(12) United States Patent
Anderson et al.

(10) Patent No.: US 12,138,302 B2
(45) Date of Patent: Nov. 12, 2024

(54) ESCHERICHIA COLI COMPOSITIONS AND METHODS THEREOF

(71) Applicant: Pfizer Inc., New York, NY (US)

(72) Inventors: Annaliesa Sybil Anderson, Upper Saddle River, NJ (US); Laurent Oliver Chorro, New York, NY (US); Robert George Konrad Donald, South Orange, NJ (US); Jacqueline Marie Lypowy, Nutley, NJ (US); Rosalind Pan, Morris Plains, NJ (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 17/509,110

(22) Filed: Oct. 25, 2021

(65) Prior Publication Data

US 2022/0152181 A1   May 19, 2022

Related U.S. Application Data

(60) Provisional application No. 63/254,195, filed on Oct. 11, 2021, provisional application No. 63/106,077, filed on Oct. 27, 2020.

(51) Int. Cl.
| | | |
|---|---|---|
| *A61K 39/108* | (2006.01) | |
| *A61K 39/00* | (2006.01) | |
| *A61P 31/04* | (2006.01) | |
| *A61P 37/04* | (2006.01) | |

(52) U.S. Cl.
CPC ...... *A61K 39/0258* (2013.01); *A61K 39/0266* (2013.01); *A61P 31/04* (2018.01); *A61P 37/04* (2018.01); *A61K 2039/6037* (2013.01)

(58) Field of Classification Search
None
See application file for complete search history.

(56) References Cited

U.S. PATENT DOCUMENTS

| | | |
|---|---|---|
| 4,709,017 A | 11/1987 | Collier et al. |
| 4,950,740 A | 8/1990 | Greenfield et al. |
| 5,340,740 A | 8/1994 | Petitte et al. |
| 5,370,872 A | 12/1994 | Cryz et al. |
| 5,614,382 A | 3/1997 | Metcalf |
| 5,656,479 A | 8/1997 | Petitte et al. |
| 5,830,510 A | 11/1998 | Petitte et al. |
| 5,843,711 A | 12/1998 | Collier et al. |
| 5,917,017 A | 6/1999 | Collier et al. |
| 6,114,168 A | 9/2000 | Samarut et al. |
| 6,194,388 B1 | 2/2001 | Krieg et al. |
| 6,207,646 B1 | 3/2001 | Krieg et al. |
| 6,214,806 B1 | 4/2001 | Krieg et al. |
| 6,218,371 B1 | 4/2001 | Krieg et al. |
| 6,239,116 B1 | 5/2001 | Krieg et al. |
| 6,339,068 B1 | 1/2002 | Krieg et al. |
| 6,455,673 B1 | 9/2002 | Collier |
| 6,500,668 B2 | 12/2002 | Samarut et al. |
| 6,749,831 B1 | 6/2004 | Bennett-Guerrero et al. |
| 7,247,307 B2 | 7/2007 | Szu et al. |
| 8,871,214 B2 | 10/2014 | Serino et al. |
| 9,060,965 B2 | 6/2015 | Costantino et al. |
| 9,492,559 B2 | 11/2016 | Emini et al. |
| 9,517,274 B2 | 12/2016 | Gu et al. |
| 9,585,950 B2 | 3/2017 | Wacker et al. |
| 9,700,612 B2 | 7/2017 | Kowarik et al. |
| 9,849,169 B2 | 12/2017 | Nagy et al. |
| 11,260,119 B2 | 3/2022 | Donald et al. |
| 2006/0228380 A1 | 10/2006 | Hausdorff et al. |
| 2007/0184071 A1 | 8/2007 | Hausdorff et al. |
| 2007/0184072 A1 | 8/2007 | Hausdorff et al. |
| 2007/0231340 A1 | 10/2007 | Hausdorff et al. |
| 2007/0231876 A1 | 10/2007 | Biemans et al. |
| 2007/0253984 A1 | 11/2007 | Kandke et al. |
| 2012/0276137 A1 | 11/2012 | Freese et al. |
| 2013/0122033 A1 | 5/2013 | De Santis et al. |
| 2015/0216996 A1 | 8/2015 | Gu et al. |
| 2015/0328328 A1 | 11/2015 | Han et al. |
| 2016/0015797 A1 | 1/2016 | Bouzari |
| 2016/0106826 A1 | 4/2016 | Ghunaim et al. |
| 2016/0136285 A1 | 5/2016 | Gozdziewicz et al. |
| 2016/0158333 A1 | 6/2016 | White et al. |
| 2016/0193330 A1 | 7/2016 | Eldridge et al. |
| 2016/0220666 A1 | 8/2016 | Eldridge et al. |
| 2016/0324950 A1 | 11/2016 | Anderson et al. |
| 2017/0260240 A1 | 9/2017 | Simon et al. |
| 2019/0275134 A1 | 9/2019 | Poolman |
| 2019/0275135 A1 | 9/2019 | Poolman |
| 2020/0002727 A1 | 1/2020 | Feary et al. |
| 2020/0061177 A1 | 2/2020 | Donald et al. |
| 2021/0268095 A1 | 9/2021 | Donald et al. |

(Continued)

FOREIGN PATENT DOCUMENTS

| | | |
|---|---|---|
| CA | 2004810 | 6/1990 |
| EP | 0 372 501 A2 | 12/1989 |

(Continued)

OTHER PUBLICATIONS

Hannan et al, "Early Severe Inflammatory Responses to Uropathogenic *E. coli* Predispose to Chronic and Recurrent Urinary Tract Infection", PLoS Pathogens 6(8):e1001042 (2010).
Hannan T., and Hunstad DA, "A Murine Model for *Escherichia coli* Urinary Tract Infection" Methods Mol Biol 1333:159-175 (2016).
Haraoka M., et al. "Neutrophil recruitment and resistance to urinary tract infection", J Infect Dis 180:1220-1229 (1999).
Hefzy, E. and Hassuna, N., "Fluoroquinolone-Resistant Sequence Type 131 Subgroups O25b and O16 Among Extraintestinal *Escherichia coli* Isolates from Community-Acquired Urinary Tract Infections", Microb Drug Resist 23:224-229 (2017).

(Continued)

*Primary Examiner* — Brian Gangle
(74) *Attorney, Agent, or Firm* — Rebecca Wright

(57) ABSTRACT

This invention relates to compositions that include a polypeptide derived from *E. coli* or a fragment thereof; and modified O-polysaccharide molecules derived from *E. coli* lipopolysaccharides and conjugates thereof, and methods of use thereof.

17 Claims, 65 Drawing Sheets

Specification includes a Sequence Listing.

(56) References Cited

U.S. PATENT DOCUMENTS

| | | |
|---|---|---|
| 2022/0168410 A1 | 6/2022 | Donald et al. |
| 2022/0202923 A1 | 6/2022 | Che et al. |

FOREIGN PATENT DOCUMENTS

| | | |
|---|---|---|
| EP | 0 413 378 B1 | 2/1991 |
| EP | 0 378 881 B1 | 6/1993 |
| EP | 0 427 347 B1 | 2/1995 |
| EP | 0 471 177 B1 | 10/1995 |
| EP | 0 594 610 B1 | 9/1998 |
| EP | 0 735 898 B1 | 3/1999 |
| EP | 0 761 231 B1 | 1/2000 |
| EP | 0 689 454 B2 | 2/2005 |
| GB | 2 220 211 A | 1/1990 |
| WO | 90/03184 A1 | 4/1990 |
| WO | 91/01146 A1 | 2/1991 |
| WO | 93/003765 A1 | 3/1993 |
| WO | 93/17712 A2 | 9/1993 |
| WO | 94/03208 A1 | 2/1994 |
| WO | 95/20657 A1 | 8/1995 |
| WO | 96/11711 A1 | 4/1996 |
| WO | 97/01640 A2 | 1/1997 |
| WO | 98/36772 A1 | 8/1998 |
| WO | 98/57659 A1 | 12/1998 |
| WO | 98/58668 A2 | 12/1998 |
| WO | 99/11241 A1 | 3/1999 |
| WO | 99/44636 A2 | 10/1999 |
| WO | 99/52549 A1 | 10/1999 |
| WO | 00/004922 A1 | 2/2000 |
| WO | 00/07621 A2 | 2/2000 |
| WO | 00/23105 A2 | 4/2000 |
| WO | 00/37105 A2 | 6/2000 |
| WO | 00/39299 A2 | 7/2000 |
| WO | 00/41720 A1 | 7/2000 |
| WO | 00/48630 A1 | 8/2000 |
| WO | 00/56358 A2 | 9/2000 |
| WO | 00/61761 A2 | 10/2000 |
| WO | 00/62800 A2 | 10/2000 |
| WO | 01/04148 A2 | 1/2001 |
| WO | 01/21152 A1 | 3/2001 |
| WO | 01/21207 A2 | 3/2001 |
| WO | 01/72337 A1 | 10/2001 |
| WO | 01/98334 A2 | 12/2001 |
| WO | 02/04496 A2 | 1/2002 |
| WO | 02/053181 A1 | 7/2002 |
| WO | 02/091998 A2 | 11/2002 |
| WO | 03/054007 A2 | 7/2003 |
| WO | 2004/081515 A2 | 9/2004 |
| WO | 2004/083251 A2 | 9/2004 |
| WO | 2006/032499 A1 | 3/2006 |
| WO | 2006/110381 A1 | 10/2006 |
| WO | 2006/134423 A2 | 12/2006 |
| WO | 2007/026190 A2 | 3/2007 |
| WO | 2008/079653 A1 | 7/2008 |
| WO | 2008/142034 A2 | 11/2008 |
| WO | 2008/143709 A2 | 11/2008 |
| WO | 2009/000826 A1 | 12/2008 |
| WO | 2010/125480 A1 | 11/2010 |
| WO | 2013/164334 A1 | 11/2013 |
| WO | 2013/188539 A2 | 12/2013 |
| WO | 2014/013375 A1 | 1/2014 |
| WO | 2014/027302 A1 | 2/2014 |
| WO | 2014/057109 A1 | 4/2014 |
| WO | 2014/072405 A1 | 5/2014 |
| WO | 2015/052344 A1 | 4/2015 |
| WO | 2015/124769 A1 | 8/2015 |
| WO | 2016/012587 A1 | 1/2016 |
| WO | 2016/115328 A1 | 7/2016 |
| WO | 2016/168324 A1 | 10/2016 |
| WO | 2016/183501 A1 | 11/2016 |
| WO | 2017/035181 A1 | 3/2017 |
| WO | 2017/085586 A1 | 5/2017 |
| WO | 2019/016187 A1 | 1/2019 |
| WO | 2019/175147 A1 | 9/2019 |
| WO | 2020/039359 A2 | 2/2020 |
| WO | 2020/191082 A1 | 9/2020 |
| WO | 2021/084429 A1 | 5/2021 |
| WO | 2021/144369 A1 | 7/2021 |
| WO | 2021/165928 A2 | 8/2021 |
| WO | 2022/090893 A2 | 5/2022 |

OTHER PUBLICATIONS

Heinrichs, D., et al., "The Assembly System for the Lipopolysaccharide R2 Core-Type of *Escherichia coli* is a hybrid of those found in *Escherichia coli* K-12 and *Salmonella enterica* Structure and function of the R2 WaaK and WaaL homologs", J Biol Chem. 273(15):8849-59 (1998).

Hong, Y. and Reeves P., "Model for the Controlled Synthesis of O-Antigen Repeat Units Involving the Waal Ligase" mSphere 1 E00074-15 (2016).

Hull et al, "Construction and Expression of Recombinant Plasmids Encoding Type 1 or D-Mannose-Resistant Pili from a Urinary Tract Infection *Escherichia coli* Isolate", Infection and Immunity 33(3):933-938 (1981).

Huttner, A., et al., "Safety, Immunogenicity, and Preliminary Clinical Efficacy of a Vaccine Against Extraintestinal Pathogenic *Escherichia coli* in Women with a History of Recurrent Urinary Tract Infection: a Randomised, Single-Blind, Placebo-Controlled Phase 1b Trial", Lancet Infect Dis, doi:10.1016/s1473-3099(17)30108-1 (2017).

Huttner, A., et al., "The Development and Early Clinical Testing of the ExPEC4V Conjugate Vaccine Against Uropathogenic *Escherichia coli*", Clin Microbiol Infect. 24(10):1046-1050 (2018).

Iebba et al, "Microevolution in fimH Gene of Mucosa-Associated *Escherichia coli* Strains Isolated from Pediatric Patients with Inflammatory Bowel Disease", Infection and Immunity 80(4):1408-1417 (2012).

Iguchi, A., et al., "A Complete View of the Genetic Diversity of the *Escherichia coli* O-antigen Biosynthesis Gene Cluster", DNA Res. 22(1):101-107 (2015).

Inoue, M., et al., "Safety, Tolerability and Immunogenicity of the ExPEC4V (JNJ-63871860) Vaccine for Prevention of invasive Extraintestinal Pathogenic *Escherichia coli* Disease: A phase 1, Randomized, Double-Blind, Placebo-Controlled Study in Healthy Japanese Participants", Hum Vaccin & Immunother. 14(9):2150-2157 (2018).

Iredell et al, "Antibiotic resistance in Enterobacteriaceae: mechanisms and clinical implications", BMJ 352:h6420 (2016).

Jiang, L., et al., "Structure and Gene Cluster of the O-antigen of *Escherichia coli* O68", Carbohydrate Research 397:27-30 (2014).

Joensen et al, "Rapid and Easy In Silico Serotyping of *Escherichia coli* Isolates by Use of Whole-Genome Sequencing Data", Journal of Clinical Microbiology 53(8):2410-2426 (2015).

Johnson S., et al., "Correlation of opsonophagocytosis and passive protection assays using human anticapsular antibodies in an infant mouse model of bacteremia for *Streptococcus pneumoniae*", J Infect Dis, 180:133-140 (1999).

Jolley et al, "Open-access bacterial population genomics: BIGSdb software, the PubMLST.org website and their applications", Wellcome Open Research 3:124 (2018).

Jonsson, K., et al., "Structural Determination of the O-antigenic Polysaccharide from *Escherichia coli* O74", Carbohydrade Research 344:1592-1595 (2009).

Kalynych, S., et al., "Structure-Guided Investigation of Lipopolysaccharide O-Antigen Chain Length Regulators Reveals Regions Critical for Modal Length Control", J Bacteriol. 193(15): 3710-3721 (2011).

Kalynych, S., et al., "Progress in Understanding the Assembly Process of Bacterial O-antigen", FEMS Microbiol Rev., 38(5):1048-1065 (2014).

Kątnik-Prastowska et al, "Glycosylation of uroplakins. Implications for bladder physiopathology", Glycoconjugate Journal 31:623-636 (2014).

Khatun et al, "Immunology of carbohydrate-based vaccines", Advanced Drug Delivery Reviews 165-166:117-126 (2020).

Kido et al, "A Single Amino Acid Substitution in a Mannosyltransferase, WbdA, Converts the *Escherichia coli* O9 Poly-

(56) References Cited

OTHER PUBLICATIONS saccharide into O9a: Generation of a New O-Serotype Group", Journal of Bacteriology 182(9):2567-2573 (2000).

King et al, "Lipopolysaccharide O antigen size distribution is determined by a chain extension complex of variable stoichiometry in *Escherichia coli* O9a", Proc. Natl. Acad. Sci. USA 111(17):6407-6412 (2014).

Kisiela et al, "Conformational inactivation induces immunogenicity of the receptor-binding pocket of a bacterial adhesin", PNAS 110(47):19089-19094 (2013).

Kisiela et al, "Conformational inactivation induces immunogenicity of the receptor-binding pocket of a bacterial adhesin—Supporting Information", 10.1073/pnas.1314395110 (2013).

Kisiela et al, "Inhibition and Reversal of Microbial Attachment by an Antibody with Parasteric Activity against the FimH Adhesin of Uropathogenic *E. coli*", PLoS Pathogens 11(5):e1004857 (2015).

Knirel, "Structure of O-Antigens", Bacterial Lipopolysaccharides, Y.A. Knirel and M.A. Valvano (eds.), Springer-Verlag/Wien 2011, Chapter 3, pp. 41-115.

Konadu, E., et al., Preparation, Characterization, and Immunological Properties in Mice of *Escherichia coli* O157 O-Specific Polysaccharide-Protein Conjugat Vaccines, Infection and Immunity, 62(11):5048-5054 (1994).

Kuo et al, "Characterization of a Recombinant Pneumolysin and Its Use as a Protein Carrier for Pneumococcal Type 18C Conjugate Vaccines", Infection and Immunity 63(7):2706-2713 (1995).

Lane, M., et al., "Expression of flagella is coincident with uropathogenic *Escherichia coli* ascension to the upper urinary tract", Proceedings of the National Academy of Sciences, 104:16669-16674 (2007).

Langermann et al, "Prevention of Mucosal *Escherichia coli* Infection by FimH-Adhesin-Based Systemic Vaccination", Science 276:607-611 (1997).

Larzabal, M., et al, "Human and Veterinary Vaccines against Pathogenic *Escherichia coli*", IntechOpen, 21 pages (2018).

Lerouge and Vanderleyden, "O-antigen structural variation: mechanisms and possible roles in animal/plant-microbe interactions", FEMS Microbiology Reviews 26(1):17-47 (2001).

Le Trong et al, "Donor strand exchange and conformational changes during *E. coli* fimbrial formation", Journal of Structural Biology 172(3):380-388 (2010).

Letrong, I., et al, "Structural Basis for Mechanical Force Regulation of the Adhesin FimH via Finger Trap-like b Sheet Twisting", Cell, 141:645-655 (2010).

Liu et al, "Identification of FimH derivatives as adjuvant vaccinated with Pac that enhance protection against *Streptococcus* mutans colonization", Molecular and Cellular Probes 45:19-25 (2019).

Ma, Z., et al., "Glycoconjugate Vaccine Containing *Escherichia coli* O157:H7 O-Antigen Linked with Maltose-Binding Protein Elicits Humoral and Cellular Responses", PLOS One, 9(8): 1-10 (2014).

Magala et al, "RMSD analysis of structures of the bacterial protein FimH identifies five conformations of its lectin domain", Proteins 88(4):593-603 (2019).

Marder et al, "Multistate Outbreak of *Escherichia coli* O157:H7 Associated with Bagged Salad", Foodborne Pathogens and Disease 11(8):593-595 (2014).

Mather, "Establishment and Characterization of Two Distinct Mouse Testicular Epithelial Cell Lines", Biology of Reproduction 23:243-252 (1980).

Mather et al, "Culture of Testicular Cells in Hormone-Supplemented Serum-Free Medium", Annals N.Y. Acad. Sci. 383:44-68 (1982).

Meiland, R., et al., "Fimch antiserum inhibits the adherence of *Escherichia coli* to cells collected by voided urine specimens of diabetic women" J Urol 171:1589-1593 (2004).

Mellata, M., et al, "Novel vaccine antigen combinations elicit protective immune responses against *Escherichia coli* sepsis", Vaccine, 34(5):656-662 (2016).

Meloni, E., et al., "Simplified low-cost production of O-antigen from *Salmonella typhimurium* Generalized Modules for Membrane Antigens (GMMA)", Journal of Biotechnology 198:46-52 (2015).

Micoli, F., et al., "A Scalable Method for O-antigen Purification Applied to Various *Salmonella serovars*", Anal Biochem, 434(1):136-145 (2013).

Milstein et al, "Hybrid hybridomas and their use in immunohistochemistry", Nature 305(5934):537-540 (1983).

Mobley H. and Alteri C., "Development of a Vaccine against *Escherichia coli* Urinary Tract Infections", Pathogens 5 (2016).

Morales-Barroso, I., et al., "Bacteraemia due to non-ESBL-producing *Escherichia coli* O25b:H4 sequence type 131: insights into risk factors, clinical features and outcomes", Int J Antimicrob Agents doi:10.1016/j.ijantimicag (2016).

Moriel, D., et al., "Identification of Protective and Broadly Conserved Vaccine Antigens from the Genome of Extraintestinal Pathogenic *Escherichia coli*", Proc Natl Acad Sci, 107(20):9072-9077 (2010).

Tchesnokova, V., et al, "Type 1 Fimbrial Adhesin FimH Elicits an Immune Response That Enhances Cell Adhesion of *Escherichia coli*", Infection and Immunity, 79(10): 3895-3904 (2011).

Thelwall et al, "Annual Epidemiological Commentary: Mandatory MRSA, MSSSA and *E. coli* bacteraemia and *C. difficile* infection data 2015/16", Jul. 7, 2016, Public Health England.

Thumbikat et al, "Bacteria-Induced Uroplakin Signaling Mediates Bladder Response to Infection", PLoS Pathogens 5(5):e1000415 (2009).

Tocilj, A., et al., "Bacterial polysaccharide co-polymerases share a common framework for control of polymer length" Nat Struct Mol Biol 15:130-138 (2008).

Uchida et al, "Mutation in the Structural Gene for Diphtheria Toxin Carried by Temperate Phage Beta", Nature New Biology 233:8-11 (1971).

Uchida et al, "Diphtheria toxin and related proteins. I. Isolation and properties of mutant proteins serologically related to diphtheria toxin", J Biol Chem 248(11):3838-3844 (1973).

Urlaub et al, "Isolation of Chinese hamster cell mutants deficient in dihydrofolate reductase activity", Proc. Natl. Acad. Sci. USA 77(7):4216-4220 (1980).

Van den Dobbelsteen et al, "Immunogenicity and safety of a tetravalent *E. coli* O-antigen bioconjugate vaccine in animal models", Vaccine 34:4152-4160 (2016).

Vetsch et al, "Chaperone-independent Folding of Type 1 Pilus Domains", J. Mol. Biol. 322(4):827-840 (2002).

Vimont, S., et al., "The CTX-M-15-producing *Escherichia coli* clone O25b: H4-ST131 has high intestine colonization and urinary tract infection abilities" PLoS One 7:e46547 (2012).

Vinogradov et al, "Structures of Lipopolysaccharides from *Klebsiella pneumoniae*: Elucidation of the Structure of the Linkage Region Between Core and Polysaccharide O Chain and Identification of the Residues at the Non-Reducing Termini of the O Chains", The Journal of Biological Chemistry 277(28):25070-25081 (2002).

Weissman et al, "Clonal analysis reveals high rate of structural mutations in fimbrial adhesins of extraintestinal pathogenic *Escherichia coli*", Mol Microbiol. 59(3):975-988 (2006).

Whitfield, C., et al., Molecular Insights Into the Assembly and Diversity of the Outer Core Oligosaccharide in Lipopolysaccharides from *Escherichia coli* and *Salmonella*, J Endotoxin Res., 9(4):244-249 (2003).

Wick et al, "Kaptive Web: User-Friendly Capsule and Lipopolysaccharide Serotype Prediction for *Klebsiella* Genomes", Journal of Clinical Microbiology 56(6):e00197-18 (2018).

Wirth et al, "Sex and virulence in *Escherichia coli*: an evolutionary perspective", Molecular Microbiology 60(5):1136-1151 (2006).

Wizemann, T., et al, "Adhesins as Targets for Vaccine Development", Emerg Infect Dis, 5(3):395-403 (1999).

Wolf, M., Occurrence, Distribution, and Associations of O and H serogroups, Colonization Factor Antigens, and Toxins of Enterotoxigenic *Escherichia coli*, Clin Microbiol Rev., 10(4):569-84 (1997).

Woodward, R., et al., "In vitro bacterial polysaccharide biosynthesis: defining the functions of Wzy and Wzz." Nat Chem Biol., 6(6):418-23 (2010).

Yinnon et al, "*Klebsiella* bacteraemia: community versus nosocomial infection", Q J Med 89(12):933-941 (1996).

(56) References Cited

OTHER PUBLICATIONS

Zhou, G., et al., "Uroplakin la is the urothelial receptor for uropathogenic *Escherichia coli*: evidence from in vitro FimH binding", J Cell Sci 114:4095-4103 (2001).
Zowawi et al, "The emerging threat of multidrug-resistant Gram-negative bacteria in urology", Nature Reviews Urology 12:570-584 (2015).
Abbanat, D., et al., "Development and Qualification of an Opsonophagocytic Killing Assay to Assess Immunogenicity of a Bioconjugated *Escherichia coli* Vaccine", Clin Vaccine Immunol 24(12):e00123-17 (2017).
Al-Hasan et al, "Antimicrobial resistance trends of *Escherichia coli* bloodstream isolates: a population-based study, 1998-2007", Journal of Antimicrobial Chemotherapy 64(1):169-174 (2009).
Alonso-Caballero, A., et al, "Mechanical architecture and folding of *E. coli* type 1 pilus domains", Nat Commun 9, 2758 (2018).
Amor, K., et al., "Distribution of core oligosaccharide types in lipopolysaccharides from *Escherichia coli*", Infect Immun 68:1116-1124 (2000).
Anderson et al, "Bloodstream Infections in Community Hospitals in the 21st Century: A Multicenter Cohort Study", PLoS One 9(3):e91713 (2014).
Appelmelk, B., et al., "Frequencies of lipopolysaccharide core types in *Escherichia coli* strains from bacteraemic patients", Microbiology 140:1119-24 (1994).
Aprikian, P., et al, "The Bacterial Fimbrial Tip Acts as a Mechanical Force Sensor", PLoS Biol 9(5):e1000617 (2011).
Baliban, S., et al., "Development of a glycoconjugate vaccine to prevent invasive *Salmonella typhimurium* infections in sub-Saharan Africa", PLoS Negl Trop Dis. 11(4): e0005493 (2017).
Bameri, Z., et al., "High Yield Expression and Modified Purification of Novel Recombinant Truncated Protein FimH. MrpH against Urinary Tract Infections by *Escherichia coli* and *Proteus mirabilis*", Journal of Clinical and Diagnostic Research 12(1): KC06-KC09 (2018).
Baraldo et al, "N19 Polyepitope as a Carrier for Enhanced Immunogenicity and Protective Efficacy of Meningococcal Conjugate Vaccines", Infection and Immunity 72(8):4884-4887 (2004).
Barnhart et al, "PapD-like chaperones provide the missing information for folding of pilin proteins", PNAS 97(14):7709-7714 (2000).
Barnhart et al, "Chaperone-Subunit-Usher Interactions Required for Donor Strand Exchange during Bacterial Pilus Assembly", Journal of Bacteriology 185(9):2723-2730 (2003).
Bauchart et al, "Pathogenomic comparison of human extraintestinal and avian pathogenic *Escherichia coli*—Search for factors involved in host specificity or zoonotic potential", Microbial Pathogenesis 49(3):105-115 (2010).
Behrens, R., et al., "Efficacy and safety of a patch vaccine containing heat-labile toxin from *Escherichia coli* against travellers' diarrhoea: a phase 3, randomised, double-blind, placebo-controlled field trial in travellers from Europe to Mexico and Guatemala", Lancet Infect Dis. 14(3):197-204 (2014).
Bennett-Guerrero, E., et al., "Preparation and Preclinical Evaluation of a Novel Liposomal Complete-Core Lipopolysaccharide Vaccine", Infect Immun. 68(11):6202-6208 (2000).
Bouckaert et al, "Receptor binding studies disclose a novel class of high-affinity inhibitors of the *Escherichia coli* FimH adhesin", Molecular Microbiology 55(2):441-455 (2005).
Bourgeois, A., et al., "Status of vaccine research and development for enterotoxigenic *Escherichia coli*", Vaccine 34(26):2880-2886 (2016).
Brown et al, "Structure of the streptococcal cell wall C5a peptidase", Proc. Natl. Acad. Sci. USA 102(51):18391-18396 (2005).
Brumbaugh, A., et al., Preventing urinary tract infection: progress toward an effective *Escherichia coli* vaccine. Expert Rev Vaccines. 11(6):663-76 (2012).
Buckles et al, "Role of the K2 Capsule in *Escherichia coli* Urinary Tract Infection and Serum Resistance", The Journal of Infectious Diseases 199(11):1689-1697 (2009).

Burns et al, "Loss of Resistance to Ingestion and Phagocytic Killing by O- and K-Mutants of a Uropathogenic *Escherichia coli* O75:K5 Strain", Infection and Immunity 67(8):3757-3762 (1999).
Céspedes et al, "Genetic Diversity and Virulence Determinants of *Escherichia coli* Strains Isolated from Patients with Crohn's Disease in Spain and Chile", Frontiers in Microbiology 8:Article 639 (2017).
Chakraborty, S., Human Experimental Challenge With Enterotoxigenic *Escherichia coli* Elicits Immune Responses to Canonical and Novel Antigens Relevant to Vaccine Development, The Journal of Infectious Diseases 218(9):1436-1446 (2018).
Chen, S., et al., "Positive selection identifies an in vivo role for FimH during urinary tract infection in addition to mannose binding", PNAS 106(52): 22439-22444 (2009).
Chen et al, "Carbapenemase-producing *Klebsiella pneumoniae*: molecular and genetic decoding", Trends in Microbiology 22(12):686-696 (2014).
Chmielewski, M., et al., "FimH-based display of functional eukaryotic proteins on bacteria surfaces", Scientific Reports 9:8410 s41598-019-44883 (2019).
Clarke et al, "Coordination of Polymerization, Chain Termination, and Export in Assembly of the *Escherichia coli* Lipopolysaccharide O9a Antigen in an ATP-binding Cassette Transporter-dependent Pathway", The Journal of Biological Chemistry 284(44):30662-30672 (2009).
Clermont, O., et al., Determination of *Escherichia coli* O Types by Allele-Specific Polymerase Chain Reaction: Application to the O types Involved in Human Septicemia, Diagn Microbiol Infect Dis. 57(2):129-36 (2007).
Cryz, S.J., "Synthesis and Characterization of a Polyvalent *Escherichia coli* O-polysaccharide-toxin A Conjugate Vaccine", Vaccine 13(5):449-453 (1995).
Cusumano et al, "Treatment and Prevention of Urinary Tract Infection with Orally Active FimH Inhibitors", Science Translational Medicine 3(109):109ra115 (2011).
Debroy, C., et al., Comparison of O-Antigen Gene Clusters of All O-Serogroups of *Escherichia coli* and Proposal for Adopting a New Nomenclature for O-Typing. PLoS One 11(1):e0147434 (2016).
Diancourt et al, "Multilocus Sequence Typing of *Klebsiella pneumoniae* Nosocomial Isolates", Journal of Clinical Microbiology 43(8):4178-4182 (2005).
Douglas et al, "Exotoxin A of Pseudomonas aeruginosa: Substitution of Glutamic Acid 553 with Aspartic Acid Drastically Reduces Toxicity and Enzymatic Activity", Journal of Bacteriology 169(11):4967-4971).
Dreux et al, "Point Mutations in FimH Adhesin of Crohn's Disease-Associated Adherent-Invasive *Escherichia coli* Enhance Intestinal Inflammatory Response", PLoS Pathogens 9(1):e1003141 (2013).
Durant, L., et al., "Identification of candidates for a subunit vaccine against extraintestinal pathogenic *Escherichia coli*", Infect Immun 75:1916-1925 (2007).
Falugi et al, "Rationally designed strings of promiscuous CD4+ T cell epitopes provide help to *Haemophilus influenzae* type b oligosaccharide: a model for new conjugate vaccines", Eur. J. Immunol. 31:3816-3824 (2001).
Feenstra et al, "Adhesion of *Escherichia coli* under flow conditions reveals potential novel effects of FimH mutations", Eur J Clin Microbiol Infect Dis 36:467-478 (2017).
Feldman, M., et al., "Engineering N-linked protein glycosylation with diverse O antigen lipopolysaccharide structures in *Escherichia coli*", Proceedings of the National Academy of Sciences of the United States of America 102:3016-3021 (2005).
Follador et al, "The diversity of *Klebsiella pneumoniae* surface polysaccharides", Microbial Genomics 2:e000073 (2016).
Forde, B., et al., "The complete genome sequence of *Escherichia coli* EC958: a high quality reference sequence for the globally disseminated multidrug resistant *E. coli* O25b:H4-ST131 clone", PLoS One, 9:e104400 (2014).
Franco, A., et al., "A Wzz (Cld) Protein Determines the Chain Length of K Lipoploysaccharide in *Escherichia coli* O8 and O9 Strains", Journal of Bacteriology 178(7):1903-1907 (1996).
Frenck, R., et al., Long-term Immunogenicity and Safety of ExPEC4V Vaccine Against Extraintestinal Pathogenic *Escherichia coli* Dis-

(56) References Cited

OTHER PUBLICATIONS ease in Healthy Participants. Presented at the American Society for Microbiology, Jun. 7-11, Atlanta, GA. (2018).
Ghosh et al, "Incidence of multidrug resistance, pathogenicity island markers, and pathoadaptive FimH mutations in uropathogenic *Escherichia coli* isolated from asymptomatic hospitalized patients", Folia Microbiologica 64(4):587-600 (2019).
Giedraitiene, A., et al., "Prevalence of O25b-ST131 clone among *Escherichia coli* strains producing CTX-M-15, CTX-M-14 and CTX-M-92 beta-lactamases", Infect Dis (Lond) 49:106-112 (2017).
Graham et al, "Characteristics of a Human Cell Line Transformed by DNA from Human Adenovirus Type 5", J. Gen. Virol. 36(1):59-74 (1977).
Green, S., et al., "Murine model of chemotherapy-induced extraintestinal pathogenic *Escherichia coli* translocation", Infect Immun 83:3243-3256 (2015).
Greenfield et al, "Biosynthesis of the Polymannose Lipopolysaccharide O-antigens from *Escherichia coli* Serotypes O8 and O9a Requires a Unique Combination of Single- and Multiple-active Site Mannosyltransferases", The Journal of Biological Chemistry 287(42):35078-35091 (2012).
Guachalla et al, "Discovery of monoclonal antibodies cross-reactive to novel subserotypes of *K. pneumoniae* O3", Scientific Reports 7:6635 (2017).
Hagan E. and Mobley H., "Uropathogenic *Escherichia coli* outer membrane antigens expressed during urinary tract infection", Infect Immun 75:3941-3949 (2007).
Han D., et al., "Regulation of the O-antigen polysaccharide chain length by Wzz—a review", Acta Microbiologica Sinica 54(9):971-976 (2014).
Motley, M. & Fries, B., "A New Take on an Old Remedy: Generating Antibodies against Multidrug-Resistant Gram-Negative Bacteria in a Postantibiotic World", mSphere, 2(5) e00397-17 (2017).
Mulford, C. and Osborn M., "An intermediate step in translocation of lipopolysaccharide to the outer membrane of *Salmonella typhimurium*", Proc Natl Acad Sci U S A 80:1159-1163 (1983).
Muller-Leonnies, S., et al., "Neutralizing and Cross-Reactive Antibodies Against Enterobacterial Lipopolysaccharide", Int J Med Microbiol., 297(5):321-40 (2007).
Munera et al, "Recognition of the N-terminal lectin domain of FimH adhesin by the usher FimD is required for type 1 pilus biogenesis", Molecular Microbiology 64(2):333-346 (2007).
Munera et al, "Specific residues in the N-terminal domain of FimH stimulate type 1 fimbriae assembly in *Escherichia coli* following the initial binding of the adhesin to FimD usher", Molecular Microbiology 69(4):911-925 (2008).
Murray, G., et al., "Regulation of *Salmonella typhimurium* lipopolysaccharide O antigen chain length is required for virulence; identification of FepE as a second Wzz", Mol Microbiol, 47:1395-1406 (2003).
Naumenko, O., "Structure and Gene Cluster of the O-antigen of *Escherichia coli* O54", Carbohydrate Research, 462:34-38 (2018).
Naumenko, O., et al., "Structural Studies on the O-polysaccharide of *Escherichia coli* O57", Carbohydrate Research 465:1-3 (2018).
Needleman et al, "A General Method Applicable to the Search for Similarities in the Amino Acid Sequence of Two Proteins", J. Mol. Biol. 48(3):443-453 (1970).
Nicolas-Chanoine et al, "*Escherichia coli* ST131, an Intriguing Clonal Group", Clinical Microbiology Reviews 27(3):543-574 (2014).
O'Brien, V., et al, "Drug and Vaccine Development for the Treatment and Prevention of Urinary Tract Infections", Microbiol Spectrum 4(1): 1-42 (2016).
Osawa, K., et al., "Modulation of O-antigen chain length by the wzz gene in *Escherichia coli* O157 influences its sensitivities to serum complement", Microbiol Immunol 57:616-623 (2013).
PCT International Search Report and Written Opinion for International Application No. PCT/IB2019/057025 dated Feb. 17, 2020.
PCT International Search Report and Written Opinion for International Application No. PCT/IB2021/051457 dated Aug. 16, 2021.
PCT International Search Report and Written Opinion for International Application No. PCT/IB2020/060081 dated Dec. 21, 2020.
PCT International Search Report and Written Opinion for International Application No. PCT/IB2021/062022 dated Jun. 3, 2022.
Pearson et al, "Improved tools for biological sequence comparison", PNAS 85:2444-2448 (1988).
Perepelov, A., et al., "Structure and Gene Cluster of the O-antigen of *Escherichia coli* O76", Carbohydrate Research, 377:14-14 (2013).
Perepelov, A., et al., "Structure and Gene Cluster of the O-antigen of *Escherichia coli* O36", Carbohydrate Research, 390:46-49 (2014).
Perepelov, A., et al., "Structure and Gene Cluster of the O-antigen of *Escherichia coli* O140", Carbohydrate Research 411:33-36 (2015).
Phalipon, A., et al., "A Synthetic Carbohydrate-Protein Conjugate Vaccine Candidate Against Shigella Flexneri 2a Infection", J Immunol., 182(4):2241-7 (2009).
Phan, M., et al., "The Serum Resistome of a Globally Disseminated Multidrug Resistant Uropathogenic *Escherichia coli* Clone", PLoS Genetics 9:e1003834 (2013).
Podschun et al, "*Klebsiella* spp. As Nosocomial Pathogens: Epidemiology, Taxonomy, Typing Methods, and Pathogenicity Factors", Clinical Microbiology Reviews 11(4):589-603 (1998).
Poolman et al., "Extraintestinal Pathogenic *Escherichi coli*, a Common Human Pathogen: Challenges for Vaccine Development and Progress in the Field", The Journal of Infectious Diseases 213:6-13 (2016).
Rabbani, S., et al., "Conformational switch of the bacterial adhesin FimH in the absence of the regulatory domain: Engineering a minimalistic allosteric system", J. Biol. Chem., 293(5): 1835-1849 (2018).
Reyes E., et al., Mechanisms of O-Antigen Structural Variation of Bacterial Lipopolysaccharide (LPS). Chapter 3, The Complex World of Polysaccharides. IntechOpen (2012).
Rodriguez et al, "Allosteric Coupling in the Bacterial Adhesive Protein FimH", The Journal of Biological Chemistry 288(33):24128-24139 (2013).
Rogers et al, "*Escherichia coli* O25b-ST131: a pandemic, multiresistant, community-associated strain", Journal of Antimicrobial Chemotherapy 66:1-14 (2011).
Ronald, L., et al, "Adaptive mutations in the signal peptide of the type 1 fimbrial adhesin of uropathogenic *Escherichia coli*" PNAS, 105(31): 10937-10942 (2008).
Ruiz-Argüello et al, "Thermostability of the human respiratory syncytial virus fusion protein before and after activation: implications for the membrane-fusion mechanism", Journal of General Virology 85(12):3677-3687 (2004).
Russo et al, "Medical and economic impact of extraintestinal infections due to *Escherichia coli*: focus on an increasingly important endemic problem", Microbes and Infection 5:449-456 (2003).
Sarkar et al, "Role of Capsule and O Antigen in the Virulence of Uropathogenic *Escherichia coli*", PLoS One 9(4): e94786 (2014).
Sato, T., et al. , "Tigecycline Nonsusceptibility Occurs Exclusively in Fluoroquinolone-Resistant *Escherichia coli* Clinical Isolates, Including the Major Multidrug-Resistant Lineages", Antimicrob Agents Chemother, O25b:H4-ST131-H30R and O1-ST648. 61 (2017).
Sauer, M., et al, "Catch-bond mechanism of the bacterial adhesin FimH", Nat. Commun. 7:10738 doi: 10.1038/ncomms10738 (2016).
Schembri et al, "Expression and purification of the mannose recognition domain of the FimH adhesin", FEMS Microbiology Letters 188:147-151 (2000).
Schrag et al, "Epidemiology of Invasive Early-Onset Neonatal Sepsis, 2005 to 2014", Pediatrics 138(6):e20162013 (2016).
Schwartz et al, "Population Dynamics and Niche Distribution of Uropathogenic *Escherichia coli* during Acute and Chronic Urinary Tract Infection", Infection and Immunity 79(10):4250-4259 (2011).
Schwartz et al, "Positively selected FimH residues enhance virulence during urinary tract infection by altering FimH conformation", PNAS 110(39):15530-15537 (2013).
Shang, W., et al., "Chemical Synthesis of the Outer Core Oligosaccharide of *Escherichia coli* R3 and Immunological Evaluation" Org Biomol Chem., 13(14):4321-4330 (2015).
Sheikh, A., et al, "Highly conserved type 1 pili promote enterotoxigenic *E. coli* pathogen-host interactions", PLoS Negl Trop Dis 11(5): e0005586 (2017).

(56) References Cited

OTHER PUBLICATIONS

Sihra, N., et al, "Nonantibiotic prevention and management of recurrent urinary tract infection", Nat Rev Urol 15: 750-776 (2018).

Sjölander et al, "ISCOMs: an adjuvant with multiple functions", Journal of Leukocyte Biology 64:713-723 (1998).

Smith, SN, "Dissemination and systemic colonization of uropathogenic *Escherichia coli* in a murine model of bacteremia" MBio 1 (2010).

Starks et al, "Optimization and qualification of an assay that demonstrates that a FimH vaccine induces functional antibody responses in women with histories of urinary tract infections", Human Vaccines & Immunotherapeutics 17(1):283-292 (2021).

Stenutz, R., et al., The Structures of *Escherichia coli* O-polysaccharide Antigens, FEMS Microbiol Rev., 30(3):382-403 (2006).

Stoll et al, "Early Onset Neonatal Sepsis: The Burden of Group B Streptococcal and *E. coli* Disease Continues", Pediatrics 127(5):817-826 (2011).

Summers et al, A Manual of Methods for Baculovirus Vectors and Insect Cell Culture Procedures; Texas Agricultural Experiment Station Bulletin No. 1555 (1987).

Szijarto, V., et al., "Diagnostic Potential of Monoclonal Antibodies Specific to the Unique O-Antigen of Multidrug-Resistant Epidemic *Escherichia coli* Clone ST131-O25b:H4", Clin Vaccine Immunol., 21(7):930-939 (2014).

Szijarto, V., et al., "Bactericidal monoclonal antibodies specific to the lipopolysaccharide O antigen from multidrug-resistant *Escherichia coli* clone ST131-O25b:H4 elicit protection in mice", Antimicrob Agents Chemother 59:3109-3116 (2015).

Taylor, C., et al., Mutations in the waaR Gene of *Escherichia coli* Which Disrupt Lipopolysaccharide Outer Core Biosynthesis Affect Cell Surface Retention of Group 2 Capsular Polysaccharides, J Bacteriol. 88(3):1165-1168 (2006).

Costantino et al, "The design of semi-synthetic and synthetic glycoconjugate vaccines", Expert Opinion Drug Discovery 6(10):1045-1066 (2011).

Franco et al, "The Wzz (Cld) Protein in *Escherichia coli*: Amino Acid Sequence Variation Determines O-Antigen Chain Length Specificity", Journal of Bacteriology 180(10):2670-2675 (1998).

Kurupati et al, "Identification of vaccine candidate antigens of an ESBL producing *Klebsiella pneumoniae* clinical strain by immunoproteome analysis", Proteomics 6:836-844 (2006).

Aucken & Pitt, "Serological relationships of the O antigens of *Klebsiella pneumoniae* O5, *Escherichia coli* O8 and a new O serotype of Serratia marcescens", FEMS Microbiology Letters 80:93-98 (1991).

Broun et al., "Catalytic Plasticity of Fatty Acid Modification Enzymes Underlying Chemical Diversity of Plant Lipids", Science 282:1315-1317 (1998).

Poolman et al., "The history of pneumococcal conjugate vaccine development: dose selection", Expert Rev. Vaccines 12(12):1379-1394 (2013).

Seffernick et al., "Melamine Deaminase and Atrazine Chlorohydrolase: 98 Percent Identical but Functionally Different", Journal of Bacteriology 183(8):2405-2410 (2001).

Whisstock & Lesk, "Prediction of protein function from protein sequence and structure", Quarterly Reviews of Biophysics 36(3):307-340 (2003).

Witkowski et al., "Conversion of a Beta-Ketoacyl Synthase to a Malonyl Decarboxylase by Replacement of the Active-Site Cysteine with Glutamine", Biochemistry 38:11643-11650 (1999).

Yampolsky & Stoltzus, "The Exchangeability of Amino Acids in Proteins", Genetics 170:1459-1472 (2005).

Kido, N., et al., "Inhibition by Succinyl Concanavalin A of Strong Adjuvant Activity of Lipopolysaccharides Which Possess Mannans as the O-Specific Polysaccharide Chains", Cellular Immunology, 1985, 92(2):328-337.

Kido, N., et al., "Potent Adjuvant Action of Lipopolysaccharides Possessing the O-Specific Polysaccharide Moieties Consisting of Mannans in Antibody Response against Protein Antigen", Cellular Immunology, 1985, 91:52-59.

Micoli, F., et al., "Potential targets for next generation antimicrobial glycoconjugate vaccines", FEMS Microbiology Reviews, 2018, 42(3):388-423.

Sugiyama, T., et al., "Generation of *Escherichia coli* O9 Serotype, a Subtype of *E. coli* O9, by Transfer of the wb* Gene Cluster of Klebsiella O3 into *E. coli* via Recombination", Journal of Bacteriology, 1998, 180(10):2775-2778.

Vinogradov, E., et al., "The structure of the core region of the lipopolysaccharide from Klebsiella pneumoniae O3: 3-Deoxy-alpha-D-manno-octulosonic acid (alpha-Kdo) residue in the outer part of the core, a common structural element of Klebsiella pneumoniae O1, O2, O3, O4, O5, O8 and O12 lipopolysaccharides", Eur. J. Biochem., 2001, 268:1722-1729.

FIG. 1A type 1 fimbriae D-mannose specific adhesin [Escherichia coli FimH J96 ELL41155.1 [E.coli J96]; 300 aa

```
  1 MKRVITLFAV LLMGWSVNAW SFACKTANGT AIPIGGGSAN VYVNLAPVVN
 51 VGQNLVVDLS TQIFCHNDYP ETITDYVTLQ RGSAYGGVLS NFSGTVKYSG
101 SSYPFPTTSE TPRVVYNSRT DKPWPVALYL TPVSSAGGVA IKAGSLIAVL
151 ILRQTNNYNS DDFQFVWNIY ANNDVVVPTG GCDVSARDVT VTLPDYPGSV
201 PIPLTVYCAK SQNLGYYLSG TTADAGNSIF TNTASFSPAQ GVGVQLTRNG
251 TIIPANNTVS LGAVGTSAVS LGLTANYART GGQVTAGNVQ SIIGVTFVYQ
(SEQ ID NO: 1)
```

FimH J96 sequence

```
  1 MKRVITLFAV LLMGWSVNAW SFACKTANGT AIPIGGGSAN VYVNLAPVVN
 51 VGQNLVVDLS TQIFCHNDYP ETITDYVTLQ RGSAYGGVLS NFSGTVKYSG
101 SSYPFPTTSE TPRVVYNSRT DKPWPVALYL TPVSSAGGVA IKAGSLIAVL
151 ILRQTNNYNS DDFQFVWNIY ANNDVVVPTG GCDVSARDVT VTLPDYPGSV
201 PIPLTVYCAK SQNLGYYLSG TTADAGNSIF TNTASFSPAQ GVGVQLTRNG
251 TIIPANNTVS LGAVGTSAVS LGLTANYART GGQVTAGNVQ SIIGVTFVYQ (SEQ ID NO: 1)
```

Fragment of FimH, corresponding to aa residues 22-300 of SEQ ID NO: 1 [mature FimH protein]

```
  1 facktangt aipigggsan vyvnlapvvn vgqnlvvdls tqifchndyp etitdyvtlq
    rgsayggvls nfsgtvkysg ssypfpttse tprvvynsrt dkpwpvalyl tpvssaggva
    ikagsliavl ilrqtnnyns ddfqfvwniy anndvvvptg gcdvsardvt vtlpdypgsv
    pipltvycak sqnlgyylsg ttadagnsif tntasfspaq gvgvqltrng tiipanntvs
    lgavgtsavs lgltanyart ggqvtagnvq siigvtfvyq 279 (SEQ ID NO: 2)
```

FimH lectin domain (SEQ ID NO: 3, which corresponds to aa residues 1-158 of SEQ ID NO: 2)

```
  1 facktangt aipigggsan vyvnlapvvn vgqnlvvdls tqifchndyp etitdyvtlq
    rgsayggvls nfsgtvkysg ssypfpttse tprvvynsrt dkpwpvalyl tpvssaggva
    ikagsliavl ilrqtnnyns ddfqfvwniy anndvvv 158 (SEQ ID NO: 3)
```

FimH pilin domain (SEQ ID NO: 4, which corresponds to aa residues 160-279 of SEQ ID NO: 2)

160 gcdvsardvt vtlpdypgsv pipltvycak sqnlgyylsg ttadagnslf tntasfspaq
gvgvqltrng tiipanntvs lgavgtsavs lgltanyart ggqvtagnvq siigvtfvyq 279
(SEQ ID NO: 4)

pSB02198 - FimH mIgK signal pept / F22..Q300 J96 FimH N28S V48C L55C N91S N249Q / 7 AA linker / FimG A1..K14 / GGHis8 in pcDNA3.1(+)
VETDTLLLWVLLLWVPGSTGFACKTASGTAIPIGGGSANVYVNLAPCVNVGQNCVVDLSTQI
FCHNDYPETITDYVTLQRGSAYGGVLSSFSGTVKYSGSSYPFPTTSETPRVVYNSRTDKPW
PVALYLTPVSSAGGVAIKAGSLIAVLILRQTNNYNSDDFQFVWNIYANNDVVVPTGGCDVSA
RDVTVTLPDYPGSVPIPLTVYCAKSQNLGYYLSGTTADAGNSIFTNTASFSPAQGVGVQLTR
QGTIIPANNTVSLGAVGTSAVSLGLTANYARTGGQVTAGNVQSIIGVTFVYQGGSSGGGAD
VTITVNGKVVAKGGHHHHHHHH (SEQ ID NO: 5)

pSB02307 - FimH mIgK signal pept / F22..Q300 J96 FimH N28S N91S N249Q / His8 in pcDNA3.1(+)
METDT LLLWV LLLWV PGSTG FACKT ASGTA IPIGG GSANV YVNLA PVVNV GQNLV
VDLST QIFCH NDYPE TITDY VTLQR GSAYG GVLSS FSGTV KYSGS SYPFP TTSET
PRVVY NSRTD KPWPV ALYLT PVSSA GGVAI KAGSL IAVLI LRQTN NYNSD DFQFV
WNIYA NNDVV VPTGG CDVSA RDVTV TLPDY PGSVP IPLTV YCAKS QNLGY YLSGT
TADAG NSIFT NTASF SPAQG VGVQL TRQGT IIPAN NTVSL GAVGT SAVSL GLTAN
YARTG GQVTA GNVQS IIGVT FVYQG GSSGG GADVT ITVNG KVVAK GGHHH HHHH
(SEQ ID NO: 6)

Number of amino acids: 310 Molecular weight: 32095.80 Theoretical pI: 7.25 pSB02083 FimH Lectin Domain Wild Type construct
METDT LLLWV LLLWV PGSTG FACKT ASGTA IPIGG GSANV YVNLA PVVNV GQNLV
VDLST QIFCH NDYPE TITDY VTLQR GSAYG GVLSS FSGTV KYSGS SYPFP TTSET
PRVVY NSRTD KPWPV ALYLT PVSSA GGVAI KAGSL IAVLI LRQTN NYNSD DFQFV
WNIYA NNDVV VPTGG HHHHHHHH (SEQ ID NO: 7)

pSB02158 FimH Lectin Domain Lock Mutant
METDTLLLWVLLLWVPGSTG FACKT ASGTA IPIGG GSANV YVNLA PCVNV GQNCV
VDLST QIFCH NDYPE TITDY VTLQR GSAYG GVLSS FSGTV KYSGS SYPFP TTSET

PRVVY NSRTD KPWPV ALYLT PVSSA GGVAI KAGSL IAVLI LRQTN NYNSD DFQFV
WNIYA NNDVV VPTGG HHHHHHHH (SEQ ID NO: 8)

FIG. 1B

FimG A1..K14 sequence
ADVTI TVNGK VVAK (SEQ ID NO: 9)

ADVT ITVNG KVVAK GGHHH HHHHH (SEQ ID NO: 21)

FIG. 1C

FimC sequence

```
  1 MSNKNVNVRK SQEITFCLLA GILMFMAMMV AGRAEAGVAL GATRVIYPAG
 51 QKQVQLAVTN NDENSTYLIQ SWVENADGVK DGRFIVTPPL FAMKGKKENT
101 LRILDATNNQ LPQDRESLFW MNVKAIPSMD KSKLTENTLQ LAIISRIKLY
151 YRPAKLALPP DQAAEKLRFR RSANSLTLIN PTPYYLTVTE LNAGTRVLEN
201 ALVPPMGEST VKLPSDAGSN ITYRTINDYG ALTPKMTGVM E (SEQ ID NO: 10)
```

FIG. 1D

| Sequence | Length | SEQ ID |
|---|---|---|
| DNKQ | 4 aa | (SEQ ID NO: 11) |
| GGSGG | 5 aa | (SEQ ID NO: 12) |
| GGSSG G | 6 aa | (SEQ ID NO: 13) |
| GGSSG GG | 7 aa | (SEQ ID NO: 14) |
| GGGSS GGG | 8 aa | (SEQ ID NO: 15) |
| GGGSG SGGG | 9 aa | (SEQ ID NO: 16) |
| GGGSG GSGGG | 10 aa | (SEQ ID NO: 17) |

FIG. 1E

FimH J96 signal sequence
MKRVI TLFAV LLMGW SVNAW S (SEQ ID NO: 18)

pSB02198 - FimH mIgK signal pept / F22..Q300 J96 FimH N28S V48C L55C N91S N249Q / 7 AA linker / FimG A1..K14 / GGHis8 in pcDNA3.1(+) [Number of amino acids: 310 Molecular weight: 32089.79 Theoretical pI: 7.23]

VETDT LLLWV LLLWV PGSTG (SEQ ID NO: 19) FACKT ASGTA IPIGG
GSANV YVNLA PCVNV GQNCV VDLST QIFCH NDYPE TITDY VTLQR
GSAYG GVLSS FSGTV KYSGS SYPFP TTSET PRVVY NSRTD KPWPV
ALYLT PVSSA GGVAI KAGSL IAVLI LRQTN NYNSD DFQFV WNIYA
NNDVV VPTGG CDVSA RDVTV TLPDY PGSVP IPLTV YCAKS QNLGY
YLSGT TADAG NSIFT NTASF SPAQG VGVQL TRQGT IIPAN NTVSL
GAVGT SAVSL GLTAN YARTG GQVTA GNVQS IIGVT FVYQ (SEQ ID NO: 20) GGSSG GG (SEQ ID NO: 14) ADVTI TVNGK VVAK GGHHH HHHHH (SEQ ID NO: 21)

pSB02307 - FimH mIgK signal pept / F22..Q300 J96 FimH N28S N91S N249Q / His8 in pcDNA3.1(+)

METDT LLLWV LLLWV PGSTG (SEQ ID NO: 22)
FACKT ASGTA IPIGG GSANV YVNLA PVVNV GQNLV VDLST QIFCH
NDYPE TITDY VTLQR GSAYG GVLSS FSGTV KYSGS SYPFP TTSET
PRVVY NSRTD KPWPV ALYLT PVSSA GGVAI KAGSL IAVLI LRQTN
NYNSD DFQFV WNIYA NNDVV VPTGG CDVSA RDVTV TLPDY PGSVP
IPLTV YCAKS QNLGY YLSGT TADAG NSIFT NTASF SPAQG VGVQL
TRQGT IIPAN NTVSL GAVGT SAVSL GLTAN YARTG GQVTA GNVQS
IIGVT FVYQ (SEQ ID NO: 23) GGSSG GG (SEQ ID NO: 14)
ADVT ITVNG KVVAK GGHHH HHHHH (SEQ ID NO: 21)

FIG. 1E continued

FIG. 1E continued pSB02083 FimH Lectin Domain Wild Type construct

METDT LLLWV LLLWV PGSTG (SEQ ID NO: 22)
    FACKT ASGTA IPIGG GSANV YVNLA PVVNV GQNLV VDLST QIFCH
    NDYPE TITDY VTLQR GSAYG GVLSS FSGTV KYSGS SYPFP TTSET
    PRVVY NSRTD KPWPV ALYLT PVSSA GGVAI KAGSL IAVLI LRQTN
    NYNSD DFQFV WNIYA NNDVV VPTGG (SEQ ID NO: 24) HHHHH HHH
    (SEQ ID NO: 25)

pSB02158 FimH Lectin Domain Lock Mutant

METDT LLLWV LLLWV PGSTG (SEQ ID NO: 22)
    FACKT ASGTA IPIGG GSANV YVNLA PCVNV GQNCV VDLST QIFCH
    NDYPE TITDY VTLQR GSAYG GVLSS FSGTV KYSGS SYPFP TTSET
    PRVVY NSRTD KPWPV ALYLT PVSSA GGVAI KAGSL IAVLI LRQTN
    NYNSD DFQFV WNIYA NNDVV VPTGG (SEQ ID NO: 26) HHHHHHHH
    (SEQ ID NO: 25)

FIG. 1F pSB01878 processed sequence:

FACKTANGTAIPIGGGSANVYVNLAPVVNVGQNLVVDLSTQIFCHNDYP
ETITDYVTLQRGSAYGGVLSNFSGTVKYSGSSYPFPTTSETPRVVYNSRTD
KPWPVALYLTPVSSAGGVAIKAGSLIAVLILRQTNNYNSDDFQFVWNIYA
NNDVVVPTGGHHHHHHHH (SEQ ID NO: 27)

NXS/T sites are indicated in bold text as these are potentially glycosylated.

pSB02083 FimH Lectin Domain Wild Type with murine IgK signal peptide

METDTLLLWVLLLWVPGSTGFACKTASGTAIPIGGGSANVYVNLAPVVNVGQNLVVDLSTQIFCHNDYP
    ETITDYVTLQRGSAYGGVLSSFSGTVKYSGSSYPFPTTSETPRVVYNSRTDKPWPVALYLTPVSSAGGVAIK
    AGSLIAVLILRQTNNYNSDDFQFVWNIYANNDVVVPTGGHHHHHHHH (SEQ ID NO: 7)

FIG. 1F continued

FIG. 1F continued pSB02158 FimH Lectin Domain Lock Mutant with murine IgK signal peptide METDTLLLWVLLLWVPGSTGFACKTASGTAIPIGGGSANVYVNLAPCVNVGQNCVVDLSTQIFCHNDYPE
TITDYVTLQRGSAYGGVLSSFSGTVKYSGSSYPFPTTSETPRVVYNSRTDKPWPVALYLTPVSSAGGVAIKAG
SLIAVLILRQTNNYNSDDFQFVWNIYANNDVVVPTGGHHHHHHHH (SEQ ID NO: 8)

FIG. 1G

Amino acid sequence of FimH of K12

FACKTANGTAIPIGGGSANV YVNLAPVVNVGQNLVVDLST QIFCHNDYPETITDYVTLQR
GSAYGGVLSNFSGTVKYSGS SYPFPTTSETPRVVYNSRTD KPWPVALYLTPVSSAGGVAI
KAGSLIAVLILRQTNNYNSD DFQFVWNIYANNDVVVPTGG CDVSARDVTVTLPDYPGSVP
IPLTVYCAKSQNLGYYLSGT TADAGNSIFTNTASFSPAQG VGVQLTRNGTIIPANNTVSL
GAVGTSAVSLGLTANYARTG GQVTAGNVQSIIGVTFVYQ* (SEQ ID NO: 28)

Amino acid sequence of FimH of UTI89, which differs from the FimH of K12

FACKTANGTAIPIGGGSANV YVNLAPAVNVGQNLVVDLST QIFCHNDYPETITDYVTLQR
GAAYGGVLSSFSGTVKYNGS SYPFPTTSETPRVVYNSRTD KPWPVALYLTPVSSAGGVAI
KAGSLIAVLILRQTNNYNSD DFQFVWNIYANNDVVVPTGG CDVSARDVTVTLPDYPGSVP
IPLTVYCAKSQNLGYYLSGT TADAGNSIFTNTASFSPAQG VGVQLTRNGTIIPANNTVSL
GAVGTSAVSLGLTANYARTG GQVTAGNVQSIIGVTFVYQ* (SEQ ID NO: 29)

FIG. 1H

Exemplary wzzB sequences include:
>O25b 2401 WzzB
MRVENNNVSGQNHDPEQIDLIDLLVQLWRGKMTIIISVIVAIALAIGYLAVAKEKWTSTAIITQP
DVGQIAGYNNAMNVIYGQAAPKVSDLQETLIGRFSSAFSALAETLDNQEEPEKLTIEPSVKN
QQLPLTVSYVGQTAEGAQMKLAQYIQQVDDKVNQELEKDLKDNIALGRKNLQDSLRTQEVV
AQEQKDLRIRQIQEALQYANQEQVTKPQVQQTEDVTQDTLFLLGSEALESMIKHEATRPLVF
SSNYYQTRQNLLDIESLKVDDLDIHAYRYVMKPTLPIRRDSPKKAITLILAVLLGGMVGAGIVL
GRNALRNYNAK (SEQ ID NO: 30)
>O25a:K5:H1 WzzB
MRVENNNVSGQNNDPEQIDLIDLLVQLWRGKMTIIISVIVAIALAIGYLAVAKEKWTSTAIITQP
DVGQIAGYNNAMNVIYGQAAPKVSDLQETLIGRFSSAFSALAETLDNQDEPEKLTIEPSVKN
QQLPLTVSYVGQTAEGAQMKLAQYIQQVDDKVNQELEKDLKDNIALGRKNLQDSLRTQEVV

AQEQKDLRIRQIQEALQYANQAQVTKPQIQQTGEDITQDTLFLLGSEALESMIKHEATRPLVF
SPNYYQTRQNLLDIESLKVDDLDIHAYRYVMKPTLPIRRDSPKKAITLILAVLLGGMVGAGIVL
GRNALRNYNAK (SEQ ID NO: 31)

>O25a ETEC ATCC WzzB
MRVENNNVSGQNHDPEQIDLIDLLVQLWRGKMTIIISVVVAIALAIGYLAVAKEKWTSTAIITQ
PDVGQIAGYNNAMNVIYGQAAPKVSDLQETLIGRFSFAFSALAETLDNQKEPEKLTIEPSVK
NQQLPLTVSYVGQTAEDAQMKLAQYIQQVDDKVNQELEKDLKDNLALGRKNLQDSLRTQE
VVAQEQKDLRIRQIQEALQYANQAQVTKPQIQQTGEDITQDTLFLLGSEALESMIKHEATRPL
VFSPNYYQTRQNLLDIENLKVDDLDIHAYRYVMKPTLPIRRDSPKKAITLILAVLLGGMVGAGI
VLGRNALRNYNSK (SEQ ID NO: 32)

>K12 W3110 WzzB
MRVENNNVSGQNHDPEQIDLIDLLVQLWRGKMTIIISVIVAIALAIGYLAVAKEKWTSTAIITQP
DVGQIAGYNNAMNVIYGQAAPKVSDLQETLIGRFSSAFSALAETLDNQEEREKLTIEPSVKN
QQLPLTVSYVGQTAEGAQMKLAQYIQQVDDKVNQELEKDLKDNIALGRKNLQDSLRTQEVV
AQEQKDLRIRQIQEALQYANQAQVTKPQIQQTGEDITQDTLFLLGSEALESMIKHEATRPLVF
SPNYYQTRQNLLDIESLKVDDLDIHAYRYVMKPMLPIRRDSPKKAITLILAVLLGGMVGAGIVL
GRNALRNYNAK (SEQ ID NO: 33)

>Salmonella LT2 WzzB
MTVDSNTSSGRGNDPEQIDLIELLLQLWRGKMTIIVAVIIAILLAVGYLMIAKEKWTSTAIITQP
DAAQVATYTNALNVLYGGNAPKISEVQANFISRFSSAFSALSEVLDNQKEREKLTIEQSVKG
QALPLSVSYVSTTAEGAQRRLAEYIQQVDEEVAKELEVDLKDNITLQTKTLQESLETQEVVA
QEQKDLRIKQIEEALRYADEAKITQPQIQQTQDVTQDTMFLLGSDALKSMIQNEATRPLVFS
PAYYQTKQTLLDIKNLKVTADTVHVYRYVMKPTLPVRRDSPKTAITLVLAVLLGGMIGAGIVL
GRNALRSYKPKAL (SEQ ID NO: 34)

Exemplary FepE sequences include:
>O25b GAR2401 FepE
MSSLNIKQGSDAHFPDYPLASPSNNEIDLLNLISVLWRAKKTVMAVVFAFACAGLLISFILPQ
KWTSAAVVTPPEPVQWQELEKSFTKLRVLDLDIKIDRTEAFNLFIKKFQSVSLLEEYLRSSPY
VMDQLKEAKIDELDLHRAIVALSEKMKAVDDNASKKKDEPSLYTSWTLSFTAPTSEEAQTVL
SGYIDYISTLVVKESLENVRNKLEIKTQFEKEKLAQDRIKTKNQLDANIQRLNYSLDIANAAGIK
KPVYSNGQAVKDDPDFSISLGADGIERKLEIEKAVTDVAELNGELRNRQYLVEQLTKAHVND
VNFTPFKYQLSPSLPVKKDGPGKAIIVILSALIGGMVACGGVLLRYAMASRKQDAMMADHLV
(SEQ ID NO: 35)

>O25a:K5:H1 FepE
MSSLNIKQGSEAHFPEYPLASPSNNEIDLLNLIEVLWRAKKTVMAVVFAFACAGLLISFILPQK
WTSAAVVTPPEPVQWQELEKTFTKLRVLDLDIKIDRTEAFNLFIKKFQSVSLLEEYLRSSPYV
MDQLKEAKIDPLDLHRAIVALSEKMKAVDDNASKKKDESALYTSWTLSFTAPTSEEAQKVLA
GYIDYISALVVKESIENVRNKLEIKTQFEKEKLAQDRIKTKNQLDANIQRLNYSLDIANAAGIKK
PVYSNGQAVKDDPDFSISLGADGIERKLEIEKAVTDVAELNGELRNRQYLVEQLTKTNINDV
NFTPFKYQLRPSLPVKKDGQGKAIIVILSALVGGMVACGGVLLRHAMASRKQDAMMADHLV
(SEQ ID NO: 36)

> O25a ETEC ATCC FepE
MSSLNIKQGSDAHFPDYPLASPSNNEIDLLNLISVLWRAKKTVMAVVFAFACAGLLISFILPQ
KWTSAAVVTPPEPVQWQELEKSFTKLRVLDLDIKIDRTEAFNLFIKKFQSVSLLEEYLRSSPY
VMDQLKEAKIDELDLHRAIVALSEKMKAVDDNASKKKDEPSLYTSWTLSFTAPTSEEAQTVL
SGYIDYISTLVVKESLENVRNKLEIKTQFEKEKLAQDRIKTKNQLDANIQRLNYSLDIANAAGIK
KPVYSNGQAVKDDPDFSISLGADGIERKLEIEKAVTDVAELNGELRNRQYLVEQLTKAHVND
VNFTPFKYQLSPSLPVKKDGPGKAIIVILSALIGGMVACGGVLLRYAMASRKQDAMMADHLV
(SEQ ID NO: 37)

> O157 FepE
MSSLNIKQGSDAHFPDYPLASPSNNEIDLLNLISVLWRAKKTVMAVVFAFACAGLLISFILPQ
KWTSAAVVTPPEPVQWQELEKTFTKLRVLDLDIKIDRTEAFNLFIKKFQSVSLLEEYLRSSPY
VMDQLKEAKIDELDLHRAIVALSEKMKAVDDNASKKKDEPSLYTSWTLSFTAPTSEEAQTVL
SGYIDYISALVVKESIENVRNKLEIKTQFEKEKLAQDRIKMKNQLDANIQRLNYSLDIANAAGIK
KPVYSNGQAVKDDPDFSISLGADGIERKLEIEKAVTDVAELNGELRNRQYLVEQLTKANIND
VNFTPFKYQLSPSLPVKKDGPGKAIIVILSALIGGMVACGSVLLRYAMASRKQDAMMADHLV
(SEQ ID NO: 38)

>Salmonella LT2 FepE
MPSLNVKQEKNQSFAGYSLPPANSHEIDLFSLIEVLWQAKRRILATVFAFACVGLLLSFLLPQ
KWTSQAIVTPAESVQWQGLERTLTALRVLDMEVSVDRGSVFNLFIKKFSSPSLLEEYLRSSP
YVMDQLKGAQIDEQDLHRAIVLLSEKMKAVDSNVGKKNETSLFTSWTLSFTAPTREEAQKV
LAGYIQYISDIVVKETLENIRNQLEIKTRYEQEKLAMDRVRLKNQLDANIQRLHYSLEIANAAGI
KRPVYSNGQAVKDDPDFSISLGADGISRKLEIEKGVTDVAEIDGDLRNRQYHVEQLAAMNV
SDVKFTPFKYQLSPSLPVKKDGPGKAIIIILAALIGGMMACGGVLLRHAMVSRKMENALAIDE
RLV (SEQ ID NO: 39)

FIG. 2A

FimH Lectin Domain
- FimH signal | FimH J96 F22..G181 | His₆ — pSB01877 — pcDNA3.1(+) or pCAG vector
- migK signal | FimH J96 F22..G181 | His₆ — pSB01878

FimCH Complex
- FimH signal | FimH J96 F22..Q300 — pSB01879 — pBudCE4.1 Dual promoter vector (CMV & EF1α)
- migK signal | FimH J96 F22..Q300 — pSB01880
- migK signal | FimC G37..E241 | GGHis₈ — pSB01881

FimH-dscG
- FimH signal | FimH J96 F22..Q300 | Linker | FimG A1..K14 | GGHis₈ — pSB01882-1888 — ADVTITVNGKVVAK
- migK signal | FimH J96 F22..Q300 | Linker | FimG A1..K14 | GGHis₈ — pSB01889-1895

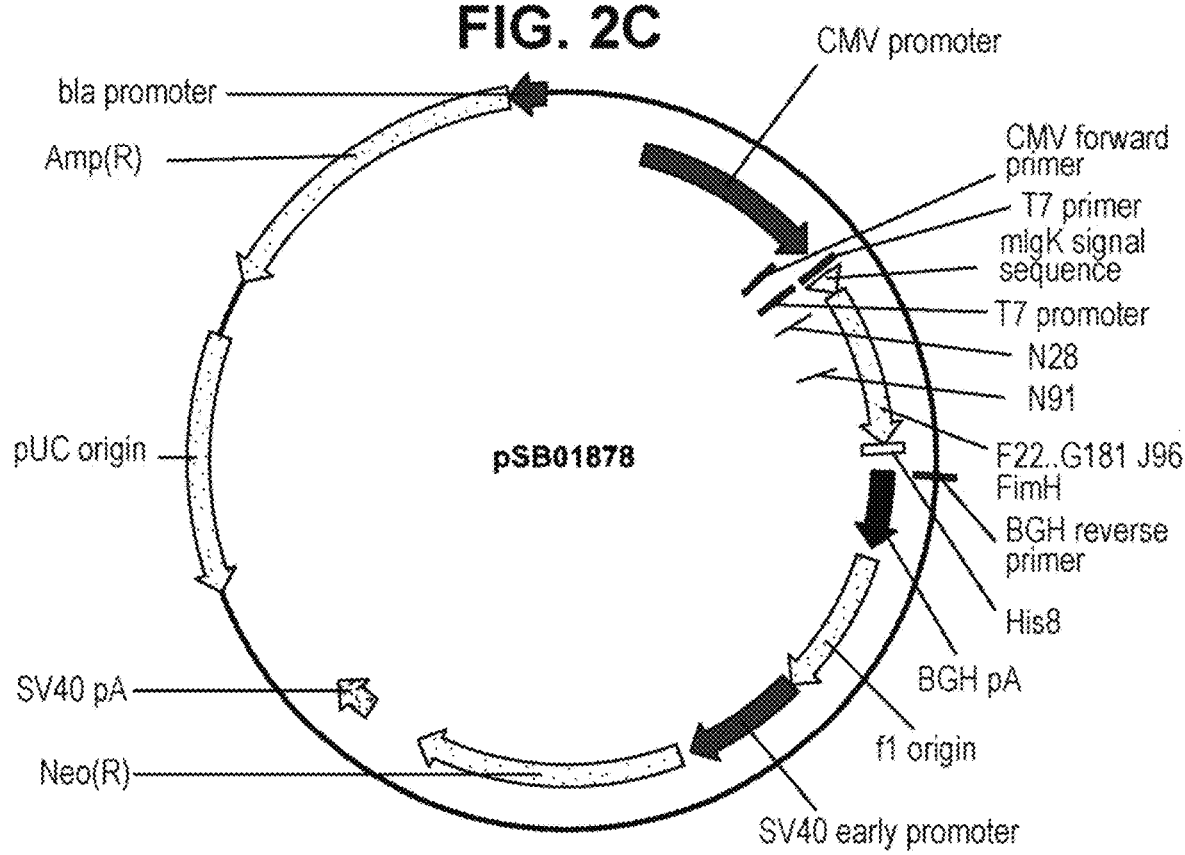
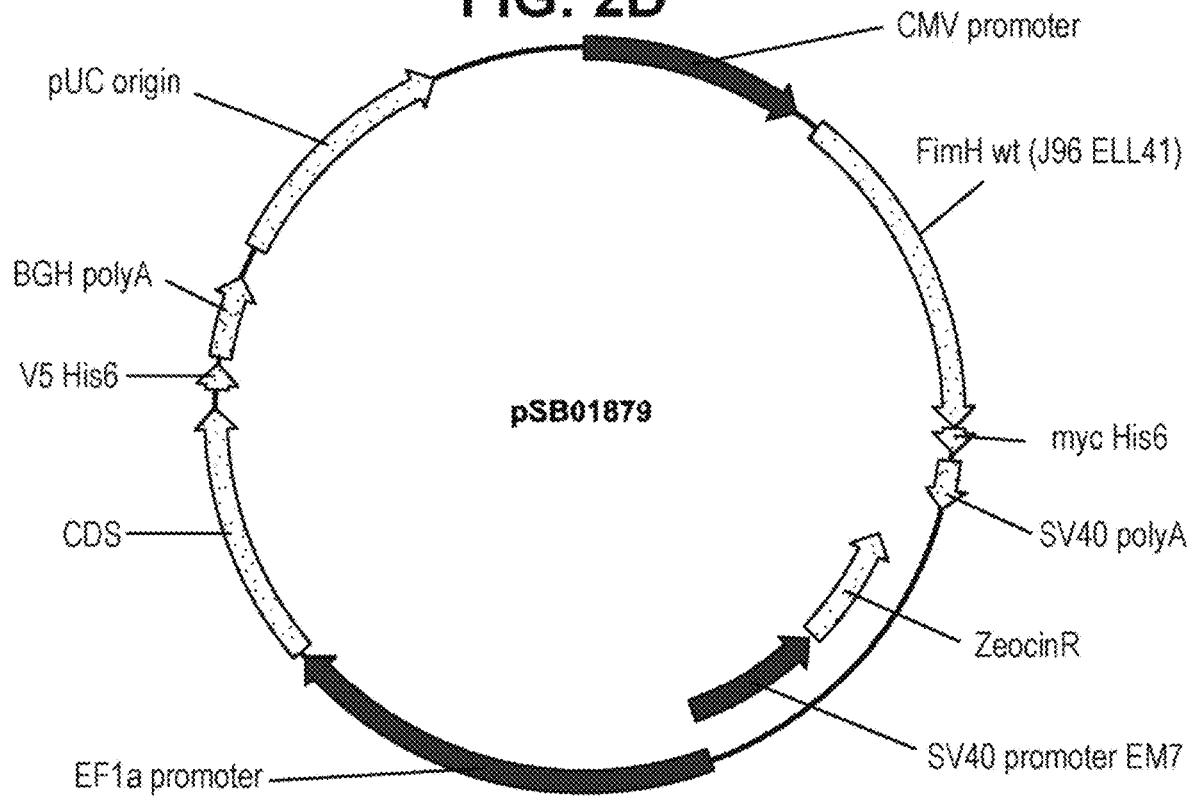

Results from Expression and Purification

FimH signal sequence    mIgK signal sequence

Results from Expression and Purification pSB02083

17 mg total yield pSB02158

10.8 mg total yield

Expression of pSB2307 FimH dscG wild type

FIG. 9A

| Serogroup | Structure |
|---|---|
| O1A, O1A1 | →3)-α-L-Rha-(1→3)-α-L-Rha-(1→4)-β-L-Rha-(1→3)-β-D-GlcNAc-(1→ \| β-D-ManNAc-(1→2) |
| O1B | →3)-α-L-Rha-(1→2)-α-L-Rha-(1→2)-α-D-Gal-(1→3)-β-D-GlcNAc-(1→ \| β-D-ManNAc-(1→2) |
| O1C | →3)-α-L-Rha-(1→2)-α-L-Rha-(1→3)-α-D-Gal-(1→3)-β-D-GlcNAc-(1→ \| β-D-ManNAc-(1→2) |
| O2 | →3)-α-L-Rha-(1→2)-α-L-Rha-(1→4)-β-L-Rha-(1→3)-β-D-GlcNAc-(1→ \| α-D-Fuc3NAc-(1→2) |
| O3 | β-L-RhaNAc(1→4)α-D-Glc-(1→4)|| →3)-β-D-GlcNAc-(1→3)-α-D-Gal-(1→3)-β-D-GlcNAc-(1→ |
| O4;K52 | →2)-α-L-Rha-(1→6)-α-D-Glc-(1→3)-α-L-FucNAc-(1→3)-β-D-GlcNAc-(1→ |
| O4;K6 | α-D-Glc-(1→3) | →2)-α-L-Rha-(1→6)-α-D-Glc-(1→3)-α-L-FucNAc-(1→3)-β-D-GlcNAc-(1→ |
| O5ab | →4)-β-D-Qui3NAc-(1→3)-β-D-Ribf-(1→4)-β-D-Gal-(1→3)-α-D-GalNAc(1→ |
| O5ac(strain 180/C3) | →2)-β-D-Qui3NAc-(1→3)-β-D-Ribf-(1→4)-β-D-Gal-(1→3)-α-D-GalNAc(1→ |
| O6;K2, K13; K15 | →4)-α-D-GalNAc-(1→3)-β-D-Man-(1→4)-β-D-Man-(1→3)-α-D-GlcNAc-(1→ \| β-D-Glc-(1→2) |
| O6;K54 | →4)-α-D-GalNAc-(1→3)-β-D-Man-(1→4)-β-D-Man-(1→3)-α-D-GlcNAc-(1→ \| α-D-GlcNAc-(1→ |
| O7 | α-L-Rha-(1→3) | →3)-β-D-Qui4NAc-(1→2)-α-D-Man-(1→4)-β-D-Gal-(1→3)-α-D-GlcNAc-(1→ |
| O10 | →3)-α-L-Rha-(1→3)-α-L-Rha-(1→3)-α-D-Gal-(1→3)-β-D-GlcNAc-(1→ \| α-D-Fuc4NAcyl-(1→2) |
| | Acyl=acetyl (60%) or (R)-3-hydroxybutyryl (40%) |
| O16 | →2)-β-D-Galf-(1→6)-α-D-Glc-(1→3)-α-L-Rha2Ac-(1→3)-α-D-GlcNAc-(1→ |
| O17 | α-D-Glc-(1→6) | →6)-α-D-Man-(1→2)-α-D-Man-(1→2)-β-D-Man-(1→3)-α-D-GlcNAc(1→ |
| O18A, O18ac | →2)-α-L-Rha-(1→6)-α-D-Glc-(1→4)-α-D-Gal-(1→4)-α-D-Gal-(1→3)-α-D-GlcNAc-(1→ \| β-D-GlcNAc-(1→3) |
| O18A1 | α-D-Glc-(1→6) | →2)-α-L-Rha-(1→6)-α-D-Glc-(1→4)-α-D-Gal-(1→3)-α-D-Gal-(1→3)-α-D-GlcNAc-(1→ \| β-D-Glc-(1→3) |
| O18B | →3)-α-L-Rha-(1→6)-α-D-Glc-(1→4)-α-D-Gal-(1→3)-α-D-Gal-(1→3)-α-D-GlcNAc-(1→ \| β-D-Glc-(1→3) |
| O18B1 | α-D-Glc-(1→4) | →3)-α-L-Rha-(1→6)-α-D-Glc-(1→4)-α-D-Gal-(1→3)-α-D-GlcNAc-(1→ \| β-D-Glc-(1→3) |
| O21 | β-D-Gal-(1→4) | →3)-β-D-Gal-(1→4)-β-D-Gal-(1→3)-α-D-GalNAc(1→3)-β-D-GlcNAc-(1→ \| β-D-GlcNAc-(1→2) |
| O23A | α-D-Glc-(1→6) | →6)-α-D-Glc-(1→3)-α-D-GalNAc-(1→3)-β-D-GalNAc-(1→ \| α-D-Glc-(1→2) |
| O24 | →7)-α-Neu5Ac-(2→3)-β-D-Glc-(1→3)-β-D-GalNAc(1→3) |

FIG. 9C

| | |
|---|---|
| O119 | β-D-RhaNAc3NFo-(1→3) \| →2)-β-D-Man-(1→3)-α-D-Gal-(1→4)-α-L-Rha-(1→3)-α-D-GlcNAc-(1→ |
| O121 | →3)-β-D-Qui4N(N-acetyl-glycyl)-(1→4)-α-D-GalNAc3AcA6N-(1→4)-α-D-GalNAcA-(1→3)-α-D-GlcNAc-(1→ |
| O124 | 4-O-[(R)-1-carboxyethyl]-β-D-Glc-(1→6)-α-D-Glc-(1→4)-α-D-Gal-(1→6)-β-D-Gal-(1→3)-β-D-GalNAc-(1→ |
| O125 | α-D-Glc-(1→3) \| →4)-β-D-GalNAc-(1→2)-α-D-Man-(1→3)-α-L-Fuc-(1→3)-α-D-GalNAc-(1→ \|β-D-Gal-(1→3) |
| O126 | →2)-β-D-Man-(1→3)-β-D-Gal-(1→3)-β-D-GlcNAc-(1→3)-α-D-GalNAc-(1→ \|α-L-Fuc-(1→2) |
| O127 | →2)-α-L-Fuc-(1→2) \| →6)-β-D-Gal-(1→3)-α-D-Gal-(1→3)-α-D-GalNAc-(1→ |
| O128 | α-L-Fuc-(1→2) \| →6)-β-D-Gal-(1→3)-β-D-GalNAc-(1→4)-α-D-Gal-(1→3)-β-D-GalNAc-(1→ |
| O136 | →4)-β-Pse5Ac7Ac-(2→4)-β-D-Gal-(1→4) |
| | -β-D-GlcNAc-(1→β-Pse5Ac7Ac=5,7-diacetamido-3,5,7,9-tetradeoxy-L-glycero-β-L-manno-nonulosonic acid |
| O138 | →2)-α-L-Rha-(1→3)-α-L-Rha-(1→4)-α-D-GalNAcA-(1→3)-β-D-GlcNAc-(1→ |
| O141 | α-L-Rha-(1→3) \| →4)-α-D-Man-(1→3)-β-D-Man6Ac-(1→3)-β-D-GlcNAc-(1→ \|β-D-GlcA-(1→2) |
| O142 | →2)-α-L-Rha-(1→6)-α-D-GalNAc-(1→4)-β-D-GalNAc-(1→3)-α-D-GalNAc-(1→ \|β-D-GlcNAc-(1→3) |
| O143 | →2)-β-D-GalA6R3,4Ac-(1→3)-α-L-Rha-(1→4)-β-D-GalA-(1→3)-β-D-GalNAc-(1→ R=1,3-dihydroxy-2-propylamino |
| O147 | →2)-α-L-Rha-(1→2)-α-L-Rha-(1→3)-β-L-Rha-(1→4)-β-D-GlcNAc-(1→ (S)-4,6Py=4,6-O-[(S)-1-carboxyethylidene]- |
| O149 | →3)-β-D-GlcNAc-(S)-4,6Py-(1→3)-α-D-GlcNAc-(1-P→6)-α-D-Glc-(1→2)-β-D-Glc-(1→3)-β-D-GlcNAc-(1→ |
| O152 | β-L-Rha-(1→4) \| →3)-α-D-GlcNAc-(1-P→6)-α-D-Glc-(1→4)-β-D-Glc-(1→3)-β-D-GalNAc-(1→ |
| O157 | →2)-α-D-Rha4NAc-(1→3)-α-L-Fuc-(1→4)-β-D-Glc-(1→3)-β-D-GalNAc-(1→ \|α-L-Rha-(1→3) |
| O158 | α-D-Glc-(1→6) \| →4)-α-D-Glc-(1→3)-β-D-GalNAc-(1→3)-α-L-Fuc-(1→3)-β-D-GlcNAc-(1→ |
| O159 | α-L-Fuc-(1→4) \| →3)-β-D-GlcNAc-(1→4)-α-D-GalA-(1→3)-α-L-Fuc-(1→3)-β-D-GalNAc-(1→ |
| O164 | β-D-Glc-(1→6)-α-D-Glc(1→4) \| →3)-β-D-Gal-(1→6)-β-D-Galf-(1→3)-β-D-GalNAc-(1→ |
| O173 | α-L-Fuc-(1→4) \| →3)-α-D-Glc-(1-P→6)-α-D-Gal-(1→2)-β-D-Glc-(1→3)-β-D-GlcNAc-(1→ |
| 62D1 | α-D-Gal(1→6) \| →2)-β-D-Qui3NAc-(1→3)-α-L-Rha-(1→3)-β-D-Gal-(1→3)-α-D-FucNAc-(1→ Suggested as Erwinia herbicola |

FIG. 10A

| | |
|---|---|
| O22 | →6)-α-D-Glc-(1→4)-β-D-GlcA-(1→4)-β-D-GalNAc3Ac-(1→3)-α-D-Gal-(1→3)-β-D-GalNAc-(1→ |
| O35 | →3)-α-L-Rha-(1→2)-α-L-Rha-(1→3)-α-L-Rha-(1→2)-β-D-GalNAcA6N-(1→2) |
| O65 | →2)-β-D-Qui3NAc-(1→4)-α-D-GalA6N-(1→4)-α-D-GalNAc-(1→4)-β-D-GalA-(1→3)-α-D-GlcNAc-(1→ | α-D-GalNAcA6N-(1→ |
| O66 | →2)-β-D-Man-(1→3)-α-D-GlcNAc-(1→2)-β-D-Glc3Ac-(1→3)-α-L-6dTal-(1→3)-α-D-GlcNAc(1→ |
| O83 | →6)-α-D-Glc-(1→4)-β-D-GlcA-(1→6)-β-D-Gal-(1→6)-β-D-Gal-(1→4)-β-D-GlcNAc-(1→ |
| O91 | →4)-α-D-Qui3NAcyl-(1→4)-β-D-Gal-(1→4)-β-D-GlcNAc-(1→4)-β-D-GlcA6NGly-(1→3)-β-D-GlcNAc-(1→ Acyl=(R)-3-hydroxybutyryl |
| O105 | β-D-Ribf-(1→3) | →4)-α-D-GlcA2Ac3Ac-(1→2)-α-L-Rha4Ac-(1→3)-β-L-Rha-(1→4)-β-L-Rha-(1→3)-β-D-GlcNAc6Ac-(1→ |
| O116 | →2)-β-D-Qui4NAc-(1→6)-α-D-GlcNAc-(1→4)-β-D-GalA-(1→3)-α-D-GalNAc-(1→ |
| O117 | →4)-β-D-GalNAc-(1→3)-α-L-Rha-(1→4)-α-D-Glc-(1→4)-α-D-GalA-(1→2)-α-L-Rha-(1→3)-α-D-GlcNAc-(1→ |
| O139 | β-D-Glc-(1→3) | →3)-α-L-Rha-(1→2)-α-L-Rha-(1→3)-α-L-Rha-(1→3)-α-D-GlcNAc-(1→ Ratnayake (1994a) |
| O153 | →2)-β-D-Ribf-(1→4)-β-D-Gal-(1→4)-α-D-GlcNAc-(1→2)-β-D-Galf-(1→5)-β-D-Galf-(1→3)-β-D-GlcNAc-(1→ |
| O167 | α-D-Galf-(1→4) | →2)-β-D-GalA6N(L)Ala-(1→3)-α-D-Glc-(1-P→4)-α-D-Glc-(1→3)-α-L-FucNAc-(1→3)-α-D-GlcNAc-(1→ |
| O172 | →3)-α-L-FucNAc-(1→4)-α-D-GlcGAc-(1→ |

FIG. 10B

| | |
|---|---|
| O8 | →2)-α-D-Man-(1→2)-α-D-Man-(1→3)-β-D-Man-(1→ |
| O9a | →2)-α-D-Man-(1→2)-α-D-Man-(1→3)-α-D-Man-(1→3)-β-D-Man-(1→ |
| O9 | →2)-[α-D-Man-(1→2)]2-α-D-Man-(1→3)-α-D-Man-(1→3)-α-D-Man-(1→ |
| O20ab | →2)-β-D-Ribf-(1→4)-α-D-Gal-(1→ Vasil'ev & Zakharova (1976) |
| O20ac | α-D-Gal-(1→3) | →2)-β-D-Ribf-(1→4)-α-D-Gal-(1→ |
| O52 | →3)-β-D-Fucf-(1→3)-β-D-6dmanHep2Ac-(1→ |
| O97 | →3)-α-L-Rha-(1→3)-β-L-Rha-(1→ || β-D-Xulf-(2→2)β-D-Xulf-(2→2) |
| O101 | →6)-α-D-GlcNAc-(1→4)-α-D-GalNAc-(1→ |

1) O25K5H1 wt
2) O25K5H1ΔwzzB
3) +O25a wzzB (homologous)
4) +O25b 2401 fepE
5) +O25a ETEC fepE
6) +Salmonella LT2 fepE
7) +O157 fepE
8) + Salmonella LT2 fepE (diluted)
9) +O111 LPS standard

FIG. 16A
SPS PAGE
FIG. 16B
O25 Immuno-Blot
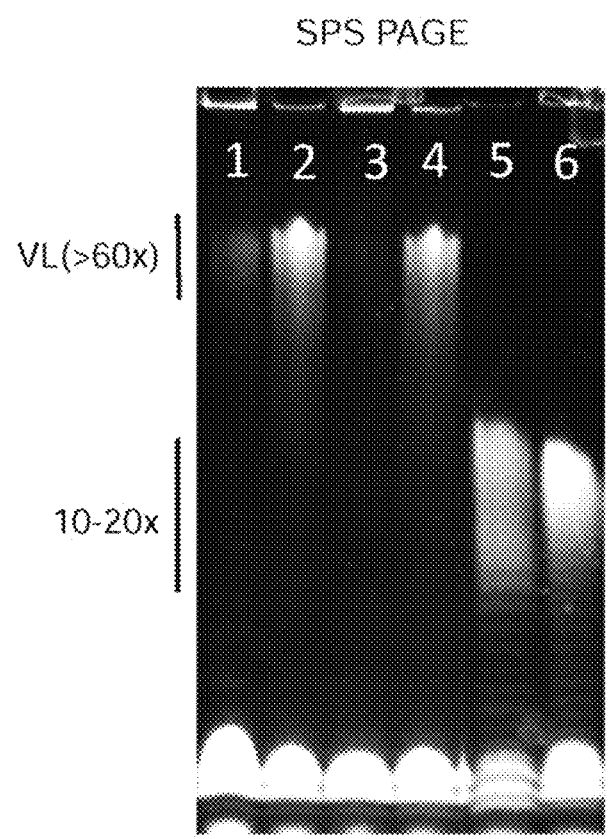
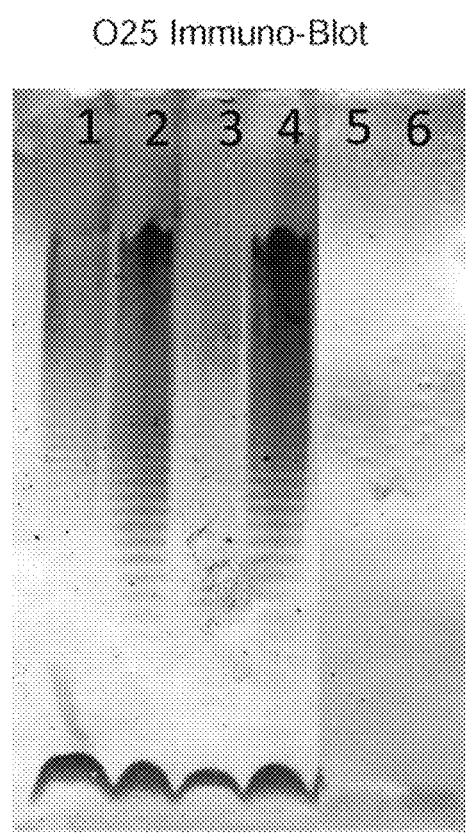

Ec O8 OPA with 3% BRC

Kp O5 hSBA with 10% hC

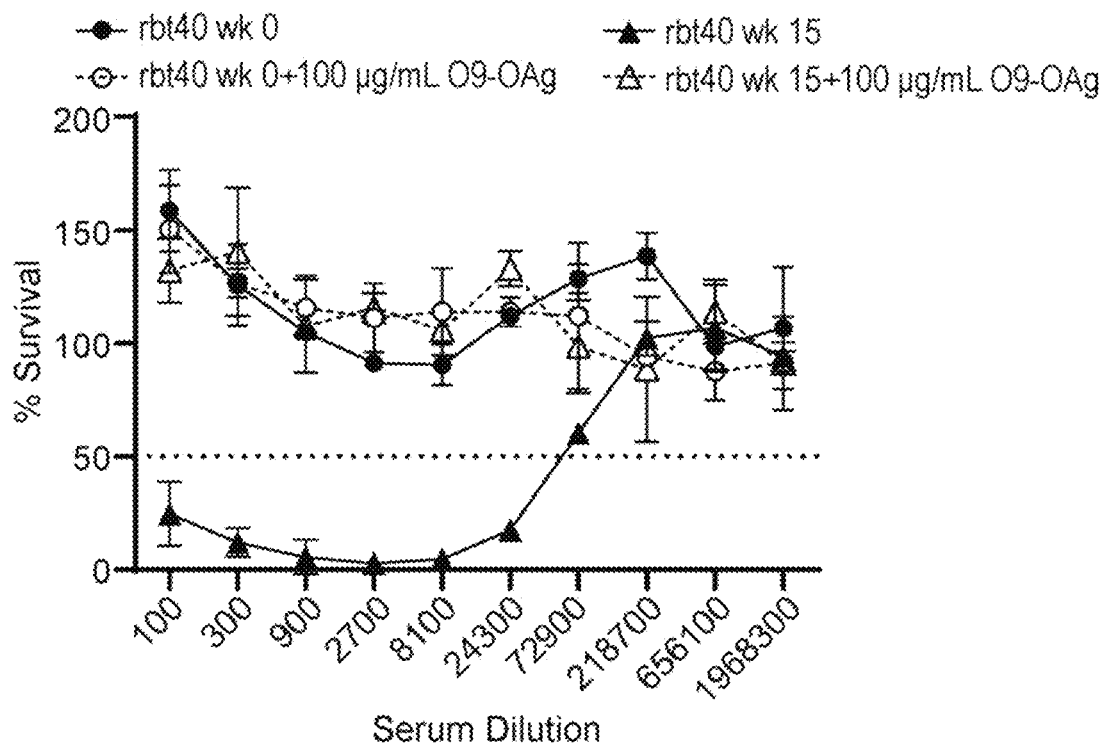
FIG. 35A  Ec O9 OPA with 3% BRC
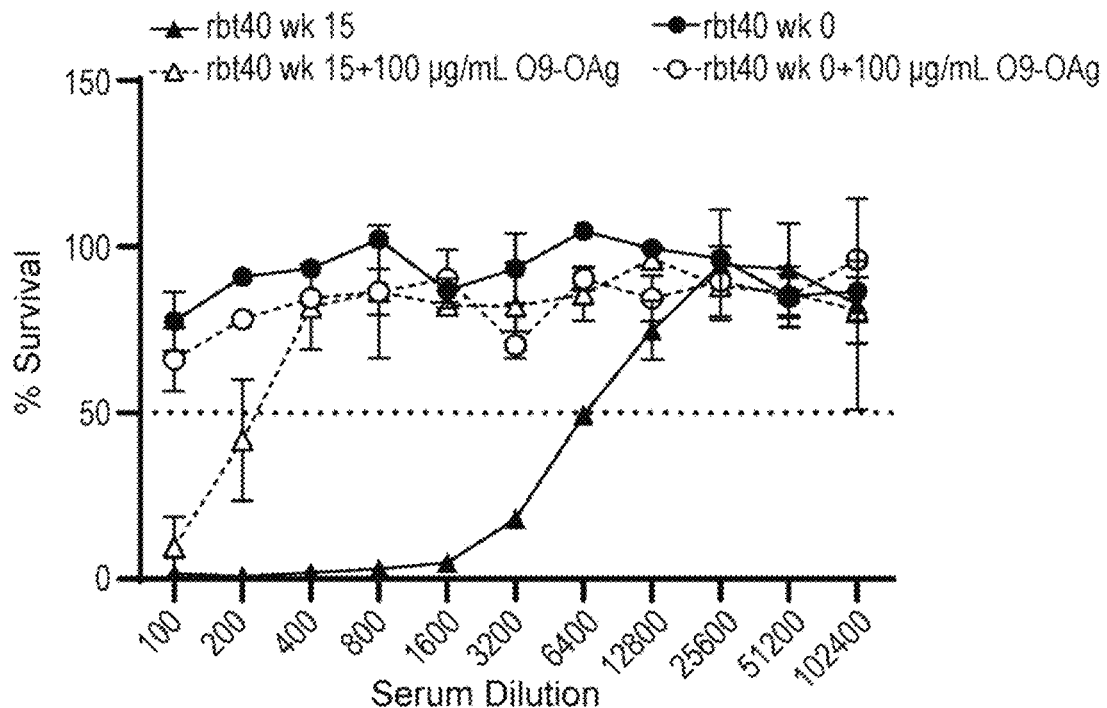
FIG. 35B  Kp O3 OPA with 15% hC

ESCHERICHIA COLI COMPOSITIONS AND METHODS THEREOF

CROSS REFERENCE TO RELATED APPLICATIONS

This application claims the benefits of U.S. Provisional Application No. 63/254,195, filed Oct. 11, 2021, U.S. Provisional Application No. 63/144,058, filed Feb. 1, 2021, and U.S. Provisional Application No. 63/106,077, filed Oct. 27, 2020. The entire content of each of the foregoing applications is incorporated herein by reference.

REFERENCE TO SEQUENCE LISTING

This application is being filed electronically via EFS-Web and includes an electronically submitted sequence listing in .txt format. The .txt file contains a sequence listing entitled "PC72671_ST25.txt" created on Oct. 26, 2020 and having a size of 160 KB. The sequence listing contained in this .txt file is part of the specification and is incorporated herein by reference in its entirety.

FIELD OF THE INVENTION

The present invention relates to new immunogenic compositions for use in a vaccine for eliciting immune responses against *E. coli* and *Klebsiella pneumoniae* serotypes in a subject.

BACKGROUND OF THE INVENTION

*Escherichia coli* is one of the most common human bacterial pathogens with clinical presentations that include blood stream infections, urinary tract infections (catheter and non-catheter associated; surgical site infections, pneumonia, and serious food poisoning related diarrhea. They are classified serologically by differences in the structure of the lipopolysaccharide-associated O-antigen (>180 known serotypes), the capsule polysaccharide K-antigen (>100 serotypes), and the flagellar H-antigen (>50 serotypes).

Urinary tract infections (UTIs) most often present as a cystitis that in some individuals can recur repeatedly following resolution. Left untreated, they can progress to pylonephritis and blood stream infections. *E. coli* infections are associated with high levels of antibiotic resistance [Al-Hasan M N, et al. The Journal of antimicrobial chemotherapy 2009; 64:169-74] with many strains being resistant to multiple antibiotics including antibiotics of last resort such as carbapenems and polymyxins [Zowawi H M, et al. Nature reviews Urology 2015; 12:570-84]. In particular, O25b serotype multilocus sequence type (MLST) 131 has emerged as a worldwide pandemic clone, causing predominantly community-onset infections with high rates of resistance to extended-spectrum cephalosporins (ESBLs) and fluoroquinolones [Rogers B A, et al. The Journal of antimicrobial chemotherapy 2011; 66:1-14; Nicolas-Chanoine M-H, et al. Clinical Microbiology Reviews 2014; 27:543-74]. *E. coli* BSI and UTI infecting strains are also known as invasive Extra-intestinal Pathogenic *E. coli* (ExPEC) or uropathogenic *E. coli* (UPEC).

Second to *E. coli*, *Klebsiella* spp. (including *K. pneumoniae* and *K. oxytoca*) are the next most common Gram-negative pathogens associated with invasive infections including UTIs, pneumonia, intra-abdominal infection, and bloodstream infection (BSI) [Nicolas-Chanoine M-H, et al. Clinical Microbiology Reviews 2014; 27:543-74; Podschun R, et al. Clin Microbiol Rev 1998; 11:589-603; Yinnon A M, et al. Q J M: monthly journal of the Association of Physicians 1996; 89:933-41; Anderson D J, et al. PLoS One 2014; 9:e91713]. *Klebsiella* maintain a profound ability to acquire antibiotic resistance through horizontally transmissible ESBL and carbapenem resistance conferring genes [Chen L, et al. Trends Microbiol 2014; 22:686-96; Iredell J, et al. Bmj 2016; 352:h6420]. Accordingly, during the last decade the prevalence of ESBL-resistant *Klebsiella* producing extended-spectrum β-lactamases (ESBL) has increased dramatically globally. *Klebsiella* spp. can express up to 8 different O-types and >80 K-types. While there are a multitude of K-antigens associated with virulent *Klebsiella* strains, only four O-antigen serotypes account for ≥80% of *Klebsiella* clinical isolates irrespective of sample site (blood, urine, sputum), infection status (invasive versus non-invasive) or the nature of acquisition (community vs nosocomial) [Follador R, et al. Microbial Genomics 2016; 2:e000073].

The increased rate of invasive multidrug-resistant (MDR) *E. coli* and *Klebsiella* infections in the vulnerable newborn population and the elderly underscores the need for vaccine-based approaches as an alternative to standard-of-care antibiotics which are becoming less effective.

SUMMARY OF THE INVENTION

To meet these and other needs, the present invention relates to compositions and methods of use thereof for producing new immunogenic compositions for use in a vaccine for eliciting immune responses against *E. coli* and *Klebsiella pneumoniae* serotypes in a subject.

In some embodiments of the methods provided herein, the subject is a mammal, preferably a human. In some particular embodiments, the human is a child, such as an infant. In some other particular embodiments, the human is a woman, particularly a pregnant woman.

The composition may be administered to the subject with or without administration of an adjuvant. The effective amount administered to the subject is an amount that is sufficient to elicit an immune response against an *E. coli* or *K. pneumoniae* antigen in the subject. Subjects that can be selected for treatment include those that are at risk for developing an *E. coli* or *K. pneumoniae* infection because of exposure or the possibility of exposure to *E. coli* or *K. pneumoniae*. Because humans may be infected with *E. coli* or *K. pneumoniae* by the age of 2, the entire birth cohort is included as a relevant population for immunization. This could be done, for example, by beginning an immunization regimen anytime from birth to 6 months of age, from 6 months of age to 5 years of age, in pregnant women (or women of child-bearing age) to protect their infants by passive transfer of antibody, infants still in utero, and subjects greater than 50 years of age.

In one aspect, the invention relates to a composition comprising a FimH polypeptide comprising amino acids having a sequence selected from the group consisting of SEQ ID NO: 5, SEQ ID NO: 6, SEQ ID NO: 7, SEQ ID NO: 8, SEQ ID NO: 27, SEQ ID NO: 110, SEQ ID NO: 111, SEQ ID NO: 112, and SEQ ID NO: 113, or any combination thereof. In some embodiments, the composition further includes a saccharide selected from any saccharide having a Formula in Table 1, preferably Formula O1A, Formula O1B, Formula O2, Formula O6, and Formula O25B, wherein n is an integer from 1 to 100, preferably 31 to 100.

In one aspect, the invention relates to a composition that includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 1, SEQ ID NO: 2, SEQ ID NO: 3, SEQ ID NO: 4, SEQ ID NO: 20, SEQ ID NO: 23, SEQ ID NO: 24, SEQ ID NO: 26, SEQ ID NO: 28, and SEQ ID NO: 29, or any combination thereof.

In another aspect, the invention relates to a composition that includes a polypeptide having at least n consecutive amino acids from any one of SEQ ID NO: 1, SEQ ID NO: 2, SEQ ID NO: 3, SEQ ID NO: 4, SEQ ID NO: 20, SEQ ID NO: 23, SEQ ID NO: 24, SEQ ID NO: 26, SEQ ID NO: 28, and SEQ ID NO: 29, wherein n is 7 or more (eg. 8, 10, 12, 14, 16, 18, 20 or more). In some embodiments, the composition further includes a saccharide selected from any one Formula in Table 1, preferably Formula O1A, Formula O1B, Formula O2, Formula O6, and Formula O25B, wherein n is an integer from 1 to 100, preferably 31 to 100.

BRIEF DESCRIPTION OF THE DRAWINGS

FIG. 1A-1H— depict amino acid sequences, including amino acid sequences for exemplary polypeptides derived from E. coli or fragments thereof; and amino acid sequences for exemplary wzzB sequences.

FIG. 9A-9C—depict structures of O-antigens synthesized by the polymerase-dependent pathway with four or less residues in the backbone.

FIG. 10A-10B—FIG. 10A depicts structures of O-antigens synthesized by the polymerase-dependent pathway with five or six residues in the backbone; FIG. 10B depicts O-antigens believed to be synthesized by the ABC-transporter-dependent pathway.

FIG. 16A-16B—depict plasmid-mediated Arabinose-inducible Expression of O25b Long O-antigen LPS in O25b O-antigen knock-out host strain. Results from an SPS PAGE are shown in FIG. 16A and results from an O25 Immuno-Blot are shown in FIG. 16B, wherein Lane 1 is from Clone 1, no arabinose; Lane 2 is from Clone 1, 0.2% arabinose; Lane 3 is from Clone 9, no Arabinose; Lane 4 is from Clone 9, 0.2% Arabinose; Lane 5 is from O55 E. coli LPS Standard; and Lane 6 is from O111 E. coli LPS Standard, in both FIG. 16A and in FIG. 16B.

(FIG. 20A) Information regarding vaccination schedule for rabbit study 1 VAC-2017-PRL-EC-0723; (FIG. 20B) vaccination schedule for rabbit study 2 VAC-2018-PRL-EC-077.

FIG. 21A depicts results from Rabbit 1-3 (Medium Activation)

FIG. 22A depicts results from Rabbit A-1 (Unconjugated Poly); FIG. 22B depicts results from Rabbit A-3 (Unconjugated Poly); FIG. 22C depicts results from Rabbit A-4 (Unconjugated Poly); FIG. 22D depicts results from Rabbit 2-1 (low activation); FIG. 22E depicts results from Rabbit 2-2 (low activation); and FIG. 22F depicts results from Rabbit 2-3 (low activation).

FIG. 23A depicts results wherein —●— represents results from O25b 2831 vs PD3 antisera; —■— represents results from O25b 2831 wt vs prebleed; —▲— represents results from O25b 2831/fepE vs PD3 antisera; —▼— represents results from O25b 2831/fepE vs prebleed. FIG. 23B depicts results wherein —●— represents results from O25b 2401 vs PD3 antisera; —■— represents results from O25b 2401 vs prebleed; —▲— represents results from O25b 2401/fepE vs PD3 antisera; —▼— represents results from O25b 2401/fepE vs prebleed.

FIG. 23C depicts results wherein -▼- represents results from *E. coli* K12 vs PD3 antisera; and -■- represents results from *E. coli* K12 vs prebleed.

FIG. 26A shows OPA titers of Rabbit 2-3 pre-immune serum (-●-) and post-immune serum wk 13 (-■-). FIG. 26B shows OPA titers of Rabbit 1-2 pre-immune serum ( -●- ) and post-immune serum wk 19 (-■- ). FIG. 26C shows Rabbit 1-2 wk 19 OPA Titer Specificity, in which OPA activity of Rabbit 1-2 immune serum is blocked by pre-incubation with 100 g/mL of purified unconjugated O25b long O-antigen polysaccharide, wherein -■- represents results from Rabbit 1-2 immune serum wk 19; and -▼- represents results from Rabbit 1-2 wk 19 w/R1 Long-OAg.

FIG. 27B and FIG. 27C show graphs depicting O-antigen O25b IgG levels elicited by unconjugated O25b long O-antigen polysaccharide (FIG. 27B, O25b Free Poly (2 µg)) and derived O25b RAC/DMSO long O-antigen glycoconjugate (FIG. 27C, O25b-CRM$_{197}$ RAC Long (2 µg)), wherein -...- (dotted line) represents Naïve CD1 O25b IgG level.

FIG. 35A-35B—depict *E. coli* serotpye O9 O-antugen immune sera is bactericidal against an invasive *K. pneumoniae* O3 isolate. Legend: Rabbit immune sera elicited by an *E. coli* serotype O9a O-antigen CRM$_{197}$ conjugate was evaluated in opsonophagocytic assays (OPAs) with an *E. coli* O9a strain (FIG. 35A) and a *K. pneumoniae* O3b strain (FIG. 35B). OPA activity against the *E. coli* O9 strain was observed after two vaccine doses (week 15) that was absent following preadsorption with unconjugated O9 polysaccharide (O9-OAg), or with matched pre-immune sera (week 0). The same rabbit immune serum also showed potent antigen-specific serum bactericidal activity (SBA) against the *K. pneumoniae* O3b strain. BRC, baby rabbit complement; hC, IgG/IgM depleted human sera used as complement source.

FIG. 36A depicts the dosing schedule of Study VAC-2019-PRL-EC-1369: between 12 and 20 CD-1 mice per group were vaccinated with 3 µg or 30 µg doses of *E. coli* FimH$_{LD}$ antigen with or without 20 µg QS21/PS80 or 50 µg AlPO$_4$ adjuvant. FIG. 36B depicts the titers after dose 3 of individual mice vaccinated with wild-type FimH$_{LD}$ or FimH$_{LD}$ lock mutant antigens which are shown as closed symbols or open symbols, respectively. p values from t-tests (unpaired Welch's correction) of log transformed neutralization titer data are indicated.

FIG. 37A. depicts the dosing schedule of Study VAC-2019-PRL-EC-1438: 20 CD-1 mice per group were vaccinated with 10 µg or 30 µg of *E. coli* FimH$_{LD}$ or FimH-DSG antigen variants with 20 µg QS21/PS80. FIG. 37B—depicts the titers after dose 3 of individual mice vaccinated with wild-type FimH$_{LD}$ or FimH$_{LD}$ lock mutant antigens which are shown as closed symbols or open symbols, respectively. p values from t-tests (unpaired Welch's correction) of log transformed neutralization titer data are indicated.

SEQUENCE IDENTIFIERS

Figure 2B:
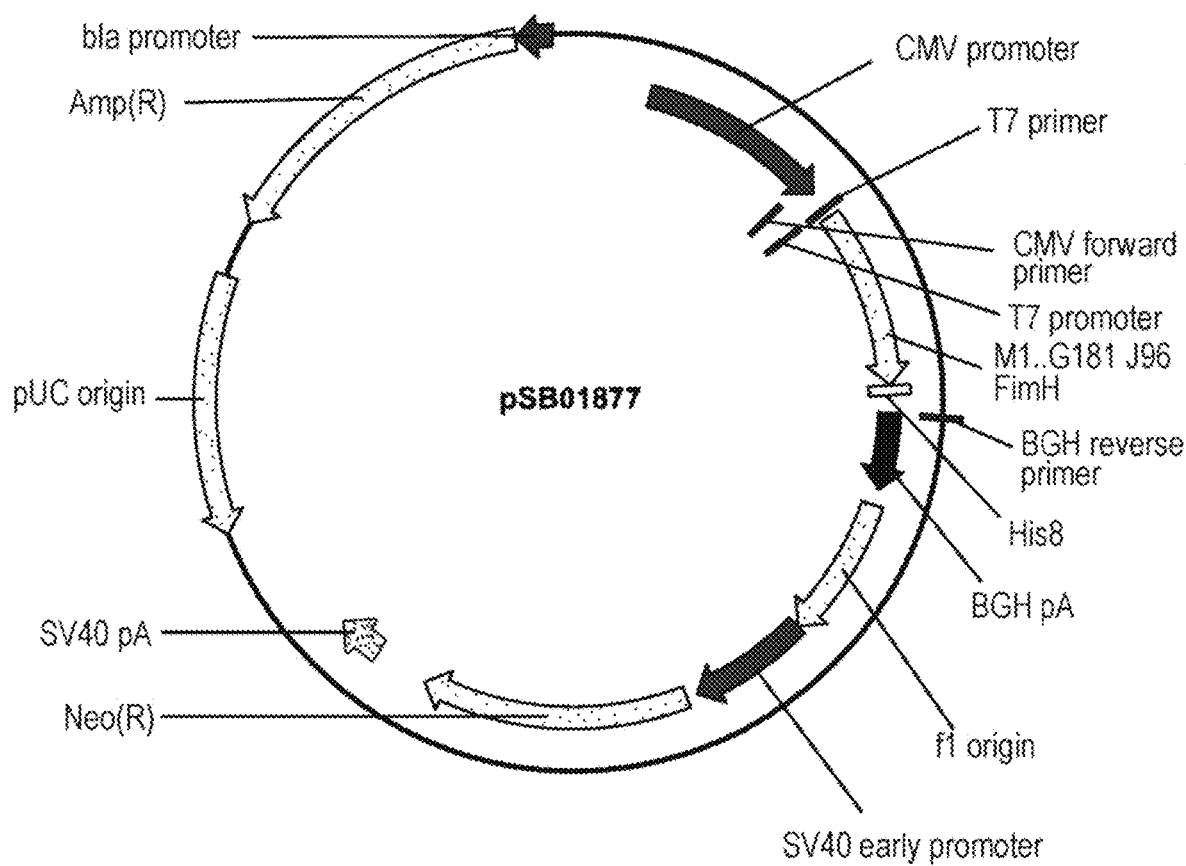
FIG. 2A-2T—depict maps of exemplary expression vectors.
Figure 2E:
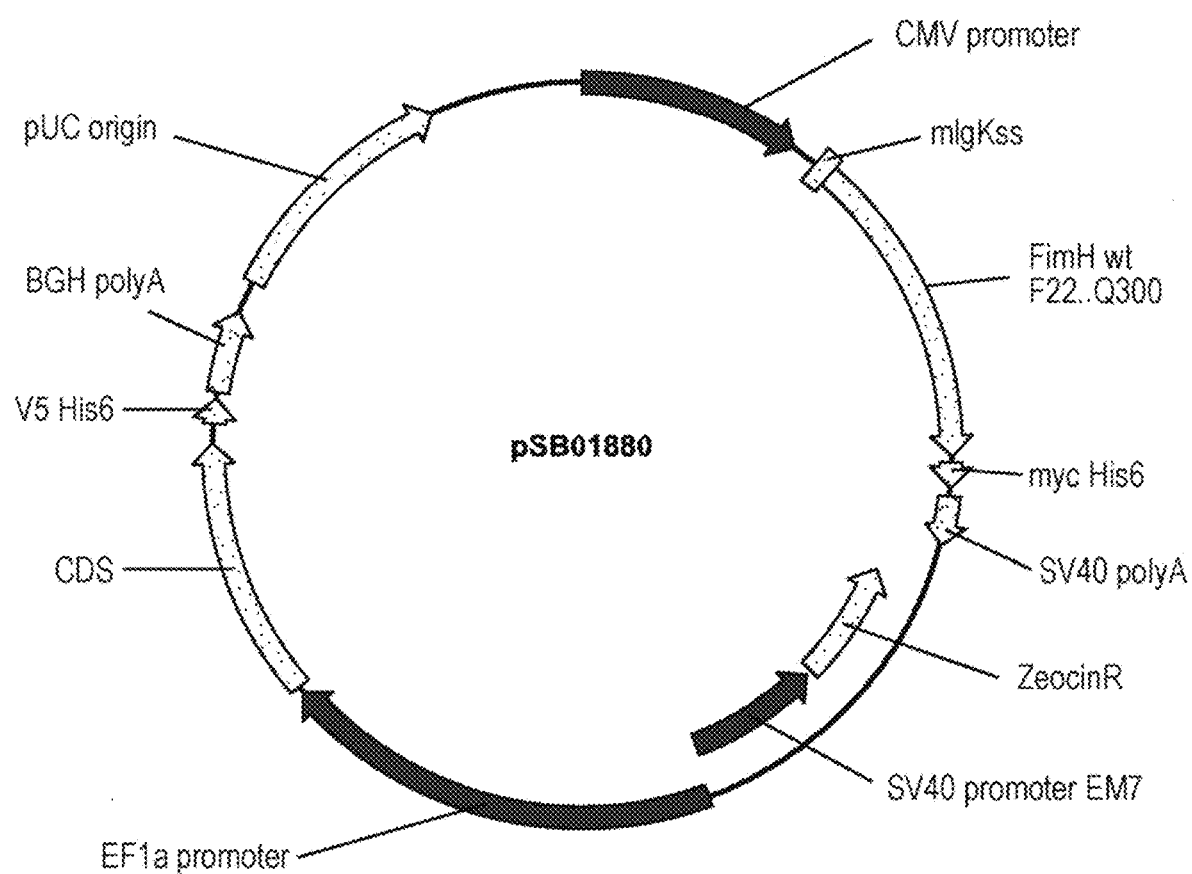
Figure 2F:
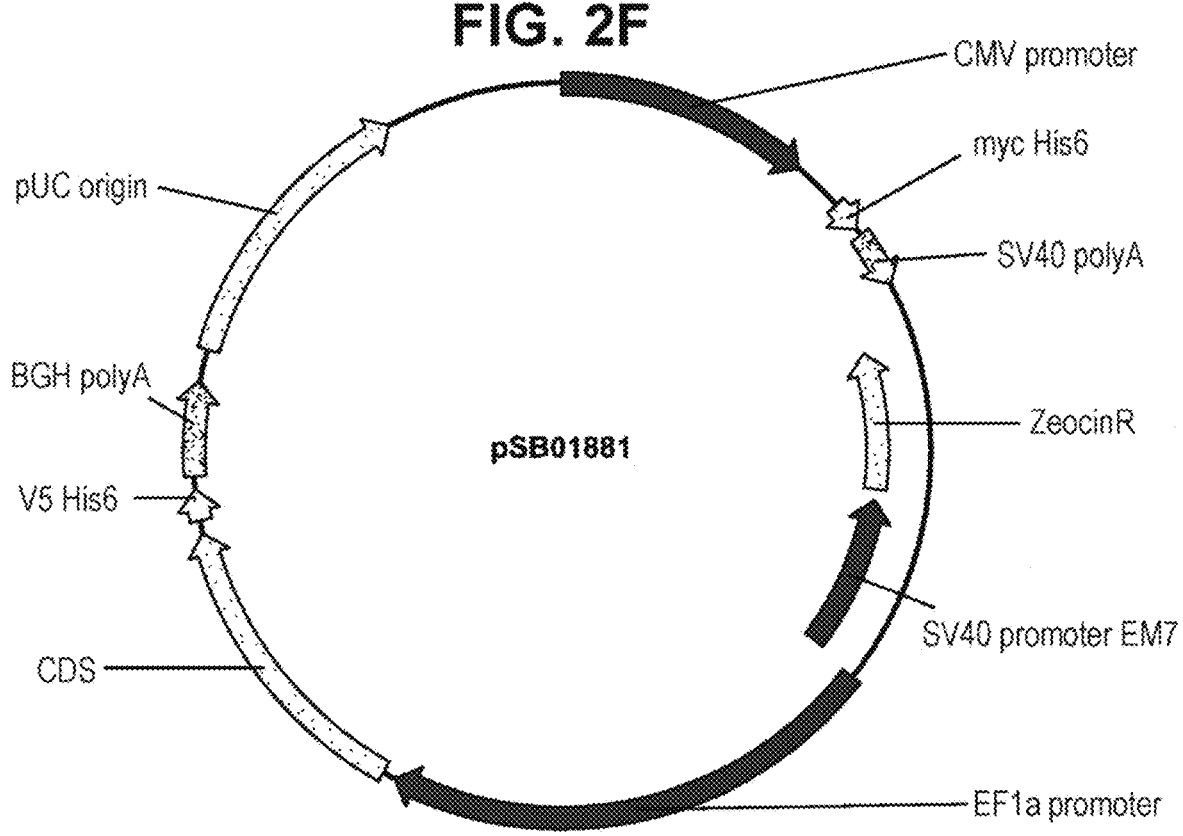
Figure 2G:
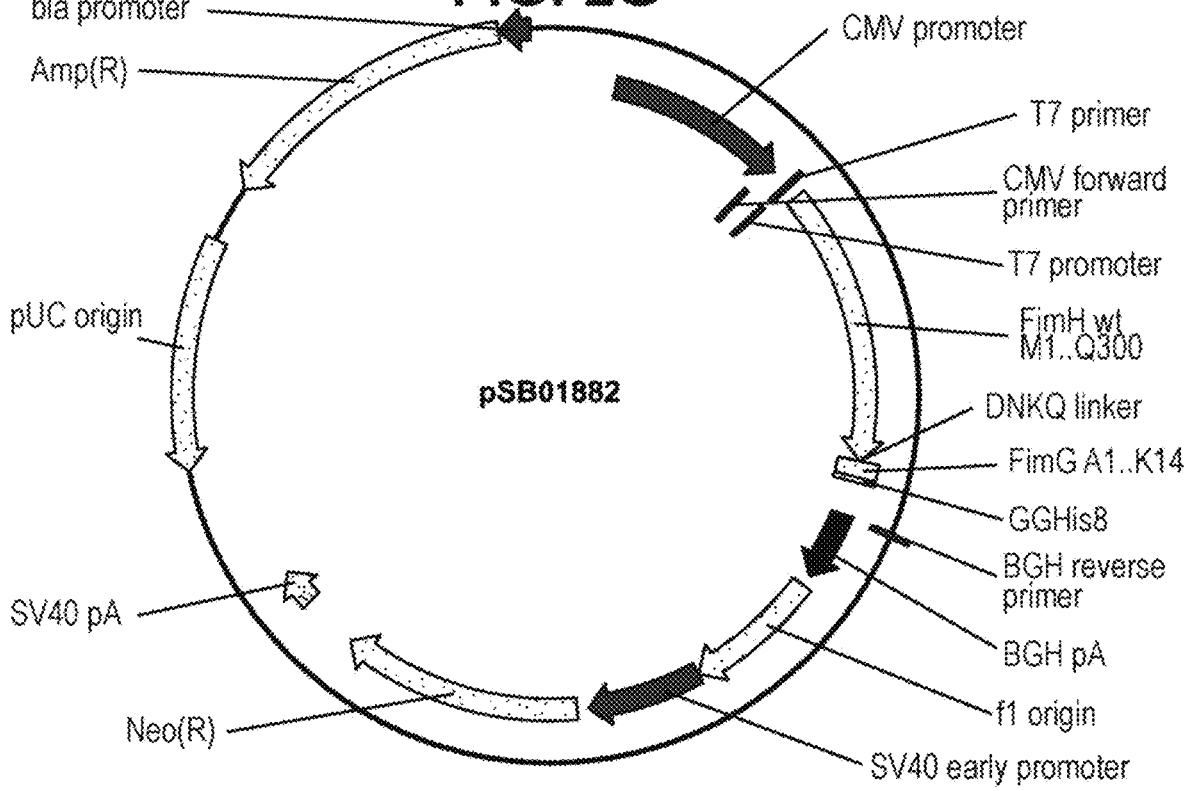
Figure 2H:
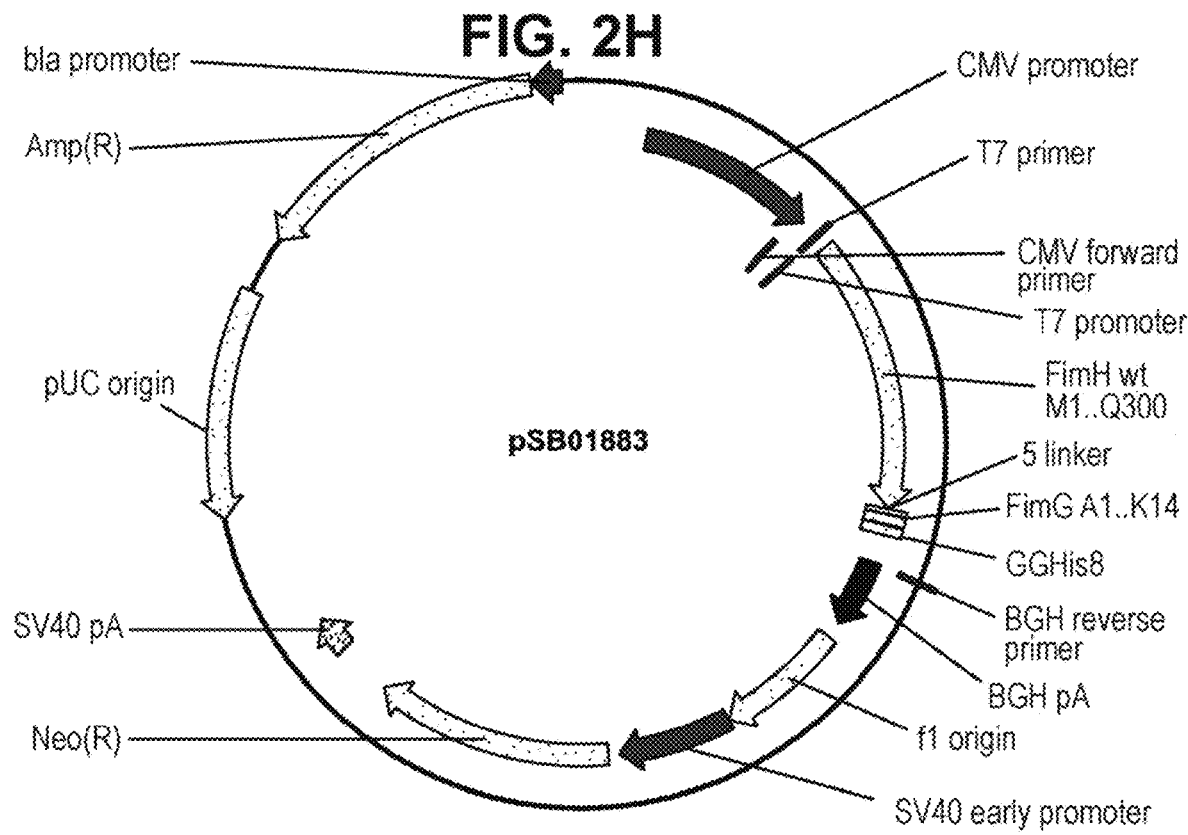
Figure 2I:
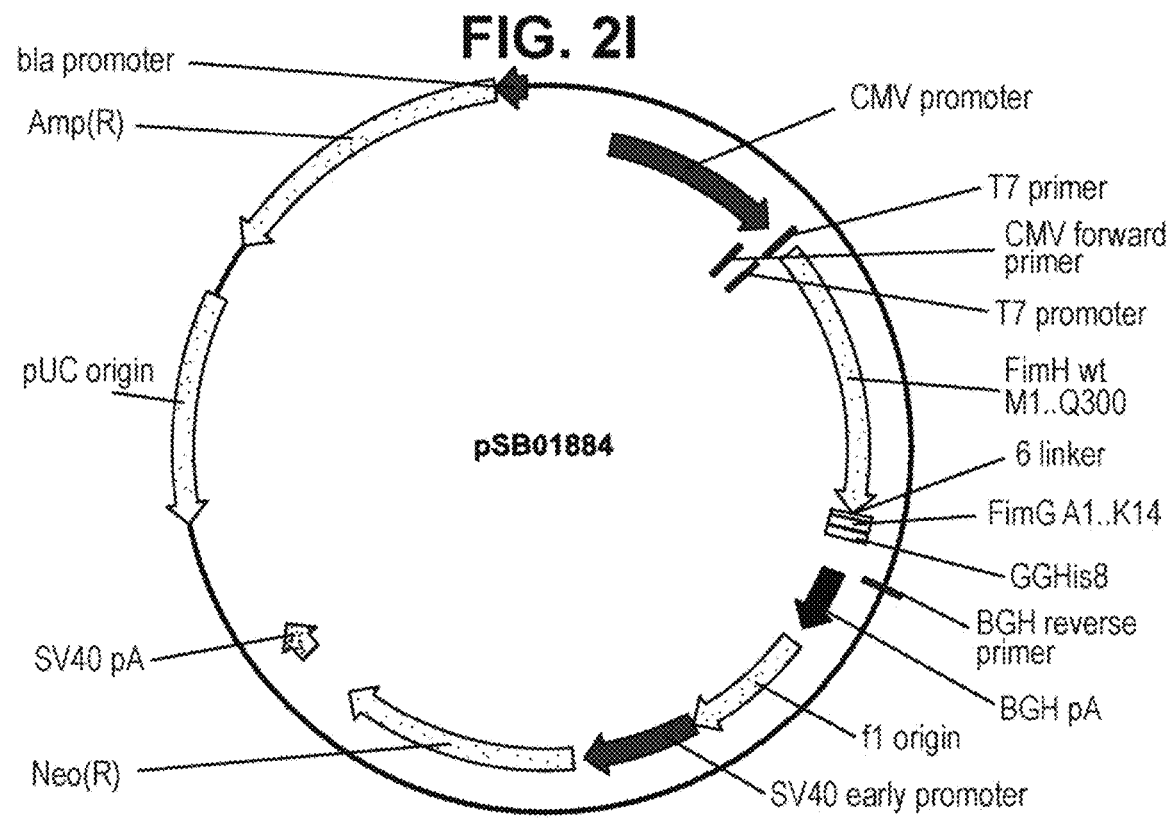
Figure 2J:
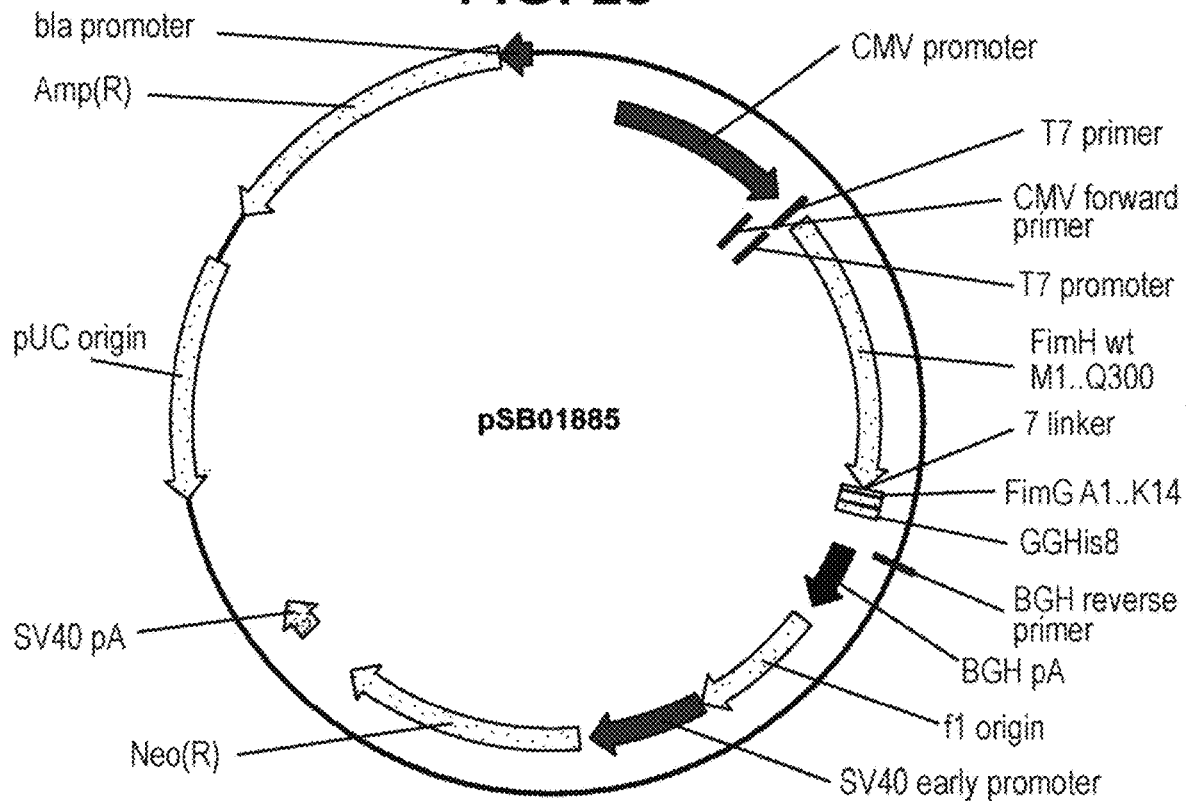
Figure 2K:
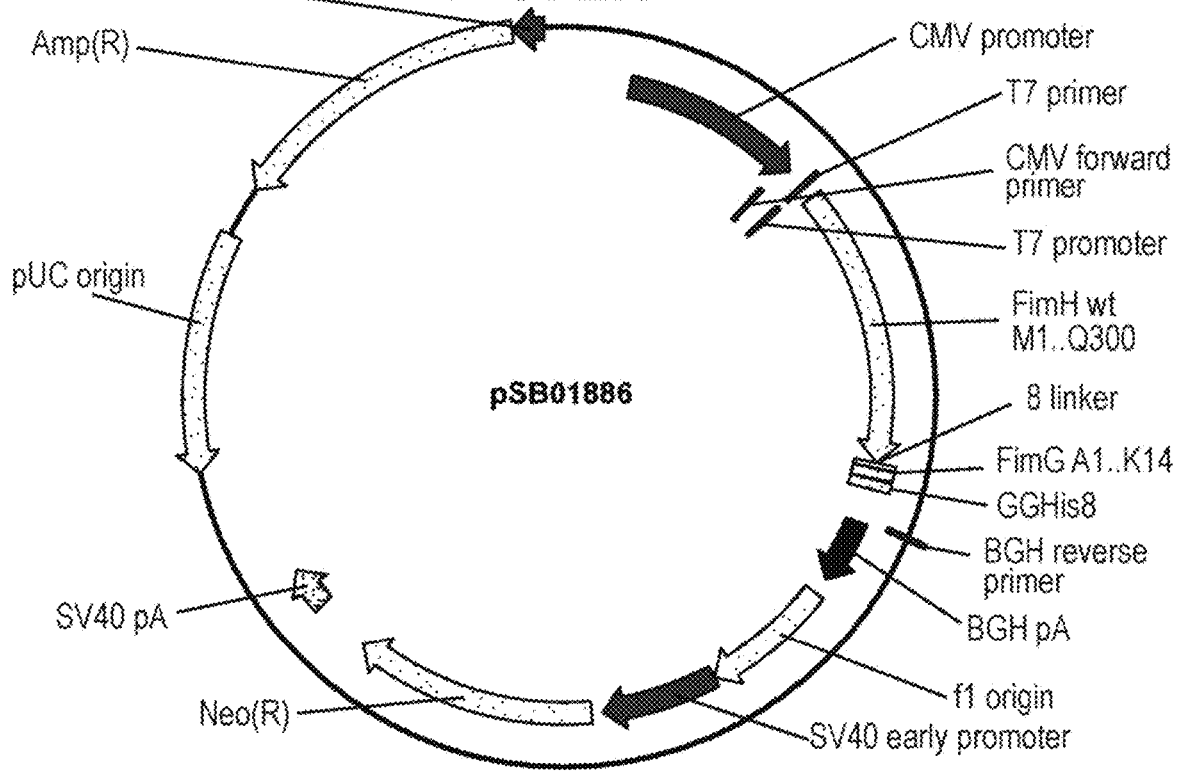
Figure 2L:
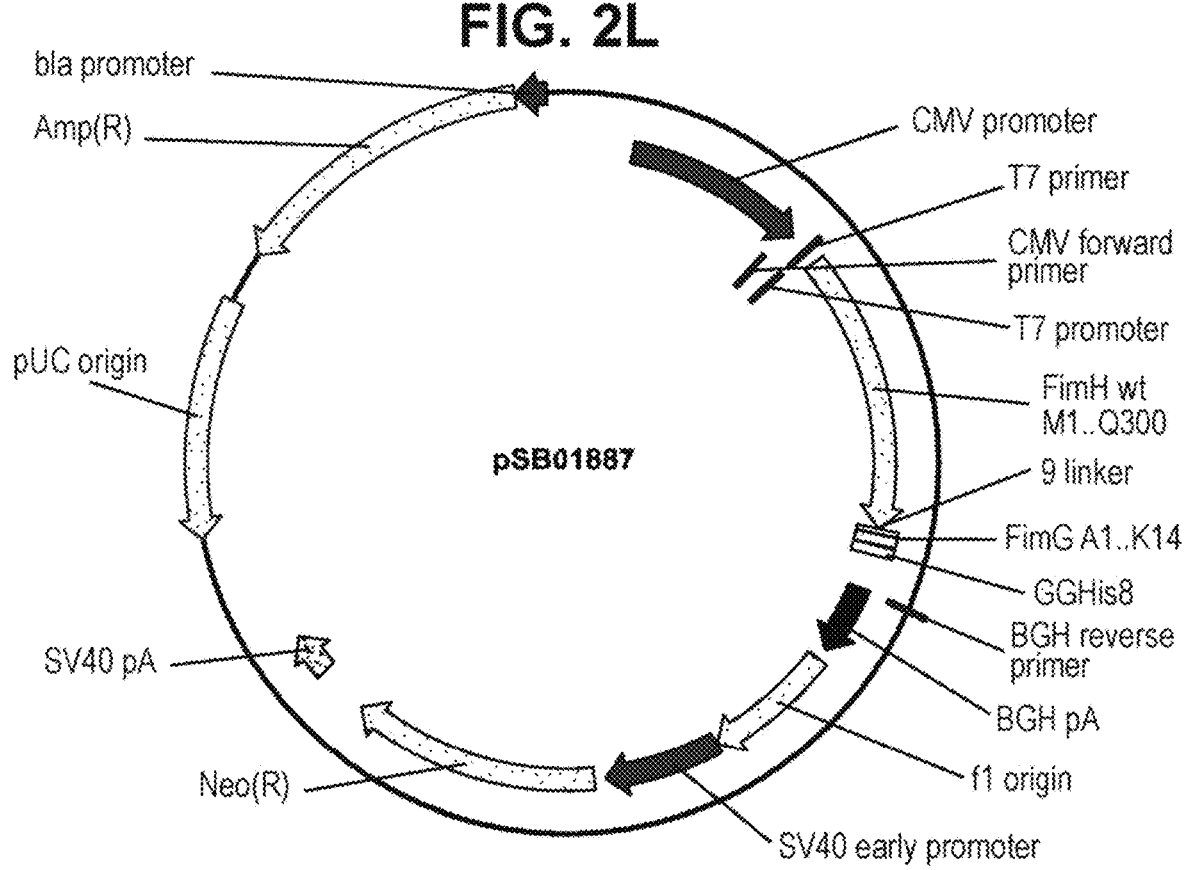
Figure 2M:
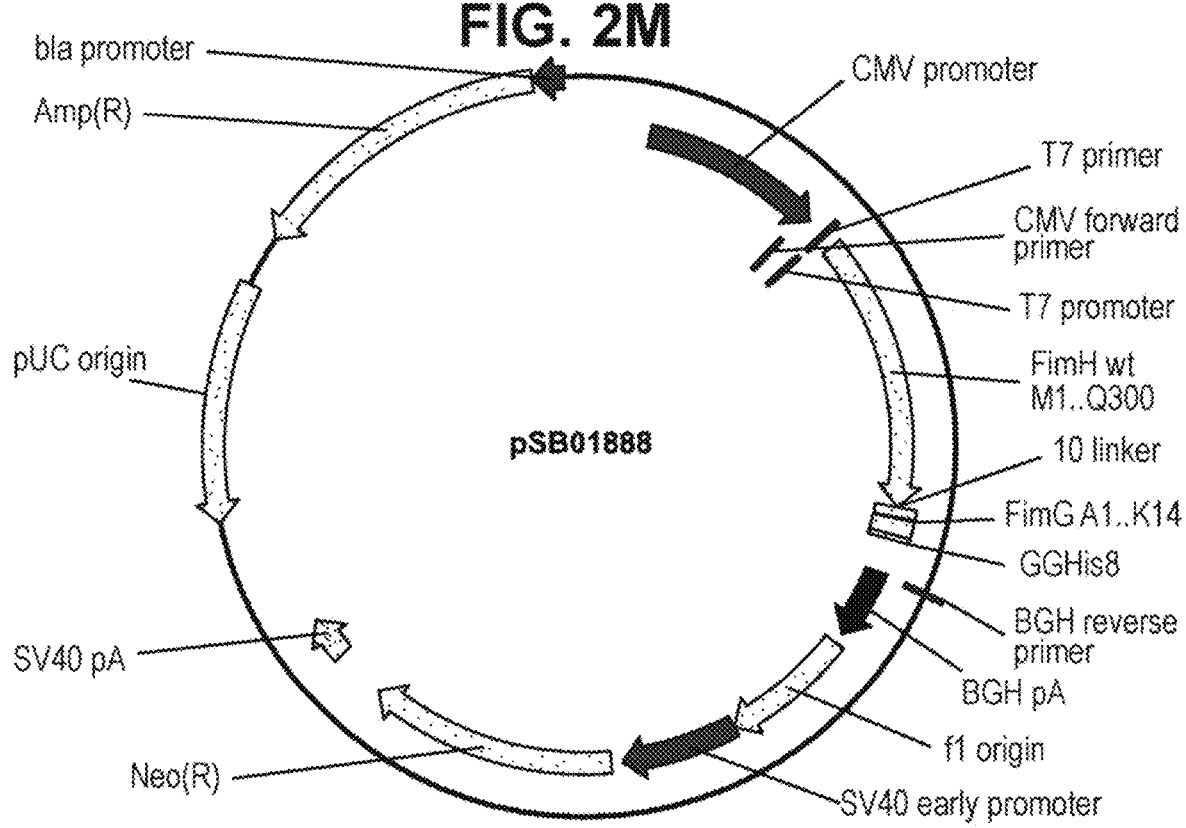
Figure 2N:
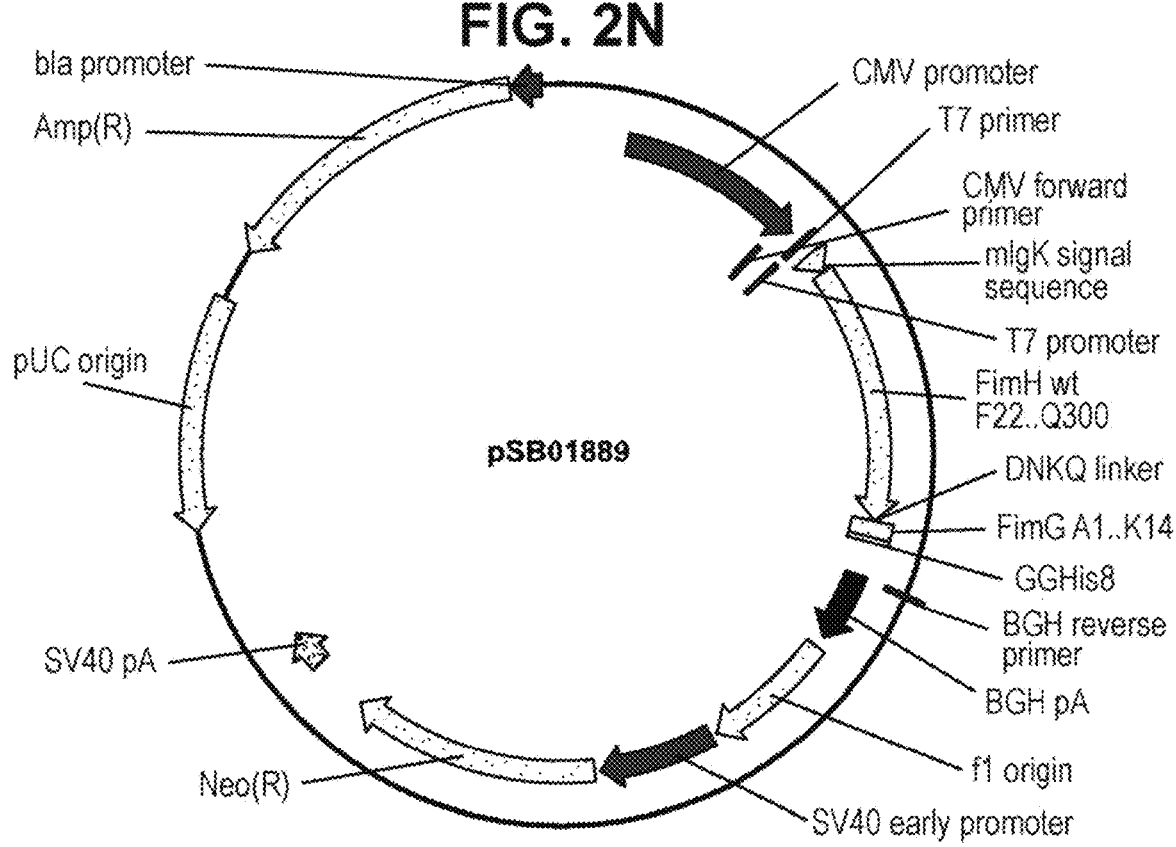
Figure 2O:
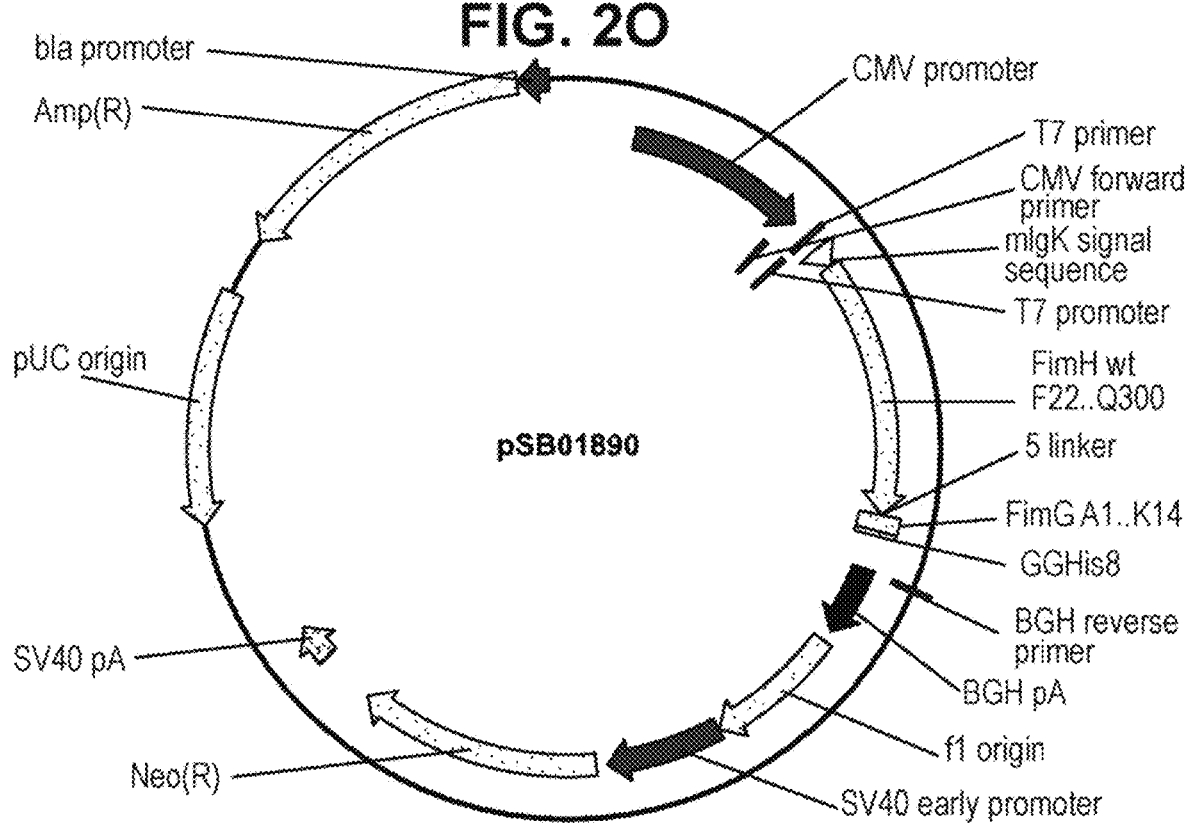
Figure 2P:
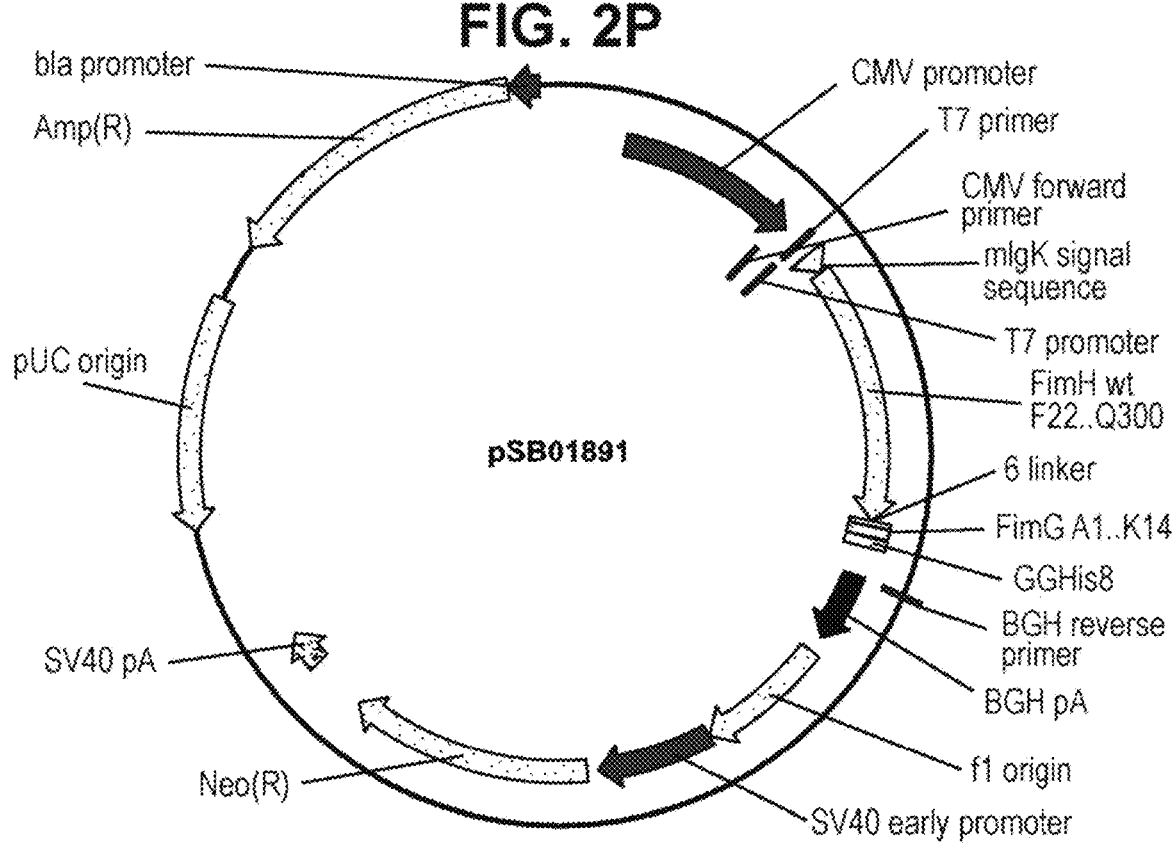
Figure 2Q:
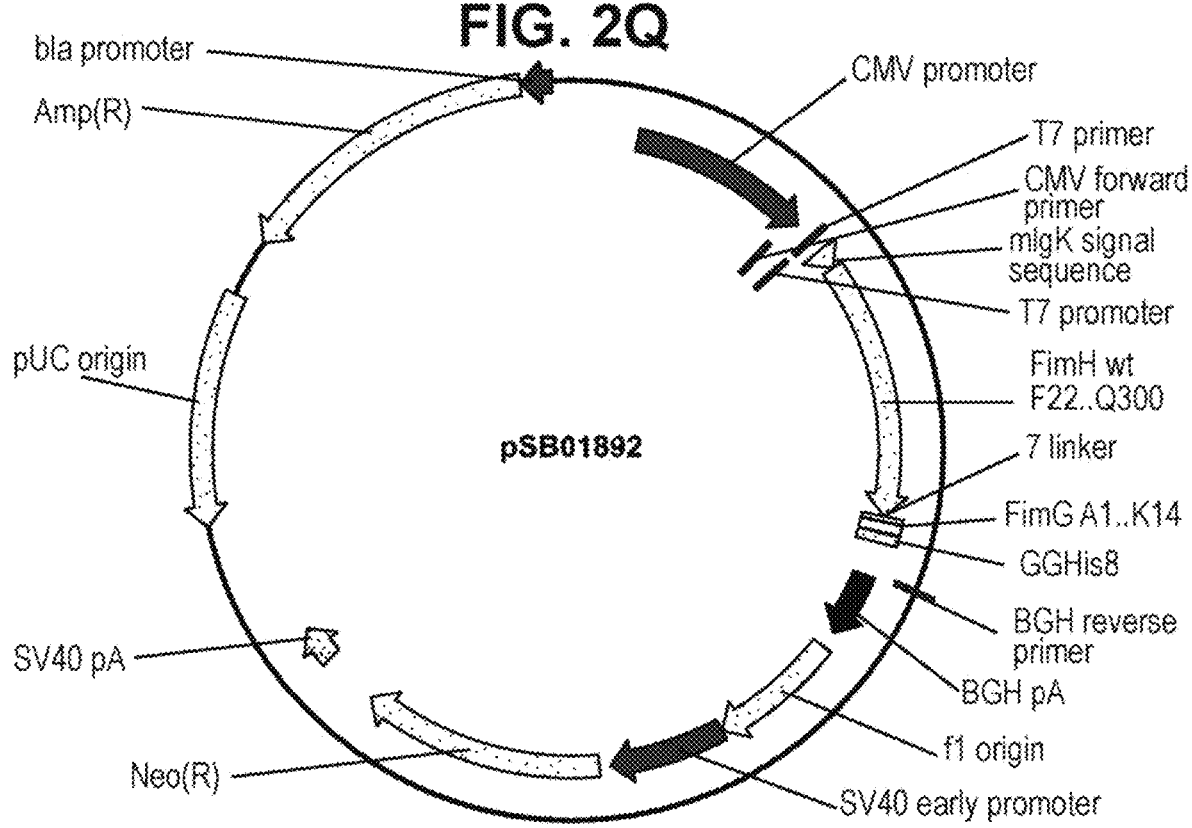
Figure 2R:
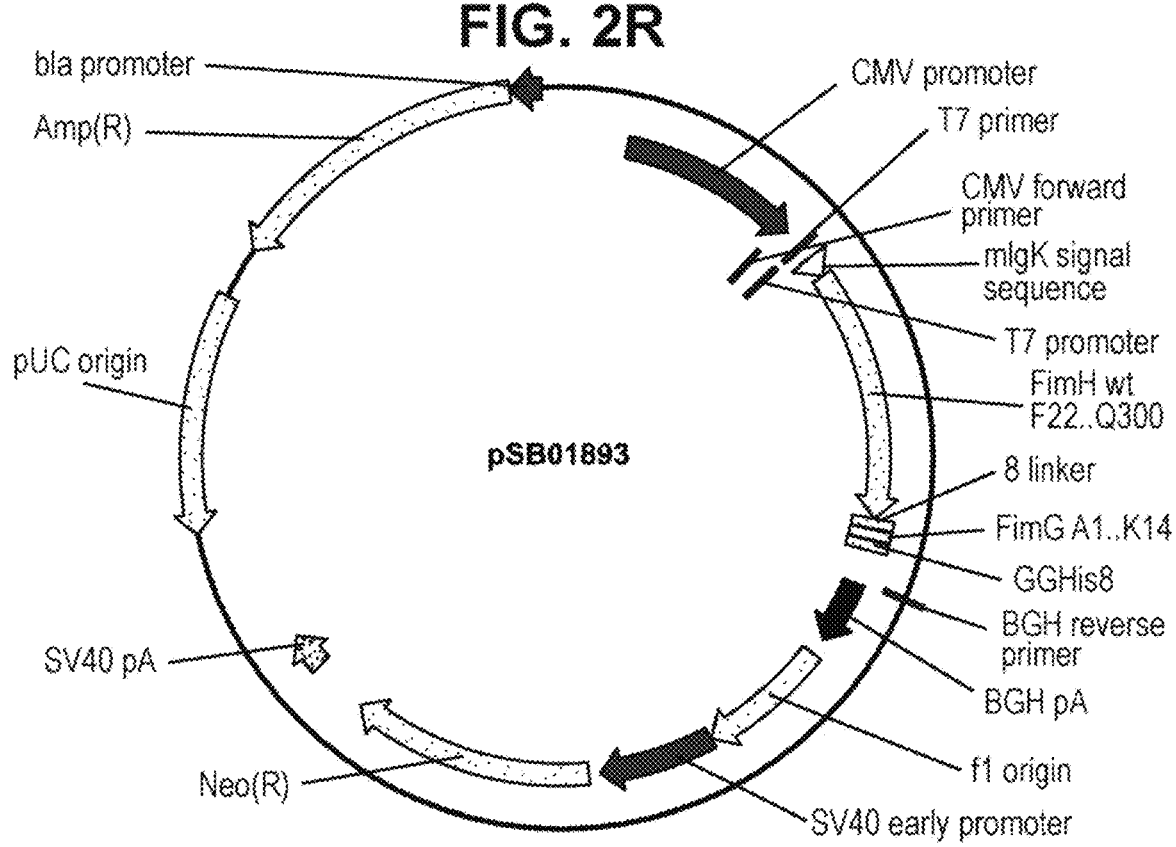
Figure 2S:
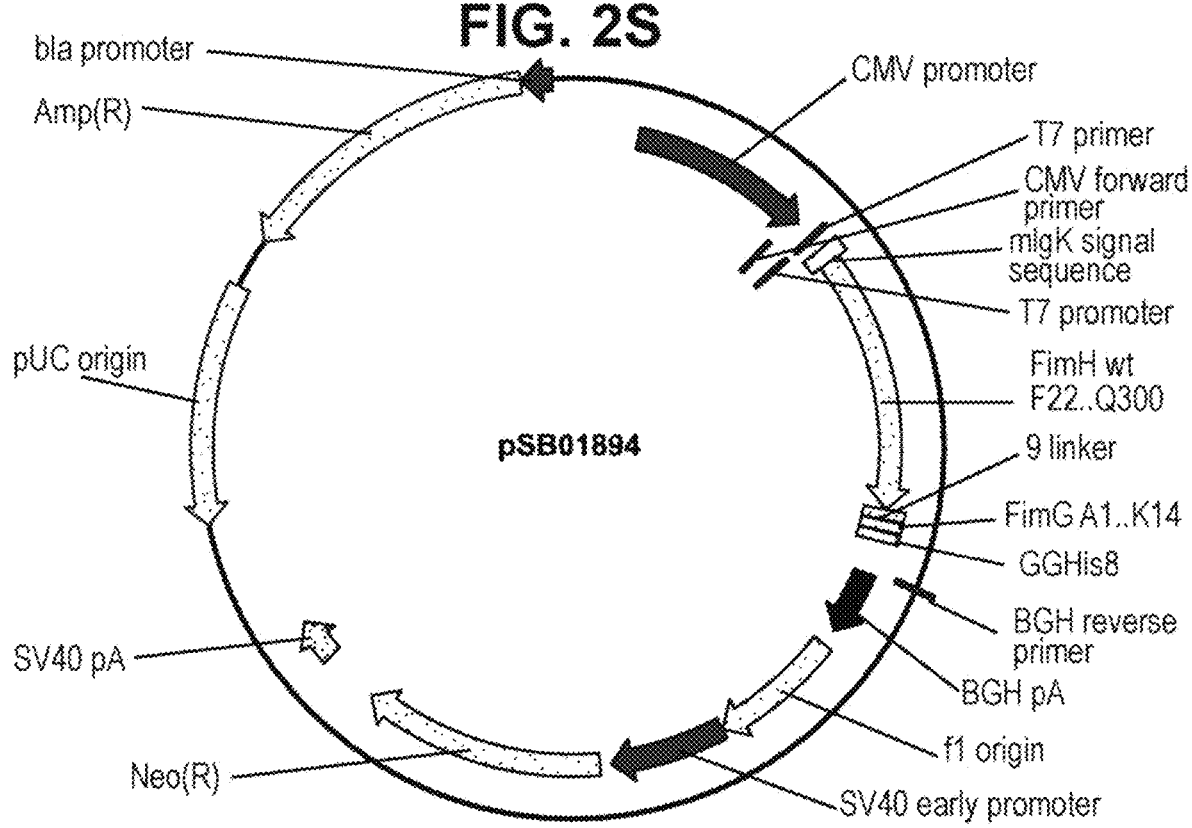

SEQ ID NO: 1 sets forth an amino acid sequence for a wild type type 1 fimbriae D-mannose specific adhesin [*Escherichia coli* FimH J96].

SEQ ID NO: 2 sets forth an amino acid sequence for a fragment of FimH, corresponding to aa residues 22-300 of SEQ ID NO: 1 (mature FimH protein).

SEQ ID NO: 3 sets forth an amino acid sequence for a FimH lectin domain.

SEQ ID NO: 4 sets forth an amino acid sequence for a FimH pilin domain.

SEQ ID NO: 5 sets forth an amino acid sequence for a polypeptide derived from *E. coli* FimH (pSB02198—FimH mIgK signal pept/F22 . . . Q300 J96 FimH N28S V48C L55C N91S N249Q/7 AA linker/FimG A1 . . . K14/GGHis8 in pcDNA3.1(+))

SEQ ID NO: 6 sets forth an amino acid sequence for a polypeptide derived from *E. coli* FimH (pSB02307—FimH mIgK signal pept/F22 . . . Q300 J96 FimH N28S N91S N249Q/His8 in pcDNA3.1(+))

SEQ ID NO: 7 sets forth an amino acid sequence for a fragment of a polypeptide derived from *E. coli* FimH (pSB02083 FimH Lectin Domain Wild Type construct)

SEQ ID NO: 8 sets forth an amino acid sequence for a fragment of a polypeptide derived from *E. coli* FimH (pSB02158 FimH Lectin Domain Lock Mutant)

SEQ ID NO: 9 sets forth an amino acid sequence for a fragment of a polypeptide derived from *E. coli* FimG (FimG A1 . . . K14)

SEQ ID NO: 10 sets forth an amino acid sequence for a fragment of a polypeptide derived from *E. coli* FimC.

SEQ ID NO: 11 sets forth an amino acid sequence for a 4 aa linker.

SEQ ID NO: 12 sets forth an amino acid sequence for a 5 aa linker.

SEQ ID NO: 13 sets forth an amino acid sequence for a 6 aa linker.

SEQ ID NO: 14 sets forth an amino acid sequence for a 7 aa linker.

SEQ ID NO: 15 sets forth an amino acid sequence for a 8 aa linker.

SEQ ID NO: 16 sets forth an amino acid sequence for a 9 aa linker.

SEQ ID NO: 17 sets forth an amino acid sequence for a 10 aa linker.

SEQ ID NO: 18 sets forth an amino acid sequence for a FimH J96 signal sequence.

SEQ ID NO: 19 sets forth an amino acid sequence for the signal peptide of SEQ ID NO: 5 (pSB02198—FimH mIgK signal pept/F22 . . . Q300 J96 FimH N28S V48C L55C N91S N249Q/7 AA linker/FimG A1 . . . K14/GGHis8 in pcDNA3.1(+)).

SEQ ID NO: 20 sets forth an amino acid sequence for a polypeptide derived from *E. coli* FimH according to SEQ ID NO: 5 (mature protein of pSB02198—FimH mIgK signal pept/F22 . . . Q300 J96 FimH N28S V48C L55C N91S N249Q/7 AA linker/FimG A1 . . . K14/GGHis8 in pcDNA3.1(+)).

SEQ ID NO: 21 sets forth an amino acid sequence for a polypeptide derived from *E. coli* FimG.

SEQ ID NO: 22 sets forth an amino acid sequence for the signal peptide of SEQ ID NO: 6 (pSB02307—FimH mIgK signal pept/F22 . . . Q300 J96 FimH N28S N91S N249Q/His8 in pcDNA3.1(+)).

SEQ ID NO: 23 sets forth an amino acid sequence for a polypeptide derived from *E. coli* FimH according to SEQ ID NO: 6 (mature protein of FimH mIgK signal pept/F22 . . . Q300 J96 FimH N28S N91S N249Q/His8 in pcDNA3.1(+)).

SEQ ID NO: 24 sets forth an amino acid sequence for a polypeptide derived from *E. coli* FimH according to SEQ ID NO: 7 (mature protein of pSB02083 FimH Lectin Domain Wild Type construct).

SEQ ID NO: 25 sets forth an amino acid sequence for a His-tag.

SEQ ID NO: 26 sets forth an amino acid sequence for a polypeptide derived from *E. coli* FimH according to SEQ ID NO: 8 (mature protein of pSB02158 FimH Lectin Domain Lock Mutant) SEQ ID NO: 27 sets forth an amino acid sequence for a polypeptide derived from *E. coli* FimH (pSB01878).

SEQ ID NO: 28 sets forth an amino acid sequence for a polypeptide derived from *E. coli* FimH (K12).

SEQ ID NO: 29 sets forth an amino acid sequence for a polypeptide derived from *E. coli* FimH (UTI89).

SEQ ID NO: 30 sets forth a O25b 2401 WzzB amino acid sequence.

SEQ ID NO: 31 sets forth a O25a:K5:H1 WzzB amino acid sequence.

SEQ ID NO: 32 sets forth a O25a ETEC ATCC WzzB amino acid sequence.

SEQ ID NO: 33 sets forth a K12 W3110 WzzB amino acid sequence.

SEQ ID NO: 34 sets forth a *Salmonella* LT2 WzzB amino acid sequence.

SEQ ID NO: 35 sets forth a O25b 2401 FepE amino acid sequence.

SEQ ID NO: 36 sets forth a O25a:K5:H1 FepE amino acid sequence.

SEQ ID NO: 37 sets forth a O25a ETEC ATCC FepE amino acid sequence.

SEQ ID NO: 38 sets forth a O157 FepE amino acid sequence.

SEQ ID NO: 39 sets forth a *Salmonella* LT2 FepE amino acid sequence.

SEQ ID NO: 40 sets forth a primer sequence for LT2wzzB_S.

SEQ ID NO: 41 sets forth a primer sequence for LT2wzzB_AS.

SEQ ID NO: 42 sets forth a primer sequence for O25bFepE_S.

SEQ ID NO: 43 sets forth a primer sequence for O25bFepE_A.

SEQ ID NO: 44 sets forth a primer sequence for wzzB P1_S.

SEQ ID NO: 45 sets forth a primer sequence for wzzB P2_AS.

SEQ ID NO: 46 sets forth a primer sequence for wzzB P3_S.

SEQ ID NO: 47 sets forth a primer sequence for wzzB P4_AS.

SEQ ID NO: 48 sets forth a primer sequence for O157 FepE_S.

SEQ ID NO: 49 sets forth a primer sequence for O157 FepE_AS.

SEQ ID NO: 50 sets forth a primer sequence for pBAD33_adaptor_S.

SEQ ID NO: 51 sets forth a primer sequence for pBAD33_adaptor_AS.

SEQ ID NO: 52 sets forth a primer sequence for JUMP-START_r.

SEQ ID NO: 53 sets forth a primer sequence for gnd_f.

SEQ ID NO: 54 sets forth an amino acid sequence for a mouse IgK signal sequence.

SEQ ID NO: 55 sets forth an amino acid sequence for a human IgG receptor FcRn large subunit p51 signal peptide.

SEQ ID NO: 56 sets forth an amino acid sequence for a human IL10 protein signal peptide.

SEQ ID NO: 57 sets forth an amino acid sequence for a human respiratory syncytial virus A (strain A2) fusion glycoprotein F0 signal peptide.

SEQ ID NO: 58 sets forth an amino acid sequence for an influenza A hemagglutinin signal peptide.

SEQ ID NOs: 59-101 set forth amino acid and nucleic acid sequences for a nanostructure-related polypeptide or fragment thereof.

SEQ ID NOs: 102-109 set forth SignalP 4.1 (DTU Bioinformatics) sequences from various species used for signal peptide predictions.

SEQ ID NO: 110 sets forth an amino acid sequence for a polypeptide derived from *E. coli* FimH (pSB02083—FimH$_{LD}$ (mIgK signal pept, N28S, N91S)).

SEQ ID NO: 111 sets forth an amino acid sequence for a polypeptide derived from *E. coli* FimH (pSB02158—FimH$_{LD}$-LM (mIgK signal pept, N28S N91S V48C L55C)).

SEQ ID NO: 112 sets forth an amino acid sequence for a polypeptide derived from *E. coli* FimH (pSB02307—FimH-DSG (mIgK signal pept, N28S N91S N249Q 7aa linker FimG A1 . . . K14)).

SEQ ID NO: 113 sets forth an amino acid sequence for a polypeptide derived from *E. coli* FimH (pSB02198—FimH-DSG-LM (mIgK signal pept, N28S N91S 249Q V48C L55C 7aa linker FimG A1 . . . K14)).

DETAILED DESCRIPTION OF THE INVENTION

The present disclosure relates to compositions comprising *E. coli* FimH polypeptides and O-antigen glycoconjugates, methods for producing and purifying the compositions, and methods of using said compositions.

In one aspect, the invention includes a composition including the FimH polypeptide or fragment thereof described herein. The composition may include a polypeptide or fragment thereof that is suitable for in vivo administration. For example, the polypeptide or fragment thereof in such a composition may have a purity of at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, by mass. In an embodiment the polypeptide in such a composition may have a purity of at least 95% by mass.

In an embodiment the polypeptide in such a composition may have a purity of at least 97% by mass. In an embodiment the polypeptide in such a composition may have a purity of at least 98% by mass. In an embodiment the polypeptide in such a composition may have a purity of at least 99% by mass. The composition may further comprise an adjuvant.

In a further aspect, the invention includes a composition for use in inducing an immune response against *E. coli* or *E. coli* infection. Use of the composition described herein for inducing an immune response against *E. coli* or *E. coli* infection and use of the composition described herein in the manufacture of a medicament for inducing an immune response against *E. coli* or *E. coli* infection, are also disclosed.

Recitation of ranges of values herein is merely intended to serve as a shorthand method of referring individually to each separate value falling within the range. Unless otherwise indicated herein, each individual value is incorporated into the specification as if it was individually recited herein. All methods described herein can be performed in any suitable order unless otherwise indicated herein or otherwise clearly contradicted by context. The use of any and all examples, or exemplary language (e.g., "such as"), provided herein is intended merely to further illustrate the disclosure and does not pose a limitation on the scope of the claims. No language in the specification should be construed as indicating any non-claimed element essential to the practice of the disclosure.

Several documents are cited throughout the text of this disclosure. Each of the documents cited herein (including all patents, patent applications, scientific publications, manufacturer's specifications, instructions, etc.), whether supra or infra, are hereby incorporated by reference in their entirety. Nothing herein is to be construed as an admission that the present disclosure was not entitled to antedate such disclosure.

Definitions

As used herein the term "about" means approximately or nearly, and in the context of a numerical value or range set forth herein in one embodiment means ±20%, +10%, 5%, or ±3% of the numerical value or range recited or claimed.

The terms "a" and "an" and "the" and similar reference used in the context of describing the disclosure (especially in the context of the claims) are to be construed to cover both the singular and the plural, unless otherwise indicated herein or clearly contradicted by context.

"Fragment", with reference to an amino acid sequence (peptide or protein), relates to a part of an amino acid sequence, i.e. a sequence which represents the amino acid sequence shortened at the N-terminus and/or C-terminus. A fragment shortened at the C-terminus (N-terminal fragment) is obtainable e.g. by translation of a truncated open reading frame that lacks the 3'-end of the open reading frame. A fragment shortened at the N-terminus (C-terminal fragment) is obtainable e.g. by translation of a truncated open reading frame that lacks the 5'-end of the open reading frame, as long as the truncated open reading frame comprises a start codon that serves to initiate translation. A fragment of an amino acid sequence comprises e.g. at least 50%, at least 60%, at least 70%, at least 80%, at least 90% of the amino acid residues from an amino acid sequence. A fragment of an amino acid sequence preferably comprises at least 6, in particular at least 8, at least 12, at least 15, at least 20, at least 30, at least 50, or at least 100 consecutive amino acids from an amino acid sequence.

As used herein, the term "wild type" or "WT" or "native" refers to an amino acid sequence that is found in nature, including allelic variations. A wild type amino acid sequence, peptide or protein has an amino acid sequence that has not been intentionally modified.

As used herein, "variants" of an amino acid sequence (peptide, protein or polypeptide), or "mutants', or reference to a "mutated" polypeptide, comprise amino acid insertion variants/mutants, amino acid addition variants/mutants, amino acid deletion variants/mutants and/or amino acid substitution variants/mutants. The term "variant" or "mutant" includes all mutants, splice variants, posttranslationally modified variants, conformations, isoforms, allelic variants, species variants, and species homologs, in particular those which are naturally occurring. The term "variant" or "mutant" includes, in particular, fragments of an amino acid sequence.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible. Amino acid addition variants comprise amino- and/or carboxy-terminal fusions of one or more amino acids, such as 1, 2, 3, 5, 10, 20, 30, 50, or more amino acids. Amino acid deletion variants are characterized by the removal of one or more amino acids from the sequence, such as by removal of 1, 2, 3, 5, 10, 20, 30, 50, or more amino acids. The deletions may be in any position of the protein. Amino acid deletion variants that comprise the deletion at the N-terminal and/or C-terminal end of the protein are also called N-terminal and/or C-terminal truncation variants. Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in peptide and protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In one embodiment, conservative amino acid substitutions include substitutions within the following groups:

glycine, alanine;
valine, isoleucine, leucine;
aspartic acid, glutamic acid;
asparagine, glutamine;
serine, threonine;
lysine, arginine; and
phenylalanine, tyrosine.

Preferably the degree of similarity, preferably identity between a given amino acid sequence and an amino acid sequence which is a variant of said given amino acid sequence will be at least about 60%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, in some embodiments continuous amino acids. In some embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS:needle, Matrix: Blosum62, Gap Open 10.0, Gap Extend 0.5.

As used herein, "sequence similarity" indicates the percentage of amino acids that either are identical or that represent conservative amino acid substitutions. "Sequence identity" between two amino acid sequences indicates the percentage of amino acids that are identical between the sequences. "Sequence identity" between two nucleic acid sequences indicates the percentage of nucleotides that are identical between the sequences.

The terms "% identical", "% identity" or similar terms are intended to refer, in particular, to the percentage of nucleotides or amino acids which are identical in an optimal alignment between the sequences to be compared. Said percentage is purely statistical, and the differences between the two sequences may be but are not necessarily randomly distributed over the entire length of the sequences to be compared. Comparisons of two sequences are usually carried out by comparing the sequences, after optimal alignment, with respect to a segment or "window of comparison", in order to identify local regions of corresponding sequences. The optimal alignment for a comparison may be carried out manually or with the aid of the local homology algorithm by Smith and Waterman, 1981, Ads App. Math. 2, 482, with the aid of the local homology algorithm by Neddleman and Wunsch, 1970, J. Mol. Biol. 48, 443, with the aid of the similarity search algorithm by Pearson and Lipman, 1988, Proc. Natl Acad. Sci. USA 88, 2444, or with the aid of computer programs using said algorithms (GAP, BESTFIT, FASTA, BLAST P, BLAST N and TFASTA in Wisconsin Genetics Software Package, Genetics Computer Group, 575 Science Drive, Madison, Wis.). In some embodiments, percent identity of two sequences is determined using the BLASTN or BLASTP algorithm, as available on the United States National Center for Biotechnology Information (NCBI) website (e.g., at blast.ncbi.nlm.nih.gov/Blast.cgi?PAGE_TYPE=BlastSearch&BLAST_SPEC=blast2seq&LINK_L OC=align2seq). In some embodiments, the algorithm parameters used for BLASTN algorithm on the NCBI website include: (i) Expect Threshold set to 10; (ii) Word Size set to 28; (iii) Max matches in a query range set to 0; (iv) Match/Mismatch Scores set to 1, -2; (v) Gap Costs set to Linear; and (vi) the filter for low complexity regions being used. In some embodiments, the algorithm parameters used for BLASTP algorithm on the NCBI website include: (i) Expect Threshold set to 10; (ii) Word Size set to 3; (iii) Max matches in a query range set to 0; (iv) Matrix set to BLOSUM62; (v) Gap Costs set to Existence: 11 Extension: 1; and (vi) conditional compositional score matrix adjustment.

Percentage identity is obtained by determining the number of identical positions at which the sequences to be compared correspond, dividing this number by the number of positions compared (e.g., the number of positions in the reference sequence) and multiplying this result by 100.

In some embodiments, the degree of similarity or identity is given for a region which is at least about 50%, at least about 60%, at least about 70%, at least about 80%, at least about 90% or about 100% of the entire length of the reference sequence. For example, if the reference nucleic acid sequence consists of 200 nucleotides, the degree of identity is given for at least about 100, at least about 120, at least about 140, at least about 160, at least about 180, or about 200 nucleotides, in some embodiments continuous nucleotides. In some embodiments, the degree of similarity or identity is given for the entire length of the reference sequence.

Homologous amino acid sequences exhibit according to the disclosure at least 40%, in particular at least 50%, at least 60%, at least 70%, at least 80%, at least 90% and preferably at least 95%, at least 98 or at least 99% identity of the amino acid residues. The amino acid sequence variants/mutants described herein may readily be prepared by the skilled person, for example, by recombinant DNA manipulation. The manipulation of DNA sequences for preparing peptides or proteins having substitutions, additions, insertions or deletions, is described in detail in Sambrook et al. (1989), for example. Furthermore, the peptides and amino acid variants described herein may be readily prepared with the aid of known peptide synthesis techniques such as, for example, by solid phase synthesis and similar methods.

In one aspect, a fragment or variant/mutant of an amino acid sequence (peptide or protein) is preferably a "functional fragment" or "functional variant". The term "functional fragment" or "functional variant/mutant" of an amino acid sequence relates to any fragment or variant/mutant exhibiting one or more functional properties identical or similar to those of the amino acid sequence from which it is derived, i.e., it is functionally equivalent. With respect to antigens or antigenic sequences, one particular function is one or more immunogenic activities displayed by the amino acid sequence from which the fragment or variant is derived. The term "functional fragment" or "functional variant/mutant", as used herein, in particular refers to a variant/mutant molecule or sequence that comprises an amino acid sequence that is altered by one or more amino acids compared to the amino acid sequence of the parent molecule or sequence and that is still capable of fulfilling one or more of the functions of the parent molecule or sequence, e.g., inducing an immune response. In one aspect, the modifications in the amino acid sequence of the parent molecule or sequence do not significantly affect or alter the characteristics of the molecule or sequence. In different embodiments, the function of the functional fragment or functional variant may be reduced but still significantly present, e.g., immunogenicity of the functional variant may be at least 50%, at least 60%, at least 70%, at least 80%, or at least 90% of the parent molecule or sequence. However, in other embodiments, immunogenicity of the functional fragment or functional variant may be enhanced compared to the parent molecule or sequence.

As used herein, "isolated" means altered or removed from the natural state. For example, a nucleic acid or a peptide naturally present in a living animal is not "isolated", but the same nucleic acid or peptide partially or completely separated from the coexisting materials of its natural state is "isolated". An isolated nucleic acid or protein can exist in substantially purified form, or can exist in a non-native environment such as, for example, a host cell.

I. Polypeptides Derived from *E. coli* and Fragments Thereof

In one aspect, disclosed herein is a mammalian cell that includes a polynucleotide that encodes a polypeptide derived from *E. coli* or a fragment thereof. The term "derived from" as used herein refers to a polypeptide that comprises an amino acid sequence of a FimH polypeptide or FimCH polypeptide complex or a fragment thereof as described herein that has been altered by the introduction of an amino acid residue substitution, deletion or addition. Preferably, the polypeptide derived from *E. coli* or a fragment thereof includes a sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to the sequence of the corresponding wild-type *E. coli* FimH polypeptide or fragment. In some embodiments, the polypeptide derived from *E. coli* or a fragment thereof has at least 85% identity to the sequence of the corresponding wild-type *E. coli* FimH polypeptide or fragment. In some embodiments, the polypeptide derived from *E. coli* or a fragment thereof has at least 90% identity to the sequence of the corresponding wild-type *E. coli* FimH polypeptide or fragment. In some embodiments, the polypeptide derived from *E. coli* or a fragment thereof has at least 95% identity to the sequence of the corresponding wild-type *E. coli* FimH polypeptide or fragment. In some embodiments, the polypeptide derived from *E. coli* or a fragment thereof has at least 98% identity to the sequence of the corresponding wild-type *E. coli* FimH polypeptide or fragment. In some embodiments, the polypeptide derived from *E. coli* or a fragment thereof has at least 99% identity to the sequence of the corresponding wild-type *E. coli* FimH polypeptide or fragment. In some embodiments, the polypeptide derived from *E. coli* or a fragment thereof has the identical total length of amino acids as the corresponding wild-type FimH polypeptide or FimCH polypeptide complex or a fragment thereof. In some embodiments, the polypeptide derived from E. coli has the identical total length of amino acids as the corresponding wild-type FimH polypeptide or FimCH polypeptide complex.

The fragments should include at least n consecutive amino acids from the sequences and, depending on the particular sequence, n is 7 or more (eg. 8, 10, 12, 14, 16, 18, 20 or more). Preferably the fragments include an epitope from the sequence. In some embodiments, the fragment includes an amino acid sequence of at least 50 consecutive amino acid residues, at least 100 consecutive amino acid residues, at least 125 consecutive amino acid residues, at least 150 consecutive amino acid residues, at least 175 consecutive amino acid residues, at least 200 consecutive amino acid residues, or at least 250 consecutive amino acid residues of the amino acid sequence of a polypeptide derived from E. coli. In some embodiments, the fragment includes an amino acid sequence of at least 50 consecutive amino acid residues of the amino acid sequence of a polypeptide derived from E. coli. In some embodiments, the fragment includes an amino acid sequence of at least 100 consecutive amino acid residues of the amino acid sequence of a polypeptide derived from E. coli. In some embodiments, the fragment includes an amino acid sequence of at least 150 consecutive amino acid residues of the amino acid sequence of a polypeptide derived from E. coli. In some embodiments, the fragment includes an amino acid sequence of at least 200 consecutive amino acid residues of the amino acid sequence of a polypeptide derived from E. coli. In some embodiments, the fragment includes an amino acid sequence of at least 250 consecutive amino acid residues of the amino acid sequence of a polypeptide derived from E. coli.

In some embodiments, the polypeptide derived from E. coli or a fragment thereof includes one or more non-classical amino acids, as compared to a corresponding wild-type E. coli FimH polypeptide or fragment.

As used herein, the term "FimH polypeptide" refers to any FimH polypeptide or fragment thereof as described herein that has been altered by the introduction of an amino acid substitution, deletion or addition, any FimH domain of the full-length wild type E. coli FimH polypeptide, any combination of domains of the full-length wild type E. coli FimH polypeptide, or the full-length E. coli FimH polypeptide. For example, in one embodiment the present disclosure provides a FimH polypeptide that is a FimH$_{LD}$ polypeptide, or a FimH-DSG polypeptide.

In some embodiments, the polypeptide derived from E. coli or a fragment thereof possess a similar or identical function as a corresponding wild-type FimH polypeptide or a fragment thereof.

In a preferred embodiment, polypeptides or polypeptide complexes or fragments thereof of the invention are isolated or purified.

In some embodiments, the polynucleotide encoding the polypeptide derived from E. coli or a fragment thereof is integrated into the genomic DNA of the mammalian cell, and, when cultured in a suitable condition, said polypeptide derived from E. coli or a fragment thereof is expressed by the mammalian cell.

In a preferred embodiment, the polypeptide derived from E. coli or a fragment thereof is soluble.

In some embodiments, the polypeptide derived from E. coli or a fragment thereof is secreted from the mammalian host cell.

In some embodiments, the polypeptide derived from E. coli or a fragment thereof may include additional amino acid residues, such as N-terminal or C-terminal extensions. Such extensions may include one or more tags, which may facilitate detection (e.g. an epitope tag for detection by monoclonal antibodies) and/or purification (e.g. a polyhistidine-tag to allow purification on a nickel-chelating resin) of the polypeptide or fragment thereof. In some embodiments, the tag includes the amino acid sequence selected from any one of SEQ ID NO: 21 and SEQ ID NO: 25. Such affinity-purification tags are known in the art. Examples of affinity-purification tags include, e.g., His tag (hexahistidine, which may, for example, bind to metal ion), maltose-binding protein (MBP), which may, for example, bind to amylose), glutathione-S-transferase (GST), which may, for example, bind to glutathione, FLAG tag, which may, for example, bind to an anti-flag antibody), Strep tag, which may, for example, bind to streptavidin or a derivative thereof). In preferred embodiments, the polypeptide derived from E. coli or a fragment thereof does not include additional amino acid residues, such as N-terminal or C-terminal extensions. In some embodiments, the polypeptide derived from E. coli or a fragment thereof described herein does not include an exogenous tag sequence.

While specific strains of E. coli may be referenced herein, it should be understood that the polypeptide derived from E. coli or a fragment thereof are not limited to specific strains unless specified.

In some embodiments, the polypeptide derived from E. coli FimH or a fragment thereof includes a phenylalanine residue at the N-terminus of the polypeptide. In some embodiments, the polypeptide derived from FimH or fragment thereof includes a phenylalanine residue within the first 20 residue positions of the N-terminus. Preferably, the phenylalanine residue is located at position 1 of the polypeptide. For example, in some embodiments, the polypeptide derived from E. coli FimH or a fragment thereof does not include an additional glycine residue at the N-terminus of the polypeptide derived from E. coli FimH or a fragment thereof.

In some embodiments, the phenylalanine residue at position 1 of the wild-type mature E. coli FimH is replaced by an aliphatic hydrophobic amino acid, such as, for example, any one of Ile, Leu and Val residues.

In some embodiments, a signal peptide may be used for expressing the polypeptide derived from E. coli or a fragment thereof. Signal sequences and expression cassettes for producing proteins are known in the art. In general, leader peptides are 5-30 amino acids long, and are typically present at the N-terminus of a newly synthesized polypeptide. The signal peptide generally contains a long stretch of hydrophobic amino acids that has a tendency to form a single alpha-helix. In addition, many signal peptides begin with a short positively charged stretch of amino acids, which may help to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. In some embodiments, the signal peptide includes the amino acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, or 100% identity to any one of SEQ ID NO: 9, SEQ ID NO: 18, SEQ ID NO: 19, and SEQ ID NO: 22. In some embodiments, the signal peptide includes the amino acid sequence having at least 99% identity to any one of SEQ ID NO: 9, SEQ ID NO: 18, SEQ ID NO: 19, and SEQ ID NO: 22. In some embodiments, the signal peptide has the amino acid sequence selected from any one of SEQ ID NO: 9, SEQ ID NO: 18, SEQ ID NO: 19, and SEQ ID NO: 22. In some embodiments, the polypeptide derived from *E. coli* or a fragment thereof described herein may include a cleavable linker. Such linkers allow for the tag to be separated from the purified complex, for example by the addition of an agent capable of cleaving the linker. Cleavable linkers are known in the art. Such linkers may be cleaved for example, by irradiation of a photolabile bond or acid-catalyzed hydrolysis. Another example of a cleavable linker includes a polypeptide linker, which incorporates a protease recognition site and may be cleaved by the addition of a suitable protease enzyme.

In some embodiments, the polypeptide derived from *E. coli* or a fragment thereof includes a modification as compared to the corresponding wild-type *E. coli* FimH polypeptide or fragment. The modification may include a covalent attachment of a molecule to the polypeptide. For example, such modifications may include glycosylation, acetylation, pegylation, phosphorylation, amidation, derivatization by known protecting/blocking groups, proteolytic cleavage, linkage to a cellular ligand or other protein, etc. In some embodiments, the polypeptide derived from *E. coli* or a fragment thereof may include a modification, such as by chemical modifications using techniques known to those of skill in the art, including, but not limited to specific chemical cleavage, acetylation, formylation, metabolic synthesis of tunicamycin, etc., as compared to a corresponding wild-type *E. coli* FimH polypeptide or fragment. In another embodiment, the modification may include a covalent attachment of a lipid molecule to the polypeptide. In some embodiments, the polypeptide does not include a covalent attachment of a molecule to the polypeptide as compared to the corresponding wild-type *E. coli* FimH polypeptide or fragment thereof.

For example, proteins and polypeptides produced in cell culture may be glycoproteins that contain covalently linked carbohydrate structures including oligosaccharide chains. These oligosaccharide chains are linked to the protein via either N-linkages or O-linkages. The oligosaccharide chains may comprise a significant portion of the mass of the glycoprotein. Generally, N-linked oligosaccharide is added to the amino group on the side chain of an asparagine residue within the target consensus sequence of Asn-X-Ser/Thr, where X may be any amino acid except proline. In some embodiments, the glycosylation site includes an amino acid sequence selected from any one of the following: asparagine-glycine-threonine (NGT), asparagine-isoleucine-threonine (NIT), asparagine-glycine-serine (NGS), asparagine-serine-threonine (NST), and asparagine-threonine-serine (NTS). The polypeptide derived from *E. coli* or a fragment thereof produced in mammalian cells may by glycosylated. The glycosylation may occur at the N-linked glycosylation signal Asn-Xaa-Ser/Thr in the sequence of the polypeptide derived from *E. coli* or a fragment thereof. "N-linked glycosylation" refers to the attachment of the carbohydrate moiety via GlcNAc to an asparagine residue in a polypeptide chain. The N-linked carbohydrate contains a common Man 1-6 (Man1-3)Manβ1-4GlcNAcβ1-4GlcNAcβ-R core structure, where R represents an asparagine residue of the produced polypeptide derived from *E. coli* or a fragment thereof.

In some embodiments, a glycosylation site in the polypeptide derived from *E. coli* or a fragment thereof is removed by a mutation within the sequence of the polypeptide derived from *E. coli* or a fragment thereof. For example, in some embodiments, the Asn residue of a glycosylation motif (Asn-Xaa-Ser/Thr) may be mutated, preferably by a substitution. In some embodiments, the residue substitution is selected from any one of Ser, Asp, Thr, and Gln.

In some embodiments, the Ser residue of a glycosylation motif may be mutated, preferably by a substitution. In some embodiments, the residue substitution is selected from any one of Asp, Thr, and Gln.

In some embodiments, the Thr residue of a glycosylation motif may be mutated, preferably by a substitution. In some embodiments, the residue substitution is selected from any one of Ser, Asp, and Gln.

In some embodiments, a glycosylation site (such as Asn-Xaa-Ser/Thr) in the polypeptide derived from *E. coli* or a fragment thereof is not removed or modified. In some embodiments, a compound to decrease or inhibit glycosylation may be added to the cell culture medium. In such embodiments, the polypeptide or protein includes at least one more unglycosylated (i.e., aglycosylated) site, that is, a completely unoccupied glycan site with no carbohydrate moiety attached thereto, or comprises at least one carbohydrate moiety less at the same potential glycosylation site than an otherwise identical polypeptide or protein which is produced by a cell under otherwise identical conditions but in the absence of a glycosylation inhibiting compound. Such compounds are known in the art and may include, but are not limited to, tunicamycin, tunicaymycin homologs, streptovirudin, mycospocidin, amphomycin, tsushimycin, antibiotic 24010, antibiotic MM 19290, bacitracin, corynetoxin, showdomycin, duimycin, 1-deoxymannonojirimycin, deoxynojirimycin, N-methyl-1-dexoymannojirimycin, brefeldin A, glucose and mannose analogs, 2-deoxy-D-glucose, 2-deoxyglucose, D-(+)-mannose, D-(+) galactose, 2-deoxy-2-fluoro-D-glucose, 1,4-dideoxy-1,4-imino-D-mannitol (DIM), fluoroglucose, fluoromannose, UDP-2-deoxyglucose, GDP-2-deoxyglucose, hydroxymethylglutaryl-CoA reductase inhibitors, 25-hydroxycholesterol, hydroxycholesterol, swainsonine, cycloheximide, puromycin, actinomycin D, monensin, m-Chlorocarbonyl-cyanide phenylhydrazone (CCCP), compactin, dolichyl-phosphoryl^-deoxyglucose, N-Acetyl-D-Glucosamine, hygoxanthine, thymidine, cholesterol, glucosamine, mannosamine, castanospermine, glutamine, bromoconduritol, conduritol epoxide and conduritol derivatives, glycosylmethyl-p-nitrophenyltriazenes, β-Hydroxynorvaline, threo-β-fluoroaspara-gine, D-(+)-Gluconic acid δ-lactone, di(2-ethyl hexyl)phosphate, tributyl phosphate, dodecyl phosphate, 2-dimethylamino ethyl ester of (diphenyl methyl)-phosphoric acid, [2-(diphenyl phosphinyloxy)ethyl]trimethyl ammonium iodide, iodoacetate, and/or fluoroacetate One of ordinary skill in the art will readily recognize or will be able to determine glycosylation-inhibiting substances that may be used in accordance with methods and compositions of the present invention without undue experimentation. In such embodiments, glycosylation of the polypeptide or fragment thereof may be controlled without the introduction of an amino acid mutation into the polypeptide or fragment thereof.

In some embodiments, the level of glycosylation (e.g., number of glycan sites that are occupied on the polypeptide or fragment thereof, the size and/or complexity of glycoform at the site, and the like) of the polypeptide or fragment thereof produced by the mammalian cell are lower than levels of glycosylation of the polypeptide or fragment thereof produced under otherwise identical conditions in an otherwise identical medium that lacks such a glycolysis-inhibiting compound and/or mutation.

In some embodiments, the sequence of a polypeptide derived from *E. coli* or a fragment thereof does not include a site of N-linked protein glycosylation. In some embodiments, the sequence of a polypeptide derived from *E. coli* or a fragment thereof does not include at least one site of N-linked protein glycosylation. In some embodiments, the sequence of a polypeptide derived from *E. coli* or a fragment thereof does not include any sites of N-linked protein glycosylation. In some embodiments, the sequence of a polypeptide derived from *E. coli* or a fragment thereof includes a site for N-linked protein glycosylation. In some embodiments, the sequence of a polypeptide derived from *E. coli* or a fragment thereof includes at most 1 site of N-linked protein glycosylation. In some embodiments, the sequence of a polypeptide derived from *E. coli* or a fragment thereof includes at most 2 sites of N-linked protein glycosylation.

A polypeptide derived from *E. coli* or a fragment thereof expressed by different cell lines or in transgenic animals may have different glycan site occupancies, glycoforms and/or glycosylation patterns compared with each other. In some embodiments, the invention encompasses a polypeptide derived from *E. coli* or a fragment thereof regardless of the glycosylation, glycan occupancy or glycoform pattern of the polypeptide derived from *E. coli* or a fragment thereof produced in a mammalian cell.

In some embodiments, the polypeptide derived from *E. coli* or a fragment thereof may be derived from an *E. coli* FimH polypeptide, wherein the amino acid residue at position 1 of the polypeptide is phenylalanine, not methionine, for example, a polypeptide having the amino acid sequence SEQ ID NO: 2. Preferably, the polypeptide derived from *E. coli* FimH comprises a phenylalanine at position 1 of the amino acid sequence of the polypeptide derived from *E. coli*. In another preferred embodiment, the polypeptide derived from *E. coli* FimH comprises the amino acid sequence SEQ ID NO: 3, preferably wherein the residue at position 1 of the amino acid sequence of the polypeptide derived from *E. coli* is phenylalanine. In some embodiments, the polypeptide derived from *E. coli* or a fragment thereof may include the amino acid sequence SEQ ID NO: 4, which may be derived from an *E. coli* FimH polypeptide.

In some embodiments, the polypeptide derived from *E. coli* or a fragment thereof includes the amino acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, or 100% identity to any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 20, SEQ ID NO: 23, SEQ ID NO: 24, SEQ ID NO: 26, SEQ ID NO: 27, SEQ ID NO: 28, SEQ ID NO: 29, SEQ ID NO: 110, SEQ ID NO: 111, SEQ ID NO: 112, and SEQ ID NO: 113. In some embodiments, the polypeptide derived from *E. coli* or a fragment thereof includes the amino acid sequence having at least 95% identity to any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 20, SEQ ID NO: 23, SEQ ID NO: 24, SEQ ID NO: 26, SEQ ID NO: 27, SEQ ID NO: 28, SEQ ID NO: 29, SEQ ID NO: 110, SEQ ID NO: 111, SEQ ID NO: 112, and SEQ ID NO: 113. In some embodiments, the polypeptide derived from *E. coli* or a fragment thereof includes the amino acid sequence having at least 99% identity to any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 20, SEQ ID NO: 23, SEQ ID NO: 24, SEQ ID NO: 26, SEQ ID NO: 27, SEQ ID NO: 28, SEQ ID NO: 29, SEQ ID NO: 110, SEQ ID NO: 111, SEQ ID NO: 112, and SEQ ID NO: 113.

In some embodiments, the polypeptide derived from *E. coli* or a fragment thereof may be derived from an *E. coli* FimG polypeptide, for example, having the amino acid sequence SEQ ID NO: 9. In some embodiments, the polypeptide derived from *E. coli* or a fragment thereof may be derived from an *E. coli* FimC polypeptide, for example, having the amino acid sequence SEQ ID NO: 10.

A. Polypeptides Derived from *E. coli* FimH and Fragments Thereof

In a preferred embodiment, the polypeptide or fragment thereof is derived from an *E. coli* FimH. In some embodiments, the polypeptide or fragment thereof includes full length *E. coli* FimH. Full length FimH includes two domains: an N-terminal lectin domain and a C-terminal pilin domain, which are connected by a short linker. In some embodiments, the full length of *E. coli* FimH includes 279 amino acids, which includes the full length of the mature protein of *E. coli* FimH. In some embodiments, the full length of *E. coli* FimH includes 300 amino acids, which includes the full length of the mature protein of *E. coli* FimH and a signal peptide sequence having 21 amino acids in length. The primary structure of the 300 amino acid-long wild type FimH is highly conserved across *E. coli* strains.

An exemplary sequence for a full-length *E. coli* FimH is SEQ ID NO: 1. The full length FimH sequence includes a sequence for a lectin domain and a sequence for a pilin domain. The lectin domain of FimH contains the carbohydrate recognition domain, which is responsible for binding to the mannosylated uroplakin 1a on the urothelial cell surface. The pilin domain is anchored to the core of the pilus via a donor strand of the subsequent FimG subunit, which is a process termed donor strand complementation.

Starting from the N-terminus, the names and in parenthesis the exemplary amino acid sequences of each domain of a full length FimH are as follows: FimH lectin (SEQ ID NO: 2) and FimH pilin (SEQ ID NO: 3).

Other suitable polypeptides and fragments thereof derived from *E. coli* FimH include variants that have various degrees of identity to any one of SEQ ID NO: 1, SEQ ID NO: 2, SEQ ID NO: 3, SEQ ID NO: 4, SEQ ID NO: 20, SEQ ID NO: 23, SEQ ID NO: 24, SEQ ID NO: 26, SEQ ID NO: 28, SEQ ID NO: 29, SEQ ID NO: 110, SEQ ID NO: 111, SEQ ID NO: 112 and SEQ ID NO: 113, such as at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to any one of SEQ ID NO: 1, SEQ ID NO: 2, SEQ ID NO: 3, SEQ ID NO: 4, SEQ ID NO: 20, SEQ ID NO: 23, SEQ ID NO: 24, SEQ ID NO: 26, SEQ ID NO: 28, SEQ ID NO: 29, SEQ ID NO: 110, SEQ ID NO: 111, SEQ ID NO: 112 and SEQ ID NO: 113. Other suitable polypeptides have least 95% identity to any one of SEQ ID NO: 1, SEQ ID NO: 2, SEQ ID NO: 3, SEQ ID NO: 4, SEQ ID NO: 20, SEQ ID NO: 23, SEQ ID NO: 24, SEQ ID NO: 26, SEQ ID NO: 28, SEQ ID NO: 29, SEQ ID NO: 110, SEQ ID NO: 111, SEQ ID NO: 112 and SEQ ID NO: 113. Other suitable polypeptides have least 99% identity to any one of SEQ ID NO: 1, SEQ ID NO: 2, SEQ ID NO: 3, SEQ ID NO: 4, SEQ ID NO: 20, SEQ ID NO: 23, SEQ ID NO: 24, SEQ ID NO: 26, SEQ ID NO: 28, SEQ ID NO: 29, SEQ ID NO: 110, SEQ ID NO: 111, SEQ ID NO: 112 and SEQ ID NO: 113. In certain embodiments, the FimH variant proteins: (i) form part of the FimH-FimC; (ii) comprise at least one epitope from SEQ ID NO: 1, SEQ ID NO: 2, SEQ ID NO: 3, SEQ ID NO: 4, SEQ ID NO: 20, SEQ ID NO: 23, SEQ ID NO: 24, SEQ ID NO: 26, SEQ ID NO: 28, SEQ ID NO: 29, SEQ ID NO: 110, SEQ ID NO: 111, SEQ ID NO: 112 and SEQ ID NO: 113; and/or (iii) may elicit antibodies in vivo which immunologically cross react with an *E. coli* FimH.

In some embodiments, the composition includes a polypeptide having at least n consecutive amino acids from any one of SEQ ID NO: 1, SEQ ID NO: 2, SEQ ID NO: 3, SEQ ID NO: 4, SEQ ID NO: 20, SEQ ID NO: 23, SEQ ID NO: 24, SEQ ID NO: 26, SEQ ID NO: 28, SEQ ID NO: 29, SEQ ID NO: 110, SEQ ID NO: 111, SEQ ID NO: 112 and SEQ ID NO: 113, wherein n is 7 or more (eg. 8, 10, 12, 14, 16, 18, 20 or more). Preferably the fragments include an epitope from the sequence. In some embodiments, composition includes a polypeptide having at least 50 consecutive amino acid residues, at least 100 consecutive amino acid residues, at least 125 consecutive amino acid residues, at least 150 consecutive amino acid residues, at least 175 consecutive amino acid residues, at least 200 consecutive amino acid residues, or at least 250 consecutive amino acid residues of the amino acid sequence of any one of SEQ ID NO: 1, SEQ ID NO: 2, SEQ ID NO: 3, SEQ ID NO: 4, SEQ ID NO: 20, SEQ ID NO: 23, SEQ ID NO: 24, SEQ ID NO: 26, SEQ ID NO: 28, SEQ ID NO: 29, SEQ ID NO: 110, SEQ ID NO: 111, SEQ ID NO: 112 and SEQ ID NO: 113. In some embodiments, composition includes a polypeptide having at least 50 consecutive amino acid residues of any one of SEQ ID NO: 1, SEQ ID NO: 2, SEQ ID NO: 3, SEQ ID NO: 4, SEQ ID NO: 20, SEQ ID NO: 23, SEQ ID NO: 24, SEQ ID NO: 26, SEQ ID NO: 28, SEQ ID NO: 29, SEQ ID NO: 110, SEQ ID NO: 111, SEQ ID NO: 112 and SEQ ID NO: 113. In some embodiments, composition includes a polypeptide having at least 100 consecutive amino acid residues of any one of SEQ ID NO: 1, SEQ ID NO: 2, SEQ ID NO: 3, SEQ ID NO: 4, SEQ ID NO: 20, SEQ ID NO: 23, SEQ ID NO: 24, SEQ ID NO: 26, SEQ ID NO: 28, SEQ ID NO: 29, SEQ ID NO: 110, SEQ ID NO: 111, SEQ ID NO: 112 and SEQ ID NO: 113. In some embodiments, composition includes a polypeptide having at least 200 consecutive amino acid residues of any one of SEQ ID NO: 1, SEQ ID NO: 2, SEQ ID NO: 3, SEQ ID NO: 4, SEQ ID NO: 20, SEQ ID NO: 23, SEQ ID NO: 24, SEQ ID NO: 26, SEQ ID NO: 28, SEQ ID NO: 29, SEQ ID NO: 110, SEQ ID NO: 111, SEQ ID NO: 112 and SEQ ID NO: 113. In some embodiments, composition includes a polypeptide having at least 250 consecutive amino acid residues of the amino acid sequence of any one of SEQ ID NO: 1, SEQ ID NO: 2, SEQ ID NO: 3, SEQ ID NO: 4, SEQ ID NO: 20, SEQ ID NO: 23, SEQ ID NO: 24, SEQ ID NO: 26, SEQ ID NO: 28, SEQ ID NO: 29, SEQ ID NO: 110, SEQ ID NO: 111, SEQ ID NO: 112 and SEQ ID NO: 113.

In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 1. In some embodiments, the composition includes a polypeptide having at least 90% identity to SEQ ID NO: 1. In some embodiments, the composition includes a polypeptide having at least 95% identity to SEQ ID NO: 1. In some embodiments, the composition includes a polypeptide having at least 99% identity to SEQ ID NO: 1. In some embodiments, the composition includes a polypeptide as set forth at SEQ ID NO: 1. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 2. In some embodiments, the composition includes a polypeptide having at least 90% identity to SEQ ID NO: 2. In some embodiments, the composition includes a polypeptide having at least 95% identity to SEQ ID NO: 2. In some embodiments, the composition includes a polypeptide having at least 99% identity to SEQ ID NO: 2. In some embodiments, the composition includes a polypeptide as set forth at SEQ ID NO: 2. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 3. In some embodiments, the composition includes a polypeptide having at least 90% identity to SEQ ID NO: 3. In some embodiments, the composition includes a polypeptide having at least 95% identity to SEQ ID NO: 3. In some embodiments, the composition includes a polypeptide having at least 99% identity to SEQ ID NO: 3. In some embodiments, the composition includes a polypeptide as set forth at SEQ ID NO: 3. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 4. In some embodiments, the composition includes a polypeptide having at least 90% identity to SEQ ID NO: 4. In some embodiments, the composition includes a polypeptide having at least 95% identity to SEQ ID NO: 4. In some embodiments, the composition includes a polypeptide having at least 99% identity to SEQ ID NO: 4. In some embodiments, the composition includes a polypeptide as set forth at SEQ ID NO: 4. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 5. In some embodiments, the composition includes a polypeptide having at least 90% identity to SEQ ID NO: 5. In some embodiments, the composition includes a polypeptide having at least 95% identity to SEQ ID NO: 5. In some embodiments, the composition includes a polypeptide having at least 99% identity to SEQ ID NO: 5. In some embodiments, the composition includes a polypeptide as set forth at SEQ ID NO: 5. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 6. In some embodiments, the composition includes a polypeptide having at least 90% identity to SEQ ID NO: 6. In some embodiments, the composition includes a polypeptide having at least 95% identity to SEQ ID NO: 6. In some embodiments, the composition includes a polypeptide having at least 99% identity to SEQ ID NO: 6. In some embodiments, the composition includes a polypeptide as set forth at SEQ ID NO: 6. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 20. In some embodiments, the composition includes a polypeptide having at least 90% identity to SEQ ID NO: 20. In some embodiments, the composition includes a polypeptide having at least 95% identity to SEQ ID NO: 20. In some embodiments, the composition includes a polypeptide having at least 99% identity to SEQ ID NO: 20. In some embodiments, the composition includes a polypeptide as set forth at SEQ ID NO: 20. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 23. In some embodiments, the composition includes a polypeptide having at least 90% identity to SEQ ID NO: 23. In some embodiments, the composition includes a polypeptide having at least 95% identity to SEQ ID NO: 23. In some embodiments, the composition includes a polypeptide having at least 99% identity to SEQ ID NO: 23. In some embodiments, the composition includes a polypeptide as set forth at SEQ ID NO: 23. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 24. In some embodiments, the composition includes a polypeptide having at least 90% identity to SEQ ID NO: 24. In some embodiments, the composition includes a polypeptide having at least 95% identity to SEQ ID NO: 24. In some embodiments, the composition includes a polypeptide having at least 99% identity to SEQ ID NO: 24. In some embodiments, the composition includes a polypeptide as set forth at SEQ ID NO: 24. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 26. In some embodiments, the composition includes a polypeptide having at least 90% identity to SEQ ID NO: 26. In some embodiments, the composition includes a polypeptide having at least 95% identity to SEQ ID NO: 26. In some embodiments, the composition includes a polypeptide having at least 99% identity to SEQ ID NO: 26. In some embodiments, the composition includes a polypeptide as set forth at SEQ ID NO: 26. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 27. In some embodiments, the composition includes a polypeptide having at least 90% identity to SEQ ID NO: 27. In some embodiments, the composition includes a polypeptide having at least 95% identity to SEQ ID NO: 27. In some embodiments, the composition includes a polypeptide having at least 99% identity to SEQ ID NO: 27. In some embodiments, the composition includes a polypeptide as set forth at SEQ ID NO: 27. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 28. In some embodiments, the composition includes a polypeptide having at least 90% identity to SEQ ID NO: 28. In some embodiments, the composition includes a polypeptide having at least 95% identity to SEQ ID NO: 28. In some embodiments, the composition includes a polypeptide having at least 99% identity to SEQ ID NO: 28. In some embodiments, the composition includes a polypeptide as set forth at SEQ ID NO: 28. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 29. In some embodiments, the composition includes a polypeptide having at least 90% identity to SEQ ID NO: 29. In some embodiments, the composition includes a polypeptide having at least 95% identity to SEQ ID NO: 29. In some embodiments, the composition includes a polypeptide having at least 99% identity to SEQ ID NO: 29. In some embodiments, the composition includes a polypeptide as set forth at SEQ ID NO: 29. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 110. In some embodiments, the composition includes a polypeptide having at least 90% identity to SEQ ID NO: 110. In some embodiments, the composition includes a polypeptide having at least 95% identity to SEQ ID NO: 110. In some embodiments, the composition includes a polypeptide having at least 99% identity to SEQ ID NO: 110. In some embodiments, the composition includes a polypeptide as set forth at SEQ ID NO: 110. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 111. In some embodiments, the composition includes a polypeptide having at least 90% identity to SEQ ID NO: 111. In some embodiments, the composition includes a polypeptide having at least 95% identity to SEQ ID NO: 111. In some embodiments, the composition includes a polypeptide having at least 99% identity to SEQ ID NO: 111. In some embodiments, the composition includes a polypeptide as set forth at SEQ ID NO: 111. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 112. In some embodiments, the composition includes a polypeptide having at least 90% identity to SEQ ID NO: 112. In some embodiments, the composition includes a polypeptide having at least 95% identity to SEQ ID NO: 112. In some embodiments, the composition includes a polypeptide having at least 99% identity to SEQ ID NO: 112. In some embodiments, the composition includes a polypeptide as set forth at SEQ ID NO: 112. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 113. In some embodiments, the composition includes a polypeptide having at least 90% identity to SEQ ID NO: 113. In some embodiments, the composition includes a polypeptide having at least 95% identity to SEQ ID NO: 113. In some embodiments, the composition includes a polypeptide having at least 99% identity to SEQ ID NO: 113. In some embodiments, the composition includes a polypeptide as set forth at SEQ ID NO: 113.

Another example of a suitable polypeptide and fragments thereof derived from *E. coli* FimH described herein is shown as SEQ ID NO: 2, which lacks the wild-type N-terminal signal sequence, and corresponds to amino acid residues 22-300 of SEQ ID NO: 1. Another example of a FimH fragment includes the entire N-terminal signal sequence and the mature protein, such as set forth in SEQ ID NO: 1.

In some embodiments, a glycosylation site in the polypeptide derived from *E. coli* or a fragment thereof is removed by a mutation within the sequence of the polypeptide derived from *E. coli* or a fragment thereof. For example, in some embodiments, the Asn residue at position 7 of a mature *E. coli* FimH polypeptide (e.g., according to the numbering of SEQ ID NO: 2) may be mutated, preferably by a substitution. In some embodiments, the Asn residue at position 7 of a lectin domain of an *E. coli* FimH polypeptide (e.g., according to the numbering of SEQ ID NO: 3) may be mutated, preferably by a substitution. In some embodiments, the residue substitution is selected from any one of Ser, Asp, Thr, and Gln.

In some embodiments, the Thr residue at position 10 of a mature *E. coli* FimH polypeptide (e.g., according to the numbering of SEQ ID NO: 2) may be mutated, preferably by a substitution. In some embodiments, the Thr residue at position 7 of a lectin domain of an *E. coli* FimH polypeptide (e.g., according to the numbering of SEQ ID NO: 3) may be mutated, preferably by a substitution. In some embodiments, the residue substitution is selected from any one of Ser, Asp, and Gln.

In some embodiments, the Asn residue at position N235 of a mature *E. coli* FimH polypeptide (e.g., according to the numbering of SEQ ID NO: 2) may be mutated, preferably by a substitution. In some embodiments, the Asn residue at position N228 of a mature *E. coli* FimH polypeptide (e.g., according to the numbering of SEQ ID NO: 2) may be mutated, preferably by a substitution. In some embodiments, the residue substitution is selected from any one of Ser, Asp, Thr, and Gln.

In some embodiments, the Asn residue at position 70 of a mature *E. coli* FimH polypeptide (e.g., according to the numbering of SEQ ID NO: 2) may be mutated, preferably by a substitution. In some embodiments, the Asn residue at position 70 of a lectin domain of an *E. coli* FimH polypeptide (e.g., according to the numbering of SEQ ID NO: 3) may be mutated, preferably by a substitution. In some embodiments, the residue substitution is selected from any one of Ser, Asp, Thr, and Gln.

In some embodiments, the Ser residue at position 72 of a mature *E. coli* FimH polypeptide (e.g., according to the numbering of SEQ ID NO: 2) may be mutated, preferably by a substitution. In some embodiments, the Ser residue at position 72 of a lectin domain of an *E. coli* FimH polypeptide (e.g., according to the numbering of SEQ ID NO: 3) may be mutated, preferably by a substitution. In some embodiments, the residue substitution is selected from any one of Asp, Thr, and Gln.

By the term "fragment" as used herein refers to a polypeptide and is defined as any discrete portion of a given polypeptide that is unique to or characteristic of that polypeptide. The term as used herein also refers to any discrete portion of a given polypeptide that retains at least a fraction of the activity of the full-length polypeptide. In certain embodiments, the fraction of activity retained is at least 10% of the activity of the full-length polypeptide. In certain embodiments, the fraction of activity retained is at least 20%, 30%, 40%, 50%, 60%, 70%, 80% or 90% of the activity of the full-length polypeptide. In certain embodiments, the fraction of activity retained is at least 95%, 96%, 97%, 98% or 99% of the activity of the full-length polypeptide. In certain embodiments, the fraction of activity retained is 100% or more of the activity of the full-length polypeptide. In some embodiments, a fragment includes at least 5, 10, 15, 20, 25, 30, 35, 40, 45, 50, 55, 60, 65, 70, 75, 80, 85, 90, 95, 100 or more consecutive amino acids of the full-length polypeptide.

B. Complex of FimH, FimC, and Fragments Thereof.

In some embodiments, the polypeptide derived from *E. coli* FimH or fragment thereof is present in a complex with polypeptide derived from *E. coli* FimC or fragment thereof. In a preferred embodiment, the polypeptide derived from *E. coli* FimH or fragment thereof and the polypeptide derived from *E. coli* FimC or fragment thereof are present in a complex, preferably in a 1:1 ratio in the complex. Without being bound by theory or mechanism, the full length FimH may be stabilized in an active conformation by the periplasmic chaperone FimC, thereby making it possible to purify full-length FimH protein. Accordingly, in some embodiments, the polypeptide or fragment thereof includes full length FimH and full length FimC.

In some embodiments, the polypeptide or fragment thereof includes a fragment of FimH and a fragment of FimC. In some embodiments, the polypeptide or fragment thereof includes full length FimH and a fragment of FimC. An exemplary sequence for *E. coli* FimC is set forth in SEQ ID NO: 10. In some embodiments, the polypeptide derived from *E. coli* or a fragment thereof includes complex-forming fragments of FimH.

A complex-forming fragment of FimH may be any part or portion of the FimH protein that retain the ability to form a complex with FimC or a fragment thereof. A suitable complex-forming fragment of FimH may also be obtained or determined by standard assays known in the art, such as co-immunoprecipitation assay, cross-linking, or co-localization by fluorescent staining, etc. SDS-PAGE or western blot may also be used (e.g., by showing that the FimH fragment and FimC or fragment thereof are in a complex as evidenced by gel electrophoresis). In certain embodiments, the complex-forming fragment of FimH (i) forms part of the FimH-FimC complex; (ii) comprises at least one epitope from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 10, SEQ ID NO: 20, SEQ ID NO: 23, SEQ ID NO: 24, SEQ ID NO: 26, SEQ ID NO: 27, SEQ ID NO: 28, SEQ ID NO: 29, SEQ ID NO: 110, and SEQ ID NO: 111; and/or (iii) may elicit antibodies in vivo which immunologically cross react with an *E. coli* FimH.

In some embodiments, the polypeptide derived from *E. coli* or a fragment thereof includes full length FimH, wherein the FimH is not complexed with FimC. In further embodiments, the polypeptide or fragment thereof includes a fragment of FimH, wherein the fragment is not complexed with FimC. In some embodiments, the polypeptide derived from *E. coli* or a fragment thereof FimC includes SEQ ID NO: 10. In some embodiments, the complex may be expressed from the same plasmid, preferably under the control of separate promoters for each polypeptide or fragment thereof.

In some embodiments, the polypeptide derived from *E. coli* FimH or a fragment thereof binds to a polypeptide derived from *E. coli* FimC or a fragment thereof, which may be engineered into the structure of the polypeptide derived from *E. coli* FimH or fragment thereof. The portion of the FimC molecule that binds to the FimH in the complex is called a "donor strand" and the mechanism of formation of the native FimH structure using the strand from FimC that binds to FimH in the FimCH complex is known as "donor strand complementation."

In some embodiments, the polypeptide derived from *E. coli* FimH or a fragment thereof may be expressed by the appropriate donor strand complemented version of FimH, wherein the amino acid sequence of FimC that interacts with FimH in the FimCH complex is itself engineered at the C-terminal end of FimH to provide the native conformation without the need for the remainder of the FimC molecule to be present. In some embodiments, the polypeptide derived from *E. coli* FimH or a fragment thereof may be expressed in the form of a complex that includes isolated domains thereof, such as the lectin binding domain and the piling domain, and such domains may be linked together covalently or non-covalently. For example, in some embodiments, the linking segment may include amino acid sequences or other oligomeric structures, including simple polymer structures.

The methods and compositions of the invention may include complexes described herein, in which said polypeptides or fragments thereof derived from *E. coli* are co-expressed or formed in a combined state.

C. Lectin Domain, Pilin Domain, and Variants Thereof

Conformation and ligand-binding properties of the lectin domain of FimH may be under the allosteric control of the pilin domain of FimH. Under static conditions, the interaction of the two domains of full length FimH stabilizes the lectin domain in a low-affinity to monomannose state (for example, $K_d$~300 µM), which is characterized by a shallow binding pocket. Binding to a mannoside ligand may induce a conformational change leading to a medium affinity state, in which the lectin and pilin domains remain in close contact. However, upon shear stress, the lectin and pilin domains may separate and induce the high-affinity state (for example, $K_d$<1.2 µM).

Because of the absence of negative allosteric regulation exerted by the pilin domain, isolated lectin domain of FimH is locked in the high-affinity state (for example, $K_d$<1.2 µM). The isolated, recombinant lectin domain, which is locked in the high-affinity state. Locking the adhesin in a low-affinity conformation (for example, $K_d$~300 µM), however, induces the production of adhesion-inhibiting antibodies. Accordingly, there is an interest in stabilizing the lectin domain in the low-affinity state.

In some embodiments, the polypeptide derived from *E. coli* or a fragment thereof includes the lectin domain of an *E. coli* FimH. Exemplary sequences for a lectin domain include any one of SEQ ID NO: 3, SEQ ID NO: 7, SEQ ID NO: 8, SEQ ID NO: 24, SEQ ID NO: 26, SEQ ID NO: 110, and SEQ ID NO: 111. In some embodiments, the lectin domain of an *E. coli* FimH includes cysteine substitutions. In a preferred embodiment, the lectin domain of an *E. coli* FimH includes cysteine substitutions within the first 50 amino acid residues of the lectin domain. In some embodiments, the lectin domain may include 1, 2, 3, 4, 5, 6, 7, 8, 9, or 10 cysteine substitutions. Preferably, the lectin domain includes 2 cysteine substitutions. See, for example, pSB02158 and pSB02198.

Other suitable polypeptides and fragments thereof derived from *E. coli* FimH include FimH lectin domain variants that have various degrees of identity to SEQ ID NO: 3, such as at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to the sequence recited in SEQ ID NO: 3. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 3. In some embodiments, the composition includes a polypeptide having at least 90% identity to SEQ ID NO: 3. In some embodiments, the composition includes a polypeptide having at least 95% identity to SEQ ID NO: 3. In some embodiments, the composition includes a polypeptide having at least 99% identity to SEQ ID NO: 3. In some embodiments, the composition includes a polypeptide as set forth at SEQ ID NO: 3. In some embodiments, the polypeptide derived from *E. coli* or a fragment thereof includes the pilin domain of an *E. coli* FimH. Other suitable polypeptides and fragments thereof derived from *E. coli* FimH include FimH pilin domain variants that have various degrees of identity to SEQ ID NO: 7, such as at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to the sequence recited in SEQ ID NO: 7. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 7. In some embodiments, the composition includes a polypeptide having at least 90% identity to SEQ ID NO: 7. In some embodiments, the composition includes a polypeptide having at least 95% identity to SEQ ID NO: 7. In some embodiments, the composition includes a polypeptide having at least 99% identity to SEQ ID NO: 7. In some embodiments, the composition includes a polypeptide as set forth at SEQ ID NO: 7. Other suitable polypeptides and fragments thereof derived from *E. coli* FimH include FimH lectin domain variants that have various degrees of identity to SEQ ID NO: 8, such as at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to the sequence recited in SEQ ID NO: 8. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 8. In some embodiments, the composition includes a polypeptide having at least 90% identity to SEQ ID NO: 8. In some embodiments, the composition includes a polypeptide having at least 95% identity to SEQ ID NO: 8. In some embodiments, the composition includes a polypeptide having at least 99% identity to SEQ ID NO: 8. In some embodiments, the composition includes a polypeptide as set forth at SEQ ID NO: 8. In some embodiments, the polypeptide derived from *E. coli* or a fragment thereof includes the pilin domain of an *E. coli* FimH. Other suitable polypeptides and fragments thereof derived from *E. coli* FimH include FimH pilin domain variants that have various degrees of identity to SEQ ID NO: 24, such as at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to the sequence recited in SEQ ID NO: 24. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 24. In some embodiments, the composition includes a polypeptide having at least 90% identity to SEQ ID NO: 24. In some embodiments, the composition includes a polypeptide having at least 95% identity to SEQ ID NO: 24. In some embodiments, the composition includes a polypeptide having at least 99% identity to SEQ ID NO: 24. In some embodiments, the composition includes a polypeptide as set forth at SEQ ID NO: 24. Other suitable polypeptides and fragments thereof derived from E. coli FimH include FimH lectin domain variants that have various degrees of identity to SEQ ID NO: 26, such as at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to the sequence recited in SEQ ID NO: 26. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 26. In some embodiments, the composition includes a polypeptide having at least 90% identity to SEQ ID NO: 26. In some embodiments, the composition includes a polypeptide having at least 95% identity to SEQ ID NO: 26. In some embodiments, the composition includes a polypeptide having at least 99% identity to SEQ ID NO: 26. In some embodiments, the composition includes a polypeptide as set forth at SEQ ID NO: 26. Other suitable polypeptides and fragments thereof derived from E. coli FimH include FimH lectin domain variants that have various degrees of identity to SEQ ID NO: 110, such as at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to the sequence recited in SEQ ID NO: 110. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 110. In some embodiments, the composition includes a polypeptide having at least 90% identity to SEQ ID NO: 110. In some embodiments, the composition includes a polypeptide having at least 95% identity to SEQ ID NO: 110. In some embodiments, the composition includes a polypeptide having at least 99% identity to SEQ ID NO: 110. In some embodiments, the composition includes a polypeptide as set forth at SEQ ID NO: 110. Other suitable polypeptides and fragments thereof derived from E. coli FimH include FimH lectin domain variants that have various degrees of identity to SEQ ID NO: 111, such as at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to the sequence recited in SEQ ID NO: 111. In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to SEQ ID NO: 111. In some embodiments, the composition includes a polypeptide having at least 90% identity to SEQ ID NO: 111. In some embodiments, the composition includes a polypeptide having at least 95% identity to SEQ ID NO: 111. In some embodiments, the composition includes a polypeptide having at least 99% identity to SEQ ID NO: 111. In some embodiments, the composition includes a polypeptide as set forth at SEQ ID NO: 111.

In some embodiments, the composition includes a polypeptide having at least n consecutive amino acids from any one of SEQ ID NO: 3, SEQ ID NO: 7, SEQ ID NO: 8, SEQ ID NO: 24, SEQ ID NO: 26, SEQ ID NO: 110, and SEQ ID NO: 111, wherein n is 7 or more (eg. 8, 10, 12, 14, 16, 18, 20 or more). Preferably the fragments include an epitope from the sequence. In some embodiments, the composition includes a polypeptide having at least 50 consecutive amino acid residues, at least 100 consecutive amino acid residues, at least 125 consecutive amino acid residues, at least 150 consecutive amino acid residues, at least 175 consecutive amino acid residues, at least 200 consecutive amino acid residues, or at least 250 consecutive amino acid residues of the amino acid sequence of any one of SEQ ID NO: 3, SEQ ID NO: 7, SEQ ID NO: 8, SEQ ID NO: 24, SEQ ID NO: 26, SEQ ID NO: 110, and SEQ ID NO: 111. In some embodiments, the composition includes a polypeptide having at least 50 consecutive amino acid residues of any one of SEQ ID NO: 3, SEQ ID NO: 7, SEQ ID NO: 8, SEQ ID NO: 24, SEQ ID NO: 26, SEQ ID NO: 110, and SEQ ID NO: 111. In some embodiments, the composition includes a polypeptide having at least 100 consecutive amino acid residues of any one of SEQ ID NO: 3, SEQ ID NO: 7, SEQ ID NO: 8, SEQ ID NO: 24, SEQ ID NO: 26, SEQ ID NO: 110, and SEQ ID NO: 111. In some embodiments, the composition includes a polypeptide having at least 150 consecutive amino acid residues of any one of SEQ ID NO: 3, SEQ ID NO: 7, SEQ ID NO: 8, SEQ ID NO: 24, SEQ ID NO: 26, SEQ ID NO: 110, and SEQ ID NO: 111. In some embodiments, the composition includes a polypeptide having at least 250 consecutive amino acid residues of the amino acid sequence of any one of SEQ ID NO: 3, SEQ ID NO: 7, SEQ ID NO: 8, SEQ ID NO: 24, SEQ ID NO: 26, SEQ ID NO: 110, and SEQ ID NO: 111.

The location and length of a lectin domain of E. coli FimH or a homologue or a variant thereof may be predicted based on pairwise alignment of its sequence to any one of SEQ ID NO: 3, SEQ ID NO: 7, SEQ ID NO: 8, SEQ ID NO: 24, SEQ ID NO: 26, SEQ ID NO: 110, and SEQ ID NO: 111, for example by aligning the amino acid sequence of a FimH to SEQ ID NO: 1, and identifying the sequence that aligns to residues 22-179 of SEQ ID NO: 1.

D. Wild-Type N-Terminal Signal Sequence

In some embodiments, the N-terminal wild type signal sequence of full-length FimH is cleaved in a host cell to produce a mature FimH polypeptide. As such, the FimH expressed by the host cell may lack the N-terminal signal sequence. In preferred embodiments, the polypeptide derived from E. coli or a fragment thereof may be encoded by a nucleotide sequence that lacks the coding sequence for the wild type N-terminal signal sequence.

In some embodiments, the polypeptide derived from E. coli or a fragment thereof includes the FimH-FimC complex forming fragments of FimH, the N-terminal signal sequence (such as, residues 1-21 of SEQ ID NO: 1), or a combination thereof. A complex-forming fragment of FimH may be any part or portion of the FimH protein that retains the ability to form a complex with FimC.

In some embodiments, the polypeptide derived from E. coli or a fragment thereof may lack between 1 and 21 amino acid residues (e.g. 1, 2, 3, 4, 5, 6, 7, 8, 9, 10, 11, 12, 13, 14, 15, 16, 17, 18, 19, 20, or 21 amino acid residues, or lack 1-21 residues, 1-20 residues, 1-15 residues, 1-10 residues, 2-20 residues, 2-15 residues, 2-10 residues, 5-20 residues, 5-15 residues, or 5-10 residues) at the N-terminus and/or C-terminus of the full-length FimH polypeptide, which may include the signal sequence, lectin domain, and pilin domain. In some embodiments, the polypeptide derived from E. coli or a fragment thereof lacks 1-21 residues at the N-terminus of the full-length FimH polypeptide. In some embodiments, the polypeptide derived from *E. coli* or a fragment thereof lacks 1-10 residues at the N-terminus of the full-length FimH polypeptide. In some embodiments, the polypeptide derived from *E. coli* or a fragment thereof lacks 5-15 residues at the N-terminus of the full-length FimH polypeptide. In some embodiments, the polypeptide derived from *E. coli* or a fragment thereof lacks 5-10 residues at the N-terminus of the full-length FimH polypeptide. In some embodiments, the polypeptide derived from *E. coli* or a fragment thereof lacks 1-21 residues at the C-terminus of the full-length FimH polypeptide. In some embodiments, the polypeptide derived from *E. coli* or a fragment thereof lacks 1-10 residues at the C-terminus of the full-length FimH polypeptide. In some embodiments, the polypeptide derived from *E. coli* or a fragment thereof lacks 5-15 residues at the C-terminus of the full-length FimH polypeptide. In some embodiments, the polypeptide derived from *E. coli* or a fragment thereof lacks 5-10 residues at the C-terminus of the full-length FimH polypeptide.

II. Nucleic Acids

In one aspect, nucleic acids encoding the polypeptide derived from *E. coli* or a fragment thereof are disclosed. One or more nucleic acid constructs encoding the polypeptide derived from *E. coli* or a fragment thereof may be used for genomic integration and subsequent expression of the polypeptide derived from *E. coli* or a fragment thereof. For example, a single nucleic acid construct encoding the polypeptide derived from *E. coli* or fragment thereof may be introduced to a host cell. Alternatively, the coding sequences for the polypeptide derived from *E. coli* or a fragment thereof may be carried by two or more nucleic acid constructs, which are then introduced into host cell simultaneously or sequentially.

For example, in one exemplary embodiment, a single nucleic acid construct encodes the lectin domain and pilin domain of an *E. coli* FimH. In another exemplary embodiment, one nucleic acid construct encodes the lectin domain and a second nucleic acid construct encodes the pilin domain of an *E. coli* FimH. In some embodiments, genomic integration is achieved.

The nucleic acid construct may comprise genomic DNA that comprises one or more introns, or cDNA. Some genes are expressed more efficiently when introns are present. In some embodiments, the nucleic acid sequence is suitable for the expression of exogenous polypeptides in said mammalian cell.

In some embodiments, the nucleic acid encoding the polypeptide or fragment thereof is codon optimized to increase the level of expression in any particular cell.

In some embodiments, the nucleic acid construct includes a signal sequence that encodes a peptide that directs secretion of the polypeptide derived from *E. coli* or a fragment thereof. In some embodiments, the nucleic acid includes the native signal sequence of the polypeptide derived from *E. coli* FimH. In some embodiments where the polypeptide derived from *E. coli* or a fragment thereof includes an endogenous signal sequence, the nucleic acid sequence encoding the signal sequence may be codon optimized to increase the level of expression of the protein in a host cell.

In some embodiments, the signal sequence is any one of the following lengths: 15, 16, 17, 18, 19, 20, 21, 22, 23, 24, 25, 26, 27, 28, 29, and 30 amino acids long. In some embodiments, the signal sequence is 20 amino acids long. In some embodiments, the signal sequence is 21 amino acids long.

In some embodiments, where the polypeptide or fragment thereof includes a signal sequence, the endogenous signal sequence naturally associated with the polypeptide may be replaced with a signal sequence not associated with the wild type polypeptide to improve the level of expression of the polypeptide or fragment thereof in cultured cells. Accordingly, in some embodiments, the nucleic acid does not include the native signal sequence of the polypeptide derived from *E. coli* or a fragment thereof. In some embodiments, the nucleic acid does not include the native signal sequence of the polypeptide derived from *E. coli* FimH. In some embodiments, the polypeptide derived from *E. coli* or a fragment thereof may be expressed with a heterologous peptide, which is preferably a signal sequence or other peptide having a specific cleavage site at the N-terminus of the mature protein or polypeptide derived from *E. coli* or a fragment thereof. For example, the polypeptide derived from *E. coli* FimH or a fragment thereof may be expressed with a heterologous peptide (e.g., IgK signal sequence), which is preferably a signal sequence or other peptide having a specific cleavage site at the N-terminus of the mature *E. coli* FimH protein. In preferred embodiments, the specific cleavage site at the N-terminus of the mature protein *E. coli* FimH occurs immediately before the initial phenylalanine residue of the mature *E. coli* FimH protein. The heterologous sequence selected is preferably one that is recognized and processed (i.e., cleaved by signal peptidase) by the host cell.

In preferred embodiments, the signal sequence is an IgK signal sequence. In some embodiments, the nucleic acid encodes the amino acid sequence SEQ ID NO: 18. In some embodiments, the nucleic acid encodes the amino acid sequence SEQ ID NO: 19. In some embodiments, the nucleic acid encodes the amino acid sequence SEQ ID NO: 22. In preferred embodiments, the signal sequence is a mouse IgK signal sequence.

Suitable mammalian expression vectors for producing the polypeptide derived from *E. coli* or fragments thereof are known in the art and may be commercially available, such as pSecTag2 expression vector from Invitrogen™. An exemplary mouse Ig Kappa signal peptide sequence includes the sequence ETDTLLLWVLLLWVPGSTG (SEQ ID NO: 54). In some embodiments, the vector includes pBudCE4.1 mammalian expression vector from Thermo Fisher. Additional exemplary and suitable vectors include the pcDNA™3.1 mammalian expression vector (Thermo Fisher).

In some embodiments, the signal sequence does not include a hemagglutinin signal sequence.

In some embodiments, the nucleic acid includes the native signal sequence of the polypeptide derived from *E. coli* or a fragment thereof. In some embodiments, the signal sequence is not an IgK signal sequence. In some embodiments, the signal sequence includes a hemagglutinin signal sequence.

In one aspect, disclosed herein are vectors that include the coding sequences for the polypeptide derived from *E. coli* or a fragment thereof. Exemplary vectors include plasmids that are able to replicate autonomously or to be replicated in a mammalian cell. Typical expression vectors contain suitable promoters, enhancers, and terminators that are useful for regulation of the expression of the coding sequence(s) in the expression construct. The vectors may also include selection markers to provide a phenotypic trait for selection of transformed host cells (such as conferring resistance to antibiotics such as ampicillin or neomycin).

Suitable promoters are known in the art. Exemplary promoters include, e.g., CMV promoter, adenovirus, EF1 a, GAPDH metallothionine promoter, SV-40 early promoter, SV-40 later promoter, murine mammary tumor virus promoter, Rous sarcoma virus promoter, polyhedrin promoter, etc. Promoters may be constitutive or inducible. One or more vectors may be used (e.g., one vector encoding all subunits or domains or fragments thereof, or multiple vectors together encoding the subunits or domains or fragments thereof).

Internal ribosome entry site (IRES) and 2A peptide sequences may also be used. IRES and 2A peptide provides alternative approaches for co-expression of multiple sequences. IRES is a nucleotide sequence that allows for translation initiation in the middle of a messenger RNA (mRNA) sequence as part of the greater process of protein synthesis. Usually, in eukaryotes, translation may be initiated only at the 5' end of the mRNA molecule. IRES elements allow expression of multiple genes in one transcript. IRES-based polycistronic vectors, which express multiple proteins from one transcript, may reduce the escape of non-expressing clones from selection. The 2A peptide allows translation of multiple proteins in a single open reading frame into a polyprotein that is subsequently cleaved into individual proteins through a ribosome-skipping mechanism. 2A peptide may provide more balanced expression of multiple protein products. Exemplary IRES sequences include, e.g., EV71 IRES, EMCV IRES, HCV IRES. For genomic integration, the integration may be site-specific or random. Site-specific recombination may be achieved by introducing homologous sequence(s) into the nucleic acid constructs described herein. Such homologous sequence substantially matches the endogenous sequence at a specific target site in the host genome. Alternatively, random integration may be used. Sometimes, the expression level of a protein may vary depending upon the integration site. Therefore, it may be desirable to select a number of clones according to recombinant protein expression level to identify a clone that achieves the desired level of expression.

Figure 2T:
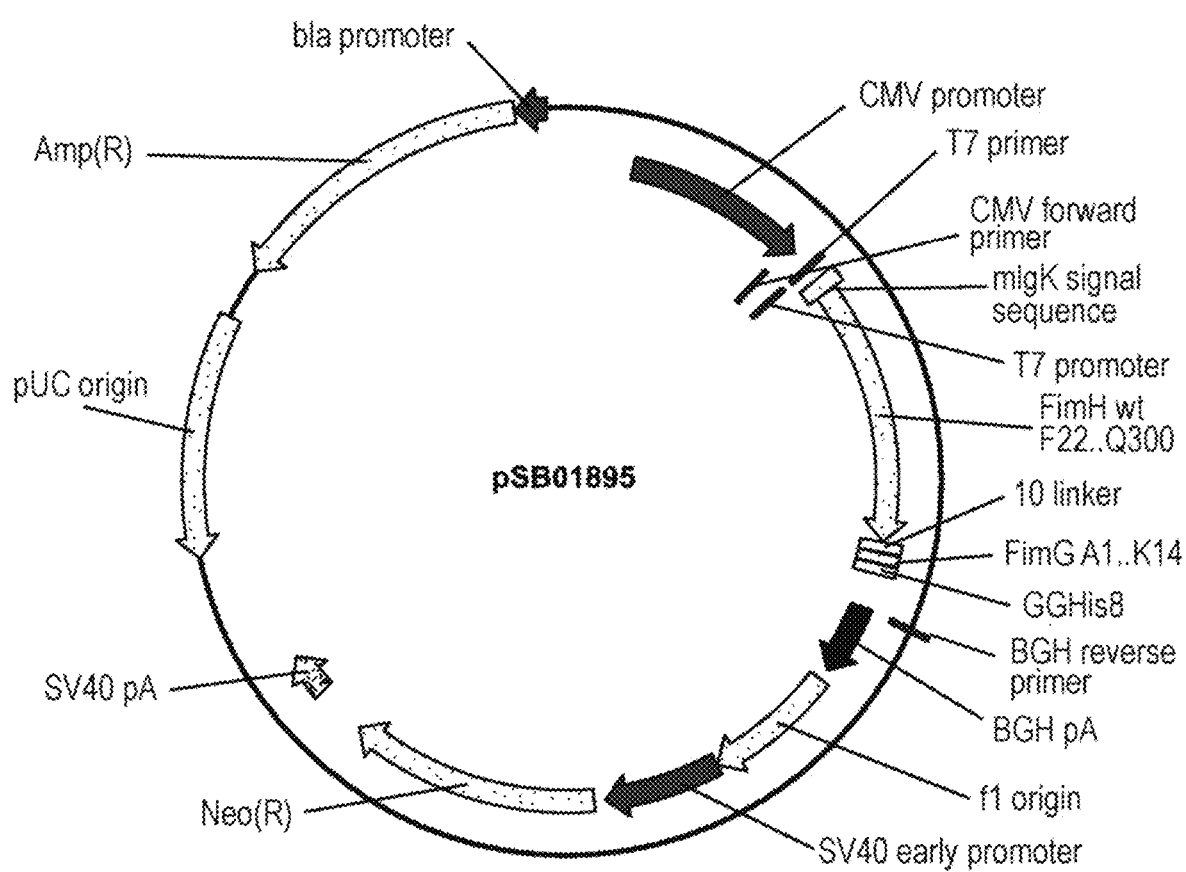

Exemplary nucleic acid constructs are further described in the figures, such as any one of FIG. 2A-2T.

In one aspect, the nucleic acid sequence encodes the amino acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9% or 100% identity to any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 20, SEQ ID NO: 23, SEQ ID NO: 24, SEQ ID NO: 26, SEQ ID NO: 27, SEQ ID NO: 28, SEQ ID NO: 29, SEQ ID NO: 110, SEQ ID NO: 111, SEQ ID NO: 112, and SEQ ID NO: 113.

III. Host Cells

In one aspect, the invention relates to cells in which the sequences encoding the polypeptide derived from *E. coli* or a fragment thereof are expressed in a mammalian host cell. In one embodiment, the polypeptide derived from *E. coli* or a fragment thereof is transiently expressed in the host cell. In another embodiment, the polypeptide derived from *E. coli* or a fragment thereof is stably integrated into the genome of the host cells, and, when cultured under a suitable condition, express the polypeptide derived from *E. coli* or a fragment thereof. In a preferred embodiment, the polynucleotide sequence is expressed with high efficiency and genomic stability.

Suitable mammalian host cells are known in the art. Preferably, the host cell is suitable for producing protein at industrial manufacturing scale. Exemplary mammalian host cells include any one of the following and derivatives thereof: Chinese Hamster Ovary (CHO) cells, COS cells (a cell line derived from monkey kidney (African green monkey), Vero cells, Hela cells, baby hamster kidney (BHK) cells, Human Embryonic Kidney (HEK) cells, NSO cells (Murine myeloma cell line), and C127 cells (nontumorigenic mouse cell line). Further exemplary mammalian host cells include mouse Sertoli (TM4), buffalo rat liver (BRL 3A), mouse mammary tumor (MMT), rat hepatoma (HTC), mouse myeloma (NSO), murine hybridoma (Sp2/0), mouse thymoma (EL4), Chinese Hamster Ovary (CHO) and CHO cell derivatives, murine embryonic (NIH/3T3, 3T3 Li), rat myocardial (H9c2), mouse myoblast (C2C12), and mouse kidney (miMCD-3). Further examples of mammalian cell lines include NSO/1, Sp2/0, Hep G2, PER.C6, COS-7, TM4, CV1, VERO-76, MDCK, BRL 3A, W138, MMT 060562, TR1, MRC5, and FS4.

Any cell susceptible to cell culture may be utilized in accordance with the present invention. In some embodiments, the cell is a mammalian cell. Non-limiting examples of mammalian cells that may be used in accordance with the present invention include BALB/c mouse myeloma line (NSO/I, ECACC No: 85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., J. Gen Virol., 36:59.1977); baby hamster kidney cells (BHK, ATCC CCL 10); Chinese hamster ovary cells +/–DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2). In some preferred embodiment, the cells are CHO cells. In some preferred embodiments, the cells are GS-cells.

Additionally, any number of commercially and non-commercially available hybridoma cell lines may be utilized in accordance with the present invention. The term "hybridoma" as used herein refers to a cell or progeny of a cell resulting from fusion of an immortalized cell and an antibody-producing cell. Such a resulting hybridoma is an immortalized cell that produces antibodies. Individual cells used to create the hybridoma can be from any mammalian source, including, but not limited to, rat, pig, rabbit, sheep, pig, goat, and human. In some embodiments, a hybridoma is a trioma cell line, which results when progeny of heterohybrid myeloma fusions, which are the product of a fusion between human cells and a murine myeloma cell line, are subsequently fused with a plasma cell. In some embodiments, a hybridoma is any immortalized hybrid cell line that produces antibodies such as, for example, quadromas (See, e.g., Milstein et al., Nature, 537:3053, 1983). One skilled in the art will appreciate that hybridoma cell lines might have different nutrition requirements and/or might require different culture conditions for optimal growth, and will be able to modify conditions as needed.

In some embodiments, the cell comprises a first gene of interest, wherein the first gene of interest is chromosomally-integrated. In some embodiments, the first gene of interest comprises a reporter gene, a selection gene, a gene of interest (e.g., encoding a polypeptide derived from *E. coli* or a fragment thereof), an ancillary gene, or a combination thereof. In some embodiments, the gene of therapeutic interest comprises a gene encoding a difficult to express (DtE) protein.

In some embodiments, the first gene of interest is located between two of the distinct recombination target sites (RTS) in a site-specific integration (SSI) mammalian cell, wherein two RTS are chromosomally-integrated within the NL1 locus or the NL2 locus. See, for example, United States Patent Application Publication No. 20200002727, for a description of the NL1 locus, the NL2 locus, the NL3 locus, the NL4 locus, the NL5 locus, and the NL6 locus. In some embodiments, the first gene of interest is located within the NL1 locus. In some embodiments, the cell comprises a second gene of interest, wherein the second gene of interest is chromosomally-integrated. In some embodiments, the second gene of interest comprises a reporter gene, a selection gene, a gene of therapeutic interest (such as a polypeptide derived from E. coli or a fragment thereof), an ancillary gene, or a combination thereof. In some embodiments, the gene of therapeutic interest comprises a gene encoding a DtE protein. In some embodiments, the second gene of interest is located between two of the RTS. In some embodiments, the second gene of interest is located within the NL1 locus or the NL2 locus. In some embodiments, the first gene of interest is located within the NL1 locus, and the second gene of interest is located within the NL2 locus. In some embodiments, the cell comprises a third gene of interest, wherein the third gene of interest is chromosomally-integrated. In some embodiments, the third gene of interest comprises a reporter gene, a selection gene, a gene of therapeutic interest (such as a polypeptide derived from E. coli or a fragment thereof), an ancillary gene, or a combination thereof. In some embodiments, the gene of therapeutic interest comprises a gene encoding a DtE protein. In some embodiments, the third gene of interest is located between two of the RTS. In some embodiments, the third gene of interest is located within the NL1 locus or the NL2 locus. In some embodiments, the third gene of interest is located within a locus distinct from the NL1 locus and the NL2 locus. In some embodiments, the first gene of interest, the second gene of interest, and the third gene of interest are within three separate loci. In some embodiments, at least one of the first genes of interest, the second gene of interest, and the third gene of interest is within the NL1 locus, and at least one of the first gene of interest, the second gene of interest, and the third gene of interest is within the NL2 locus. In some embodiments, the cell comprises a site-specific recombinase gene. In some embodiments, the site-specific recombinase gene is chromosomally-integrated.

In some embodiments, the present disclosure provides a mammalian cell comprising at least four distinct RTS, wherein the cell comprises (a) at least two distinct RTS are chromosomally-integrated within the NL1 locus or NL2 locus; (b) a first gene of interest is integrated between the at least two RTS of (a), wherein the first gene of interest comprises a reporter gene, a gene encoding a DtE protein, an ancillary gene or a combination thereof; (c) and a second gene of interest is integrated within a second chromosomal locus distinct from the locus of (a), wherein the second gene of interest comprises a reporter gene, a gene encoding a DtE protein (such as a polypeptide derived from E. coli or a fragment thereof), an ancillary gene or a combination thereof. In some embodiments, the present disclosure provides a mammalian cell comprising at least four distinct RTS, wherein the cell comprises (a) at least two distinct RTS are chromosomally-integrated within the Fer1L4 locus; (b) at least two distinct RTS are chromosomally-integrated within the NL1 locus or the NL2 locus; (c) a first gene of interest is chromosomally-integrated within the Fer1L4 locus, wherein the first gene of interest comprises a reporter gene, a gene encoding a DtE protein, an ancillary gene or a combination thereof; and (d) a second gene of interest is chromosomally-integrated within the within the NL1 locus or NL2 locus of (b), wherein the second gene of interest comprises a reporter gene, a gene encoding a DtE protein (such as a polypeptide derived from E. coli or a fragment thereof), an ancillary gene or a combination thereof.

In some embodiments, the present disclosure provides a mammalian cell comprising at least six distinct RTS, wherein the cell comprises (a) at least two distinct RTS and a first gene of interest are chromosomally-integrated within the Fer1 L4 locus; (b) at least two distinct RTS and a second gene of interest are chromosomally-integrated within the NL1 locus; and (c) at least two distinct RTS and a third gene of interest are chromosomally-integrated within the NL2 locus.

As referred to herein, the terms "in operable combination," "in operable order," and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced. In some embodiments, a gene of interest is operably linked to a promoter, wherein the gene of interest is chromosomally-integrated into the host cell. In some embodiments, the gene of interest is operably linked to a heterologous promoter; where in the gene of interest is chromosomally-integrated into the host cell. In some embodiments, an ancillary gene is operably linked to a promoter, wherein the ancillary gene is chromosomally-integrated into the host cell genome. In some embodiments, the ancillary gene is operably linked to a heterologous promoter; where in the ancillary gene is chromosomally-integrated into the host cell genome. In some embodiments, a gene encoding a DtE protein is operably linked to a promoter, wherein the gene encoding a DtE protein is chromosomally-integrated into the host cell genome. In some embodiments, the gene encoding a DtE protein is operably linked to a heterologous promoter, where in the gene encoding a DtE protein is chromosomally-integrated into the host cell genome. In some embodiments, a recombinase gene is operably linked to a promoter, wherein the recombinase gene is chromosomally-integrated into the host cell. In some embodiments, the recombinase gene is operably linked to a promoter, where in the recombinase gene is not integrated into the host cell genome. In some embodiments, a recombinase gene is operably linked to a heterologous promoter, wherein the recombinase gene is not chromosomally-integrated into the host cell genome. In some embodiments, the recombinase gene is operably linked to a heterologous promoter, wherein the recombinase gene is not chromosomally-integrated into the host cell genome.

As referred to herein, the term "chromosomally-integrated" or "chromosomal integration" refers to the stable incorporation of a nucleic acid sequence into the chromosome of a host cell, e.g. a mammalian cell. i.e., a nucleic acid sequence that is chromosomally-integrated into the genomic DNA (gDNA) of a host cell, e.g. a mammalian cell. In some embodiments, a nucleic acid sequence that is chromosomally-integrated is stable. In some embodiments, a nucleic acid sequence that is chromosomally-integrated is not located on a plasmid or a vector. In some embodiments, a nucleic acid sequence that is chromosomally-integrated is not excised. In some embodiments, chromosomal integration is mediated by the clustered regularly interspaced short palindromic repeats (CRISPR) and CRISPR associated protein (Cas) gene editing system (CRISPR/CAS).

In some embodiments, the host cells are suitable for growth in suspension cultures. Suspension competent host cells are generally monodisperse or grow in loose aggregates without substantial aggregation. Suspension competent host cells include cells that are suitable for suspension culture without adaptation or manipulation (e.g., hematopoietic cells, lymphoid cells) and cells that have been made suspension competent by modification or adaptation of attachment-dependent cells (e.g., epithelial cells, fibroblasts).

In some embodiments, the expression level or activity of the polypeptide derived from *E. coli* or fragment thereof is increased by at least 2-fold, at least 3 fold, at least 5 fold, at least 10 fold, at least 20 fold, at least 30 fold, at least 40 fold, at least 50 fold, at least 60 fold, at least 70 fold, at least 75 fold, at least 80 fold, at least 90 fold, at least 100 fold, as compared to expression of the polypeptide derived from *E. coli* or a fragment thereof in a bacterial cell, such as, for example, an *E. coli* host cell. In some embodiments, the expression level of the polypeptide derived from *E. coli* or fragment thereof is increased by at least 2-fold as compared to expression of the polypeptide derived from *E. coli* or a fragment thereof in an *E. coli* host cell. In some embodiments, the expression level of the polypeptide derived from *E. coli* or fragment thereof is increased by at least 50-fold as compared to expression of the polypeptide derived from *E. coli* or a fragment thereof in an *E. coli* host cell. In some embodiments, the expression level of the polypeptide derived from *E. coli* or fragment thereof is increased by at least 100-fold as compared to expression of the polypeptide derived from *E. coli* or a fragment thereof in an *E. coli* host cell.

The host cells described herein are suitable for large scale culture. For example, the cell cultures may be 10 L, 30 L, 50 L, 100 L, 150 L, 200 L, 300 L, 500 L, 1000 L, 2000 L, 3000 L, 4000 L, 5000 L, 10,000 L or larger. In some embodiments, the cell culture size may range from 10 L to 5000 L, from 10 L to 10,000 L, from 10 L, to 20,000 L, from 10 l, to 50,000 L, from 40 l, to 50,000 L, from 100 L to 50,000 L, from 500 L to 50,000 L, from 1000 L to 50,000 L, from 2000 L to 50,000 L, from 3000 l, to 50,000 L, from 4000 L to 50,000 L, from 4500 L to 50,000 L, from 1000 L to 10,000 L, from 1000 L to 20,000 L, from 1000 L to 25,000 L, from 1000 L to 30,000 L, from 15 L to 2000 L, from 40 L to 1000 L, from 100 L to 500 L, from 200 L to 400 L, or any integer there between. Media components for cell culture are known in the art, and may include, e.g., buffer, amino acid content, vitamin content, salt content, mineral content, serum content, carbon source content, lipid content, nucleic acid content, hormone content, trace element content, ammonia content, co-factor content, indicator content, small molecule content, hydrolysate content and enzyme modulator content.

The terms "medium", "cell culture medium" and "culture medium" as used herein refer to a solution containing nutrients which nourish growing mammalian cells. Typically, such solutions provide essential and non-essential amino acids, vitamins, energy sources, lipids, and trace elements required by the cell for minimal growth and/or survival. Such a solution may also contain supplementary components that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), inorganic compounds present at high final concentrations (e.g., iron), amino acids, lipids, and/or glucose or other energy source. In some embodiments, a medium is advantageously formulated to a pH and salt concentration optimal for cell survival and proliferation. In some embodiments, a medium is a feed medium that is added after the beginning of the cell culture.

In some embodiments, cells may be grown in one of a variety of chemically defined media, wherein the components of the media are both known and controlled. In some embodiments, cells may be grown in a complex medium, in which not all components of the medium are known and/or controlled. Chemically defined growth media for mammalian cell culture have been extensively developed and published over the last several decades. All components of defined media are well characterized, and so defined media do not contain complex additives such as serum or hydrolysates. Early media formulations were developed to permit cell growth and maintenance of viability with little or no concern for protein production. More recently, media formulations have been developed with the express purpose of supporting highly productive recombinant protein producing cell cultures. Such media are preferred for use in the method of the invention. Such media generally comprises high amounts of nutrients and in particular of amino acids to support the growth and/or the maintenance of cells at high density. If necessary, these media can be modified by the skilled person for use in the method of the invention. For example, the skilled person may decrease the amount of phenylalanine, tyrosine, tryptophan and/or methionine in these media for their use as base media or feed media in a method as disclosed herein.

Not all components of complex media are well characterized, and so complex media may contain additives such as simple and/or complex carbon sources, simple and/or complex nitrogen sources, and serum, among other things. In some embodiments, complex media suitable for the present invention contains additives such as hydrolysates in addition to other components of defined medium as described herein. In some embodiments, defined media typically includes roughly fifty chemical entities at known concentrations in water. Most of them also contain one or more well-characterized proteins such as insulin, IGF-1, transferrin or BSA, but others require no protein components and so are referred to as protein-free defined media. Typical chemical components of the media fall into five broad categories: amino acids, vitamins, inorganic salts, trace elements, and a miscellaneous category that defies neat categorization.

Cell culture medium may be optionally supplemented with supplementary components. The term "supplementary components" as used herein refers to components that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, and/or glucose or other energy source. In some embodiments, supplementary components may be added to the initial cell culture. In some embodiments, supplementary components may be added after the beginning of the cell culture. Typically, trace elements refer to a variety of inorganic salts included at micromolar or lower levels. For example, commonly included trace elements are zinc, selenium, copper, and others. In some embodiments, iron (ferrous or ferric salts) can be included as a trace element in the initial cell culture medium at micromolar concentrations. Manganese is also frequently included among the trace elements as a divalent cation ($MnCl_2$ or $MnSO_4$) in a range of nanomolar to micromolar concentrations. Numerous less common trace elements are usually added at nanomolar concentrations.

In some embodiments, the medium used in the method of the invention is a medium suitable for supporting high cell density, such as for example $1\times10^6$ cells/mL, $5\times10^6$ cells/mL, $1\times10^7$ cells/mL, $5\times10^7$ cells/mL, $1\times10^8$ cells/mL or $5\times10^8$ cells/mL, in a cell culture. In some embodiments, the cell culture is a mammalian cell fed-batch culture, preferably a CHO cells fed-batch culture.

In some embodiments, the cell culture medium comprises phenylalanine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises tyrosine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises tryptophan at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises methionine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises leucine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises serine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises threonine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises glycine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises two of phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises phenylalanine and tyrosine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises phenylalanine and tryptophan at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises phenylalanine and methionine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises tyrosine and tryptophan at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises tyrosine and methionine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises tryptophan and methionine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises three of phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises phenylalanine, tyrosine and tryptophan at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises phenylalanine, tyrosine and methionine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises phenylalanine, tryptophan and methionine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises tyrosine, tryptophan and methionine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises four of phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises phenylalanine, tyrosine, tryptophan and methionine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises five of phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises six of phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises seven of phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM. In some embodiments, the cell culture medium further comprises at least 1, 2, 3, 4, 5, 6, 7, 8, 9, 10, 11, 12 or 13 of glycine, valine, leucine, isoleucine, proline, serine, threonine, lysine, arginine, histidine, aspartate, glutamate and asparagine at a concentration above 2 mM, 3 mM, 4 mM, 5 mM, 10 mM, 15 mM, preferably 2 mM. In some embodiments, the cell culture medium further comprises at least 5 of glycine, valine, leucine, isoleucine, proline, serine, threonine, lysine, arginine, histidine, aspartate, glutamate and asparagine at a concentration above 2 mM, 3 mM, 4 mM, 5 mM, 10 mM, 15 mM, preferably 2 mM. In some embodiments, the cell culture medium further comprises glycine, valine, leucine, isoleucine, proline, serine, threonine, lysine, arginine, histidine, aspartate, glutamate and asparagine at a concentration above 2 mM, 3 mM, 4 mM, 5 mM, 10 mM, 15 mM, preferably 2 mM. In some embodiments, the cell culture medium further comprises at least 1, 2, 3, 4, 5, 6, 7, 8, or 9 of valine, isoleucine, proline, lysine, arginine, histidine, aspartate, glutamate and asparagine at a concentration above 2 mM, 3 mM, 4 mM, 5 mM, 10 mM, 15 mM, preferably 2 mM. In some embodiments, the cell culture medium further comprises at least 5 of valine, isoleucine, proline, lysine, arginine, histidine, aspartate, glutamate and asparagine at a concentration above 2 mM, 3 mM, 4 mM, 5 mM, 10 mM, 15 mM, preferably 2 mM. In some embodiments, the cell culture medium further comprises valine, isoleucine, proline, lysine, arginine, histidine, aspartate, glutamate and asparagine at a concentration above 2 mM, 3 mM, 4 mM, 5 mM, 10 mM, 15 mM, preferably 2 mM. In some embodiments, the cell culture medium comprises serine at a concentration above 3 mM, 5 mM, 7 mM, 10 mM, 15 mM or 20 mM, preferably 10 mM. In some embodiments, the cell culture medium comprises valine at a concentration above 3 mM, 5 mM, 7 mM, 10 mM, 15 mM or 20 mM, preferably 10 mM. In some embodiments, the cell culture medium comprises cysteine at a concentration above 3 mM, 5 mM, 7 mM, 10 mM, 15 mM or 20 mM, preferably 10 mM. In some embodiments, the cell culture medium comprises isoleucine at a concentration above 3 mM, 5 mM, 7 mM, 10 mM, 15 mM or 20 mM, preferably 10 mM. In some embodiments, the cell culture medium comprises leucine at a concentration above 3 mM, 5 mM, 7 mM, 10 mM, 15 mM or 20 mM, preferably 10 mM. In some embodiments, the above cell culture medium is for use in a method as disclosed herein. In some embodiments, the above cell culture medium is used in a method as disclosed herein as a base media. In some embodiments, the above cell culture medium is used a method as disclosed herein as a feed media.

IV. Method of Producing

In one aspect, the invention includes a method of producing a polypeptide derived from *E. coli* or a fragment thereof. The method includes culturing a mammalian cell under a suitable condition, thereby expressing the polypeptide derived from *E. coli* or a fragment thereof. The method may further include harvesting the polypeptide derived from *E. coli* or a fragment thereof from the culture. The process may further include purifying the polypeptide derived from *E. coli* or a fragment thereof.

In some embodiments, the method produces the polypeptide or fragment thereof at a yield as 0.1 g/L to 0.5 g/L.

In some embodiments, the cells may be grown in batch or fed-batch cultures, where the culture is terminated after sufficient expression of the polypeptide, after which the expressed polypeptide is harvested and optionally purified. In some embodiments, the cells may be grown in perfusion cultures, where the culture is not terminated and new nutrients and other components are periodically or continuously added to the culture, during which the expressed polypeptide is periodically or continuously harvested.

In some embodiments, the cells may be grown in small scale reaction vessels ranging in volume from a few milliliters to several liters. In some embodiments, the cells may be grown in large scale commercial bioreactors ranging in volume from approximately least 1 liter to 10, 100, 250, 500, 1,000, 2,500, 5,000, 8,000, 10,000, 12,000 liters or more, or any volume in between.

The temperature of the cell culture will be selected based primarily on the range of temperatures at which the cell culture remains viable, at which a high level of polypeptide is produced, the temperature at which production or accumulation of metabolic waste products is minimized, and/or any combination of these or other factors deemed important by the practitioner. As one non-limiting example, CHO cells grow well and produce high levels or protein or polypeptide at approximately 37° C. In general, most mammalian cells grow well and/or can produce high levels or protein or polypeptide within a range of about 25° C. to 42° C., although methods taught by the present disclosure are not limited to these temperatures. Certain mammalian cells grow well and/or can produce high levels or protein or polypeptide within the range of about 35° C. to 40° C. In certain embodiments, the cell culture is grown at a temperature of 20° C., 21° C., 22° C., 23'C, 24'C, 25'C, 26'C, 27'C, 28'C, 29'C, 30'C, 31° C., 32'C, 33° C., 34° C., 35° C., 36° C., 37° C., 38° C., 39° C., 40° C., 41° C., 42° C., 43° C., 44° C., or 45° C. at one or more times during the cell culture process.

The terms "culture" and "cell culture" as used herein refer to a cell population that is suspended in a medium under conditions suitable to survival and/or growth of the cell population. As will be clear to those of ordinary skill in the art, in some embodiments, these terms as used herein refer to the combination comprising the cell population and the medium in which the population is suspended. In some embodiments, the cells of the cell culture comprise mammalian cells.

The present invention may be used with any cell culture method that is amenable to the desired process (e.g., production of a recombinant protein (e.g., antibody)). As a non-limiting example, cells may be grown in batch or fed-batch cultures, where the culture is terminated after sufficient expression of the recombinant protein (e.g., antibody), after which the expressed protein (e.g., antibody) is harvested. Alternatively, as another non-limiting example, cells may be grown in batch-refeed, where the culture is not terminated and new nutrients and other components are periodically or continuously added to the culture, during which the expressed recombinant protein (e.g., antibody) is harvested periodically or continuously. Other suitable methods (e.g., spin-tube cultures) are known in the art and can be used to practice the present invention.

In some embodiments, a cell culture suitable for the present invention is a fed-batch culture. The term "fed-batch culture" as used herein refers to a method of culturing cells in which additional components are provided to the culture at a time or times subsequent to the beginning of the culture process. Such provided components typically comprise nutritional components for the cells which have been depleted during the culturing process. A fed-batch culture is typically stopped at some point and the cells and/or components in the medium are harvested and optionally purified. In some embodiments, the fed-batch culture comprises a base medium supplemented with feed media.

Cells may be grown in any convenient volume chosen by the practitioner. For example, cells may be grown in small scale reaction vessels ranging in volume from a few milliliters to several liters. Alternatively, cells may be grown in large scale commercial Bioreactors ranging in volume from approximately at least 1 liter to 10, 50, 100, 250, 500, 1000, 2500, 5000, 8000, 10,000, 12,000, 15000, 20000 or 25000 liters or more, or any volume in between.

The temperature of a cell culture will be selected based primarily on the range of temperatures at which the cell culture remains viable and the range in which a high level of desired product (e.g., a recombinant protein) is produced. In general, most mammalian cells grow well and can produce desired products (e.g., recombinant proteins) within a range of about 25° C. to 42° C., although methods taught by the present disclosure are not limited to these temperatures. Certain mammalian cells grow well and can produce desired products (e.g., recombinant proteins or antibodies) within the range of about 35° C. to 40° C. In certain embodiments, a cell culture is grown at a temperature of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., or 45° C. at one or more times during the cell culture process. Those of ordinary skill in the art will be able to select appropriate temperature or temperatures in which to grow cells, depending on the particular needs of the cells and the particular production requirements of the practitioner. The cells may be grown for any amount of time, depending on the needs of the practitioner and the requirement of the cells themselves. In some embodiment, the cells are grown at 37° C. In some embodiments, the cells are grown at 36.5° C.

In some embodiments, the cells may be grown during the initial growth phase (or growth phase) for a greater or lesser amount of time, depending on the needs of the practitioner and the requirement of the cells themselves. In some embodiments, the cells are grown for a period of time sufficient to achieve a predefined cell density. In some embodiments, the cells are grown for a period of time sufficient to achieve a cell density that is a given percentage of the maximal cell density that the cells would eventually reach if allowed to grow undisturbed. For example, the cells may be grown for a period of time sufficient to achieve a desired viable cell density of 1, 5, 10, 15, 20, 25, 30, 35, 40, 45, 50, 55, 60, 65, 70, 75, 80, 85, 90, 95 or 99 percent of maximal cell density. In some embodiments, the cells are grown until the cell density does not increase by more than 15%, 14%, 13%, 12%, 11%, 10%, 9%, 8%, 7%, 6%, 5%, 4%, 3%, 2% or 1% per day of culture. In some embodiments, the cells are grown until the cell density does not increase by more than 5% per day of culture.

In some embodiment the cells are allowed to grow for a defined period of time. For example, depending on the starting concentration of the cell culture, the temperature at which the cells are grown, and the intrinsic growth rate of the cells, the cells may be grown for 0, 1, 2, 3, 4, 5, 6, 7, 8, 9, 10, 11, 12, 13, 14, 15, 16, 17, 18, 19, 20 or more days, preferably for 4 to 10 days. In some cases, the cells may be allowed to grow for a month or more. The practitioner of the present invention will be able to choose the duration of the initial growth phase depending on protein production requirements and the needs of the cells themselves.

The cell culture may be agitated or shaken during the initial culture phase in order to increase oxygenation and dispersion of nutrients to the cells. In accordance with the present invention, one of ordinary skill in the art will understand that it can be beneficial to control or regulate certain internal conditions of the bioreactor during the initial growth phase, including but not limited to pH, temperature, oxygenation, etc.

At the end of the initial growth phase, at least one of the culture conditions may be shifted so that a second set of culture conditions is applied and a metabolic shift occurs in the culture. A metabolic shift can be accomplished by, e.g., a change in the temperature, pH, osmolality or chemical inductant level of the cell culture. In one non-limiting embodiment, the culture conditions are shifted by shifting the temperature of the culture. However, as is known in the art, shifting temperature is not the only mechanism through which an appropriate metabolic shift can be achieved. For example, such a metabolic shift can also be achieved by shifting other culture conditions including, but not limited to, pH, osmolality, and sodium butyrate levels. The timing of the culture shift will be determined by the practitioner of the present invention, based on protein production requirements or the needs of the cells themselves.

When shifting the temperature of the culture, the temperature shift may be relatively gradual. For example, it may take several hours or days to complete the temperature change. Alternatively, the temperature shift may be relatively abrupt. For example, the temperature change may be complete in less than several hours. Given the appropriate production and control equipment, such as is standard in the commercial large-scale production of polypeptides or proteins, the temperature change may even be complete within less than an hour.

In some embodiments, once the conditions of the cell culture have been shifted as discussed above, the cell culture is maintained for a subsequent production phase under a second set of culture conditions conducive to the survival and viability of the cell culture and appropriate for expression of the desired polypeptide or protein at commercially adequate levels.

As discussed above, the culture may be shifted by shifting one or more of a number of culture conditions including, but not limited to, temperature, pH, osmolality, and sodium butyrate levels. In some embodiments, the temperature of the culture is shifted. According to this embodiment, during the subsequent production phase, the culture is maintained at a temperature or temperature range that is lower than the temperature or temperature range of the initial growth phase. As discussed above, multiple discrete temperature shifts may be employed to increase cell density or viability or to increase expression of the recombinant protein.

In some embodiments, the cells may be maintained in the subsequent production phase until a desired cell density or production titer is reached. In another embodiment of the present invention, the cells are allowed to grow for a defined period of time during the subsequent production phase. For example, depending on the concentration of the cell culture at the start of the subsequent growth phase, the temperature at which the cells are grown, and the intrinsic growth rate of the cells, the cells may be grown for 1, 2, 3, 4, 5, 6, 7, 8, 9, 10, 11, 12, 13, 14, 15, 16, 17, 18, 19, 20 or more days. In some cases, the cells may be allowed to grow for a month or more. The practitioner of the present invention will be able to choose the duration of the subsequent production phase depending on polypeptide or protein production requirements and the needs of the cells themselves.

The cell culture may be agitated or shaken during the subsequent production phase in order to increase oxygenation and dispersion of nutrients to the cells. In accordance with the present invention, one of ordinary skill in the art will understand that it can be beneficial to control or regulate certain internal conditions of the bioreactor during the subsequent growth phase, including but not limited to pH, temperature, oxygenation, etc.

In some embodiments, the cells express a recombinant protein and the cell culture method of the invention comprises a growth phase and a production phase.

In some embodiments, step (ii) of any of the methods disclosed herein is applied during the totality of the cell culture method. In some embodiments, step (ii) of any of the methods disclosed herein is applied during a part of the cell culture method. In some embodiments, step (ii) is applied until a predetermined viable cell density is obtained.

In some embodiments, the cell culture method of the invention comprises a growth phase and a production phase and step (ii) is applied during the growth phase. In some embodiments, the cell culture method of the invention comprises a growth phase and a production phase and step (ii) is applied during a part of the growth phase. In some embodiments, the cell culture method of the invention comprises a growth phase and a production phase and step (ii) is applied during the growth phase and the production phase.

In step (ii) of any of the methods disclosed herein, the term "maintaining" can refer to maintaining the concentration of amino acid or metabolite below C1 or C2 for the entire culture process (until harvesting) or for a part of the culture process such as for example the growth phase, a part of the growth phase or until a predetermined cell density is obtained.

In some embodiments of any of the above mentioned methods, cell growth and/or productivity are increased as compared to a control culture, said control culture being identical except that it does not comprise step (ii).

In some embodiments of any of the above mentioned methods, the method of the invention is a method for improving cell growth. In some embodiment, the method of the invention is a method for improving cell growth in high density cell culture at high cell density.

High cell density as used herein refers to cell density above $1\times10^6$ cells/mL, $5\times10^6$ cells/mL, $1\times10^7$ cells/mL, $5\times10^7$ cells/mL, $1\times10^8$ cells/mL or $5\times10^8$ cells/mL, preferably above $1\times10^7$ cells/mL, more preferably above $5\times10^7$ cells/mL.

In some embodiments, the method of the invention is a method for improving cell growth in a cell culture where cell density is above $1\times10^6$ cells/mL, $5\times10^6$ cells/mL, $1\times10^7$ cells/mL, $5\times10^7$ cells/mL, $1\times10^8$ cells/mL or $5\times10^8$ cells/mL. In some embodiments, the method of the invention is a method for improving cell growth in a cell culture where maximum cell density is above $1\times10^6$ cells/mL, $5\times10^6$ cells/mL, $1\times10^7$ cells/mL, $5\times10^7$ cells/mL, $1\times10^8$ cells/mL or $5\times10^8$ cells/mL.

In some embodiments, cell growth is determined by viable cell density (VCD), maximum viable cell density, or Integrated viable cell count (IVCC). In some embodiments, cell growth is determined by maximum viable cell density.

The term "viable cell density" as used herein refers to the number of cells present in a given volume of medium. Viable cell density can be measured by any method known to the skilled person. Preferably, Viable cell density is measured using an automated cell counter such as Bioprofile Flex®. The term maximum cell density as used herein refers to the maximum cell density achieved during the cell culture. The term "cell viability" as used herein refers to the ability of cells in culture to survive under a given set of culture conditions or experimental variations. Those of ordinary skill in the art will appreciate that one of many methods for determining cell viability are encompassed in this invention. For example, one may use a dye (e.g., trypan blue) that does not pass through the membrane of a living cell, but can pass through the disrupted membrane of a dead or dying cell in order to determine cell viability.

The term "Integrated viable cell count (IVCC)" as used herein refers to as the area under the viable cell density (VCD) curve. IVCC can be calculated using the following formula: $IVCC_{t+1}=IVCC_t+(VCD_t+VCD_{t+1})*(\Delta t)/2$, where $\Delta t$ is the time difference between t and t+1 time points. $IVCC_{t=0}$ can be assumed negligible. $VCD_t$ and $VCD_{t+1}$ are viable cell densities at t and t+1 time points.

The term "titer" as used herein refers, for example, to the total amount of recombinantly expressed protein produced by a cell culture in a given amount of medium volume. Titer is typically expressed in units of grams of protein per liter of medium.

In some embodiments, cell growth is increased by at least 5%, 10%, 15%, 20% or 25% as compared to the control culture. In some embodiments, cell growth is increased by at least 10% as compared to the control culture. In some embodiments, cell growth is increased by at least 20% as compared to the control culture.

In some embodiments, the productivity is determined by titer and/or volumetric productivity.

The term "titer" as used herein refers, for example, to the total amount of recombinantly expressed protein produced by a cell culture in a given amount of medium volume. Titer is typically expressed in units of grams of protein per liter of medium.

In some embodiments, the productivity is determined by titer. In some embodiments, the productivity is increased by at least 5%, 10%, 15%, 20% or 25% as compared to the control culture. In some embodiments, the productivity is increased by at least 10% as compared to a control culture. In some embodiments, the productivity is increased by at least 20% as compared to a control culture.

In some embodiments, the maximum cell density of the cell culture is greater than $1\times10^6$ cells/mL, $5\times10^6$ cells/mL, $1\times10^7$ cells/mL, $5\times10^7$ cells/mL, $1\times10^8$ cells/mL or $5\times10^8$ cells/mL. In some embodiments, the maximum cell density of the cell culture is greater than $5\times10^6$ cells/mL. In some embodiments, the maximum cell density of the cell culture is greater than $1\times10^8$ cells/mL.

V. Purification

In some embodiments, the method for producing a polypeptide derived from *E. coli* or a fragment thereof includes isolating and/or purifying the polypeptide derived from *E. coli* or a fragment thereof. In some embodiments, the expressed polypeptide derived from *E. coli* or a fragment thereof is secreted into the medium and thus cells and other solids may be removed by centrifugation and/or filtration.

The polypeptide derived from *E. coli* or a fragment thereof produced in accordance with the methods described herein may be harvested from host cells and purified using any suitable method known to the skilled person. Suitable methods for purifying the polypeptide or fragment thereof include precipitation and various types of chromatography, such as hydrophobic interaction, ion exchange, affinity, chelation, and size exclusion, all of which are known in the art. Suitable purification schemes may include two or more of these or other suitable methods. In some embodiments, one or more of the polypeptide or fragments thereof derived from *E. coli* may include a "tag" that facilitates purification, such as an epitope tag or a HIS tag, Strep tag. Such tagged polypeptides may conveniently be purified, for example from conditioned media, by chelating chromatography or affinity chromatography. Optionally, the tag sequence may be cleaved post-purification.

In some embodiments, the polypeptide derived from *E. coli* or a fragment thereof may include a tag for affinity purification. Affinity purification tags are known in the art. Examples include, e.g., His tag (binds to metal ion), an antibody, maltose-binding protein (MBP) (binds to amylose), glutathione-S-transferase (GST) (binds to glutathione), FLAG tag, Strep tag (binds to streptavidin or a derivative thereof).

In a preferred embodiment, the polypeptide derived from *E. coli* or a fragment thereof does not include a purification tag.

In some embodiments, the yield of the polypeptide derived from *E. coli* or a fragment thereof is at least about 1 mg/L, at least about 2 mg/L, at least about 3 mg/L, at least about 4 mg/L, at least about 5 mg/L, at least about 6 mg/L, at least about 7 mg/L, at least about 8 mg/L, at least about 9 mg/L, at least about 10 mg/L, at least about 11 mg/L, at least about 12 mg/L, at least about 13 mg/L, at least about 14 mg/L, at least about 15 mg/L, at least about 16 mg/L, at least about 17 mg/L, at least about 18 mg/L, at least about 19 mg/L, at least about 20 mg/L, at least about 25 mg/L, at least about 30 mg/L, at least about 35 mg/L, at least about 40 mg/L, at least about 45 mg/L, at least about 50 mg/L, at least about 55 mg/L, at least about 60 mg/L, at least about 65 mg/L, at least about 70 mg/L, at least about 75 mg/L, at least about 80 mg/L, at least about 85 mg/L, at least about 90 mg/L, at least about 95 mg/L, or at least about 100 mg/L.

In some embodiments, the culture is at least about 10 liters in size, e.g., a volume of at least about 10 L, at least about 20 L, at least about 30 L, at least about 40 L, at least about 50 L, at least about 60 L, at least about 70 L, at least about 80 L, at least about 90 L, at least about 100 L, at least about 150 L, at least about 200 L, at least about 250 L, at least about 300 L, at least about 400 L, at least about 500 L, at least about 600 L, at least about 700 L, at least about 800 L, at least about 900 L, at least about 1000 L, at least about 2000 L, at least about 3000 L, at least about 4000 L, at least about 5000 L, at least about 6000 L, at least about 10,000 L, at least about 15,000 L, at least about 20,000 L, at least about 25,000 L, at least about 30,000 L, at least about 35,000 L, at least about 40,000 L, at least about 45,000 L, at least about 50,000 L, at least about 55,000 L, at least about 60,000 L, at least about 65,000 L, at least about 70,000 L, at least about 75,000 L, at least about 80,000 L, at least about 85,000 L, at least about 90,000 L, at least about 95,000 L, at least about 100,000 L, etc.

VI. Compositions and Formulations

In one aspect, the invention includes a composition that includes a polypeptide derived from *E. coli* or a fragment thereof. In some embodiments, the composition elicits an immune response, including antibodies, that may confer immunity to pathogenic species of *E. coli*.

In some embodiments, the composition includes the polypeptide derived from *E. coli* or fragment thereof as the only antigen. In some embodiments, the composition does not include a conjugate.

In some embodiments, the composition includes the polypeptide derived from *E. coli* or fragment thereof and an additional antigen. In some embodiments, the composition includes the polypeptide derived from *E. coli* or fragment thereof and an additional *E. coli* antigen. In some embodiments, the composition includes the polypeptide derived from *E. coli* or fragment thereof and a glycoconjugate from *E. coli*.

In some embodiments, the polypeptide or a fragment thereof is derived from *E. coli* FimH.

In some embodiments, the composition includes a polypeptide derived from *E. coli* FimC or a fragment thereof.

In some embodiments, the composition includes a polypeptide derived from *E. coli* FimH or a fragment thereof; and a polypeptide derived from *E. coli* FimC or a fragment thereof.

In one aspect, the invention includes a composition including a polypeptide derived from *E. coli* FimH or a fragment thereof; and a saccharide comprising a structure selected from any one of Formula O1 (e.g., Formula O1A, Formula O1B, and Formula O1C), Formula O2, Formula O3, Formula O4 (e.g., Formula O4:K52 and Formula O4:K6), Formula O5 (e.g., Formula O5ab and Formula O5ac (strain 180/C3)), Formula O6 (e.g., Formula O6:K2; K13; K15 and Formula O6:K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62$D_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 1 to 100.

In some embodiments, the composition includes any one of the saccharides disclosed herein. In preferred embodiments, the composition includes any one of the conjugates disclosed herein.

In some embodiments, the composition includes at least one glycoconjugate from *E. coli* serotype O25, preferably serotype O25b. In one embodiment, the composition includes at least one glycoconjugate from *E. coli* serotype O1, preferably serotype O1a. In one embodiment, the composition includes at least one glycoconjugate from *E. coli* serotype O2. In one embodiment, the composition includes at least one glycoconjugate from *E. coli* serotype O6.

In one embodiment, the composition comprises at least one glycoconjugate selected from any one of the following *E. coli* serotypes O25, O1, O2, and O6, preferably O25b, O1a, O2, and O6. In one embodiment, the composition comprises at least two glycoconjugates selected from any one of the following *E. coli* serotypes O25, O1, O2, and O6, preferably O25b, O1a, O2, and O6. In one embodiment, the composition comprises at least three glycoconjugates selected from any one of the following *E. coli* serotypes O25, O1, O2, and O6, preferably O25b, O1a, O2, and O6. In one embodiment, the composition comprises a glycoconjugate from each of the following *E. coli* serotypes O25, O1, O2, and O6, preferably O25b, O1a, O2, and O6.

In a preferred embodiment, the glycoconjugate of any of the above compositions is individually conjugated to $CRM_{197}$. In another preferred embodiment, the glycoconjugate of any of the above compositions is individually conjugated to SCP.

Accordingly, in some embodiments, the composition includes a polypeptide derived from *E. coli* or a fragment thereof; and an O-antigen from at least one *E. coli* serotype. In a preferred embodiment, the composition includes a polypeptide derived from *E. coli* or a fragment thereof; and an O-antigen from more than 1 *E. coli* serotype. For example, the composition may include an O-antigen from two different *E. coli* serotypes (or "v", valences) to 12 different serotypes (12v). In one embodiment, the composition includes a polypeptide derived from *E. coli* or a fragment thereof; and an O-antigen from 3 different serotypes. In one embodiment, the composition includes a polypeptide derived from *E. coli* or a fragment thereof; and an O-antigen from 4 different *E. coli* serotypes. In one embodiment, the composition includes an O-antigen from 5 different *E. coli* serotypes. In one embodiment, the composition includes a polypeptide derived from *E. coli* or a fragment thereof; and an O-antigen from 6 different *E. coli* serotypes. In one embodiment, the composition includes a polypeptide derived from *E. coli* or a fragment thereof; and an O-antigen from 7 different *E. coli* serotypes. In one embodiment, the composition includes a polypeptide derived from *E. coli* or a fragment thereof; and an O-antigen from 8 different *E. coli* serotypes. In one embodiment, the composition includes a polypeptide derived from *E. coli* or a fragment thereof; and an O-antigen from 9 different *E. coli* serotypes. In one embodiment, the composition includes a polypeptide derived from *E. coli* or a fragment thereof; and an O-antigen from 10 different *E. coli* serotypes. In one embodiment, the composition includes a polypeptide derived from *E. coli* or a fragment thereof; and an O-antigen from 11 different *E. coli* serotypes. In one embodiment, the composition includes a polypeptide derived from *E. coli* or a fragment thereof; and an O-antigen from 12 different serotypes. In one embodiment, the composition includes a polypeptide derived from *E. coli* or a fragment thereof; and an O-antigen from 13 different serotypes. In one embodiment, the composition includes a polypeptide derived from *E. coli* or a fragment thereof; and an O-antigen from 14 different serotypes. In one embodiment, the composition includes a polypeptide derived from *E. coli* or a fragment thereof; and an O-antigen from 15 different serotypes. In one embodiment, the composition includes a polypeptide derived from *E. coli* or a fragment thereof; and an O-antigen from 16 different serotypes. In one embodiment, the composition includes a polypeptide derived from *E. coli* or a fragment thereof; and an O-antigen from 17 different serotypes. In one embodiment, the composition includes a polypeptide derived from *E. coli* or a fragment thereof; and an O-antigen from 18 different serotypes. In one embodiment, the composition includes a polypeptide derived from *E. coli* or a fragment thereof; and an O-antigen from 19 different serotypes. In one embodiment, the composition includes a polypeptide derived from *E. coli* or a fragment thereof; and an O-antigen from 20 different serotypes.

Preferably, the number of *E. coli* saccharides can range from 1 serotype (or "v", valences) to 26 different serotypes (26v). In one embodiment there is one serotype. In one embodiment there are 2 different serotypes. In one embodiment there are 3 different serotypes. In one embodiment there are 4 different serotypes. In one embodiment there are 5 different serotypes. In one embodiment there are 6 different serotypes. In one embodiment there are 7 different serotypes. In one embodiment there are 8 different serotypes. In one embodiment there are 9 different serotypes. In one embodiment there are 10 different serotypes. In one embodiment there are 11 different serotypes. In one embodiment there are 12 different serotypes. In one embodiment there are 13 different serotypes. In one embodiment there are 14 different serotypes. In one embodiment there are 15 different serotypes. In one embodiment there are 16 different serotypes. In one embodiment there are 17 different serotypes. In one embodiment there are 18 different serotypes. In one embodiment there are 19 different serotypes. In one embodiment there are 20 different serotypes. In one embodiment there are 21 different serotypes. In one embodiment there are 22 different serotypes. In one embodiment there are 23 different serotypes. In one embodiment there are 24 different serotypes. In an embodiment there are 25 different serotypes. In one embodiment there are 26 different serotypes. The saccharides are conjugated to a carrier protein to form glycoconjugates as described herein.

In one aspect, the composition includes a polypeptide derived from *E. coli* or a fragment thereof; and a glycoconjugate that includes an O-antigen from at least one *E. coli* serogroup, wherein the O-antigen is conjugated to a carrier protein. In one embodiment, the composition includes a polypeptide derived from *E. coli* or a fragment thereof; and an O-antigen from more than 1 *E. coli* serotype, wherein each O-antigen is conjugated to a carrier protein. In one embodiment, the composition includes a polypeptide derived from *E. coli* or a fragment thereof; and an O-antigen from 2 different *E. coli* serotypes, wherein each O-antigen is conjugated to a carrier protein. In one embodiment, the composition includes a polypeptide derived from *E. coli* or a fragment thereof; and an O-antigen from 3 different *E. coli* serotypes, wherein each O-antigen is conjugated to a carrier protein. In one embodiment, the composition includes a polypeptide derived from *E. coli* or a fragment thereof; and an O-antigen from 4 different *E. coli* serotypes, wherein each O-antigen is conjugated to a carrier protein. In one embodiment, the composition includes a polypeptide derived from *E. coli* or a fragment thereof; and an O-antigen from 5 different *E. coli* serotypes, wherein each O-antigen is conjugated to a carrier protein. In one embodiment, the composition includes a polypeptide derived from *E. coli* or a fragment thereof; and an O-antigen from 6 different *E. coli* serotypes, wherein each O-antigen is conjugated to a carrier protein. In one embodiment, the composition includes a polypeptide derived from *E. coli* or a fragment thereof; and an O-antigen from 7 different *E. coli* serotypes, wherein each O-antigen is conjugated to a carrier protein. In one embodiment, the composition includes a polypeptide derived from *E. coli* or a fragment thereof; and an O-antigen from 8 different *E. coli* serotypes, wherein each O-antigen is conjugated to a carrier protein. In one embodiment, the composition includes a polypeptide derived from *E. coli* or a fragment thereof; and an O-antigen from 9 different *E. coli* serotypes, wherein each O-antigen is conjugated to a carrier protein. In one embodiment, the composition includes an O-antigen from a polypeptide derived from *E. coli* or a fragment thereof; and 10 different *E. coli* serotypes, wherein each O-antigen is conjugated to a carrier protein. In one embodiment, the composition includes an O-antigen from a polypeptide derived from *E. coli* or a fragment thereof; and 11 different *E. coli* serotypes, wherein each O-antigen is conjugated to a carrier protein. In one embodiment, the composition includes a polypeptide derived from *E. coli* or a fragment thereof; and an O-antigen from 12 different serotypes, wherein each O-antigen is conjugated to a carrier protein. In one embodiment, the composition includes a polypeptide derived from *E. coli* or a fragment thereof; and an O-antigen from 13 different serotypes, wherein each O-antigen is conjugated to a carrier protein. In one embodiment, the composition includes a polypeptide derived from *E. coli* or a fragment thereof; and an O-antigen from 14 different serotypes, wherein each O-antigen is conjugated to a carrier protein. In one embodiment, the composition includes a polypeptide derived from *E. coli* or a fragment thereof; and an O-antigen from 15 different serotypes, wherein each O-antigen is conjugated to a carrier protein. In one embodiment, the composition includes a polypeptide derived from *E. coli* or a fragment thereof; and an O-antigen from 16 different serotypes, wherein each O-antigen is conjugated to a carrier protein. In one embodiment, the composition includes a polypeptide derived from *E. coli* or a fragment thereof; and an O-antigen from 17 different serotypes, wherein each O-antigen is conjugated to a carrier protein. In one embodiment, the composition includes a polypeptide derived from *E. coli* or a fragment thereof; and an O-antigen from 18 different serotypes, wherein each O-antigen is conjugated to a carrier protein. In one embodiment, the composition includes a polypeptide derived from *E. coli* or a fragment thereof; and an O-antigen from 19 different serotypes, wherein each O-antigen is conjugated to a carrier protein. In one embodiment, the composition includes a polypeptide derived from *E. coli* or a fragment thereof; and an O-antigen from 20 different serotypes, wherein each O-antigen is conjugated to a carrier protein.

In another aspect, the composition includes an O-polysaccharide from at least one *E. coli* serotype. In a preferred embodiment, the composition includes an O-polysaccharide from more than 1 *E. coli* serotype. For example, the composition may include an O-polysaccharide from two different *E. coli* serotypes to 12 different *E. coli* serotypes. In one embodiment, the composition includes an O-polysaccharide from 3 different *E. coli* serotypes. In one embodiment, the composition includes an O-polysaccharide from 4 different *E. coli* serotypes. In one embodiment, the composition includes an O-polysaccharide from 5 different *E. coli* serotypes. In one embodiment, the composition includes an O-polysaccharide from 6 different *E. coli* serotypes. In one embodiment, the composition includes an O-polysaccharide from 7 different *E. coli* serotypes. In one embodiment, the composition includes an O-polysaccharide from 8 different *E. coli* serotypes. In one embodiment, the composition includes an O-polysaccharide from 9 different *E. coli* serotypes. In one embodiment, the composition includes an O-polysaccharide from 10 different *E. coli* serotypes. In one embodiment, the composition includes an O-polysaccharide from 11 different *E. coli* serotypes. In one embodiment, the composition includes an O-polysaccharide from 12 different serotypes. In one embodiment, the composition includes an O-polysaccharide from 13 different serotypes. In one embodiment, the composition includes an O-polysaccharide from 14 different serotypes. In one embodiment, the composition includes an O-polysaccharide from 15 different serotypes. In one embodiment, the composition includes an O-polysaccharide from 16 different serotypes. In one embodiment, the composition includes an O-polysaccharide from 17 different serotypes. In one embodiment, the composition includes an O-polysaccharide from 18 different serotypes. In one embodiment, the composition includes an O-polysaccharide from 19 different serotypes. In one embodiment, the composition includes an O-polysaccharide from 20 different serotypes.

In a preferred embodiment, the composition includes an O-polysaccharide from at least one *E. coli* serotype, wherein the O-polysaccharide is conjugated to a carrier protein. In a preferred embodiment, the composition includes an O-polysaccharide from more than 1 *E. coli* serotype, wherein each O-polysaccharide is conjugated to a carrier protein. For example, the composition may include an O-polysaccharide from two different *E. coli* serotypes to 12 different *E. coli* serotypes, wherein each O-polysaccharide is conjugated to a carrier protein. In one embodiment, the composition includes an O-polysaccharide from 3 different *E. coli* serotypes, wherein each O-polysaccharide is conjugated to a carrier protein. In one embodiment, the composition includes an O-polysaccharide from 4 different *E. coli* serotypes, wherein each O-polysaccharide is conjugated to a carrier protein. In one embodiment, the composition includes an O-polysaccharide from 5 different *E. coli* serotypes, wherein each O-polysaccharide is conjugated to a carrier protein. In one embodiment, the composition includes an O-polysaccharide from 6 different *E. coli* serotypes, wherein each O-polysaccharide is conjugated to a carrier protein. In one embodiment, the composition includes an O-polysaccharide from 7 different *E. coli* serotypes, wherein each O-polysaccharide is conjugated to a carrier protein. In one embodiment, the composition includes an O-polysaccharide from 8 different *E. coli* serotypes, wherein each O-polysaccharide is conjugated to a carrier protein. In one embodiment, the composition includes an O-polysaccharide from 9 different *E. coli* serotypes, wherein each O-polysaccharide is conjugated to a carrier protein. In one embodiment, the composition includes an O-polysaccharide from 10 different *E. coli* serotypes, wherein each O-polysaccharide is conjugated to a carrier protein. In one embodiment, the composition includes an O-polysaccharide from 11 different *E. coli* serotypes, wherein each O-polysaccharide is conjugated to a carrier protein. In one embodiment, the composition includes an O-polysaccharide from 12 different serotypes, wherein each O-polysaccharide is conjugated to a carrier protein. In one embodiment, the composition includes an O-polysaccharide from 13 different serotypes, wherein each O-polysaccharide is conjugated to a carrier protein. In one embodiment, the composition includes an O-polysaccharide from 14 different serotypes, wherein each O-polysaccharide is conjugated to a carrier protein. In one embodiment, the composition includes an O-polysaccharide from 15 different serotypes, wherein each O-polysaccharide is conjugated to a carrier protein. In one embodiment, the composition includes an O-polysaccharide from 16 different serotypes, wherein each O-polysaccharide is conjugated to a carrier protein. In one embodiment, the composition includes an O-polysaccharide from 17 different serotypes, wherein each O-polysaccharide is conjugated to a carrier protein. In one embodiment, the composition includes an O-polysaccharide from 18 different serotypes, wherein each O-polysaccharide is conjugated to a carrier protein. In one embodiment, the composition includes an O-polysaccharide from 19 different serotypes, wherein each O-polysaccharide is conjugated to a carrier protein. In one embodiment, the composition includes an O-polysaccharide from 20 different serotypes, wherein each O-polysaccharide is conjugated to a carrier protein.

In a most preferred embodiment, the composition includes an O-polysaccharide from at least one *E. coli* serotype, wherein the O-polysaccharide is conjugated to a carrier protein, and wherein the O-polysaccharide includes the O-antigen and core saccharide. In a preferred embodiment, the composition includes an O-polysaccharide from more than 1 *E. coli* serotype, wherein each O-polysaccharide is conjugated to a carrier protein, and wherein the O-polysaccharide includes the O-antigen and core saccharide. For example, the composition may include an O-polysaccharide from two different *E. coli* serotypes to 12 different *E. coli* serotypes, wherein each O-polysaccharide is conjugated to a carrier protein, and wherein the O-polysaccharide includes the O-antigen and core saccharide. In one embodiment, the composition includes an O-polysaccharide from 3 different *E. coli* serotypes, wherein each O-polysaccharide is conjugated to a carrier protein, and wherein the O-polysaccharide includes the O-antigen and core saccharide. In one embodiment, the composition includes an O-polysaccharide from 4 different *E. coli* serotypes, wherein each O-polysaccharide is conjugated to a carrier protein, and wherein the O-polysaccharide includes the O-antigen and core saccharide. In one embodiment, the composition includes an O-polysaccharide from 5 different *E. coli* serotypes, wherein each O-polysaccharide is conjugated to a carrier protein, and wherein the O-polysaccharide includes the O-antigen and core saccharide. In one embodiment, the composition includes an O-polysaccharide from 6 different *E. coli* serotypes, wherein each O-polysaccharide is conjugated to a carrier protein, and wherein the O-polysaccharide includes the O-antigen and core saccharide. In one embodiment, the composition includes an O-polysaccharide from 7 different *E. coli* serotypes, wherein each O-polysaccharide is conjugated to a carrier protein, and wherein the O-polysaccharide includes the O-antigen and core saccharide. In one embodiment, the composition includes an O-polysaccharide from 8 different *E. coli* serotypes, wherein each O-polysaccharide is conjugated to a carrier protein, and wherein the O-polysaccharide includes the O-antigen and core saccharide. In one embodiment, the composition includes an O-polysaccharide from 9 different *E. coli* serotypes, wherein each O-polysaccharide is conjugated to a carrier protein, and wherein the O-polysaccharide includes the O-antigen and core saccharide. In one embodiment, the composition includes an O-polysaccharide from 10 different *E. coli* serotypes, wherein each O-polysaccharide is conjugated to a carrier protein, and wherein the O-polysaccharide includes the O-antigen and core saccharide. In one embodiment, the composition includes an O-polysaccharide from 11 different *E. coli* serotypes, wherein each O-polysaccharide is conjugated to a carrier protein, and wherein the O-polysaccharide includes the O-antigen and core saccharide. In one embodiment, the composition includes an O-polysaccharide from 12 different serotypes, wherein each O-polysaccharide is conjugated to a carrier protein, and wherein the O-polysaccharide includes the O-antigen and core saccharide. In one embodiment, the composition includes an O-polysaccharide from 13 different serotypes, wherein each O-polysaccharide is conjugated to a carrier protein, and wherein the O-polysaccharide includes the O-antigen and core saccharide. In one embodiment, the composition includes an O-polysaccharide from 14 different serotypes, wherein each O-polysaccharide is conjugated to a carrier protein, and wherein the O-polysaccharide includes the O-antigen and core saccharide. In one embodiment, the composition includes an O-polysaccharide from 15 different serotypes, wherein each O-polysaccharide is conjugated to a carrier protein, and wherein the O-polysaccharide includes the O-antigen and core saccharide. In one embodiment, the composition includes an O-polysaccharide from 16 different serotypes, wherein each O-polysaccharide is conjugated to a carrier protein, and wherein the O-polysaccharide includes the O-antigen and core saccharide. In one embodiment, the composition includes an O-polysaccharide from 17 different serotypes, wherein each O-polysaccharide is conjugated to a carrier protein, and wherein the O-polysaccharide includes the O-antigen and core saccharide. In one embodiment, the composition includes an O-polysaccharide from 18 different serotypes, wherein each O-polysaccharide is conjugated to a carrier protein, and wherein the O-polysaccharide includes the O-antigen and core saccharide. In one embodiment, the composition includes an O-polysaccharide from 19 different serotypes, wherein each O-polysaccharide is conjugated to a carrier protein, and wherein the O-polysaccharide includes the O-antigen and core saccharide. In one embodiment, the composition includes an O-polysaccharide from 20 different serotypes, wherein each O-polysaccharide is conjugated to a carrier protein, and wherein the O-polysaccharide includes the O-antigen and core saccharide. In a preferred embodiment, the carrier protein is $CRM_{197}$.

In another preferred embodiment, the composition includes a polypeptide derived from *E. coli* or a fragment thereof; and an O-polysaccharide conjugated to $CRM_{197}$, wherein the O-polysaccharide includes Formula O25a, wherein n is at least 40, and the core saccharide. In a preferred embodiment, the composition further includes an O-polysaccharide conjugated to $CRM_{197}$, wherein the O-polysaccharide includes Formula O25b, wherein n is at least 40, and the core saccharide. In another embodiment, the composition further includes an O-polysaccharide conjugated to $CRM_{197}$, wherein the O-polysaccharide includes Formula O1a, wherein n is at least 40, and the core saccharide. In another embodiment, the composition further includes an O-polysaccharide conjugated to $CRM_{197}$, wherein the O-polysaccharide includes Formula O2, wherein n is at least 40, and the core saccharide. In another embodiment, the composition further includes an O-polysaccharide conjugated to $CRM_{197}$, wherein the O-polysaccharide includes Formula O6, wherein n is at least 40, and the core saccharide.

In another embodiment, the composition further includes an O-polysaccharide conjugated to $CRM_{197}$, wherein the O-polysaccharide includes Formula O17, wherein n is at least 40, and the core saccharide. In another embodiment, the composition further includes an O-polysaccharide conjugated to $CRM_{197}$, wherein the O-polysaccharide includes Formula O15, wherein n is at least 40, and the core saccharide. In another embodiment, the composition further includes an O-polysaccharide conjugated to $CRM_{197}$, wherein the O-polysaccharide includes Formula O18A, wherein n is at least 40, and the core saccharide. In another embodiment, the composition further includes an O-polysaccharide conjugated to $CRM_{197}$, wherein the O-polysaccharide includes Formula O75, wherein n is at least 40, and the core saccharide. In another embodiment, the composition further includes an O-polysaccharide conjugated to $CRM_{197}$, wherein the O-polysaccharide includes Formula O4, wherein n is at least 40, and the core saccharide. In another embodiment, the composition further includes an O-polysaccharide conjugated to $CRM_{197}$, wherein the O-polysaccharide includes Formula O16, wherein n is at least 40, and the core saccharide. In another embodiment, the composition further includes an O-polysaccharide conjugated to $CRM_{197}$, wherein the O-polysaccharide includes Formula O13, wherein n is at least 40, and the core saccharide. In another embodiment, the composition further includes an O-polysaccharide conjugated to $CRM_{197}$, wherein the O-polysaccharide includes Formula O7, wherein n is at least 40, and the core saccharide.

In another embodiment, the composition further includes an O-polysaccharide conjugated to $CRM_{197}$, wherein the O-polysaccharide includes Formula O8, wherein n is at least 40, and the core saccharide. In another embodiment, the O-polysaccharide includes Formula O8, wherein n is 1-20, preferably 2-5, more preferably 3. Formula O8 is shown, e.g., in FIG. 10B. In another embodiment, the composition further includes an O-polysaccharide conjugated to $CRM_{197}$, wherein the O-polysaccharide includes Formula O9, wherein n is at least 40, and the core saccharide. In another embodiment, the O-polysaccharide includes Formula O9, wherein n is 1-20, preferably 4-8, more preferably 5. Formula O9 is shown, e.g., in FIG. 10B. In another embodiment, the O-polysaccharide includes Formula O9a, wherein n is 1-20, preferably 4-8, more preferably 5. Formula O9a is shown, e.g., in FIG. 10B.

In some embodiments, the O-polysaccharide includes selected from any one of Formula O20ab, Formula O20ac, Formula O52, Formula O97, and Formula O101, wherein n is 1-20, preferably 4-8, more preferably 5. See, e.g., FIG. 10B.

As described above, the composition may include a polypeptide derived from *E. coli* or a fragment thereof; and any combination of conjugated O-polysaccharides (antigens). In one exemplary embodiment, the composition includes a polysaccharide that includes Formula O25b, a polysaccharide that includes Formula O1A, a polysaccharide that includes Formula O2, and a polysaccharide that includes Formula O6. More specifically, such as a composition that includes: (i) an O-polysaccharide conjugated to $CRM_{197}$, wherein the O-polysaccharide includes Formula O25b, wherein n is at least 40, and the core saccharide; (ii) an O-polysaccharide conjugated to $CRM_{197}$, wherein the O-polysaccharide includes Formula O1a, wherein n is at least 40, and the core saccharide; (iii) an O-polysaccharide conjugated to $CRM_{197}$, wherein the O-polysaccharide includes Formula O2, wherein n is at least 40, and the core saccharide; and (iv) an O-polysaccharide conjugated to $CRM_{197}$, wherein the O-polysaccharide includes Formula O6, wherein n is at least 40, and the core saccharide.

In one embodiment, the composition includes a polypeptide derived from *E. coli* or a fragment thereof; and at least one O-polysaccharide derived from any *E. coli* serotype, wherein the serotype is not O25a. For example, in one embodiment, the composition does not include a saccharide that includes the Formula O25a. Such a composition may include, for example, an O-polysaccharide that includes Formula O25b, an O-polysaccharide that includes Formula O1A, an O-polysaccharide that includes Formula O2, and an O-polysaccharide that includes Formula O6.

In one embodiment, the composition includes a polypeptide derived from *E. coli* or a fragment thereof; and an O-polysaccharide from 2 different *E. coli* serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 3 different *E. coli* serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 4 different *E. coli* serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 5 different *E. coli* serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 6 different *E. coli* serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 7 different *E. coli* serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 8 different *E. coli* serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 9 different *E. coli* serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 10 different *E. coli* serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 11 different *E. coli* serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 12 different serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 13 different serotypes, wherein each O-polysaccharide is conjugated to $CRM_{197}$ and wherein the O-polysaccharide includes the O-antigen and core saccharide. In one embodiment, the composition includes a polypeptide derived from *E. coli* or a fragment thereof; and an O-polysaccharide from 14 different serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 15 different serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 16 different serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 17 different serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 18 different serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 19 different serotypes, wherein each O-polysaccharide is conjugated to $CRM_{197}$, and wherein the O-polysaccharide includes the O-antigen and core saccharide. In one embodiment, the composition includes a polypeptide derived from *E. coli* or a fragment thereof; and an O-polysaccharide from 20 different serotypes, wherein each O-polysaccharide is conjugated to $CRM_{197}$, and wherein the O-polysaccharide includes the O-antigen and core saccharide.

In one aspect, the invention relates to a composition that includes a polypeptide derived from *E. coli* or a fragment thereof; and a conjugate including a saccharide covalently bound to a carrier protein, wherein the saccharide includes Formula O25b, wherein n is 15±2. In one aspect, the invention relates to a composition that includes a polypeptide derived from *E. coli* or a fragment thereof; and a conjugate including a saccharide covalently bound to a carrier protein, wherein the saccharide includes Formula O25b, wherein n is 17±2. In one aspect, the invention relates to a composition that includes a polypeptide derived from *E. coli* or a fragment thereof; and a conjugate including a saccharide covalently bound a carrier protein, wherein the saccharide includes Formula O25b, wherein n is 55±2. In another aspect, the invention relates to a composition that includes a polypeptide derived from *E. coli* or a fragment thereof; and a conjugate including a saccharide covalently bound a carrier protein, wherein the saccharide includes Formula O25b, wherein n is 51±2. In one embodiment, the saccharide further includes the *E. coli* R1 core saccharide moiety. In another embodiment, the saccharide further includes the *E. coli* K12 core saccharide moiety. In another embodiment, the saccharide further includes the KDO moiety. Preferably, the carrier protein is $CRM_{197}$. In one embodiment, the conjugate is prepared by single end linked conjugation. In one embodiment, the conjugate is prepared by reductive amination chemistry, preferably in DMSO buffer. In one embodiment, the saccharide is conjugated to the carrier protein through a (2-((2-oxoethyl)thio)ethyl) carbamate (eTEC) spacer. Preferably, the composition further includes a pharmaceutically acceptable diluent.

In one embodiment, the immunogenic composition elicits IgG antibodies in humans, said antibodies being capable of binding an *E. coli* serotype O25B polysaccharide at a concentration of at least 0.2 μg/ml, 0.3 μg/ml, 0.35 μg/ml, 0.4 μg/ml or 0.5 μg/ml as determined by ELISA assay. Therefore, comparison of OPA activity of pre- and post-immunization serum with the immunogenic composition of the invention can be conducted and compared for their response to serotype O25B to assess the potential increase of responders. In one embodiment, the immunogenic composition elicits IgG antibodies in humans, said antibodies being capable of killing *E. coli* serotype O25B as determined by in vitro opsonophagocytic assay. In one embodiment, the immunogenic composition elicits functional antibodies in humans, said antibodies being capable of killing *E. coli* serotype O25B as determined by in vitro opsonophagocytic assay. In one embodiment, the immunogenic composition of the invention increases the proportion of responders against *E. coli* serotype O25B (i.e., individual with a serum having a titer of at least 1:8 as determined by in vitro OPA) as compared to the pre-immunized population. In one embodiment, the immunogenic composition elicits a titer of at least 1:8 against *E. coli* serotype O25B in at least 50% of the subjects as determined by in vitro opsonophagocytic killing assay. In one embodiment, the immunogenic composition of the invention elicits a titer of at least 1:8 against *E. coli* serotype O25B in at least 60%, 70%, 80%, or at least 90% of the subjects as determined by in vitro opsonophagocytic killing assay. In one embodiment, the immunogenic composition of the invention significantly increases the proportion of responders against *E. coli* serotypes O25B (i.e., individual with a serum having a titer of at least 1:8 as determined by in vitro OPA) as compared to the pre-immunized population. In one embodiment, the immunogenic composition of the invention significantly increases the OPA titers of human subjects against *E. coli* serotype O25B as compared to the pre-immunized population.

In one aspect, the invention relates to a composition that includes a polypeptide derived from *E. coli* or a fragment thereof; and a conjugate including a saccharide covalently bound a carrier protein, wherein the saccharide includes Formula O1a, wherein n is 39±2. In another aspect, the invention relates to a composition that includes a polypeptide derived from *E. coli* or a fragment thereof; and a conjugate including a saccharide covalently bound a carrier protein, wherein the saccharide includes Formula O1a, wherein n is 13±2. In one embodiment, the saccharide further includes the *E. coli* R1 core saccharide moiety. In one embodiment, the saccharide further includes the KDO moiety. Preferably, the carrier protein is $CRM_{197}$. In one embodiment, the conjugate is prepared by single end linked conjugation. In one embodiment, the conjugate is prepared by reductive amination chemistry, preferably in DMSO buffer. In one embodiment, the saccharide is conjugated to the carrier protein through a (2-((2-oxoethyl)thio)ethyl) carbamate (eTEC) spacer. Preferably, the composition further includes a pharmaceutically acceptable diluent.

In one embodiment, the immunogenic composition elicits IgG antibodies in humans, said antibodies being capable of binding an *E. coli* serotype O1A polysaccharide at a concentration of at least 0.2 μg/ml, 0.3 μg/ml, 0.35 μg/ml, 0.4 μg/ml or 0.5 μg/ml as determined by ELISA assay. Therefore, comparison of OPA activity of pre- and post-immunization serum with the immunogenic composition of the invention can be conducted and compared for their response to serotype O1A to assess the potential increase of responders. In one embodiment, the immunogenic composition elicits IgG antibodies in humans, said antibodies being capable of killing *E. coli* serotype O1A as determined by in vitro opsonophagocytic assay. In one embodiment, the immunogenic composition elicits functional antibodies in humans, said antibodies being capable of killing *E. coli* serotype O1A as determined by in vitro opsonophagocytic assay. In one embodiment, the immunogenic composition of the invention increases the proportion of responders against *E. coli* serotype O1A (i.e., individual with a serum having a titer of at least 1:8 as determined by in vitro OPA) as compared to the pre-immunized population. In one embodiment, the immunogenic composition elicits a titer of at least 1:8 against *E. coli* serotype O1A in at least 50% of the subjects as determined by in vitro opsonophagocytic killing assay. In one embodiment, the immunogenic composition of the invention elicits a titer of at least 1:8 against *E. coli* serotype O1A in at least 60%, 70%, 80%, or at least 90% of the subjects as determined by in vitro opsonophagocytic killing assay. In one embodiment, the immunogenic composition of the invention significantly increases the proportion of responders against *E. coli* serotypes O1A (i.e., individual with a serum having a titer of at least 1:8 as determined by in vitro OPA) as compared to the pre-immunized population. In one embodiment, the immunogenic composition of the invention significantly increases the OPA titers of human subjects against *E. coli* serotype O1A as compared to the pre-immunized population.

In one aspect, the invention relates to a composition that includes a polypeptide derived from *E. coli* or a fragment thereof; and a conjugate including a saccharide covalently bound a carrier protein, wherein the saccharide includes Formula O2, wherein n is 43±2. In another aspect, the invention relates to a composition that includes a polypeptide derived from *E. coli* or a fragment thereof; and a conjugate including a saccharide covalently bound a carrier protein, wherein the saccharide includes Formula O2, wherein n is 47±2. In another aspect, the invention relates to a composition that includes a conjugate including a saccharide covalently bound a carrier protein, wherein the saccharide includes Formula O2, wherein n is 17±2. In another aspect, the invention relates to a composition that includes a conjugate including a saccharide covalently bound a carrier protein, wherein the saccharide includes Formula O2, wherein n is 18±2. In one embodiment, the saccharide further includes the *E. coli* R1 core saccharide moiety. In another embodiment, the saccharide further includes the *E. coli* R4 core saccharide moiety. In another embodiment, the saccharide further includes the KDO moiety. Preferably, the carrier protein is $CRM_{197}$. In one embodiment, the conjugate is prepared by single end linked conjugation. In one embodiment, the conjugate is prepared by reductive amination chemistry, preferably in DMSO buffer. In one embodiment, the saccharide is conjugated to the carrier protein through a (2-((2-oxoethyl)thio)ethyl)carbamate (eTEC) spacer. Preferably, the composition further includes a pharmaceutically acceptable diluent.

In one embodiment, the immunogenic composition elicits IgG antibodies in humans, said antibodies being capable of binding an *E. coli* serotype O2 polysaccharide at a concentration of at least 0.2 µg/ml, 0.3 µg/ml, 0.35 µg/ml, 0.4 µg/ml or 0.5 µg/ml as determined by ELISA assay. Therefore, comparison of OPA activity of pre- and post-immunization serum with the immunogenic composition of the invention can be conducted and compared for their response to serotype O2 to assess the potential increase of responders. In one embodiment, the immunogenic composition elicits IgG antibodies in humans, said antibodies being capable of killing *E. coli* serotype O2 as determined by in vitro opsonophagocytic assay. In one embodiment, the immunogenic composition elicits functional antibodies in humans, said antibodies being capable of killing *E. coli* serotype O2 as determined by in vitro opsonophagocytic assay. In one embodiment, the immunogenic composition of the invention increases the proportion of responders against *E. coli* serotype O2 (i.e., individual with a serum having a titer of at least 1:8 as determined by in vitro OPA) as compared to the pre-immunized population. In one embodiment, the immunogenic composition elicits a titer of at least 1:8 against *E. coli* serotype O2 in at least 50% of the subjects as determined by in vitro opsonophagocytic killing assay. In one embodiment, the immunogenic composition of the invention elicits a titer of at least 1:8 against *E. coli* serotype O2 in at least 60%, 70%, 80%, or at least 90% of the subjects as determined by in vitro opsonophagocytic killing assay. In one embodiment, the immunogenic composition of the invention significantly increases the proportion of responders against *E. coli* serotypes O2 (i.e., individual with a serum having a titer of at least 1:8 as determined by in vitro OPA) as compared to the pre-immunized population. In one embodiment, the immunogenic composition of the invention significantly increases the OPA titers of human subjects against *E. coli* serotype O2 as compared to the pre-immunized population.

In one aspect, the invention relates to a composition that includes a polypeptide derived from *E. coli* or a fragment thereof; and a conjugate including a saccharide covalently bound a carrier protein, wherein the saccharide includes Formula O6, wherein n is 42±2. In another aspect, the invention relates to a composition that includes a polypeptide derived from *E. coli* or a fragment thereof; and a conjugate including a saccharide covalently bound a carrier protein, wherein the saccharide includes Formula O6, wherein n is 50±2. In another aspect, the invention relates to a composition that includes a conjugate including a saccharide covalently bound a carrier protein, wherein the saccharide includes Formula O6, wherein n is 17±2. In another aspect, the invention relates to a composition that includes a conjugate including a saccharide covalently bound a carrier protein, wherein the saccharide includes Formula O6, wherein n is 18±2. In one embodiment, the saccharide further includes the *E. coli* R1 core saccharide moiety. In one embodiment, the saccharide further includes the KDO moiety. Preferably, the carrier protein is $CRM_{197}$. In one embodiment, the conjugate is prepared by single end linked conjugation. In one embodiment, the conjugate is prepared by reductive amination chemistry, preferably in DMSO buffer. In one embodiment, the saccharide is conjugated to the carrier protein through a (2-((2-oxoethyl)thio)ethyl) carbamate (eTEC) spacer. Preferably, the composition further includes a pharmaceutically acceptable diluent.

In one embodiment, the immunogenic composition elicits IgG antibodies in humans, said antibodies being capable of binding an *E. coli* serotype O6 polysaccharide at a concentration of at least 0.2 pg/ml, 0.3 pg/ml, 0.35 pg/ml, 0.4 pg/ml or 0.5 pg/ml as determined by ELISA assay. Therefore, comparison of OPA activity of pre- and post-immunization serum with the immunogenic composition of the invention can be conducted and compared for their response to serotype O6 to assess the potential increase of responders. In one embodiment, the immunogenic composition elicits IgG antibodies in humans, said antibodies being capable of killing *E. coli* serotype O6 as determined by in vitro opsonophagocytic assay. In one embodiment, the immunogenic composition elicits functional antibodies in humans, said antibodies being capable of killing *E. coli* serotype O6 as determined by in vitro opsonophagocytic assay. In one embodiment, the immunogenic composition of the invention increases the proportion of responders against *E. coli* serotype O6 (i.e., individual with a serum having a titer of at least 1:8 as determined by in vitro OPA) as compared to the pre-immunized population. In one embodiment, the immunogenic composition elicits a titer of at least 1:8 against *E. coli* serotype O6 in at least 50% of the subjects as determined by in vitro opsonophagocytic killing assay. In one embodiment, the immunogenic composition of the invention elicits a titer of at least 1:8 against *E. coli* serotype O6 in at least 60%, 70%, 80%, or at least 90% of the subjects as determined by in vitro opsonophagocytic killing assay. In one embodiment, the immunogenic composition of the invention significantly increases the proportion of responders against *E. coli* serotypes O6 (i.e., individual with a serum having a titer of at least 1:8 as determined by in vitro OPA) as compared to the pre-immunized population. In one embodiment, the immunogenic composition of the invention significantly increases the OPA titers of human subjects against *E. coli* serotype O6 as compared to the pre-immunized population.

In one aspect, the composition includes a polypeptide derived from *E. coli* or a fragment thereof; and a conjugate including a saccharide covalently bound to a carrier protein, wherein the saccharide includes a structure selected from any one of Formula O1 (e.g., Formula O1A, Formula O1B, and Formula O1C), Formula O2, Formula O3, Formula O4 (e.g., Formula O4:K52 and Formula O4:K6), Formula O5 (e.g., Formula O5ab and Formula O5ac (strain 180/C3)), Formula O6 (e.g., Formula O6:K2; K13; K15 and Formula O6:K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62$D_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 1 to 100, preferably from 31 to 90. In one embodiment, the saccharide further includes the *E. coli* R1 core saccharide moiety. In one embodiment, the saccharide further includes the *E. coli* R2 core saccharide moiety. In one embodiment, the saccharide further includes the *E. coli* R3 core saccharide moiety. In another embodiment, the saccharide further includes the *E. coli* R4 core saccharide moiety. In one embodiment, the saccharide further includes the *E. coli* K12 core saccharide moiety. In another embodiment, the saccharide further includes the KDO moiety. Preferably, the carrier protein is $CRM_{197}$. In one embodiment, the conjugate is prepared by single end linked conjugation. In one embodiment, the conjugate is prepared by reductive amination chemistry, preferably in DMSO buffer. In one embodiment, the saccharide is conjugated to the carrier protein through a (2-((2-oxoethyl)thio)ethyl)carbamate (eTEC) spacer. Preferably, the composition further includes a pharmaceutically acceptable diluent. In one embodiment, the composition further includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29 additional conjugates to at most 30 additional conjugates, each conjugate including a saccharide covalently bound to a carrier protein, wherein the saccharide includes a structure selected from any one of said Formulas.

A. Saccharide

In one embodiment, the saccharide is produced by expression (not necessarily overexpression) of different Wzz proteins (e.g., WzzB) to control of the size of the saccharide.

As used herein, the term "saccharide" refers to a single sugar moiety or monosaccharide unit as well as combinations of two or more single sugar moieties or monosaccharide units covalently linked to form disaccharides, oligosaccharides, and polysaccharides. The saccharide may be linear or branched.

In one embodiment, the saccharide is produced in a recombinant Gram-negative bacterium. In one embodiment, the saccharide is produced in a recombinant *E. coli* cell. In one embodiment, the saccharide is produced in a recombinant *Salmonella* cell. Exemplary bacteria include *E. coli* O25K5H1, *E. coli* BD559, *E. coli* GAR2831, *E. coli* GAR865, *E. coli* GAR868, *E. coli* GAR869, *E. coli* GAR872, *E. coli* GAR878, *E. coli* GAR896, *E. coli* GAR1902, *E. coli* O25a ETC NR-5, *E. coli* O157:H7:K–, *Salmonella enterica* serovar *Typhimurium* strain LT2, *E. coli* GAR2401, *Salmonella enterica* serotype *Enteritidis* CVD 1943, *Salmonella enterica* serotype *Typhimurium* CVD 1925, *Salmonella enterica* serotype Paratyphi A CVD 1902, and *Shigella flexneri* CVD 1208S. In one embodiment, the bacterium is not *E. coli* GAR2401. This genetic approach towards saccharide production allows for efficient production of O-polysaccharides and O-antigen molecules as vaccine components.

The term "wzz protein," as used herein, refers to a chain length determinant polypeptide, such as, for example, wzzB, wzz, $wzz_{SF}$, $wZZ_{ST}$, fepE, $wzz_{fepE}$, wzz1 and wzz2. The GenBank accession numbers for the exemplary wzz gene sequences are AF011910 for E4991/76, AF011911 for F186, AF011912 for M70/1-1, AF011913 for 79/311, AF011914 for Bi7509-41, AF011915 for C664-1992, AF011916 for C258-94, AF011917 for C722-89, and AF011919 for EDL933. The GenBank accession numbers for the G7 and Bi316-41 wzz genes sequences are U39305 and U39306, respectively. Further GenBank accession numbers for exemplary wzz gene sequences are NP_459581 for *Salmonella enterica* subsp. *enterica* serovar *Typhimurium* str. LT2 FepE; AIG66859 for *E. coli* O157:H7 Strain EDL933 FepE; NP_461024 for *Salmonella enterica* subsp. *enterica* serovar *Typhimurium* str. LT2 WzzB. NP_416531 for *E. coli* K-12 substr. MG1655 WzzB, NP_415119 for *E. coli* K-12 substr. MG1655 FepE. In preferred embodiments, the wzz family protein is any one of wzzB, wzz, $wzz_{SF}$, $wZZ_{ST}$, fepE, $wzz_{fepE}$, wZZ1 and wzz2, most preferably wzzB, more preferably fepE.

Exemplary wzzB sequences include sequences set forth in SEQ ID Nos: 30-34. Exemplary FepE sequences include sequences set forth in SEQ ID Nos: 35-39.

In some embodiments, a modified saccharide (modified as compared to the corresponding wild-type saccharide) may be produced by expressing (not necessarily overexpressing) a wzz family protein (e.g., fepE) from a Gram-negative bacterium in a Gram-negative bacterium and/or by switching off (i.e., repressing, deleting, removing) a second wzz gene (e.g., wzzB) to generate high molecular weight saccharides, such as lipopolysaccharides, containing intermediate or long O-antigen chains. For example, the modified saccharides may be produced by expressing (not necessarily overexpressing) wzz2 and switching off wzz1. Or, in the alternative, the modified saccharides may be produced by expressing (not necessarily overexpressing) wzzfepE and switching off wzzB. In another embodiment, the modified saccharides may be produced by expressing (not necessarily overexpressing) wzzB but switching off wzzfepE. In another embodiment, the modified saccharides may be produced by expressing fepE. Preferably, the wzz family protein is derived from a strain that is heterologous to the host cell.

In some embodiments, the saccharide is produced by expressing a wzz family protein having an amino acid sequence that is at least 30%, 50%, 70%, 75%, 80%, 85%, 90%, 95%, 98%, 99% or 100% sequence identity to any one of SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, and SEQ ID NO: 39. In one embodiment, the wzz family protein includes a sequence selected from any one of SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, and SEQ ID NO: 39. Preferably, the wzz family protein has at least 30%, 50%, 70%, 75%, 80%, 85%, 90%, 95%, 98%, 99% or 100% sequence identity to SEQ ID NO: 30, SEQ ID NO: 31, SEQ ID NO: 32, SEQ ID NO: 33, SEQ ID NO: 34. In some embodiments, the saccharide is produced by expressing a protein having an amino acid sequence that is at least 30%, 50%, 70%, 75%, 80%, 85%, 90%, 95%, 98%, 99% or 100% sequence identity to an fepE protein.

In one aspect, the invention relates to saccharides produced by expressing a wzz family protein, preferably fepE, in a Gram-negative bacterium to generate high molecular weight saccharides containing intermediate or long O-antigen chains, which have an increase of at least 1, 2, 3, 4, or 5 repeating units, as compared to the corresponding wild-type O-polysaccharide. In one aspect, the invention relates to saccharides produced by a Gram-negative bacterium in culture that expresses (not necessarily overexpresses) a wzz family protein (e.g., wzzB) from a Gram-negative bacterium to generate high molecular weight saccharides containing intermediate or long O-antigen chains, which have an increase of at least 1, 2, 3, 4, or 5 repeating units, as compared to the corresponding wild-type O-antigen. See description of O-polysaccharides and O-antigens below for additional exemplary saccharides having increased number of repeat units, as compared to the corresponding wild-type saccharides. A desired chain length is the one which produces improved or maximal immunogenicity in the context of a given vaccine construct.

In another embodiment, the saccharide includes any one Formula selected from Table 1, wherein the number of repeat units n in the saccharide is greater than the number of repeat units in the corresponding wild-type O-polysaccharide by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more repeat units. Preferably, the saccharide includes an increase of at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 repeat units, as compared to the corresponding wild-type O-polysaccharide. See, for example, Table 24. Methods of determining the length of saccharides are known in the art. Such methods include nuclear magnetic resonance, mass spectroscopy, and size exclusion chromatography, as described in Example 13.

In a preferred embodiment, the invention relates to a saccharide produced in a recombinant *E. coli* host cell, wherein the gene for an endogenous wzz O-antigen length regulator (e.g., wzzB) is deleted and is replaced by a (second) wzz gene from a Gram-negative bacterium heterologous to the recombinant *E. coli* host cell (e.g., *Salmonella* fepE) to generate high molecular weight saccharides, such as lipopolysaccharides, containing intermediate or long O-antigen chains. In some embodiments, the recombinant *E. coli* host cell includes a wzz gene from *Salmonella*, preferably from *Salmonella enterica*.

In one embodiment, the host cell includes the heterologous gene for a wzz family protein as a stably maintained plasmid vector. In another embodiment, the host cell includes the heterologous gene for a wzz family protein as an integrated gene in the chromosomal DNA of the host cell. Methods of stably expressing a plasmid vector in an *E. coli* host cell and methods of integrating a heterologous gene into the chromosome of an *E. coli* host cell are known in the art. In one embodiment, the host cell includes the heterologous genes for an O-antigen as a stably maintained plasmid vector. In another embodiment, the host cell includes the heterologous genes for an O-antigen as an integrated gene in the chromosomal DNA of the host cell. Methods of stably expressing a plasmid vector in an *E. coli* host cell and a *Salmonella* host cell are known in the art. Methods of integrating a heterologous gene into the chromosome of an *E. coli* host cell and a *Salmonella* host cell are known in the art. In one aspect, the recombinant host cell is cultured in a medium that comprises a carbon source. Carbon sources for culturing *E. coli* are known in the art. Exemplary carbon sources include sugar alcohols, polyols, aldol sugars or keto sugars including but not limited to arabinose, cellobiose, fructose, glucose, glycerol, inositol, lactose, maltose, mannitol, mannose, rhamnose, raffinose, sorbitol, sorbose, sucrose, trehalose, pyruvate, succinate and methylamine. In a preferred embodiment, the medium includes glucose. In some embodiments, the medium includes a polyol or aldol sugar, for example, mannitol, inositol, sorbose, glycerol, sorbitol, lactose and arabinose as the carbon source. All of the carbon sources may be added to the medium before the start of culturing, or it may be added step by step or continuously during culturing.

An exemplary culture medium for the recombinant host cell includes an element selected from any one of $KH_2PO_4$, $K_2HPO_4$, $(NH_4)_2SO_4$, sodium citrate, $Na_2SO_4$, aspartic acid, glucose, $MgSO_4$, $FeSO_4\cdot7H_2O$, $Na_2MoO_4\cdot2H_2O$, $H_3BO_3$, $CoCl_2\cdot6H_2O$, $CuCl_2\cdot2H_2O$, $MnCl_2\cdot4H_2O$, $ZnCl_2$ and $CaCl_2\cdot2H_2O$. Preferably, the medium includes $KH_2PO_4$, $K_2HPO_4$, $(NH_4)_2SO_4$, sodium citrate, $Na_2SO_4$, aspartic acid, glucose, $MgSO_4$, $FeSO_4\cdot7H_2O$, $Na_2MoO_4\cdot2H_2O$, $H_3BO_3$, $CoCl_2\cdot6H_2O$, $CuCl_2\cdot2H_2O$, $MnCl_2\cdot4H_2O$, $ZnCl_2$ and $CaCl_2\cdot2H_2O$.

The medium used herein may be solid or liquid, synthetic (i.e. man-made) or natural, and may include sufficient nutrients for the cultivation of the recombinant host cell. Preferably, the medium is a liquid medium.

In some embodiments, the medium may further include suitable inorganic salts. In some embodiments, the medium may further include trace nutrients. In some embodiments, the medium may further include growth factors. In some embodiments, the medium may further include an additional carbon source. In some embodiments, the medium may further include suitable inorganic salts, trace nutrients, growth factors, and a supplementary carbon source. Inorganic salts, trace nutrients, growth factors, and supplementary carbon sources suitable for culturing E. coli are known in the art.

In some embodiments, the medium may include additional components as appropriate, such as peptone, N—Z Amine, enzymatic soy hydrosylate, additional yeast extract, malt extract, supplemental carbon sources and various vitamins. In some embodiments, the medium does not include such additional components, such as peptone, N—Z Amine, enzymatic soy hydrosylate, additional yeast extract, malt extract, supplemental carbon sources and various vitamins.

Illustrative examples of suitable supplemental carbon sources include, but are not limited to other carbohydrates, such as glucose, fructose, mannitol, starch or starch hydrolysate, cellulose hydrolysate and molasses; organic acids, such as acetic acid, propionic acid, lactic acid, formic acid, malic acid, citric acid, and fumaric acid; and alcohols, such as glycerol, inositol, mannitol and sorbitol.

In some embodiments, the medium further includes a nitrogen source. Nitrogen sources suitable for culturing E. coli are known in the art. Illustrative examples of suitable nitrogen sources include, but are not limited to ammonia, including ammonia gas and aqueous ammonia; ammonium salts of inorganic or organic acids, such as ammonium chloride, ammonium nitrate, ammonium phosphate, ammonium sulfate and ammonium acetate; urea; nitrate or nitrite salts, and other nitrogen-containing materials, including amino acids as either pure or crude preparations, meat extract, peptone, fish meal, fish hydrolysate, corn steep liquor, casein hydrolysate, soybean cake hydrolysate, yeast extract, dried yeast, ethanol-yeast distillate, soybean flour, cottonseed meal, and the like.

In some embodiments, the medium includes an inorganic salt. Illustrative examples of suitable inorganic salts include, but are not limited to salts of potassium, calcium, sodium, magnesium, manganese, iron, cobalt, zinc, copper, molybdenum, tungsten and other trace elements, and phosphoric acid.

In some embodiments, the medium includes appropriate growth factors. Illustrative examples of appropriate trace nutrients, growth factors, and the like include, but are not limited to coenzyme A, pantothenic acid, pyridoxine-HCl, biotin, thiamine, riboflavin, flavine mononucleotide, flavine adenine dinucleotide, DL-6,8-thioctic acid, folic acid, Vitamin $B_{12}$, other vitamins, amino acids such as cysteine and hydroxyproline, bases such as adenine, uracil, guanine, thymine and cytosine, sodium thiosulfate, p- or r-aminobenzoic acid, niacinamide, nitriloacetate, and the like, either as pure or partially purified chemical compounds or as present in natural materials. The amounts may be determined empirically by one skilled in the art according to methods and techniques known in the art.

In another embodiment, the modified saccharide (as compared to the corresponding wild-type saccharide) described herein is synthetically produced, for example, in vitro. Synthetic production or synthesis of the saccharides may facilitate the avoidance of cost- and time-intensive production processes. In one embodiment, the saccharide is synthetically synthesized, such as, for example, by using sequential glycosylation strategy or a combination of sequential glycosylations and [3+2] block synthetic strategy from suitably protected monosaccharide intermediates. For example, thioglycosides and glycosyl trichloroacetimidate derivatives may be used as glycosyl donors in the glycosylations. In one embodiment, a saccharide that is synthetically synthesized in vitro has the identical structure to a saccharide produced by recombinant means, such as by manipulation of a wzz family protein described above.

The saccharide produced (by recombinant or synthetic means) includes a structure derived from any E. coli serotype including, for example, any one of the following E. coli serotypes: O1 (e.g., O1A, O1B, and O1C), O2, O3, O4 (e.g., O4:K52 and O4:K6), O5 (e.g., O5ab and O5ac (strain 180/C3)), O6 (e.g., O6:K2; K13; K15 and O6:K54), O7, O8, O9, O10, O11, O12, O13, O14, O15, O16, O17, O18 (e.g., O18A, O18ac, O18A1, O18B, and O18B1), O19, O20, O21, O22, O23 (e.g., O23A), O24, O25 (e.g., O25a and O25b), O26, O27, O28, O29, O30, O32, O33, O34, O35, O36, O37, O38, O39, O40, O41, O42, O43, O44, O45 (e.g., O45 and O45rel), O46, O48, O49, O50, O51, O52, O53, O54, O55, O56, O57, O58, O59, O60, O61, O62, 62D$_1$, O63, O64, O65, O66, O68, O69, O70, O71, O73 (e.g., O73 (strain 73-1)), O74, O75, O76, O77, O78, O79, O80, O81, O82, O83, O84, O85, O86, O87, O88, O89, O90, O91, O92, O93, O95, O96, O97, O98, O99, O100, O101, O102, O103, O104, O105, O106, O107, O108, O109, O110, O111, O112, O113, O114, O115, O116, O117, O118, O119, O120, O121, O123, O124, O125, O126, O127, O128, O129, O130, O131, O132, O133, O134, O135, O136, O137, O138, O139, O140, O141, O142, O143, O144, O145, O146, O147, O148, O149, O150, O151, O152, O153, O154, O155, O156, O157, O158, O159, O160, O161, O162, O163, O164, O165, O166, O167, O168, O169, O170, O171, O172, O173, O174, O175, O176, O177, O178, O179, O180, O181, O182, O183, O184, O185, O186, and O187.

The individual polysaccharides are typically purified (enriched with respect to the amount of polysaccharide-protein conjugate) through methods known in the art, such as, for example, dialysis, concentration operations, diafiltration operations, tangential flow filtration, precipitation, elution, centrifugation, precipitation, ultra-filtration, depth filtration, and/or column chromatography (ion exchange chromatography, multimodal ion exchange chromatography, DEAE, and hydrophobic interaction chromatography). Preferably, the polysaccharides are purified through a method that includes tangential flow filtration.

Purified polysaccharides may be activated (e.g., chemically activated) to make them capable of reacting (e.g., either directly to the carrier protein or via a linker such as an eTEC spacer) and then incorporated into glycoconjugates of the invention, as further described herein.

In one preferred embodiment, the saccharide of the invention is derived from an *E. coli* serotype, wherein the serotype is O25a. In another preferred embodiment, the serotype is O25b. In another preferred embodiment, the serotype is O1A. In another preferred embodiment, the serotype is O2. In another preferred embodiment, the serotype is O6. In another preferred embodiment, the serotype is O17. In another preferred embodiment, the serotype is O15. In another preferred embodiment, the serotype is O18A. In another preferred embodiment, the serotype is O75. In another preferred embodiment, the serotype is O4. In another preferred embodiment, the serotype is O16. In another preferred embodiment, the serotype is O13. In another preferred embodiment, the serotype is O7. In another preferred embodiment, the serotype is O8. In another preferred embodiment, the serotype is O9.

As used herein, reference to any of the serotypes listed above, refers to a serotype that encompasses a repeating unit structure (O-unit, as described below) known in the art and is unique to the corresponding serotype. For example, the term "O25a" serotype (also known in the art as serotype "O25") refers to a serotype that encompasses Formula O25 shown in Table 1. As another example, the term "O25b" serotype refers to a serotype that encompasses Formula O25b shown in Table 1.

As used herein, the serotypes are referred generically herein unless specified otherwise such that, for example, the term Formula "O18" refers generically to encompass Formula O18A, Formula O18ac, Formula 18A1, Formula O18B, and Formula O18B1.

As used herein, the term "O1" refers generically to encompass the species of Formula that include the generic term "O1" in the Formula name according to Table 1, such as any one of Formula O1A, Formula O1A1, Formula O1B, and Formula O1C, each of which is shown in Table 1. Accordingly, an "O1 serotype" refers generically to a serotype that encompasses any one of Formula O1A, Formula O1A1, Formula O1B, and Formula O1C.

As used herein, the term "O6" refers generically to species of Formula that include the generic term "O6" in the Formula name according to Table 1, such as any one of Formula O6:K2; K13; K15; and O6:K54, each of which is shown in Table 1. Accordingly, an "O6 serotype" refers generically to a serotype that encompasses any one of Formula O6:K2; K13; K15; and O6:K54.

Other examples of terms that refer generically to species of a Formula that include the generic term in the Formula name according to Table 1 include: "O4", "O5", "O18", and "O45".

As used herein, the term "O2" refers to Formula O2 shown in Table 1. The term "O2 O-antigen" refers to a saccharide that encompasses Formula O2 shown in Table 1.

As used herein, reference to an O-antigen from a serotype listed above refers to a saccharide that encompasses the formula labeled with the corresponding serotype name. For example, the term "O25B O-antigen" refers to a saccharide that encompasses Formula O25B shown in Table 1.

As another example, the term "O1 O-antigen" generically refers to a saccharide that encompasses a Formula including the term "O1," such as the Formula O1A, Formula O1A1, Formula O1B, and Formula O1C, each of which are shown in Table 1. As another example, the term "O6 O-antigen" generically refers to a saccharide that encompasses a Formula including the term "O6," such as Formula O6:K2; Formula O6:K13; Formula O6:K15 and Formula O6:K54, each of which are shown in Table 1.

B. O-Polysaccharide

As used herein, the term "O-polysaccharide" refers to any structure that includes an O-antigen, provided that the structure does not include a whole cell or Lipid A. For example, in one embodiment, the O-polysaccharide includes a lipopolysaccharide wherein the Lipid A is not bound. The step of removing Lipid A is known in the art and includes, as an example, heat treatment with addition of an acid. An exemplary process includes treatment with 1% acetic acid at 100° C. for 90 minutes. This process is combined with a process of isolating Lipid A as removed. An exemplary process for isolating Lipid A includes ultracentrifugation.

In one embodiment, the O-polysaccharide refers to a structure that consists of the O-antigen, in which case, the O-polysaccharide is synonymous with the term O-antigen. In one preferred embodiment, the O-polysaccharide refers to a structure that includes repeating units of the O-antigen, without the core saccharide. Accordingly, in one embodiment, the O-polysaccharide does not include an *E. coli* R1 core moiety. In another embodiment, the O-polysaccharide does not include an *E. coli* R2 core moiety. In another embodiment, the O-polysaccharide does not include an *E. coli* R3 core moiety. In another embodiment, the O-polysaccharide does not include an *E. coli* R4 core moiety. In another embodiment, the O-polysaccharide does not include an *E. coli* K12 core moiety. In another preferred embodiment, the O-polysaccharide refers to a structure that includes an O-antigen and a core saccharide. In another embodiment, the O-polysaccharide refers to a structure that includes an O-antigen, a core saccharide, and a KDO moiety.

Methods of purifying an O-polysaccharide, which includes the core oligosaccharide, from LPS are known in the art. For example, after purification of LPS, purified LPS may be hydrolyzed by heating in 1% (v/v) acetic acid for 90 minutes at 100 degrees Celsius, followed by ultracentrifugation at 142,000×g for 5 hours at 4 degrees Celsius. The supernatant containing the O-polysaccharide is freeze-dried and stored at 4 degrees Celsius. In certain embodiments, deletion of capsule synthesis genes to enable simple purification of O-polysaccharide is described.

The O-polysaccharide can be isolated by methods including, but not limited to mild acid hydrolysis to remove lipid A from LPS. Other embodiments may include use of hydrazine as an agent for O-polysaccharide preparation. Preparation of LPS can be accomplished by known methods in the art.

In certain embodiments, the O-polysaccharides purified from wild-type, modified, or attenuated Gram-negative bacterial strains that express (not necessarily overexpress) a Wzz protein (e.g., wzzB) are provided for use in conjugate vaccines. In preferred embodiments, the O-polysaccharide chain is purified from the Gram-negative bacterial strain expressing (not necessarily overexpressing) wzz protein for use as a vaccine antigen either as a conjugate or complexed vaccine.

In one embodiment, the O-polysaccharide has a molecular weight that is increased by about 1-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 26-fold, 27-fold, 28-fold, 29-fold, 30-fold, 31-fold, 32-fold, 33-fold, 34-fold, 35-fold, 36-fold, 37-fold, 38-fold, 39-fold, 40-fold, 41-fold, 42-fold, 43-fold, 44-fold, 45-fold, 46-fold, 47-fold, 48-fold, 49-fold, 50-fold, 51-fold, 52-fold, 53-fold, 54-fold, 55-fold, 56-fold, 57-fold, 58-fold, 59-fold, 60-fold, 61-fold, 62-fold, 63-fold, 64-fold, 65-fold, 66-fold, 67-fold, 68-fold, 69-fold, 70-fold, 71-fold, 72-fold, 73-fold, 74-fold, 75-fold, 76-fold, 77-fold, 78-fold, 79-fold, 80-fold, 81-fold, 82-fold, 83-fold, 84-fold, 85-fold, 86-fold, 87-fold, 88-fold, 89-fold, 90-fold, 91-fold, 92-fold, 93-fold, 94-fold, 95-fold, 96-fold, 97-fold, 98-fold, 99-fold, 100-fold or more, as compared to the corresponding wild-type O-polysaccharide. In a preferred embodiment, the O-polysaccharide has a molecular weight that is increased by at least 1-fold and at most 5-fold, as compared to the corresponding wild-type O-polysaccharide. In another embodiment, the O-polysaccharide has a molecular weight that is increased by at least 2-fold and at most 4-fold, as compared to the corresponding wild-type O-polysaccharide. An increase in molecular weight of the O-polysaccharide, as compared to the corresponding wild-type O-polysaccharide, is preferably associated with an increase in number of O-antigen repeat units. In one embodiment, the increase in molecular weight of the O-polysaccharide is due to the wzz family protein.

In one embodiment, the O-polysaccharide has a molecular weight that is increased by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 kDa or more, as compared to the corresponding wild-type O-polysaccharide. In one embodiment, the O-polysaccharide of the invention has a molecular weight that is increased by at least 1 and at most 200 kDa, as compared to the corresponding wild-type O-polysaccharide. In one embodiment, the molecular weight is increased by at least 5 and at most 200 kDa. In one embodiment, the molecular weight is increased by at least 10 and at most 200 kDa. In one embodiment, the molecular weight is increased by at least 12 and at most 200 kDa. In one embodiment, the molecular weight is increased by at least 15 and at most 200 kDa. In one embodiment, the molecular weight is increased by at least 18 and at most 200 kDa. In one embodiment, the molecular weight is increased by at least 20 and at most 200 kDa. In one embodiment, the molecular weight is increased by at least 21 and at most 200 kDa. In one embodiment, the molecular weight is increased by at least 22 and at most 200 kDa. In one embodiment, the molecular weight is increased by at least 30 and at most 200 kDa. In one embodiment, the molecular weight is increased by at least 1 and at most 100 kDa. In one embodiment, the molecular weight is increased by at least 5 and at most 100 kDa. In one embodiment, the molecular weight is increased by at least 10 and at most 100 kDa. In one embodiment, the molecular weight is increased by at least 12 and at most 100 kDa. In one embodiment, the molecular weight is increased by at least 15 and at most 100 kDa. In one embodiment, the molecular weight is increased by at least 20 and at most 100 kDa. In one embodiment, the molecular weight is increased by at least 1 and at most 75 kDa. In one embodiment, the molecular weight is increased by at least 5 and at most 75 kDa. In one embodiment, the molecular weight is increased by at least 10 and at most 75 kDa. In one embodiment, the molecular weight is increased by at least 12 and at most 75 kDa. In one embodiment, the molecular weight is increased by at least 15 and at most 75 kDa. In one embodiment, the molecular weight is increased by at least 18 and at most 75 kDa. In one embodiment, the molecular weight is increased by at least 20 and at most 75 kDa. In one embodiment, the molecular weight is increased by at least 30 and at most 75 kDa. In one embodiment, the molecular weight is increased by at least 10 and at most 90 kDa. In one embodiment, the molecular weight is increased by at least 12 and at most 85 kDa. In one embodiment, the molecular weight is increased by at least 10 and at most 75 kDa. In one embodiment, the molecular weight is increased by at least 10 and at most 70 kDa. In one embodiment, the molecular weight is increased by at least 10 and at most 60 kDa. In one embodiment, the molecular weight is increased by at least 10 and at most 50 kDa. In one embodiment, the molecular weight is increased by at least 10 and at most 49 kDa. In one embodiment, the molecular weight is increased by at least 10 and at most 48 kDa. In one embodiment, the molecular weight is increased by at least 10 and at most 47 kDa. In one embodiment, the molecular weight is increased by at least 10 and at most 46 kDa. In one embodiment, the molecular weight is increased by at least 20 and at most 45 kDa. In one embodiment, the molecular weight is increased by at least 20 and at most 44 kDa. In one embodiment, the molecular weight is increased by at least 20 and at most 43 kDa. In one embodiment, the molecular weight is increased by at least 20 and at most 42 kDa. In one embodiment, the molecular weight is increased by at least 20 and at most 41 kDa. Such an increase in molecular weight of the O-polysaccharide, as compared to the corresponding wild-type O-polysaccharide, is preferably associated with an increase in number of O-antigen repeat units. In one embodiment, the increase in molecular weight of the O-polysaccharide is due to the wzz family protein. See, for example, Table 21.

In another embodiment, the O-polysaccharide includes any one Formula selected from Table 1, wherein the number of repeat units n in the O-polysaccharide is greater than the number of repeat units in the corresponding wild-type O-polysaccharide by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more repeat units. Preferably, the saccharide includes an increase of at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 repeat units, as compared to the corresponding wild-type O-polysaccharide. See, for example, Table 21.

C. O-Antigen

The O-antigen is part of the lipopolysaccharide (LPS) in the outer membrane of Gram-negative bacteria. The O-antigen is on the cell surface and is a variable cell constituent. The variability of the O-antigen provides a basis for serotyping of Gram-negative bacteria. The current *E. coli* serotyping scheme includes O-polysaccharides 1 to 181.

The O-antigen includes oligosaccharide repeating units (O-units), the wild type structure of which usually contains two to eight residues from a broad range of sugars. The O-units of exemplary *E. coli* O-antigens are shown in Table 1, see also FIG. 9A-9C and FIG. 10A-10B. In one embodiment, the saccharide of the invention may be one oligosaccharide unit. In one embodiment, the saccharide of the invention is one repeating oligosaccharide unit of the relevant serotype. In such embodiments, the saccharide may include a structure selected from any one of Formula O1a, Formula O2, Formula O6, Formula O8, Formula O9a, Formula O9, Formula O20ab, Formula O20ac, Formula O25b, Formula O52, Formula O97, and Formula O101. In a further embodiment, the saccharide may include a structure selected from any one of Formula O1a, Formula O2, Formula O6, and Formula O25b.

In one embodiment, the saccharide of the invention may be oligosaccharides. Oligosaccharides have a low number of repeat units (typically 5-15 repeat units) and are typically derived synthetically or by hydrolysis of polysaccharides. In such embodiments, the saccharide may include a structure selected from any one of Formula O1a, Formula O2, Formula O6, Formula O8, Formula O9a, Formula O9, Formula O20ab, Formula O20ac, Formula O25b, Formula O52, Formula O97, and Formula O101. In a further embodiment, the saccharide may include a structure selected from any one of Formula O1a, Formula O2, Formula O6, and Formula O25b.

Preferably, all of the saccharides of the present invention and in the immunogenic compositions of the present invention are polysaccharides. High molecular weight polysaccharides may induce certain antibody immune responses due to the epitopes present on the antigenic surface. The isolation and purification of high molecular weight polysaccharides are preferably contemplated for use in the conjugates, compositions and methods of the present invention.

In some embodiments, the number of repeat O units in each individual O-antigen polymer (and therefore the length and molecular weight of the polymer chain) depends on the wzz chain length regulator, an inner membrane protein. Different wzz proteins confer different ranges of modal lengths (4 to >100 repeat units). The term "modal length" refers to the number of repeating O-units. Gram-negative bacteria often have two different Wzz proteins that confer two distinct OAg modal chain lengths, one longer and one shorter. The expression (not necessarily the overexpression) of wzz family proteins (e.g., wzzB) in Gram-negative bacteria may allow for the manipulation of O-antigen length, to shift or to bias bacterial production of O-antigens of certain length ranges, and to enhance production of high-yield large molecular weight lipopolysaccharides. In one embodiment, a "short" modal length as used herein refers to a low number of repeat O-units, e.g., 1-20. In one embodiment, a "long" modal length as used herein refers to a number of repeat O-units greater than 20 and up to a maximum of 40. In one embodiment, a "very long" modal length as used herein refers to greater than 40 repeat O-units.

In one embodiment, the saccharide produced has an increase of at least 10 repeating units, 15 repeating units, 20 repeating units, 25 repeating units, 30 repeating units, 35 repeating units, 40 repeating units, 45 repeating units, 50 repeating units, 55 repeating units, 60 repeating units, 65 repeating units, 70 repeating units, 75 repeating units, 80 repeating units, 85 repeating units, 90 repeating units, 95 repeating units, or 100 repeating units, as compared to the corresponding wild-type O-polysaccharide.

In another embodiment, the saccharide of the invention has an increase of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more repeat units, as compared to the corresponding wild-type O-polysaccharide. Preferably, the saccharide includes an increase of at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 repeat units, as compared to the corresponding wild-type O-polysaccharide. See, for example, Table 21. Methods of determining the length of saccharides are known in the art. Such methods include nuclear magnetic resonance, mass spectroscopy, and size exclusion chromatography, as described in Example 13.

Methods of determining the number of repeat units in the saccharide are also known in the art. For example, the number of repeat units (or "n" in the Formula) may be calculated by dividing the molecular weight of the polysaccharide (without the molecular weight of the core saccharide or KDO residue) by the molecular weight of the repeat unit (i.e., molecular weight of the structure in the corresponding Formula, shown for example in Table 1, which may be theoretically calculated as the sum of the molecular weight of each monosaccharide within the Formula). The molecular weight of each monosaccharide within the Formula is known in the art. The molecular weight of a repeat unit of Formula O25b, for example, is about 862 Da. The molecular weight of a repeat unit of Formula O1a, for example, is about 845 Da. The molecular weight of a repeat unit of Formula O2, for example, is about 829 Da. The molecular weight of a repeat unit of Formula O6, for example, is about 893 Da. When determining the number of repeat units in a conjugate, the carrier protein molecular weight and the protein:polysaccharide ratio is factored into the calculation. As defined herein, "n" refers to the number of repeating units (represented in brackets in Table 1) in a polysaccharide molecule. As is known in the art, in biological macromolecules, repeating structures may be interspersed with regions of imperfect repeats, such as, for example, missing branches. In addition, it is known in the art that polysaccharides isolated and purified from natural sources such as bacteria may be heterogenous in size and in branching. In such a case, n may represent an average or median value for n for the molecules in a population.

In one embodiment, the O-polysaccharide has an increase of at least one repeat unit of an O-antigen, as compared to the corresponding wild-type O-polysaccharide. The repeat units of O-antigens are shown in Table 1. In one embodiment, the O-polysaccharide includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more total repeat units. Preferably, the saccharide has a total of at least 3 to at most 80 repeat units. In another embodiment, the O-polysaccharide has an increase of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more repeat units, as compared to the corresponding wild-type O-polysaccharide.

In one embodiment, the saccharide includes an O-antigen wherein n in any of the O-antigen formulas (such as, for example, the Formulas shown in Table 1 (see also FIG. 9A-9C and FIG. 10A-10B)) is an integer of at least 1, 2, 3, 4, 5, 10, 20, 21, 22, 23, 24, 25, 26, 27, 28, 29, 30, 31, 32, 33, 34, 35, 36, 37, 38, 39, 40, and at most 200, 100, 99, 98, 97, 96, 95, 94, 93, 92, 91, 90, 89, 88, 87, 86, 81, 80, 79, 78, 77, 76, 75, 74, 73, 72, 71, 70, 69, 68, 67, 66, 65, 60, 59, 58, 57, 56, 55, 54, 53, 52, 51, or 50. Any minimum value and any maximum value may be combined to define a range. Exemplary ranges include, for example, at least 1 to at most 1000; at least 10 to at most 500; and at least 20 to at most 80, preferably at most 90. In one preferred embodiment, n is at least 31 to at most 90. In a preferred embodiment, n is 40 to 90, more preferably 60 to 85.

In one embodiment, the saccharide includes an O-antigen wherein n in any one of the O-antigen Formulas is at least 1 and at most 200. In one embodiment, n in any one of the O-antigen Formulas is at least 5 and at most 200. In one embodiment, n in any one of the O-antigen Formulas is at least 10 and at most 200. In one embodiment, n in any one of the O-antigen Formulas is at least 25 and at most 200. In one embodiment, n in any one of the O-antigen Formulas is at least 50 and at most 200. In one embodiment, n in any one of the O-antigen Formulas is at least 75 and at most 200. In one embodiment, n in any one of the O-antigen Formulas is at least 100 and at most 200. In one embodiment, n in any one of the O-antigen Formulas is at least 125 and at most 200. In one embodiment, n in any one of the O-antigen Formulas is at least 150 and at most 200. In one embodiment, n in any one of the O-antigen Formulas is at least 175 and at most 200. In one embodiment, n in any one of the O-antigen Formulas is at least 1 and at most 100. In one embodiment, n in any one of the O-antigen Formulas is at least 5 and at most 100. In one embodiment, n in any one of the O-antigen Formulas is at least 10 and at most 100. In one embodiment, n in any one of the O-antigen Formulas is at least 25 and at most 100. In one embodiment, n in any one of the O-antigen Formulas is at least 50 and at most 100. In one embodiment, n in any one of the O-antigen Formulas is at least 75 and at most 100. In one embodiment, n in any one of the O-antigen Formulas is at least 1 and at most 75. In one embodiment, n in any one of the O-antigen Formulas is at least 5 and at most 75. In one embodiment, n in any one of the O-antigen Formulas is at least 10 and at most 75. In one embodiment, n in any one of the O-antigen Formulas is at least 20 and at most 75. In one embodiment, n in any one of the O-antigen Formulas is at least 25 and at most 75. In one embodiment, n in any one of the O-antigen Formulas is at least 30 and at most 75. In one embodiment, n in any one of the O-antigen Formulas is at least 40 and at most 75. In one embodiment, n in any one of the O-antigen Formulas is at least 50 and at most 75. In one embodiment, n in any one of the O-antigen Formulas is at least 30 and at most 90. In one embodiment, n in any one of the O-antigen Formulas is at least 35 and at most 85. In one embodiment, n in any one of the O-antigen Formulas is at least 35 and at most 75. In one embodiment, n in any one of the O-antigen Formulas is at least 35 and at most 70. In one embodiment, n in any one of the O-antigen Formulas is at least 35 and at most 60. In one embodiment, n in any one of the O-antigen Formulas is at least 35 and at most 50. In one embodiment, n in any one of the O-antigen Formulas is at least 35 and at most 49. In one embodiment, n in any one of the O-antigen Formulas is at least 35 and at most 48. In one embodiment, n in any one of the O-antigen Formulas is at least 35 and at most 47. In one embodiment, n in any one of the O-antigen Formulas is at least 35 and at most 46. In one embodiment, n in any one of the O-antigen Formulas is at least 36 and at most 45. In one embodiment, n in any one of the O-antigen Formulas is at least 37 and at most 44. In one embodiment, n in any one of the O-antigen Formulas is at least 38 and at most 43. In one embodiment, n in any one of the O-antigen Formulas is at least 39 and at most 42. In one embodiment, n in any one of the O-antigen Formulas is at least 39 and at most 41.

For example, in one embodiment, n in the saccharide is 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90, most preferably 40. In another embodiment, n is at least 35 to at most 60. For example, in one embodiment, n is any one of 35, 36, 37, 38, 39, 40, 41, 42, 43, 44, 45, 46, 47, 48, 49, 50, 51, 52, 53, 54, 55, 56, 57, 58, 59, and 60, preferably 50. In another preferred embodiment, n is at least 55 to at most 75. For example, in one embodiment, n is 55, 56, 57, 58, 59, 60, 61, 62, 63, 64, 65, 66, 67, 68, or 69, most preferably 60.

The saccharide structure may be determined by methods and tools known art, such as, for example, NMR, including 1D, 1H, and/or 13C, 2D TOCSY, DQF-COSY, NOESY, and/or HMQC.

In some embodiments, the purified polysaccharide before conjugation has a molecular weight of between 5 kDa and 400 kDa. In other such embodiments, the saccharide has a molecular weight of between 10 kDa and 400 kDa; between 5 kDa and 400 kDa; between 5 kDa and 300 kDa; between 5 kDa and 200 kDa; between 5 kDa and 150 kDa; between 10 kDa and 100 kDa; between 10 kDa and 75 kDa; between 10 kDa and 60 kDa; between 10 kDa and 40 kDa; between 10 kDa and 100 kDa; 10 kDa and 200 kDa; between 15 kDa and 150 kDa; between 12 kDa and 120 kDa; between 12 kDa and 75 kDa; between 12 kDa and 50 kDa; between 12 and 60 kDa; between 35 kDa and 75 kDa; between 40 kDa and 60 kDa; between 35 kDa and 60 kDa; between 20 kDa and 60 kDa; between 12 kDa and 20 kDa; or between 20 kDa and 50 kDa. In further embodiments, the polysaccharide has a molecular weight of between 7 kDa to 15 kDa; 8 kDa to 16 kDa; 9 kDa to 25 kDa; 10 kDa to 100; 10 kDa to 60 kDa; 10 kDa to 70 kDa; 10 kDa to 160 kDa; 15 kDa to 600 kDa; 20 kDa to 1000 kDa; 20 kDa to 600 kDa; 20 kDa to 400 kDa; 30 kDa to 1,000 KDa; 30 kDa to 60 kDa; 30 kDa to 50 kDa or 5 kDa to 60 kDa. Any whole number integer within any of the above ranges is contemplated as an embodiment of the disclosure.

As used herein, the term "molecular weight" of polysaccharide or of carrier protein-polysaccharide conjugate refers to molecular weight calculated by size exclusion chromatography (SEC) combined with multiangle laser light scattering detector (MALLS).

A polysaccharide can become slightly reduced in size during normal purification procedures. Additionally, as described herein, polysaccharide can be subjected to sizing techniques before conjugation. Mechanical or chemical sizing maybe employed. Chemical hydrolysis may be conducted using acetic acid. Mechanical sizing may be conducted using High Pressure Homogenization Shearing. The molecular weight ranges mentioned above refer to purified polysaccharides before conjugation (e.g., before activation).

TABLE 1

E. coli serogroups/serotypes and O-unit moieties

| Serogroup/Serotype | Moiety Structure (O-unit) | Moiety structure referred to herein as: |
|---|---|---|
| O1A, O1A1 | [→3)-α-L-Rha-(1→3)-α-L-Rha-(1→3)-β-L-Rha-(1→4)-β-D-GlcNAc-(1→ \| β-D-ManNac-(1→2) ]$_n$ | Formula O1A |

TABLE 1-continued

*E. coli* serogroups/serotypes and O-unit moieties

| Serogroup/ Serotype | Moiety Structure (O-unit) | Moiety structure referred to herein as: |
|---|---|---|
| O1B | [→3)-α-L-Rha-(1→2)-α-L-Rha-(1→2)-α-D-Gal-(1→3)-β-D-GlcNAc-(1→\|β-D-ManNAc-(1→2) ]$_n$ | Formula O1B |
| O1C | [→3)-α-L-Rha-(1→)-α-L-Rha-(1→3)-α-D-Gal-(1→3)-β-D-GlcNAc-(1→\|β-D-ManNAc-(1→2) ]$_n$ | Formula O1C |
| O2 | [→3)-α-L-Rha-(1→2)-α-L-Rha-(1→3)-β-L-Rha-(1→4)-β-D-GlcNAc-(1→ \| α-D-Fuc3NAc-(1→2) ]$_n$ | Formula O2 |
| O3 | [β-L-RhaNAc(1→4)α-D-Glc-(1→4)\| \| →3)-β-D-GlcNAc-(1→3)-α-D-Gal-(1→3)-β-D-GlcNAc-(1→ ]$_n$ | Formula O3 |
| O4:K52 | [→2)-α-L-Rha-(1→6)-α-D-Glc-(1→3)-α-L-FucNAc-(1→3)-β-D-GlcNAc(1→ ]$_n$ | Formula O4:K52 |
| O4:K6 | [α-D-Glc-(1→3) \| →2)-α-L-Rha-(1→6)-α-D-Glc-(1→3)-α-L-FucNAc-(1→3)-β-D-GlcNAc(1→ ]$_n$ | Formula O4:K6 |
| O5ab | [→4)-β-D-Qui3NAc-(1→3)-β-D-Ribf-(1→4)-β-D-Gal-(1→3)-α-D-GalNAc-(1→]$_n$ | Formula O5ab |
| O5ac (strain 180/C3) | [→2)-β-D-Qui3NAc-(1→3)-β-D-Ribf-(1→4)-β-D-Gal-(1→3)-α-D-GalNAc-(1→ ]$_n$ | Formula O5ac (strain 180/C3) |
| O6:K2; K13; K15 | [→4)-α-D-GalNAc-(1→3)-β-D-Man-(1→4)-β-D-Man-(1→3)-α-D-GlcNAc-(1→ \| β-D-Glc-(1→2) ]$_n$ | Formula O6: K2; K13; K15 |
| O6:K54 | [→4)-α-D-GalNAc-(1→3)-β-D-Man-(1→4)-β-D-Man-(1→3)-α-D-GlcNAc-(1→\|β-D-GlcNAc-(1→2) ]$_n$ | Formula O6: K54 |
| O7 | [α-L-Rha-(1→3) \| →3)-β-D-Qui4NAc-(1→2)-α-D-Man-(1→4)-β-D-Gal-(1→3)-α-D-GlcNAc-(1→ ]$_n$ | Formula O7 |
| O10 | [→3)-α-L-Rha-(1→3)-α-L-Rha-(1→3)-α-D-Gal-(1→3)-β-D-GlcNac-(1→ \| α-D-Fuc4NAcyl-(1→2) Acyl=acetyl (60%) or (R)-3-hydroxybutyryl (40%) ]$_n$ | Formula O10 |
| O16 | [→2)-β-D-Galf-(1→6)-α-D-Glc-(1→3)-α-L-Rha2Ac-(1→3)-α-D-GlcNAc-(1→ ]$_n$ | Formula O16 |
| O17 | [α-D-Glc-(1→6) \| →6)-α-D-Man-(1→2)-α-D-Man-(1→2)-β-D-Man-(1→3)-α-D-GlcNAc(1→ ]$_n$ | Formula O17 |
| O18A, O18ac | [→2)-α-L-Rha-(1→6)-α-D-Glc-(1→4)-α-D-Gal-(1→3)-α-D-GlcNAc-(1→ \| β-D-GlcNAc-(1→3) ]$_n$ | Formula O18A, Formula O18ac |
| O18A1 | [α-D-Glc-(1→6) \| →2)-α-L-Rha-(1→6)-α-D-Glc-(1→4)-α-D-Gal-(1→3)-α-D-GlcNAc-(1→ \| β-D-GlcNAc-(1→3) ]$_n$ | Formula O18A1 |
| O18B | [→3)-α-L-Rha-(1→6)-α-D-Glc-(1→4)-α-D-Gal-(1→3)-α-D-GlcNAc-(1→ \| β-D-Glc-(1→3) ]$_n$ | Formula O18B |
| O18B1 | [α-D-Glc-(1→4) \| →3)-α-L-Rha-(1→6)-α-D-Glc-(1→4)-α-D-Gal-(1→3)-α-D-GlcNAc-(1→ \| β-D-Glc-(1→3) ]$_n$ | Formula O18B1 |
| O21 | [β-D-Gal-(1→4) \| →3)-β-D-Gal-(1→4)-β-D-Glc-(1→3)-β-D-GalNAc-(1→ \| β-D-GlcNAc-(1→2) ]$_n$ | Formula O21 |
| O23A | [α-D-Glc-(1→6) \| →6)-α-D-Glc-(1→4)-β-D-Gal-(1→3)-α-D-GalNAc-(1→3)-β-D-GlcNAc-(1→ \| β-D-GlcNAc(1→3) ]$_n$ | Formula O23A |
| O24 | [→7)-α-Neu5Ac-(2→3)-β-D-Glc-(1→3)-β-D-GalNAc-(1→ \| α-D-Glc-(1→2) ]$_n$ | Formula O24 |
| O25/O25a | [β-D-Glc-(1→6) \| →4)-α-D-Glc-(1→3)-α-L-FucNAc-(1→3)-β-D-GlcNAc-(1→ \| α-L-Rha-(1→3) ]$_n$ | Formula O25a |
| O25b | β-Glcp-<br>1<br>↓<br>6<br>[α-Rhap-(1→3)-α-Glcp-(1→3)-α-Rhap2OAc-(1→3)-β-GlcpNAc-]$_n$ | Formula O25b |
| O26 | [→3)-α-L-Rha-(1→4)-α-L-FucNAc-(1→3)-β-D-GlcNAc-(1→ ]$_n$ | Formula O26 |
| O28 | [→2)-(R)-Gro-1-P→4)-β-D-GlcNAc-(1→3)-β-D-Galf2Ac-(1→3)-α-D-GlcNAc-(1→ ]$_n$ | Formula O28 |
| O36 | [α-L-Rhap-(1→2)-α-L-Fucp<br>1<br>↓<br>3<br>→4)-α-D-Manp-(1→3)-α-L-Fucp-(1→3)-β-D-GlcpNAc-(1→]n | Formula O36 |
| O44 | [α-D-Glc-(1→4) \| →6)-α-D-Man-(1→2)-α-D-Man-(1→2)-β-D-Man-(1→3)-α-D-GlcNAc(1→ ]$_n$ | Formula O44 |
| O45 | [→2)-β-D-Glc-(1→3)-α-L-6dTal2Ac-(1→3)-α-D-FucNAc-(1→ ]$_n$ | Formula O45 |
| O45rel | [→2)-β-D-Glc-(1→3)-α-L-6dTal2Ac-(1→3)-α-D-GlcNAc-(1→ ]$_n$ | Formula O45rel |
| O54 | [→4)-α-d-GalpA-(1 → 2)-α-l-Rhap-(1 → 2)-β-d-Ribf-(1 → 4)-β-d-Galp-(1 → 3)-β-d-GlcpNAc-(1→]n | Formula O54 |

TABLE 1-continued

*E. coli* serogroups/serotypes and O-unit moieties

| Serogroup/Serotype | Moiety Structure (O-unit) | Moiety structure referred to herein as: |
|---|---|---|
| O55 | [→6)-β-D-GlcNAc-(1→3)-αD-Gal-(1→3)-β-D-GalNAc-(1→ \| α-Col-(1→2)-β-D-Gal-(1→3) ]$_n$ | Formula O55 |
| O56 | [→7)-α-Neu5Ac-(2→3)-β-D-Glc-(1→3)-β-D-GlcNAc-(1→ \| α-D-Gal-(1→2) ]$_n$ | Formula O56 |
| O57 | [→3)-α-D-Galp-(1→3)-α-L-FucpNAc-(1→3)-α-D-GlcpNAc-(1→]n<br>　　　　　　　　2　　　　　　　　4<br>　　　　　　　　↑　　　　　　　　↑<br>　　　　　　　　1　　　　　　　　1<br>　　　　α-D-GalpA2/3Ac　　β-D-Glcp | Formula O57 |
| O58 | [3-O-[(R)-1-carboxyethyl]-α-L-Rha-(1→3) \| →4)-α-D-Man-(1→4)-α-D-Man2Ac-(1→3)-β-D-GlcNAc-(1→ ]$_n$ | Formula O58 |
| O64 | [β-D-Gal-(1→6) \| →3)-α-D-ManNAc-(1→3)-β-D-GlcA-(1→3)-β-D-Gal-(1→3)-β-D-GlcNAc(1→ ]$_n$ | Formula O64 |
| O68 | [α-L-Rhap　　　α-D-Glcp<br>　　1　　　　　　1<br>　　↓　　　　　　↓<br>　　3　　　　　　3<br>→6)-α-D-Manp-(1→2)-α-D-Manp-(1→2)-α-D-Manp-(1→2)-β-D-Manp-(1→3)-α-D-GlcpNAC-(1→]n | Formula O68 |
| O69 | [→2)-α-L-Rha-(1→2)-α-L-Rha-(1→2)-α-D-Gal-(1→3)-β-D-GlcNAc-(1→ ]$_n$ | Formula O69 |
| O73 (Strain 73-1) | [α-D-Glc-(1→3) \| →4)-α-D-Man-(1→2)-α-D-Man-(1→2)-β-D-Man-(1→3)-α-D-GalNAc(1→ ]$_n$ | Formula O73 (Strain 73-1) |
| O74 | →6)-α-D-GlcpNAc-(1→4)-β-D-GalpA-(1→3)-β-D-GlcpNAc-(1→]n<br>　　　　　　　\|<br>[β-D-Fucp3NAc-(1→3) | Formula O74 |
| O75 | [β-D-Man-(1→4) \| →3)-α-D-Gal-(1→4)-α-L-Rha-(1→3)-β-D-GlcNAc-(1→ ]$_n$ | Formula O75 |
| O76 | [→4)-β-D-GlcpA-(1→4)-β-D-GalpNAc3Ac-(1→4)-α-D-GalpNAc-(1→3)-β-D-GalpNAc-(1→]n | Formula O76 |
| O77 | [→6)-α-D-Man-(1→2)-α-D-Man-(1→2)-β-D-Man-(1→3)-α-D-GlcNAc-(1→ ]$_n$ | Formula O77 |
| O78 | [→4)-β-D-GlcNAc-(1→4)-β-D-Man-(1→4)-α-D-Man-(1→3)-β-D-GlcNAc-(1→ ]$_n$ | Formula O78 |
| O86 | [α-D-Gal-(1→3) \| →4)-α-L-Fuc-(1→2)-β-D-Gal-(1→3)-α-D-GalNAc-(1→3)-β-D-GalNAc-(1→ ]$_n$ | Formula O86 |
| O88 | [α-L-6dTal-(1→3) \| →4)-α-D-Man-(1→3)-α-D-Man-(1→3)-β-D-GlcNAc-(1→ ]$_n$ | Formula O88 |
| O90 | [→4)-α-L-Fuc2/3Ac-(1→2)-β-D-Gal-(1→3)-α-D-GalNAc-(1→3)-β-D-GalNAc-(1→ ]$_n$ | Formula O90 |
| O98 | [→3)-α-L-QuiNAc-(1→4)-α-D-GalNAcA-(1→3)-α-L-QuiNAc-(1→3)-β-D-GlcNAc-(1→ ]$_n$ | Formula O98 |
| O104 | [→4)-α-D-Gal-(1→4)-α-Neu5,7,9Ac$_3$-(2→3)-β-D-Gal-(1→3)-β-D-GalNAc-(1→]$_n$ | Formula O104 |
| O111 | [α-Col-(1→6) \| →4)-α-D-Glc-(1→4)-α-D-Gal-(1→3)-β-D-GlcNAc-(1→ \| α-Col-(1→3) ]$_n$ | Formula O111 |
| O113 | [→4)-α-D-GalNAc-(1→4)-α-D-GalA-(1→3)-α-D-Gal-(1→3)-β-D-GlcNAc-(1→ \| β-D-Gal-(1→3) ]$_n$ | Formula O113 |
| O114 | [→4)-β-D-Qui3N(N-acetyl-L-seryl)-(1→3)-β-D-Ribf-(1→4)-β-D-Gal-(1→3)-α-D-GlcNAc(1→ ]$_n$ | Formula O114 |
| O119 | [β-D-RhaNAc3NFo-(1→3) \| →2)-β-D-Man-(1→3)-α-D-Gal-(1→4)-α-L-Rha-(1→3)-α-D-GlcNAc-(1→ ]$_n$ | Formula O119 |
| O121 | [→3)-β-D-Qui4N(N-acetyl-glycyl)-(1→4)-α-D-GalNAc3AcA6N-(1→4)-α-D-GalNAcA-(1→3)-α-D-GlcNAc-(1→ ]$_n$ | Formula O121 |
| O124 | [4-O-[(R)-1-carboxyethyl]-β-D-Glc-(1→6)-α-D-Glc(1→4) \|→3)-α-D-Gal-(1→6)-β-D-Galf-(1→3)-β-D-GalNAc-(1→ ]$_n$ | Formula O124 |
| O125 | [α-D-Glc-(1→3) \| →4)-β-D-GalNAc-(1→2)-α-D-Man-(1→3)-α-L-Fuc-(1→3)-α-D-GalNAc-(1→ \| β-D-Gal-(1→3) ]$_n$ | Formula O125 |
| O126 | [→2)-β-D-Man-(1→3)-β-D-Gal-(1→3)-α-D-GlcNAc-(1→3)-β-D-GlcNAc-(1→ \| α-L-Fuc-(1→2) ]$_n$ | Formula O126 |
| O127 | [→2)-α-L-Fuc-(1→2)-β-D-Gal-(1→3)-α-D-GalNAc-(1→3)-α-D-GalNAc-(1→ ]$_n$ | Formula O127 |

TABLE 1-continued

E. coli serogroups/serotypes and O-unit moieties

| Serogroup/Serotype | Moiety Structure (O-unit) | Moiety structure referred to herein as: |
|---|---|---|
| O128 | [α-L-Fuc-(1→2) \| →6)-β-D-Gal-(1→3)-β-D-GalNAc-(1→4)-α-D-Gal-(1→3)-β-D-GalNAc-(1→ ]$_n$ | Formula O128 |
| O136 | [→4)-β-Pse5Ac7Ac-(2→4)-β-D-Gal-(1→4)-β-D-GlcNAc-(1→β-Pse5Ac7Ac=5,7-diacetamido-3,5,7,9-tetradeoxyl-L-glycero-β-L-manno-nonulosonic acid ]$_n$ | Formula O136 |
| O138 | [→2)-α-L-Rha-(1→3)-α-L-Rha-(1→4)-α-D-GalNAcA-(1→3)-β-D-GlcNAc-(1→ ]$_n$ | Formula O138 |
| O140 | [α-D-Galf-(1→2)-α-L-Rhap<br>1<br>↓<br>4<br>→3)-β-D-Galp-(1→4)-α-D-Glcp-(1→4)-β-D-GlcpA-(1→3)-β-D-GalpNAc-(1→]n | Formula O140 |
| O141 | [α-L-Rha-(1→3) \|→4)-α-D-Man-(1→3)-α-D-Man6Ac-(1→3)-β-D-GlcNAc-(1→ \| β-D-GlcA-(1→2) ]$_n$ | Formula O141 |
| O142 | [→2)-α-L-Rha-(1→6)-α-D-GalNAc-(1→4)-α-D-GalNAc-(1→3)-α-D-GalNAc-(1→ \| β-D-GlcNAc-(1→3) ]$_n$ | Formula O142 |
| O143 | [→2)-β-D-GalA6R3,4Ac-(1→3)-α-D-GalNAc-(1→4)-β-D-GlcA-(1→3)-β-D-GlcNAc-(1→ R=1,3-dihydroxy-2-propylamino ]$_n$ | Formula O143 |
| O147 | [→2)-α-L-Rha-(1→2)-α-L-Rha-(1→4)-β-D-GalA-(1→3)-β-D-GalNAc-(1→ ]$_n$ | Formula O147 |
| O149 | [→3)-β-D-GlcNAc-(S)-4,6Py-(1→3)-β-L-Rha-(1→4)-β-D-GlcNAc-(1→ (S)-4,6Py=4,6-O-[(S)-1-carboxyethylidene]- ]$_n$ | Formula O149 |
| O152 | [β-L-Rha-(1→4) \| →3)-α-D-GlcNAc-(1-P→6)-α-D-Glc-(1→2)-β-D-Glc-(1→3)-β-D-GlcNAc-(1→ ]$_n$ | Formula O152 |
| O157 | [→2)-α-D-Rha4NAc-(1→3)-α-L-Fuc-(1→4)-β-D-Glc-(1→3)-α-D-GalNAc-(1→ ]$_n$ | Formula O157 |
| O158 | [α-D-Glc-(1→6) \| →4)-α-D-Glc-(1→3)-α-D-GalNAc-(1→3)-β-D-GalNAc-(1→ \| α-L-Rha-(1→3) ]$_n$ | Formula O158 |
| O159 | [α-L-Fuc-(1→4) \| →3)-β-D-GlcNAc-(1→4)-α-D-GalA-(1→3)-α-L-Fuc-(1→3)-β-D-GlcNAc-(1→ ]$_n$ | Formula O159 |
| O164 | [β-D-Glc-(1→6)-α-D-Glc(1→4) \| →3)-β-D-Gal-(1→6)-β-D-Galf-(1→3)-β-D-GalNAc-(1→ ]$_n$ | Formula O164 |
| O173 | [α-L-Fuc-(1→4) \| →3)-α-D-Glc-(1-P→6)-α-D-Glc-(1→2)-β-D-Glc-(1→3)-β-D-GlcNAc-(1→]$_n$ | Formula O173 |
| 62D$_1$ Suggested as *Erwinia herbicola* | [α-D-Gal(1→6) \| →2)-β-D-Qui3NAc-(1→3)-α-L-Rha-(1→3)-β-D-Gal-(1→3)-α-D-FucNAc-(1→ ]$_n$ | Formula 62D$_1$ |
| O22 | [→6)-α-D-Glc-(1→4)-β-D-GlcA-(1→4)-β-D-GalNAc3Ac-(1→3)-α-D-Gal-(1→3)-β-D-GalNAc-(1→]$_n$ | Formula O22 |
| O35 | [→3)-α-L-Rha-(1→2)-α-L-Rha-(1→3)-α-L-Rha-(1→2)-α-L-Rha-(1→3)-β-D-GlcNAc-(1→ \| α-D-GalNAcA6N-(1→2) ]$_n$ | Formula O35 |
| O65 | [→2)-β-D-Qui3NAc-(1→4)-α-D-GalA6N-(1→4)-α-D-GalNAc-(1→4)-β-D-GalA-(1→3)-α-D-GlcNAc-(1→ ]$_n$ | Formula O65 |
| O66 | [→2)-β-D-Man-(1→3)-α-D-GlcNAc-(1→2)-β-D-Glc3Ac-(1→3)-α-L-6dTal-(1→3)-α-D-GlcNAc(1→ ]$_n$ | Formula O66 |
| O83 | [→6)-α-D-Glc-(1→4)-β-D-GlcA-(1→6)-β-D-Gal-(1→4)-β-D-Gal-(1→4)-β-D-GlcNAc-(1→ ]$_n$ | Formula O83 |
| O91 | [→4)-α-D-Qui3NAcyl-(1→4)-β-D-Gal-(1→4)-β-D-GlcNAc-(1→4)-β-D-GlcA6NGly-(1→3)-β-D-GlcNAc-(1→ Acyl=(R)-3-hydroxybutyryl]$_n$ | Formula O91 |
| O105 | [β-D-Ribf-(1→3) \|→4)-α-D-GlcA2Ac3Ac-(1→2)-α-L-Rha4Ac-(1→3)-β-L-Rha-(1→4)-β-L-Rha-(1→3)-β-D-GlcNAc6Ac-(1→ ]$_n$ | Formula O105 |
| O116 | [→2)-β-D-Qui4NAc-(1→6)-α-D-GlcNAc-(1→4)-α-D-GalNAc-(1→4)-α-D-GalA-(1→3)-β-D-GlcNAc-(1→ ]$_n$ | Formula O116 |
| O117 | [→4)-β-D-GalNAc-(1→3)-α-L-Rha-(1→4)-α-D-Glc-(1→4)-β-D-Gal-(1→3)-α-D-GalNAc-(1→]$_n$ | Formula O117 |
| O139 | [β-D-Glc-(1→3) \| →3)-α-L-Rha-(1→4)-α-D-GalA-(1→2)-α-L-Rha-(1→3)-α-L-Rha-(1→2)-α-L-Rha-(1→3)-α-D-GlcNAc-(1→ ]$_n$ | Formula O139 |
| O153 | [→2)-β-D-Ribf-(1→4)-β-D-Gal-(1→4)-α-D-GlcNAc-(1→4)-β-D-Gal-(1→3)-α-D-GlcNAc-(1→ ]$_n$ | Formula O153 |
| O167 | [α-D-Galf-(1→4) \| →2)-β-D-GalA6N(L)Ala-(1→3)-α-D-GlcNAc-(1→2)-β-D-Galf-(1→5)-β-D-Galf-(1→3)-β-D-GlcNAc-(1→ ]$_n$ | Formula O167 |
| O172 | [→3)-α-L-FucNAc-(1→4)-α-D-Glc6Ac-(1-P→4)-α-D-Glc-(1→3)-α-L-FucNAc-(1→3)-α-D-GlcNAc-(1→ ]$_n$ | Formula O172 |
| O8 | [→2)-α-D-Man-(1→2)-α-D-Man-(1→3)-β-D-Man-(1→ ]$_n$ | Formula O8 |
| O9a | [→2)-α-D-Man-(1→2)-α-D-Man-(1→3)-α-D-Man-(1→3)-α-D-Man-(1→ ]$_n$ | Formula O9a |

TABLE 1-continued

E. coli serogroups/serotypes and O-unit moieties

| Serogroup/Serotype | Moiety Structure (O-unit) | Moiety structure referred to herein as: |
|---|---|---|
| O9 | [→2)-[α-D-Man-(1→2)]$_2$-α-D-Man-(1→3)-α-D-Man-(1→3)-α-D-Man-(1→ ]$_n$ | Formula O9 |
| O20ab | [→2)-β-D-Ribf-(1→4)-α-D-Gal-(1→ ]$_n$ | Formula O20ab |
| O20ac | [α-D-Gal-(1→3) | →2)-β-D-Ribf-(1→4)-α-D-Gal-(1→ ]$_n$ | Formula O20ac |
| O52 | [→3)-β-D-Fucf-(1→3)-β-D-6dmanHep2Ac-(1→ ]$_n$ | Formula O52 |
| O97 | [→3)-α-L-Rha-(1→3)-β-L-Rha-(1→ ‖ β-D-Xulf-(2→2)β-D-Xulf-(2→2) ]$_n$ | Formula O97 |

† β-D-6dmanHep2Ac is 2-O-acetyl-6-deoxy-β-D-manno-heptopyranosyl.
‡ β-D-Xulf is β-D-threo-pentofuranosyl.

D. Core Oligosaccharide

The core oligosaccharide is positioned between Lipid A and the O-antigen outer region in wild-type E. coli LPS. More specifically, the core oligosaccharide is the part of the polysaccharide that includes the bond between the O-antigen and the lipid A in wild type E. coli. This bond includes a ketosidic bond between the hemiketal function of the innermost 3-deoxy-d-manno-oct-2-ulosonic acid (KDO)) residue and a hydroxyl-group of a GlcNAc-residue of the lipid A. The core oligosaccharide region shows a high degree of similarity among wild-type E. coli strains. It usually includes a limited number of sugars. The core oligosaccharide includes an inner core region and an outer core region.

More specifically, the inner core is composed primarily of L-glycero-D-manno-heptose (heptose) and KDO residues. The inner core is highly conserved. A KDO residue includes the following Formula KDO:

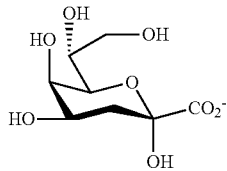

Figure 24:
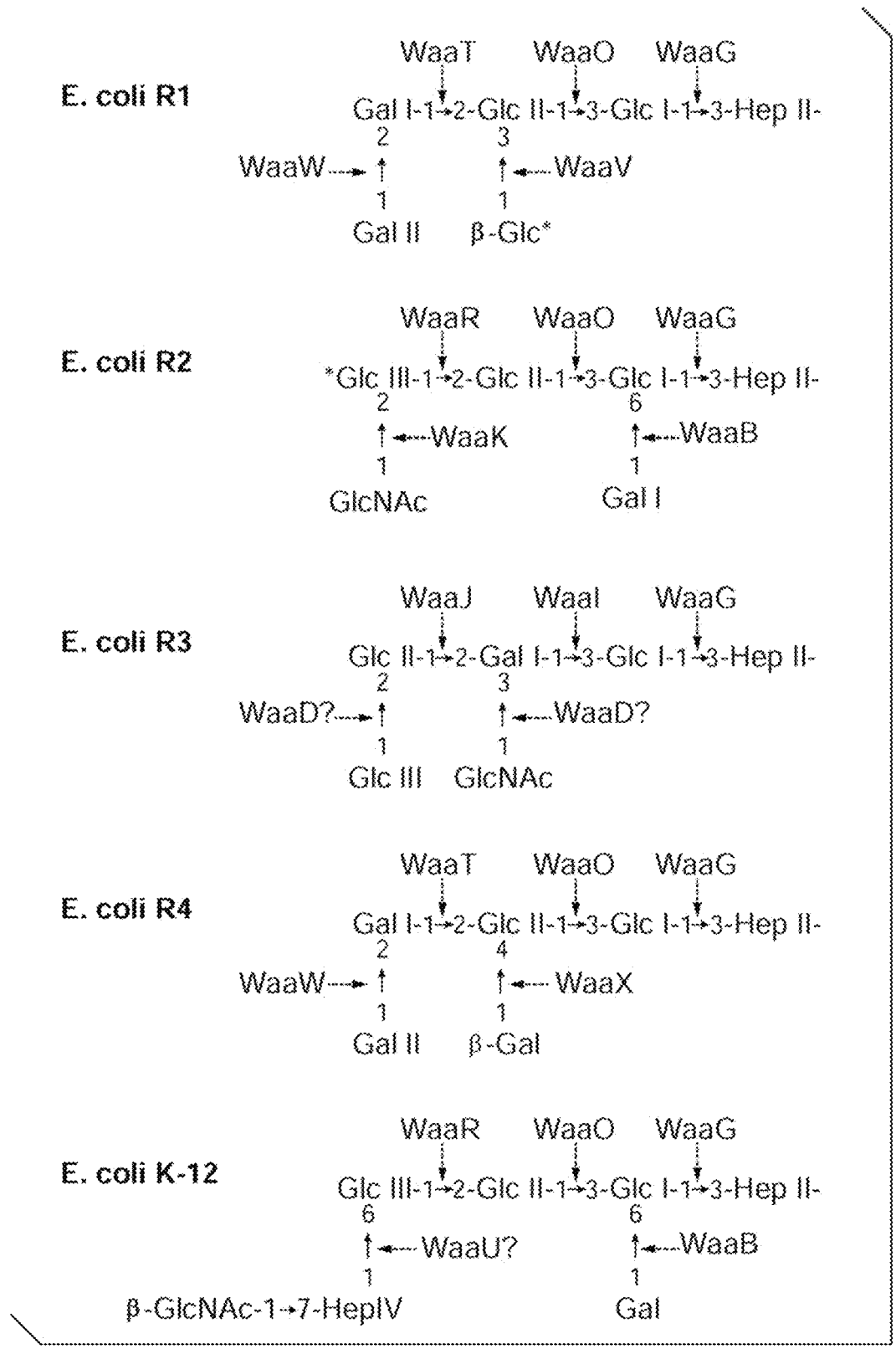
FIG. 24—depicts generalized structures of the carbohydrate backbone of the outer core oligosaccharides of the five known chemotypes. All glycoses are in the α-anomeric configuration unless otherwise indicated. The genes whose products catalyse formation of each linkage are indicated in dashed arrows. An asterisk denotes the residue of the core oligosaccharide to which attachment of O-antigen occurs.

The outer region of the core oligosaccharide displays more variation than the inner core region, and differences in this region distinguish the five chemotypes in E. coli: R1, R2, R3, R4, and K-12. See FIG. 24, which illustrates generalized structures of the carbohydrate backbone of the outer core oligosaccharides of the five known chemotypes. HepII is the last residue of the inner core oligosaccharide. While all of the outer core oligosaccharides share a structural theme, with a (hexose)$_3$ carbohydrate backbone and two side chain residues, the order of hexoses in the backbone and the nature, position, and linkage of the side chain residues can all vary. The structures for the R1 and R4 outer core oligosaccharides are highly similar, differing in only a single β-linked residue.

The core oligosaccharides of wild-type E. coli are categorized in the art based on the structures of the distal oligosaccharide, into five different chemotypes: E. coli R1, E. coli R2, E. coli R3, E. coli R4, and E. coli K12.

In a preferred embodiment, the compositions described herein include glycoconjugates in which the O-polysaccharide includes a core oligosaccharide bound to the O-antigen. In one embodiment, the composition induces an immune response against at least any one of the core E. coli chemotypes E. coli R1, E. coli R2, E. coli R3, E. coli R4, and E. coli K12. In another embodiment, the composition induces an immune response against at least two core E. coli chemotypes. In another embodiment, the composition induces an immune response against at least three core E. coli chemotypes. In another embodiment, the composition induces an immune response against at least four core E. coli chemotypes. In another embodiment, the composition induces an immune response against all five core E. coli chemotypes.

In another preferred embodiment, the compositions described herein include glycoconjugates in which the O-polysaccharide does not include a core oligosaccharide bound to the O-antigen. In one embodiment, such a composition induces an immune response against at least any one of the core E. coli chemotypes E. coli R1, E. coli R2, E. coli R3, E. coli R4, and E. coli K12, despite the glycoconjugate having an O-polysaccharide that does not include a core oligosaccharide.

E. coli serotypes may be characterized according to one of the five chemotypes. Table 2 lists exemplary serotypes characterized according to chemotype. The serotypes in bold represent the serotypes that are most commonly associated with the indicated core chemotype. Accordingly, in a preferred embodiment, the composition induces an immune response against at least any one of the core E. coli chemotypes E. coli R1, E. coli R2, E. coli R3, E. coli R4, and E. coli K12, which includes an immune response against any one of the respective corresponding E. coli serotypes.

TABLE 2

Core Chemotype and associated E. coli Serotype

| Core chemotype | Serotype |
|---|---|
| R1 | O25a, O6, O2, O1, O75, O4, O16, O8, O18, O9, O13, O20, O21, O91, and O163. |
| R2 | O21, O44, O11, O89, O162, O9 |
| R3 | O25b, O15, O153, O21, O17, O11, O159, O22, O86, O93 |
| R4 | O2, O1, O86, O7, O102, O160, O166 |
| K-12 | O25b, O16 |

In some embodiments, the composition includes a saccharide that includes a structure derived from a serotype having an R1 chemotype, e.g., selected from a saccharide having Formula O25a, Formula O6, Formula O2, Formula O1, Formula O75, Formula O4, Formula O16, Formula O8, Formula O18, Formula O9, Formula O13, Formula O20, Formula O21, Formula O91, and Formula O163, wherein n is 1 to 100. In some embodiments, the saccharide in said composition further includes an E. coli R1 core moiety, e.g., shown in FIG. 24.-

In some embodiments, the composition includes a saccharide that includes a structure derived from a serotype having an R1 chemotype, e.g., selected from a saccharide having Formula O25a, Formula O6, Formula O2, Formula O1, Formula O75, Formula O4, Formula O16, Formula O18, Formula O13, Formula O20, Formula O21, Formula O91, and Formula O163, wherein n is 1 to 100, preferably 31 to 100, preferably from 31 to 90 more preferably 35 to 90, most preferably 35 to 65. In some embodiments, the saccharide in said composition further includes an *E. coli* R1 core moiety in the saccharide.

In some embodiments, the composition includes a saccharide that includes a structure derived from a serotype having an R2 chemotype, e.g., selected from a saccharide having Formula O21, Formula O44, Formula O11, Formula O89, Formula O162, and Formula O9, wherein n is 1 to 100, preferably 31 to 100, preferably from 31 to 90, more preferably 35 to 90, most preferably 35 to 65. In some embodiments, the saccharide in said composition further includes an *E. coli* R2 core moiety, e.g., shown in FIG. 24.

In some embodiments, the composition includes a saccharide that includes a structure derived from a serotype having an R3 chemotype, e.g., selected from a saccharide having Formula O25b, Formula O15, Formula O153, Formula O21, Formula O17, Formula O11, Formula O159, Formula O22, Formula O86, and Formula O93, wherein n is 1 to 100, preferably 31 to 100, preferably from 31 to 90, more preferably 35 to 90, most preferably 35 to 65. In some embodiments, the saccharide in said composition further includes an *E. coli* R3 core moiety, e.g., shown in FIG. 24.

In some embodiments, the composition includes a saccharide that includes a structure derived from a serotype having an R4 chemotype, e.g., selected from a saccharide having Formula O2, Formula O1, Formula O86, Formula O7, Formula O102, Formula O160, and Formula O166, wherein n is 1 to 100, preferably 31 to 100, preferably from 31 to 90, more preferably 35 to 90, most preferably 35 to 65. In some embodiments, the saccharide in said composition further includes an *E. coli* R4 core moiety, e.g., shown in FIG. 24.

In some embodiments, the composition includes a saccharide that includes a structure derived from a serotype having an K-12 chemotype (e.g., selected from a saccharide having Formula O25b and a saccharide having Formula O16), wherein n is 1 to 1000, preferably 31 to 100, preferably from 31 to 90, more preferably 35 to 90, most preferably 35 to 65. In some embodiments, the saccharide in said composition further includes an *E. coli* K-12 core moiety, e.g., shown in FIG. 24.

In some embodiments, the saccharide includes the core saccharide. Accordingly, in one embodiment, the O-polysaccharide further includes an *E. coli* R1 core moiety. In another embodiment, the O-polysaccharide further includes an *E. coli* R2 core moiety. In another embodiment, the O-polysaccharide further includes an *E. coli* R3 core moiety. In another embodiment, the O-polysaccharide further includes an *E. coli* R4 core moiety. In another embodiment, the O-polysaccharide further includes an *E. coli* K12 core moiety.

In some embodiments, the saccharide does not include the core saccharide. Accordingly, in one embodiment, the O-polysaccharide does not include an *E. coli* R1 core moiety. In another embodiment, the O-polysaccharide does not include an *E. coli* R2 core moiety. In another embodiment, the O-polysaccharide does not include an *E. coli* R3 core moiety. In another embodiment, the O-polysaccharide does not include an *E. coli* R4 core moiety. In another embodiment, the O-polysaccharide does not include an *E. coli* K12 core moiety.

E. Conjugated O-Antigens

Chemical linkage of O-antigens or preferably O-polysaccharides to protein carriers may improve the immunogenicity of the O-antigens or O-polysaccharides. However, variability in polymer size represents a practical challenge for production. In commercial use, the size of the saccharide can influence the compatibility with different conjugation synthesis strategies, product uniformity, and conjugate immunogenicity. Controlling the expression of a Wzz family protein chain length regulator through manipulation of the O-antigen synthesis pathway allows for production of a desired length of O-antigen chains in a variety of Gram-negative bacterial strains, including *E. coli*.

In one embodiment, the purified saccharides are chemically activated to produce activated saccharides capable of reacting with the carrier protein. Once activated, each saccharide is separately conjugated to a carrier protein to form a conjugate, namely a glycoconjugate. As used herein, the term "glycoconjugate" refers to a saccharide covalently linked to a carrier protein. In one embodiment a saccharide is linked directly to a carrier protein. In another embodiment, a saccharide is linked to a protein through a spacer/linker. Conjugates may be prepared by schemes that bind the carrier to the O-antigen at one or at multiple sites along the O-antigen, or by schemes that activate at least one residue of the core oligosaccharide.

In one embodiment, each saccharide is conjugated to the same carrier protein. If the protein carrier is the same for 2 or more saccharides in the composition, the saccharides may be conjugated to the same molecule of the carrier protein (e.g., carrier molecules having 2 or more different saccharides conjugated to it).

In a preferred embodiment, the saccharides are each individually conjugated to different molecules of the protein carrier (each molecule of protein carrier only having one type of saccharide conjugated to it). In said embodiment, the saccharides are said to be individually conjugated to the carrier protein.

The chemical activation of the saccharides and subsequent conjugation to the carrier protein can be achieved by the activation and conjugation methods disclosed herein. After conjugation of the polysaccharide to the carrier protein, the glycoconjugates are purified (enriched with respect to the amount of polysaccharide-protein conjugate) by a variety of techniques. These techniques include concentration/diafiltration operations, precipitation/elution, column chromatography, and depth filtration. After the individual glycoconjugates are purified, they are compounded to formulate the immunogenic composition of the present invention.

Activation. The present invention further relates to activated polysaccharides produced from any of the embodiments described herein wherein the polysaccharide is activated with a chemical reagent to produce reactive groups for conjugation to a linker or carrier protein. In some embodiments, the saccharide of the invention is activated prior to conjugation to the carrier protein. In some embodiments, the degree of activation does not significantly reduce the molecular weight of the polysaccharide. For example, in some embodiments, the degree of activation does not cleave the polysaccharide backbone. In some embodiments, the degree of activation does not significantly impact the degree of conjugation, as measured by the number of lysine residues modified in the carrier protein, such as, $CRM_{197}$ (as determined by amino acid analysis). For example, in some embodiments, the degree of activation does not significantly increase the number of lysine residues modified (as deter mined by amino acid analysis) in the carrier protein by 3-fold, as compared to the number of lysine residues modified in the carrier protein of a conjugate with a reference polysaccharide at the same degree of activation. In some embodiments, the degree of activation does not increase the level of unconjugated free saccharide. In some embodiments, the degree of activation does not decrease the optimal saccharide/protein ratio.

In some embodiments, the activated saccharide has a percentage of activation wherein moles of thiol per saccharide repeat unit of the activated saccharide is between 1-100%, such as, for example, between 2-80%, between 2-50%, between 3-30%, and between 4-25%. The degree of activation is at least 1%, 2%, 3%, 4%, 5%, 6%, 7%, 8%, 9%, 10%, 11%, 12%, 13%, 14%, 15%, 16%, 17%, 18%, 19%, ≥20%, ≥30%, ≥40%, ≥50%, ≥60%, ≥70%, ≥80%, or ≥90%, or about 100%. Preferably, the degree of activation is at most 50%, more preferably at most 25%. In one embodiment, the degree of activation is at most 20%. Any minimum value and any maximum value may be combined to define a range.

In one embodiment, the polysaccharide is activated with 1-cyano-4-dimethylamino pyridinium tetrafluoroborate (CDAP) to form a cyanate ester. The activated polysaccharide is then coupled directly or via a spacer (linker) group to an amino group on the carrier protein (preferably $CRM_{197}$ or tetanus toxoid).

For example, the spacer may be cystamine or cysteamine to give a thiolated polysaccharide which could be coupled to the carrier via a thioether linkage obtained after reaction with a maleimide-activated carrier protein (for example using N-[Y-maleimidobutyrloxy]succinimide ester (GMBS)) or a haloacetylated carrier protein (for example using iodoacetimide, N-succinimidyl bromoacetate (SBA; SIB), N-succinimidyl(4-iodoacetyl)aminobenzoate (SIAB), sulfosuccinimidyl(4-iodoacetyl)aminobenzoate (sulfo-SIAB), N-succinimidyl iodoacetate (SIA), or succinimidyl 3-[bromoacetamido]proprionate (SBAP)). In one embodiment, the cyanate ester (optionally made by CDAP chemistry) is coupled with hexane diamine or adipic acid dihydrazide (ADH) and the amino-derivatised saccharide is conjugated to the carrier protein (e.g., $CRM_{197}$) using carbodiimide (e.g., EDAC or EDC) chemistry via a carboxyl group on the protein carrier.

Other suitable techniques for conjugation use carbodiimides, hydrazides, active esters, norborane, p-nitrobenzoic acid, N-hydroxysuccinimide, S—NHS, EDC, TSTU. Conjugation may involve a carbonyl linker which may be formed by reaction of a free hydroxyl group of the saccharide with CDI followed by reaction with a protein to form a carbamate linkage. This may involve reduction of the anomeric terminus to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein (CDI chemistry).

Molecular weight. In some embodiments, the glycoconjugate comprises a saccharide having a molecular weight of between 10 kDa and 2,000 kDa. In other embodiments, the saccharide has a molecular weight of between 50 kDa and 1,000 kDa. In other embodiments, the saccharide has a molecular weight of between 70 kDa and 900 kDa. In other embodiments, the saccharide has a molecular weight of between 100 kDa and 800 kDa. In other embodiments, the saccharide has a molecular weight of between 200 kDa and 600 kDa. In further embodiments, the saccharide has a molecular weight of 100 kDa to 1000 kDa; 100 kDa to 900 kDa; 100 kDa to 800 kDa; 100 kDa to 700 kDa; 100 kDa to 600 kDa; 100 kDa to 500 kDa; 100 kDa to 400 kDa; 100 kDa to 300 kDa; 150 kDa to 1,000 kDa; 150 kDa to 900 kDa; 150 kDa to 800 kDa; 150 kDa to 700 kDa; 150 kDa to 600 kDa; 150 kDa to 500 kDa; 150 kDa to 400 kDa; 150 kDa to 300 kDa; 200 kDa to 1,000 kDa; 200 kDa to 900 kDa; 200 kDa to 800 kDa; 200 kDa to 700 kDa; 200 kDa to 600 kDa; 200 kDa to 500 kDa; 200 kDa to 400 kDa; 200 kDa to 300; 250 kDa to 1,000 kDa; 250 kDa to 900 kDa; 250 kDa to 800 kDa; 250 kDa to 700 kDa; 250 kDa to 600 kDa; 250 kDa to 500 kDa; 250 kDa to 400 kDa; 250 kDa to 350 kDa; 300 kDa to 1,000 kDa; 300 kDa to 900 kDa; 300 kDa to 800 kDa; 300 kDa to 700 kDa; 300 kDa to 600 kDa; 300 kDa to 500 kDa; 300 kDa to 400 kDa; 400 kDa to 1,000 kDa; 400 kDa to 900 kDa; 400 kDa to 800 kDa; 400 kDa to 700 kDa; 400 kDa to 600 kDa; 500 kDa to 600 kDa. In one embodiment, the glycoconjugate having such a molecular weight is produced by single-end conjugation. In another embodiment, the glycoconjugate having such a molecular weight is produced by reductive amination chemistry (RAC) prepared in aqueous buffer. Any whole number integer within any of the above ranges is contemplated as an embodiment of the disclosure.

In some embodiments, the glycoconjugate of the invention has a molecular weight of between 400 kDa and 15,000 kDa; between 500 kDa and 10,000 kDa; between 2,000 kDa and 10,000 kDa; between 3,000 kDa and 8,000 kDa; or between 3,000 kDa and 5,000 kDa. In other embodiments, the glycoconjugate has a molecular weight of between 500 kDa and 10,000 kDa. In other embodiments, glycoconjugate has a molecular weight of between 1,000 kDa and 8,000 kDa. In still other embodiments, the glycoconjugate has a molecular weight of between 2,000 kDa and 8,000 kDa or between 3,000 kDa and 7,000 kDa. In further embodiments, the glycoconjugate of the invention has a molecular weight of between 200 kDa and 20,000 kDa; between 200 kDa and 15,000 kDa; between 200 kDa and 10,000 kDa; between 200 kDa and 7,500 kDa; between 200 kDa and 5,000 kDa; between 200 kDa and 3,000 kDa; between 200 kDa and 1,000 kDa; between 500 kDa and 20,000 kDa; between 500 kDa and 15,000 kDa; between 500 kDa and 12,500 kDa; between 500 kDa and 10,000 kDa; between 500 kDa and 7,500 kDa; between 500 kDa and 6,000 kDa; between 500 kDa and 5,000 kDa; between 500 kDa and 4,000 kDa; between 500 kDa and 3,000 kDa; between 500 kDa and 2,000 kDa; between 500 kDa and 1,500 kDa; between 500 kDa and 1,000 kDa; between 750 kDa and 20,000 kDa; between 750 kDa and 15,000 kDa; between 750 kDa and 12,500 kDa; between 750 kDa and 10,000 kDa; between 750 kDa and 7,500 kDa; between 750 kDa and 6,000 kDa; between 750 kDa and 5,000 kDa; between 750 kDa and 4,000 kDa; between 750 kDa and 3,000 kDa; between 750 kDa and 2,000 kDa; between 750 kDa and 1,500 kDa; between 1,000 kDa and 15,000 kDa; between 1,000 kDa and 12,500 kDa; between 1,000 kDa and 10,000 kDa; between 1,000 kDa and 7,500 kDa; between 1,000 kDa and 6,000 kDa; between 1,000 kDa and 5,000 kDa; between 1,000 kDa and 4,000 kDa; between 1,000 kDa and 2,500 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; or between 2,000 kDa and 3,000 kDa. In one embodiment, the glycoconjugate having such a molecular weight is produced by eTEC conjugation described herein. In another embodiment, the glycoconjugate having such a molecular weight is produced by reductive amination chemistry (RAC). In another embodiment, the glycoconjugate having such a molecular weight is produced by reductive amination chemistry (RAC) prepared in DMSO.

In further embodiments, the glycoconjugate of the invention has a molecular weight of between 1,000 kDa and 20,000 kDa; between 1,000 kDa and 15,000 kDa; between 2,000 kDa and 10,000 kDa; between 2000 kDa and 7,500 kDa; between 2,000 kDa and 5,000 kDa; between 3,000 kDa and 20,000 kDa; between 3,000 kDa and 15,000 kDa; between 3,000 kDa and 12,500 kDa; between 4,000 kDa and 10,000 kDa; between 4,000 kDa and 7,500 kDa; between 4,000 kDa and 6,000 kDa; or between 5,000 kDa and 7,000 kDa. In one embodiment, the glycoconjugate having such a molecular weight is produced by reductive amination chemistry (RAC). In another embodiment, the glycoconjugate having such a molecular weight is produced by reductive amination chemistry (RAC) prepared in DMSO. In another embodiment, the glycoconjugate having such a molecular weight is produced by eTEC conjugation described herein.

In further embodiments, the glycoconjugate of the invention has a molecular weight of between 5,000 kDa and 20,000 kDa; between 5,000 kDa and 15,000 kDa; between 5,000 kDa and 10,000 kDa; between 5,000 kDa and 7,500 kDa; between 6,000 kDa and 20,000 kDa; between 6,000 kDa and 15,000 kDa; between 6,000 kDa and 12,500 kDa; between 6,000 kDa and 10,000 kDa or between 6,000 kDa and 7,500 kDa.

The molecular weight of the glycoconjugate may be measured by SEC-MALLS. Any whole number integer within any of the above ranges is contemplated as an embodiment of the disclosure. The glycoconjugates of the invention may also be characterized by the ratio (weight/weight) of saccharide to carrier protein. In some embodiments, the ratio of polysaccharide to carrier protein in the glycoconjugate (w/w) is between 0.5 and 3 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0). In other embodiments, the saccharide to carrier protein ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the saccharide to carrier protein ratio (w/w) is between 0.8 and 1.2. In a preferred embodiment, the ratio of polysaccharide to carrier protein in the conjugate is between 0.9 and 1.1. In some such embodiments, the carrier protein is $CRM_{197}$.

The glycoconjugates may also be characterized by their molecular size distribution ($K_d$). Size exclusion chromatography media (CL-4B) can be used to determine the relative molecular size distribution of the conjugate. Size Exclusion Chromatography (SEC) is used in gravity fed columns to profile the molecular size distribution of conjugates. Large molecules excluded from the pores in the media elute more quickly than small molecules. Fraction collectors are used to collect the column eluate. The fractions are tested colorimetrically by saccharide assay. For the determination of $K_d$, columns are calibrated to establish the fraction at which molecules are fully excluded ($V_o$), ($K_d=0$), and the fraction representing the maximum retention ($V_i$), ($K_d=1$). The fraction at which a specified sample attribute is reached ($V_e$), is related to Kd by the expression, $K_d=(V_e-V_o)/(V_i-V_o)$.

Free saccharide. The glycoconjugates and immunogenic compositions of the invention may include free saccharide that is not covalently conjugated to the carrier protein, but is nevertheless present in the glycoconjugate composition. The free saccharide may be non-covalently associated with (i.e., non-covalently bound to, adsorbed to, or entrapped in or with) the glycoconjugate. In a preferred embodiment, the glycoconjugate comprises at most 50%, 45%, 40%, 35%, 30%, 25%, 20% or 15% of free polysaccharide compared to the total amount of polysaccharide. In a preferred embodiment the glycoconjugate comprises less than about 25% of free polysaccharide compared to the total amount of polysaccharide. In a preferred embodiment the glycoconjugate comprises at most about 20% of free polysaccharide compared to the total amount of polysaccharide. In a preferred embodiment the glycoconjugate comprises at most about 15% of free polysaccharide compared to the total amount of polysaccharide. In another preferred embodiment, the glycoconjugate comprises at most about 20%, 19%, 18%, 17%, 16%, 15%, 14%, 13%, 12%, 11%, 10%, 9%, 8%, 7%, 6%, 5%, 4%, 3%, 2%, or 1% of free polysaccharide compared to the total amount of polysaccharide. In a preferred embodiment the glycoconjugate comprises less than about 8% of free polysaccharide compared to the total amount of polysaccharide. In a preferred embodiment the glycoconjugate comprises at most about 6% of free polysaccharide compared to the total amount of polysaccharide. In a preferred embodiment the glycoconjugate comprises at most about 5% of free polysaccharide compared to the total amount of polysaccharide. See, for example, Table 19, Table 20, Table 21, Table 22, Table 23, Table 24, and Table 25.

Covalent linkage. In other embodiments, the conjugate comprises at least one covalent linkage between the carrier protein and saccharide for every 5 to 10 saccharide repeat units; every 2 to 7 saccharide repeat units; every 3 to 8 saccharide repeat units; every 4 to 9 saccharide repeat units; every 6 to 11 saccharide repeat units; every 7 to 12 saccharide repeat units; every 8 to 13 saccharide repeat units; every 9 to 14 saccharide repeat units; every 10 to 15 saccharide repeat units; every 2 to 6 saccharide repeat units, every 3 to 7 saccharide repeat units; every 4 to 8 saccharide repeat units; every 6 to 10 saccharide repeat units; every 7 to 11 saccharide repeat units; every 8 to 12 saccharide repeat units; every 9 to 13 saccharide repeat units; every 10 to 14 saccharide repeat units; every 10 to 20 saccharide repeat units; every 4 to 25 saccharide repeat units or every 2 to 25 saccharide repeat units. In frequent embodiments, the carrier protein is $CRM_{197}$. In another embodiment, at least one linkage between carrier protein and saccharide occurs for every 2, 3, 4, 5, 6, 7, 8, 9, 10, 11, 12, 13, 14, 15, 16, 17, 18, 19, 20, 21, 22, 23, 24 or 25 saccharide repeat units of the polysaccharide. In one embodiment, the carrier protein is $CRM_{197}$. Any whole number integer within any of the above ranges is contemplated as an embodiment of the disclosure.

Lysine residues. Another way to characterize the glycoconjugates of the invention is by the number of lysine residues in the carrier protein (e.g., $CRM_{197}$) that become conjugated to the saccharide which can be characterized as a range of conjugated lysines (degree of conjugation). The evidence for lysine modification of the carrier protein, due to covalent linkages to the polysaccharides, can be obtained by amino acid analysis using routine methods known to those of skill in the art. Conjugation results in a reduction in the number of lysine residues recovered, compared to the carrier protein starting material used to generate the conjugate materials. In a preferred embodiment, the degree of conjugation of the glycoconjugate of the invention is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In one embodiment, the degree of conjugation of the glycoconjugate of the invention is about 2, about 3, about 4, about 5, about 6, about 7, about 8, about 9, about 10, about 11, about 12, about 13, about 14 or about 15. In a preferred embodiment, the degree of conjugation of the glycoconjugate of the invention is between 4 and 7. In some such embodiments, the carrier protein is $CRM_{197}$.

The frequency of attachment of the saccharide chain to a lysine on the carrier protein is another parameter for characterizing the glycoconjugates of the invention. For example, in some embodiments, at least one covalent linkage between the carrier protein and the polysaccharide for every 4 saccharide repeat units of the polysaccharide. In another embodiment, the covalent linkage between the carrier protein and the polysaccharide occurs at least once in every 10 saccharide repeat units of the polysaccharide. In another embodiment, the covalent linkage between the carrier protein and the polysaccharide occurs at least once in every 15 saccharide repeat units of the polysaccharide. In a further embodiment, the covalent linkage between the carrier protein and the polysaccharide occurs at least once in every 25 saccharide repeat units of the polysaccharide.

O-acetylation. In some embodiments, the saccharides of the invention are O-acetylated. In some embodiments, the glycoconjugate comprises a saccharide which has a degree of O-acetylation of between 10-100%, between 20-100%, between 30-100%, between 40-100%, between 50-100%, between 60-100%, between 70-100%, between 75-100%, 80-100%, 90-100%, 50-90%, 60-90%, 70-90% or 80-90%. In other embodiments, the degree of O-acetylation is 10%, ≥20%, ≥30%, ≥40%, ≥50%, ≥60%, ≥70%, ≥80%, or ≥90%, or about 100%. By % of O-acetylation it is meant the percentage of a given saccharide relative to 100% (where each repeat unit is fully acetylated relative to its acetylated structure). In some embodiments, the glycoconjugate is prepared by reductive amination. In some embodiments, the glycoconjugate is a single-end-linked conjugated saccharide, wherein the saccharide is covalently bound to a carrier protein directly. In some embodiments, the glycoconjugate is covalently bound to a carrier protein through a (2-((2-oxoethyl)thio)ethyl) carbamate (eTEC) spacer.

REDUCTIVE AMINATION. In one embodiment, the saccharide is conjugated to the carrier protein by reductive amination (such as described in U.S. Patent Appl. Pub. Nos. 2006/0228380, 2007/0231340, 2007/0184071 and 2007/0184072, WO 2006/110381, WO 2008/079653, and WO 2008/143709).

Reductive amination includes (1) oxidation of the saccharide, (2) reduction of the activated saccharide and a carrier protein to form a conjugate. Before oxidation, the saccharide is optionally hydrolyzed. Mechanical or chemical hydrolysis may be employed. Chemical hydrolysis may be conducted using acetic acid.

The oxidation step may involve reaction with periodate. The term "periodate" as used herein refers to both periodate and periodic acid. The term also includes both metaperiodate ($IO_4^-$) and orthoperiodate ($IO_6^{5-}$) and the various salts of periodate (e.g., sodium periodate and potassium periodate). In one embodiment the polysaccharide is oxidized in the presence of metaperiodate, preferably in the presence of sodium periodate ($NaIO_4$). In another embodiment the polysaccharide is oxidized in the presence of orthoperiodate, preferably in the presence of periodic acid.

In one embodiment, the oxidizing agent is a stable nitroxyl or nitroxide radical compound, such as piperidine-N-oxy or pyrrolidine-N-oxy compounds, in the presence of an oxidant to selectively oxidize primary hydroxyls. In said reaction, the actual oxidant is the N-oxoammonium salt, in a catalytic cycle. In an aspect, said stable nitroxyl or nitroxide radical compound are piperidine-N-oxy or pyrrolidine-N-oxy compounds. In an aspect, said stable nitroxyl or nitroxide radical compound bears a TEMPO (2,2,6,6-tetramethyl-1-piperidinyloxy) or a PROXYL (2,2,5,5-tetramethyl-1-pyrrolidinyloxy) moiety. In an aspect, said stable nitroxyl radical compound is TEMPO or a derivative thereof. In an aspect, said oxidant is a molecule bearing a N-halo moiety. In an aspect, said oxidant is selected from any one of N-ChloroSuccinimide, N-Bromosuccinimide, N-Iodosuccinimide, Dichloroisocyanuric acid, 1,3,5-trichloro-1,3,5-triazinane-2,4,6-trione, Dibromoisocyanuric acid, 1,3,5-tribromo-1,3,5-triazinane-2,4,6-trione, Diiodoisocyanuric acid and 1,3,5-triiodo-1,3,5-triazinane-2,4,6-trione. Preferably said oxidant is N-Chlorosuccinimide.

Following the oxidation step of the saccharide, the saccharide is said to be activated and is referred to as "activated" herein below. The activated saccharide and the carrier protein may be lyophilised (freeze-dried), either independently (discrete lyophilization) or together (co-lyophilized). In one embodiment the activated saccharide and the carrier protein are co-lyophilized. In another embodiment the activated polysaccharide and the carrier protein are lyophilized independently.

In one embodiment the lyophilization takes place in the presence of a non-reducing sugar, possible non-reducing sugars include sucrose, trehalose, raffinose, stachyose, melezitose, dextran, mannitol, lactitol and palatinit.

The next step of the conjugation process is the reduction of the activated saccharide and a carrier protein to form a conjugate (so-called reductive amination), using a reducing agent. Suitable reducing agents include the cyanoborohydrides, such as sodium cyanoborohydride, sodium triacetoxyborohydride or sodium or zinc borohydride in the presence of Bronsted or Lewis acids), amine boranes such as pyridine borane, 2-Picoline Borane, 2,6-diborane-methanol, dimethylamine-borane, t-BuMe'PrN—BH3, benzylamine-BH3 or 5-ethyl-2-methylpyridine borane (PEMB), borane-pyridine, or borohydride exchange resin. In one embodiment the reducing agent is sodium cyanoborohydride.

In an embodiment, the reduction reaction is carried out in aqueous solvent (e.g; selected from PBS, MES, HEPES, Bis-tris, ADA, PIPES, MOPSO, BES, MOPS, DIPSO, MOBS, HEPPSO, POPSO, TEA, EPPS, Bicine or HEPB, at a pH between 6.0 and 8.5, 7.0 and 8.0, or 7.0 and 7.5), in another embodiment the reaction is carried out in aprotic solvent. In an embodiment, the reduction reaction is carried out in DMSO (dimethylsulfoxide) or in DMF (dimethylformamide) solvent. The DMSO or DMF solvent may be used to reconstitute the activated polysaccharide and carrier protein which has been lyophilized.

At the end of the reduction reaction, there may be unreacted aldehyde groups remaining in the conjugates, these may be capped using a suitable capping agent. In one embodiment this capping agent is sodium borohydride ($NaBH_4$). Following the conjugation (the reduction reaction and optionally the capping), the glycoconjugates may be purified (enriched with respect to the amount of polysaccharide-protein conjugate) by a variety of techniques known to the skilled person. These techniques include dialysis, concentration/diafiltration operations, tangential flow filtration precipitation/elution, column chromatography (DEAE or hydrophobic interaction chromatography), and depth filtration. The glycoconjugates maybe purified by diafiltration and/or ion exchange chromatography and/or size exclusion chromatography. In an embodiment, the glycoconjugates are purified by diafiltration or ion exchange chromatography or size exclusion chromatography. In one embodiment the glycoconjugates are sterile filtered.

In a preferred embodiment, a glycoconjugate from an *E. coli* serotype is selected from any one of O25B, O1, O2, and O6 is prepared by reductive amination. In a preferred embodiment, the glycoconjugates from *E. coli* serotypes O25B, O1, O2, and O6 are prepared by reductive amination.

In one aspect, the invention relates to a conjugate that includes a carrier protein, e.g., $CRM_{197}$, linked to a saccharide of Formula O25B, presented by

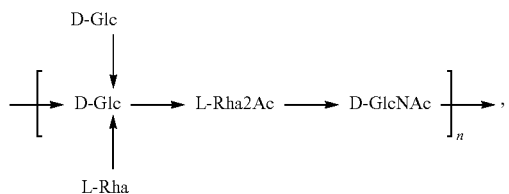

wherein n is any integer greater than or equal to 1. In a preferred embodiment, n is an integer of at least 31, 32, 33, 34, 35, 36, 37, 38, 39, 40, and at most 200, 100, 99, 98, 97, 96, 95, 94, 93, 92, 91, 90, 89, 88, 87, 86, 81, 80, 79, 78, 77, 76, 75, 74, 73, 72, 71, 70, 69, 68, 67, 66, 65, 60, 59, 58, 57, 56, 55, 54, 53, 52, 51, or 50. Any minimum value and any maximum value may be combined to define a range. Exemplary ranges include, for example, at least 1 to at most 1000; at least 10 to at most 500; and at least 20 to at most 80. In one preferred embodiment, n is at least 31 to at most 90, more preferably 40 to 90, most preferably 60 to 85.

In another aspect, the invention relates to a conjugate that includes a carrier protein, e.g., $CRM_{197}$, linked to a saccharide having any one of the following structures shown in Table 1 (see also FIG. 9A-9C and FIG. 10A-10B), wherein n is an integer greater than or equal to 1.

Without being bound by theory or mechanism, in some embodiments, a stable conjugate is believed to require a level of saccharide antigen modification that is balanced against preserving the structural integrity of the critical immunogenic epitopes of the antigen.

Activation and formation of an Aldehyde. In some embodiments, the saccharide of the invention is activated and results in the formation of an aldehyde. In such embodiments wherein the saccharide is activated, the percentage (%) of activation (or degree of oxidation (DO)) (see, e.g., Example 31) refers to moles of a saccharide repeat unit per moles of aldehyde of the activated polysaccharide. For example, in some embodiments, the saccharide is activated by periodate oxidation of vicinal diols on a repeat unit of the polysaccharide, resulting in the formation of an aldehyde. Varying the molar equivalents (meq) of sodium periodate relative to the saccharide repeat unit and temperature during oxidation results in varying levels of degree of oxidation (DO).

The saccharide and aldehyde concentrations are typically determined by colorimetric assays. An alternative reagent is TEMPO (2,2,6,6-tetramethylpiperidine 1-oxyl radical)-N-chlorosuccinimide (NCS) combination, which results in the formation of aldehydes from primary alcohol groups.

In some embodiments, the activated saccharide has a degree of oxidation wherein the moles of a saccharide repeat unit per moles of aldehyde of the activated saccharide is between 1-100, such as, for example, between 2-80, between 2-50, between 3-30, and between 4-25. The degree of activation is at least 1, 2, 3, 4, 5, 6, 7, 8, 9, 10, 11, 12, 13, 14, 15, 16, 17, 18, 19, ≥20, 30, ≥40, ≥50, ≥60, ≥70, ≥80, or ≥90, or about 100. Preferably, the degree of oxidation (DO) is at least 5 and at most 50, more preferably at least 10 and at most 25. In one embodiment, the degree of activation is at least 10 and at most 25. Any minimum value and any maximum value may be combined to define a range. A degree of oxidation value may be represented as percentage (%) of activation. For example, in one embodiment, a DO value of 10 refers to one activated saccharide repeat unit out of a total of 10 saccharide repeat units in the activated saccharide, in which case the DO value of 10 may be represented as 10% activation.

In some embodiments, the conjugate prepared by reductive amination chemistry includes a carrier protein and a saccharide, wherein the saccharide includes a structure selected from any one of Formula O1 (e.g., Formula O1A, Formula O1B, and Formula O1C), Formula O2, Formula O3, Formula O4 (e.g., Formula O4:K52 and Formula O4:K6), Formula O5 (e.g., Formula O5ab and Formula O5ac (strain 180/C3)), Formula O6 (e.g., Formula O6:K2; K13; K15 and Formula O6:K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62$D_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187. In some embodiments, the saccharide in the conjugate includes a Formula, wherein n is an integer from 1 to 1000, from 5 to 1000, preferably 31 to 100, more preferably 35 to 90, most preferably 35 to 65.

SINGLE-END LINKED CONJUGATES. In some embodiments, the conjugate is single-end-linked conjugated saccharide, wherein the saccharide is covalently bound at one end of the saccharide to a carrier protein. In some embodiments, the single-end-linked conjugated polysaccharide has a terminal saccharide. For example, a conjugate is single-end linked if one of the ends (a terminal saccharide residue) of the polysaccharide is covalently bound to a carrier protein. In some embodiments, the conjugate is single-end linked if a terminal saccharide residue of the polysaccharide is covalently bound to a carrier protein through a linker. Such linkers may include, for example, a cystamine linker (A1), a 3,3'-dithio bis(propanoic dihydrazide) linker (A4), and a 2,2'-dithio-N,N'-bis(ethane-2,1-diyl) bis(2-(aminooxy)acetamide) linker (A6).

In some embodiments, the saccharide is conjugated to the carrier protein through a 3-deoxy-d-manno-oct-2-ulosonic acid (KDO) residue to form a single-end linked conjugate. See, for example, Example 26, Example 27, Example 28, and FIG. 17.

In some embodiments, the conjugate is preferably not a bioconjugate. The term "bioconjugate" refers to a conjugate between a protein (e.g., a carrier protein) and an antigen, e.g., an O antigen (e.g., O25B) prepared in a host cell background, wherein host cell machinery links the antigen to the protein (e.g., N-links). Glycoconjugates include bioconjugates, as well as sugar antigen (e.g., oligo- and polysaccharides)-protein conjugates prepared by means that do not require preparation of the conjugate in a host cell, e.g., conjugation by chemical linkage of the protein and saccharide.

Thiol Activated Saccharides. In some embodiments, the saccharide of the invention is thiol activated. In such embodiments wherein the saccharide is thiol activated, the percentage (%) of activation refers to moles of thiol per saccharide repeat unit of the activated polysaccharide. The saccharide and thiol concentrations are typically determined by Ellman's assay for quantitation of sulfhydryls. For example, in some embodiments, the saccharide includes activation of 2-Keto-3-deoxyoctanoic acid (KDO) with a disulfide amine linker. See, for example, Example 10 and FIG. 31. In some embodiments, the saccharide is covalently bound to a carrier protein through a bivalent, heterobifunctional linker (also referred to herein as a "spacer"). The linker preferably provides a thioether bond between the saccharide and the carrier protein, resulting in a glycoconjugate referred to herein as a "thioether glycoconjugate." In some embodiments, the linker further provides carbamate and amide bonds, such as, for example, (2-((2-oxoethyl) thio)ethyl) carbamate (eTEC). See, for example, Example 21.

In some embodiments, the single-end linked conjugate includes a carrier protein and a saccharide, wherein the saccharide includes a structure selected from any one of Formula O1 (e.g., Formula O1A, Formula O1B, and Formula O1C), Formula O2, Formula O3, Formula O4 (e.g., Formula O4:K52 and Formula O4:K6), Formula O5 (e.g., Formula O5ab and Formula O5ac (strain 180/C3)), Formula O6 (e.g., Formula O6:K2; K13; K15 and Formula O6:K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D$_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187. In some embodiments, the saccharide in the conjugate includes a Formula, wherein n is an integer from 1 to 1000, from 5 to 1000, preferably 31 to 100, more preferably 35 to 90, most preferably 35 to 65.

For example, in one embodiment, the single-end linked conjugate includes a carrier protein and a saccharide having a structure selected from Formula O8, Formula O9a, Formula O9, Formula O20ab, Formula O20ac, Formula O52, Formula O97, and Formula O101, wherein n is an integer from 1 to 10.

F. eTEC Conjugates

In one aspect, the invention relates generally to glycoconjugates comprising a saccharide derived from *E. coli* described above covalently conjugated to a carrier protein through a (2-((2-oxoethyl)thio)ethyl)carbamate (eTEC) spacer (as described, for example, in U.S. Pat. No. 9,517,274 and International Patent Application Publication WO2014027302, incorporated by reference herein in their entireties), including immunogenic compositions comprising such glycoconjugates, and methods for the preparation and use of such glycoconjugates and immunogenic compositions. Said glycoconjugates comprise a saccharide covalently conjugated to a carrier protein through one or more eTEC spacers, wherein the saccharide is covalently conjugated to the eTEC spacer through a carbamate linkage, and wherein the carrier protein is covalently conjugated to the eTEC spacer through an amide linkage. The eTEC spacer includes seven linear atoms (i.e., —C(O)NH(CH$_2$)$_2$SCH$_2$C (O)—) and provides stable thioether and amide bonds between the saccharide and carrier protein.

The eTEC linked glycoconjugates of the invention may be represented by the general formula (I):

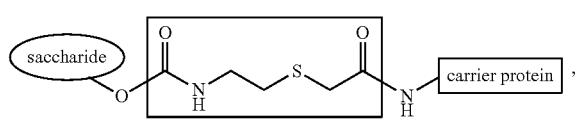

(I)

where the atoms that comprise the eTEC spacer are contained in the central box.

In said glycoconjugates of the invention, the saccharide may be a polysaccharide or an oligosaccharide.

The carrier proteins incorporated into the glycoconjugates of the invention are selected from the group of carrier proteins generally suitable for such purposes, as further described herein or known to those of skill in the art. In particular embodiments, the carrier protein is CRM$_{197}$.

In another aspect, the invention provides a method of making a glycoconjugate comprising a saccharide described herein conjugated to a carrier protein through an eTEC spacer, comprising the steps of a) reacting a saccharide with a carbonic acid derivative in an organic solvent to produce an activated saccharide; b) reacting the activated saccharide with cystamine or cysteamine or a salt thereof, to produce a thiolated saccharide; c) reacting the thiolated saccharide with a reducing agent to produce an activated thiolated saccharide comprising one or more free sulfhydryl residues; d) reacting the activated thiolated saccharide with an activated carrier protein comprising one or more α-haloacetamide groups, to produce a thiolated saccharide-carrier protein conjugate; and e) reacting the thiolated saccharide-carrier protein conjugate with (i) a first capping reagent capable of capping unconjugated α-haloacetamide groups of the activated carrier protein; and/or (ii) a second capping reagent capable of capping unconjugated free sulfhydryl residues of the activated thiolated saccharide; whereby an eTEC linked glycoconjugate is produced.

In frequent embodiments, the carbonic acid derivative is 1,1'-carbonyl-di-(1,2,4-triazole) (CDT) or 1,1'-carbonyldiimidazole (CDI). Preferably, the carbonic acid derivative is CDT and the organic solvent is a polar aprotic solvent, such as dimethylsulfoxide (DMSO). In preferred embodiments, the thiolated saccharide is produced by reaction of the activated saccharide with the bifunctional symmetric thioalkylamine reagent, cystamine or a salt thereof. Alternatively, the thiolated saccharide may be formed by reaction of the activated saccharide with cysteamine or a salt thereof. The eTEC linked glycoconjugates produced by the methods of the invention may be represented by general Formula (I).

In frequent embodiments, the first capping reagent is N-acetyl-L-cysteine, which reacts with unconjugated α-haloacetamide groups on lysine residues of the carrier protein to form an S-carboxymethylcysteine (CMC) residue covalently linked to the activated lysine residue through a thioether linkage.

In other embodiments, the second capping reagent is iodoacetamide (IAA), which reacts with unconjugated free sulfhydryl groups of the activated thiolated saccharide to provide a capped thioacetamide. Frequently, step e) comprises capping with both a first capping reagent and a second capping reagent. In certain embodiments, step e) comprises capping with N-acetyl-L-cysteine as the first capping reagent and IAA as the second capping reagent.

In some embodiments, the capping step e) further comprises reaction with a reducing agent, for example, DTT, TCEP, or mercaptoethanol, after reaction with the first and/or second capping reagent.

The eTEC linked glycoconjugates and immunogenic compositions of the invention may include free sulfhydryl residues. In some instances, the activated thiolated saccharides formed by the methods provided herein will include multiple free sulfhydryl residues, some of which may not undergo covalent conjugation to the carrier protein during the conjugation step. Such residual free sulfhydryl residues are capped by reaction with a athiol-reactive capping reagent, for example, iodoacetamide (IAA), to cap the potentially reactive functionality. Other thiol-reactive capping reagents, e.g., maleimide containing reagents and the like are also contemplated.

In addition, the eTEC linked glycoconjugates and immunogenic compositions of the invention may include residual unconjugated carrier protein, which may include activated carrier protein which has undergone modification during the capping process steps.

In some embodiments, step d) further comprises providing an activated carrier protein comprising one or more α-haloacetamide groups prior to reacting the activated thiolated saccharide with the activated carrier protein. In frequent embodiments, the activated carrier protein comprises one or more α-bromoacetamide groups.

In another aspect, the invention provides an eTEC linked glycoconjugate comprising a saccharide described herein conjugated to a carrier protein through an eTEC spacer produced according to any of the methods disclosed herein.

In some embodiments, the carrier protein is CRM$_{197}$ and the covalent linkage via an eTEC spacer between the CRM$_{197}$ and the polysaccharide occurs at least once in every 4, 10, 15 or 25 saccharide repeat units of the polysaccharide.

For each of the aspects of the invention, in particular embodiments of the methods and compositions described herein, the eTEC linked glycoconjugate comprises a saccharide described herein, such as, a saccharide derived from *E. coli*.

In another aspect, the invention provides a method of preventing, treating or ameliorating a bacterial infection, disease or condition in a subject, comprising administering to the subject an immunologically effective amount of an immunogenic composition of the invention, wherein said immunogenic composition comprises an eTEC linked glycoconjugate comprising a saccharide described herein. In some embodiments, the saccharide is derived from *E. coli*.

In some embodiments, the eTEC linked glycoconjugate comprises a carrier protein and a saccharide, in which said saccharide comprises a structure selected from any one of Formula O1 (e.g., Formula O1A, Formula O1B, and Formula O1C), Formula O2, Formula O3, Formula O4 (e.g., Formula O4:K52 and Formula O4:K6), Formula O5 (e.g., Formula O5ab and Formula O5ac (strain 180/C3)), Formula O6 (e.g., Formula O6:K2; K13; K15 and Formula O6:K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D$_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187. In some embodiments, the saccharide in the conjugate includes a Formula, wherein n is an integer from 1 to 1000, from 5 to 1000, preferably 31 to 100, more preferably 35 to 90, most preferably 35 to 65.

The number of lysine residues in the carrier protein that become conjugated to the saccharide can be characterized as a range of conjugated lysines. For example, in some embodiments of the immunogenic compositions, the CRM$_{197}$ may comprise 4 to 16 lysine residues out of 39 covalently linked to the saccharide. Another way to express this parameter is that about 10% to about 41% of CRM$_{197}$ lysines are covalently linked to the saccharide. In other embodiments, the CRM$_{197}$ may comprise 2 to 20 lysine residues out of 39 covalently linked to the saccharide. Another way to express this parameter is that about 5% to about 50% of CRM$_{197}$ lysines are covalently linked to the saccharide.

In frequent embodiments, the carrier protein is CRM$_{197}$ and the covalent linkage via an eTEC spacer between the CRM$_{197}$ and the polysaccharide occurs at least once in every 4, 10, 15 or 25 saccharide repeat units of the polysaccharide.

In other embodiments, the conjugate comprises at least one covalent linkage between the carrier protein and saccharide for every 5 to 10 saccharide repeat units; every 2 to 7 saccharide repeat units; every 3 to 8 saccharide repeat units; every 4 to 9 saccharide repeat units; every 6 to 11 saccharide repeat units; every 7 to 12 saccharide repeat units; every 8 to 13 saccharide repeat units; every 9 to 14 saccharide repeat units; every 10 to 15 saccharide repeat units; every 2 to 6 saccharide repeat units, every 3 to 7 saccharide repeat units; every 4 to 8 saccharide repeat units; every 6 to 10 saccharide repeat units; every 7 to 11 saccharide repeat units; every 8 to 12 saccharide repeat units; every 9 to 13 saccharide repeat units; every 10 to 14 saccharide repeat units; every 10 to 20 saccharide repeat units; or every 4 to 25 saccharide repeat units. In another embodiment, at least one linkage between carrier protein and saccharide occurs for every 2, 3, 4, 5, 6, 7, 8, 9, 10, 11, 12, 13, 14, 15, 16, 17, 18, 19, 20, 21, 22, 23, 24 or 25 saccharide repeat units of the polysaccharide.

G. Carrier Proteins

A component of the glycoconjugate of the invention is a carrier protein to which the saccharide is conjugated. The terms "protein carrier" or "carrier protein" or "carrier" may be used interchangeably herein. Carrier proteins should be amendable to standard conjugation procedures.

One component of the conjugate is a carrier protein to which the O-polysaccharide is conjugated. In one embodiment, the conjugate includes a carrier protein conjugated to the core oligosaccharide of the O-polysaccharide (see FIG. 24). In one embodiment, the conjugate includes a carrier protein conjugated to the O-antigen of the O-polysaccharide.

The terms "protein carrier" or "carrier protein" or "carrier" may be used interchangeably herein. Carrier proteins should be amendable to standard conjugation procedures.

In a preferred embodiment, the carrier protein of the conjugates is independently selected from any one of TT, DT, DT mutants (such as CRM$_{197}$), *H. influenzae* protein D, PhtX, PhtD, PhtDE fusions (particularly those described in WO 01/98334 and WO 03/54007), detoxified pneumolysin, PorB, N19 protein, PspA, OMPC, toxin A or B of *C. Difficile* and PsaA. In an embodiment, the carrier protein of the conjugates of the invention is DT (Diphtheria toxoid). In another embodiment, the carrier protein of the conjugates of the invention is TT (tetanus toxoid). In another embodiment, the carrier protein of the conjugates of the invention is PD (*Haemophilus influenzae* protein D—see, e.g., EP 0 594 610 B). In some embodiments, the carrier protein includes poly(L-lysine) (PLL).

In a preferred embodiment, the saccharides are conjugated to CRM$_{197}$ protein. The CRM$_{197}$ protein is a nontoxic form of diphtheria toxin but is immunologically indistinguishable from the diphtheria toxin. CRM$_{197}$ is produced by *C. diphtheriae* infected by the nontoxigenic phage β197tox⁻ created by nitrosoguanidine mutagenesis of the toxigenic corynephage beta. The CRM$_{197}$ protein has the same molecular weight as the diphtheria toxin but differs therefrom by a single base change (guanine to adenine) in the structural gene. This single base change causes an amino acid substitution glutamic acid for glycine) in the mature protein and eliminates the toxic properties of diphtheria toxin. The CRM$_{197}$ protein is a safe and effective T-cell dependent carrier for saccharides.

Accordingly, in some embodiments, the conjugates of the invention include CRM$_{197}$ as the carrier protein, wherein the saccharide is covalently linked to CRM$_{197}$.

In a preferred embodiment, the carrier protein of the glycoconjugates is selected in the group consisting of DT (Diphtheria toxin), TT (tetanus toxoid) or fragment C of TT, CRM197 (a nontoxic but antigenically identical variant of diphtheria toxin), other DT mutants (such as CRM176, CRM228, CRM 45 (Uchida et al J. Biol. Chem. 218; 3838-3844, 1973), CRM9, CRM45, CRM102, CRM103 or CRM107; and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or 4,950,740; mutation of at least one or more residues Lys 516, Lys 526, Phe 530 and/or Lys 534 and other mutations disclosed in U.S. Pat. No. 5,917,017 or 6,455,673; or fragment disclosed in U.S. Pat. No. 5,843,711), pneumococcal pneumolysin (Kuo et al (1995) Infect Immun 63; 2706-13) including ply detoxified in some fashion for example dPLY-GMBS (WO 04081515, PCT/EP2005/010258) or dPLY-formol, PhtX, including PhtA, PhtB, PhtD, PhtE (sequences of PhtA, PhtB, PhtD or PhtE are disclosed in WO 00/37105 or WO 00/39299) and fusions of Pht proteins for example PhtDE fusions, PhtBE fusions, Pht A-E (WO 01/98334, WO 03/54007, WO2009/000826), OMPC (meningococcal outer membrane protein—usually extracted from N. meningitidis serogroup B—EP0372501), PorB (from N. meningitidis), PD (Haemophilus influenzae protein D—see, e.g., EP 0 594 610 B), or immunologically functional equivalents thereof, synthetic peptides (EP0378881, EP0427347), heat shock proteins (WO 93/17712, WO 94/03208), pertussis proteins (WO 98/58668, EP0471 177), cytokines, lymphokines, growth factors or hormones (WO 91/01146), artificial proteins comprising multiple human CD4+ T cell epitopes from various pathogen derived antigens (Falugi et al (2001) Eur J Immunol 31; 3816-3824) such as N19 protein (Baraldoi et al (2004) Infect Immun 72; 4884-7) pneumococcal surface protein PspA (WO 02/091998), iron uptake proteins (WO 01/72337), toxin A or B of C. difficile (WO 00/61761), transferrin binding proteins, pneumococcal adhesion protein (PsaA), recombinant Pseudomonas aeruginosa exotoxin A (in particular non-toxic mutants thereof (such as exotoxin A bearing a substitution at glutamic acid 553 (Uchida Cameron D M, RJ Collier. 1987. J. Bacteriol. 169:4967-4971)). Other proteins, such as ovalbumin, keyhole limpet hemocyanin (KLH), bovine serum albumin (BSA) or purified protein derivative of tuberculin (PPD) also can be used as carrier proteins. Other suitable carrier proteins include inactivated bacterial toxins such as cholera toxoid (e.g., as described in Int'l Patent Application No. WO 2004/083251), E. coli LT, E. coli ST, and exotoxin A from Pseudomonas aeruginosa.

In some embodiments, the carrier protein is selected from any one of, for example, CRM$_{197}$, diphtheria toxin fragment B (DTFB), DTFB C8, Diphtheria toxoid (DT), tetanus toxoid (TT), fragment C of TT, pertussis toxoid, cholera toxoid, or exotoxin A from Pseudomonas aeruginosa; detoxified Exotoxin A of P. aeruginosa (EPA), maltose binding protein (MBP), flagellin, detoxified hemolysin A of S. aureus, clumping factor A, clumping factor B, Cholera toxin B subunit (CTB), Streptococcus pneumoniae Pneumolysin and detoxified variants thereof, C. jejuni AcrA, C. jejuni natural glycoproteins and Streptococcal C5a peptidase (SCP). In one embodiment, the carrier protein is detoxified Pseudomonas exotoxin (EPA). In another embodiment, the carrier protein is not detoxified Pseudomonas exotoxin (EPA). In one embodiment, the carrier protein is flagellin. In another embodiment, the carrier protein is not flagellin.

In a preferred embodiment, the carrier protein of the glycoconjugates is independently selected from the group consisting of TT, DT, DT mutants (such as CRM$_{197}$), H. influenzae protein D, PhtX, PhtD, PhtDE fusions (particularly those described in WO 01/98334 and WO 03/54007), detoxified pneumolysin, PorB, N19 protein, PspA, OMPC, toxin A or B of C. Difficile and PsaA. In an embodiment, the carrier protein of the glycoconjugates of the invention is DT (Diphtheria toxoid). In another embodiment, the carrier protein of the glycoconjugates of the invention is TT (tetanus toxoid). In another embodiment, the carrier protein of the glycoconjugates of the invention is PD (Haemophilus influenzae protein D—see, e.g., EP 0 594 610 B).

In a preferred embodiment, the capsular saccharides of the invention are conjugated to CRM$_{197}$ protein. The CRM$_{197}$ protein is a nontoxic form of diphtheria toxin but is immunologically indistinguishable from the diphtheria toxin. CRM$_{197}$ is produced by C. diphtheriae infected by the nontoxigenic phage β197tox-created by nitrosoguanidine mutagenesis of the toxigenic corynephage beta (Uchida, T. et al. 1971, Nature New Biology 233:8-11). The CRM$_{197}$ protein has the same molecular weight as the diphtheria toxin but differs therefrom by a single base change (guanine to adenine) in the structural gene. This single base change causes an amino acid substitution glutamic acid for glycine) in the mature protein and eliminates the toxic properties of diphtheria toxin. The CRM$_{197}$ protein is a safe and effective T-cell dependent carrier for saccharides. Further details about CRM$_{197}$ and production thereof can be found e.g. in U.S. Pat. No. 5,614,382

Accordingly, in frequent embodiments, the glycoconjugates of the invention comprise CRM$_{197}$ as the carrier protein, wherein the capsular polysaccharide is covalently linked to CRM$_{197}$.

In a further embodiment, the carrier protein of the glycoconjugates is SCP (Streptococcal C5a Peptidase). All human isolates of β-hemolytic streptococci produce a highly conserved cell-wall protein SCP (Streptococcal C5a Peptidase) that specifically inactivates C5a. The scp genes encode a polypeptide containing between 1,134 and 1,181 amino acids (Brown et al., PNAS, 2005, vol. 102, no. 51 pages 18391-18396). The first 31 residues are the export signal presequence and are removed upon passing through the cytoplasmic membrane. The next 68 residues serve as a pro-sequence and must be removed to produce active SCP. The next 10 residues can be removed without loss of protease activity. At the other end, starting with Lys-1034, are four consecutive 17-residue motifs followed by a cell sorting and cell-wall attachment signal. This combined signal is composed of a 20-residue hydrophilic sequence containing an LPTTND sequence, a 17-residue hydrophobic sequence, and a short basic carboxyl terminus.

SCP can be divided in domains (see FIG. 1B of Brown et al., PNAS, 2005, vol. 102, no. 51 pages 18391-18396). These domains are the Pre/Pro domain (which comprises the export signal presequence (commonly the first 31 residues) and the pro-sequence (commonly the next 68 residues)), the protease domain (which is splitted in two part (protease part 1 commonly residues 89-333/334 and protease domain part 2 and commonly residues 467/468-583/584), the protease-associated domain (PA domain) (commonly residues 333/334-467/468), three fibronectin type III (Fn) domains (Fn1, commonly residues 583/584-712/713; Fn2, commonly residues 712/713-928/929/930; commonly Fn3, residues 929/930-1029/1030/1031) and a cell wall anchor domain (commonly redisues 1029/1030/1031 to the C-terminus).

In an embodiment, the carrier protein of the glycoconjugates of the invention is an SCP from GBS (SCPB). An example of SCPB is provided at SEQ. ID. NO: 3 of WO97/26008. See also SEQ ID NO: 3 of WO00/34487.

In another embodiment, the carrier protein of the glycoconjugate of the invention is an SCP from GAS (SCPA). Examples of SCPA can be found at SEQ. ID. NO:1 and SEQ. ID. NO:2 of WO97/26008. See also SEQ ID NOs: 1, 2 and 23 of WO00/34487.

In a further embodiment, the carrier protein of the glycoconjugate of the invention is an SCP as set forth in SEQ ID NO: 150 or 151 of WO2014/136064.

H. Dosages of the Compositions Dosage regimens may be adjusted to provide the optimum desired response.

For example, a single dose of the polypeptide derived from *E. coli* or fragment thereof may be administered, several divided doses may be administered overtime, or the dose may be proportionally reduced or increased as indicated by the exigencies of the situation. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Determining appropriate dosages and regimens for administration of the therapeutic protein are well-known in the relevant art and would be understood to be encompassed by the skilled artisan once provided the teachings disclosed herein.

In some embodiments, the amount of the polypeptide derived from *E. coli* or fragment thereof in the composition, may range from about 10 µg to about 300 µg of each protein antigen. In some embodiments, the amount of the polypeptide derived from *E. coli* or fragment thereof in the composition may range from about 20 µg to about 200 µg of each protein antigen.

The amount of glycoconjugate(s) in each dose is selected as an amount which induces an immunoprotective response without significant, adverse side effects in typical vaccines. Such amount will vary depending upon which specific immunogen is employed and how it is presented.

The amount of a particular glycoconjugate in an immunogenic composition can be calculated based on total polysaccharide for that conjugate (conjugated and non-conjugated). For example, a glycoconjugate with 20% free polysaccharide will have about 80 µg of conjugated polysaccharide and about 20 µg of non-conjugated polysaccharide in a 100 µg polysaccharide dose. The amount of glycoconjugate can vary depending upon the *E. coli* serotype. The saccharide concentration can be determined by the uronic acid assay.

The "immunogenic amount" of the different polysaccharide components in the immunogenic composition, may diverge and each may comprise about 1.0 µg, about 2.0 µg, about 3.0 µg, about 4.0 µg, about 5.0 µg, about 6.0 µg, about 7.0 µg, about 8.0 µg, about 9.0 µg, about 10.0 µg, about 15.0 µg, about 20.0 µg, about 30.0 µg, about 40.0 µg, about 50.0 µg, about 60.0 µg, about 70.0 µg, about 80.0 µg, about 90.0 µg, or about 100.0 µg of any particular polysaccharide antigen. Generally, each dose will comprise 0.1 µg to 100 µg of polysaccharide for a given serotype, particularly 0.5 µg to 20 µg, more particularly 1 µg to 10 µg, and even more particularly 2 µg to 5 µg. Any whole number integer within any of the above ranges is contemplated as an embodiment of the disclosure. In one embodiment, each dose will comprise 1 µg, 2 µg, 3 µg, 4 µg, 5 µg, 6 µg, 7 µg, 8 µg, 9 µg, 10 µg, 15 µg or 20 µg of polysaccharide for a given serotype.

Carrier protein amount. Generally, each dose will comprise 5 µg to 150 µg of carrier protein, particularly 10 µg to 100 µg of carrier protein, more particularly 15 µg to 100 µg of carrier protein, more particularly 25 µg to 75 µg of carrier protein, more particularly 30 µg to 70 µg of carrier protein, more particularly 30 µg to 60 µg of carrier protein, more particularly 30 µg to 50 µg of carrier protein and even more particularly 40 µg to 60 µg of carrier protein. In one embodiment, said carrier protein is $CRM_{197}$. In one embodiment, each dose will comprise about 25 µg, about 26 µg, about 27 µg, about 28 µg, about 29 µg, about 30 µg, about 31 µg, about 32 µg, about 33 µg, about 34 µg, about 35 µg, about 36 µg, about 37 µg, about 38 µg, about 39 µg, about 40 µg, about 41 µg, about 42 µg, about 43 µg, about 44 µg, about 45 µg, about 46 µg, about 47 µg, about 48 µg, about 49 µg, about 50 µg, about 51 µg, about 52 µg, about 53 µg, about 54 µg, about 55 µg, about 56 µg, about 57 µg, about 58 µg, about 59 µg, about 60 µg, about 61 µg, about 62 µg, about 63 µg, about 64 µg, about 65 µg, about 66 µg, about 67 µg, 68 µg, about 69 µg, about 70 µg, about 71 µg, about 72 µg, about 73 µg, about 74 µg or about 75 µg of carrier protein. In one embodiment, said carrier protein is $CRM_{197}$. In another embodiment, said carrier protein is SCP.

I. Adjuvant

In some embodiments, the immunogenic compositions disclosed herein may further comprise at least one, two or three adjuvants. In some embodiments, the immunogenic compositions disclosed herein may further comprise at least one adjuvant. In some embodiments, the immunogenic compositions disclosed herein may further comprise one adjuvant. In some embodiments, the immunogenic compositions disclosed herein may further comprise two adjuvants. The term "adjuvant" refers to a compound or mixture that enhances the immune response to an antigen. Antigens may act primarily as a delivery system, primarily as an immune modulator or have strong features of both. Suitable adjuvants include those suitable for use in mammals, including humans.

Examples of known suitable delivery-system type adjuvants that can be used in humans include, but are not limited to, alum (e.g., aluminum phosphate, aluminum sulfate or aluminum hydroxide), calcium phosphate, liposomes, oil-in-water emulsions such as MF59 (4.3% w/v squalene, 0.5% w/v polysorbate 80 (Tween 80), 0.5% w/v sorbitan trioleate (Span 85)), water-in-oil emulsions such as Montanide, and poly(D,L-lactide-co-glycolide) (PLG) microparticles or nanoparticles.

In an embodiment, the immunogenic compositions disclosed herein comprise aluminum salts (alum) as adjuvant (e.g., aluminum phosphate, aluminum sulfate or aluminum hydroxide). In a preferred embodiment, the immunogenic compositions disclosed herein comprise aluminum phosphate or aluminum hydroxide as adjuvant. In an embodiment, the immunogenic compositions disclosed herein comprise from 0.1 mg/mL to 1 mg/mL or from 0.2 mg/mL to 0.3 mg/mL of elemental aluminum in the form of aluminum phosphate. In an embodiment, the immunogenic compositions disclosed herein comprise about 0.25 mg/mL of elemental aluminum in the form of aluminum phosphate.

Examples of known suitable immune modulatory type adjuvants that can be used in humans include, but are not limited to, saponin extracts from the bark of the Aquilla tree (QS21, Quil A), TLR4 agonists such as MPLA (Monophosphoryl Lipid A), 3DMPL (3-O-deacylated MPL) or GLA-AQ, LT/CT mutants, cytokines such as the various interleukins (e.g., IL-2, IL-12) or GM-CSF, ASO1, and the like.

Examples of known suitable immune modulatory type adjuvants with both delivery and immune modulatory features that can be used in humans include, but are not limited to, ISCOMS (see, e.g., Sjolander et al. (1998) J. Leukocyte Biol. 64:713; WO 90/03184, WO 96/11711, WO 00/48630, WO 98/36772, WO 00/41720, WO 2006/134423 and WO 2007/026190) or GLA-EM which is a combination of a TLR4 agonist and an oil-in-water emulsion.

For veterinary applications including but not limited to animal experimentation, one can use Complete Freund's Adjuvant (CFA), Freund's Incomplete Adjuvant (IFA), Emulsigen, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-di-palmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further exemplary adjuvants to enhance effectiveness of the immunogenic compositions disclosed herein include, but are not limited to (1) oil-in-water emulsion formulations (with or without other specific immunostimulating agents such as muramyl peptides (see below) or bacterial cell wall components), such as for example (a) SAF, containing 10% Squalane, 0.4% Tween 80, 5% pluronic-blocked polymer L121, and thr-MDP either microfluidized into a submicron emulsion or vortexed to generate a larger particle size emulsion, and (b) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), preferably MPL+CWS (DETOX™); (2) saponin adjuvants, such as QS21, STIMULON™ (Cambridge Bioscience, Worcester, Mass.), ABISCO® (Isconova, Sweden), or ISCOMA-TRIX® (Commonwealth Serum Laboratories, Australia), may be used or particles generated therefrom such as ISCOMs (immunostimulating complexes), which ISCOMS may be devoid of additional detergent (e.g., WO 00/07621); (3) Complete Freund's Adjuvant (CFA) and Incomplete Freund's Adjuvant (IFA); (4) cytokines, such as interleukins (e.g., IL-1, IL-2, IL-4, IL-5, IL-6, IL-7, IL-12 (e.g., WO 99/44636)), interferons (e.g., gamma interferon), macrophage colony stimulating factor (M-CSF), tumor necrosis factor (TNF), etc.; (5) monophosphoryl lipid A (MPL) or 3-O-deacylated MPL (3dMPL) (see, e.g., GB2220211, EP0689454) (see, e.g., WO 00/56358); (6) combinations of 3dMPL with, for example, QS21 and/or oil-in-water emulsions (see, e.g., EP0835318, EP0735898, EP0761231); (7) a polyoxyethylene ether or a polyoxyethylene ester (see, e.g., WO 99/52549); (8) a polyoxyethylene sorbitan ester surfactant in combination with an octoxynol (e.g., WO 01/21207) or a polyoxyethylene alkyl ether or ester surfactant in combination with at least one additional non-ionic surfactant such as an octoxynol (e.g., WO 01/21152); (9) a saponin and an immunostimulatory oligonucleotide (e.g., a CpG oligonucleotide) (e.g., WO 00/62800); (10) an immunostimulant and a particle of metal salt (see, e.g., WO 00/23105); (11) a saponin and an oil-in-water emulsion (e.g., WO 99/11241); (12) a saponin (e.g., QS21)+3dMPL+1M2 (optionally+a sterol) (e.g., WO 98/57659); (13) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc.

In another embodiment, the adjuvant is a liposomal QS21 formulation as set forth in Example 35. In a further embodiment, the adjuvant is a liposomal MPLA formulation as set forth in Example 35. In a still further embodiment, the adjuvant is a liposomal MPLA/QS21 formulation as set forth in Example 35.

In an embodiment of the present invention, the immunogenic compositions as disclosed herein comprise a CpG Oligonucleotide as adjuvant. A CpG oligonucleotide as used herein refers to an immunostimulatory CpG oligodeoxynucleotide (CpG ODN), and accordingly these terms are used interchangeably unless otherwise indicated. Immunostimulatory CpG oligodeoxynucleotides contain one or more immunostimulatory CpG motifs that are unmethylated cytosine-guanine dinucleotides, optionally within certain preferred base contexts. The methylation status of the CpG immunostimulatory motif generally refers to the cytosine residue in the dinucleotide. An immunostimulatory oligonucleotide containing at least one unmethylated CpG dinucleotide is an oligonucleotide which contains a 5' unmethylated cytosine linked by a phosphate bond to a 3' guanine, and which activates the immune system through binding to Toll-like receptor 9 (TLR-9). In another embodiment the immunostimulatory oligonucleotide may contain one or more methylated CpG dinucleotides, which will activate the immune system through TLR9 but not as strongly as if the CpG motif(s) was/were unmethylated. CpG immunostimulatory oligonucleotides may comprise one or more palindromes that in turn may encompass the CpG dinucleotide. CpG oligonucleotides have been described in a number of issued patents, published patent applications, and other publications, including U.S. Pat. Nos. 6,194,388; 6,207,646; 6,214,806; 6,218,371; 6,239,116; and 6,339,068.

In an embodiment of the present invention, the immunogenic compositions as disclosed herein comprise any of the CpG Oligonucleotide described at page 3, line 22, to page 12, line 36, of WO 2010/125480.

Different classes of CpG immunostimulatory oligonucleotides have been identified. These are referred to as A, B, C and P class, and are described in greater detail at page 3, line 22, to page 12, line 36, of WO 2010/125480. Methods of the invention embrace the use of these different classes of CpG immunostimulatory oligonucleotides.

VII. Nanoparticles

In another aspect, disclosed herein is an immunogenic complex that includes 1) a nanostructure; and 2) at least one fimbrial polypeptide antigen or fragment thereof. Preferably, the fimbrial polypeptide or fragment thereof is derived from E. coli fimbrial H (fimH). In a preferred embodiment, the fimbrial polypeptide is selected from any one of the fimbrial polypeptides described above. For example, the fimbrial polypeptide may comprise any one amino acid sequence selected from SEQ ID NOs:1-10, 18, 20, 21, 23, 24, 26-29 and 110-113.

In some embodiments, the antigen is fused or conjugated to the nanostructure exterior to stimulate development of adaptive immune responses to the displayed epitopes. In some embodiments, the immunogenic complex further includes an adjuvant or other immunomodulatory compounds attached to the exterior and/or encapsulated in the cage interior to help tailor the type of immune response generated for each pathogen.

In some embodiments, the nanostructure includes a single assembly including a plurality of identical first nanostructure-related polypeptides.

In alternative embodiments, the nanostructure includes a plurality assembly, including a plurality of identical first nanostructure-related polypeptides and a plurality of second assemblies, each second assembly comprising a plurality of identical second nanostructure-related polypeptides.

Various nanostructure platforms can be employed in generating the immunogenic compositions described herein. In some embodiments, the nanostructures employed are formed by multiple copies of a single subunit. In some embodiments, the nanostructures employed are formed by multiple copies of multiple different subunits.

The nanostructures are typically ball-like shaped, and/or have rotational symmetry (e.g., with 3-fold and 5-fold axis), e.g., with an icosahedral structure exemplified herein.

In some embodiments, the antigen is presented on self-assembling nanoparticles such as self-assembling nanostructures derived from ferritin (FR), E2p, Qβ, and I3-01. E2p is a redesigned variant of dihydrolipoyl acyltransferase from *Bacillus stearothermophilus*. I3-01 is an engineered protein that may self-assemble into hyperstable nanoparticles. Sequences of the subunits of these proteins are known in the art. In a first aspect, disclosed herein is a nanostructure-related polypeptide comprising an amino acid sequence that is at least 75% identical over its length, and identical at least at one identified interface position, to the amino acid sequence of a nanostructure-related polypeptide selected from the group consisting of SEQ ID NOS: 59-92. The nanostructure-related polypeptides can be used, for example, to prepare the nanostructures. The nanostructure-related polypeptides were designed for their ability to self-assemble in pairs to form nanostructures, such as icosahedral nanostructures.

In some embodiments, the nanostructure includes (a) a plurality of first assemblies, each first assembly comprising a plurality of identical first nanostructure-related polypeptides, wherein the first nanostructure-related polypeptides comprise the amino acid sequence of a nanostructure-related polypeptide selected from the group consisting of SEQ ID NOS: 59-92; and (b) a plurality of second assemblies, each second assembly comprising a plurality of identical second nanostructure-related polypeptides, wherein the second nanostructure-related polypeptides comprise the amino acid sequence of a nanostructure-related polypeptide selected from the group consisting of SEQ ID NOS: 59-92, and wherein the second nanostructure-related polypeptide differs from the first nanostructure-related polypeptide; wherein the plurality of first assemblies non-covalently interact with the plurality of second assemblies to form a nanostructure.

The nanostructures include symmetrically repeated, non-natural, non-covalent polypeptide-polypeptide interfaces that orient a first assembly and a second assembly into a nanostructure, such as one with an icosahedral symmetry.

SEQ ID NOS: 59-92 provide the amino acid sequence of exemplary nanostructure-related polypeptides. The number of interface residues for the exemplary nanostructure-related polypeptides of SEQ ID NO:59-92 range from 4-13 residues. In various embodiments, the nanostructure-related polypeptides comprise an amino acid sequence that is at least 75%, 80%, 85%, 90%, 91%, 92%, 93%, 94%, 95%, 96%, 97%, 98%, or 99% identical over its length, and identical at least at 1, 2, 3, 4, 5, 6, 7, 8, 9, 10, 11, 12, or 13 identified interface positions (depending on the number of interface residues for a given nanostructure-related polypeptide), to the amino acid sequence of a nanostructure-related polypeptide selected from the group consisting of SEQ ID NOS: 59-92. In other embodiments, the nanostructure-related polypeptides comprise an amino acid sequence that is at least 75%, 80%, 85%, 90%, 91%, 92%, 93%, 94%, 95%, 96%, 97%, 98%, or 99% identical over its length, and identical at least at 20%, 25%, 33%, 40%, 50%, 60%, 70%, 75%, 80%, 90%, or 100% of the identified interface positions, to the amino acid sequence of a nanostructure-related polypeptide selected from the group consisting of SEQ ID NOS: 59-92. In further embodiments, the nanostructure-related polypeptides include a nanostructure-related polypeptide having the amino acid sequence of a nanostructure-related polypeptide selected from the group consisting of SEQ ID NOS: 59-98.

In one non-limiting embodiment, the nanostructure-related polypeptides can be modified to facilitate covalent linkage to a "cargo" of interest. In one non-limiting example, the nanostructure-related polypeptides can be modified, such as by introduction of various cysteine residues at defined positions to facilitate linkage to one or more antigens of interest, such that a nanostructure of the nanostructure-related polypeptides would provide a scaffold to provide a large number of antigens for delivery as a vaccine to generate an improved immune response.

In some embodiments, some or all native cysteine residues that are present in the nanostructure-related polypeptides but not intended to be used for conjugation may be mutated to other amino acids to facilitate conjugation at defined positions. In another non-limiting embodiment, the nanostructure-related polypeptides may be modified by linkage (covalent or non-covalent) with a moiety to help facilitate "endosomal escape." For applications that involve delivering molecules of interest to a target cell, such as targeted delivery, a critical step can be escape from the endosome-a membrane-bound organelle that is the entry point of the delivery vehicle into the cell. Endosomes mature into lysosomes, which degrade their contents. Thus, if the delivery vehicle does not somehow "escape" from the endosome before it becomes a lysosome, it will be degraded and will not perform its function. There are a variety of lipids or organic polymers that disrupt the endosome and allow escape into the cytosol. Thus, in this embodiment, the nanostructure-related polypeptides can be modified, for example, by introducing cysteine residues that will allow chemical conjugation of such a lipid or organic polymer to the monomer or resulting assembly surface. In another non-limiting example, the nanostructure-related polypeptides can be modified, for example, by introducing cysteine residues that will allow chemical conjugation of fluorophores or other imaging agents that allow visualization of the nanostructures in vitro or in vivo.

Surface amino acid residues on the nanostructure-related polypeptides can be mutated in order to improve the stability or solubility of the protein subunits or the assembled nanostructures. As will be known to one of skill in the art, if the nanostructure-related polypeptide has significant sequence homology to an existing protein family, a multiple sequence alignment of other proteins from that family can be used to guide the selection of amino acid mutations at non-conserved positions that can increase protein stability and/or solubility, a process referred to as consensus protein design (9).

Surface amino acid residues on the nanostructure-related polypeptides can be mutated to positively charged (Arg, Lys) or negatively charged (Asp, Glu) amino acids in order to endow the protein surface with an overall positive or overall negative charge. In one non-limiting embodiment, surface amino acid residues on the nanostructure-related polypeptides can be mutated to endow the interior surface of the self-assembling nanostructure with a high net charge. Such a nanostructure can then be used to package or encapsulate a cargo molecule with the opposite net charge due to the electrostatic interaction between the nanostructure interior surface and the cargo molecule. In one non-limiting embodiment, surface amino acid residues on the nanostructure-related polypeptides can be mutated primarily to Arginine or Lysine residues in order to endow the interior surface of the self-assembling nanostructure with a net positive charge. Solutions containing the nanostructure-related polypeptides can then be mixed in the presence of a nucleic acid cargo molecule such as a dsDNA, ssDNA, dsRNA, ssRNA, cDNA, miRNA, siRNA, shRNA, piRNA, or other nucleic acid in order to encapsulate the nucleic acid inside the self-assembling nanostructure. Such a nanostructure could be used, for example, to protect, deliver, or concentrate nucleic acids.

In one embodiment, the nanostructure has icosahedral symmetry. In this embodiment, the nanostructure may comprise 60 copies of the first nanostructure-related polypeptide and 60 copies of the second nanostructure-related polypeptide. In one such embodiment, the number of identical first nanostructure-related polypeptides in each first assembly is different than the number of identical second nanostructure-related polypeptides in each second assembly. For example, in one embodiment, the nanostructure comprises twelve first assemblies and twenty second assemblies; in this embodiment, each first assembly may; for example, comprise five copies of the identical first nanostructure-related polypeptide, and each second assembly may, for example, comprise three copies of the identical second nanostructure-related polypeptide. In another embodiment, the nanostructure comprises twelve first assemblies and thirty second assemblies; in this embodiment, each first assembly may, for example, comprise five copies of the identical first nanostructure-related polypeptide, and each second assembly may, for example, comprise two copies of the identical second nanostructure-related polypeptide. In a further embodiment, the nanostructure comprises twenty first assemblies and thirty second assemblies; in this embodiment, each first assembly may, for example, comprise three copies of the identical first nanostructure-related polypeptide, and each second assembly may, for example, comprise two copies of the identical second nanostructure-related polypeptide. All of these embodiments are capable of forming synthetic nanomaterials with regular icosahedral symmetry.

VIII. Combination with a Saccharide and/or Polypeptide or Fragment Thereof Derived from *Klebsiella pneumoniae*

*Klebsiella pneumoniae* (*K. pneumoniae*) is a Gram-negative pathogen, known to cause urinary tract infections, bacteremia, and sepsis. Multidrug-resistant *Klebsiella pneumoniae* infections are an increasing cause of mortality in vulnerable populations at risk. The O-antigen serotypes are highly prevalent among strains causing invasive disease globally and derived O-antigen glycoconjugates are attractive as vaccine antigens.

In one aspect, any of the compositions disclosed herein may further comprise at least one saccharide that is, or is derived from, at least one *K. pneumoniae* serotype selected from O1 (and d-Gal-III variants), O2 (and d-Gal-III variants), O2ac, O3, O4, O5, O7, O8, and O12. In a preferred embodiment, any of the compositions disclosed herein may further comprise a polypeptide derived from *K. pneumoniae* selected from a polypeptide derived from *K. pneumoniae* Type I fimbrial protein or an immunogenic fragment thereof; or a polypeptide derived from *K. pneumoniae* Type III fimbrial protein or an immunogenic fragment thereof; or a combination thereof.

As is known in the art, *K. pneumoniae* O1 and O2 O-antigens and their corresponding v1 and v2 subtypes are polymeric galactans that differ in the structures of their repeat units. *K. pneumoniae* O1 and O2 antigens contain homopolymer galactose units (or galactans). *K. pneumoniae* O1 and O2 antigens each contain D-galactan I units (sometimes referred to as the O2a repeat unit), but O1 antigens differ in that O1 antigens have a D-galactan II cap structure. D-galactan III (d-Gal-III) is a variant of D-galactan I. Structures of the base galactans I and III that define the two distinct serotype O2 subtypes, O2v1 and O2v2; and structures of the derived chimeras resulting from capping by galactan II which yields subtypes O1v1 and O1v2, are shown in Kelly S D, et al. *J Biol Chem* 2019; 294:10863-76; and Clarke B R, et al. J Biol Chem 2018; 293:4666-79.

In some embodiments, the saccharide derived from *K. pneumoniae* O1 includes a repeat unit of [→3)-β-D-Galp-(1→3)-α-D-Galp-(1→]. In some embodiments, the saccharide derived from *K. pneumoniae* O1 includes a repeat unit of [→3)-α-D-Galp-(1→3)-β-D-Galp-(1→]. In some embodiments, the saccharide derived from *K. pneumoniae* O1 includes a repeat unit of [→3)-β-D-Galf-(1→3)-α-D-Galp-(1→], and a repeat unit of [→3)-α-D-Galp-(1→3)-β-D-Galp-(1→]. In some embodiments, the saccharide derived from *K. pneumoniae* O1 includes a repeat unit of →3)-β-D-Galf-(1→3)-[α-D-Galp-(1→4)]-α-D-Galp-(1→] (referred to as the D-Gal-III repeat unit). (Kol O., et al. (1992) Carbohydr. Res. 236, 339-344; Whitfield C., et al. (1991) J. Bacteriol. 173, 1420-1431).

In some embodiments, the saccharide derived from *K. pneumoniae* O2 includes a repeat unit of [→3)-α-D-Galp-(1→3)-β-D-Galf-(1→] (which may be an element of *K. pneumoniae* serotype O2a antigen). In some embodiments, the saccharide derived from *K. pneumoniae* O2 includes a repeat unit of [→3)-β-D-GlcpNAc-(1→5)-β-D-Galf-(1→] (which may be an element of *K. pneumoniae* serotype O2c antigen). In some embodiments, the saccharide derived from *K. pneumoniae* O2 includes a modification of the O2a repeat unit by side chain addition of (1→4)-linked Galp residues (which may be an element of the *K. pneumoniae* O2afg antigen). In some embodiments, the saccharide derived from *K. pneumoniae* O2 includes a modification of the O2a repeat unit by side chain addition of (1→2)-linked Galp residues (which may be an element of the *K. pneumoniae* O2aeh antigen). (Whitfield C., et al. (1992) J. Bacteriol. 174, 4913-4919).

Without being bound by mechanism or theory, O-antigen polysaccharide structure of *K. pneumoniae* serotypes O3 and O5 are disclosed in the art to be identical to those of *E. coli* serotypes O9a (Formula O9a) and O8 (Formula O8), respectively.

In some embodiments, the saccharide derived from *K. pneumoniae* O4 includes a repeat unit of [→4)-α-D-Galp-(1→2)-β-D-Ribf-(1→)]. In some embodiments, the saccharide derived from *K. pneumoniae* O7 includes a repeat unit of [→2-α-L-Rhap-(1→2)-β-D-Ribf-(1→3)-α-L-Rhap-(1→3)-α-L-Rhap-(1→]. In some embodiments, the saccharide derived from *K. pneumoniae* O8 serotype includes the same repeat-unit structure as *K. pneumoniae* O2a, but is nonstoichiometrically O-acetylated. In some embodiments, the saccharide derived from *K. pneumoniae* O12 serotype includes a repeat unit of [α-Rhap-(1→3)-β-GlcpNAc] disaccharide repeat unit.

In one aspect, the invention includes a composition including a polypeptide derived from *E. coli* FimH or a fragment thereof; and at least one saccharide that is, or derived from, at least one *K. pneumoniae* serotype selected from O1 (and d-Gal-III variants), O2 (and d-Gal-III variants), O2ac, O3, O4, O5, O7, O8, and O12. In some embodiments, the composition includes saccharides from or derived from one or more of serotypes O1, O2, O3, and O5, or a combination thereof. In some embodiments, the composition includes saccharides from or derived from each of serotypes O1, O2, O3, and O5.

In another aspect, the invention includes a composition including at least one saccharide that is, or is derived from, at least one *K. pneumoniae* serotype selected from O1 (and d-Gal-III variants), O2 (and d-Gal-III variants), O2ac, O3, O4, O5, O7, O8, and O12; and a saccharide derived from an *E. coli* O-antigen having a structure selected from any one of Formula O1 (e.g., Formula O1A, Formula O1B, and Formula O1C), Formula O2, Formula O3, Formula O4 (e.g., Formula O4:K52 and Formula O4:K6), Formula O5 (e.g., Formula O5ab and Formula O5ac (strain 180/C3)), Formula O6 (e.g., Formula O6:K2; K13; K15 and Formula O6:K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D$_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 1 to 100. In some embodiments, the composition includes a saccharide from or derived from one or more of *K. pneumoniae* serotypes O1, O2, O3 and O5, or a combination thereof. In some embodiments, the composition includes a saccharide from or derived from each of *K. pneumoniae* serotypes O1, O2, O3 and O5. In some embodiments, the composition includes a saccharide derived from an *E. coli* O-antigen having Formula O9 and does not include a saccharide derived from *K. pneumoniae* serotype O3. In some embodiments, the composition includes a saccharide derived from an *E. coli* O-antigen having Formula O8 and does not include a saccharide derived from *K. pneumoniae* serotype O5.

In another aspect, the invention relates to a composition including a polypeptide derived from *E. coli* FimH or a fragment thereof; at least one saccharide that is, or derived from, at least one *K. pneumoniae* serotype selected from O1 (and d-Gal-III variants), O2 (and d-Gal-III variants), O2ac, O3, O4, O5, O7, O8, and O12; and a saccharide having a structure selected from any one of Formula O1 (e.g., Formula O1A, Formula O1B, and Formula O1C), Formula O2, Formula O3, Formula O4 (e.g., Formula O4:K52 and Formula O4:K6), Formula O5 (e.g., Formula O5ab and Formula O5ac (strain 180/C3)), Formula O6 (e.g., Formula O6:K2; K13; K15 and Formula O6:K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D$_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 1 to 100, preferably from 31 to 90. In some embodiments, the composition includes a saccharide derived from an *E. coli* O-antigen having Formula O9 and does not include a saccharide derived from *K. pneumoniae* serotype O3. In some embodiments, the composition includes a saccharide derived from an *E. coli* O-antigen having Formula O8 and does not include a saccharide derived from *K. pneumoniae* serotype O5.

In some embodiments, the composition includes at least one saccharide derived from any one *K. pneumoniae* type selected from the group consisting of O1, O2, O3, and O5.

In some embodiments, the composition includes at least one saccharide derived from *K. pneumoniae* type O1. In one aspect of this embodiment, the *K. pneumoniae* O-antigen is selected from subtype v1 (O1v1) or subtype v2 (O1v2). In one aspect of this embodiment, the *K. pneumoniae* O-antigen is selected from subtype v1 (O1v1) and subtype v2 (O1v2). In some embodiments, the composition includes at least one saccharide derived from *K. pneumoniae* type O2. In one aspect of this embodiment, the *K. pneumoniae* O-antigen is selected from subtype v1 (O2v1) or subtype v2 (O2v2). In one aspect of this embodiment, the *K. pneumoniae* O-antigen is selected from subtype v1 (O2v1) and subtype v2 (O2v2). In another aspect, the *K. pneumoniae* O-antigen is selected from the group consisting of: a) serotype O1 subtype v1 (O1v), b) serotype O1 subtype v2 (O1v2), c) serotype O2 subtype v1 (O2v1), and d) serotype O2 subtype v2 (O2v2). In one aspect of this embodiment, the *K. pneumoniae* O-antigen is subtype v1 (O1v1). In one aspect of this embodiment, the *K. pneumoniae* O-antigen is subtype v2 (O1v2). In one aspect of this embodiment, the *K. pneumoniae* O-antigen is subtype v1 (O2v1). In one aspect of this embodiment, the *K. pneumoniae* O-antigen is subtype v2 (O2v2). In another aspect of this embodiment, the composition comprises one, two, three or four *K. pneumoniae* O-antigen selected from the group consisting of: a) serotype O1 subtype v1 (O1v1), b) serotype O1 subtype v2 (O1v2), c) serotype O2 subtype v1 (O2v1), and d) serotype O2 subtype v2 (O2v2). In some embodiments, the composition includes a combination of saccharides derived from *K. pneumoniae*, wherein a first saccharide is derived from any one of *K. pneumoniae* types selected from the group consisting of O1, O2, O3, and O5; and a second saccharide is derived from a saccharide is derived from any one of *K. pneumoniae* types selected from the group consisting of O1 (and d-Gal-III variants), O2 (and d-Gal-III variants), O2ac, O3, O4, O5, O7, O8, and O12. For example, in some embodiments, the composition includes at least one saccharide derived from *K. pneumoniae* type O1 and at least one saccharide derived from *K. pneumoniae* type O2. In a preferred embodiment, the saccharide derived from *K. pneumoniae* is conjugated to a carrier protein; and the saccharide derived from *E. coli* is conjugated to a carrier protein.

In another aspect, the invention includes a composition including a polypeptide derived from *E. coli* FimH or a fragment thereof; and at least one saccharide derived from any one *K. pneumoniae* type selected from the group consisting of O1, O2, O3, and O5.

In another aspect, the invention includes at least one saccharide derived from any one *K. pneumoniae* type selected from the group consisting of O1, O2, O3, and O5; and at least one saccharide derived from *E. coli* having a structure selected from any one of Formula O1 (e.g., Formula O1A, Formula O1B, and Formula O1C), Formula O2, Formula O3, Formula O4 (e.g., Formula O4:K52 and Formula O4:K6), Formula O5 (e.g., Formula O5ab and Formula O5ac (strain 180/C3)), Formula O6 (e.g., Formula O6:K2; K13; K15 and Formula O6:K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D$_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula mula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187. In some embodiments, the composition includes a saccharide derived from an *E. coli* O-antigen having Formula O9 and does not include a saccharide derived from *K. pneumoniae* serotype O3. In some embodiments, the composition includes a saccharide derived from an *E. coli* O-antigen having Formula O8 and does not include a saccharide derived from *K. pneumoniae* serotype O5.

In some embodiments, the composition includes at least one saccharide derived from *K. pneumoniae* type O1; and at least one saccharide derived from *E. coli* having a structure selected from the group consisting of Formula O8 and Formula O9. In another embodiment, the composition includes at least one saccharide derived from *K. pneumoniae* type O2; and at least one saccharide derived from *E. coli* having a structure selected from the group consisting of Formula O8 and Formula O9. In another embodiment, the composition includes at least one saccharide derived from *K. pneumoniae* type O1; at least one saccharide derived from *K. pneumoniae* type O2; and at least one saccharide derived from *E. coli* having a structure selected from the group consisting of Formula O8 and Formula O9.

In one embodiment, the invention provides a method of inducing an immune response to *K. pneumoniae* in a subject comprising administering to the subject an immunologically effective amount of an immunogenic composition comprising at least one glycoconjugate from *E. coli* serotype O8 or O9, wherein said immunogenic composition does not comprise glycoconjugates from *K. pneumoniae* serotype O5 or O3. In one aspect, the composition includes a saccharide derived from an *E. coli* O-antigen having Formula O8 and does not include a saccharide derived from *K. pneumoniae* serotype O5. In another aspect, the composition includes a saccharide derived from an *E. coli* O-antigen having Formula O9 and does not include a saccharide derived from *K. pneumoniae* serotype O3.

In another embodiment, the invention provides a method of inducing an immune response to *E. coli* in a subject comprising administering to the subject an immunologically effective amount of an immunogenic composition comprising at least one glycoconjugate from *K. pneumoniae* serotype O5 or O3, or a variant thereof, wherein said immunogenic composition does not comprise glycoconjugates from *E. coli* serotype O8 or O9. In one aspect, the composition includes a saccharide derived from *K. pneumoniae* serotype O5 and does not include a saccharide derived from an *E. coli* O-antigen having Formula O8. In another aspect, the composition includes a saccharide derived from *K. pneumoniae* serotype O3 and does not include a saccharide derived from an *E. coli* O-antigen having Formula O9.

In some embodiments, the composition includes at least one saccharide that is, or is derived from, at least one *K. pneumoniae* serotype selected from O1 (and d-Gal-III variants), O2 (and d-Gal-III variants), O2ac, O3, O4, O5, O7, O8, and O12; at least one saccharide derived from *E. coli* having a structure selected from the group consisting of Formula O8 and Formula O9. In some embodiments, the composition includes at least one saccharide that is, or derived from, at least one *K. pneumoniae* serotype selected from O1 (and d-Gal-III variants), O2 (and d-Gal-III variants), O2ac, O3, O4, O5, O7, O8, and O12; at least one saccharide derived from *E. coli* having a structure selected from the group consisting of Formula O1A, Formula O1B, Formula O2, Formula O6, and Formula O25B.

In some embodiments, the composition further includes a polypeptide derived from *K. pneumoniae* selected from a polypeptide derived from *K. pneumoniae* Type I fimbrial protein or an immunogenic fragment thereof; or a polypeptide derived from *K. pneumoniae* Type III fimbrial protein or an immunogenic fragment thereof, or a combination thereof. The sequences of said polypeptides are known in the art.

IX. Uses of the Compositions

In one aspect, the disclosure provides use of the compositions described herein, nucleic acids encoding *E. coli* FimH polypeptides or vectors for expressing them, or compositions comprising a polypeptide or nucleic acids as a medicament, or in the manufacture of a medicament, for eliciting an immune response against *E. coli* or *K. pneumoniae* or for preventing *E. coli* or *K. pneumoniae* infection in a subject.

In other aspects, the present disclosure provides a method of eliciting an immune response against *E. coli* or *K. pneumoniae* in a subject, such as a human, comprising administering to the subject an effective amount of a composition described herein or a nucleic acid molecule encoding an *E. coli* or *K. pneumoniae* polypeptide. The present disclosure also provides a method of preventing *E. coli* or *K. pneumoniae* infection in a subject, comprising administering to the subject an effective amount of a pharmaceutical composition, such as a vaccine, comprising a *E. coli* or *K. pneumoniae* composition described herein.

As used herein, "subject" means a mammal, preferably a human. In some particular embodiments, the human is a child, such as an infant. In some other particular embodiments, the human is a woman, particularly a pregnant woman. The compositions of the invention may be administered to the subject with or without administration of an adjuvant. The effective amount administered to the subject is an amount that is sufficient to elicit an immune response against an *E. coli* or *K. pneumoniae* antigen in the subject. Subjects that can be selected for treatment include those that are at risk for developing an *E. coli* or *K. pneumoniae* infection because of exposure or the possibility of exposure to *E. coli* or *K. pneumoniae*. Because humans may be infected with *E. coli* or *K. pneumoniae* by the age of 2, the entire birth cohort is included as a relevant population for immunization. This could be done, for example, by beginning an immunization regimen anytime from birth to 6 months of age, from 6 months of age to 5 years of age, in pregnant women (or women of child-bearing age) to protect their infants by passive transfer of antibody, infants still in utero, and subjects greater than 50 years of age.

Administration of the compositions provided by the present disclosure, such as pharmaceutical compositions, can be carried out using standard routes of administration. Non-limiting embodiments include parenteral administration, such as intradermal, intramuscular, subcutaneous, transcutaneous, mucosal, or oral administration.

The total dose of the composition provided to a subject during one administration can be varied as is known to the skilled practitioner.

It is also possible to provide one or more booster administrations of one or more of the vaccine compositions. If a boosting vaccination is performed, typically, such a boosting vaccination will be administered to the same subject at a moment between one week and 10 years, preferably between two weeks and six months, after administering the composition to the subject for the first time (which is in such cases referred to as "priming vaccination"). In alternative boosting regimens, it is also possible to administer different vectors, e.g., one or more adenovirus, or other vectors such as modified vaccinia virus of Ankara (MVA), or DNA, or protein, to the subject after the priming vaccination. It is, for instance, possible to administer to the subject a recombinant viral vector hereof as a prime, and boosting with a composition described herein.

In certain embodiments, the administration comprises a priming administration and at least one booster administration. In certain other embodiments, the administration is provided annually. In still other embodiments, the administration is provided annually together with an influenza vaccine.

The vaccines provided by the present disclosure may be used together with one or more other vaccines. For example, in adults they may be used together with an influenza vaccine, Prevnar, tetanus vaccine, diphtheria vaccine, and pertussis vaccine. For pediatric use, vaccines provided by the present disclosure may be used with any other vaccine indicated for pediatric patients.

EXAMPLES

In order that this invention may be better understood, the following examples are set forth. These examples are for purposes of illustration only and are not to be construed as limiting the scope of the invention in any manner. The following Examples illustrate some embodiments of the invention.

Example 1

Bacterial fimbrial adhesins FimH and FmlH allow *Escherichia coli* to exploit distinct urinary tract microenvironments through recognition of specific host cell glycoproteins. FimH binds to manosylated uroplakin receptors in the uroepithelium whereas FmlH binds to galactose or N-acetylgalactosamine O-glycans on epithelial surface proteins in the kidney and inflamed bladder. FimH fimbriae also play a role in colonization of enterotoxigenic *E. coli* (ETEC) and multidrug-resistant invasive *E. coli* in the gut through binding to highly mannosylated proteins on the intestinal epithelia.

Full length FimH is composed of two domains: the N-terminal lectin domain and the C-terminal pilin domain, which are connected by a short linker. The lectin domain of FimH contains the carbohydrate recognition domain, which is responsible for binding to the mannosylated uroplakin 1a on the urothelial cell surface. The pilin domain is anchored to the core of the pilus via a donor strand of the subsequent FimG subunit, which is a process termed donor strand complementation.

Conformation and ligand-binding properties of the lectin domain of FimH are under the allosteric control of the pilin domain of FimH. Under static conditions, the interaction of the two domains of full length FimH stabilizes the lectin domain in the low-affinity to monomannose (for example, $K_d$~300 µM) state, which is characterized by a shallow binding pocket. Binding to a mannoside ligand induces a conformational change leading to a medium affinity state, where the lectin and pilin domains remain in close contact. However, upon shear stress, the lectin and pilin domains separate, thereby inducing the high-affinity state (for example, $K_d$<1.2 µM).

Because of the absence of negative allosteric regulation exerted by the pilin domain, the isolated lectin domain of FimH is locked in the high-affinity state. The isolated, recombinant lectin domain, which is locked in the high-affinity state, exhibits high stability. Locking the adhesin in a low-binding conformation, however, induces the production of adhesion-inhibiting antibodies. Accordingly, there is an interest in stabilizing the lectin domain in the low-affinity state.

Table 3 sets forth the FimH constructs used to make various constructs to address these needs.

TABLE 3

Summary of FimH constructs

| Construct | Plasmid | Signal sequence | Protein Description | Linker | Additional protein variant | Backbone | Mass |
|---|---|---|---|---|---|---|---|
| FimH lectin domain | pSB01877 | FimH signal sequence | FimH J96 F22 . . . G181 | none | none | pcDNA3.1(+) or pCAG vector | |
| FimH lectin domain | pSB01878 | mIgK signal sequence | FimH J96 F22 . . . G181 | none | none | pcDNA3.1(+) or pCAG vector | Fully reduced mass, with His-tag: 18117.48 Observed non-reduced mass, with His-tag: 18117.90 Mass without tag: 17022.08 |

TABLE 3-continued

Summary of FimH constructs

| Construct | Plasmid | Signal sequence | Protein Description | Linker | Additional protein variant | Backbone | Mass |
|---|---|---|---|---|---|---|---|
| FimH/C | pSB01879 | FimH signal sequence | FimH J96 F22 . . . Q300 | none | none | pBudCE4.1 Dual promoter vector (CMV & EF1α) | |
| FimH/C | pSB01880 | mIgK signal sequence | FimH J96 F22 . . . Q300 | none | none | pBudCE4.1 Dual promoter vector (CMV & EF1α) | |
| FimH/C | pSB01881 | mIgK signal sequence | FimC G37 . . . E241 (according to SEQ ID NO: 18) | none | none | pBudCE4.1 Dual promoter vector (CMV & EF1α) | |
| FimH-dscG | pSB01882 | FimH signal sequence | FimH J96 F22 . . . Q300 | DNKQ | FimG A1 . . . K14 (SEQ ID NO: 17) | | |
| FimH-dscG | pSB01883 | FimH signal sequence | FimH J96 F22 . . . Q300 | GGSGG | FimG A1 . . . K14 (SEQ ID NO: 17) | | |
| FimH-dscG | pSB01884 | FimH signal sequence | FimH J96 F22 . . . Q300 | GGSSGG | FimG A1 . . . K14 (SEQ ID NO: 17) | | |
| FimH-dscG | pSB01885 | FimH signal sequence | FimH J96 F22 . . . Q300 | GGSSGGG | FimG A1 . . . K14 (SEQ ID NO: 17) | N-terminus residue at W20, and therefore does not appear to have been processed at preferred position; a small amount of protein present exhibiting preferred processing as indicated by the small amount of the FACK peptide being detected | |
| FimH-dscG | pSB01886 | FimH signal sequence | FimH J96 F22 . . . Q300 | GGGSSGGG | FimG A1 . . . K14 (SEQ ID NO: 17) | | |
| FimH-dscG | pSB01887 | FimH signal sequence | FimH J96 F22 . . . Q300 | GGGSGSGGG | FimG A1 . . . K14 (SEQ ID NO: 17) | | |
| FimH-dscG | pSB01888 | FimH signal sequence | FimH J96 F22 . . . Q300 | GGGSGGSGGG | FimG A1 . . . K14 (SEQ ID NO: 17) | | |

TABLE 3-continued

Summary of FimH constructs

| Construct | Plasmid | Signal sequence | Protein Description | Linker | Additional protein variant | Backbone | Mass |
|---|---|---|---|---|---|---|---|
| FimH-dscG | pSB01889 | mIgK signal sequence | FimH J96 F22 . . . Q300 | DNKQ | FimG A1 . . . K14 (SEQ ID NO: 17) | | |
| FimH-dscG | pSB01890 | mIgK signal sequence | FimH J96 F22 . . . Q300 | GGSGG | FimG A1 . . . K14 (SEQ ID NO: 17) | | |
| FimH-dscG | pSB01891 | mIgK signal sequence | FimH J96 F22 . . . Q300 | GGSSGG | FimG A1 . . . K14 (SEQ ID NO: 17) | | |
| FimH-dscG | pSB01892 | mIgK signal sequence | FimH J96 F22 . . . Q300 | GGSSGGG | FimG A1 . . . K14 (SEQ ID NO: 17) | appears to have had the signal peptide processed with the F22 being the preferred N-terminal residue; identity of the peptide was confirmed by MS/MS | |
| FimH-dscG | pSB01893 | mIgK signal sequence | FimH J96 F22 . . . Q300 | GGGSSGGG | FimG A1 . . . K14 (SEQ ID NO: 17) | | |
| FimH-dscG | pSB01894 | mIgK signal sequence | FimH J96 F22 . . . Q300 | GGGSGSGGG | FimG A1 . . . K14 (SEQ ID NO: 17) | | |
| FimH-dscG | pSB01895 | mIgK signal sequence | FimH J96 F22 . . . Q300 | GGGSGGSGGG | FimG A1 . . . K14 (SEQ ID NO: 17) | | |
| FimH lectin domain | pSB02081 | mIgK signal sequence | F22 . . . G181 J96 FimH N28Q N91S/ His8 in pcDNA3.1(+) | | | | |
| FimH lectin domain | pSB02082 | mIgK signal sequence | F22 . . . G181 J96 FimH N28Q N91S/ His8 in pcDNA3.1(+) | | | | |
| FimH lectin domain | pSB02083 | mIgK signal sequence | F22 . . . G181 J96 FimH N28S N91S/ His8 in pcDNA3.1(+) | | | | |
| FimH lectin domain | pSB02088 | mIgK signal sequence | F22 . . . G181 J96 FimH V48C L55C/ His8 in pcDNA3.1(+) | | | | |

TABLE 3-continued

Summary of FimH constructs

| Construct | Plasmid | Signal sequence | Protein Description | Linker | Additional protein variant | Backbone | Mass |
|---|---|---|---|---|---|---|---|
| FimH lectin domain | pSB02089 | mIgK signal sequence | F22 . . . G181 J96 FimH N28Q V48C L55C N91S/ His8 in pcDNA3.1(+) | | | | |
| FimH lectin domain | pSB02158 | mIgK signal sequence | F22 . . . G181 J96 FimH N28S V48C L55C N91S/ His8 in pcDNA3.1(+) | | | | |
| FimH-dscG | pSB02159 | | | | | | |
| FimH-dscG | pSB02198 | mIgK signal sequence | FimH mIgK signal pept/ F22 . . . Q300 J96 FimH N28S V48C L55C N91S N249Q/7 AA linker/ FimG A1 . . . K14/ GGHis8 in pcDNA3.1(+) | | | | |
| FimH-dscG | pSB02199 | mIgK signal sequence | FimH mIgK signal pept/ F22 . . . Q300 J96 FimH N28S V48C L55C N91S N256Q/7 AA linker/ FimG A1 . . . K14/ GGHis8 in pcDNA3.1(+) | | | | |
| FimH-dscG | pSB02200 | mIgK signal sequence | FimH mIgK signal pept/ F22 . . . Q300 J96 FimH N28S V48C L55C N91S N249Q N256Q/7 AA linker/ FimG A1 . . . K14/ GGHis8 in pcDNA3.1(+) | | | | |
| FimH-dscG | pSB02304 | mIgK signal sequence | FimH mIgK signal pept/ F22 . . . Q300 J96 FimH N28S V48C L55C N91S T251A/7 AA linker/ FimG A1 . . . K14/ GGHis8 in pcDNA3.1(+) | | | | |

TABLE 3-continued

Summary of FimH constructs

| Construct | Plasmid | Signal sequence | Protein Description | Linker | Additional protein variant | Backbone | Mass |
|---|---|---|---|---|---|---|---|
| FimH-dscG | pSB02305 | mIgK signal sequence | FimH mIgK signal pept/ F22 . . . Q300 J96 FimH N28S V48C L55C N91S T258A/7 AA linker/ FimG A1 . . . K14/ GGHis8 in pcDNA3.1(+) | | | | |
| FimH-dscG | pSB02306 | mIgK signal sequence | FimH mIgK signal pept/ F22 . . . Q300 J96 FimH N28S V48C L55C N91S T251A T258A/7 AA linker/ FimG A1 . . . K14/ GGHis8 in pcDNA3.1(+) | | | | |
| FimH-dscG | pSB02307 | mIgK signal sequence | FimH mIgK signal pept/ F22 . . . Q300 J96 FimH N28S N91S N249Q/7 AA linker/ FimG A1 . . . K14/ GGHis8 in pcDNA3.1(+) | | | | |
| FimH-dscG | pSB02308 | mIgK signal sequence | FimH mIgK signal pept/ F22 . . . Q300 J96 FimH N28S N91S N256Q/7 AA linker/ FimG A1 . . . K14/ GGHis8 in pcDNA3.1(+) | | | | |

All of the FimH constructs studied were monomeric proteins of expected molecular weight.

TABLE 4

| Protein | Sedimentation Coefficient, S | $M_{w,app}$ | $M_{w,expected}$ | Homogeneity |
|---|---|---|---|---|
| *E.coli* expression | | | | |
| Cytosolic FimH-LD | 1.9 S | 18 kDa | 18 kDa | 98% |
| Periplasmic FimH-LD | 1.9 S | 18 kDa | 18 kDa | 98% |
| FimH-LD lock mutant | 2.0 S | 19 kDa | 18 kDa | 97% |
| Mammalian expression | | | | |
| FimH-LD | 1.9 S | 18 kDa | 18 kDa | >99% |
| FimH-LD lock mutant | 1.9 S | 18 kDa | 18 kDa | 98% |
| FimH wild type | 2.7 S | 36 kDa | 34 kDa | 96% |
| FimH lock mutant | 2.7 S | 34 kDa | 34 kDa | 94% |

Expected molecular weight of FimC-FimH complex is 53.1 kDa;
Expected molecular weight of FimC is 24 kDa.

Example 2: Mammalian Expression of FimH Lectin Binding Domain

The present non-limiting example relates to producing a polypeptide derived from *E. coli* or a fragment thereof in a HEK cell line. The yields were relatively high, as compared to expression of the polypeptide derived from *E. coli* or a fragment thereof in an *E. coli* host cell.

To accomplish the production of FimH variants from mammalian cells, a SignalP prediction algorithm was used to analyze different heterologous signal sequences for secretion of proteins and fragments. The wild type FimH leader sequence was also analyzed. The predictions indicated that the wild type FimH leader sequence may work for secretion of the FimH variants in mammalian cells, however, the secreted variant was predicted to be cleaved at the W20 residue of the full-length wild type FimH (see SEQ ID NO: 1), rather than the F22 residue of the full-length wild type FimH (see SEQ ID NO: 1). A hemagglutinin signal sequence was predicted not to work. The murine IgK signal sequence was predicted to produce an N-terminus of F22 of SEQ ID NO: 1, or F1 residue of the mature protein.

Based on these analyses, DNA was synthesized and recombinantly produced constructs to express the FimH lectin binding domain with the wild-type FimH leader. Constructs were also prepared to express the FimH lectin binding domain with the mIgK signal sequence. Affinity purification tags, such as His tag, were introduced to the C-terminus of the polypeptide derived from E. coli or a fragment thereof to facilitate purification.

The expression plasmid was transfected into HEK host cells, namely EXP1293 mammalian cells.

The polypeptides or fragments thereof derived from E. coli were successfully expressed. For example, the preferred N-terminal processing using the mIgK signal sequence fused to the mature start of FimH at F22 was demonstrated for the pSB01892 FimHdscG construct by MS. The processing is believed correct for the lectin domain construct pSB01878 and the mass spec data supports this.

The preferred N-terminal processing (i.e., processing at F22 of SEQ ID NO: 1) was not shown with the native FimH leader peptide.

pSB01877 and pSB01878 constructs are in pcDNA3.1(+) mammalian expression vectors. The cells were diluted and subsequently used in 20 ml transfections. 1 ug/ml DNA for each construct was used and transfected cells in 125 ml flasks using Expifectamine protocol. After 72 hours, the cell viability was still good so the expression was allowed to continue until 96 hours. Samples were taken at 72 hours and ran 10 ul of each on SDS PAGE gels to check for expression.

Figure 4:
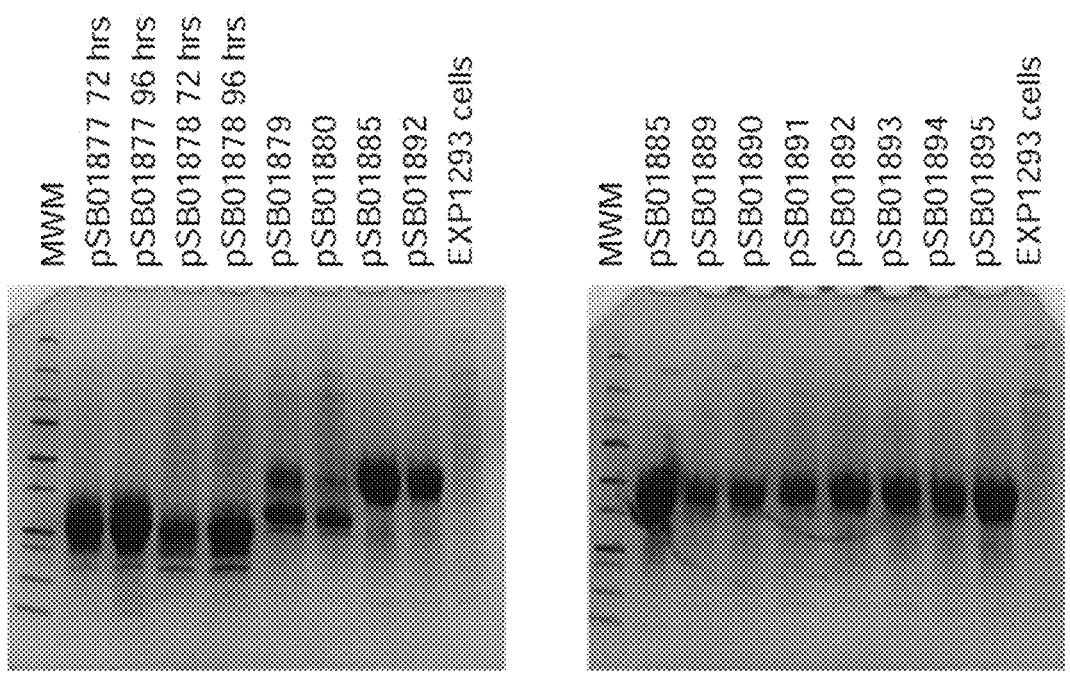
FIG. 4—depicts results from expression and purification.

After 96 hours, conditioned media was harvested and 0.25 ml of Nickel Excel resin was added with batch binding O/N at 4° C. with rotation. Eluted in TrisCl pH8.0, NaCl, imidazole. See FIG. 4.

pSB01878 has expected mass consistent with N-terminal F22. Glycosylation present on 1 or 2 sites (+1 mass from each deamidation of N-D).

Figure 5:
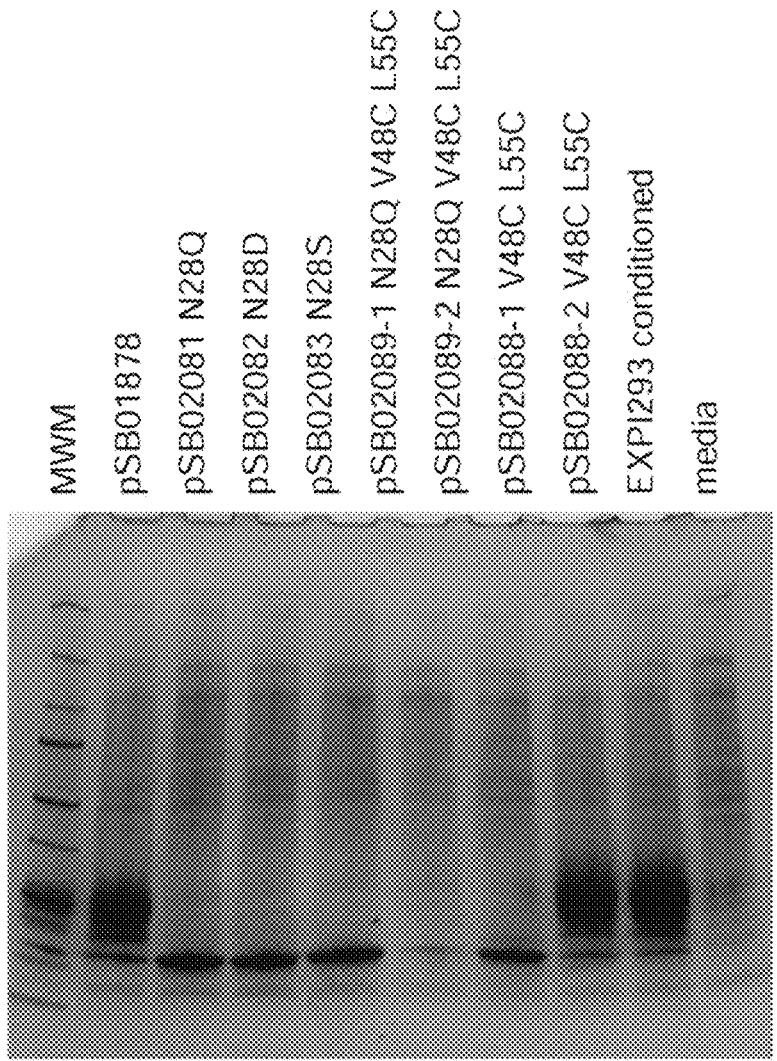
FIG. 5—depicts results from expression.

Glycosylation mutants were constructed. See, for example, pSB02081, pSB02082, pSB02083, pSB02088, and pSB02089. The glycosylation mutants expressed the polypeptides of interest. See FIG. 5 for results.

Figure 6A:
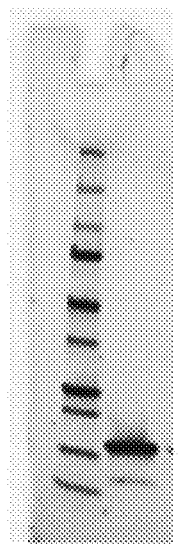
FIG. 6A-6C—depict pSB02083 and pSB02158 SEC pools and affinities, including yields.
Figure 6B:
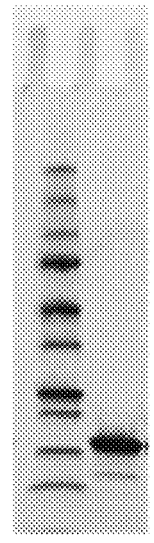

A FimH lectin domain lock mutant was also constructed. See, for example, pSB02158. Results of the expression of the pSB02158 construct is shown in FIG. 6B.

Figure 6C:
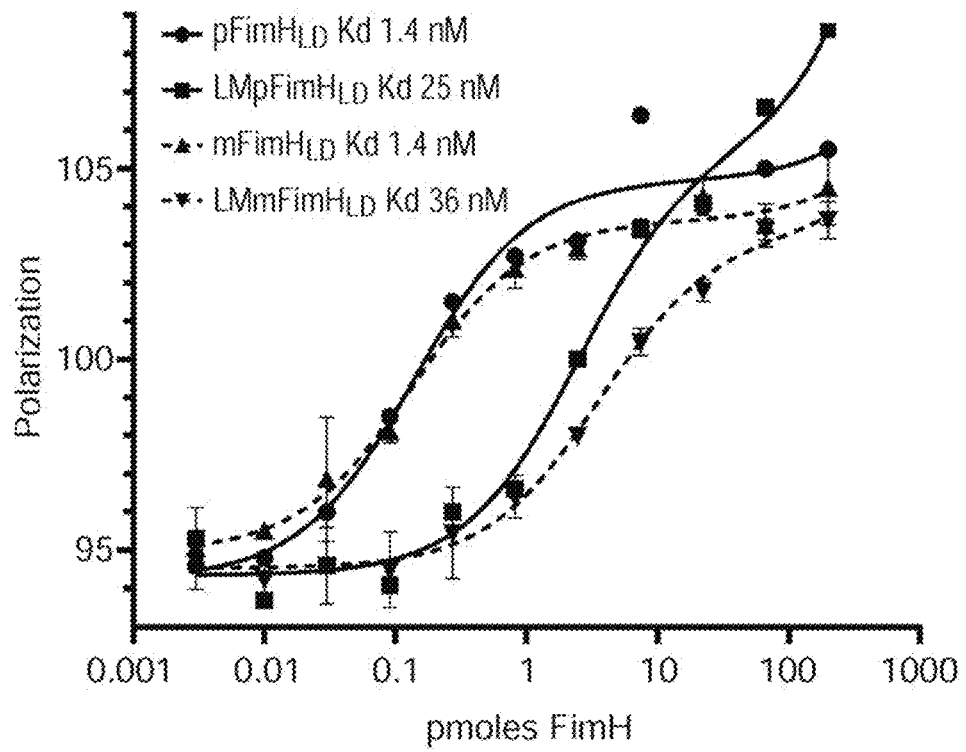

Fluorescence polarization assay using 0.5 pmoles fluorescein-conjugated aminophenyl-mannopyranoside (APMP). The assay was performed at room temperature, 300 RPM for 64 hrs. Results shown in FIG. 6C.

Example 3: Mammalian Expression of FimH/C Complex, pSB01879 and pSB01880

For production of the FimH/C complex, dual expression constructs of the FimC under the EF1alpha promoter and the FimH with either the wild type or mIgK signal peptide were prepared. These were cloned into a pBudCE4.1 mammalian expression vector (ThermoFisher) and a C-term His tag was added to the FimC. The FimC variant was designed for secretion using the mIgK signal peptide as it resulted in a positive prediction to yield the G37 FimC as the first residue of the mature protein based on SignalP analysis.

More specifically, these constructs were designed to have the FimC fragment under the EF1alpha promoter in the vector pBudCE4.1 and the FimH fragment inserts under the CMV promoter in the same vector. The vector pBudCE4.1 is an expression vector from Thermo Fisher that has 2 promoters for expression in mammalian cells. The FimC fragment insert (pSB01881 insert) was subcloned by digesting with NotI and XhoI and subcloning into the pBudCE4.1 vector at the same sites. These were plated onto 2×YT zeocin 50 ug/ml plates. Colonies were inoculated into 2×YT with zeocin 50 ug/ml, grew overnight at 37° C. and plasmid prepped. These were digested with NotI and XhoI to check for insert and all colonies had insert size of ~722 bp.

pSB01881 was digested with HindIII and BamHI and the pSB01879 insert and pSB01880 insert DNA was digested with HindIII and BamHI. These fragments were gel isolated and subcloned into the pSB01881 vector and plated onto 2×YTzeo50 ug/ml plates. Colonies from each were inoculated into 2×YT zeo50 ug/ml, grown overnight at 37° C., plasmid prepped and digested with NotI and XhoI to test for FimC insert and HindIII and BamHI to test for FimH inserts. All clones had expected sized inserts at both cloning sites. The pSB01879-1 and pSB01880-1 clones were subsequently used for expression.

The FimH/FimC complex has been demonstrated to express in EXP1293 cells as well. Expression may be optimized by switching promoters, such as EF1a, CAG, Ub, Tub, or other promoters.

The preferred N-terminal processing (i.e., processing at F22 of SEQ ID NO: 1) was not shown with the native FimH leader peptide.

Exemplary results from SignalP 4.1 (DTU Bioinformatics) used for signal peptide predictions are shown below. Additional signal peptides are predicted to produce the preferred N-terminus of Phe at position 1 of the mature FimH polypeptide or fragment thereof. The following is only a representative sample set of 4 common signal sequences.

The following signal peptide sequences were predicted to yield the preferred N-terminus of Phe at position 1 of the mature FimH polypeptide or fragment thereof:

TABLE 5

|  | signal peptide sequence | SEQ ID NO: |
|---|---|---|
| >sp\|P55899\|FCGRN_HUMAN IgG receptor FcRn large subunit p51 OS = Homo sapiens OX = 9606 GN = FCGRT PE = 1 SV = 1 | MGVPRPQPWALGLLLFLLPGSLG | SEQ ID NO: 55 |

TABLE 5-continued

| | signal peptide sequence | SEQ ID NO: |
|---|---|---|
| >tr\|Q6FGW4\|Q6FGW4_HUMAN IL10 protein OS = Homo sapiens OX = 9606 GN = IL10 PE = 2 SV = 1 | MHSSALLCCLVLLTGVRA | SEQ ID NO: 56 |

The following signal peptide sequences were NOT predicted to yield the preferred N-terminus of Phe at position 1 of the mature FimH polypeptide or fragment thereof:

TABLE 6

| | signal peptide sequence | SEQ ID NO: |
|---|---|---|
| >sp\|P03420\|FUS_HRSVA Fusion glycoprotein F0 OS = Human respiratory syncytial virus A (strain A2) OX = 11259 GN = F PE = 1 SV = 1 | MELLILKANAITTILTAVTFCFASG | SEQ ID NO: 57 |
| >sp\|P03451\|HEMA_I57A0 Hemagglutinin OS = Influenza A virus (strain A/Japan/305/1957 H2N2) OX = 387161 GN = HA PE = 1 SV = 1 | MAIIYLILLFTAVRG | SEQ ID NO: 58 |

TABLE 7

SignalP 4.1 used for predictions

| | Fusion sequence |
|---|---|
| >sp\|P55899\|FCGRN_HUMAN IgG receptor FcRn large subunit p51 OS = Homo sapiens OX = 9606 GN = FCGRT PE = 1 SV = 1 MGVPRPQPWALGLLLLFLLPGSLGAESHLSLLY HLTAVSSPAPGTPAFWVSGWLGPQQYLS YNSLRGEAEPCGAWVWENQVSWYWEKETT DLRIKEKLFLEAFKALGGKGPYTLQGLLGCE LGPDNTSVPTAKFALNGEEFMNFDLKQGTWG GDWPEALAISQRWQQQDKAANKELTFLLF SCPHRLREHLERGRGNLEWKEPPSMRLKARPS SPGFSVLTCSAFSFYPPELQLRFLRNGL AAGTGQGDFGPNSDGSFHASSSLTVKSGDEH HYCCIVQHAGLAQPLRVELESPAKSSVLV VGIVIGVLLLTAAAVGGALLWRRMRSGLPAP WISLRGDDTGVLLPTPGEAQDADLKDVNV IPATA (SEQ ID NO: 102) | The signal peptide from the protein listed in the respective left column is shown below in CAPITAL LETTERS. The N-terminus of FimH is depicted in lower case. MGVPRPQPWALGLLLLFLLPGSLGfacktangtaipigggs anvyvnlapvvnvgqnlvvdls (SEQ ID NO: 103) # Measure Position Value Cutoff signal peptide? max. C  24      0.664 max. Y  24      0.788 max. S   9      0.966 mean S  1-23    0.935 D       1-23    0.867  0.450    YES Name = Sequence SP = 'YES' Cleavage site between pos. 23 and 24: SLG-FA D = 0.867 D-cutoff = 0.450 Networks = SignalP-noTM |
| >sp\|P03420\|FUS_HRSVA Fusion glycoprotein F0 OS = Human respiratory syncytial virus A (strain A2) OX = 11259 GN = F PE = 1 SV = 1 MELLILKANAITTILTAVTFCFASGQNITEEFYQ STCSAVSKGYLSALRTGWYTSVITIE LSNIKENKCNGTDAKVKLIKQELDKYKNAVTE LQLLMQSTPPTNNRARRELPRFMNYTLN NAKKTNVTLSKKRKRRFLGFLLGVGSAIASG VAVSKVLHLEGEVNKIKSALLSTNKAVVS LSNGVSVLTSKVLDLKNYIDKQLLPIVNKQSC SISNIETVIEFQQKNNRLLEITREFSVN AGVTTPVSTYMLTNSELLSLINDMPITNDQKK LMSNNVQIVRQQSYSIMSIIKEEVLAYV VQLPLYGVIDTPCWKLHTSPLCTTNTKEGSNI CLTRTDRGWYCDNAGSVSFFPQAETCKV QSNRVFCDTMNSLTLPSEINLCNVDIFNPKYD CKIMTSKTDVSSSVITSLGAIVSCYGKT KCTASNKNRGIIKTFSNGCDYVSNKGMDTVS VGNTLYYVNKQEGKSLYVKGEPIINFYDP | The signal peptide from the protein listed in the respective left column is shown below in CAPITAL LETTERS. The N-terminus of FimH is depicted in lower case. MELLILKANAITTILTAVTFCFASGfacktangtaipigggsanvy vnlapvvnvgqnlvvdls (SEQ ID NO: 105) # Measure Position Value Cutoff signal peptide? max. C  28      0.188 max. Y  28      0.263 max. S  11      0.478 mean S  1-27    0.387 D       1-27    0.312  0.500    NO Name = Sequence SP = 'NO' D = 0.312 D-cutoff = 0.500 Networks = SignalP-TM |

TABLE 7-continued

SignalP 4.1 used for predictions

| | Fusion sequence |
|---|---|
| LVFPSDEFDASISQVNEKINQSLAFIRKSDELL<br>HNVNAGKSTTNIMITTIIIVIIVILLS<br>LIAVGLLLYCKARSTPVTLSKDQLSGINNIAFS<br>N (SEQ ID NO: 104) | |
| >tr\|Q6FGW4\|Q6FGW4_HUMAN IL 10 protein<br>OS = Homo sapiens OX = 9606 GN = IL10<br>PE = 2 SV = 1<br>MHSSALLCCLVLLTGVRASPGQGTQSENSC<br>THFPGNLPNMLRDLRDAFSRVKTFFQMKDQ<br>LDNLLLKESLLEDFKGYLGCQALSEMIQFYLE<br>EVMPQAENQDPDIKAHVNSLGENLKTLR<br><br>LRLRRCHRFLPCENKSKAVEQVKNAFNKLQE<br>KGIYKAMSEFDIFINYIEAYMTMKIRN (SEQ ID<br>NO: 106) | The signal peptide from the protein listed in the respective left column is shown below in CAPITAL LETTERS. The N-terminus of FimH is depicted in lower case.<br>MHSSALLCCLVLLTGVRAfacktangtaipigggsanvyvnlapvv nvgqnlvvdls (SEQ ID NO: 107)<br># Measure Position Value Cutoff signal peptide?<br>  max. C  19      0.726<br>  max. Y  19      0.829<br>  max. S   4      0.973<br>  mean S  1-18    0.947<br>     D   1-18    0.893  0.450       YES<br>Name=Sequence SP = 'YES' Cleavage site between pos. 18 and 19: VRA-FA D = 0.893 D-cutoff = 0.450<br>Networks = SignalP-noTM |
| >sp\|P03451\|HEMA_157A0 Hemagglutinin<br>OS = Influenza A virus (strain A/Japan/<br>305/1957H2N2) OX = 387161 GN = HA<br>PE = 1 SV = 1<br>MAIIYLILLFTAVRGDQICIGYHANNSTEKVDT<br>NLERNVTVTHAKDILEKTHNGKLCKLN<br>GIPPLELGDCSIAGWLLGNPECDRLLSVPEW<br><br>SYIMEKENPRDGLCYPGSFNDYEELKHLL<br>SSVKHFEKVKILPKDRWTQHTTTGGSRACAV<br>SGNPSFFRNMVWLTKEGSDYPVAKGSYNN<br>TSGEQMLIIWGVHHPIDETEQRTLYQNVGTY<br>VSVGTSTLNKRSTPEIATRPKVNGQGGRM<br>EFSWTLLDMWDTINFESTGNLIAPEYGFKISK<br>RGSSGIMKTEGTLENCETKCQTPLGAIN<br>TTLPFHNVHPLTIGECPKYVKSEKLVLATGLR<br>NVPQIESRGLFGAIAGFIEGGWQGMVDG<br>WYGYHHSNDQGSGYAADKESTQKAFDGITN<br>KVNSVIEKMNTQFEAVGKEFGNLERRLENL<br>NKRMEDGFLDVWTYNAELLVLMENERTLDF<br>HDSNVKNLYDKVRMQLRDNVKELGNGCFEF<br>YHKCDDECMNSVKNGTYDYPKYEEESKLNR<br>NEIKGVKLSSMGVYQILAIYATVAGSLSLA<br>IMMAGISFWMCSNGSLQCRICI (SEQ ID NO: 108) | The signal peptide from the protein listed in the respective left column is shown below in CAPITAL LETTERS. The N-terminus of FimH is depicted in lower case.<br>MAIIYLILLFTAVRGfacktangtaipigggsanvyvnlapvvnvgq nlvvdls (SEQ ID NO: 109)<br># Measure Position Value Cutoff signal peptide?<br>  max. C  18      0.524<br>  max. Y  18      0.690<br>  max. S   1      0.951<br>  mean S  1-17    0.895<br>     D   1-17    0.800  0.450       YES<br>Name=Sequence SP = 'YES' Cleavage site between pos. 17 and 18: GFA-CK D = 0.800 D-cutoff = 0.450<br>Networks = SignalP-noTM |

Example 4: Mammalian Expression of Donor Strand Complement Fusion of FimH with the FimG Peptide Several linker lengths were tested. Recombinant expression with these linkers fusing the FimH to the N-terminal FimG peptide in both the wild type FimH and the mIgK signal peptide fused to F22 of FimH were prepared.

The FimH donor strand complement FimG constructs have also been shown to have robust expression in EXP1293 cells.

The preferred N-terminal processing (i.e., processing at F22 of SEQ ID NO: 1) was not shown with the native FimH leader peptide.

For the donor strand complement constructs, oligonucleotides were designed to produce base constructs in pcDNA3.1(+) that contained the various linkers and FimG peptide. A unique BstEII site was incorporated at G294 V295 T296 residues, according to the numbering of SEQ ID NO: 1 of FimH. The same BstEII site was incorporated in the linkers to produce base constructs.

The base constructs for pSB01882-01895 were constructed. Primers were used to PCR amplify pcDNA3.1(+) with ACCUPRIME PFX DNA Polymerase (Thermo Fisher), digest the PCR products with NdeI (in CMV promoter) and BamHI and cloned into pcDNA3.1(+) that was digested with NdeI and BamHI and gel isolated to remove the fragment.

Another transient transfection was performed with pSB01877, 01878, 01879, 01880, 01885, and 01892 alongside EXP1293 cells as control.

Figure 3:
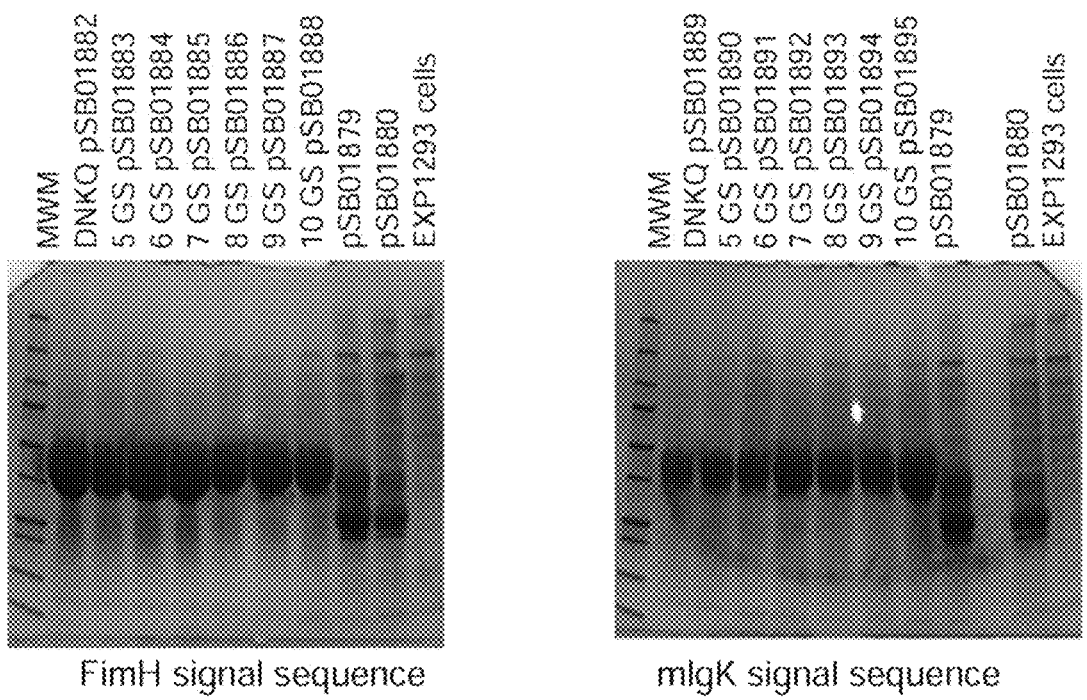
FIG. 3—depicts results from expression and purification.

Constructs pSB01882 through pSB01895 were used in transient transfection expression tests in EXP1293 cells from Thermo Fisher as per the manufacturer's protocol. See FIG. 3, which shows the results following expression in 20 mL EXP1293 cells, 72 hours, 10 ul of conditioned media loaded; high levels of expression observed; the FimH/FimC complex present following expression from pSB01879 & pSB01880 constructs; 20 ml conditioned media batch bound to Nickel Excel, 40 CV wash, elution in Imdidazole.

Figure 7:
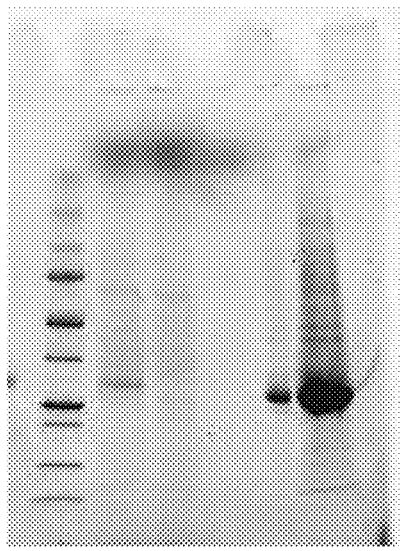
FIG. 7—depicts results from expression of pSB2198 FimH dscG Lock Mutant construct.
Figure 8:
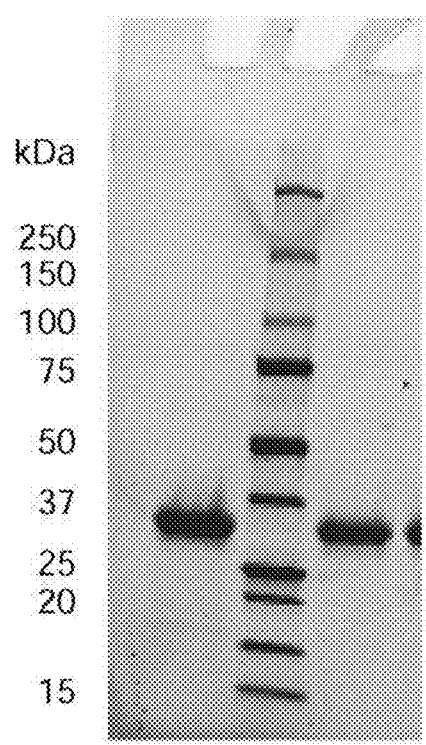
FIG. 8—depicts results from expression of pSB2307 FimH dscG wild type.
Figure 9B:

Additional FimH-donor strand complement constructs were prepared. See, for example, pSB02198, pSB02199, pSB02200, pSB02304, pSB02305, pSB02306, pSB02307, pSB02308 constructs. The expression of pSB2198 FimH dscG lock mutant construct is shown in FIG. 7. The pSB2198 FimH dscG Lock Mutant yielded 12 mg/L from transient expression.

According to Vi-CELL XR 2.04 (Beckman Coulter, Inc.), the following were observed (actual cell type used for expression was HEK cells):

TABLE 8

| Sample | Cell type parameter entered | Viability (%) | Total cells/ml (×10$^6$) | Viable cells/ml (×10$^6$) | Avg. diam. (microns) |
|---|---|---|---|---|---|
| EXPI P13 | CHO | 97.8 | 3.56 | 3.48 | 19.33 |
| pSB01882 | CHO | 90.9 | 4.98 | 4.53 | 17.39 |
| pSB01889 | CHO | 89.2 | 5.23 | 4.67 | 17.14 |
| cells | CHO | 88.9 | 6.66 | 5.92 | 16.91 |
| Expi Start | CHO | 93.7 | 3.35 | 3.14 | 18.72 |
| Samples at harvest - 85-86 hours after transfection: | | | | | |
| 1877 | SF-9 | 57.3 | 4.32 | 2.48 | 16.00 |
| pSB01878 | SF-9 | 57.6 | 3.88 | 2.24 | 15.49 |
| pSB01879 | SF-9 | 59.1 | 5.24 | 3.10 | 15.32 |
| pSB01880 | SF-9 | 56.8 | 5.97 | 3.39 | 15.10 |
| pSB01885 | SF-9 | 63.1 | 6.95 | 4.39 | 16.08 |
| pSB01892 | SF-9 | 56.2 | 4.89 | 2.75 | 15.91 |
| 187772 | SF-9 | 79.5 | 5.14 | 4.09 | 18.36 |
| 187872 | SF-9 | 72.6 | 5.26 | 3.81 | 17.35 |
| expicont | SF-9 | 75.5 | 4.95 | 3.74 | 18.62 |

Example 5: Molecular Weight Fragments are with Processed Signal Peptide

TABLE 9

**pSB01877 FimH J96 ELL41155.1 [*E. coli* J96] Analysis**

| Analysis | Fragment 15-189 | Entire Protein |
|---|---|---|
| Length | 175 aa | 189 aa |
| Molecular Weight | 18948.34 | 20522.36 m.w. |
| 1 microgram = | 52.775 pMoles | 48.727 pMoles |
| Molecular Extinction Coefficient | 35800 | 35800 |
| 1 A(280) corr. to: | 0.53 mg/ml | 0.57 mg/ml |
| A[280] of 1 mg/ml | 1.89 AU | 1.74 AU |
| Isoelectric Point | 6.81 | 8 |
| Charge at pH 7 | −0.48 | 1.52 |

**pSB01878 FimH J96 ELL41155.1 [*E. coli* J96] Analysis**

| Analysis | Fragment 21-188 | Entire Protein |
|---|---|---|
| Length | 168 aa | 188 aa |
| Molecular Weight | 18117.48 | 20344.08 m.w. |
| 1 microgram = | 55.195 pMoles | 49.154 pMoles |
| Molecular Extinction Coefficient | 24420 | 35800 |
| 1 A(280) corr. to: | 0.74 mg/ml | 0.57 mg/ml |
| A[280] of 1 mg/ml | 1.35 AU | 1.76 AU |
| Isoelectric Point | 6.81 | 6.29 |
| Charge at pH 7 | −0.48 | −2.47 |

**pSB01885 FimH J96 ELL41155.1 [*E. coli* J96] Analysis**

| Analysis | Fragment 20-331 | Entire Protein |
|---|---|---|
| Length | 312 aa | 331 aa |
| Molecular Weight | 32406.19 | 34537.79 m.w. |
| 1 microgram = | 30.858 pMoles | 28.954 pMoles |
| Molecular Extinction Coefficient | 38030 | 43720 |

TABLE 9-continued

| | | |
|---|---|---|
| 1 A(280) corr. to: | 0.85 mg/ml | 0.79 mg/ml |
| A[280] of 1 mg/ml | 1.17 AU | 1.27 AU |
| Isoelectric Point | 7.25 | 8.32 |
| Charge at pH 7 | 0.5 | 2.5 |

**pSB01892 FimH J96 ELL41155.1 [*E. coli* J96] Analysis**

| Analysis | Fragment 21-330 | Entire Protein |
|---|---|---|
| Length | 310 aa | 330 aa |
| Molecular Weight | 32132.91 | 34359.51 m.w. |
| 1 microgram = | 31.121 pMoles | 29.104 pMoles |
| Molecular Extinction Coefficient | 32340 | 43720 |
| 1 A(280) corr. to: | 0.99 mg/ml | 0.79 mg/ml |
| A[280] of 1 mg/ml | 1.01 AU | 1.27 AU |
| Isoelectric Point | 7.25 | 6.51 |
| Charge at pH 7 | 0.5 | −1.49 |

**pSB01893 FimH J96 ELL41155.1 [*E. coli* J96] Analysis**

| Analysis | Entire Protein |
|---|---|
| Length | 331 aa |
| Molecular Weight | 34416.56 |
| 1 microgram = | 29.056 pMoles |
| Molecular Extinction Coefficient | 43720 |
| 1 A(280) corr. to: | 0.79 mg/ml |
| A[280] of 1 mg/ml | 1.27 AU |
| Isoelectric Point | 6.51 |
| Charge at pH 7 | −1.49 |

**pSB01894 FimH J96 ELL41155.1 [*E. coli* J96] Analysis**

| Analysis | Fragment 21-332 | Entire Protein |
|---|---|---|
| Length | 312 aa | 332 aa |
| Molecular Weight | 32247.01 | 34473.61 m.w. |
| 1 microgram = | 31.011 pMoles | 29.008 pMoles |
| Molecular Extinction Coefficient | 32340 | 43720 |
| 1 A(280) corr. to: | 1.00 mg/ml | 0.79 mg/ml |
| A[280] of 1 mg/ml | 1.00 AU | 1.27 AU |
| Isoelectric Point | 7.25 | 6.51 |
| Charge at pH 7 | 0.5 | −1.49 | pSB02083

| Analysis | Fragment 21-188 | Entire Protein |
|---|---|---|
| Length | 168 aa | 188 aa |
| Molecular Weight | 18063.42 | 20290.02 m.w. |
| 1 microgram = | 55.361 pMoles | 49.285 pMoles |
| Molar Extinction coefficient | 24420 | 35800 |
| 1 A(280) corr. to: | 0.74 mg/ml | 0.57 mg/ml |
| A[280] of 1 mg/ml | 1.35 AU | 1.76 AU |
| Isoelectric Point | 6.81 | 6.29 |
| Charge at pH 7 | −0.48 | −2.47 | pSB02198

| | |
|---|---|
| | FimH PSB 2198 |
| | 1.45 mg/ml |
| | 5 ml |
| Sample | 20190918 SS |
| Volume (mls) | 25 |
| Conc. (mg/ml) | 1.45 |
| Total Amount (mgs) | 36.25 |
| Aliquots | 5 ml x5 |
| Yield | 12 mg/L |
| Buffer: 50 mM TrisCl | |
| pH 8.0, 300 mM NaCl | |

TABLE 9-continued pSB02307

| | Fim H 2307<br>0.48 mg/ml<br>5 ml |
|---|---|
| Sample Name | 20190918 SS |
| Volume (mls) | 22.5 mls |
| Conc. (mg/ml) | 0.48 mg/ml |
| Total Amount (mgs) | 10.8 mg |
| Yield | 3.6 mg/L |
| Buffer: 50 mM TrisCI pH 8.0, 300 mM NaCl | |

Example 6: The N-Terminal α-Amino Group of Phe1 (According to the Numbering of SEQ ID NO: 2) in the FimH Mature Protein Provides Critical Polar Recognition for D-Mannose Without being bound by theory or mechanism, it is suggested that the correct signal peptide cleavage just ahead of Phe1 (according to the numbering of SEQ ID NO: 2) of the FimH mature protein is important to express functional FimH protein. Changes at the N-terminal α-amino group, such as by adding an amino acid at the N-terminus ahead of Phe1 of the FimH protein can abolish the hydrogen bond interactions with O2-, O5- and O6-atoms of the D-mannose and introduce steric repulsion with D-mannose, thereby blocking mannose binding. This is confirmed with our experimental observation that adding an extra Gly residue ahead of the Phe1 of SEQ ID NO: 2 leads to no detection of mannose binding.

Following an analysis of the crystal structure of FimH bound to D-mannose, the following were observed: The N-Terminal α-amino group of Phe1 along with sidechains of Asp54 of the FimH according to the numbering of SEQ ID NO: 2 and Gln133 of the FimH according to the numbering of SEQ ID NO: 2 provide critical polar recognition motifs for D-mannose, and mutations and changes of these polar interactions lead to no mannose binding.

Example 7: The Sidechain of Phe1 in FimH does not Interact Directly with D-Mannose but is Rather Buried Inside of FimH, Suggesting that Phe1 can be Replaced by Other Residues, e.g. Aliphatic Hydrophobic Residues (Ile, Leu, or Val)

Analysis of crystal structures of FimH in complex with D-mannose and its analogs (e.g. PDB ID: 1QUN) shows that the sidechain of Phe1 (according to the numbering of SEQ ID NO: 2) does not interact directly with D-mannose but rather stabilizes the binding pocket by stacking its aromatic rings with the sidechains of Val56, Tyr95, Gln133 and Phe144 (according to the numbering of SEQ ID NO: 2).

Figure 11:
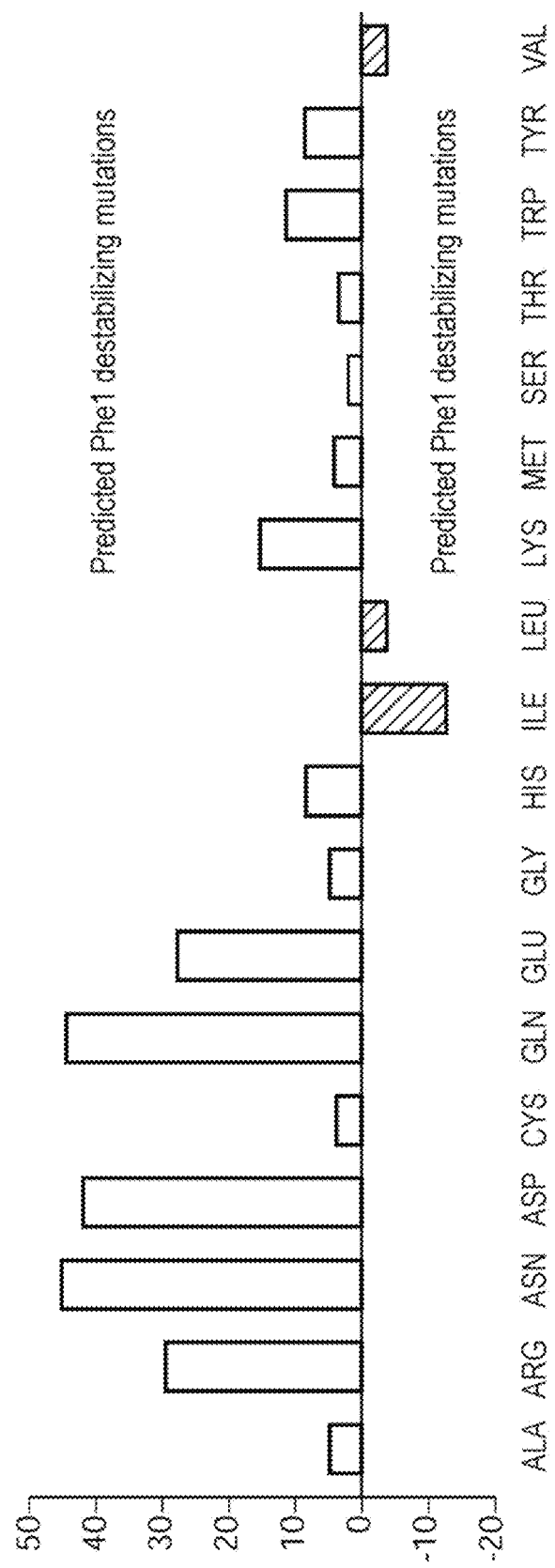
FIG. 11—depicts computational mutagenesis scanning of Phe1 with other amino acids having aliphatic hydrophobic sidechains, e.g. Ile, Leu and Val, that may stabilize the FimH protein and accommodate mannose binding.

Alternative N-terminal residue instead of Phe may stabilize the FimH protein, accommodate mannose binding, and allow correct signal peptide cleavage. Such residues may be identified by suitable method known in the art, such as by visual inspection of a crystal structure of FimH, or more quantitative selection using computational protein design software, such as BioLuminate™ [BioLuminate, Schrodinger LLC, New York, 2017], Discovery Studio™ [Discovery Studio Modeling Environment, Dassault Systemes, San Diego, 2017], MOE™ [Molecular Operating Environment, Chemical Computing Group Inc., Montreal, 2017], and Rosetta™ [Rosetta, University of Washington, Seattle, 2017]. An illustrative example is shown FIG. 9A-9C. The replacement amino acids can be aliphatic hydrophobic amino acids (e.g. Ile, Leu and Val). FIG. 11 depicts computational mutagenesis scanning of Phe1 with other amino acids having aliphatic hydrophobic sidechains, e.g. Ile, Leu and Val, which may stabilize the FimH protein and accommodate mannose binding.

Example 8: Mutations of Asn7 According to the Numbering of SEQ ID NO: 2 in a FimH Protein can Remove the Putative N-Glycosylation Site and Prevent Deamidation, without Impacting Mannose, mAb21, or mAb475 Binding Over-expression of secreted E. coli FimH from mammalian cell lines may lead to N-linked glycosylation at residue Asn7, according to the numbering of SEQ ID NO: 2. In addition, residue Asn7 is solvent exposed and followed with a Gly residue, making it very prone to deamidation.

Analysis of crystal structures of FimH in complex with D-mannose and its analogs (e.g. PDB ID: 1QUN) indicates that Asn7 is more than 20 Å away from the mannose binding site and a mutation at the site should not impact mannose binding. Thus, mutations of Asn7 to other amino acids (e.g. Ser, Asp and Gln) can effectively remove the putative N-glycosylation site and prevent deamidation.

Example 9: E. coli and S. enterica Strains

Clinical strains and derivatives are listed in Table 10. Additional reference strains included: O25K5H1, a clinical O25a serotype strain; and S. enterica serovar Typhimurium strain LT2.

Gene knockouts in E. coli strains removing the targeted open-reading frame but leaving a short scar sequence were constructed.

The hydrolyzed O-antigen chain and core sugars are indicated subsequently as O-Polysaccharide (OPS) for simplicity.

TABLE 10

E. coli Strains

| Strain | Strain Alias | Genotype | Serotype |
|---|---|---|---|
| GAR2401 | PFEEC0100 | wt (blood isolate) | O25b |
| '2401 ΔwzzB | — | ΔwzzB | O25b |
| '2401ΔAraAΔ(OPS) | — | ΔAraA Δ(rflB-wzzB) | OPS- |
| O25K5H1 | PFEEC0101 | wt | O25a |
| O25K5H1ΔwzzB | | ΔwzzB | O25a |
| BD559 | — | W3110 ΔAraA ΔfhuA ΔrecA | OPS- |
| BD559ΔwzzB | — | W3110ΔAraA ΔfhuA ΔrecAΔwzzB | OPS- |
| BD559Δ(OPS) | — | BD559 Δ(rflB-wzzB) | OPS- |
| GAR2831 | PFEEC0102 | wt (blood isolate) | O25b |
| GAR865 | PFEEC0103 | wt (blood isolate) | O2 |
| GAR868 | PFEEC0104 | wt (blood isolate) | O2 |
| GAR869 | PFEEC0105 | wt (blood isolate) | O15 |
| GAR872 | PFEEC0106 | wt (blood isolate) | O1 |
| GAR878 | PFEEC0107 | wt (blood isolate) | O75 |
| GAR896 | PFEEC0108 | wt (blood isolate) | O15 |
| GAR1902 | PFEEC0109 | wt (blood isolate) | O6 |
| Atlas187913 | PFEEC0068 | wt (blood isolate) | O25b |
| Salmonella enterica serovar Typhimurium strain LT2 | — | wt | N/A |

Example 10: Oligonucleotide Primers for wzzB, fepE and O-Antigen Gene Cluster Cloning

TABLE 11

Oligonucleotide Primers

| Name | Primer Sequence | Comments |
|---|---|---|
| LT2wzzB_S | GAAGCAAACCGTACGCGTAAAG (SEQ ID NO: 40) | based on Genbank GCA_000006945.2 |
| LT2wzzB_AS | CGACCAGCTCTTACACGGCG (SEQ ID NO: 41) | *Salmonella enterica* serovar Typhimurium strain LT2 |
| O25bFepE_S | GAAATAGGACCACTAATAAATACACAAATTAAT AAC (SEQ ID NO: 42) | Based on Genbank GCA_000285655.3 |
| O25bFepE_A | ATAATTGACGATCCGGTTGCC (SEQ ID NO: 43) | O25b E0958 strain ST131 assembly and O25b GAR2401 WGS data |
| wzzB P1_S | GCTATTTACGCCCTGATTGTCTTTTGT (SEQ ID NO: 44) | based on *E. coli* K-12 strain sequence, |
| wzzB P2_AS | ATTGAGAACCTGCGTAAACGGC (SEQ ID NO: 45) | Genbank MG1655 NC_000913.3 or W3110 |
| wzzB P3_S | TGAAGAGCGGTTCAGATAACTTCC (SEQ ID NO: 46) (UDP-glucose-6-dehydrogenase) | assembly GCA_000010245.1 |
| wzzB P4_AS | CGATCCGGAAACCTCCTACAC (SEQ ID NO: 47) (Phosphoribosyl-AMP cyclohydrolase/ Phosphoribosyl-ATP pyrophosphohydrolase) | |
| O157 FepE_S | GATTATTCGCGCAACGCTAAACAGAT (SEQ ID NO: 48) | *E. coli* O157 fepE (based on Genbank |
| O157 FepE_AS | TGATCATTGACGATCCGGTAGCC (SEQ ID NO: 49) | EDL933 strain GCA_000732965.1) |
| pBAD33_adaptor_S | CGGTAGCTGTAAAGCCAGGGGCGGTAGCGTG GTTTAAACCCAAGCAACAGATCGGCGTCGTCG GTATGGA (SEQ ID NO: 50) | Adaptor has central PmeI site and homology to conserved 5' OAg |
| pBAD33_adaptor_AS | AGCTTCCATACCGACGACGCCGATCTGTTGCT TGGGTTTAAACCACGCTACCGCCCCTGGCTTT ACAGCTACCGAGCT (SEQ ID NO: 51) | operon promoter and 3' gnd gene sequences |
| JUMPSTART_r | GGTAGCTGTAAAGCCAGGGGCGGTAGCGTG (SEQ ID NO: 52) | Universal Jumpstart (OAg operon promoter) |
| gnd_f | CCATACCGACGACGCCGATCTGTTGCTTGG (SEQ ID NO: 53) | Universal 3' OAg (gnd) operon antisense primer |

Example 11: Plasmids

Figure 12A:
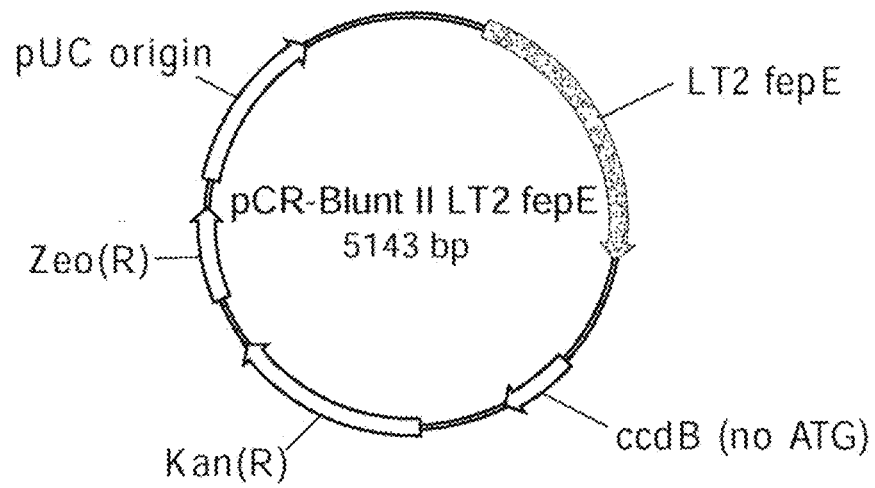
FIG. 12A-12B—depict plasmids: a pUC replicon plasmid, 500-700× copies per cell, Chain length regulator (FIG. 12A); and P15a replicon plasmid, 10-12× copies per cell, O-antigen operon (FIG. 12B).
Figure 12B:
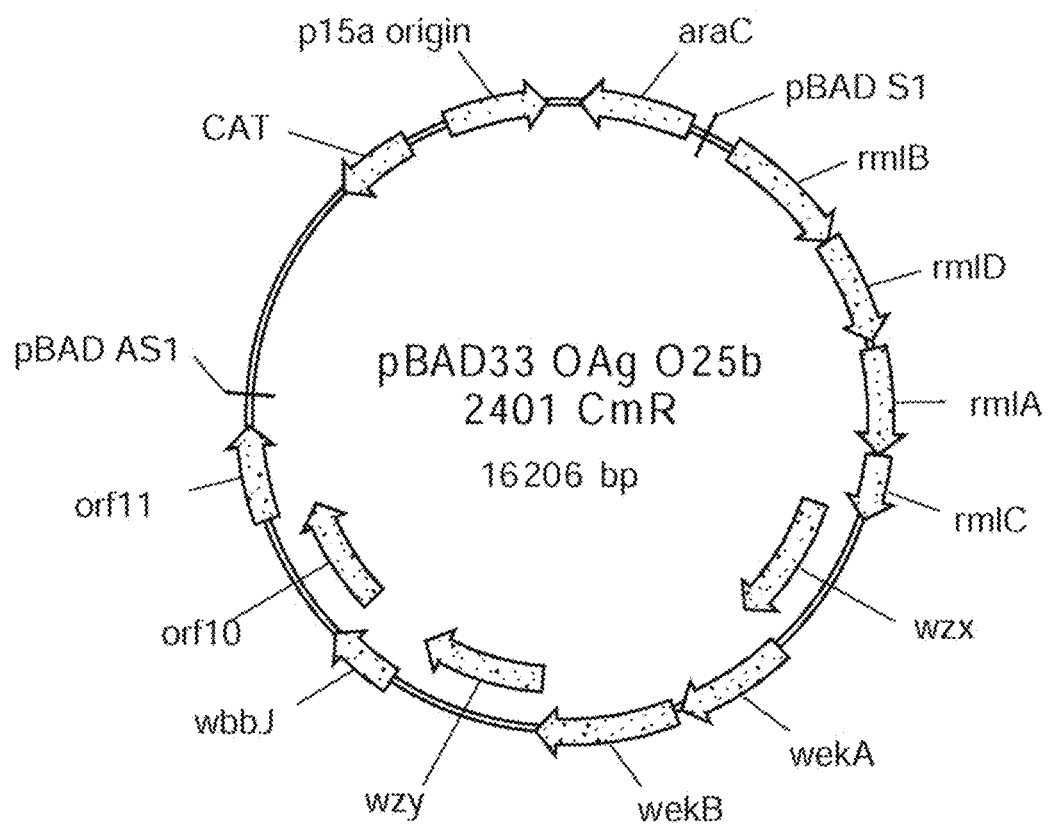

Plasmid vectors and subclones are listed in Table 12. PCR fragments harboring various *E. coli* and *Salmonella* wzzB and fepE genes were amplified from purified genomic DNA and subcloned into the high copy number plasmid provided in the Invitrogen PCR®Blunt cloning kit FIG. 12A-12B. This plasmid is based on the pUC replicon. Primers P3 and P4 were used to amplify *E. coli* wzzB genes with their native promoter, and are designed to bind to regions in proximal and distal genes encoding UDP-glucose-6-dehydrogenase and phosphoribosyladenine nucleotide hydrolase respectively (annotated in Genbank MG1655 NC_000913.3). A PCR fragment containing *Salmonella* fepE gene and promoter were amplified using primers previously described. Analogous *E. coli* fepE primers were designed based on available Genbank genome sequences or whole genome data generated internally (in case of GAR2401 and O25K5H1). Low copy number plasmid pBAD33 was used to express O-antigen biosynthetic genes under control of the arabinose promoter. The plasmid was first modified to facilitate cloning (via Gibson method) of long PCR fragments amplified using universal primers homologous to the 5' promoter and 3' 6-phosphogluconate dehydrogenase (gnd) gene Table 12. The pBAD33 subclone containing the O25b biosynthetic operon is illustrated in FIG. 12A-12B.

TABLE 12

Plasmids

| Name | Replicon | Resistance marker | Comments |
|---|---|---|---|
| PCR ®Blunt II TOPO | pUC | KanR | Invitrogen PCR cloning vector |
| pBAD33 | P15a | CamR | Arabinose inducible vector |
| pBAD33-OAg | P15a | CamR | OAg operon Gibson cloning vector |
| pBAD33-O25b | P15a | CamR | O25b OAg expression plasmid |
| pBAD33-O21 | P15a | CamR | O21 OAg expression plasmid |

TABLE 12-continued

Plasmids

| Name | Replicon | Resistance marker | Comments |
|---|---|---|---|
| pBAD33-O16 | P15a | CamR | O16 OAg expression plasmid |
| pBAD33-O75 | P15a | CamR | O75 OAg expression plasmid |
| pBAD33-O1 | P15a | CamR | O1 OAg expression plasmid |
| pBAD33-O2 | P15a | CamR | O2 OAg expression plasmid |
| pTOPO-O25b 2401 wzzB | pUC | KanR | GAR 2401 gDNA template |
| pTOPO-O25b 2401 fepE | pUC | KanR | |
| pTOPO-K12 wzzB | pUC | KanR | E. coli K-12 strain gDNA template |
| pTOPO-O25a wzzB | pUC | KanR | E. coli O25a strain O25K5H1 |
| pTOP0-O25a fepE | pUC | KanR | gDNA template |
| pTOPO-Salmonella LT2 wzzB | pUC | KanR | Salmonella enterica serovar Typhimurium strain LT2 gDNA template |
| pTOPO-Salmonella LT2 fepE | pUC | KanR | |
| pTOPO-O25a ETEC wzzB | pUC | KanR | O25a ETEC strain gDNA |
| pTOPO-O25a ETEC fepE | pUC | KanR | purchased from ATCC ("NR-5" E2539-C1) |
| pTOPO-O157fepE | pUC | KanR | O157:H7:K- Shigella toxin strain DNA purchased from ATCC (EDL933 #43895D-5) |

Example 12: O-Antigen Purification

The fermentation broth was treated with acetic acid to a final concentration of 1-2% (final pH of 4.1). The extraction of OAg and delipidation were achieved by heating the acid treated broth to 100° C. for 2 hours. At the end of the acid hydrolysis, the batch was cooled to ambient temperature and 14% NH$_4$OH was added to a final pH of 6.1. The neutralized broth was centrifuged and the centrate was collected. To the centrate was added CaCl$_2$ in sodium phosphate and the resulting slurry was incubated for 30 mins at room temperature. The solids were removed by centrifugation and the centrate was concentrated 12-fold using a 10 kDa membrane, followed by two diafiltrations against water. The retentate which contained OAg was then purified using a carbon filter. The carbon filtrate was diluted 1:1 (v/v) with 4.0M ammonium sulfate. The final ammonium sulfate concentration was 2M. The ammonium sulfate treated carbon filtrate was further purified using a membrane with 2M ammonium sulfate as the running buffer. The OAg was collected in the flow through. For the long OAg the HIC filtrate was concentrated and then buffer exchanged against water (20 diavolumes) using a 5 kDa membrane. For the short (native) OAg polysaccharide, the MWCO was further reduced to enhance yield.

Example 13: Conjugation of O25b Long O-Antigen to CRM$_{197}$

The first set of long chain O25b polysaccharide-CRM$_{197}$ conjugates were produced using periodate oxidation followed by conjugation using reductive amination chemistry (RAC) (Table 14). Conjugate variants with three activation levels (low, medium and high) by varying the oxidation levels. Conjugates were produced by reacting the lyophilized activated polysaccharides with lyophilized CRM$_{197}$, reconstituted in DMSO medium, using sodium cyanoborohydride as the reducing agent. Conjugation reactions were carried out at 23° C. for 24 hrs, followed by capping using sodium borohydride for 3 hrs. Following the conjugation quenching step, conjugates were purified by ultrafiltration/diafiltration with 100K MWCO regenerated cellulose membrane, using 5 mM Succinate/0.9% NaCl, pH 6.0. Final filtration of the conjugates were performed using a 0.22 μm membrane.

Unless expressly stated otherwise, the conjugates disclosed throughout the following Examples include a core saccharide moiety.

Long O-Antigen Expression Conferred by Heterologous Polymerase Chain Length Regulators.

Initial E. coli strain construction focused on the O25 serotype. Goal was to overexpress heterologous wzzB or fepE genes to see if they confer longer chain length in O25 wzzB knockout strains. First, blood isolates were screened by PCR to identify strains of the O25a and O25b subtype. Next, strains were screened for sensitivity to ampicillin. A single ampicillin-sensitive O25b isolate GAR2401 was identified into which a wzzB deletion was introduced. Similarly, a wzzB deletion was made in O25a strain O25K5H1. For genetic complementation of these mutations, wzzB genes from GAR 2401 and O25K5H1 were subcloned into the high copy PCR-Blunt II cloning vector and introduced into both strains by electroporation. Additional wzzB genes from E. coli K-12 and S. enterica serovar Typhimurium LT2 were similarly cloned and transferred; likewise fepE genes from E. coli O25K5H1, GAR 2401, O25a ETEC NR-5, O157:H7:K- and S. enterica serovar Typhimurium LT2.

Figure 13A:
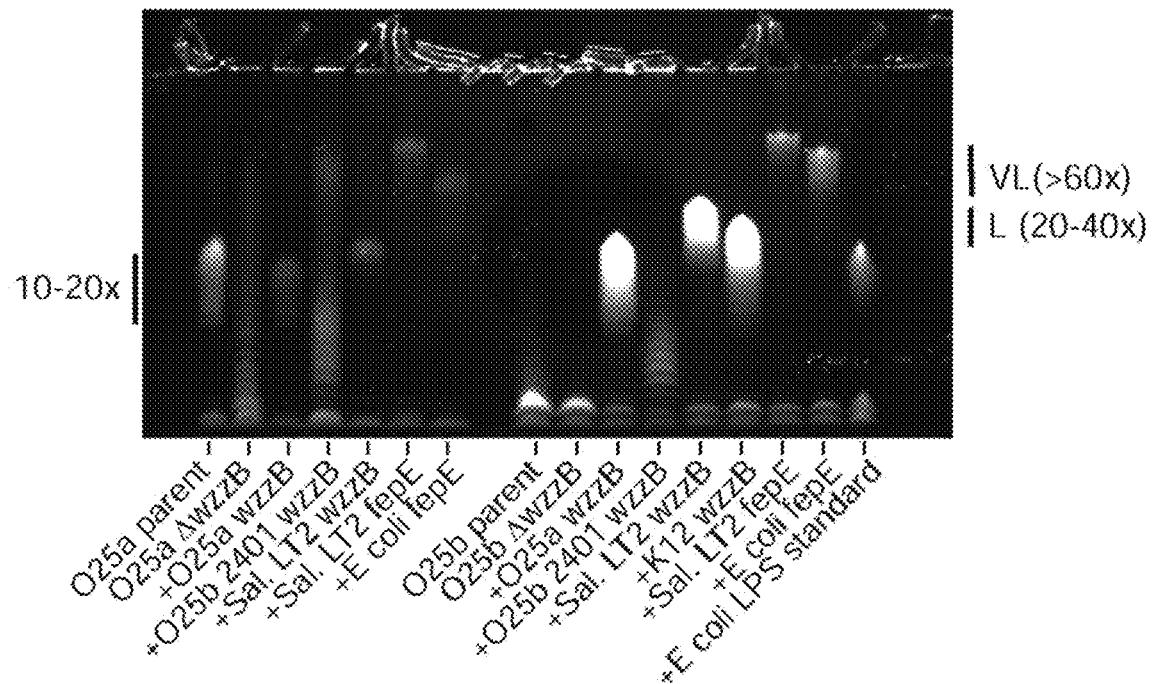
FIG. 13A-13B—depict modulation of O-antigen chain length in serotype O25a and O25b strains by plasmid-based expression of heterologous wzzB and fepE chain length regulators. Genetic complementation of LPS expression in plasmid transformants of wzzB knockout strains O25K5H1 (O25a) and GAR2401 (O25b) is shown. On the left side of FIG. 13A, LPS profiles of plasmid transformants of O25a O25K5HΔwzzB are shown; and on the right, analogous profiles of O25b GAR 2401ΔwzzB transformants. An immunoblot of a replicate gel probed with O25-specific sera (Statens Serum Institut) is shown in FIG. 13B. O25a ΔwxxB (Knock out) background associated with Lanes 1-7; O25b 2401 ΔwzzB (Knock out) background associated with Lanes 8-15.
Figure 13B:
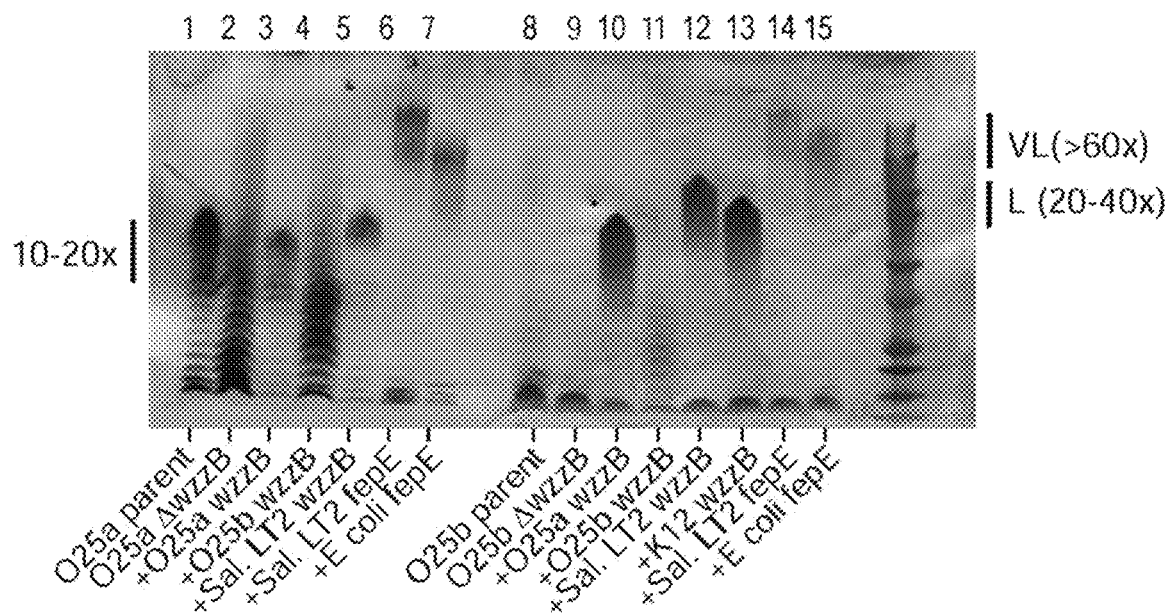

Bacteria were grown overnight in LB medium and LPS was extracted with phenol, resolved by SDS PAGE (4-12% acrylamide) and stained. Each well of the gel was loaded with LPS extracted from the same number of bacterial cells (approximately 2 OD$_{600}$ units). Size of LPS was estimated from an internal native E. coli LPS standard and by counting the ladder discernable from a subset of samples showing a broad distribution of chain lengths (differing by one repeat unit). On the left side of FIG. 13A, LPS profiles of plasmid transformants of O25a O25K5HΔwzzB are shown; and on the right, analogous profiles of O25b GAR 2401ΔwzzB transformants. An immunoblot of a replicate gel probed with O25-specific sera is shown in FIG. 13B.

Results from this experiment show that introduction of the homologous wzzB gene into the E. coli O25aΔwzzB host restores expression of short O25 LPS (10-20x), as does the Salmonella LT2 wzzB. Introduction of the O25b wzzB gene from GAR2401 does not, suggesting the WzzB enzyme from this strain is defective. A comparison of E. coli WzzB amino acid sequences suggests that A210E and P253S substitutions may be responsible. Significantly, *Salmonella* LT2 fepE and *E. coli* fepE from O25a O25K5H1 conferred the ability to express very long (VL) OAg LPS, with the *Salmonella* LT2 fepE resulting in OAg exceeding in size that conferred by *E. coli* fepE.

Figure 14:
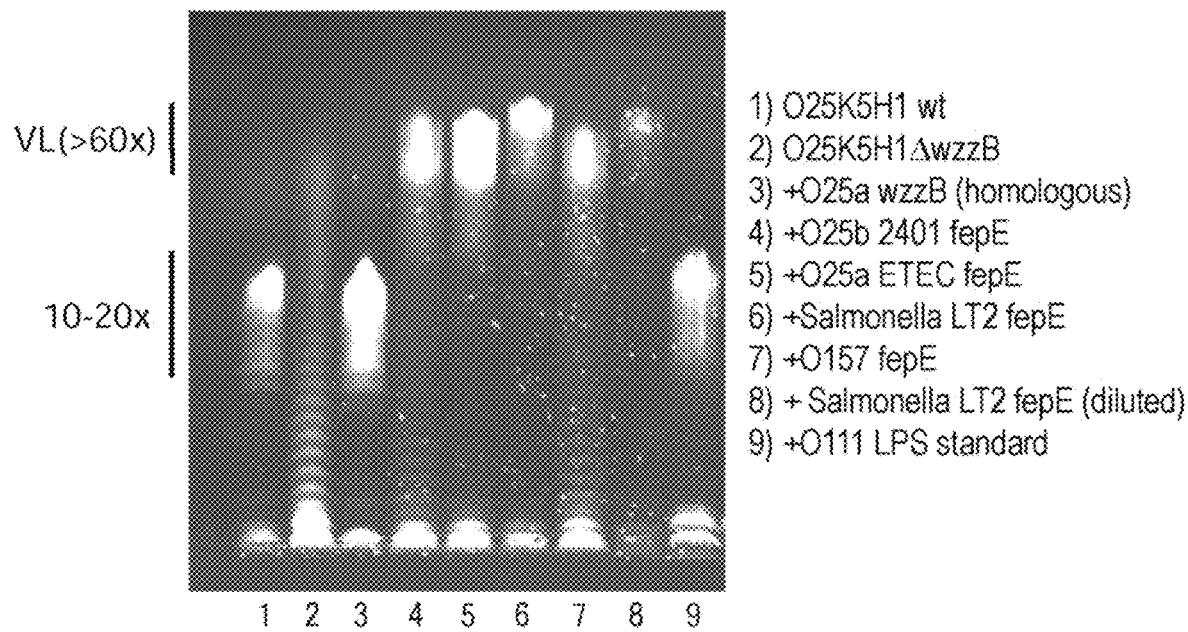
FIG. 14—depicts long chain O-antigen expression conferred by E. coli and Salmonella fepE plasmids in host O25K5H1ΔwzzB.

A similar pattern of expression was observed with GAR2401ΔwzzB transformants: *E. coli* O25a or K12 strain wzzB restored ability to produce short LPS. The *Salmonella* LT2 fepE generated the longest LPS, the *E. coli* fepE a slightly shorter LPS, while the *Salmonella* LT2 wzzB yielded an intermediate sized long LPS (L). The ability of other *E. coli* fepE genes to produce very long LPS was assessed in a separate experiment with transformants of *E. coli* O25aΔwzzB. The fepE genes from GAR2401, an O25a ETEC strain and an O157 *Shigella* toxin producing strain also conferred the ability to produce very long LPS, but not as long as the LPS generated with the *Salmonella* LT2 fepE (FIG. 14).

Figure 15:
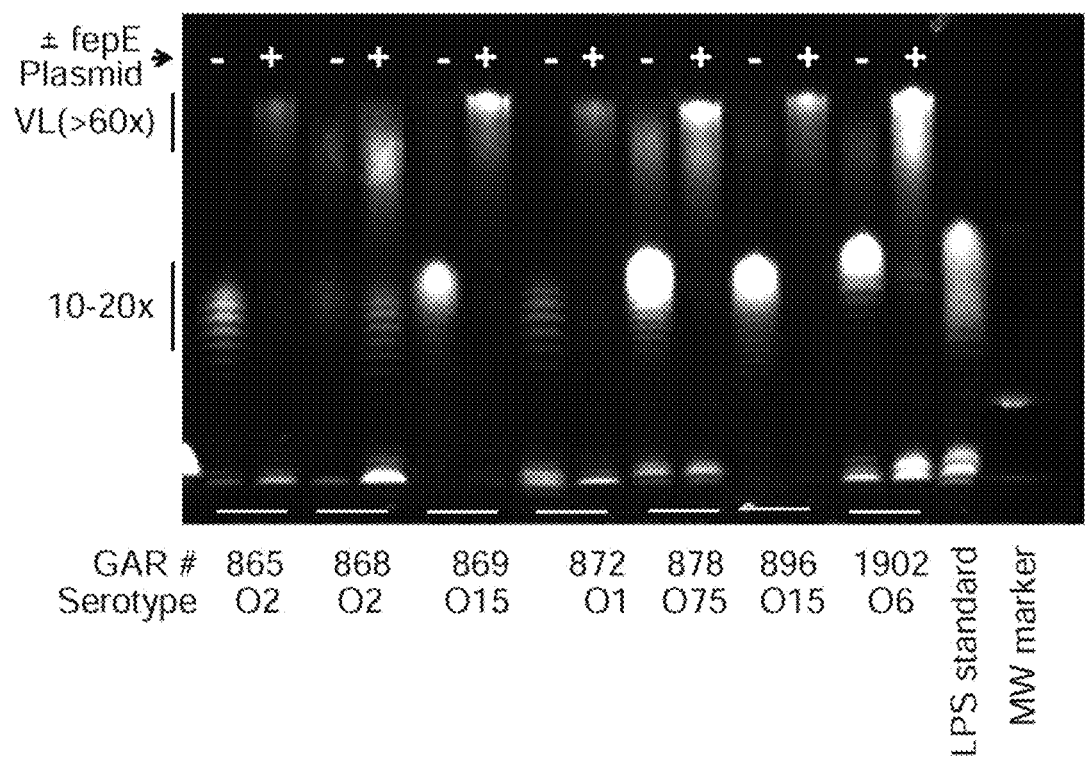
FIG. 15—depicts that Salmonella fepE expression generates Long O-antigen LPS in a variety of clinical isolates.

Having established in serotype O25a and O25b strains that *Salmonella* LT2 fepE generates the longest LPS of the polymerase regulators evaluated, we next sought to determine whether it would also produce very long LPS in other *E. coli* serotypes. Wild-type bacteremia isolates of serotype O1, O2, O6, O15 and O75 were transformed with the *Salmonella* fepE plasmid and LPS extracted. The results shown in FIG. 15 confirm that *Salmonella* fepE can confer the ability to make very long LPS in other prevalent serotypes associated with blood-infections. Results also show that plasmid-based expression of *Salmonella* fepE appears to override the control of chain length normally exerted by endogenous wzzB in these strains.

Plasmid-Based Expression of O-Antigens in a Common *E. coli* Host Strain.

From the perspective of bioprocess development, the ability to produce O-antigens of different serotypes in a common *E. coli* host instead of multiple strains would greatly simplify the manufacturing of individual antigens. To this end, O-antigen gene clusters from different serotypes were amplified by PCR and cloned into a low-copy number plasmid (pBAD33) under control of an arabinose regulated promoter. This plasmid is compatible (can coexist) with the *Salmonella* LT2 fepE plasmid in *E. coli* as it harbors a different (p15a) replicon and different selectable marker (chloramphenicol vs kanamycin). In a first experiment, a pBAD33 O25b operon plasmid subclone was cotransfected with the *Salmonella* LT2 fepE plasmid into GAR2401ΔwzzB and transformants grown in the presence or absence of 0.2% arabinose. Results shown in FIG. 16A-16B demonstrated that very long O-antigen LPS was produced in an arabinose-dependent manner.

Figure 17:
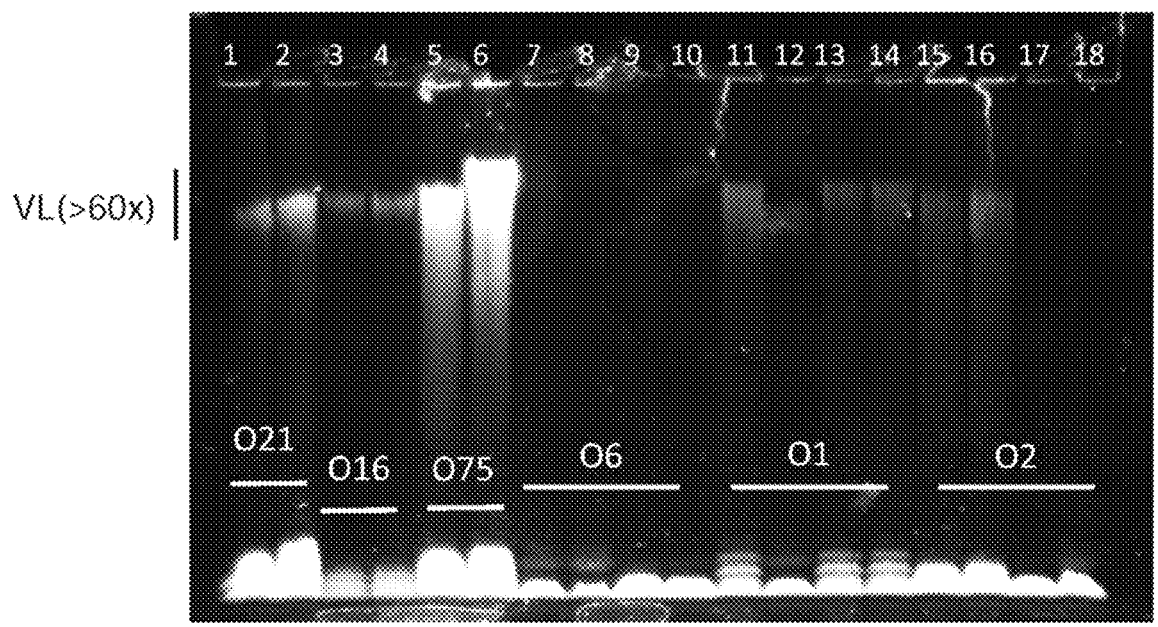
FIG. 17—depicts plasmid-mediated Arabinose-inducible Expression of Long O-antigen LPS in common host strain.

O-antigen gene clusters cloned from other serotypes were similarly evaluated and the results shown in FIG. 17. Co-expression of *Salmonella* LT2 fepE and pBAD33-OAg plasmids resulted in detectable long chain LPS corresponding to O1, O2 (for two out of four clones), O16, O21 and O75 serotypes. For unknown reasons, the pBAD33-O6 plasmid failed to yield detectable LPS in all four isolates tested. Although expression level was variable, results show that expression of long chain O-antigens in a common host is feasible. However, in some cases further optimization to improve expression may be required, for example by modification of plasmid promoter sequences.

Figure 18:
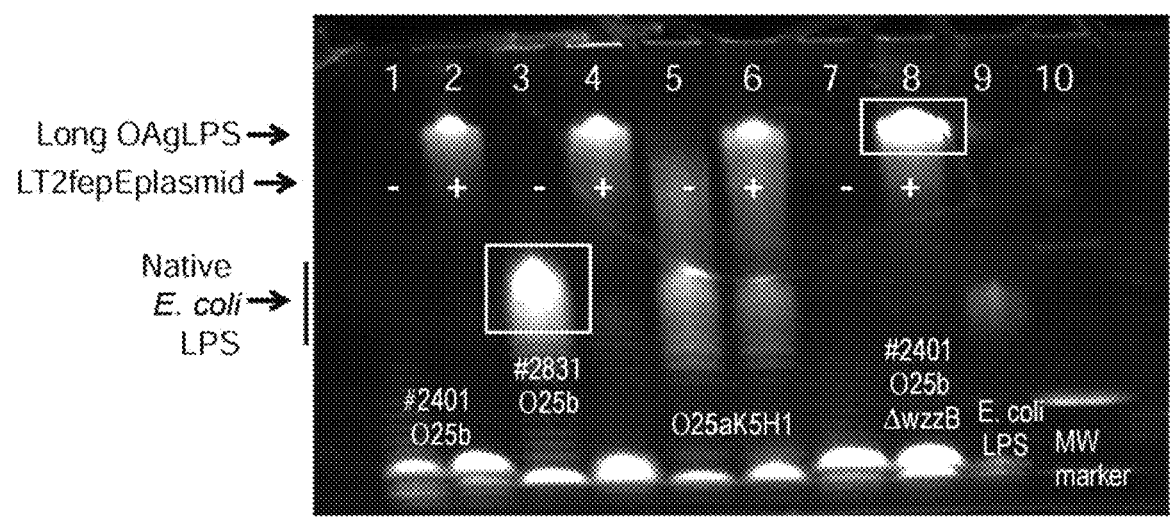
FIG. 18—depicts expression of O25 O-antigen LPS in Exploratory Bioprocess strains.
Figure 19A:
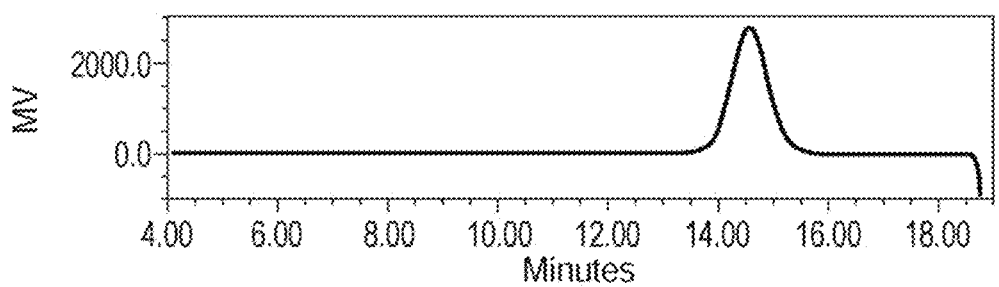
FIG. 19A-19B—depict SEC profiles and properties of short (FIG. 19A, Strain 1 O25b wt 2831) and long O25b O-antigens (FIG. 19B, Strain 2 O25b 2401ΔwzzB/LT2 FepE) purified from strains GAR2831 and '2401ΔwzzB/fepE.
Figure 19B:
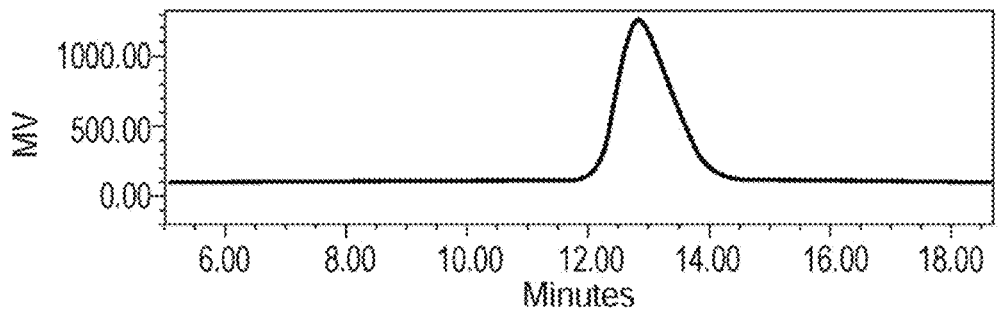

The profiles of LPS from different serotype O25 *E. coli* strains with or without the *Salmonella* LT2 fepE plasmid are shown in FIG. 18. Two strains were studied for fermentation, extraction and purification of O-antigens: GAR2831, for the production of native short O25b OAg; and GAR2401ΔwzzB/fepE, for the production of long O25b OAg. The corresponding short and long form LPSs shown in the FIG. 18 SDS-PAGE gel are highlighted in red. Polysaccharides were extracted directly from fermented bacteria with acetic acid and purified. Size exclusion chromatography profiles of purified short and long or very long O25b polysaccharides are shown in FIG. 19A-19B. The properties of two lots of short polysaccharide (from GAR2831) are compared with a single very long polysaccharide preparation (from strain GAR2401ΔwzzB/fepE). The molecular mass of the long O-antigen is 3.3-fold greater than that of the short O-antigen, and the number of repeat units was estimated to be ~65 (very long) vs ~20. See Table 13.

TABLE 13

| Poly Lot # | Native | Native | Modified (long chain) |
|---|---|---|---|
| Poly Lot # | 709766-24A | 709722-24B | 709766-25A |
| Poly MW (kDa) | 17.3 | 16.3 | 55.3 |
| # Repeat Units | 20 | 19 | 64 |

The very long O25b O-antigen polysaccharide was conjugated to diphtheria toxoid $CRM_{197}$ using a conventional reductive amination process. Three different lots of glycoconjugate were prepared with varying degree of periodate activation: medium (5.5%), low (4.4%) and high (8.3%). The resulting preparations and unconjugated polysaccharide were shown to be free of endotoxin contamination) (Table 14).

Figure 20A:
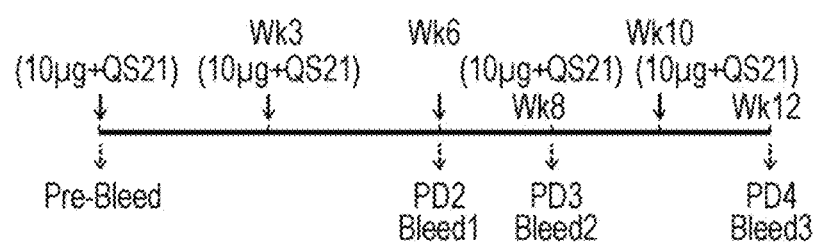
FIG. 20A-20B—depict vaccination schedules in rabbits.

Groups of four rabbits (New Zealand White females) were each vaccinated with 10 mcg of glycoconjugate and 20 mcg of QS21 adjuvant and serum sampled (VAC-2017-PRL-EC-0723) according to the schedule shown in FIG. 20A. It is worth noting that a 10 mcg dose is at the low end of the range customarily given to rabbits in the evaluation of bacterial glycoconjugates (20-50 mcg is more typical). A group of rabbits was also vaccinated in a separate study (VAC-2017-PRL-GB-0698) with unconjugated polysaccharide using the same dose (10 mcg polysaccharide+20 mcg QS21 adjuvant) and identical administration schedule.

Figure 21A:
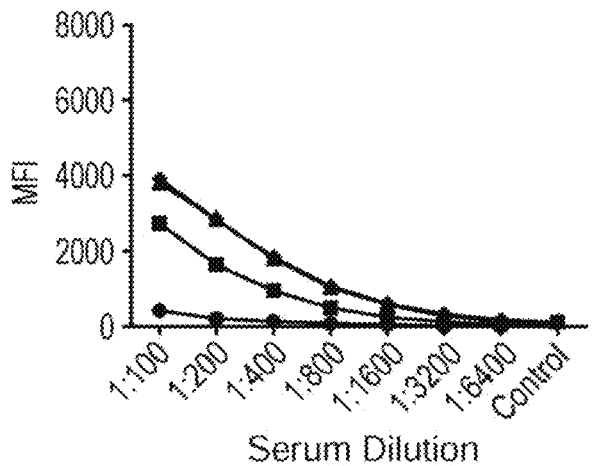
FIG. 21A-21A—depict O25b Glycoconjugate IgG responses, wherein —●— represents results from Prebleed; —■— Bleed 1 (6 wk); —▲— Bleed 2 (8 wk); —◆— Bleed 3 (12 wk).
Figure 21B:
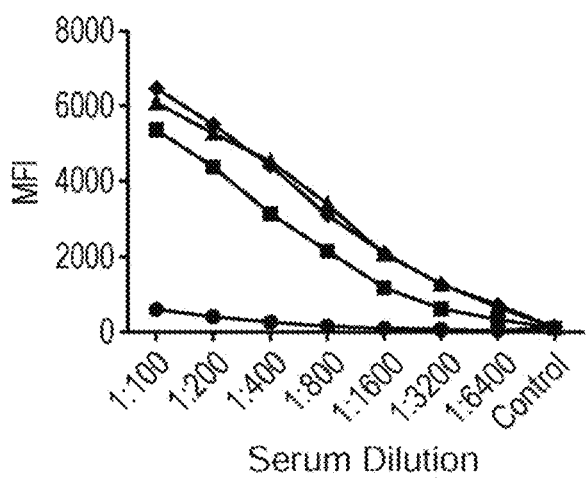
FIG. 21B depicts results from Rabbit 2-3 (Low Activation)
Figure 21C:
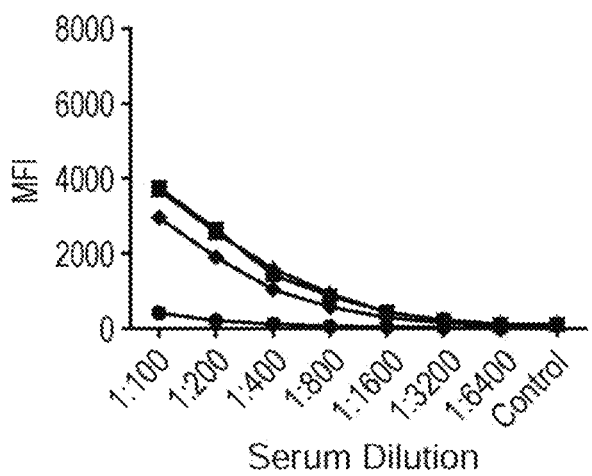
FIG. 21C depicts results from Rabbit 3-1 (High Activation).

Rabbit antibody responses to the three O25b glycoconjugate preparations were evaluated in a LUMINEX assay in which carboxy beads were coated with methylated human serum albumin prebound with unconjugated O25b long polysaccharide. The presence of O25b-specific IgG antibodies in serum samples was detected with a phycoerythrin (PE)-labelled anti-IgG secondary antibody. The profiles of immune responses observed in sera sampled at week 0 (pre-immune), week 6 (post-dose 2, PD2), week 8 (post-dose 3, PD3) and week 12 (post-dose 4, PD4) in best-responding rabbits (one from each group of four) are shown in FIG. 21A-21C. No significant pre-immune serum IgG titers were detected in any of the 12 rabbits. In contrast, O25b antigen-specific antibody responses were detected in post-vaccination sera from rabbits in all three groups, with the low-activation glycoconjugate group responses trending slightly higher than the medium or high activation glycoconjugate groups. Maximal responses were observed by the post-dose 3 timepoint. One rabbit in the low activation group and one rabbit from the high activation group failed to respond to vaccination (non-responders).

Figure 22A:
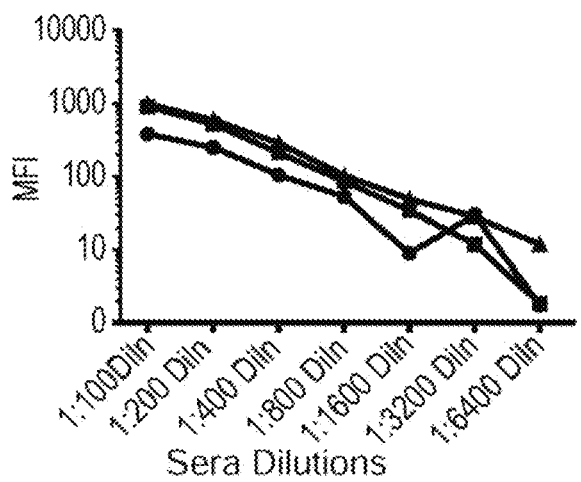
FIG. 22A-22F—depict IgG responses to O25b Long O-antigen Glycoconjugate, i.e., Low activation O25b CRM$_{197}$ gate (FIG. 22D-22F, wherein —●— represents results from Prebleed from Rabbit 2-1, —■— Week 12 Antisera from Rabbit 2-1) vs unconjugated polysaccharide, i.e., free O25b polysaccharide (FIG. 22A-22C, wherein —●— represents results from Prebleed from Rabbit A —■— Week 6 Antisera from Rabbit A-1, —▲— Week 8 Antisera from Rabbit A-1). Note that MFIs are plotted on log scale to highlight differences between pre-immune and immune antibodies in the <1000 MFI range.
Figure 22B:
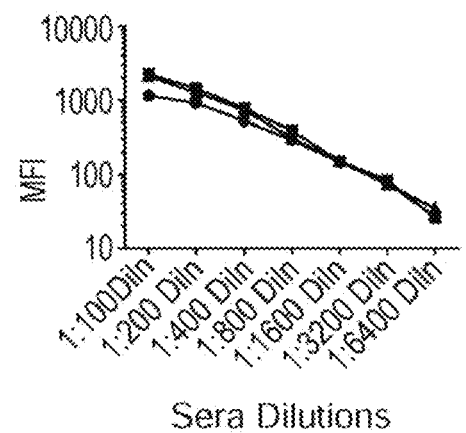
Figure 22C:
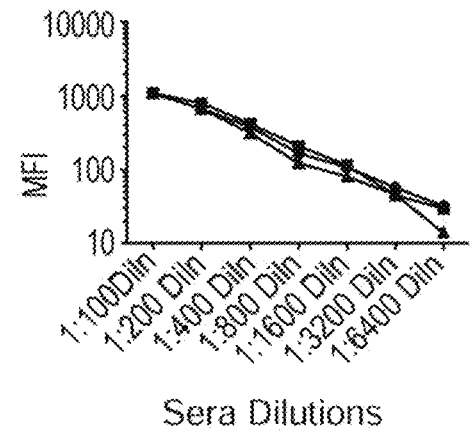
Figure 22D:
Figure 22E:
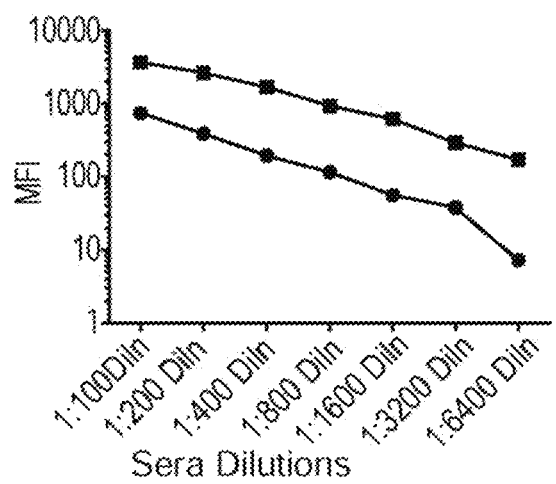
Figure 22F:
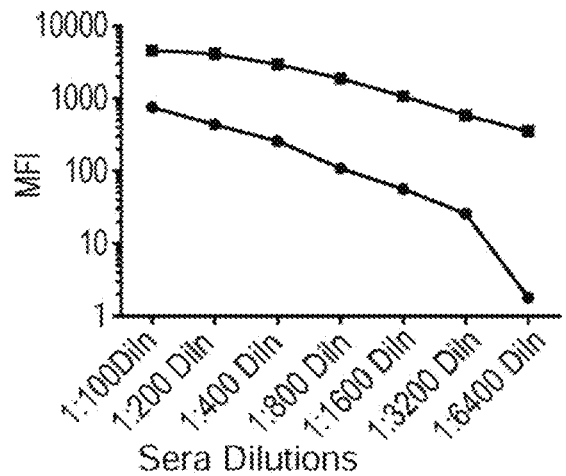

To assess the impact of $CRM_{197}$ carrier protein conjugation on immunogenicity of the long O25b OAg polysaccharide, the presence of antibodies in sera from rabbits vaccinated with unconjugated polysaccharide was compared with sera from rabbits vaccinated with the low activation $CRM_{197}$ glycoconjugate FIG. 22A-22F. Remarkably, the free polysaccharide was not immunogenic, eliciting virtually no IgG responses in immune vs preimmune sera (FIG. 22A). In contrast, O25b OAg-specific IgG mean fluorescence intensity values (MFIs) of approximately ten-fold above preimmune serum levels were observed in PD4 sera from three out of four rabbits vaccinated with O25b OAg-$CRM_{197}$, across a range of serum dilutions (from 1:100 to 1:6400). These results demonstrate the necessity of carrier protein conjugation to generate IgG antibodies to the O25b OAg polysaccharide at the 10 mcg dose level.

Bacteria grown on TSA plates were suspended in PBS, adjusted to $OD_{600}$ of 2.0 and fixed in 4% paraformaldehyde in PBS. After blocking in 4% BSA/PBS for 1 h, bacteria were incubated with serial dilutions of pre-immune and PD3 immune sera in 2% BSA/PBS, and bound IgG detected with PE-labeled secondary F(ab) antibody.

Specificity of the O25b antibodies elicited by the O25b OAg-$CRM_{197}$ was demonstrated in flow cytometry experiments with intact bacteria. Binding of IgG to whole cells was detected with PE-conjugated $F(ab')_2$ fragment goat anti-rabbit IgG in an Accuri flow cytometer.

Figure 23A:
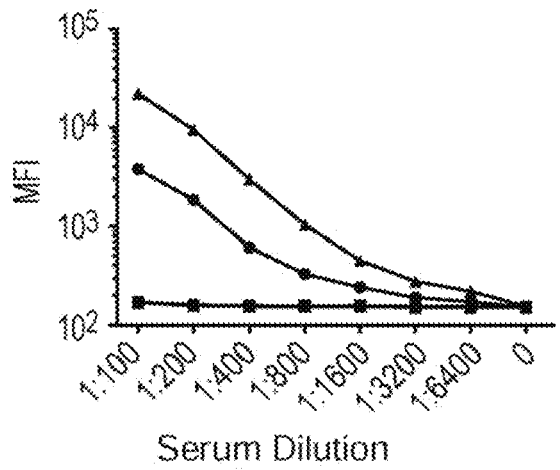
FIG. 23A-23C—depict surface expression of native vs long O25b O-antigen detected with O25b antisera.
Figure 23B:
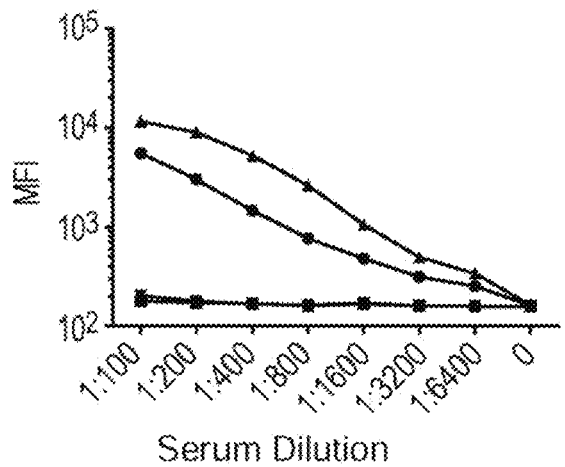
Figure 23C:
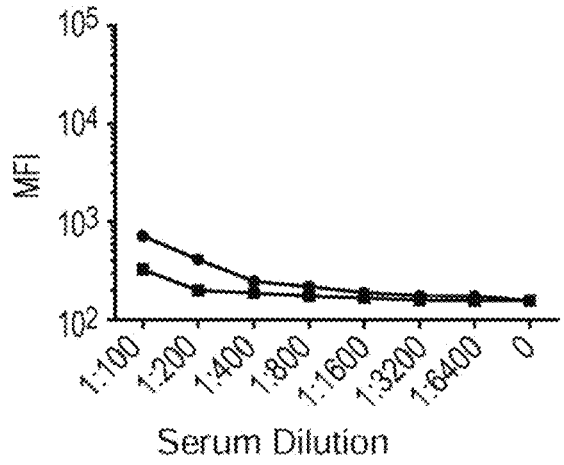

As shown in FIG. 23A-23C, pre-immune rabbit antibodies failed to bind to wild-type serotype O25b isolates GAR2831 and GAR2401 or to a K-12 *E. coli* strain, whereas matched PD3 antibodies stained the O25b bacteria in a concentration dependent manner. Negative control K-12 strain which lacks the ability to express OAg showed only very weak binding of PD3 antibodies, most likely due to the presence of exposed inner core oligosaccharide epitopes on its surface. Introduction of the *Salmonella* fepE plasmid into the wild-type O25b isolates resulted in significantly enhanced staining, consistent with the higher density of immunogenic epitopes provided by the longer OAg polysaccharide.

Conclusion: The results described show that not only is *Salmonella* fepE the determinant of very long O-antigen polysaccharides in *Salmonella* species, but that it also can confer on *E. coli* strains of different O-antigen serotypes the ability to make very long OAgs. This property can be exploited to produce O-antigen vaccine polysaccharides with improved properties for bioprocess development, by facilitating purification and chemical conjugation to appropriate carrier proteins, and by potentially enhancing immunogenicity through the formation of higher molecular weight complexes.

Example 14: Initial Rabbit Studies Generated First Polyclonal Antibody Reagents and IgG Responses to RAC O25b OAg-$CRM_{197}$ Long chain O25b polysaccharide-$CRM_{197}$ conjugates were produced using periodate oxidation followed by conjugation using reductive amination chemistry (RAC) (Table 14). See also Table 24.

TABLE 14

| $CRM_{197}$ conjugate | 132242-28 Medium 5.5% activation | 132242-27 Low 4.5% activation | 132242-29 High 8.3% activation | 709766-29 Free O25b polysaccharide |
|---|---|---|---|---|
| Polysaccharide concentration (mg/mL) | 0.7 | 0.6 | 0.67 | 1 |
| Endotoxin (EU/ug) | 0.02 | 0.02 | 0.02 | <0.6EU |
| Matrix | 5 uM Succinate buffer/saline, pH 6.0 | | | |

Figure 25:
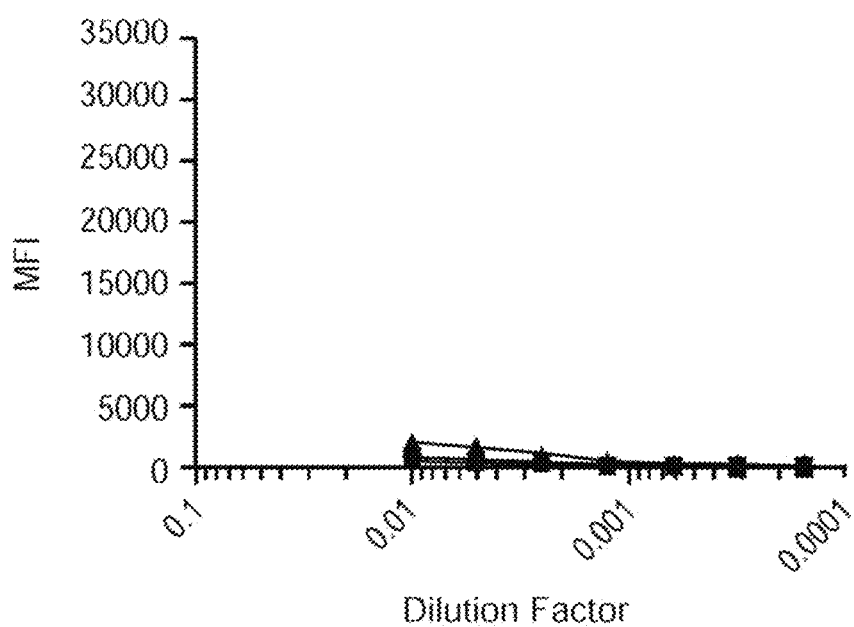
FIG. 25—depicts that unconjugated free O25b polysaccharide is not immunogenic (dLIA), wherein -●- represents results from Week 18 (1 wk=PD4) Antisera from 4-1; -■- represents results from Week 18 (1 wk=PD4) Antisera from 4-2; -▲- represents results from Week 18 (1 wk=PD4) Antisera from 5-1; -▼- represents results from Week 18 (1 wk=PD4) Antisera from 5-2; -*- represents results from Week 18 (1 wk=PD4) Antisera from 6-1; -▲- represents results from Week 18 (1 wk=PD4) Antisera from 6-2.

In Rabbit Study 1 (VAC-2017-PRL-EC-0723) (also described above in Example 13)—five (5) rabbits/group, with 10 ug L-, M- or H-activation RAC (+QS21) received a composition according to the schedule shown in FIG. 20A. Unconjugated free O25b polysaccharide was observed not to be immunogenic in a follow-up rabbit Study (VAC-2017-PRL-GB-0698) (see FIG. 25).

Figure 20B:
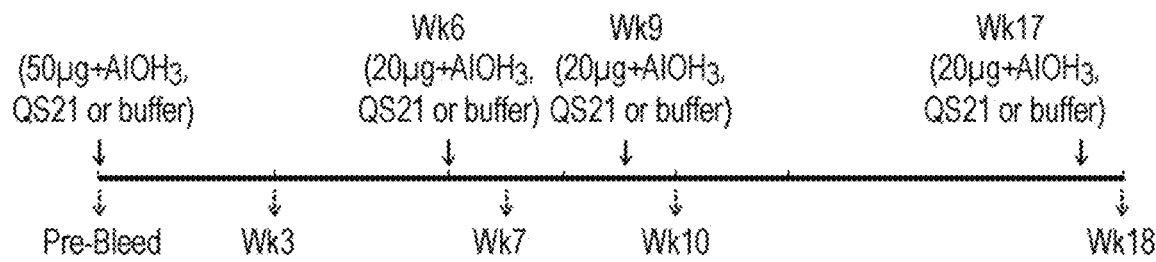

In Rabbit Study 2 (VAC-2018-PRL-EC-077)—2 rabbits/group, with L-RAC ($AlOH_3$, QS21, or no adjuvant) received a composition according to the schedule shown in FIG. 20B.

Rabbits 4-1, 4-2, 5-1, 5-2, 6-1, and 6-2 received the very long unconjugated O25b polysaccharide described in Example 13, and week 18 sera were tested.

More specifically, a composition including 50 ug unconjugated O25b, 100 ug $AlOH_3$ adjuvant was administered to Rabbit 4-1. A composition including 50 ug unconjugated O25b, 100 ug $AlOH_3$ adjuvant was administered to Rabbit 4-2. A composition including 50 ug unconjugated O25b, 50 ug QS-21 adjuvant was administered to Rabbit 5-1. A composition including 50 ug unconjugated O25b, 50 ug QS-21 adjuvant was administered to Rabbit 5-2. A composition including 50 ug unconjugated O25b, no adjuvant was administered to Rabbit 6-1. A composition including 50 ug unconjugated O25b, no adjuvant was administered to Rabbit 6-2.

Example 15: Rabbit Studies with O25b RAC Conjugate: dLIA Serum Dilution Titers

Rabbit Study 2 (VAC-2018-PRL-EC-077) O25b dLIA serum dilution titers vs best responding rabbit from study 1 (VAC-2017-PRL-EC-0723). For these experiments a modified direct binding Luminex assay was implemented in which a polylysine conjugate of O25b long O-antigen was passively adsorbed onto the Luminex carboxy beads instead of the methylated serum albumin long O-antigen mixture described previously. The use of the polylysine-O25b conjugate improved the sensitivity of the assay and the quality of IgG concentration dependent responses, permitting determination of serum dilution titers through use of curve-fitting (four parameter non-linear equation). O25b IgG titers in sera from highest titer rabbit from first study is compared with sera from second study rabbits in Table 15.

TABLE 15

|  | O25b-CRM Low Activation Conjugate with Alum Adjuvant (EC$_{50}$ as serum dilution) | | O25b-CRM Low Activation Conjugate with QS21 Adjuvant (EC$_{50}$ as serum dilution) | | O25b-CRM Low Activation Conjugate without Adjuvant (EC$_{50}$ as serum dilution) | |
| --- | --- | --- | --- | --- | --- | --- |
|  | Rabbit 1-1 | Rabbit 1-2 | Rabbit 2-1 | Rabbit 2-2 | Rabbit 3-1 | Rabbit 3-2 |
| Week 3 Antisera (3 wks after primary) | ~1:200 | ~1:200 | <1:100 | <1:100 | ~1:200 | ~1:200 |
| Week 7 Antisera (1 wk after boost 1) | 1:1600 | 1:4000 | 1:250 | 1:500 | 1:250 | 1:1500 |
| Week 10 Antisera (1 wk after boost 2) | 1:1100 | 1:1900 | 1:250 | 1:500 | 1:800 | 1:1200 |
| Week 18 Antisera (1 wk after boost 4) | 1:1600 | 1:4000 | 1:1300 | 1:1200 | 1:1400 | 1:1600 |

Average of 6 replicates of best antisera from rabbit 2-3 (assay standard from first study) EC$_{50}$ = 1:1700

Higher doses in second rabbit study (50/20 ug vs 10 ug) did not improve IgG titers.

Two month rest boosts IgG responses (not observed with shorter intervals).

Alum appears to enhance IgG response in rabbits compared with QS21 or no adjuvant.

An opsonophagocytic assay (OPA) with baby rabbit complement (BRC) and HL60 cells as source of neutrophils was established to measure the functional immunogenicity of O-antigen glycoconjugates. Pre-frozen bacterial stocks of *E. coli* GAR2831 were grown in Luria broth (LB) media at 37° C. Cells were pelleted and suspended to a concentration of 1 OD$_{600}$ unit per ml in PBS supplemented with 20% glycerol and frozen. Pre-titered thawed bacteria were diluted to $0.5 \times 10^5$ CFU/ml in HBSS (Hank's Balanced Salt Solution) with 1% Gelatin) and 10 μL ($10^3$ CFU) combined with 20 μL of serially diluted sera in a U-bottomed tissue culture microplate and the mixture shaken at 700 rpm BELLCO Shaker) for 30 min at 37° C. in a 5% CO$_2$ incubator. 10 μl of 2.5% complement (Baby Rabbit Serum, PEL-FREEZ 31061-3, prediluted in HBG) and 20 μL of HL-60 cells ($0.75 \times 10^7$/ml) and 40 μL of HBG added to the U-bottomed tissue culture microplate and the mixture shaken at 700 rpm BELLCO Shaker) for 45 min at 37° C. in a 5% CO$_2$ incubator. Subsequently, 10 μL of each 100 μL reaction was transferred into the corresponding wells of a pre-wetted MILLIPORE MULTISCREENHTS HV filter plate prepared by applying 100 μL water, filter vacuumed, and applying 150 μL of 50% LB. The filter plate was vacuum filtered and incubated overnight at 37° C. in a 5% CO$_2$ incubator. The next day the colonies were enumerated after fixing, staining, and destaining with COOMASSIE dye and Destain solutions, using an IMMUNOSPOT® analyzer and IMMUNO-CAPTURE software. To establish the specificity of OPA activity, immune sera were preincubated with 100 μg/mL purified long O25b O-antigen prior to combining with the other assay components in the OPA reaction. The OPA assay includes control reactions without HL60 cells or complement, to demonstrate dependence of any observed killing on these components.

Figure 26A:
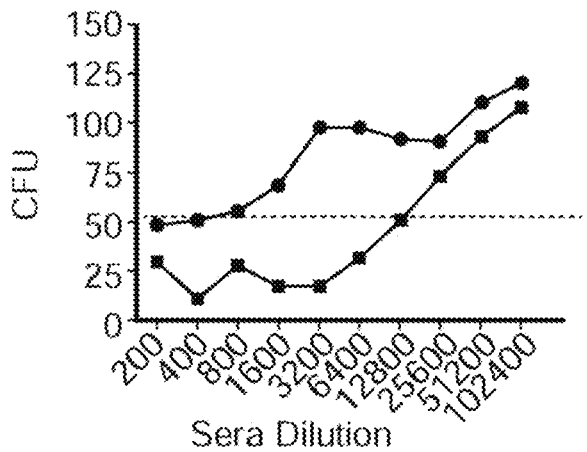
FIG. 26A-26C—depict graphs illustrating the specificity of BRC Rabbit O25b RAC conjugate immune sera OPA titers.
Figure 26B:
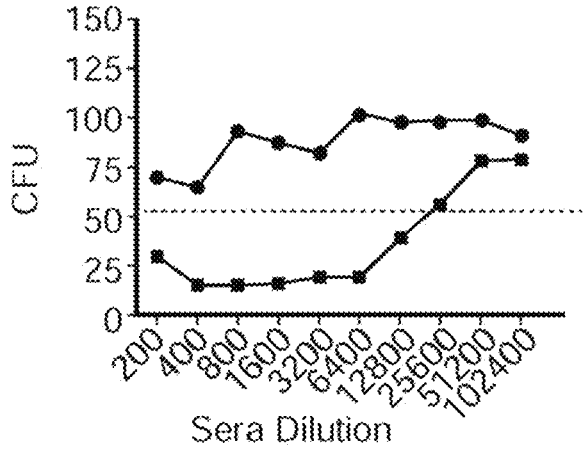

Matched pre-immune and post-vaccination serum samples from representative rabbits from both rabbit studies were evaluated in the assay and serum dilution titers determined (Table 16, FIG. 26A-26B). Preincubation with unconjugated O25b long O-antigen polysaccharide blocked bactericidal activity demonstrating specificity of the OPA (FIG. 19C). Table 16 OPA titers Rabbit 2-3 was dosed as follows: Rabbit 2-3 dosing: 10/10/10/10 ug RAC conjugate+QS21, post-dose (PD) 4 bleed. Rabbit 1-2 was dosed as follows: 50/20/20/20 ug RAC conjugate+Al(OH)$_3$, PD4 bleed.

TABLE 16

| Sample | Titer |
| --- | --- |
| Rabbit 2-3 Pre-immune serum | 537 |
| Rabbit 2-3 wk 13 serum (terminal bleed) | 13686 |
| Rabbit 1-2 Pre-immune serum | <200 |
| Rabbit 1-2 wk 19 serum (terminal bleed) | 22768 |

Figure 27A:
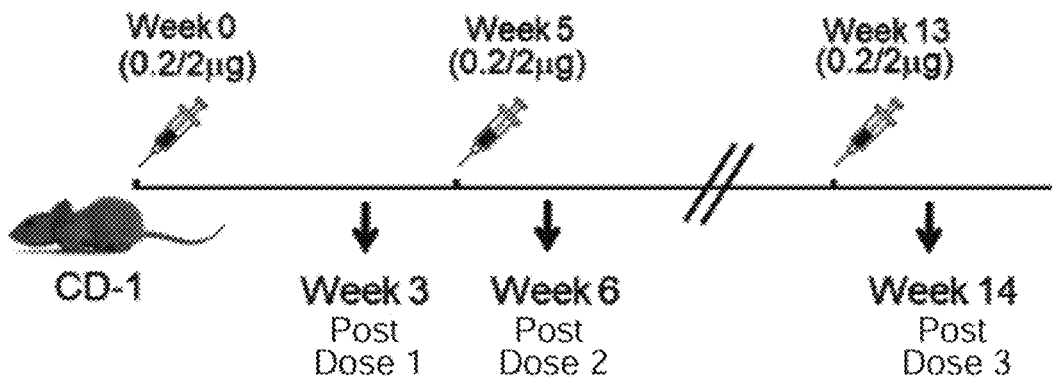
FIG. 27A-27C—FIG. 27A depicts an illustration of an exemplary administration schedule.
Figure 27B:
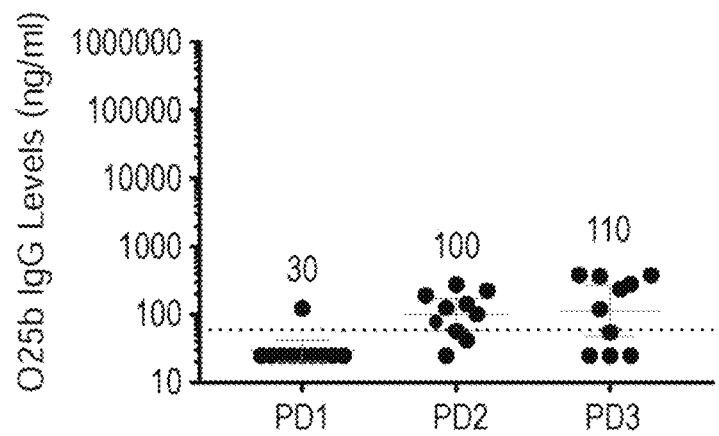
Figure 27C:
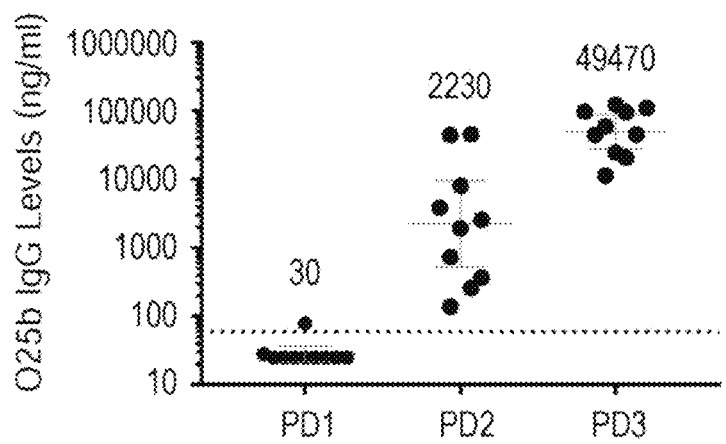

Example 16: O-Antigen O25b IgG Levels Elicited by Unconjugated O25b Long O-Antigen Polysaccharide and Derived O25b RAC/DMSO Long O-Antigen Glycoconjugate Groups of ten CD-1 mice were dosed by sub-cutaneous injection with 0.2 or 2.0 μg/animal of O25b RAC/DMSO long O-antigen glycoconjugate at weeks 0, 5 and 13, with bleeds taken at week 3 (post-dose 1, PD1), week 6 (post-dose 2, PD2) and week 13 (post-dose 3, PD3) timepoints for immunogenicity testing. Levels of antigen-specific IgG were determined by quantitative Luminex assay (see details in Example 15) with O25b-specific mouse mAb as internal standard. Baseline IgG levels (dotted line) were determined in serum pooled from 20x randomly selected unvaccinated mice. The free unconjugated O25b long O-antigen polysaccharide immunogen did not induce IgG above baseline levels at any timepoint. In contrast, IgG responses were observed after two doses of O25b-CRM197 RAC long conjugate glycoconjugate: robust uniform IgG responses were observed by PD3, with intermediate and more variable IgG levels at PD2. GMT IgG values (ng/ml) are indicated with 95% CI error bars. See FIG. 27A-27C.

Example 17: Specificity of the O25b Baby Rabbit Complement (BRC) OPA

Figure 26C:
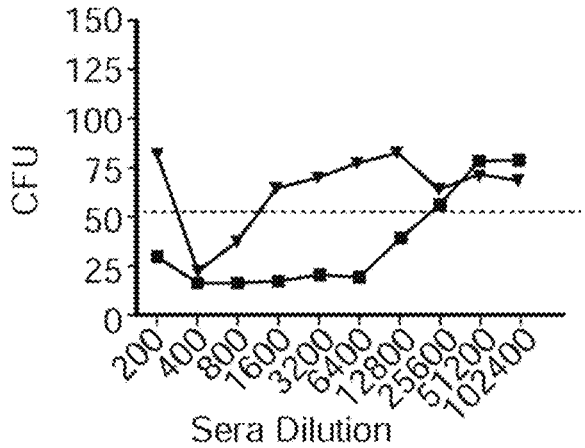

A-B) O25b RAC/DMSO long O-antigen post-immune serum from rabbits 2-3 and 1-2 (but not matched pre-immune control serum) shows bactericidal OPA activity. C) OPA activity of immune serum from rabbit 1-2 was blocked by pre-incubation with 100 µg/mL long O-antigen O25b polysaccharide. Strain GAR2831 bacteria were incubated with HL60s, 2.5% BRC and serial dilutions of serum for 1 h at 37° C. and surviving bacteria enumerated by counting microcolonies (CFUs) on filter plates. See FIG. 26A-26C.

Figure 28A:
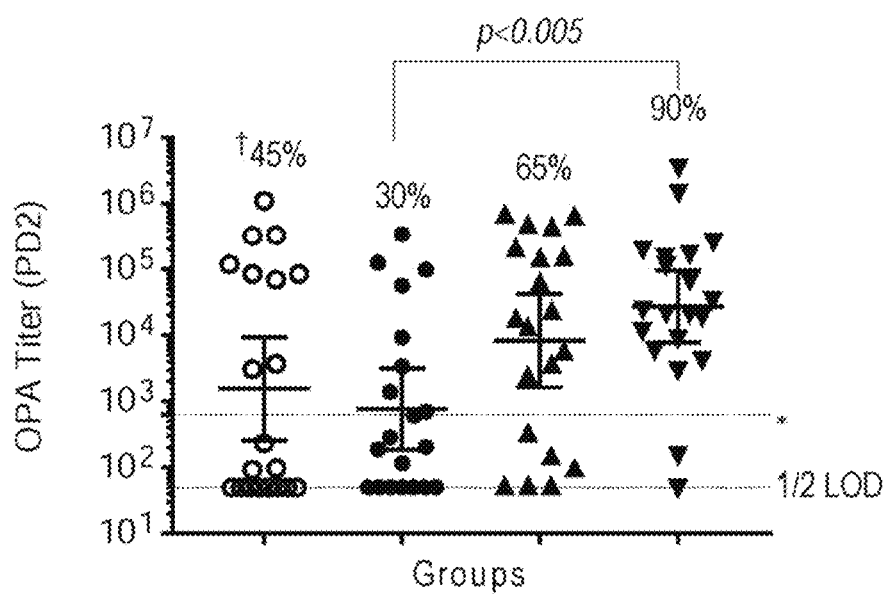
FIG. 28A-28B—depict graphs showing OPA immunogenicity of RAC, eTEC O25b long glycoconjugates, and single end glycoconjugates post dose 2 (FIG. 28A) and post dose 3 (FIG. 28B), wherein -○- represents results from single end short 2 µg; -●- single end long 2 µg; -▲- RAC/DMSO long 2 µg; -▼- eTEC long 2 µg; * Background control (n=20). †Responder rates are % mice with titers >2× unvaccinated baseline.
Figure 28B:
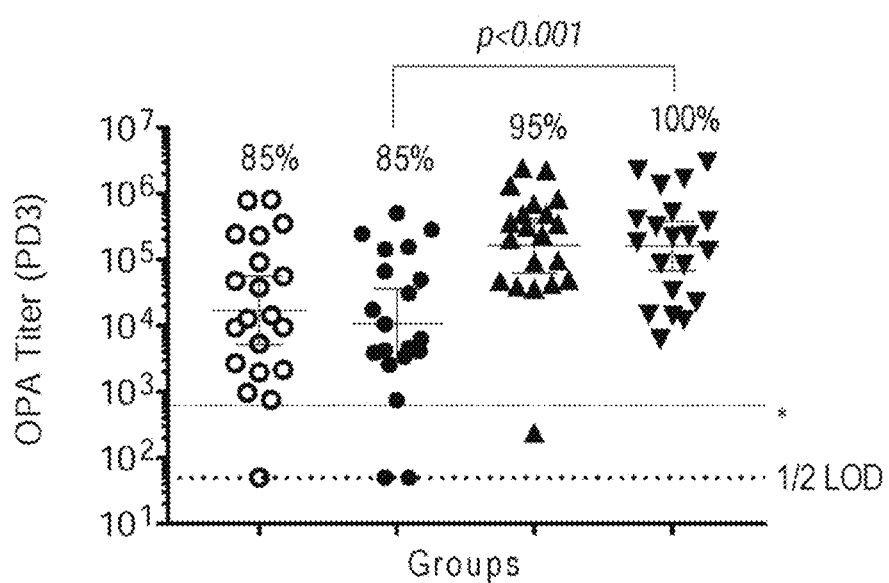

Example 18: RAC and eTEC O25b Long Glycoconjugates are More Immunogenic than Single End Glycoconjugates BRC OPA assay with carbapenem-resistant fluoroquinlone-resistant MDR strain Atlas187913. Groups of 20 CD-1 mice were vaccinated with 2 µg of glycoconjugate according to the same schedule as shown in FIG. 28A-28B and OPA responses determined at post-dose 2 (PD2) (FIG. 28A) and post-dose 3 (PD3) (FIG. 28B) timepoints. Bars indicate GMTs with 95% CI. Responder rates above unvaccinated baseline are indicated. Log transformed data from different groups were evaluated to assess if differences were statistically significant using unpaired t-test with Welch's correction (Graphpad Prism). Results are summarized in the Table 17. See FIG. 28A-28B. In mice that were vaccinated with 2 µg of eTEC O1a long glycoconjugates, OPA titers against O1a, PD2 and PD3 (data not shown), were observed to be greater than the OPA titers against O25b, PD2 and PD3, respectively, shown in Table 17.

TABLE 17

| DESCRIPTION | % Responders (n/N)* | GEOMEAN TITER PD2 | % Responders (n/N)* | GEOMEAN TITER PD3 |
|---|---|---|---|---|
| Single end short, 2 µg | 45 (9/20) | 1,552 | 85 (17/20) | 17,070 |
| Single end long, 2 µg | 30 (6/20) | 763 | 85 (17/20) | 10,838 |
| RAC/DMSO long, 2 µg | 65 (13/20) | 8,297 | 95 (19/20) | 163,210 |
| eTEC (10%) long, 2 µg | 90 (18/20) | 27,368 | 100 (19/19) | 161,526 |

Figure 29:
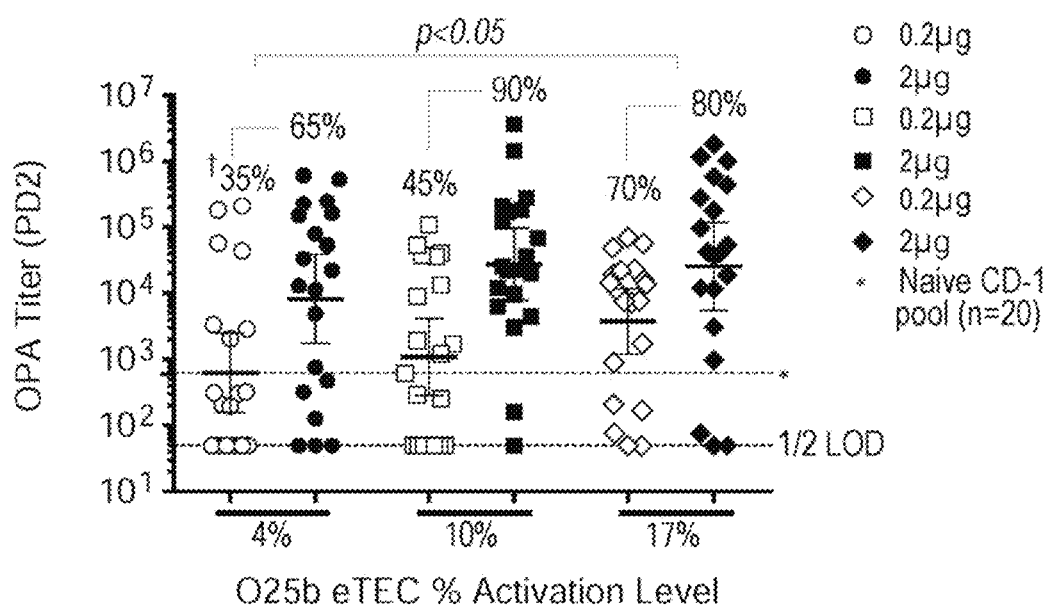
FIG. 29—depicts graph showing OPA immunogenicity of eTEC chemistry and modified levels of polysaccharide activation. tResponder rates are % mice with titers >2× unvaccinated baseline.

Example 19: OPA Immunogenicity of eTEC Chemistry May be Improved by Modifying Levels of Polysaccharide Activation BRC OPA assay with carbapenem-resistant fluoroquinlone-resistant MDR strain Atlas187913. Groups of 20 CD-1 mice were vaccinated with 0.2 µg or 2 µg of the indicated long O25b eTEC glycoconjugate and OPA responses determined at PD2 timepoint. Aggregated log transformed data from 4% activation vs 17% activation groups were evaluated to confirm that differences in OPA responses were statistically significant using unpaired t-test with Welch's correction (Graphpad Prism). GMTs and responder rates for individual groups are summarized in Table 18. See FIG. 29.

TABLE 18

| Description | % Responders (n/N) | GeoMean Titer |
|---|---|---|
| eTEC long 4% activation (0.2 µg) | 35 (7/20) | 628 |
| eTEC long 4% activation (0.2 µg) | 65 (13/20) | 8,185 |
| eTEC long 10% activation (0.2 µg) | 45 (9/20) | 1,085 |
| eTEC long 10% activation (0.2 µg) | 90 (18/20) | 27,368 |
| eTEC long 17% activation (0.2 µg) | 70 (14/20) | 3,734 |
| eTEC long 17% activation (0.2 µg) | 80 (16/20) | 25,461 |

Figure 30A:
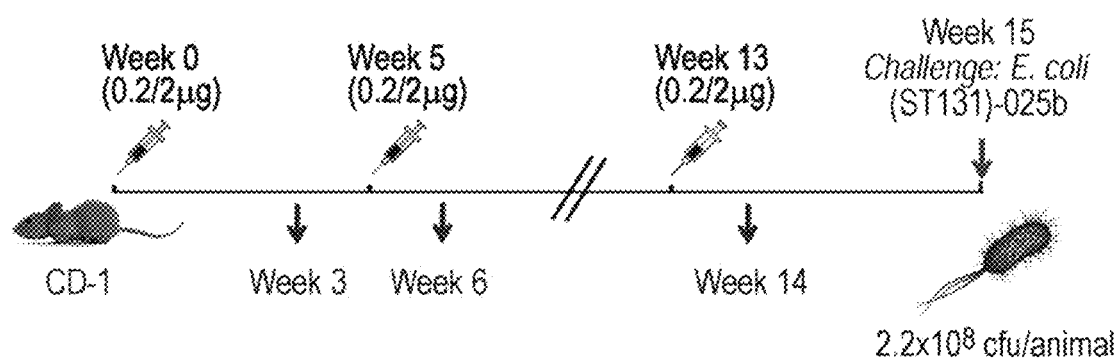
FIG. 30A-30B—depict an illustration of an exemplary administration schedule (FIG. 30A); and a graph depicting protection of mice immunized with doses of *E. coli* eTEC conjugates from lethal challenge with O25b isolate (FIG. 30B), wherein -◇- represents eTEC Long Chain 17% activation; -△- eTEC represents Long Chain 10% activation; -▽- represents eTEC Long Chain 4% activation; -□- represents O25b Polysaccharide; -○- represents unvaccinated controls.
Figure 30B:
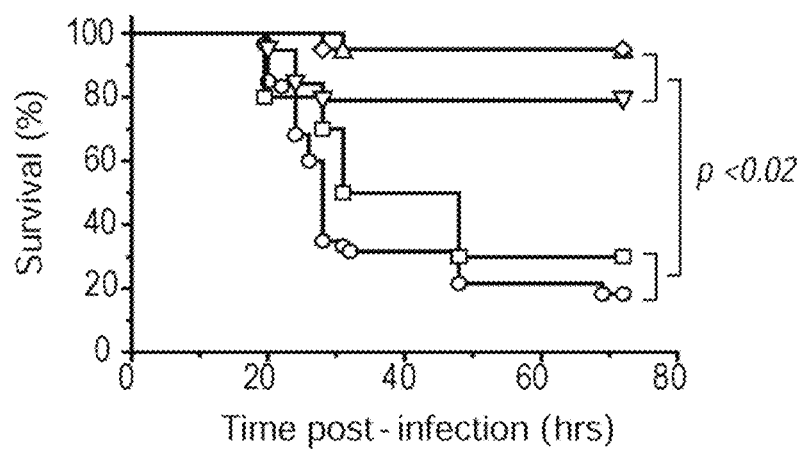

Example 20: Challenge Study Indicates Long E. coli O25b eTEC Conjugates Elicit Protection after Three Doses Groups of 20× CD-1 mice immunized with a 2 µg dose according to the indicated schedule were challenged IP with $1\times10^9$ bacteria of strain GAR2831. Subsequent survival was monitored for six days. Groups of mice vaccinated with eTEC glycoconjugates activated at 4%, 10% or 17% levels were protected from lethal infection, whereas unvaccinated control mice or mice vaccinated with 2 µg unconjugated O25b long polysaccharide were not. See FIG. 30A-30B.

Example 21: Process for Preparation of eTEC Linked Glycoconjugates

Activation of Saccharide and Thiolation with Cystamine dihydrochloride. The saccharide is reconstituted in anhydrous dimethylsulfoxide (DMSO). Moisture content of the solution is determined by Karl Fischer (KF) analysis and adjusted to reach a moisture content of 0.1 and 1.0%, typically 0.5%.

To initiate the activation, a solution of 1,1'-carbonyl-di-1,2,4-triazole (CDT) or 1,1'-carbonyldiimidazole (CDI) is freshly prepared at a concentration of 100 mg/mL in DMSO. The saccharide is activated with various amounts of CDT/CDI (1-10 molar equivalents) and the reaction is allowed to proceed for 1-5 hours at rt or 35° C. Water was added to quench any residual CDI/CDT in the activation reaction solution. Calculations are performed to determine the added amount of water and to allow the final moisture content to be 2-3% of total aqueous. The reaction was allowed to proceed for 0.5 hour at rt. Cystamine dihydrochloride is freshly prepared in anhydrous DMSO at a concentration of 50 mg/mL. The activated saccharide is reacted with 1-2 mol. eq. of cystamine dihydrochloride. Alternatively, the activated saccharide is reacted with 1-2 mol. eq. of cysteamine hydrochloride. The thiolation reaction is allowed to proceed for 5-20 hours at rt, to produce a thiolated saccharide. The thiolation level is determined by the added amount of CDT/CDI.

Reduction and Purification of Activated Thiolated Saccharide. To the thiolated saccharide reaction mixture a solution of tris(2-carboxyethyl)phosphine (TCEP), 3-6 mol. eq., is added and allowed to proceed for 3-5 hours at rt. The reaction mixture is then diluted 5-10-fold by addition to pre-chilled 10 mM sodium phosphate monobasic, and filtered through a 5 µm filter. Dialfiltration of thiolated saccharide is performed against 30-40-fold diavolume of pre-chilled 10 mM sodium phosphate monobasic. An aliquot of activated thiolated saccharide retentate is pulled to determine the saccharide concentration and thiol content (Ellman) assays.

Activation and Purification of Bromoacetylated Carrier Protein. Free amino groups of the carrier protein are bromoacteylated by reaction with a bromoacetylating agent, such as bromoacetic acid N-hydroxysuccinimide ester (BAANS), bromoacetylbromide, or another suitable reagent.

The carrier protein (in 0.1M Sodium Phosphate, pH 8.0±0.2) is first kept at 8±3° C., at about pH 7 prior to activation. To the protein solution, the N-hydroxysuccinimide ester of bromoacetic acid (BAANS) as a stock dimethylsulfoxide (DMSO) solution (20 mg/mL) is added in a ratio of 0.25-0.5 BAANS:protein (w/w). The reaction is gently mixed at 5±3° C. for 30-60 minutes. The resulting bromoacetylated (activated) protein is purified, e.g., by ultrafiltration/diafiltration using 10 kDa MWCO membrane using 10 mM phosphate (pH 7.0) buffer. Following purification, the protein concentration of the bromoacetylated carrier protein is estimated by Lowry protein assay.

The extent of activation is determined by total bromide assay by ion-exchange liquid chromatography coupled with suppressed conductivity detection (ion chromatography). The bound bromide on the activated bromoacetylated protein is cleaved from the protein in the assay sample preparation and quantitated along with any free bromide that may be present. Any remaining covalently bound bromine on the protein is released by conversion to ionic bromide by heating the sample in alkaline 2-mercaptoethanol.

Activation and Purification of Bromoacetylated $CRM_{197}$. $CRM_{197}$ was diluted to 5 mg/mL with 10 mM phosphate buffered 0.9% NaCl pH 7 (PBS) and then made 0.1 M $NaHCO_3$ pH 7.0 using 1 M stock solution. BAANS was added at a $CRM_{197}$: BAANS ratio 1:0.35 (w:w) using a BAANS stock solution of 20 mg/mL DMSO. The reaction mixture was incubated at between 3° C. and 11° C. for 30 mins-1 hour then purified by ultrafiltration/diafiltration using a 10K MWCO membrane and 10 mM Sodium Phosphate/0.9% NaCl, pH 7.0. The purified activated $CRM_{197}$ was assayed by the Lowry assay to determine the protein concentration and then diluted with PBS to 5 mg/mL. Sucrose was added to 5% wt/vol as a cryoprotectant and the activated protein was frozen and stored at −25° C. until needed for conjugation. Bromoacetylation of lysine residues of $CRM_{197}$ was very consistent, resulting in the activation of 15 to 25 lysines from 39 lysines available. The reaction produced high yields of activated protein.

Conjugation of Activated Thiolated Saccharide to Bromoacetylated Carrier Protein. Bromoacetylated carrier protein and activated thiolated saccharide are subsequently added. The saccharide/protein input ratio is 0.8±0.2. The reaction pH is adjusted to 9.0±0.1 with 1 M NaOH solution. The conjugation reaction is allowed to proceed at 5° C. for 20±4 hours.

Capping of Residual Reactive Functional Groups. The unreacted bromoacetylated residues on the carrier protein are quenched by reacting with 2 mol. eq. of N-acetyl-L-cysteine as a capping reagent for 3-5 hours at 5° C. Residual free sulfhydryl groups are capped with 4 mol. eq. of iodoacetamide (IAA) for 20-24 hours at 5° C.

Purification of eTEC-linked Glycoconjugate. The conjugation reaction (post-IAA-capped) mixture is filtered through 0.45 µm filter. Ultrafiltration/dialfiltration of the glycoconjugate is performed against 5 mM succinate-0.9% saline, pH 6.0. The glycoconjugate retentate is then filtered through 0.2 µm filter. An aliquot of glycoconjugate is pulled for assays. The remaining glycoconjugate is stored at 5° C. See Table 21, Table 22, Table 23, Tale 24, and Table 25.

Example 22: Preparation of *E. coli*-O25B ETEC Conjugates

Activation Process—Activation of *E. coli*-O25b Lipopolysaccharide. The lyophilized *E. coli*-O25b polysaccharide was reconstituted in anhydrous dimethylsulfoxide (DMSO). Moisture content of the lyophilized O25b/DMSO solution was determined by Karl Fischer (KF) analysis. The moisture content was adjusted by adding WFI to the O25b/DMSO solution to reach a moisture content of 0.5%.

To initiate the activation, 1,1'-carbonyldiimidazole (CDI) was freshly prepared as 100 mg/mL in DMSO solution. *E. coli*-O25b polysaccharide was activated with various amounts of CDI prior to the thiolation step. The CDI activation was carried out at rt or 35° C. for 1-3 hours. Water was added to quench any residual CDI in the activation reaction solution. Calculations are performed to determine the added amount of water and to allow the final moisture content to be 2-3% of total aqueous. The reaction was allowed to proceed for 0.5 hour at rt.

Thiolation of Activated *E. coli*-O25b Polysaccharide. Cystamine-dihydrochloride was freshly prepared in anhydrous DMSO and 1-2 mol. eq. of cystamine dihydrochloride was added to the activated polysaccharide reaction solution. The reaction was allowed to proceed for 20±4 hours at rt.

Figure 32A:
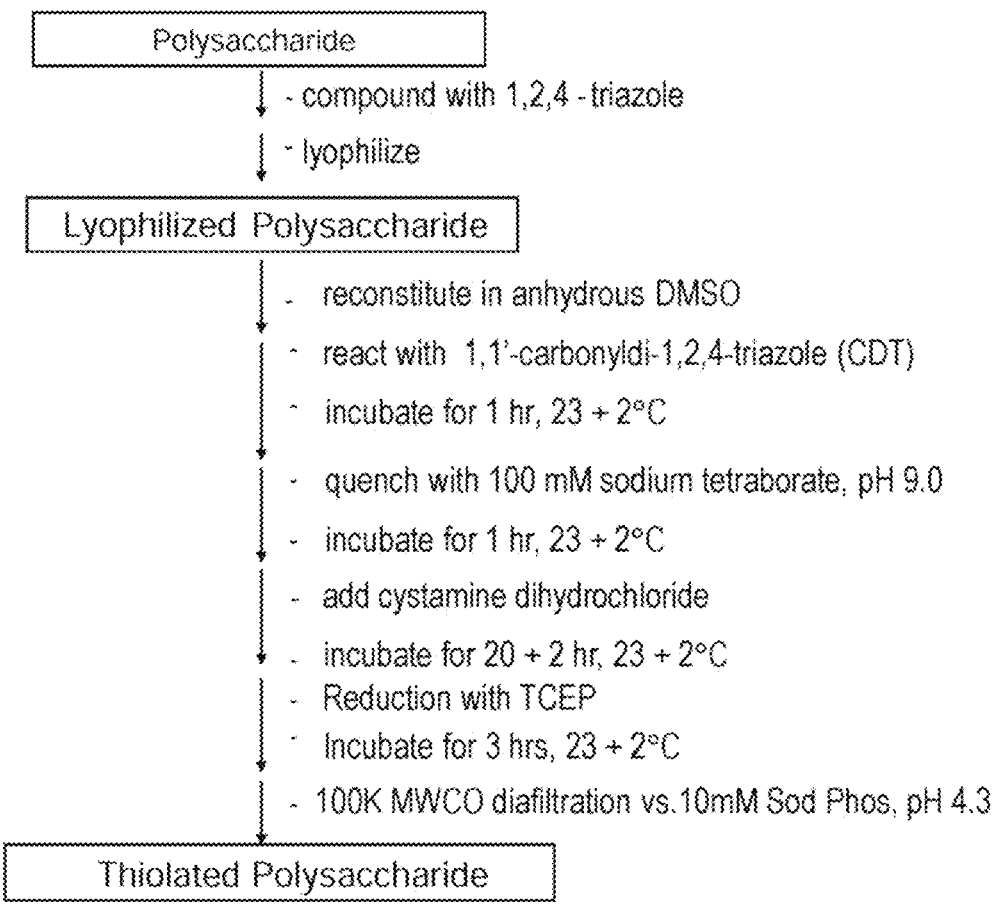
FIG. 32A-32B—depict an exemplary process flow diagram for the activation (FIG. 32A) and conjugation (FIG. 32B) processes used in the preparation of *E. coli* glycoconjugate to CRM$_{197}$.

Reduction and Purification of Activated Thiolated *E. coli*-O25b Polysaccharide. To the thiolated saccharide reaction mixture a solution of tris(2-carboxyethyl)phosphine (TCEP), 3-6 mol. eq., was added and allowed to proceed for 3-5 hours at rt. The reaction mixture was then diluted 5-10-fold by addition to pre-chilled 10 mM sodium phosphate monobasic and filtered through a 5 µm filter. Dialfiltration of thiolated saccharide was performed against 40-fold diavolume of pre-chilled 10 mM sodium phosphate monobasic with 5K MWCO ultrafilter membrane cassettes. The thiolated O25b polysaccharide retentate was pulled for both saccharide concentration and thiol (Ellman) assays. A flow diagram of the activation process is provided in FIG. 32A).

Conjugation Process—Conjugation of Thiolated *E. coli*-O25b Polysaccharide to Bromoacetylated $CRM_{197}$. The $CRM_{197}$ carrier protein was activated separately by bromoacetylation, as described in Example 21, and then reacted with the activated *E. coli*-O25b polysaccharide for the conjugation reaction. Bromoacetylated $CRM_{197}$ and thiolated O25b polysaccharide were mixed together in a reaction vessel. The saccharide/protein input ratio was 0.8±0.2. The reaction pH was adjusted to 8.0-10.0. The conjugation reaction was allowed to proceed at 5° C. for 20±4 hours.

Capping of Reactive Groups on Bromoacetylated $CRM_{197}$ and Thiolated *E. coli*-O25b Polysaccharide. The unreacted bromoacetylated residues on $CRM_{197}$ proteins were capped by reacting with 2 mol. eq. of N-acetyl-L-cysteine for 3-5 hours at 5° C., followed by capping any residual free sulfhydryl groups of the thiolated O25b-polysaccharide with 4 mol. eq. of iodoacetamide (IAA) for 20-24 hours at 5° C.

Purification of eTEC-linked *E. coli*-O25b Glycoconjugate. The conjugation solution was filtered through a 0.45 µm or 5 µm filter. Dialfiltration of the O25b glycoconjugate was carried out with 100K MWCO ultrafilter membrane cassettes. Diafiltration was performed against 5 mM succinate-0.9% saline, pH 6.0. The *E. coli*-O25b glycoconjugate 100K retentate was then filtered through a 0.22 µm filter and stored at 5° C.

Figure 32B:
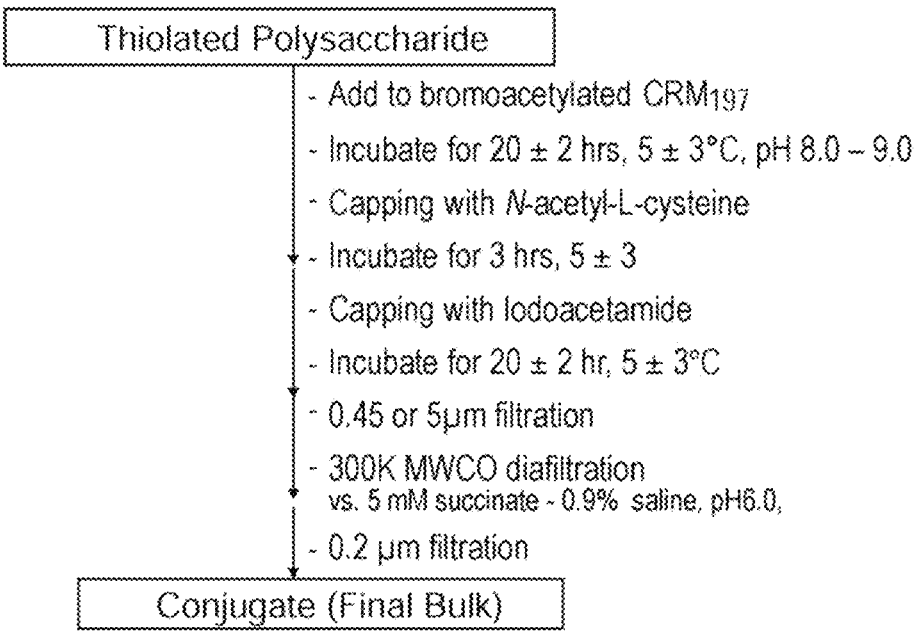

A flow diagram of the conjugation process is provided in FIG. 32B.

Results

The reaction parameters and characterization data for several batches of *E. coli*-O25b eTEC glycoconjugates are shown in Table 19. The CDI activation-thiolation with cystamine dihydrochloride generated glycoconjugates having from 41 to 92% saccharide yields and <5 to 14% free saccharides. See also Table 21, Table 22, Table 23, Table 24 and Table 25.

TABLE 19

Experimental Parameters and Characterization Data of
E. coli-O25b eTEC Conjugates

| | Conjugate Batch | | | | | |
|---|---|---|---|---|---|---|
| | O25b-1A | O25b-2B | O25b-3C | O25b-4D | O25b-5E | O25b-6F |
| Activation level (mol of thiol/mol of polysaccharide), % | 10 | 20 | 22 | 17 | 25 | 24 |
| Input Sacc/Prot Ratio | 0.8 | 0.8 | 0.8 | 0.8 | 0.8 | 0.8 |
| Saccharide yield (%) | 56 | 57 | 79 | 92 | 41 | 59 |
| Output Sacc/Prot Ratio | 0.88 | 1 | 1.18 | 1.32 | 2.9 | 1.4 |
| Free Saccharide, % | 8 | <5 | 6 | 5 | 14 | 5 |
| Free Protein, % | <1 | <1 | <1 | <1 | <1 | <1 |
| Conjugate Mw, kDa | 1057 | 4124 | 2259 | 2306 | 1825 | 1537 |
| Total CMCA | 3 | na | na | 7.2 | na | na |

Example 23: Procedure for the Preparation of *E. coli* O-Antigen Polysaccharide-CRM197 eTEC Conjugates (Applied to O-Antigens from *E. coli* Serotypes O25b, O1a, O2, and O6)

Activation of polysaccharide. The *E. coli* O-antigen polysaccharide is reconstituted in anhydrous dimethylsulfoxide (DMSO). To initiate the activation, various amounts of 1,1'-carbonyldiimidazole (CDI) (1-10 molar equivalents) is added to the polysaccharide solution and the reaction is allowed to proceed for 1-5 hours at rt or 35° C. Then, water (2-3%, v/v) was added to quench any residual CDI in the activation reaction solution. After the reaction was allowed to proceed for 0.5 hour at rt, 1-2 mol. eq. of cystamine dihydrochloride is added. The reaction is allowed to proceed for 5-20 hours at rt, and then treated with 3-6 mol. eq of tris(2-carboxyethyl)phosphine (TCEP) to produce a thiolated saccharide. The thiolation level is determined by the added amount of CDI.

The reaction mixture is then diluted 5-10-fold by addition to pre-chilled 10 mM sodium phosphate monobasic, and filtered through a 5 μm filter. Dialfiltration of thiolated saccharide is performed against 30-40-fold diavolume of pre-chilled 10 mM sodium phosphate monobasic. An aliquot of activated thiolated saccharide retentate is pulled to determine the saccharide concentration and thiol content (Ellman) assays.

Activation of Carrier Protein ($CRM_{197}$). The $CRM_{197}$ (in 0.1M Sodium Phosphate, pH 8.0±0.2) is first kept at 8±3° C., at about pH 8 prior to activation. To the protein solution, the N-hydroxysuccinimide ester of bromoacetic acid (BAANS) as a stock dimethylsulfoxide (DMSO) solution (20 mg/mL) is added in a ratio of 0.25-0.5 BAANS:protein (w/w). The reaction is gently mixed at 5±3° C. for 30-60 minutes. The resulting bromoacetylated (activated) protein is purified, e.g., by ultrafiltration/diafiltration using 10 kDa MWCO membrane using 10 mM phosphate (pH 7.0) buffer. Following purification, the protein concentration of the bromoacetylated carrier protein is estimated by Lowry protein assay.

Conjugation. Activated $CRM_{197}$ and activated *E. coli* O-antigen polysaccharide are subsequently added to a reactor and mixed. The saccharide/protein input ratio is 1±0.2. The reaction pH is adjusted to 9.0±0.1 with 1 M NaOH solution. The conjugation reaction is allowed to proceed at 5° C. for 20±4 hours. The unreacted bromoacetylated residues on the carrier protein are quenched by reacting with 2 mol. eq. of N-acetyl-L-cysteine as a capping reagent for 3-5 hours at 5° C. Residual free sulfhydryl groups are capped with 4 mol. eq. of iodoacetamide (IAA) for 20-24 hours at 5° C. Then, the reaction mixture is purified using ultrafiltration/dialfiltration performed against 5 mM succinate-0.9% saline, pH 6.0. The purified conjugate is then filtered through 0.2 μm filter. See Table 21, Table 22, Table 23, Table 24 and Table 25.

Example 24: General Procedure—Conjugation of O-Antigen (from *E. coli* Serotypes O1, O2, O6, 25b) Polysaccharide by Reductive Mination Chemistry (RAC) Conjugation in Dimethylsulfoxide (RAC/DMSO)

Activating Polysaccharide. Polysaccharide oxidation was carried out in 100 mM sodium phosphate buffer (pH 6.0±0.2) by sequential addition of calculated amount of 500 mM sodium phosphate buffer (pH 6.0) and water for injection (WFI) to give final polysaccharide concentration of 2.0 g/L. If required, the reaction pH was adjusted to pH 6.0, approximately. After pH adjustment, the reaction temperature was cooled to 4° C. Oxidation was initiated by the addition of approximately 0.09-0.13 molar equivalents of sodium periodate. The oxidation reaction was performed at 5±3° C. for 20±4 hrs, approximately.

Concentration and diafiltration of the activated polysaccharide was carried out using 5K MWCO ultrafiltration cassettes. Diafiltration was performed against 20-fold diavolumes of WFI. The purified activated polysaccharide was then stored at 5±3° C. The purified activated saccharide is characterized, inter alia, by (i) saccharide concentration by colorimetric assay; (ii) aldehyde concentration by colorimetric assay; (iii) degree of oxidation; and (iv) molecular weight by SEC-MALLS.

Compounding Activated Polysaccharide with Sucrose Excipient, and Lyophilizing.

The activated polysaccharide was compounded with sucrose to a ratio of 25 grams of sucrose per gram of activated polysaccharide. The bottle of compounded mixture was then lyophilized. Following lyophilization, bottles containing lyophilized activated polysaccharide were stored at −20±5° C. Calculated amount of CRM$_{197}$ protein was shell-frozen and lyophilized separately. Lyophilized CRM$_{197}$ was stored at −20±5° C.

Reconstituting Lyophilized Activated Polysaccharide and Carrier Protein.

Lyophilized activated polysaccharide was reconstituted in anhydrous dimethyl sulfoxide (DMSO). Upon complete dissolution of polysaccharide, an equal amount of anhydrous DMSO was added to lyophilized CRM$_{197}$ for reconstitution.

Conjugating and Capping. Reconstituted activated polysaccharide was combined with reconstituted CRM$_{197}$ in the reaction vessel, followed by mixing thoroughly to obtain a clear solution before initiating the conjugation with sodium cyanoborohydride. The final polysaccharide concentration in reaction solution was approximately 1 g/L. Conjugation was initiated by adding 0.5-2.0 MEq of sodium cyanoborohydride to the reaction mixture and incubating at 23±2° C. for 20-48 hrs. The conjugation reaction was terminated by adding 2 MEq of sodium borohydride (NaBH$_4$) to cap unreacted aldehydes. This capping reaction continued at 23±2° C. for 3±1 hrs.

Purifying the Conjugate. The conjugate solution was diluted 1:10 with chilled 5 mM succinate-0.9% saline (pH 6.0) in preparation for purification by tangential flow filtration using 100-300K MWCO membranes. The diluted conjugate solution was passed through a 5 μm filter, and diafiltration was performed using 5 mM succinate/0.9% saline (pH 6.0) as the medium. After the diafiltration was completed, the conjugate retentate was transferred through a 0.22 μm filter. The conjugate was diluted further with 5 mM succinate/0.9% saline (pH 6), to a target saccharide concentration of approximately 0.5 mg/mL. Alternatively, the conjugate is purified using 20 mM Histidine-0.9% saline (pH 6.5) by tangential flow filtration using 100-300K MWCO membranes. Final 0.22 μm filtration step was completed to obtain the immunogenic conjugate. See Table 21, Table 22, Table 23, Table 24 and Table 25.

Example 25: Conjugation in Aqueous Buffer (RAC/Aqueous), as Applied to from *E. coli* Serotypes O25B, O1A, O2, and O6

Polysaccharides activation and diafiltration was performed in the same manner as the one for DMSO based conjugation.

The filtered activated saccharide was compounded with CRM$_{197}$ at a polysaccharide to protein mass ratio ranging from 0.4 to 2 w/w depending on the serotype. This input ratio was selected to control the polysaccharide to CRM$_{197}$ ratio in the resulting conjugate. The compounded mixture was then lyophilized. Upon conjugation, the polysaccharide and protein mixture was dissolved in 0.1M sodium phosphate buffer at the polysaccharide concentration ranging from 5 to 25 g/L depending on the serotype, pH was adjusted between 6.0 to 8.0 depending on the serotype. Conjugation was initiated by adding 0.5-2.0 MEq of sodium cyanoborohydride to the reaction mixture and incubating at 23±2° C. for 20-48 hrs. The conjugation reaction was terminated by adding 1-2 MEq of sodium borohydride (NaBH$_4$) to cap unreacted aldehydes.

Alternatively, the filtered activated saccharide and calculated amount of CRM$_{197}$ protein was shell-frozen and lyophilized separately, and then combined upon dissolving in 0.1M sodium phosphate buffer, subsequent conjugation can then be proceeded as described above.

TABLE 20

Summary of results from both conjugations prepared in DMSO and aqueous buffer

|  | RAC/DMSO | RAC/Aqueous |
|---|---|---|
| Poly MW (kDa) | 48K | 46K |
| Degree of Oxidation (DO) | 12 | 12 |
| Saccharide/Protein Ratio | 0.8 | 1.0 |
| % Free Saccharide | <5% | 32% |
| Conjugate MW by SEC-MALLS, kDa | 7950 | 260 |

Figure 31:
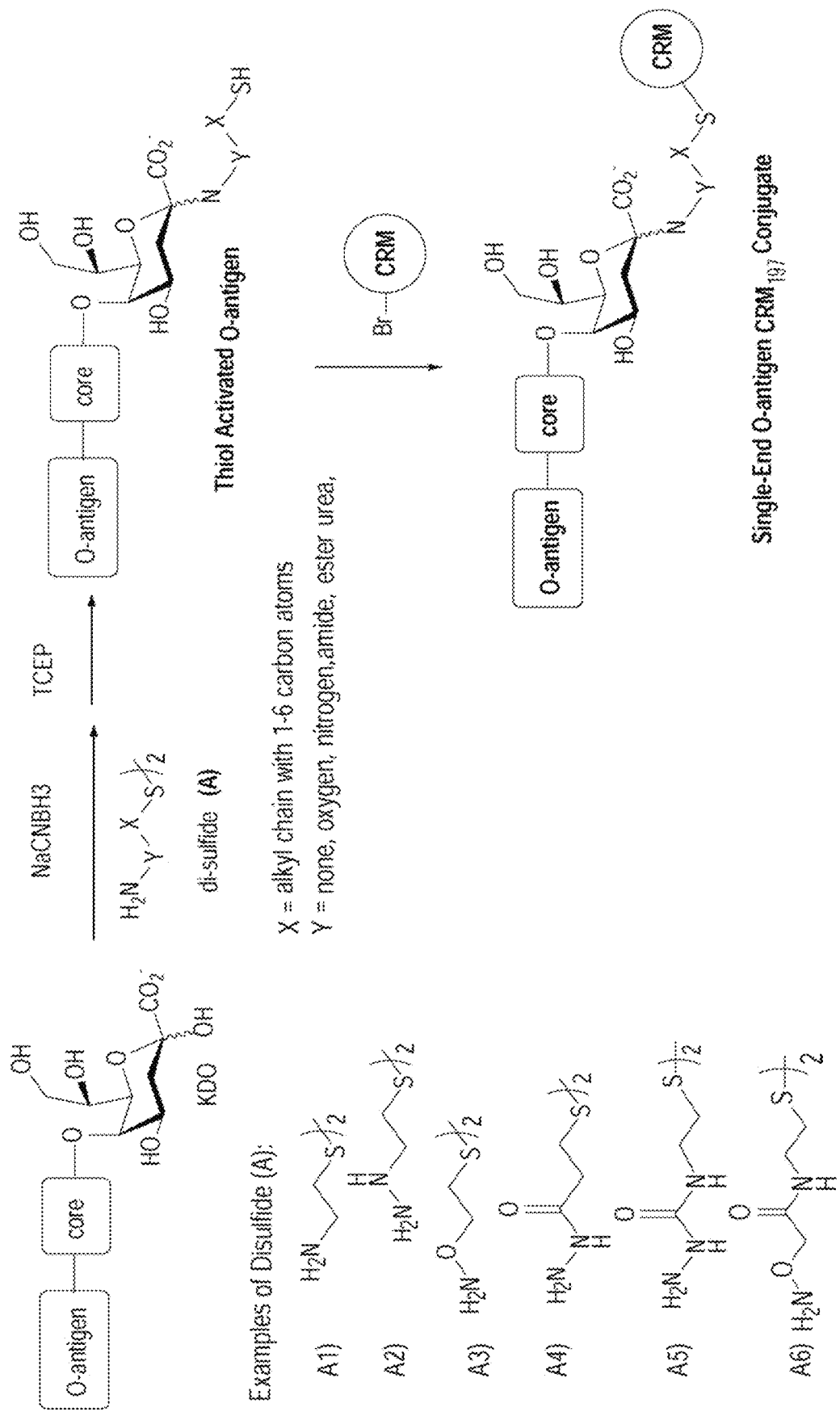
FIG. 31—depicts a schematic illustrating an exemplary preparation of single-ended conjugates, wherein the conjugation process involves selective activation of 2-Keto-3-deoxyoctanoic acid (KDO) with a disulfide amine linker, upon unmasking of a thiol functional group. The KDO is then conjugated to bromo activated CRM$_{197}$ protein as depicted in FIG. 31 (Preparation of Single-Ended Conjugates).

Example 26: Procedure for the Preparation of *E. coli* O-Antigen Polysaccharide-CRM$_{197}$ Single-Ended Conjugates Lipopolysaccharides (LPS), which are common components of the outer membrane of Gram-negative bacteria, comprise lipid A, the core region, and the O-antigen (also refer to as the O-specific polysaccharide or O-polysaccharide). Different serotype of O-antigen repeating units differ in their composition, structure and serological features. The O-antigen used in this invention is attached to the core domain which contains a sugar unit called 2-Keto-3-deoxyoctanoic acid (KDO) at its chain terminus. Unlike some conjugation methods based on random activation of the polysaccharide chain (e.g. activation with sodium periodate, or carbodiimide). This invention discloses a conjugation process involving selective activation of KDO with a disulfide amine linker, upon unmasking of thiol functional group, it is then conjugated to bromo activated CRM$_{197}$ protein as depicted in FIG. 31 (Preparation of Single-Ended Conjugates).

Conjugation based on cystamine linker (A1). O-antigen polysaccharide and cystamine (50-250 mol. eq of KDO) were mixed in phosphate buffer, adjust pH to 6.0-7.0. To the mixture, sodium cyanoborohydride (NaCNBH$_3$) (5-30 mol. eq of KDO) was added and the mixture was stirred at 37° C. for 48-72 hrs. Upon cooling to room temperature and diluted with equal volume of phosphate buffer, the mixture was treated with tris(2-carboxyethyl)phosphine (TCEP) (1.2 mol, eq of cystamine added). The mixture was then purified through diafiltration using 5 KDa MWCO membrane against 10 mM sodium phosphate monobasic solution, to furnish thiol containing O-antigen polysaccharide. The thiol content can be determined by Ellman assays.

The conjugation was then proceeded by mixing above thiol activated O-antigen polysaccharide with bromo activated CRM$_{197}$ protein at a ratio of 0.5-2.0. The pH of the reaction mixture is adjusted to 8.0-10.0 with 1 M NaOH solution. The conjugation reaction was proceeded at 5° C. for 24±4 hours. The unreacted bromo residues on the carrier protein were quenched by reacting with 2 mol. eq. of N-acetyl-L-cysteine for 3-5 hours at 5° C. The addition of 3 mol. eq. of iodoacetamide (related to N-acetyl-L-Cysteine added) wad then followed to cap the residual free sulfhydryl groups. This capping reaction was proceeded for another 3-5 hours at 5° C., and pH of both capping steps was maintained at 8.0-10.0 by addition of 1M NaOH. The resulting conjugate was obtained after ultrafiltration/dialfiltration using 30 KDa MWCO membrane against 5 mM succinate-0.9% saline, pH 6.0. See Table 21, Table 22, Table 23, Table 24 and Table 25.

Example 27: Conjugation Based on 3,3'-Dithio Bis(Propanoic Dihydrazide) Linker (A4)

O-antigen polysaccharide and 3,3'-dithio bis(propanoic dihydrazide) (5-50 mol. eq of KDO) were mixed in acetate buffer, adjust pH to 4.5-5.5. To the mixture, sodium cyanoborohydride (NaCNBH$_3$) (5-30 mol. eq of KDO) was added and the mixture was stirred at 23-37° C. for 24-72 hrs. The mixture was then treated with tris(2-carboxyethyl)phosphine (TCEP) (1.2 mol, eq of 3,3'-dithio bis(propanoicdihydrazide) linker added). The mixture was then purified through diafiltration using 5 KDa MWCO membrane against 10 mM sodium phosphate monobasic solution, to furnish thiol containing O-antigen polysaccharide. The thiol content can be determined by Ellman assays.

The conjugation was then proceeded by mixing above thiol activated O-antigen polysaccharide with bromo activated CRM$_{197}$ protein at a ratio of 0.5-2.0. The pH of the reaction mixture is adjusted to 8.0-10.0 with 1 M NaOH solution. The conjugation reaction was proceeded at 5° C. for 24±4 hours. The unreacted bromo residues on the carrier protein were quenched by reacting with 2 mol. eq. of N-acetyl-L-cysteine for 3-5 hours at 5° C. The addition of 3 mol. eq. of iodoacetamide (related to N-acetyl-L-Cysteine added) wad then followed to cap the residual free sulfhydryl groups. This capping reaction was proceeded for another 3-5 hours at 5° C., and pH of both capping steps was maintained at 8.0-10.0 by addition of 1M NaOH. The resulting conjugate was obtained after ultrafiltration/dialfiltration using 30 KDa MWCO membrane against 5 mM succinate-0.9% saline, pH 6.0.

Example 28: Conjugation Based on 2,2'-Dithio-N,N'-Bis(Ethane-2,1-Diyl)Bis(2-(Aminooxy)Acetamide) Linker (A6)

O-antigen polysaccharide and 2,2'-dithio-N,N'-bis(ethane-2,1-diyl)bis(2-(aminooxy)acetamide) (5-50 mol. eq of KDO) were mixed in acetate buffer, adjust pH to 4.5-5.5. The mixture was then stirred at 23-37° C. for 24-72 hrs, followed by the addition of sodium cyanoborohydride (NaCNBH$_3$) (5-30 mol. eq of KDO) and the mixture was stirred for another 3-24 hrs. The mixture was then treated with tris(2-carboxyethyl)phosphine (TCEP) (1.2 mol, eq of linker added). The mixture was then purified through diafiltration using 5 KDa MWCO membrane against 10 mM sodium phosphate monobasic solution, to furnish thiol containing O-antigen polysaccharide. The thiol content can be determined by Ellman assays.

The conjugation was then proceeded by mixing above thiol activated O-antigen polysaccharide with bromo activated CRM$_{197}$ protein at a ratio of 0.5-2.0. The pH of the reaction mixture is adjusted to 8.0-10.0 with 1 M NaOH solution. The conjugation reaction was proceeded at 5° C. for 24±4 hours. The unreacted bromo residues on the carrier protein were quenched by reacting with 2 mol. eq. of N-acetyl-L-cysteine for 3-5 hours at 5° C. The addition of 3 mol. eq. of iodoacetamide (related to N-acetyl-L-Cysteine added) was then followed to cap the residual free sulfhydryl groups. This capping reaction was proceeded for another 3-5 hours at 5° C., and pH of both capping steps was maintained at 8.0-10.0 by addition of 1M NaOH. The resulting conjugate was obtained after ultrafiltration/dialfiltration using 30 KDa MWCO membrane against 5 mM succinate-0.9% saline, pH 6.0.

Example 29A: Preparation of Bromo Activated CRM$_{197}$

The CRM$_{197}$ was prepared in 0.1M Sodium Phosphate, pH 8.0±0.2 solution, and was cooled to 5±3° C. To the protein solution, the N-hydroxysuccinimide ester of bromoacetic acid (BAANS) as a stock dimethylsulfoxide (DMSO) solution (20 mg/mL) is added in a ratio of 0.25-0.5 BAANS:protein (w/w). The reaction is gently mixed at 5±3° C. for 30-60 minutes. The resulting bromoacetylated (activated) protein is purified, e.g., by ultrafiltration/diafiltration using 10 kDa MWCO membrane using 10 mM phosphate (pH 7.0) buffer. Following purification, the protein concentration of the bromoacetylated carrier protein is estimated by Lowry protein assay.

TABLE 21

O1a Conjugates

| | Conjugate Lot# | | | | |
|---|---|---|---|---|---|
| | 132240-112-2 | 132242-106 | 132242-124 | 132242-127 | 132242-130 |
| Poly Lot# | 709756-160 | 709756-160 | 709756-160 | 710958-116 | 710958-116 |
| Poly Type | | Long Chain | | Short Chain | |
| Poly MW (kDa) | 33 | 33 | 33 | 11 | 11 |
| Variant | eTEC | Single-End | RAC/DMSO | Single-End | RAC/DMSO |
| Activation | 8% SH | 2.1% SH | DO: 13 | 6.4% SH | DO: 16 |
| | | Conjugate Data | | | |
| Yield (%) | 30 | 26 | 77 | 45 | 35 |
| SPRatio | 0.6 | 0.5 | 1.0 | 0.7 | 0.6 |
| Free Sacc (%) | 9 | 9 | 20 | 5 | 6 |
| MW (kDa) | 1035 | 331 | 1284 | 280 | 2266 |
| Sacc Conc (mg · mL) | 0.31 | 0.37 | 0.58 | 0.59 | 0.37 |
| Endotoxin (EU/ug) | 0.03 | 0.02 | 0.01 | 0.01 | 0.01 |
| Buffer | | 5 mM Succ/Saline, pH 6.0 | | | |

TABLE 22

O2 Conjugates

| | Conjugate Lot# | | | | |
|---|---|---|---|---|---|
| | 00709749-0003-1 | 132242-161 | 132242-152 | 132242-159 | 132242-157 |
| Poly Lot# | 709766-33 | 709766-65 | | 710958-141-2 | |
| Poly Type | | Long Chain | | Short Chain | |
| Poly MW (kDa) | 36 | 39 | | 14 | |
| Variant | eTEC | Single-End | RAC/DMSO | Single-End | RAC/DMSO |
| Activation | 6.8% SH | 1.6% SH | DO: 17 | 6.3% SH | DO: 19 |
| | | Conjugate Data | | | |
| Yield (%) | 26 | 33 | 50 | 38 | 36 |
| SPRatio | 1.5 | 0.8 | 0.8 | 1.0 | 0.6 |
| Free Sacc (%) | 11 | 24% | <5 | <5 | 6 |
| MW (kDa) | 1161 | 422 | 3082 | 234 | 1120 |
| Endotoxin (EU/ug) | 0.025 | 0.02 | 0.01 | 0.01 | 0.01 |
| Buffer | | 5 mM Succ/Saline, pH 6.0 | | | |

TABLE 23

O6 Conjugates

| | Conjugate Lot# | | | | |
|---|---|---|---|---|---|
| | 132240-117-1 | 132242-134 | 132242-137 | 132242-146 | 132242-145 |
| Poly Lot# | | 710958-121-1 | | 710958-143-3 | |
| Poly Type | | Long Chain | | Short Chain | |
| Poly MW (kDa) | | 44 | | 15 | |
| Variant | eTEC | Single-End | RAC/DMSO | Single-End | RAC/DMSO |
| Activation | 18% SH | 2.2% SH | DO: 16.5 | 6.1% SH | DO: 22 |
| | | Conjugate Data | | | |
| Yield (%) | 27 | 23 | 58 | 48 | 30 |
| SPRatio | 0.78 | 0.6 | 0.82 | 0.7 | 0.6 |
| Free Sacc (%) | 9 | 4 | 4 | <5 | 8 |
| MW (kDa) | 1050 | 340 | 1910 | 256 | 2058 |
| Sacc Conc (mg · mL) | 0.39 | 0.45 | 0.59 | 0.88 | 0.41 |
| Endotoxin (EU/ug) | 0.03 | 0.02 | 0.01 | 0.004 | 0.005 |
| Buffer | | 5 mM Succ/Saline, pH 6.0 | | | |

TABLE 24

O25b Conjugates

| | Conjugate Lot# | | | | | | | | |
|---|---|---|---|---|---|---|---|---|---|
| | 132242-28 | 132242-98 | 132240-73-1-1 | 132240-62-1 | 132240-81 | 132242-116 | 132242-121 | 132242-27 | 132242-29 |
| Poly Lot# | 709766-28 | 709766-29 | 709766-30 | 709766-30 | 709766-30 | 710958-117/118 | 710958-117/118 | 709766-28 | 709766-28 |
| Poly type | | | Long Chain | | | Short Chain | | Long Chain | Long Chain |
| Poly MW (kDa) | 51 | 48 | 48 | 48 | 48 | 14 | 14 | 51 | 51 |
| Variant | RAC/DMSO | Single-End | eTEC | eTEC | eTEC | Single-End | RAC/DMSO | RAC/DMSO | RAC/DMSO |
| Activation | DO: 18 | 2.4% SH | 10% SH | 4% SH | 17% SH | 6.6% SH | DO: 17 | 21 | 12 |
| | | | | Conjugate Data | | | | | |
| Yield (%) | 82 | 26 | 56 | 32 | 92 | 28 | 18 | 71 | 80 |
| SPRatio | 0.9 | 0.82 | 0.88 | 0.64 | 1.32 | 0.7 | 0.36 | 0.81 | 0.84 |
| Free Sacc (%) | 7.2 | 5 | <5 | 11 | <5 | <5 | <5 | 8.3 | <5 |
| Conjugate MW (kDa) | 4415 | 840 | 1057 | 1029 | 2306 | 380 | 9114 | 3303 | 7953 |
| Sacc Conc (mg · mL) | 0.7 | 0.4 | 0.43 | 0.36 | 0.9 | 0.45 | 0.19 | 0.6 | 0.67 |

TABLE 24-continued

O25b Conjugates

| | Conjugate Lot# | | | | | | | | |
|---|---|---|---|---|---|---|---|---|---|
| | 132242-28 | 132242-98 | 132240-73-1-1 | 132240-62-1 | 132240-81 | 132242-116 | 132242-121 | 132242-27 | 132242-29 |
| Endotoxin (EU/ug) | 0.01 | 0.02 | 0.08 | 0.08 | 0.01 | 0.01 | 0.01 | 0.02 | 0.22 |
| Conjugate (DS) Buffer matrix | 5 mM Succ/Saline, pH 6.0 | | | | | | | | |

TABLE 25

O25b K-12 Conjugates

| | Conjugate Lot# | |
|---|---|---|
| | 709749-015-2 | 709744-0016 |
| Poly Lot# | 710958-137 | |
| Poly Type | Long Chain (K12) | |
| Poly MW (kDa) | 44 | |
| Variant | eTEC | RAC/DMSO |
| Activation | SH: 24% | DO: 19 |
| Conjugate Data | | |
| Yield (%) | 59% | 33% |
| SPRatio | 1.4 | 0.83 |
| Free Sacc (%) | 5% | 5.2% |
| MW (kDa) | 1537 | 4775 |
| Sacc Conc (mg · mL) | 0.91 | 0.29 |
| Endotoxin (EU/ug) | 0.08 | 0.01 |
| Buffer | 5 mM Succ/Saline, pH 6.0 | |

Table 26

Exemplary embodiments:

| E. coli serotype O25b-TT conjugate | E. coli serotype O6-TT conjugate |
|---|---|
| Volume: 41 mL | Volume: 42 mL |
| Sacc Conc (Anthrone): 1.122 mg/mL (92% yield) | Sacc Conc (Anthrone): 0.790 mg/mL (66% yield) |
| Protein Conc (Lowry): 1.133 mg/mL | Protein Conc (Lowry): 1.895 mg/mL |
| SPRatio: 0.99 | SPRatio: 0.42 |
| Free Sacc (DOC): 74.7% | Free Sacc (DOC): <5% |
| The product obtained was concentrated to 15 mL using MWCO regenerated cellulose membranes and diafiltration was performed against saline (40X diavolumes). Filtered through 0.22 um filter and analyzed. | MW (kDa): 1192 |
| | Endotoxin (EU/ug:) 0.022 |
| Volume: 27 mL | |
| Sacc Conc (Anthrone): 1.041 mg/mL (56% yield) | |
| Protein Conc (Lowry): 1.012 mg/mL | |
| SPRatio: 1.03 | |
| Free Sacc (DOC): 60.6% (poly recovery 100%) | |

Example 29B: Preparation of E. coli O—Ag-TT Conjugates

E. coli serotype O25b long polysaccharide, Lot #709766-30 (about 6.92 mg/mL, MW: about 39 kDa), 50 mg, lyophilized was used for Tetanus Toxoid (TT) conjugation. E. coli serotype O1a long polysaccharide 710958-142-3 (about 6.3 mg/mL, MW: about 44.3 kDa) (50 mg, 7.94 mL) was lyophilized.

E. coli serotype O6 long polysaccharide, 710758-121-1 (about 16.8 mg/mL, MW: about 44 kDa) (50 mg, 2.98 mL) was lyophilized.

Each of the lyophilized polysaccharides listed above was dissolved in WFI to make at approx 5-10 mg/mL to it, 0.5 mL (100 mg (1-cyano-4-dimethylaminopyridinum tetrafluoroborate (CDAP) solution in 1 mL acetonitrile) was added and stirred at RT. Triethylamine (TEA) 0.2M (2 mL) was added and stirred at RT.

Preparation of Tetanus toxoid (TT): TT (100 mg, 47 ml) was concentrated to approximately 20 mL and washed twice with saline (2×50 mL) using filteration tubes. After that it was diluted with HEPES and saline to make final HEPES conc as about 0.25M. TT was prepared as described above and pH of the reaction was adjusted to about 9.1-9.2. The reaction mixture was stirred at RT.

After 20-24 hrs the reaction was quenched with Glycine (0.5 mL). After that it was concentrated to using MWCO regenerated cellulose membranes and diafiltration was performed against saline. Filtered and analyzed. See Table 26.

Example 30: Additional Results from O-Antigen Fermentation, Purification, and Conjugation The exemplary processes described below is generally applicable to all E. coli serotypes. The production of each polysaccharide included a batch production fermentation followed by chemical inactivation prior to downstream purification.

Strains and storage. Strains employed for biosynthesis of short chain O-antigen were clinical wild type strains of E. coli. Long chain O-antigen was produced with derivatives of the short chain-producers that had been engineered by the Wanner-Datsenko method to possess a deletion of the native wzzb gene and were complemented by the "long-chain" extender function fepE from Salmonella. The fepE function was expressed from its native promoter on either a high copy colE1-based "topo" vector or a low copy derivative of the colE1-based vector pET30a, from which the T7 promoter region had been deleted.

Cell banks were prepared by growing cells in either animal free LB or minimal medium to an $OD_{600}$ of at least 3.0. The broth was then diluted in fresh medium and combined with 80% glycerol to obtain a 20% glycerol final concentration with 2.0 $OD_{600}$/mL.

Media used for seed culture and fermentation. The seed and fermentation medium employed share the following formulation: $KH_2PO_4$, $K_2HPO_4$, $(NH_4)_2SO_4$, sodium citrate, $Na_2SO_4$, aspartic acid, glucose, $MgSO_4$, $FeSO_4\text{-}7H_2O$, $Na_2MoO_4\text{-}2H_2O$, $H_3BO_3$, $CoCl_2\text{-}6H_2O$, $CuCl_2\text{-}2H_2O$, $MnCl_2\text{-}4H_2O$, $ZnCl_2$ and $CaCl_2\text{-}2H_2O$.

Seed and fermentation conditions. Seeds were inoculated at 0.1% from a single seed vial. The seed flask was incubated at 37° C. for 16-18 hours and typically achieved 10-20 $OD_{600}$/mL.

Fermentation was performed in a 10 L stainless steel, steam in place fermentor.

Inoculation of the fermentor was typically 1:1000 from a 10 $OD_{600}$ seed. The batch phase, which is the period during which growth proceeds on the 10 g/L batched glucose, typically lasts 8 hours. Upon glucose exhaustion, there was a sudden rise in dissolved oxygen, at which point glucose was fed to the fermentation. The fermentation typically then proceeds for 16-18 hours with harvest giving >120 $OD_{600}$/mL.

Initial evaluation of short/long chain O-antigen production for serotypes O1a, O2, O6 and O25b. Wild type strains for O1a, O2, O6 and O25b were fermented in a supplemented minimal medium in batch mode to an $OD_{600}$=15-20. Upon glucose exhaustion, which results in a sudden decrease in oxygen consumption, a growth limiting glucose feed was applied from a glucose solution for 16-18 hours. Cell densities of 124-145 $OD_{600}$ units/mL were reached. The pH of the harvest broths was subsequently adjusted to about 3.8 and heated to 95° C. for 2 hours. The hydrolyzed broth was then cooled to 25° C., brought to pH 6.0 and centrifuged to remove solids. The resulting supernatant was then applied to a SEC-HPLC column for quantitation of the O-antigen. Productivities in the range of 2240-4180 mg/L were obtained. The molecular weight of purified short-chain O-antigen from these batches was found to range from 10-15 kDa. It was also noted that SEC chromatography of the O2 and O6 hydrolysates revealed a distinct and separable contaminating polysaccharide that was not evident in the O1a and O25b hydrolysates.

Long chain versions of the O1a, O2, O6 and O25b O-antigens where accessed through fermentation of a wzzb deletion version of each strain which carried a heterologous, complementing fepE gene on a high-copy, kanamycin-selectable topo plasmid. Fermentation was performed as for the short chain, albeit with kanamycin selection. The final cell densities observed at 124-177 $OD_{600}$/mL were associated with O-antigen productivities of 3500-9850 mg/L. The complementation-based synthesis of long chain O-antigen was at least as productive as in the parental short chain strain and in some cases more so. The molecular weights of purified O-antigen polysaccharide were 33-49 kDa or about 3 times the size of the corresponding short chain.

It was noted that the long chain hydrolysates for O2 and O6 showed evidence of a contaminating polysaccharide peak that, in the case of long chain antigen, was observed as a shoulder on the main O-antigen peak; O1 and O25b showed no evidence of production of a contaminating polysaccharide, as was seen earlier with the short chain parent.

Growth rate suppression was found to be associated with the presence of the topo replicon absent the fepE. Additionally, the Δwzzb mutation itself had not adverse effect on growth rate, indicating that the disturbed growth rates were conveyed by the plasmid vector.

Evaluation of strains for production of O11, O13, O16, O21 and O75 O-antigen. Multiple wild-type strains of serotypes O11, O13, O16, O21 and O75 were evaluated for their propensity to produce unwanted polysaccharide in fermentation by SEC-HPLC. Strains for O11, O13, O16, O21 and O75 were selected as absent contaminating polysaccharide, as well as for their ability to produce ≥1000 mg/L O-antigen and for the display of an antibiotic sensitivity profile that allowed Wanner-Datsenko recombineering for introduction of the Δwzzb trait.

Chloramphenicol-selectable versions of topo-fepE and pET-fepE were constructed that allowed for the introduction of fepE into the O11, O13, O16, O21 and O75 Δwzzb strains that in general were found to be kanamycin-resistant. The resulting topo-fepE and pET-fepE bearing strains were fermented with chloramphenicol selection and the supernatant from acid-hydrolyzed broth was evaluated by SEC-HPLC. Both the high (topo) and low copy (pET) fepE constructs directed the synthesis of O-antigen with productivities for each that were equivalent to the parental wild-type. Expression of potentially interfering polysaccharides was not observed.

An evaluation of growth rates for wzzb plasmid-bearing strains showed that the O11, O13 and O21 were retarded by the presence of topo-fepE but not by pET-fepE; strains O16 and O75 strains showed acceptable growth rates irrespective of replicon choice.

TABLE 27

| O-antigen type | IHMA type | short (SC) or long chain (LC) | fep E plasmid type | marker | final cell density $OD_{600}$ | final Oag productivity (mg/L) | MW-kDa | SEC impurity |
|---|---|---|---|---|---|---|---|---|
| O1a | wt | SC | None | None | 125 | 2550 | 11 | N |
| O1a | Δwzzb/fepE | LC | topo | Kana | 130 | 5530 | 33 | N |
| O1a | Δwzzb/fepE | LC | pET | Kana | Not done (ND) | ND | ND | ND |
| O2 | wt | SC | None | None | 127 | 2240 | 13 | Y |
| O2 | Δwzzb/fepE | LC | topo | Kana | 177 | 3750 | 49 | Y |
| O2 | x | LC | pET | x | NA | NA | NA | NA |
| O6 | wt | SC | None | None | 145 | 4180 | 16 | Y |
| O6 | Δwzzb/fepE | LC | topo | Kana | 124 | 9850 | 44 | Y |
| O6 | Δwzzb/fepE | LC | pET | Kana | ND | ND | ND | ND |
| O11 | wt | SC | None | None | 194 | 4720 | x | N |
| O11 | Δwzzb/fepE | LC | topo | Kana | 142 | 7220 | x | N |
| O11 | x | LC | pET | x | NA | NA | NA | NA |
| O13 | wt | SC | None | x | 113 | 4770 | x | N |
| O13 | Δwzzb/fepE | LC | topo | cam | 101 | 4680 | x | N |
| O13 | Δwzzb/fepE | LC | pET | cam | 108 | 4600 | x | N |
| O16 | wt | SC | None | x | 154 | 1870 | x | N |
| O16 | Δwzzb/fepE | LC | topo | cam | 129 | 1180 | x | N |
| O16 | Δwzzb/fepE | LC | pET | cam | 137 | 1280 | x | N |
| O21 | wt | SC | None | x | 140 | 1180 | x | N |

TABLE 27-continued

| O-antigen type | IHMA type | short (SC) or long chain (LC) | fep E plasmid type | marker | final cell density $OD_{600}$ | final Oag productivity (mg/L) | MW-kDa | SEC impurity |
|---|---|---|---|---|---|---|---|---|
| O21 | ΔwzzB/fepE | LC | topo | cam | ND | ND | x | N |
| O21 | ΔwzzB/fepE | LC | pET | cam | 131 | 820 | x | N |
| O25b | 2831 | SC | None | None | 126 | 3550 | 10 | N |
| O25b | ΔwzzB/fepE | LC | topo | Kana | 152 | 3500 | 49 | N |
| O25b | x | LC | pET | x | NA | NA | NA | NA |
| O75 | wt | SC | None | x | 149 | 1690 | x | N |
| O75 | ΔwzzB/fepE | LC | topo | cam | 132 | 1500 | x | N |
| O75 | ΔwzzB/fepE | LC | pET | cam | 138 | 1520 | x | N |

The purification process for the polysaccharides included acid hydrolysis to release the O-antigens. A crude suspension of serotype specific *E. coLi* culture in fermentation reactor was directly treated with acetic acid to the final pH of 3.5±0.5 and the acidified broth was heated to the temperature of 95±5° C. for at least one hour. This treatment cleaves the labile linkage between KDO, at the proximal end of the oligosaccharide and the lipid A, thus releasing the O—Ag chain. The acidified broth that contains the released O—Ag was cooled to 20±10° C. before being neutralized to pH 7±1.0 using $NH_4OH$. The process further included several centrifugation, filtration, and concentration/diafiltration operations steps.

TABLE 28

| Serotype (core) | Description | Expected Poly size | Titer (g/L) | Purified Poly M.W. (kDa) | Number of Repeat Units | Increase in M.W. (kDa) over short | NMR | Purified Conjugate M.W. (kDa) | Conjugation Lot # |
|---|---|---|---|---|---|---|---|---|---|
| O25b (R1) | ΔwzzB + LT2FepE | Long | 5.3 | 47 | 55 | 34 | ✓ | 5365 | 132242-28 (RAC/DMSO) |
| | | | | | | | | 1423 | 132242-98 (Single-end) |
| | | | | | | | | 1258 | 132240-73-1-1 (eTEC) |
| | ΔwzzB + O25a wzzB | Short | 2.3 | 13/14 | 15 | NA | ✓ | 380 | 132242-116 (Single-end) |
| | | | | | | | | 9114 | 132242-121 (RAC/DMSO) |
| O25b (K12) | ΔwzzB + LT2FepE | Long | 3.5 | 44 | 51 | 27 | ✓ | 1537 | 709749-015-2 (eTEC) |
| | | | | | | | | 4775 | 709744-0016 (RAC/DMSO) |
| | wt | Short | 3.5 | 17 | 17 | NA | ✓ | | |
| O1a (R1) | ΔwzzB + LT2FepE | Long | 5.5 | 33 | 39 | 22 | ✓ | 1035 | 132240-112-2 (eTEC) |
| | | | | | | | | 331 | 132242-106 (Single-end) |
| | | | | | | | | 1284 | 132242-124 (RAC/DMSO) |
| | wt | Short | 2.5 | 11 | 13 | NA | ✓ | 280 | 132242-127 (Single-end) |
| | | | | | | | | 2266 | 132242-130 (RAC/DMSO) |
| O2 (R1) | ΔwzzB + LT2FepE | Long | 4.9 | 36 | 43 | 22 | ✓ | 1161 | 00707947-0003-1 eTEC) |
| | | | | 39 | 47 | 25 | | 422 | 132242-161 (single-end) |
| | | | | | | | | 3082 | 132242-152 (RAC/DMSO) |
| | wt | Short | 2.8 | 14 | 17 | NA | ✓ | 234 | 132242-159 (single-end) |
| | | | | | | | | 1120 | 1322421-157 (RAC/DMSO) |
| O2 (R4) | ΔwzzB + LT2FepE | Long | 5.1 | NA | NA | NA | NA | | |
| | wt | Short | 2.1 | 14.7 | 18 | NA | ✓ | | |

TABLE 28-continued

| Serotype (core) | Description | Expected Poly size | Titer (g/L) | Purified Poly M.W. (kDa) | Number of Repeat Units | Increase in M.W. (kDa) over short | NMR | Purified Conjugate M.W. (kDa) | Conjugation Lot # |
|---|---|---|---|---|---|---|---|---|---|
| O6 (R1) | ΔwzzB + LT2FepE | Long | 6.9 | 37.2 | 42 | 22.2 | ✓ | | |
| | wt | Short | 3.5 | 15 | 17 | NA | ✓ | 256 | 132242-146 (Single-end_ |
| | | | | | | | | 2058 | 123342-145 (RAC/DMSO) |
| O6 (R1) | ΔwzzB + LT2FepE | Long | 8.4 | 44.4 | 50 | 28.2 | ✓ | 1050 | 132240-117-1 (eTEC) |
| | | | | | | | | 340 | 132242-134 (Single-end) 132242-137 |
| | | | | | | | | 1910 | (RAC/DMSO) |
| | wt | Short | 3.6 | 16.2 | 18 | NA | ✓ | | |

Example 31: Conjugation Towards O-Antigen (O4, O11, O21, O75) Studied (RAC/DMSO)

TABLE 29

O4 conjugates

| | Conjugate Lot# | | |
|---|---|---|---|
| | 709744-70 | 709744-73 | 709744-72 |
| Poly Lot# | | 709740-168 | |
| Poly MW (kDa) | | 52 | |
| DO | 26 | 19 | 15 |
| Act poly Mw (kDa) | | 51 | |
| Conjugation | | | |
| Input SP | 1.0 | 1.0 | 1.0 |
| SPRatio | 0.85 | 1.0 | 1.0 |
| Free Sacc (%) | <5% | <5% | <5% |
| MW (kDa) | 4764 | 4758 | 3423 |
| Yield (%) | 72 | 80 | 82 |
| Endotoxin (EU/ug) | 0.003 | 0.001 | 0.005 |

TABLE 30

O11 conjugates

| | Conjugate Lot# | | | |
|---|---|---|---|---|
| | 709744-64 | 709744-66 | 709744-65 | 709744-67 |
| Poly Lot# | | 709740-162 | | |
| Poly MW (kDa) | | 39 | | |
| DO | 21 | | 14 | |
| Act poly Mw (kDa) | | 40 | | |
| Conjugation | | | | |
| Input SP | 1.0 | 1.3 | 1.0 | 1.3 |
| SPRatio | 0.5 | 0.64 | 0.65 | 0.75 |
| Free Sacc (%) | <5% | <5% | <5% | <5% |
| MW (kDa) | 10520 | 7580 | 4814 | 4338 |
| Yield (%) | 30 | 30 | 44 | 38 |
| Endotoxin (EU/ug) | 0.005 | 0.005 | 0.005 | 0.005 |

TABLE 31

O21 conjugates

| | Conjugate Lot# | | | | |
|---|---|---|---|---|---|
| | 709749-113 | 709749-111 | 709749-112 | 709749-115 | 709749-116 |
| Poly Lot# | | | 709740-165 | | |
| Poly MW (kDa) | | | 40 | | |
| DO | 25 | | 18 | | 15 |
| Act poly Mw (KDa) | 40 | | 41 | | 40 |
| Conjugation | | | | | |
| Input SP | 1.0 | 1.0 | 0.8 | 1.0 | 1.25 |
| SPRatio | 0.6 | 0.6 | 0.5 | 0.9 | 1.1 |
| Free Sacc (%) | 6% | 5% | <5% | 12% | 7% |
| MW (kDa) | 6920 | 5961 | 9729 | 2403 | 1960 |
| Yield (%) | 31 | 36 | 37 | 52 | 54 |
| Endotoxin (EU/ug) | 0.02 | 0.02 | 0.03 | 0.01 | 0.009 |

TABLE 32

O75 conjugates

| | Conjugate Lot# | | |
|---|---|---|---|
| | 709749-101 | 709749-102 | 709749-103 |
| Poly Lot# | | 709766-080B | |
| Poly MW (kDa) | | 48 | |
| DO | 18 | | 25 |
| Act poly Mw (kDa) | 43 | | 44 |
| Conjugation | | | |
| Input SP | 1.0 | 0.8 | 1.0 |
| SPRatio | 0.94 | 0.76 | 0.78 |
| Free Sacc (%) | <5% | 6% | 6% |
| MW (kDa) | 2304 | 2427 | 5229 |
| Yield (%) | 62 | 65 | 45 |
| Endotoxin (EU/ug) | 0.02 | 0.01 | 0.01 |

Example 32: PILL Conjugates Prepared

TABLE 33

| | Serotype | | | |
|---|---|---|---|---|
| | O11 | O75 | O21 | O4 |
| | Conjugate Lot# | | | |
| | 00707779-0413 | 00707779-0414 | 00707779-0415 | 00707779-0416 |
| Poly Lot# | 709740-162 | 709766-080B | 709740-165 | 709740-168 |
| Poly MW (kDa) | 39 | 48 | 40 | 52 |
| Conjugate Data | | | | |
| SPRatio | 13.5 | 16.8 | 18.1 | 21.2 |
| Free Sacc (%) | 9.8% | <5% | <5% | 6.9% |
| Sacc Conc | 789 µg/mL | 676 µg/mL | 978 µg/mL | 837 µg/mL |
| PLL Conc | 58.3 µg/mL | 40.3 µg/mL | 54.0 µg/mL | 39.4 µg/mL |
| Endotoxin (EU/ug) | 0.002 | 0.002 | 0.005 | 0.004 |
| Conjugate (DS) Matrix | 1X PBS, 1M NaCl | | | |

Example 33: Stable Mammalian Cell Expression of E. coli Polypeptides

Stable CHO clones expressing FimH GSD or FimH LD were generated using a SSI (Site Specific Integration) stable expression system. The host CHO cell is an engineered cell line from a CHOK1SV GS-KO background (see, for example, United States Patent Application 20200002727, for a description of the CHOK1 SV GS-KO host cell line). Briefly a landing pad with green fluorescent protein (GFP) gene surrounded by two FRT sites were targeted into a transcription hot spot in the genome of the host cell. The GFP gene can be exchanged with GS gene and the gene of interest which are also surrounded by FRT sites from the LVEC vector co-expressed with flippase recombinase (FLPe). This system not only has growth and productivity profiles that compare favorably with random integration but also displays genotypic and phenotypic stability to at least 100 generations.

As referred to herein, the term "FRT site" refers to a nucleotide sequence at which the product of the flippase (FLP) gene of the yeast 2 µm plasmid, FLP recombinase, can catalyze a site-specific recombination. A variety of non-identical FRT sites are known to the art. The sequences of the various FRT sites are similar in that they all contain identical 13-base pair inverted repeats flanking an 8-base pair asymmetric core region in which the recombination occurs. It is the asymmetric core region that is responsible for the directionality of the site and for the variation among the different FRT sites. Illustrative (non-limiting) examples of these include the naturally occurring FRT (F), and several mutant or variant FRT sites such as FRT F1 and FRT F2.

As referred to herein, the term "landing pad" refers to a nucleic acid sequence comprising a first recombination target site chromosomally-integrated into a host cell. In some embodiments, a landing site comprises two or more recombination target sites chromosomally-integrated into a host cell. In some embodiments, the cell comprises 1, 2, 3, 4, 5, 6, 7, or 8 landing pads. In some embodiments, the cell comprises 1, 2, or 3 landing pads. In some embodiments, the cell comprises 4 landing pads. In some embodiments, landing pads are integrated at up to 1, 2, 3, 4, 5, 6, 7, or 8 distinct chromosomal loci. In some embodiments, landing pads are integrated at up to 1, 2, or 3 distinct chromosomal loci. In some embodiments, landing pads are integrated at 4 distinct chromosomal loci.

The LVEC expression vector for FimH GSD or FimH LD and the FLPe expression vector were co-transfected into a SSI host cell by electroporation either with BioRad Gene Pulser Xcell or Amaxa 4D-Nucleofector. Then cells were cultured in media without glutamine to select cells that has GS gene integrated at the landing pad site. Usually cells recover in 2-3 weeks. Then single cell cloning were carried out in 96 well plates either by FACS or limiting dilution. Titers from wells with cells were ranked to narrow down to top 48 clones. A second round of fed batch screening in 24 deep-well plates was conducted to narrow down the clones to top 12. A third round of fed batch screening in Ambr15 was executed to narrow down the clones to top 3. Ambr250 experiments were used to identify the best clone. Master cell bank and working cell bank were generated for the top clone after its identification.

Example 34: Cell Line Development and Production Reactor Expression of FimH-DSG WT and $FimH_{LD}$ WT Proteins The example described herein, describes an exemplary production of both FimH-DSG WT and $FimH_{LD}$ WT proteins from stable CHO cell lines, where the coding sequences for each protein has been stably intergraded into the CHO genome.

In a production bioreactor setting, the stable CHO cell lines selected were able to produce the target protein at around 1 gram per liter of culture for FimH-DSG WT, and 250 miligrams per liter of culture for $FimH_{LD}$ WT. The seed train for the production reactor was continuously scaled up from vial thaw of a working cell bank and expanded in shake flasks using an inoculation viable cell density of 0.3×10^6 cells/ml through three passage cycles in shake flasks to provide enough cells for the production reactor. The cells were grown at 36.5 deg C., at 5% $CO_2$ for three-four days.

The production reactor was seeded from the final shake flask, targeting an inoculation cell density of 1×10^6 cells/ml. The production reactor was grown at 36.5 deg C. for seven days, using a pH of 7.05 (+/−0.15), and targeting a $CO_2$ saturation of 5-10%. pH is controlled by sodium/potassium bicarbonate for base control, and $CO_2$ sparge for acid control. Dissolved oxygen is controlled at a setpoint of 40% using pure oxygen through the sparge. The temperature was adjusted to 31 deg C. on day seven. The reactor was fed on day 1 using a feed strategy that adds feed in correlation to the viable cell density, this is achieved by using a feed factor of 0.75 in order to ensure feed components do not run out during the run. The feed is then added continuously to provide the desired volume of feed over the course of the day.

The production reactor was harvested on day 13, and the harvest culture was centrifuged and 0.22 µm filtered, prior to downstream processing.

Example 35: Immunogenicity of FimH Antigens and O-Antigen Combinations in Mice E. coli FimH lectin binding domain ($FimH_{LD}$) and full-length (FimH-DSG or FimCH) variants were evaluated in mouse immunogenicity studies that assessed the ability of elicited antibodies to neutralize the binding of fimbriated E. coli to mannosylated ligands. Wild-type FimH antigens that were secreted and purified at high yield from mammalian cells were similarly immunogenic in mice as analogous native antigens purified at low yield from the E. coli periplasm. By comparison, full-length FimH antigens containing both the lectin and pillin domains were significantly more immunogenic than $FimH_{LD}$. Use of an adjuvant formulation containing QS21 was required to generate robust functional immune responses to these fimbrial antigens. A follow-up study investigated the immunogenicity of FimH in combination with a four-valent O-antigen glycoconjugate mixture and different adjuvants. After a second dose, mice vaccinated with a liposomal QS21 formulation induced consistently higher functional responses to the combined antigens in both FimH neutralization and O-antigen-specific OPA assays compared with groups dosed with no adjuvant or liposomal monophosphoryl lipid A (MPLA).

Animal Immunogenicity. 6-8 week old CD-1 mice were obtained from Charles River and groups of 10 or 20 animals were dosed subcutaneously (SC) with 0.1 mL of test antigen or buffer control. Polyclonal anti-FimH rabbit control serum was prepared by immunizing rabbits with three doses of E. coli $FimH_{LD}$ antigen with 100 µg complete Freund's adjuvant (at wk 0) followed by antigen in 100 µg incomplete Freund's adjuvant (at wks 4 and 8) (Covance). Each vaccination administered 0.5 mLs containing 50 µg of antigen at two sites (sub-cutaneous-Dorsal).

Adjuvant Formulations. Diluent for unadjuvanted antigens was 10 mM phosphate buffer, pH 6.1. For $AlPO_4$, 50 µg (100 µL of a 0.5 mg/ml suspension) was given per mouse dose. The default dose of Quillaja saponaria-21 (QS21) used in preclinical studies was 20 µg per mouse from a stock containing 5.1 mg/mL QS-21, 5 mM Succinate, 60 mM NaCl, 0.1% PS80, pH 5.6. Liposomal formulations of monophosphoryl Lipid A (MPLA, Synthetic, PHAD®, Avanti) and QS21 were prepared with 1,2-dioleoyl-sn-glycero-3-phosphocholine (DOPC) and cholesterol (Avanti polar lipids). Liposomal MPLA was used at 5 µg per dose from stock comprising 15 mM phosphate buffer, pH 6.1, 4 mg/mL DOPC, 1 mg/mL Cholesterol, 0.2 mg/mL MPLA (Lot 00714551-0018-2XLipoMPL), having a liposomal particle size of 71 nm determined by dynamic light scattering. A liposomal MPLA/QS21 formulation was used at 5 µg each per dose from stock comprising 15 mM phosphate buffer, pH 6.1, 4 mg/mL DOPC, 1 mg/mL Cholesterol, 0.2 mg/mL MPLA, and 0.2 mg/mL QS-21 (Lot 00714551-0018-2XLipoMQ), having particle size of 75 nm for MPLA-QS21 liposomes determined by dynamic light scattering.

Expression Plasmids and Derived FimH Fimbrial Antigens used in Immunogenicity Studies. The following expression plasmids were used to generate recombinant protein for mouse experiments:

```
>pSB02083 -- FimH_LD (mIgK signal pept, N28S, N91S),
processed protein sequence:
                                     (SEQ ID NO: 110)
FACKTASGTAIPIGGGSANVYVNLAPCVNVGQNCVVDLSTQIFCHNDYPE

TITDYVTLQRGSAYGGVLSSFSGTVKYSGSSYPFPTTSETPRVVYNSRTD

KPWPVALYLTPVSSAGGVAIKAGSLIAVLILRQTNNYNSDDFQFVWNIYA

NNDVVVPTGGCDVSARDVTVTLPDYPGSVPIPLTVYCAKSQNLGYYLSGT

TADAGNSIFTNTASFSPAQGVGVQLTRQGTIIPANNTVSLGAVGTSAVSL

GLTANYARTGGQVTAGNVQSIIGVTFVYQGGSSGGGADVTITVNGKVVAK

GGHHHHHHHH;

>pSB02158 -- FimH_LD-LM (mIgK signal pept, N28S N91S
V48C L55C), processed protein sequence:
                                     (SEQ ID NO: 111)
FACKTASGTAIPIGGGSANVYVNLAPCVNVGQNCVVDLSTQIFCHNDYPE

TITDYVTLQRGSAYGGVLSSFSGTVKYSGSSYPFPTTSETPRVVYNSRTD

KPWPVALYLTPVSSAGGVAIKAGSLIAVLILRQTNNYNSDDFQFVWNIYA

NNDVVVPTGGHHHHHHHH;

>pSB02307 - FimH-DSG (mIgK signal pept, N28S N91S
N249Q 7aa linker FimG A1 . . . K14),
processed protein sequence:
                                     (SEQ ID NO: 112)
FACKTASGTAIPIGGGSANVYVNLAPVVNVGQNLVVDLSTQIFCHNDYPE

TITDYVTLQRGSAYGGVLSSFSGTVKYSGSSYPFPTTSETPRVVYNSRTD

KPWPVALYLTPVSSAGGVAIKAGSLIAVLILRQTNNYNSDDFQFVWNIYA

NNDVVVPTGGCDVSARDVTVTLPDYPGSVPIPLTVYCAKSQNLGYYLSGT

TADAGNSIFTNTASFSPAQGVGVQLTRQGTIIPANNTVSLGAVGTSAVSL

GLTANYARTGGQVTAGNVQSIIGVTFVYQGGSSGGGADVTITVNGKVVAK

GGHHHHHHHH;

>pSB02198 - FimH-DSG-LM (mIgK signal pept, N28S
N91S 249Q V48C L55C 7aa linker FimG A1 . . . K14),
processed protein sequence:
                                     (SEQ ID NO: 113)
FACKTASGTAIPIGGGSANVYVNLAPVVNVGQNLVVDLSTQIFCHNDYPE

TITDYVTLQRGSAYGGVLSSFSGTVKYSGSSYPFPTTSETPRVVYNSRTD

KPWPVALYLTPVSSAGGVAIKAGSLIAVLILRQTNNYNSDDFQFVWNIYA

NNDVVVPTGGHHHHHHHH.
```

Amino acid numbering is based on the full-length amino acid sequence of the J96 strain FimH, whereas academic publications use numbering based on the N-terminal Phenylalanine (in position 21) that is exposed after signal peptide processing. Other mutations remove glycosylation site asparagine residues in the lectin domain (N28S and N91S), in the pilin domain of the full-length FimH-DSG construct (N249Q). The donor-strand G peptide that is added to the C-terminus stabilizes FimH. The 7 amino acid linker length was optimized for mammalian expression as described in the above Examples.

FimH Whole Cell Neutralization Assays. FimH neutralization assays were developed to measure the inhibition by serum antibodies of the binding of fimbriated E. coli to mannoside ligands. Ligands were either microplate-immobilized yeast mannan or bladder 5637 cells that express the mannosylated uroplakin receptor UPIa.

For the yeast mannan assay black microtiter 96-well plates (Maxisorb, Nunc) were coated with 20 μg/ml of yeast mannan (Sigma-Aldrich) in PBS buffer. The wells were blocked with 1% bovine serum albumin (BSA, Sigma-Aldrich) in PBS for 20 min. The human bladder epithelial cell line 5637 was obtained from ATCC (ATCC HTB-9). Cells were grown on black tissue-culture microplates (Greiner) in RPMI 1640 (Sigma, St Louis, MO) supplemented with 10% fetal bovine serum (FBS, Sigma), 2.0 g/l sodium bicarbonate (Sigma) and 0.3 g/l I-glutamine, grown at 37° C. with 5% $CO_2$ and utilized between passages 10 and 24. Surface expression of Uroplakin 1a receptor was confirmed by immunofluorescence staining with polyclonal antibody (Novus #NBP214694). E. coli serotype O25b UTI strain PFEEC0547 was serially passaged in 10 mL static LB cultures at 37° C. to induce FimH expression. Expression of FimH on the bacterial surface was confirmed by flow cytometry with rabbit immune serum to $FimH_{LD}$ antigen. Specificity of bacterial binding to mannan or bladder cells was established by the inclusion of negative control compound methyl α-D-mannopyranoside (Sigma) which reduced binding by >95% at 50 mM levels. Eight-step two-fold serial dilutions of test sera starting at 1:100 (in PBS, 0.1% BSA) were co-incubated with $1 \times 10^7$ E. coli for 1 h at 37° C. before adding to immobilized yeast mannan or 5637 cell monolayers. Serially diluted anti-$FimH_{LD}$ rabbit serum was used as an internal standard on each plate. Plates were incubated for 1 h at 37° C. before washing away unbound bacteria. Bound E. coli were stained for 45 min at RT with 3 μg/ml of an O25b-specific mAb conjugated to Alexafluor 488. The mAb was reconstructed from variable light and heavy chain sequences of O25b antibody 3E9-11 (Nagy E, Nagy G, Szijarto V, et al. Antibodies to multi-drug resistant Escherichia coli: Arsanis Biosciences GmbH, Austria. 2014:76pp). The human pTT5 IgG expression plasmid was used as cloning vector. The fluorescence intensity of individual wells was read on a ClarioStar Plus instrument. $IC_{50}$ inhibition values were interpolated using sigmoidal dose response variable-slope curve fitting (Graphpad Prism). Titers are the reciprocal of the serum dilution at which half-maximal inhibition is observed. A vaccine antigen responder was defined as a neutralizing titer that exceeds 80% inhibition at the starting serum dilution of 1:100. In addition, the serum dilution titration of binding activity must satisfy variable slope sigmoidal curve fitting parameters ($R^2$>0.95, with interpolated Log IC50 value or trigger an experimental repeat with a broader dilution until resolved). The statistical significance (p-value) of differences in responses between groups was determined using an unpaired t-test with Welch's correction applied to log-transformed data.

For experiments involving mice vaccinated with multivalent O-antigen conjugates of different serotypes the yeast mannan assay was adapted for use with the Bactiter Glo detection reagent (Promega), to avoid potential interference by elicited anti-O—Ag IgG with bacterial detection. In this case detection is based on photon emission catalyzed by firefly luciferase following release of ATP from permeabilized viable bacteria. Use of this reagent simplified detection by eliminating the wash step and facilitated implementation of a higher throughput 384-well assay format with liquid handling automation (Bravo, Agilent). The miniaturized assay reduced reaction volumes from 100 μL to 30 μL and the required number of bacteria from $1 \times 10^7$ per well to $1 \times 10^6$. After diluting 1:1 in PBS, Bactiter Glo was added to all wells and after mixing, read on the ClarioStar reader in luminometer mode. The serotype O6:K2 E. coli UTI strain CFT073 (ATCC® 700928™) was selected for use in the semi-automated 384-well assay due to its enhanced sensitivity compared with O25b UTI strain PFEEC0547. Both strains yielded similar results in bridging studies comparing individual serum titers in a subset of mouse vaccination groups (data not shown).

E. coli O—Ag Mouse IgG Direct Luminex Immunoassay (dLIA). Long chain E. coli O—Ag polysaccharides of serotypes O25b, O1a, O2 and O6 produced in-house by eBPD (Pfizer) were conjugated to poly-L-lysine and then to Luminex bead microspheres with EDC/NHS. Use of beads with distinct spectral addresses for each O-antigen enabled four-fold multiplexing. Beads were incubated with serially diluted individual mouse sera or control mAbs with shaking at 4° C. for 18 h. After washing, bound serotype-specific IgG was detected with a PE-conjugated goat anti-mouse IgG mouse secondary antibody (90 min RT incubation). Microplates were read on a FlexMap 3D instrument (Biorad). Serotype specific mouse IgG mAbs with similar binding properties (generated in-house) were used as internal standards to quantify IgG levels. Plots of standard curves for each mAb yielded overlapping linear slope profiles across 103 serum dilutions (log luminescence vs log serum dilution). A lower limit of quantitation (LLOQ) for the 4-plex IgG dLIA of 0.15259 ug/mL was calculated from standard curve bias, which was the same for each of the four antigens.

E. coli Opsonophagocytic Assays (OPA). Clinical E. coli invasive blood isolates were obtained from the Pfizer-sponsored Antimicrobial Testing Leadership and Surveillance (ATLAS) database which is maintained by the International Health Management associates (IHMA) clinical lab. Strains were genotypically characterized by WGS using the Illumina Miseq platform, including in-silico serotyping for prediction of O-antigen and K-capsule types. Serotype O1a, O2, O6 and O25b strains that express both O-antigen and K-antigens when grown in Dulbecco's Modified Eagle's medium (DMEM) under cell-banking conditions were used as test strains, as well as multidrug-resistant unencapsulated strains representing O6 and O25b serotypes. O-antigen expression was confirmed by flow cytometry with antigen-specific monoclonal or polyclonal antibodies generated in-house. K1-antigen expression was confirmed using K1-capsule mAb mAb13D9-151 (obtained from NRC, Canada). K2-antigen expression was detected with K2-typing serum (Statens Serum Institute). Expression of the K5 heparosan capsule was confirmed by increased surface exposure of underlying O-antigen upon treatment with heparinase. The following E. coli clinical strains were developed for OPA assays:

O1a:K1 (PFEEC0435, ST-95),
O2:K1 (PFEEC0146, ST-95, Ticarcillin/Clavulanic $Acid^R$), O6:K- (PFEEC0412, ST-127, Ticarcillin/Clavulanic Acid[R], ESBL),
O6:K2 (PFEEC0150, ST-127),
O25b:K- (PFEEC0068, ST-131, Imipenem[R], fluoroquinolone[R]),
O25b:K5 (PFEEC0066, ST-131, fluorquinolone[R]).

Pre-frozen bacterial stocks of were grown in DMEM to an $OD_{600}$ of between 0.5 and 1.0 and glycerol added to a final concentration 20% prior to freezing. Pre-titered thawed bacteria were diluted to $1\times10^5$ CFU/ml in OPA buffer (Hanks Balanced Salt Solution (Life Technologies), 0.1% gelatin, 1 mM $MgCl_2$, 2.5 mM $CaCl_2$) and 20 µL (103 CFU) of the bacterial suspension was opsonized with 10 µL of serially diluted sera for 30 min at RT in a 384-well tissue culture microplate. Conditions, such as the need for the opsonization step, the level of baby rabbit complement, the length of assay incubation, and HL60 to bacteria ratio, varied slightly and was optimized according to the assay strain used. Subsequently, 10 µl of 2-6% complement (Baby Rabbit Serum, Pel-Freez) and 10 µL of HL-60 cells (at 100-200:1 ratio) were added to each well and the mixture shaken at 2000 rpm for 45-60 min at 37° C. in a 5% $CO_2$ incubator. Ten µL of each 50 µL reaction was transferred into the corresponding wells of a prewetted 384-well Millipore MultiScreen HTS HV filter plate containing 50 µL water. After vacuum filtering the liquid, 50 µL of 50% DMEM was applied and filtered and plate incubated overnight at 37° C. in a sealed zip-lock bag. The next day the colonies were enumerated after staining with Coomassie dye using an ImmunoSpot® analyzer and ImmunoCapture software. To establish the specificity of OPA activity, immune sera were preincubated with 20 µg/mL of the homologous serotype purified O-antigen prior to the opsonization step. The OPA assay includes control reactions without HL60 cells or complement, to demonstrate dependence of any observed killing on these components. Individual serum OPA titers were calculated using variable slope curve fitting (Excel). Combined data were plotted using GraphPad Prism to generate GMTs and associated p values for significance (unpaired t-test with Welch's correction from log transformed data).

Results

Mouse Immunogenicity Studies. A first study was designed to evaluate the immunogenicity of recombinant $FimH_{LD}$ antigens expressed and purified from the E. coli periplasm at different dose levels and with different adjuvants. Purification of $FimH_{LD}$ was based on a previously described method (Schembri M A, Hasman H, Klemm P. Expression and purification of the mannose recognition domain of the FimH adhesin. FEMS microbiology letters 2000; 188:147-51). A second study compared the activity of E. coli $FimH_{LD}$ with mammalian expressed variants of $FimH_{LD}$ and full-length FimH-DsG. Finally, a third study investigated immunogenicity of combinations of FimH-DsG with a 4-valent long O-antigen glycoconjugate mixture and different adjuvant formulations.

Figure 36A:
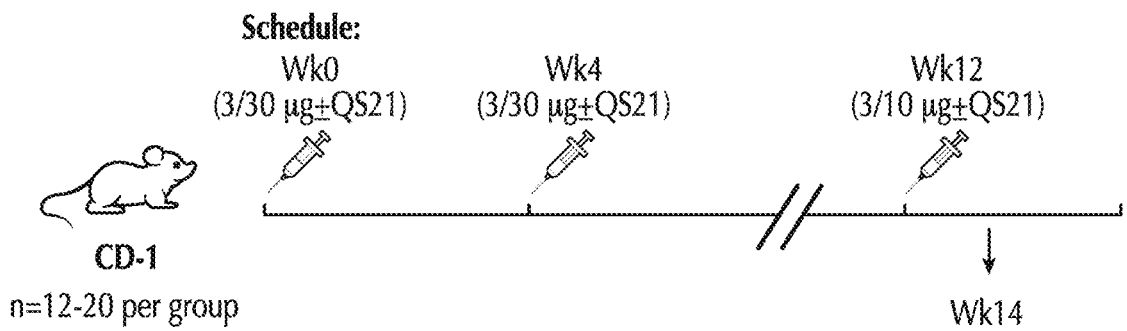
FIG. 36A-36B—depict that the *E. coli* FimH$_{LD}$ Antigen requires a potent adjuvant to elicit neutralizing antibodies.
Figure 36B:
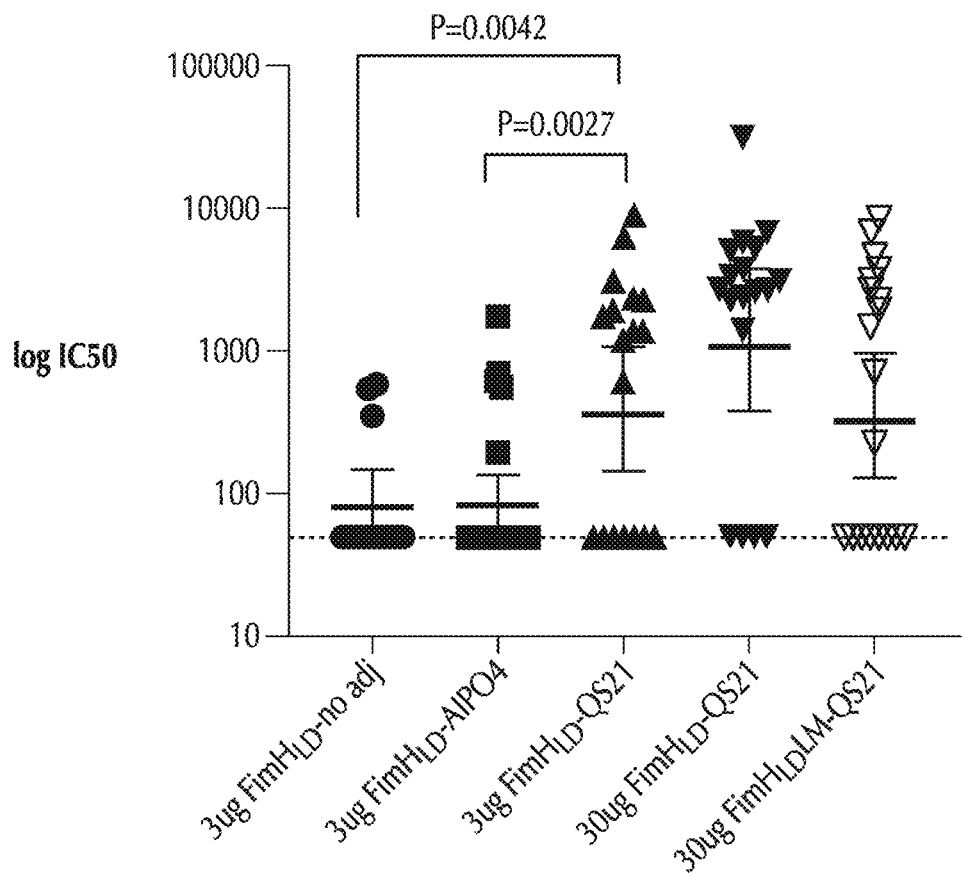

Immunogenicity of FimH Antigens. Induction of functional anti-FimH antibodies induced by the various FimH constructs was assessed using neutralization assays similar to those described previously based on inhibition of binding by E. coli to surface immobilized yeast mannan (Kisiela D I, Avagyan H, Friend D, et al. Inhibition and Reversal of Microbial Attachment by an Antibody with Parasteric Activity against the FimH Adhesin of Uropathogenic E. coli. PLOS Pathogens 2015; 11:e1004857) or bladder epithelial cells (Langermann S, Palaszynski S, Barnhart M, et al. Prevention of mucosal Escherichia coli infection by FimH-adhesin-based systemic vaccination. Science 1997; 276:607-11; Starks C M, Miller M M, Broglie P M, et al. Optimization and Qualification of an Assay that Demonstrates that a FimH Vaccine Induces Functional Antibody Responses in Women with Histories of Urinary Tract Infections. Human Vaccines & Immunotherapeutics 2020:1-10). The functional potency of antigen variants was quantified by determining serum neutralization titers that prevent the binding of fimbriated bacteria to the yeast mannoside ligands. The titer is defined as the reciprocal of the serum dilution at which 50% of bacteria are bound to the assay microplate in an eight-point two-fold titration of vaccinated animal sera. Results of an initial study with $FimH_{LD}$ antigens purified from E. coli are shown in FIG. 36A and FIG. 36B and Table 34. The vaccination schedule is shown in FIG. 36A and individual mouse reponses plotted in FIG. 36B.

Mouse Immunogenicity Experiment
1—Comparison of Different E. coli

Periplasmic Produced FimH Constructs. After vaccination with three 3 µg doses of the $FimH_{LD}$ antigen, only 25% of mice in the unadjuvanted group or group adjuvanted with 50 µg of $AlPO_4$ yielded neutralizing antibody titers in the yeast mannan assay. In contrast, 61% of mice in the group adjuvanted with 20 µg QS21/PS80, yielded neutralizing titers. In this case the geometric mean titer (GMT) was 5-fold higher (p value of <0.05) than the other groups. At the 30 µg $FimH_{LD}$ dose level with QS21/PS80, a further three-fold increase in GMT and a 78% seroresponder rate was observed. In this adjuvant context, the presence of the disulfide mutation, designed and predicted to enhance functional immunogenicity by locking the $FimH_{LD}$ antigen in an open conformation (Rodriguez V B, Kidd B A, Interlandi G, et al. Allosteric coupling in the bacterial adhesive protein FimH. J Biol Chem 2013; 288:24128-39; Kisiela D I, Rodriguez V B, Tchesnokova V, et al. Conformational inactivation induces immunogenicity of the receptor-binding pocket of a bacterial adhesin. Proceedings of the National Academy of Sciences of the United States of America 2013; 110:19089-94) did not improve immunogenicity compared with the wild-type $FimH_{LD}$ construct. An approximately three-fold lower GMT was observed for the lock-mutant compared with wild-type that bordered on statistical significance (p=0.09). A key observation from this study is that the E. coli $FimH_{LD}$ antigen requires a potent QS21 adjuvant formulation to elicit robust levels of neutralizing antibodies in mice.

TABLE 34

VAC-2019-PRL-EC-1369 Neutralizing Titer GMTs and Responder Rates

| Vaccination Group | % Responders | # of Responders | Geometric mean ($IC_{50}$) titers |
|---|---|---|---|
| 3 ug $FimH_{LD}$ no adjuvant | 25 | 3/12 | 88 |
| 3 ug $FimH_{LD}$ $AlPO_4$ | 25 | 5/20 | 93 |
| 3 ug $FimH_{LD}$ QS21/PS80 | 61 | 11/18 | 495 |
| 30 ug $FimH_{LD}$ QS21/PS80 | 78 | 14/18 | 1486 |
| 30 ug $FimH_{LD}LM^a$- QS21 | 58 | 11/19 | 459 |

[a]LM is the duslfide lock mutation V48C L55C

Figure 37A:
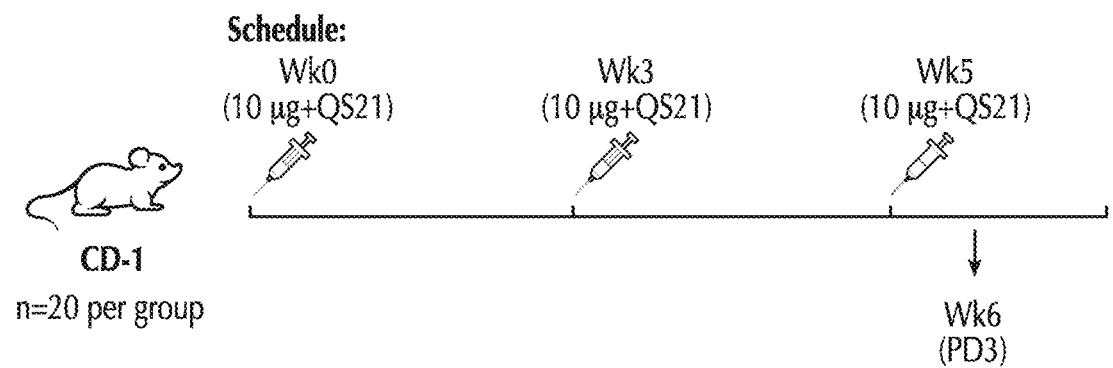
FIG. 37A-37B—demonstrates that FimH-DSG variants are more immunogenic than FimH$_L$D constructs.
Figure 37B:
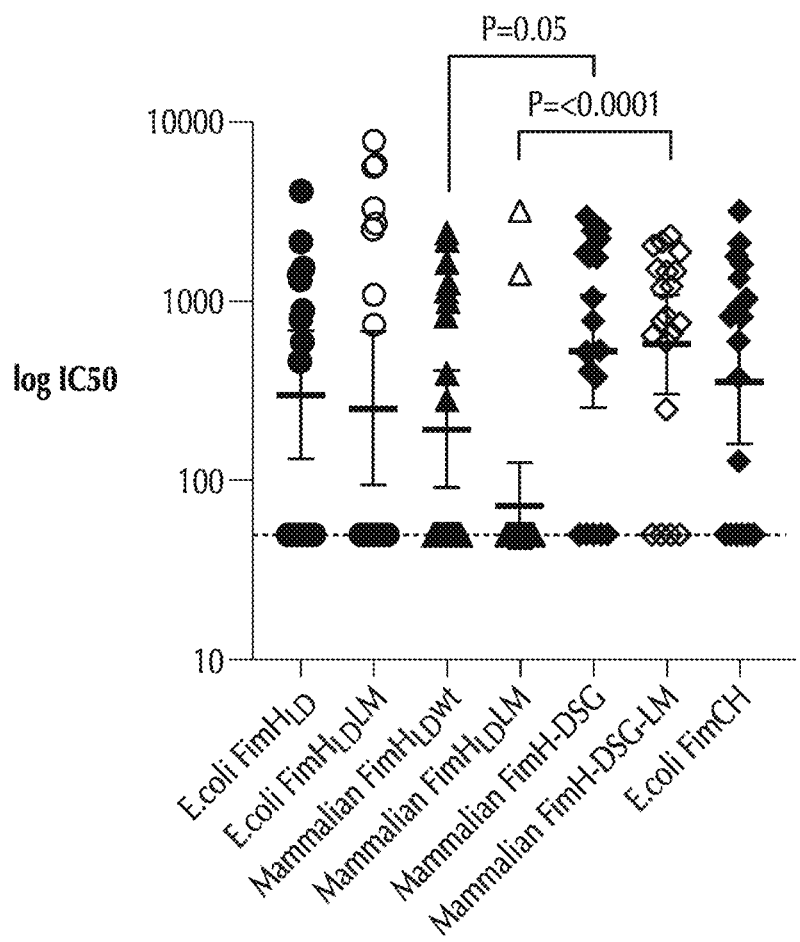

Immuogenicity of Periplasmic Compared to Mammalian Produced FimH Constructs. In the second study the immunogenicity of $FimH_{LD}$ and full-length FimH proteins expressed in E. coli were compared with analogous variants expressed in Expi293 mammalian cells. E. coli-expressed full-length FimH complexed with its periplasmic chaperone FimC was used as a benchmark. Neutralization data comparing the relative level of functional antibody induction by E. coli vs mammalian expressed antigens with or without the lock-mutation after three vaccinations are shown in FIG. 37A and FIG. 37B and Table 35. Antigens were dosed at 10 μg each with 20 μg QS21/PS80 according to the schedule shown in FIG. 37B. The E. coli-expressed FimH$_{LD}$ group of mice yielded a neutralization assay GMT of 300 and 55% responder rate, which was not statistically different from the analogous mammalian expressed FimH$_L$D group (with GMT of 194 and 45% responder rate). The mammalian full-length FimH-DSG was significantly more immunogenic than its FimH$_{LD}$ counterpart, showing a two-fold higher GMT (529 vs 194) and improved seroresponder rate (75% vs 45%). As with the first study, the presence of the lock mutation offered no benefit in terms of generating a functional neutralizing response, either in the context of FimH$_{LD}$ (E. coli or mammalian expressed) or full-length FimH-DSG. Mammalian expressed FimH-DSG (with or without the lock mutation) also presented as more immunogenic than the E. coli FimCH antigen, although the differences were not statistically significant. Taken together these results identified full-length FimH-DSG, as the antigen of choice for subsequent investigation. We speculate that the presence of the FimH pilin domain in this construct, in complex with the C-terminal FimG donor strand peptide, may provide additional functional epitopes and/or enhanced stability.

TABLE 35

VAC-2019-PRL-EC-1438 Neutralizing Titer GMTs and Responder Rates

| Vaccination Group | % Responders | # of responders | Geometric mean (IC$_{50}$) titers |
|---|---|---|---|
| Periplasmic- FimH$_{LD}$ | 55 | 11/20 | 300 |
| Periplasmic- FimH$_{LD}$-LM | 40 | 8/20 | 254 |
| Mammalian- FimH$_{LD}$ | 45 | 9/20 | 194 |
| Mammalian- FimH$_{LD}$-LM | 10 | 2/20 | 73 |
| Mammalian FimH-DSG | 75 | 15/20 | 529 |
| Mammalian FimH-DSG-LM | 80 | 16/20 | 579 |
| Periplasmic- FimCH | 67 | 12/18 | 354 |

Figure 38:
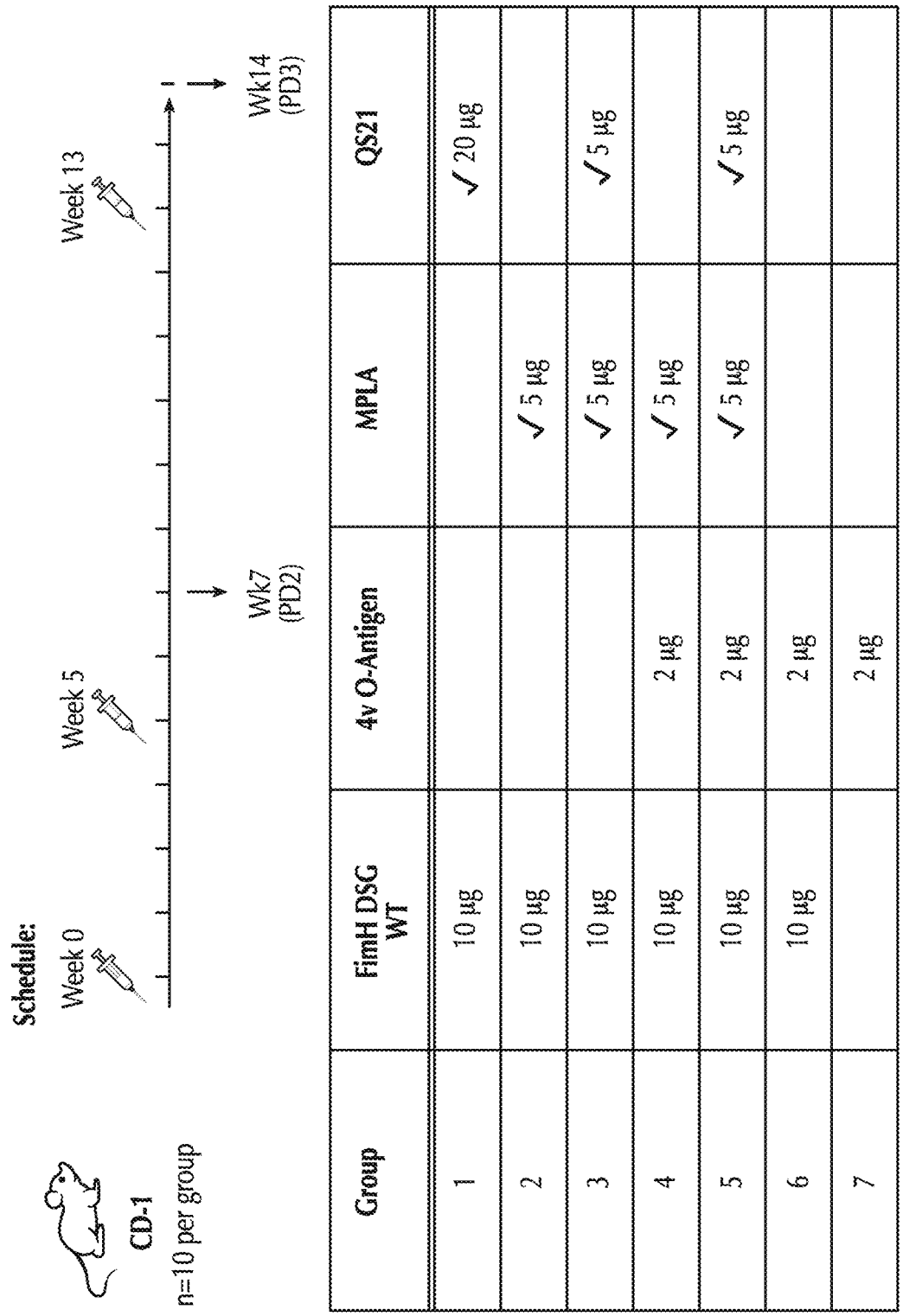
FIG. 38—depicts the schedule and dosing for a FimH-DSG and O-antigen combination and adjuvant formulation study (Study VAC-2020-PRL-EC-1679).

Immunogenicity of Coformulated Mammalian-generated FimH-DSG and 4-valent O-antigen Glycoconjugate in Mice. The third mouse study was designed to assess the impact of combined O-antigen and adjuvant formulations on FimH-DSG immunogenicity. Long O-antigen glycoconjugates of CRM$_{197}$ representing four most prevalent serotypes O25b, O1a, O2 and O6 were mixed and administered at a dose of 2 μg each as a baseline control group (FIG. 38). Other vaccine groups evaluated the impact on immunogenicity of three adjuvants with 10 μg of FimH-DSG, either individually or in combination with the four-valent O-antigens. Adjuvants were the default 20 μg QS21/PS80 per dose formulation (used in FimH studies 1 and 2); a liposomal synthetic MPLA formulation (5 μg per dose); and a liposomal synthetic MPLA/QS21 formulation (at 5 μg each per dose). Sera were tested in functional FimH neutralization and O-antigen specific opsonophagocytic (OPA) assays at post-dose 2 (PD2) and post-dose 3 (PD3) timepoints.

Figure 39A:
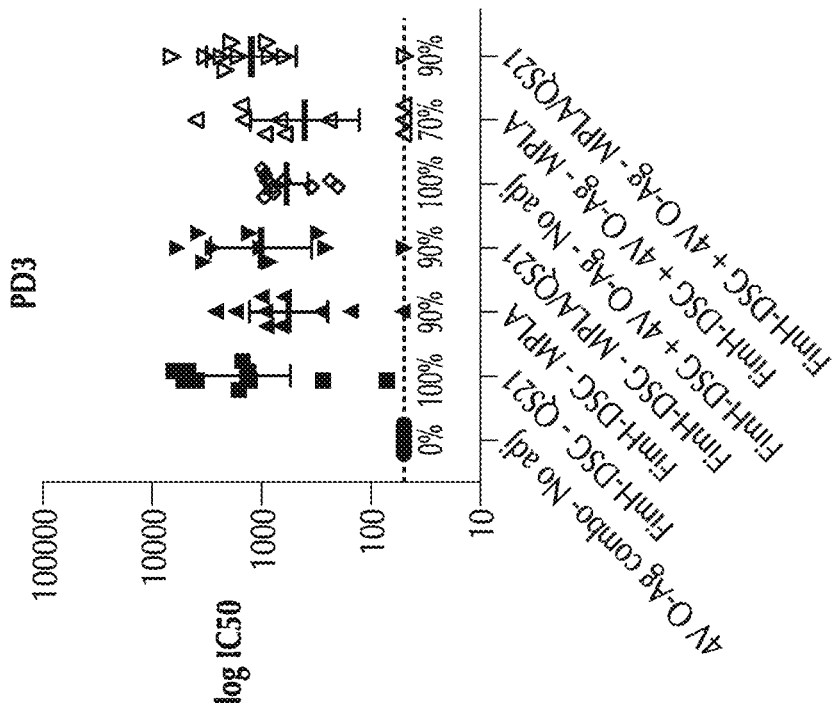
FIG. 39A-39B—depict Study VAC-2020-PRL-EC-1679 which demonstrates the influence of adjuvant and FimH-DSG and 4-valent O-antigen combinations on FimH neutralization. Yeast mannan assay binding neutralization titers at PD2 (FIG. 39A) and PD3 (FIG. 39B) timepoints. Closed symbols reflect mice vaccinated with O-antigens or FimH-DSG antigens only; open symbols are mice in groups vaccinated with FimH-DSG O-antigen combinations as labeled on x-axis.
Figure 39B:
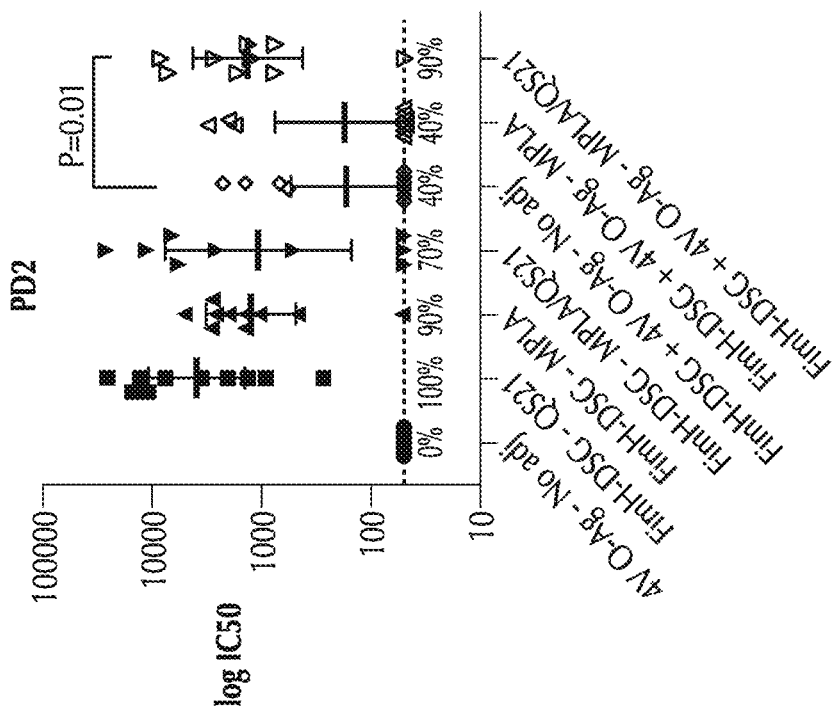

Results of yeast manan FimH binding neutralization assays at P2 and P3 timepoints are shown in FIG. 39A and FIG. 39B with GMTs and responder rates summarized in Table 36.

TABLE 36

VAC-2020-PRL-EC-1679 Combination Study Yeast Mannan Binding Neutralization Assay Responder Rates and GMTs

| | % Responders | | Geomean of IC50s | | # of responders (out of 10) | |
|---|---|---|---|---|---|---|
| Vaccination Group | PD2 | PD3 | PD2 | PD3 | PD2 | PD3 |
| 4plex O-antigen combo-No adjuvant | 0 | 0 | 50 | 50 | 0 | 0 |
| FimH-DSG (10 μg)-QS21 (20 μg) | 100 | 100 | 3938 | 1457 | 10 | 10 |
| FimH-DSG (10 μg)-MPLA (5 μg) | 90 | 90 | 1243 | 559 | 9 | 9 |
| FimH-DSG (10 μg)-MPLA/QS21 (5 μg/5 μg) | 70 | 90 | 1075 | 990 | 7 | 9 |

TABLE 36

VAC-2020-PRL-EC-1679 Combination Study Yeast Mannan Binding Neutralization Assay Responder Rates and GMTs

| | % Responders | | Geomean of IC50s | | # of responders (out of 10) | |
|---|---|---|---|---|---|---|
| Vaccination Group | PD2 | PD3 | PD2 | PD3 | PD2 | PD3 |
| FimH-DSG (10 μg) + 4plex O-antigen combo-No adjuvant | 40 | 100 | 169 | 581 | 4 | 10 |
| FimH-DSG (10 μg) + 4plex O-antigen combo-MPLA (5 μg) | 40 | 70 | 176 | 397 | 4 | 8 |
| FimH-DSG (10 μg) + 4plex O-antigen combo-MPLA/QS21 (5 μg/5 μg) | 90 | 90 | 1332 | 1223 | 9 | 9 |

As antibody responses to individual FimH and monovalent serotype O25b antigens were sub-maximal after two doses in previous experiments, it was anticipated that the PD2 timepoint would best differentiate effects of vaccine antigen and adjuvant composition. Indeed, by PD3 responder rates and FimH neutralizing GMTs were not significantly different between any of the groups (p>0.05). At PD2, the liposomal adjuvant formulations had no significant effect on groups with FimH-DSG alone. In contrast, for the groups vaccinated with combined FimH-DSG/O-antigens, significantly lower FimH neutralizing GMTs were observed with the no adjuvant or liposomal MPLA groups, compared with the group of mice vaccinated with liposomal MPLA/QS21 or any of the FimH-DSG alone groups. PD1 sera were also tested but none of the mice showed neutralizing titers.

Figure 40A:
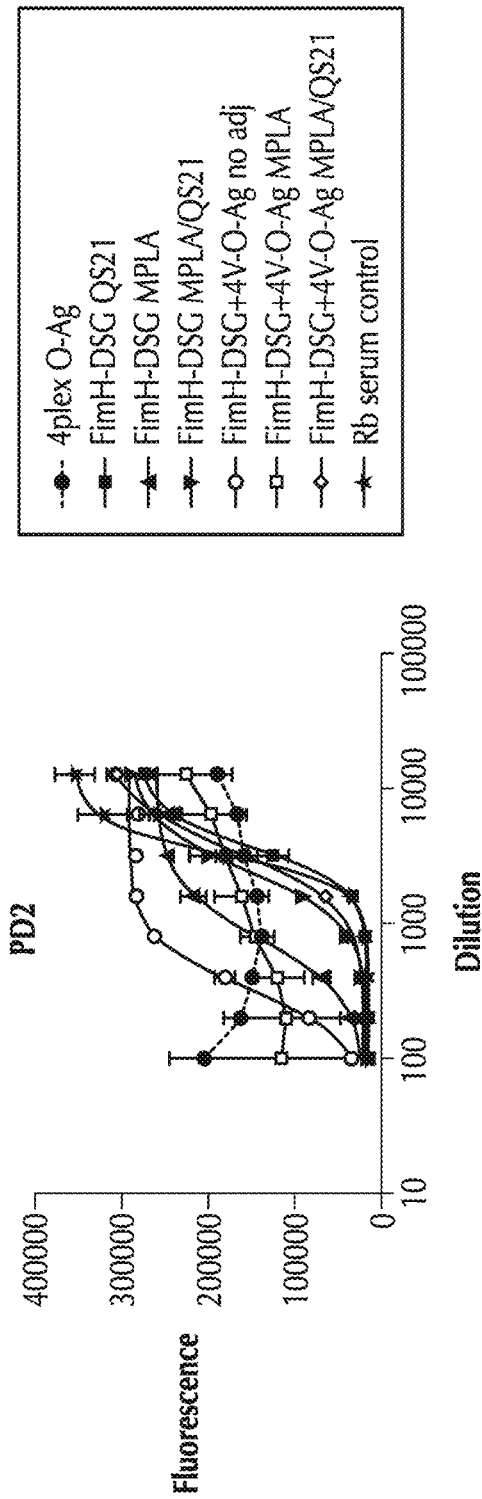
FIG. 40A-40B—depict results of bladder assay with mouse serum pools corroborate yeast mannan assay data with individual mouse sera. Bladder cell binding inhibition curves from pooled mouse sera (n=10). Details are same as in the legend to FIG. 39A-39B. Rabbit anti-FimH positive control serum titrations are also shown, as an invariant assay reference standard.
Figure 40B:
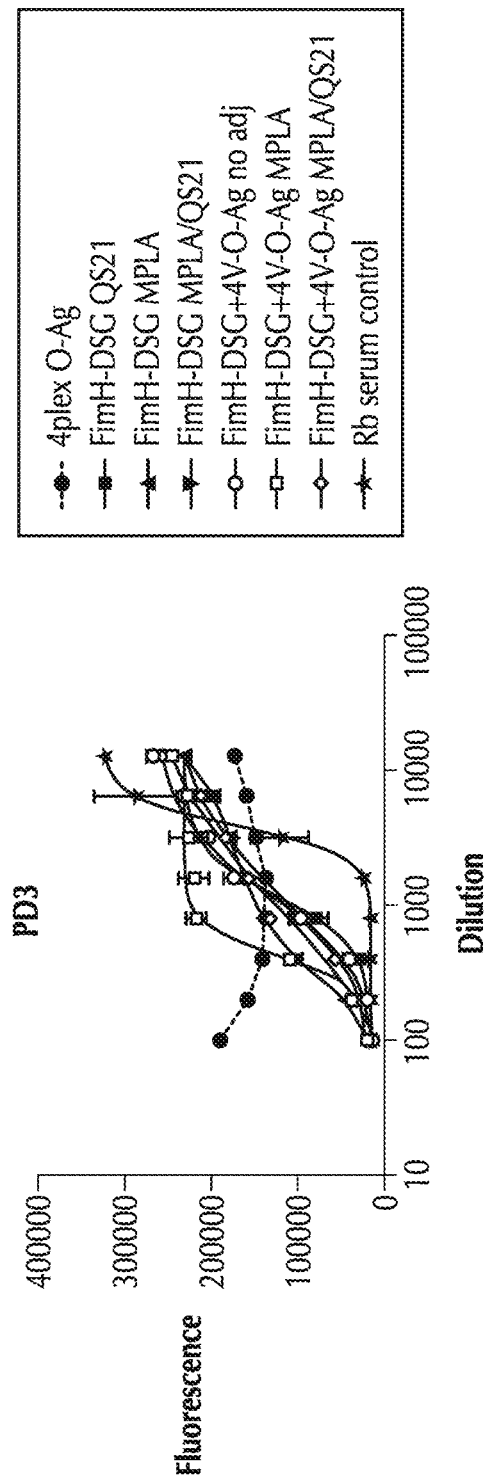

The bladder cell binding neutralization assay was used to test sera pooled from each vaccine group at PD2 and PD3 timepoints. Bladder 5637 cells constitutively express the mannosylated uroplakin receptor UPIa which is a natural ligand for FimH (Thumbikat P, Berry R E, Zhou G, et al. Bacteria-induced uroplakin signaling mediates bladder response to infection. PLoS pathogens 2009; 5:e1000415-e; Kctnik-Prastowska I, Lis J, Matejuk A. Glycosylation of uroplakins. Implications for bladder physiopathology. Glycoconjugate journal 2014; 31:623-36). Results shown in FIG. 40A and FIG. 40B and Table 37 were consistent with the findings of the yeast mannan neutralization assay run with individual sera. Again, combined FimH-DSG/O-antigens formulated with liposomal MPLA or no adjuvant generated significantly weaker neutralizing responses than the liposomal MPLA/QS21 group, which responded similarly to the groups of mice vaccinated with QS21/PS80 or liposomal MPLA/QS21 and FimH-DSG without O-antigens. A minor difference between the mannan and bladder neutralization assay data was a trend in the latter toward weaker responses with the liposomal MPLA formulation for groups vaccinated with either FimH-DSG only or combined FimH-DSG/O-antigens.

TABLE 37

VAC-2020-PRL-EC-1679 Bladder Cell Neutralization Titers with Mouse Serum Pools

|  | Vaccination Group | |
| --- | --- | --- |
|  | PD2 IC50 | PD3 IC50 |
| 4V O-Ag | Inactive | Inactive |
| FimH-DSG QS21 | 3656 | 1140 |
| FimH-DSG MPLA | 775 | 750-1000[a] |
| FimH-DSG MPLA/QS21 | 2458 | 1198 |
| FimH-DSG + 4V O-Ag no adj | 337 | 1177 |
| FimH-DSG + 4V O-Ag MPLA | Inactive | 434 |
| FimH-DSG + 4V O-Ag MPLA/QS21 | 3447 | 931 |
| Rabbit serum control | 3266 | 3809 |

[a]$IC_{50}$ titer estimate due to poor fit of biphasic curve with variable slope equation.

Figure 41:
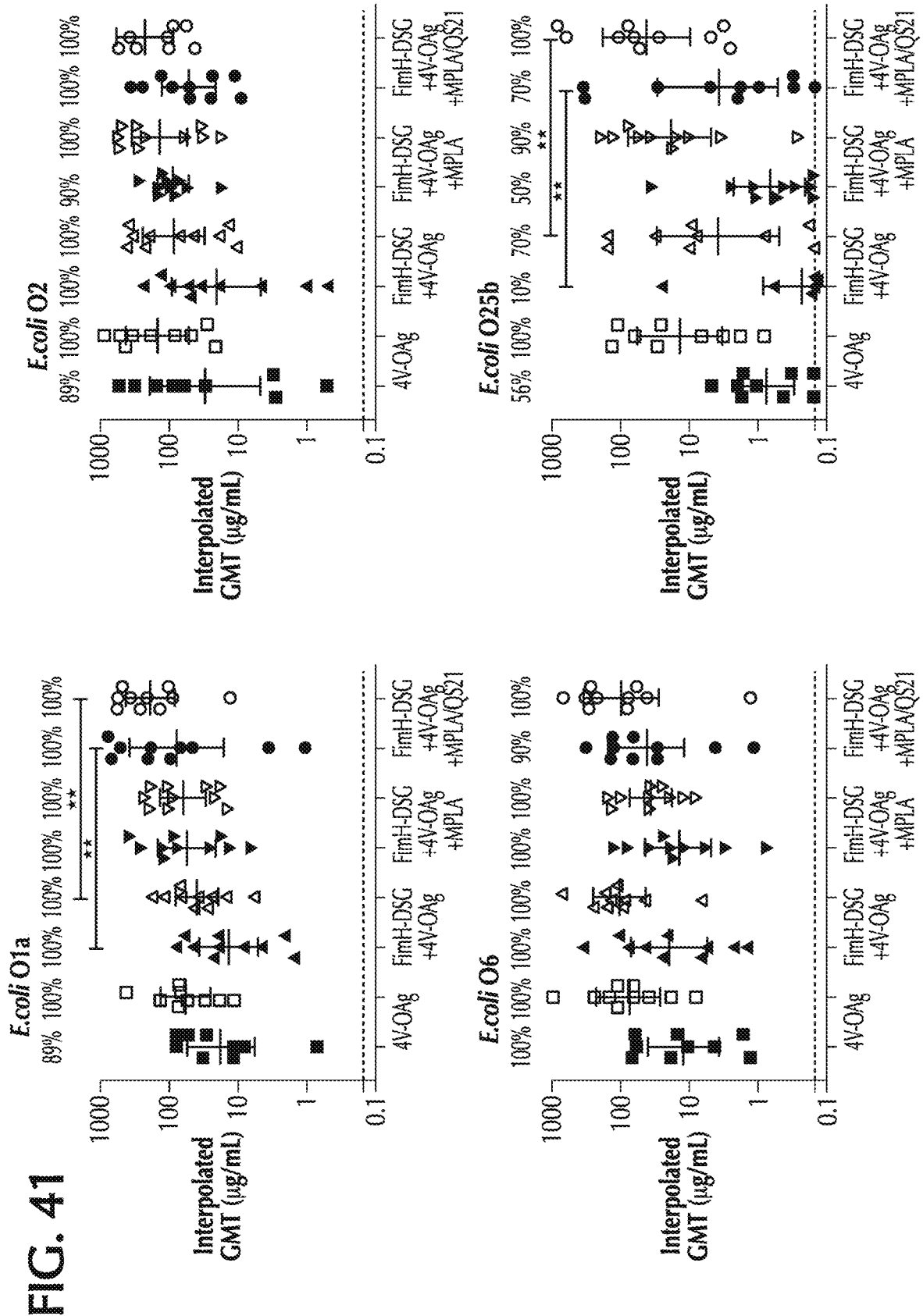
FIG. 41—depicts the influence of adjuvant and FimH-DSG on O-Antigen specific serum IgG levels. Closed and open symbols represent PD2 and PD3 timepoint values, respectively. Ten pre-vaccinated CD-1 mice per group were pooled to determine the baseline IgG level for each antigen. The GMT of each pre-vaccinated pool was <the lower limit of quantitation (O.15 µg/mL, dotted line), determined from standard curve bias analysis. Responder rates are indicated as the percentage of mice per group that show greater than a 5-fold increase in titer over baseline. Differences in antibody titers between groups were analyzed by unpaired t test with Welch's correction **P<0.05.

Levels of O-antigen specific total IgGs generated with the 4-plex dLIA after vaccination of four groups of mice with the 4-valent O-antigens alone or in combination with FimH-DSG and liposomal adjuvants are shown in FIG. 41 and Table 38. Serotype O25b-specific IgG responses after two doses were markedly lower than those elicited by serotype O1a, O2 and O6 O-antigens, which is consistent with results of previous conjugate chemistry studies with monovalent O-antigens (not shown) and reported preclinical studies with tetravalent bioconjugate O-antigens (van den Dobbelsteen G, Faé K C, Serroyen J, et al. Immunogenicity and safety of a tetravalent *E. coli* O-antigen bioconjugate vaccine in animal models. Vaccine 2016; 34:4152-60). The lowest level of anti-O—Ag IgG across the O25b groups at PD2 was observed with the unadjuvanted FimH-DSG and O-antigen combination, which yielded only a single titer exceeding the five-fold over baseline IgG responder threshold; in comparison, the unadjuvanted O-antigen only group generated higher responder rates of 56% (5/9), although the difference in GMTs (0.79 vs 0.24 µg/mL IgG) between the two groups was not statistically significant (p>0.5). At PD2, the liposomal MPLA/QS21 adjuvant significantly enhanced the immunogenicity of the FimH-DSG and O-antigen combination by inducing a 16-fold increase in GMT (3.84 vs 0.24) and improved responder rate (70% vs 10%); a significant increase in GMT was also observed at PD3 (40.78 vs 3.75). A responder is defined as mouse with serum that yields a complete dilution dependent killing response that meets variable slope curve fitting criteria. Despite higher responder rates and titers across the groups than for serotype O25b, serotype O1a IgG titers for the FimH-DSG and O-antigen combination were also significantly improved at PD2 and PD3 by liposomal MPLA/QS21 by 5.9 and 4.6-fold, respectively. The impact of the MPLA/QS21 on o2 and O6 O-antigens was less pronounced than for O1a and O25b due to smaller differences overall in GMTs between the vaccination groups.

TABLE 38

VAC-2020-PRL-EC-1679: Influence of Adjuvant and FimH-DSG on O-antigen Specific Serum IgG GMTs

| Vaccination Group | O1a | | O2 | | O6 | | O25b | |
| --- | --- | --- | --- | --- | --- | --- | --- | --- |
|  | PD2 | PD3 | PD2 | PD3 | PD2 | PD3 | PD2 | PD3 |
| 4v O-Ag | 13.86 | 56.72 | 21.96 | 145.99 | 9.66 | 74.25 | 0.79 | 13.73 |
| FimH-DSG + 4v O-Ag no adjuvant | 13.42 | 39.05 | 20.56 | 86.81 | 19.19 | 101.48 | 0.24 | 3.75 |
| FimH-DSG + 4v O-Ag in liposomal MPLA | 54.48 | 61.59 | 89.69 | 138.18 | 13.86 | 35.15 | 0.68 | 19.05 |
| FimH-DSG + 4v O-Ag in liposomal MPLA/QS21 | 79.59 | 181.73 | 52.82 | 230.35 | 39.64 | 94.34 | 3.84 | 40.78 |

Functional bactericidal antibodies induced by individual O-antigens of the 4-valent composition were assessed in OPA assays with invasive clinical strains. Selection of OPA strains was based on a combination of factors: expression of both O-antigen and K-capsule under in vitro growth conditions and/or multidrug-resistance; and the ability to identify compatible baby rabbit serum complement capable of facilitating bactericidal killing in the presence of neutrophil-like HL60 cells and O-antigen specific antibodies. While *E. coli* O-antigens are considered to be the primary determinant for preventing non-specific killing by serum complement, K1, K2 and K5-capsular antigens have also been shown to play a role in resisting phagocytosis in whole blood (Sarkar S, Ulett G C, Totsika M, et al. Role of Capsule and O Antigen in the Virulence of Uropathogenic *Escherichia coli*. PLoS ONE 2014; 9:e94786; Burns S M, Hull S I. Loss of resistance to ingestion and phagocytic killing by O(−) and K(−) mutants of a uropathogenic *Escherichia coli* O75:K5 strain. Infection and immunity 1999; 67:3757-62; Buckles E L, Wang X, Lane M C, et al. Role of the K2 Capsule in *Escherichia coli* Urinary Tract Infection and Serum Resistance. The Journal of infectious diseases 2009; 199:10.1086/598524).

Figure 42:
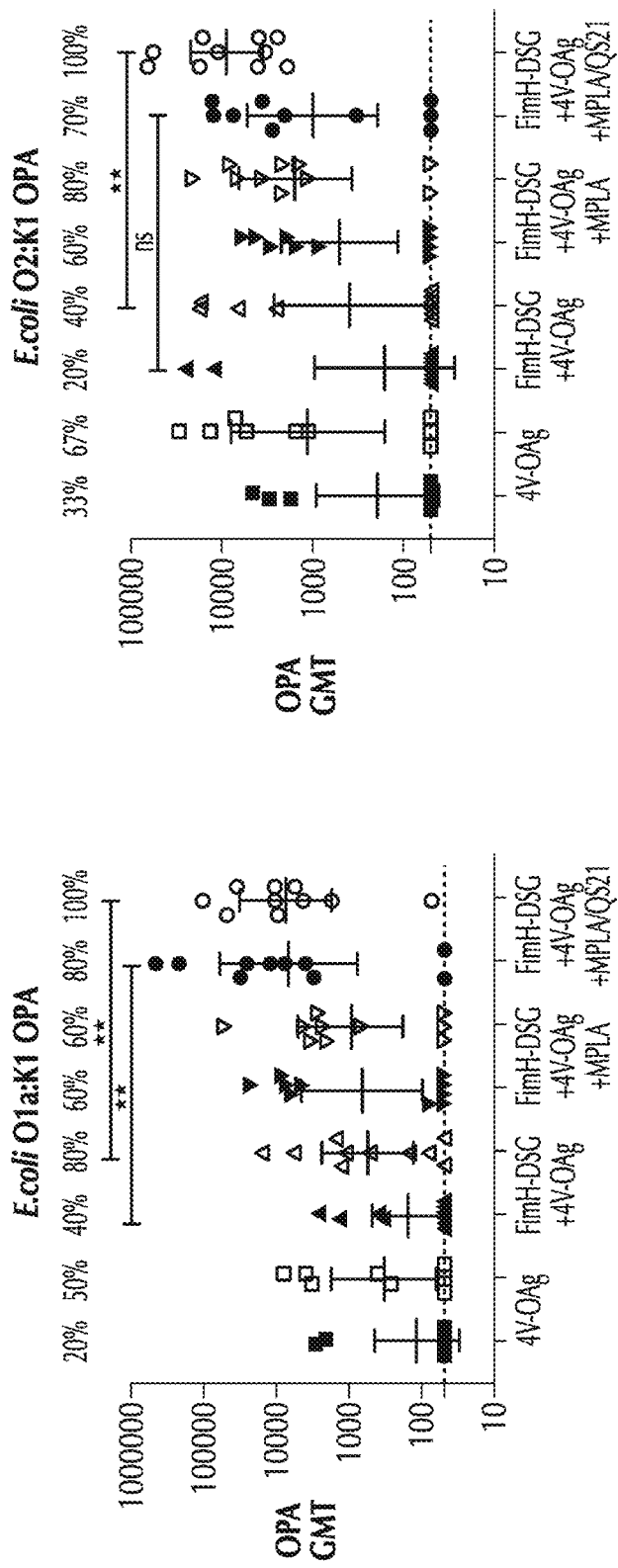
FIG. 42—depicts the influence of adjuvant and FimH-DSG on O-antigen-specific serum OPA titers. Details are same as for FIG. 41. Dotted lines reflect baseline titers from mouse pre-vaccination serum pools (½×LOD or 50, n=10). Closed and open symbols represent PD2 and PD3 timepoint values, respectively.
Figure 42:
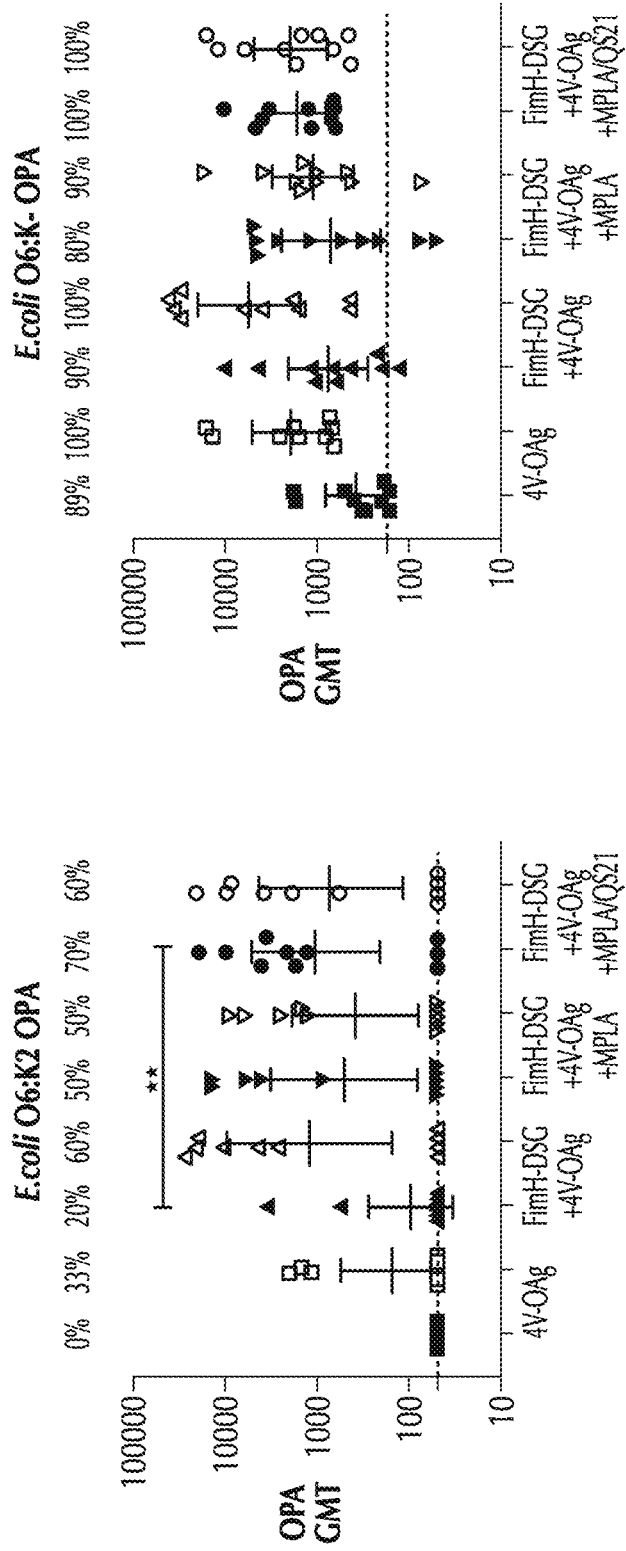
Figure 42:
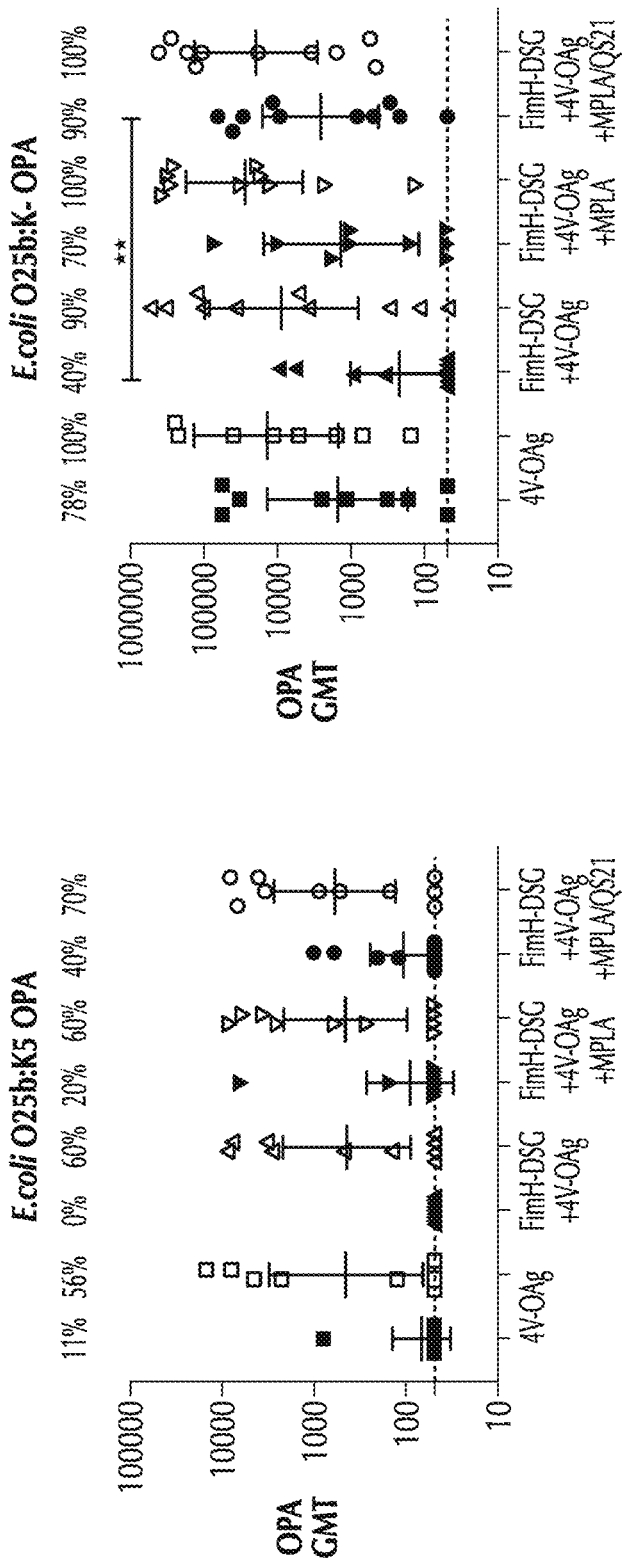

Results of OPA assays with four encapsulated O1a, O2, O6 and O25b strains and two multidrug-resistant unencapsulated O6 and O25b strains are shown in FIG. 42 and Table 39. With the exception of the O6:K− strain assay which exhibited a relatively high baseline titer of 174 for pre-vaccination sera, sera from unvaccinated mice for all other strains generated titers that were at the limit of assay detection (LOD) or 100, the starting serum dilution. Individual OPA responses to the four-valent O-antigens largely parallel the IgG binding antibody titers (FIG. 41, Table 38). For example, the significant positive impact of the liposomal MPLA/QS21 formulation on the immunogenicity of the FimH-DSG 4-valent O-antigen combination was confirmed in OPAs with encapsulated serotype O1a, O2, and O6 strains, which reported responder rates of 70% or greater after two vaccine doses. In contrast, only after a third dose did the O25b:K5 OPA strain report titers reaching this level of functional activity with the MPLA/QS21 formulation. Compared with their encapsulated O6:K1 and O25b:K5 counterparts, unencapsulated O6 and O25b strains generated higher OPA titers and responder rates, especially among non-adjuvanted groups of mice vaccinated with O-antigens alone or the combined FimH-DSG/4-valent O-antigens. This greater sensitivity is consistent with the absence of respective K2 or K5 capsules shown previously to confer resistance to phagocytosis (Burns S M, Hull S I. Loss of resistance to ingestion and phagocytic killing by O(-) and K(-) mutants of a uropathogenic *Escherichia coli* O75:K5 strain. Infection and immunity 1999; 67:3757-62; Buckles E L, Wang X, Lane M C, et al. Role of the K2 Capsule in *Escherichia coli* Urinary Tract Infection and Serum Resistance. The Journal of infectious diseases 2009; 199:10.1086/598524).

*E. coli* and *K. pneumoniae* polymannan O-antigens involves a different mechanism of O-unit translocation and chain synthesis than other *E. coli* O-antigens. In this case chain elongation is regulated by the biosynthetic WbdA-WbdD complex (King J D, Berry S, et al. Proceedings of the National Academy of Sciences 2014; 111:6407-12), which is distinct from the Wzx/Wzy-dependent pathway where chain length is controlled by WzzB or FepE enzymes. As a consequence, the native polymannan O-antigens can only be produced in their short form, which requires different bioprocesses methods for purification and carrier protein conjugation than the engineered long *E. coli* O-antigens. The same mechanism and limitation applies to the predominant

TABLE 39

VAC-2020-PRL-EC-1679: Influence of Adjuvant and FimH-DSG on O-antigen Specific Serum OPA GMTs

| Vaccination Group | O1a:K1 OPA | | O2:K1 OPA | | O6:K2 | | O6:K- | | O25b:K5 | | O25b:K- | |
|---|---|---|---|---|---|---|---|---|---|---|---|---|
| | PD2 | PD3 | PD2 | PD3 | PD2 | PD3 | PD2 | PD3 | PD2 | PD3 | PD2 | PD3 |
| 4v O-Ag | 119 | 348 | 191 | 1108 | 50 | 155 | 383 | 1931 | 68 | 461 | 1516 | 14260 |
| FimH-DSG + 4v O-Ag no adjuvant | 157 | 575 | 161 | 385 | 98 | 1256 | 760 | 5375 | 50 | 443 | 223 | 9000 |
| FimH-DSG + 4v O-Ag in liposomal MPLA | 675 | 979 | 499 | 1525 | 510 | 388 | 714 | 1104 | 91 | 457 | 1382 | 28204 |
| FimH-DSG + 4v O-Ag in liposomal MPLA/QS21 | 6978 | 7714 | 984 | 8610 | 1064 | 737 | 1681 | 1961 | 110 | 606 | 2593 | 19462 |

Conclusion

Taken together, the results of these studies support the use of mammalian-produced FimH-DSG (or derived mutant variants) in combination with O-antigen glycoconjugates and QS21 adjuvant as a vaccine composition to prevent invasive *E. coli* infections. Such a formulation may be advantageous for preventing recurrent UTI infections and sepsis in elderly patients. Results confirm the benefit of QS21 adjuvant for enhancing the functional immune response to FimH-DSG and the long O25b O-antigen, which are individually less immunogenic than analogous serotype O1a, O2, and O6 O-antigen glycoconjugates in mice.

Example 36: Antibodies Elicited by CRM197 Conjugates of *E. coli* Serotype O8 and O9 O-Antigens Show Cross-Protective Bactericidal Activity Against *K. pneumoniae* Serotype O5 and O3 Invasive Isolates This Example demonstrates that antibodies elicited by short single-end native $CRM_{197}$ polymannan conjugates of *E. coli* serotype O8 and O9 O-antigens are bactericidal and cross-protective against *Klebsiella* O5 and O3 strains that express equivalent or related O-antigens. *E. coli* and *K. pneumoniae* share common polymannan O-antigens which are synthesized by enzymes encoded by highly homologous biosynthetic gene clusters. The *E. coli* O8 and O9 O-antigen polysaccharides are linear mannose homopolymers whose repeat units differ in their monosaccharide linkages and in the number of residues. Their counterparts in *K. pneumoniae* are the serotype O5 and O3 O-antigens. Biosynthesis of the

*K. pneumoniae* serotype O1 and O2 O-antigens, which are polygalactans comprised of galactose residues.

Figure 33:
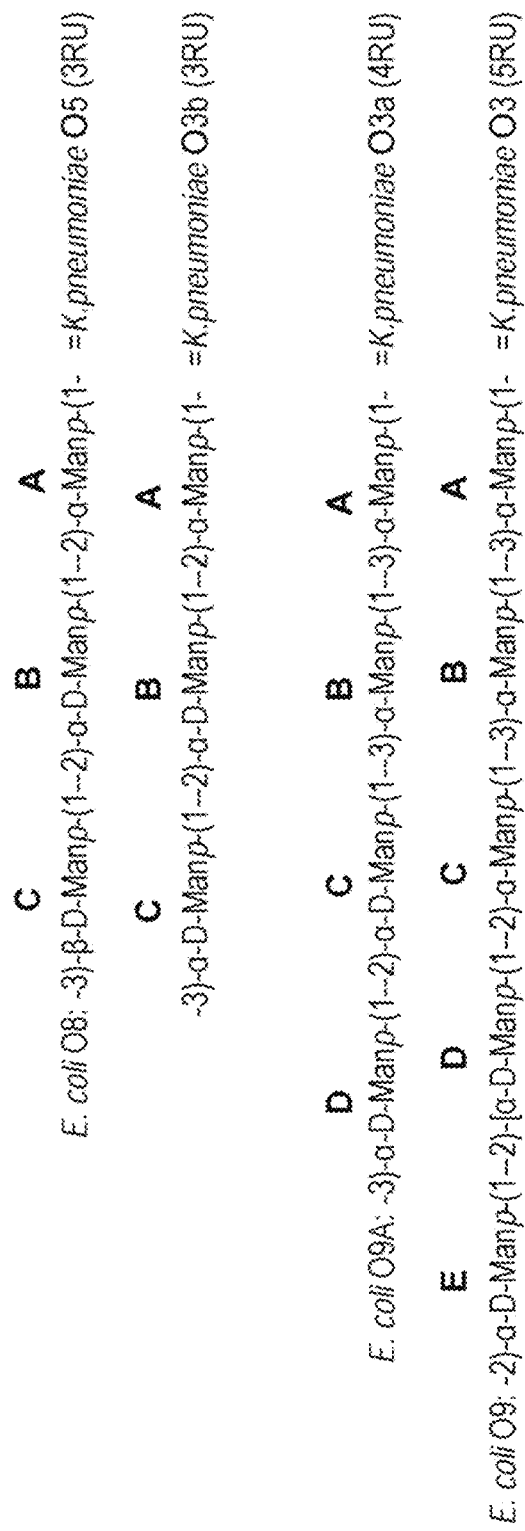
FIG. 33—depicts structures of the repeat unit (RU) of *E. coli* and *K. pneumoniae* polymannan O-antigens. Legend: Trimeric *E. coli* O8 and *K. pneumoniae* O5 are identical, as are the terameric *E. coli* O9A/*K. pneumoniae* O3a and pentameric *E. coli* O9/*K. pneumoniae* O3. Differentiation of the *K. pneumoniae* O3 subtypes at the level of biosynthetic enzyme sequences is described in Guachalla L M et al. (Scientific Reports 2017; 7:6635).

The structural relationship between these O-antigens and their subtypes is shown in FIG. 33. The *E. coli* O8 and *K. pneumoniae* O5 O-antigens are identical (Vinogradov E, et al. J Biol Chem 2002; 277:25070-81). *E. coli* O9 and *K. pneumoniae* O3 O-antigens share common tetrameric O9a/O3a and pentameric O9/O3 repeat unit subtypes, while the trimeric O3b subtype is only found in *K. pneumoniae*. These subtypes can be identified serologically and genotypically (Guachalla L M, et al. Scientific Reports 2017; 7:6635). Serotype O3a loci are distinguished by a single point mutation in wbdA (C80R). An analogous point mutation in the *E. coli* O9 wbdA enzyme (C55R) converts the O9 polysaccharide into O9a (Kido N, Kobayashi H. Journal of bacteriology 2000; 182:2567-73). The O3b subtype has sufficient nucleotide divergence in the sequence of the WbdD enzyme to necessitate a separate reference sequence. The Kaptive web algorithm (Wick R R, et al. J Clin Microbiol 2018; 56), implemented into Pfizer's BigSdb whole genome sequencing (WGS) pipeline, designates O3 loci as either O3/O3a (covered by the same reference sequence) or O3b.

Materials and Methods a. Production of *E. coli* Serotype O8 and O9 $CRM_{197}$ Immune Sera in Rabbits Two groups of four female New Zealand White rabbits each were used for the study run at Covance. Animals received 10 μg/animal of serotype O8 or O9 $CRM_{197}$ conjugate per dose with CFA/IFA as adjuvant. Native O8 and O9 O-antigens were conjugated using single-end chemistry. Each 1 mL dose of 10 μg of antigen was split across two subcutaneous vaccination sites. Vaccinations were given at weeks 0, 6 and 14, with blood draws at weeks 7 and 15, which correspond to post-dose two (PD2) and post-dose three (PD3) timepoints.

b. Bacterial Strains

*E. coli* and *K. pneumoniae* clinical isolates were obtained from the Pfizer-sponsored Antimicrobial Testing Leadership and Surveillance (ATLAS) collection which is maintained by the International Health Management Associates (IHMA) clinical lab. Strains were genotypically characterized by whole genome sequencing (WGS) using the Miseq platform (Illumina). WGS data was used to generate multi-locus-sequence type (MLST) information using established *E. coli* and *K. pneumoniae* schemes integrated into the BigDdb platform (Wirth T, et al. Molecular microbiology 2006; 60:1136-51; Jolley K A, et al. Wellcome Open Res 2018; 3:124; Diancourt L, et al. Journal of clinical microbiology 2005; 43:4178-82). Embedded in silico serotyping algorithms for *E. coli* and *K. pneumoniae* were used to predict O-antigen serotype (Wick R R, et al. J Clin Microbiol 2018; 56; Joensen K G, et al. J Clin Microbiol 2015; 53:2410-26).

TABLE 40

Clinical isolates used for O-antigen production or development of bactericidal assays

| ID | Species | MLST ST | Serotype (subtype) | Source |
|---|---|---|---|---|
| EC0130 | *E. coli* | 162 | O8 | Blood |
| EC0423 | *E. coli* | 46 | O9a | Blood |
| EC0305 | *E. coli* | 448 | O8 | Blood |
| KP0121 | *K. pneumoniae* | 279 | O5 | Blood |
| EC0611 | *E. coli* | New | O9a | UTI, Kidney |
| KP0009 | *K. pneumoniae* | 37 | O3b | UTI, Bladder | c. *E. coli* O8 and O9 $CRM_{197}$ conjugates

Serotype O8 and O9a O-antigen polysaccharides were extracted and purified from strains EC0130 and EC0423, respectively (Table 40). The conjugation process involves selective activation of the Kdo monosaccharide present on the reducing end of the short native *E. coli* O8 and O9 O-antigens with a disulfide amine linker. Upon unmasking of thiol functional group, it is then conjugated to bromo activated $CRM_{197}$ protein as described Example 26 set forth herein.

d. Bactericidal Assays

Pre-frozen *E. coli* and *K. pneumoniae* stocks were prepared by growing strains in DMEM or LB media to an $OD_{600}$ of between 0.5 and 1.0 and glycerol was added to a final concentration of 20% prior to freezing. Specific assay conditions varied according to conditions optimized for each bacterial strain. Pre-titered thawed bacteria were diluted to $1 \times 10^5$ CFU/ml in OPA buffer (Hanks Balanced Salt Solution (Life Technologies) and 0.1% gelatin) and 20 μL (103 CFU) of the bacterial suspension was opsonized with 20 μL of serially diluted sera for 30 min at RT in a tissue culture microplate. Subsequently, 10 μl of complement (Baby Rabbit Serum or IgG/IgM depleted human serum, Pel-Freez) and 20 μL of HL-60 cells (at 100-200:1 ratio) were added to each well with OPA buffer to a final volume of 100 μL. The reaction mixture was shaken for 60 min at 37° C. in a 5% $CO_2$ incubator. In some cases, bacteria were directly combined with complement and HL60s without the pre-opsonization step and shaken for 60 min at 37° C. under 5% $CO_2$. After the incubation, 10 μL of each reaction was transferred into the corresponding wells of a prewetted Millipore MultiScreen HTS HV filter plate containing 100 μL water. After vacuum filtering the liquid, 100 μL of 50% bacterial growth media was applied and filtered, and the plate incubated overnight at 37° C. in a sealed zip-lock bag. The next day microcolonies were enumerated after staining with Coomassie dye using an ImmunoSpot® analyzer and ImmunoCapture software. In the case of the *E. coli* serotype O9 assay, the OPA was miniaturized for 50 μL reaction reactions volumes in the 384-well format. To establish the specificity of OPA activity, immune sera were preincubated with purified O-antigen polysaccharide prior to the opsonization step. The OPA assay included control reactions without HL60 cells or complement, to demonstrate dependence of any observed killing on these components. For the *Klebsiella* serotype O5 assay where presence of HL60s had no impact, serum bactericidal reactions were run in the absence of effector cells.

Results a. *E. coli* and *K. pneumoniae* Strain Selection for Bactericidal Assays Bacterial clinical strains were initially selected after confirming O-antigen expression by LPS profiling (by SDS-PAGE), and O-antigen surface accessibility by flow cytometry with O-antigen specific rabbit antisera. Next, empiric screening of serum complement was done to identify individual compatible lots across a range of concentrations that provided a suitable balance of low levels of non-specific killing combined with a high degree of susceptibility in the presence of immune sera. Additional assay optimization parameters included adjusting the ratio of HL60 effector cell to bacteria, shaker speed, presence/absence of plate sealer and inclusion of an opsonization preincubation step.

b. *E. coli* O8 and *K. pneumoniae* O5 O-Antigen Immune Serum Cross-Protection and Specificity

Figure 34A:
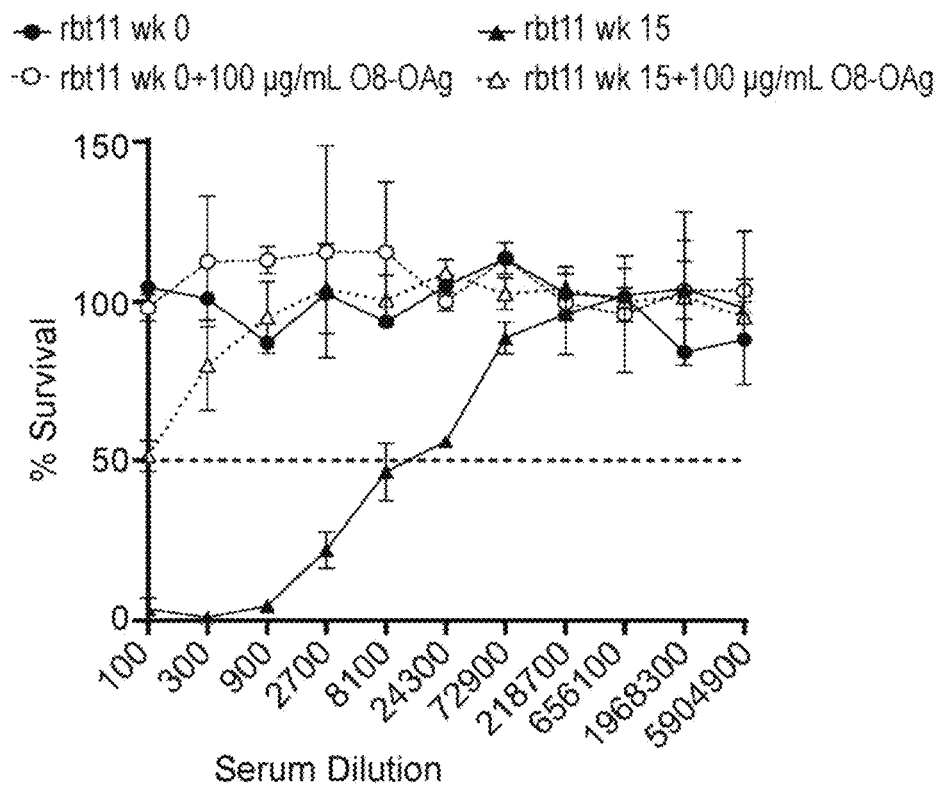
FIG. 34A-34B—depict *E. coli* serotype O8 immune sera is bactericidal against an invasive *K. pneumoniae* serotype O5 strai. Legend: Rabbit immune sera elicited by an *E. coli* serotype O8 O-antigen CRM$_{197}$ conjugate was evaluated in bactericidal assays with an *E. coli* O8 strain (FIG. 34A) and a *K. pneumoniae* O5 strain (FIG. 34B). Potent opsonophagocytic assay (OPA) activity against an *E. coli* O8 strain was observed after two vaccine doses (week 15) that was absent following preadsorption with unconjugated O8 polysaccharide (O8-OAg), or with matched pre-immune sera (week 0). The same rabbit immune serum showed antigen-specific serum bactericidal activity (SBA) against the *K. pneumoniae* O5 strain. BRC—baby rabbit complement, hC—IgG/IgM depleted human sera as complement source.
Figure 34B:
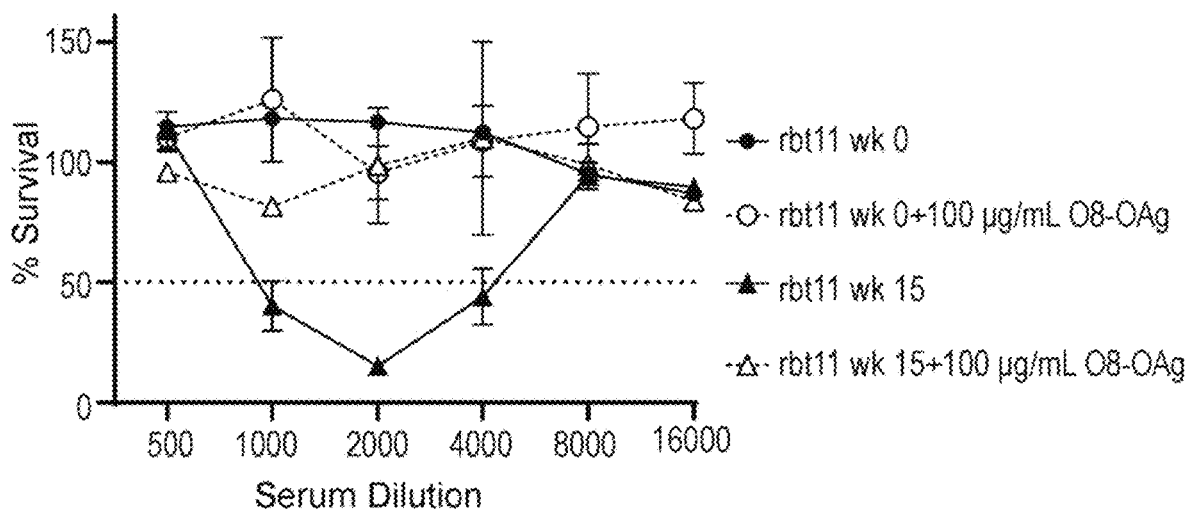

*E. coli* O8 strain EC0305 and *K. pneumoniae* O5 strain KP0121 were selected for assay development. Both are blood isolates. EC0305 is resistant to cephalosporins and tetracycline while KP0121 is resistant to ampicillin. An OPA assay was developed for the *E. coli* O8 strain EC0305 with conditions including 3.0% BRC, a 1:100 bacteria to HL60 ratio, and a single step 60 min OPA incubation reaction. As the bactericidal activity of the *K. pneumoniae* O5 strain KP0121 in the presence of immune sera was found to be independent of HL60 effector cells, an SBA was developed. In this case, the SBA reaction required the use of 10% depleted human serum as source of complement. Results of bactericidal assays with these *E. coli* O8 and *K. pneumoniae* O5 strains are shown in FIG. 34A-34B. In the *E. coli* serotype O8 OPA, rabbit immune serum generated after two doses of O8-$CRM_{197}$ conjugate showed potent O-antigen specific killing that was blocked by preadsorption of the immune serum with free O8 O-antigen polysaccharide. Complete killing was observed at serum dilutions of less than 1:1000. Matched pre-immune sera from the same rabbit was inactive. The same rabbit sera was evaluated in the *K. pneumoniae* O5 SBA, and found to be similarly bactericidal at a 1:2000 serum dilution. Killing was blocked by free O8 O-antigen and absent with the pre-immune serum. In this case a serum matrix prozone masked SBA activity at serum dilutions of less than 1:1000.

c. *E. coli* O9 and *K. pneumoniae* O3 OPA O-Antigen Immune Serum Cross-Protection and Specificity

*E. coli* O9a strain EC0611 and *K. pneumoniae* O3b strain KP0009 were selected for assay development. EC0611 is resistant to ampicillin, while KP0009 is resistant to cephalosporins, fluoroquinolones, and tetracycline. Both are UTI isolates from kidney and bladder infections, respectively.

The O9a O-antigen used to generate the CRM$_{197}$ conjugate and resulting immune serum has the tetrametic polymannan repeat unit structure and is identical to the O9a EC0611 assay strain O-antigen; however, it is structurally heterologous to the *K. pneumoniae* O3b O-antigen KP0009 assay strain, which is predicted to express the shorter trimeric repeat unit based on the sequence of its wbdD gene (See FIG. 33). Results of OPAs with the *E. coli* O9a and *K. pneumoniae* O3b strains show that anti-*E. coli* O9a immune serum is potent against both (FIG. 35A-35B). Complete killing in the OPAs was observed at serum dilutions of less than 1:8,000 for the *E. coli* O9a strain and at less than 1:1, 600 for the *Klebsiella* O3b strain. Specificity was demonstrated by the lack of activity upon preadsorption of serum with free O9a O-antigen and with the matched-pre-immune serum.

Conclusion

*E. coli* serotype O8 and O9 polymannan CRM$_{197}$ conjugates elicit functional antibodies that are capable of killing not only homologous *E. coli* clinical strains but also *Klebsiella* serotype O5 and O3 strains in bactericidal assays. Results confirm that these conjugates elicit antibodies that are cross-protective against isolates of both species expressing structurally related polymannan O-antigens.

The following clauses describe additional embodiments of the invention:

C1. A composition comprising a polypeptide derived from FimH or a fragment thereof; and a saccharide comprising a structure selected from any one of Formula O1 (e.g., Formula O1A, Formula O1B, and Formula O1C), Formula O2, Formula O3, Formula O4 (e.g., Formula O4:K52 and Formula O4:K6), Formula O5 (e.g., Formula O5ab and Formula O5ac (strain 180/C3)), Formula O6 (e.g., Formula O6:K2; K13; K15 and Formula O6:K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56 Formula O57, Formula O58, Formula O59, Formula O60, Formula O61, Formula O62, Formula 62D$_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 1 to 100.

C2. The composition according to clause C1, wherein the saccharide comprises a structure selected from Formula O1 (e.g., Formula O1A, Formula O1B, and Formula O1C), Formula O2, Formula O3, Formula O4 (e.g., Formula O4:K52 and Formula O4:K6), Formula O5 (e.g., Formula O5ab and Formula O5ac (strain 180/C3)), Formula O6 (e.g., Formula O6:K2; K13; K15 and Formula O6:K54), Formula O7, Formula O10, Formula O16, Formula O17, Formula O18 (e.g., Formula O18A, Formula O18ac, Formula O18A1, Formula O18B, and Formula O18B1), Formula O21, Formula O23 (e.g., Formula O23A), Formula O24, Formula O25 (e.g., Formula O25a and Formula O25b), Formula O26, Formula O28, Formula O44, Formula O45 (e.g., Formula O45 and Formula O45rel), Formula O55, Formula O56, Formula O58, Formula O64, Formula O69, Formula O73 (e.g., Formula O73 (strain 73-1)), Formula O75, Formula O77, Formula O78, Formula O86, Formula O88, Formula O90, Formula O98, Formula O104, Formula O111, Formula O113, Formula O114, Formula O119, Formula O121, Formula O124, Formula O125, Formula O126, Formula O127, Formula O128, Formula O136, Formula O138, Formula O141, Formula O142, Formula O143, Formula O147, Formula O149, Formula O152, Formula O157, Formula O158, Formula O159, Formula O164, Formula O173, Formula 62D$_1$, Formula O22, Formula O35, Formula O65, Formula O66, Formula O83, Formula O91, Formula O105, Formula O116, Formula O117, Formula O139, Formula O153, Formula O167, and Formula O172, wherein n is an integer from 20 to 100.

C3. The composition according to clause C2, wherein the saccharide comprises a structure selected from Formula O1 (e.g., Formula O1A, Formula O1B, and Formula O1C), Formula O2, Formula O3, Formula O4 (e.g., Formula O4:K52 and Formula O4:K6), Formula O5 (e.g., Formula O5ab and Formula O5ac (strain 180/C3)), Formula O6 (e.g., Formula O6:K2; K13; K15 and Formula O6:K54), Formula O7, Formula O10, Formula O16, Formula O17, Formula O18 (e.g., Formula O18A, Formula O18ac, Formula O18A1, Formula O18B, and Formula O18B1), Formula O21, Formula O23 (e.g., Formula O23A), Formula O24, Formula O25 (e.g., Formula O25a and Formula O25b), Formula O26, Formula O28, Formula O44, Formula O45 (e.g., Formula O45 and Formula O45rel), Formula O55, Formula O56, Formula O58, Formula O64, Formula O69, Formula O73 (e.g., Formula O73 (strain 73-1)), Formula O75, Formula O77, Formula O78, Formula O86, Formula O88, Formula O90, Formula O98, Formula O104, Formula O111, Formula O113, Formula O114, Formula O119, Formula O121, Formula O124, Formula O125, Formula O126, Formula O127, Formula O128, Formula O136, Formula O138, Formula O141, Formula O142, Formula O143, Formula O147, Formula O149, Formula O152, Formula O157, Formula O158, Formula O159, Formula O164, Formula O173, and Formula 62D$_1$, wherein n is an integer from 20 to 100.

C4. The composition according to clause C2, comprising a structure selected from Formula O1 (e.g., Formula O1A, Formula O1B, and Formula O1C), Formula O2, Formula O6 (e.g., Formula O6:K2; K13; K15 and Formula O6:K54), Formula O15, Formula O16, Formula O21, Formula O25 (e.g., Formula O25a and Formula O25b), and Formula O75.

C5. The composition according to clause C2, comprising a structure selected from Formula O4, Formula O11, Formula O21, and Formula O75.

C6. The composition according to clause C1, wherein the saccharide does not comprise a structure selected from Formula O8, Formula O9a, Formula O9, Formula O20ab, Formula O20ac, Formula O52, Formula O97, and Formula O101.

C7. The composition according to clause C1, wherein the saccharide does not comprise a structure selected from Formula O12.

C8. The composition according to clause C4, wherein the saccharide is produced by expressing a wzz family protein in a Gram-negative bacterium to generate said saccharide.

C9. The composition according to clause C8, wherein the wzz family protein is selected from the group consisting of wzzB, wzz, wzz$_{SF}$, wZZ$_{ST}$, fepE, wzz$_{fepE}$, wzz1 and wzz2.

C10. The composition according to clause C8, wherein the wzz family protein is wzzB.

C11. The composition according to clause C8, wherein the wzz family protein is fepE.

C12. The composition according to clause C8, wherein the wzz family protein is wzzB and fepE.

C13. The composition according to clause C8, wherein the wzz family protein is derived from *Salmonella enterica*.

C14. The composition according to clause C8, wherein the wzz family protein comprises a sequence selected from any one of SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, and SEQ ID NO: 39.

C15. The composition according to clause C8, wherein the wzz family protein comprises a sequence having at least 90% sequence identity to any one of SEQ ID NO: 30, SEQ ID NO: 31, SEQ ID NO: 32, SEQ ID NO: 33, SEQ ID NO: 34.

C16. The composition according to clause C8, wherein the wzz family protein comprises a sequence selected from any one of SEQ ID NO: 35, SEQ ID NO: 36, SEQ ID NO: 37, SEQ ID NO: 38, and SEQ ID NO: 39.

C17. The composition according to clause C1, wherein the saccharide is synthetically synthesized.

C18. The composition according to any one of clauses C1 to C17, wherein the saccharide further comprises an *E. coli* R1 moiety.

C19. The composition according to any one of clauses C1 to C17, wherein the saccharide further comprises an *E. coli* R2 moiety.

C20. The composition according to any one of clauses C1 to C17, wherein the saccharide further comprises an *E. coli* R3 moiety.

C21. The composition according to any one of clauses C1 to C17, wherein the saccharide further comprises an *E. coli* R4 moiety.

C22. The composition according to any one of clauses C1 to C17, wherein the saccharide further comprises an *E. coli* K-12 moiety.

C23. The composition according to any one of clauses C1 to C22, wherein the saccharide further comprises a 3-deoxy-d-manno-oct-2-ulosonic acid (KDO) moiety.

C24. The composition according to any one of clauses C1 to C17, wherein the saccharide does not further comprise an *E. coli* R1 moiety.

C25. The composition according to any one of clauses C1 to C17, wherein the saccharide does not further comprise an *E. coli* R2 moiety.

C26. The composition according to any one of clauses C1 to C17, wherein the saccharide does not further comprise an *E. coli* R3 moiety.

C27. The composition according to any one of clauses C1 to C17, wherein the saccharide does not further comprise an *E. coli* R4 moiety.

C28. The composition according to any one of clauses C1 to C17, wherein the saccharide does not further comprise an *E. coli* K-12 moiety.

C29. The composition according to any one of clauses C1 to C22, wherein the saccharide does not further comprise a 3-deoxy-d-manno-oct-2-ulosonic acid (KDO) moiety.

C30. The composition according to any one of clauses C1 to C23, wherein the saccharide does not comprise a Lipid A.

C31. The composition according to any one of clauses C1 to C30, wherein the polysaccharide has a molecular weight of between 10 kDa and 2,000 kDa, or between 50 kDa and 2,000 kDa.

C32. The composition according to any one of clauses C1 to C31, wherein the saccharide has an average molecular weight of 20-40 kDa.

C33. The composition according to any one of clauses C1 to C32, wherein the saccharide has an average molecular weight of 40,000 to 60,000 kDa.

C34. The composition according to any one of clauses C1 to C33, wherein n is an integer 31 to 90.

C35. A composition comprising a polypeptide derived from FimH or fragment thereof; and a conjugate comprising a saccharide covalently bound a carrier protein, wherein the saccharide is derived from *E. coli*.

C36. A composition comprising a polypeptide derived from FimH or fragment thereof; and a conjugate comprising a saccharide according to any one of clause C1 to clause C34, covalently bound a carrier protein.

C37. A composition comprising a polypeptide derived from FimH or fragment thereof; and a conjugate according to any one of clause C35 to clause C36, wherein the carrier protein is selected from any one of poly(L-lysine), CRM$_{197}$, diphtheria toxin fragment B (DTFB), DTFB C8, Diphtheria toxoid (DT), tetanus toxoid (TT), fragment C of TT, pertussis toxoid, cholera toxoid, or exotoxin A from *Pseudomonas aeruginosa*; detoxified Exotoxin A of *P. aeruginosa* (EPA), maltose binding protein (MBP), detoxified hemolysin A of *S. aureus*, clumping factor A, clumping factor B, Cholera toxin B subunit (CTB), *Streptococcus pneumoniae* Pneumolysin and detoxified variants thereof, *C. jejuni* AcrA, *C. jejuni* natural glycoproteins and Streptococcal C5a peptidase (SCP).

C38. The composition according to any one of clause C35 to clause C37, wherein the carrier protein is CRM$_{197}$.

C39. The composition according to any one of clause C35 to clause C37, wherein the carrier protein is tetanus toxoid (TT).
C40. The composition according to any one of clause C35 to clause C37, wherein the carrier protein is poly(L-lysine).
C41. The composition according to any one of clause C35 to clause C39, wherein the conjugate is prepared by reductive amination.
C42. The composition according to any one of clause C35 to clause C39, wherein the conjugate is prepared by CDAP chemistry.
C43. The composition according to any one of clause C35 to clause C39, wherein the conjugate is a single-end linked conjugated saccharide.
C44. The composition according to any one of clause C35 to clause C39, wherein the saccharide is conjugated to the carrier protein through a (2-((2-oxoethyl)thio)ethyl)carbamate (eTEC) spacer.
C45. The composition according to clause C44, wherein the saccharide is conjugated to the carrier protein through a (2-((2-oxoethyl)thio)ethyl)carbamate (eTEC) spacer, wherein the saccharide is covalently linked to the eTEC spacer through a carbamate linkage, and wherein the carrier protein is covalently linked to the eTEC spacer through an amide linkage.
C46. The composition according to any one of clause C44 to clause C45, wherein the $CRM_{197}$ comprises 2 to 20, or 4 to 16, lysine residues covalently linked to the polysaccharide through an eTEC spacer.
C47. The composition according to any one of clause C35 to clause C46, wherein the saccharide:carrier protein ratio (w/w) is between 0.2 and 4.
C48. The composition according to any one of clause C35 to clause C46, wherein the ratio of saccharide to protein is at least 0.5 and at most 2.
C49. The composition according to any one of clause C35 to clause C46, wherein the ratio of saccharide to protein is between 0.4 and 1.7
C50. The composition according to any one of clause C43 to clause C49, wherein the saccharide is conjugated to the carrier protein through a 3-deoxy-d-manno-oct-2-ulosonic acid (KDO) residue.
C51. A composition comprising a polypeptide derived from FimH or fragment thereof; and a conjugate comprising a saccharide covalently bound a carrier protein, wherein the saccharide comprises a structure selected from Formula O8, Formula O9a, Formula O9, Formula O20ab, Formula O20ac, Formula O52, Formula O97, and Formula O101, wherein n is an integer from 1 to 10.
C52. A composition comprising a polypeptide derived from FimH or fragment thereof; and a saccharide according to any one of clause C1 to clause C34, and a pharmaceutically acceptable diluent.
C53. A composition comprising a polypeptide derived from FimH or fragment thereof; and a conjugate according to any one of clause C35 to clause C51, and a pharmaceutically acceptable diluent.
C54. The composition according to clause C53, comprising at most about 25% free saccharide as compared to the total amount of saccharide in the composition.
C55. The composition according to any one of clause C52 to clause C53, further comprising an adjuvant.
C56. The composition according to any one of clause C52 to clause C53, further comprising aluminum.
C57. The composition according to any one of clause C52 to clause C53, further comprising QS-21.
C58. The composition according to any one of clause C52 to clause C53, further comprising a CpG oligonucleotide.
C59. The composition according to any one of clause C52 to clause C53, wherein the composition does not include an adjuvant.
C60. A composition comprising a polypeptide derived from FimH or fragment thereof; and a saccharide derived from E. coli, conjugated to a carrier protein through a (2-((2-oxoethyl)thio)ethyl)carbamate (eTEC) spacer, wherein the polysaccharide is covalently linked to the eTEC spacer through a carbamate linkage, and wherein the carrier protein is covalently linked to the eTEC spacer through an amide linkage.
C61. The composition according to clause C60, wherein the saccharide is an O-antigen derived from E. coli.
C62. The composition according to clause C60, further comprising a pharmaceutically acceptable excipient, carrier or diluent.
C63. The composition according to clause C60, wherein the saccharide is an O-antigen derived from E. coli.
C64. A composition comprising a polypeptide derived from FimH or fragment thereof; and a saccharide according to any one of clause C1 to clause C17, conjugated to a carrier protein through a (2-((2-oxoethyl)thio)ethyl)carbamate (eTEC) spacer, wherein the polysaccharide is covalently linked to the eTEC spacer through a carbamate linkage, and wherein the carrier protein is covalently linked to the eTEC spacer through an amide linkage.
C65. A composition comprising a polypeptide derived from FimH or fragment thereof; and (i) a conjugate of an E. coli O25B antigen covalently coupled to a carrier protein, (ii) a conjugate of an E. coli O1A antigen covalently coupled to a carrier protein, (iii) a conjugate of an E. coli O2 antigen covalently coupled to a carrier protein, and (iv) a conjugate of an O6 antigen covalently coupled to a carrier protein, wherein the E. coli O25B antigen comprises the structure of Formula O25B, wherein n is an integer greater than 30.
C66. The composition of clause C65, wherein the carrier protein is selected from any one of poly(L-lysine), $CRM_{197}$, diphtheria toxin fragment B (DTFB), DTFB C8, Diphtheria toxoid (DT), tetanus toxoid (TT), fragment C of TT, pertussis toxoid, cholera toxoid, or exotoxin A from *Pseudomonas aeruginosa*; detoxified Exotoxin A of *P. aeruginosa* (EPA), maltose binding protein (MBP), detoxified hemolysin A of *S. aureus*, clumping factor A, clumping factor B, Cholera toxin B subunit (CTB), *Streptococcus pneumoniae* Pneumolysin and detoxified variants thereof, *C. jejuni* AcrA, *C. jejuni* natural glycoproteins and Streptococcal C5a peptidase (SCP).
C67. A composition comprising a polypeptide derived from FimH or fragment thereof; and (i) a conjugate of an E. coli O25B antigen covalently coupled to a carrier protein, (ii) a conjugate of an E. coli O4 antigen covalently coupled to a carrier protein, (iii) a conjugate of an E. coli O11 antigen covalently coupled to a carrier protein, and (iv) a conjugate of an O21 antigen covalently coupled to a carrier protein, wherein the E. coli O25B antigen comprises the structure of Formula O75, wherein n is an integer greater than 30.
C68. The composition of clause C67, wherein the carrier protein is selected from any one of poly(L-lysine), $CRM_{197}$, diphtheria toxin fragment B (DTFB), DTFB C8, Diphtheria toxoid (DT), tetanus toxoid (TT), fragment C of TT, pertussis toxoid, cholera toxoid, or exotoxin A from *Pseudomonas aeruginosa*; detoxified Exotoxin A of *P. aeruginosa* (EPA), maltose binding protein (MBP), detoxified hemolysin A of *S. aureus*, clumping factor A, clumping factor B, Cholera toxin B subunit (CTB), *Streptococcus pneumoniae*

Pneumolysin and detoxified variants thereof, *C. jejuni* AcrA, *C. jejuni* natural glycoproteins and Streptococcal C5a peptidase (SCP).

C69. A method of making a composition comprising a polypeptide derived from FimH or fragment thereof; and a conjugate comprising a saccharide conjugated to a carrier protein through a (2-((2-oxoethyl)thio)ethyl)carbamate (eTEC) spacer, comprising the steps of a) reacting a saccharide with 1,1'-carbonyl-di-(1,2,4-triazole) (CDT) or 1,1'-carbonyldiimidazole (CDI), in an organic solvent to produce an activated saccharide; b) reacting the activated saccharide with cystamine or cysteamine or a salt thereof, to produce a thiolated saccharide; c) reacting the thiolated saccharide with a reducing agent to produce an activated thiolated saccharide comprising one or more free sulfhydryl residues; d) reacting the activated thiolated saccharide with an activated carrier protein comprising one or more α-haloacetamide groups, to produce a thiolated saccharide-carrier protein conjugate; and e) reacting the thiolated saccharide-carrier protein conjugate with (i) a first capping reagent capable of capping unconjugated α-haloacetamide groups of the activated carrier protein; and/or (ii) a second capping reagent capable of capping unconjugated free sulfhydryl residues; whereby an eTEC linked glycoconjugate is produced, wherein the saccharide is derived from *E. coli*; further comprising expressing a polynucleotide encoding a polypeptide derived from FimH or fragment thereof in a recombinant mammalian cell, and isolating said polypeptide or fragment thereof.

C70. The method according to clause C69, comprising making the composition according to any one of clause C1 to clause C34.

C71. The method according to any of one clause C69 to clause C70, wherein the capping step e) comprises reacting the thiolated saccharide-carrier protein conjugate with (i) N-acetyl-L-cysteine as a first capping reagent, and/or (ii) iodoacetamide as a second capping reagent.

C72. The method according to any of one clause C69 to clause C71, further comprising a step of compounding the saccharide by reaction with triazole or imidazole to provide a compounded saccharide, wherein the compounded saccharide is shell frozen, lyophilized and reconstituted in an organic solvent prior to step a).

C73. The method according to any of one clause C69 to clause C72, further comprising purification of the thiolated polysaccharide produced in step c), wherein the purification step comprises diafiltration.

C74. The method according to any of one clause C69 to clause C73, wherein the method further comprises purification of the eTEC linked glycoconjugate by diafiltration.

C75. The method according to any of one clause C69 to clause C74, wherein the organic solvent in step a) is a polar aprotic solvent selected from any one of dimethyl sulfoxide (DMSO), dimethylformamide (DMF), dimethylacetamide (DMA), N-methyl-2-pyrrolidone (NMP), acetonitrile, 1,3-Dimethyl-3,4,5,6-tetrahydro-2(1H)-pyrimidinone (DMPU) and hexamethylphosphoramide (HMPA), or a mixture thereof.

C76. A medium comprising $KH_2PO_4$, $K_2HPO_4$, $(NH_4)_2SO_4$, sodium citrate, $Na_2SO_4$, aspartic acid, glucose, $MgSO_4$, $FeSO_4 \cdot 7H_2O$, $Na_2MoO_4 \cdot 2H_2O$, $H_3BO_3$, $CoCl_2 \cdot 6H_2O$, $CuCl_2 \cdot 2H_2O$, $MnCl_2 \cdot 4H_2O$, $ZnCl_2$ and $CaCl_2 \cdot 2H_2O$.

C77. The medium according to clause C76, wherein the medium is used for culturing *E. coli*.

C78. A method for producing a saccharide according to any one of clause C1 to clause C34, comprising culturing a recombinant *E. coli* in a medium; producing said saccharide by culturing said cell in said medium; whereby said cell produces said saccharide.

C79. The method according to clause C78, wherein the medium comprises an element selected from any one of $KH_2PO_4$, $K_2HPO_4$, $(NH_4)_2SO_4$, sodium citrate, $Na_2SO_4$, aspartic acid, glucose, $MgSO_4$, $FeSO_4 \cdot 7H_2O$, $Na_2MoO_4 \cdot 2H_2O$, $H_3BO_3$, $CoCl_2 \cdot 6H_2O$, $CuCl_2 \cdot 2H_2O$, $MnCl_2 \cdot 4H_2O$, $ZnCl_2$ and $CaCl_2 \cdot 2H_2O$.

C80. The method according to clause C78, wherein the medium comprises soy hydrolysate.

C81. The method according to clause C78, wherein the medium comprises yeast extract.

C82. The method according to clause C78, wherein the medium does not further comprise soy hydrolysate and yeast extract.

C83. The method according to clause C78, wherein the *E. coli* cell comprises a heterologous wzz family protein selected from any one of wzzB, wzz, $wzz_{SF}$, $wZZ_{ST}$, fepE, $wzz_{fepE}$, wZZ1 and wzz2.

C84. The method according to clause C78, wherein the *E. coli* cell comprises a *Salmonella enterica* wzz family protein selected from any one of wzzB, wzz, $wzz_{SF}$, $wZZ_{ST}$, fepE, $wzz_{fepE}$, wzz1 and wzz2.

C85. The method according to clause C84, wherein the wzz family protein comprises a sequence selected from any one of SEQ ID NO: 20, SEQ ID NO: 21, SEQ ID NO: 22, SEQ ID NO: 23, SEQ ID NO: 24, SEQ ID NO: 15, SEQ ID NO: 16, SEQ ID NO: 17, SEQ ID NO: 18, and SEQ ID NO: 19.

C86. The method according to clause C78, wherein the culturing produces a yield of >120 $OD_{600}$/mL.

C87. The method according to clause C78, further comprising purifying the saccharide.

C88. The method according to clause C78, wherein the purifying step comprises any one of the following: dialysis, concentration operations, diafiltration operations, tangential flow filtration, precipitation, elution, centrifugation, precipitation, ultra-filtration, depth filtration, and column chromatography (ion exchange chromatography, multimodal ion exchange chromatography, DEAE, and hydrophobic interaction chromatography).

C89. A method for inducing an immune response in a mammal comprising administering to the subject a composition according to any one of clause C1 to clause C68.

C90. The method according to clause C89, wherein the immune response comprises induction of an anti-*E. coli* O-specific polysaccharide serum antibody.

C91. The method according to clause C89, wherein the immune response comprises induction of an anti-*E. coli* IgG antibody.

C92. The method according to clause C89, wherein the immune response comprises induction of bactericidal activity against *E. coli*.

C93. The method according to clause C89, wherein the immune response comprises induction of opsonophagocytic antibodies against *E. coli*.

C94. The method according to clause C89, wherein the immune response comprises a geometric mean titer (GMT) level of at least 1,000 to 200,000 after initial dosing.

C95. The method according to clause C89, wherein the composition comprises a saccharide comprising the Formula O25, wherein n is an integer 40 to 100, wherein the immune response comprises a geometric mean titer (GMT) level of at least 1,000 to 200,000 after initial dosing.

C96. The method according to clause C89, wherein the mammal is at risk of any one of the conditions selected from urinary tract infection, cholecystitis, cholangitis, diarrhea, hemolytic uremic syndrome, neonatal meningitis, urosepsis, intra-abdominal infection, meningitis, complicated pneumonia, wound infection, post-prostate biopsy-related infection, neonatal/infant sepsis, neutropenic fever, and other blood stream infection; pneumonia, bacteremia, and sepsis.

C97. The method according to clause C89, wherein the mammal is has any one of the conditions selected from urinary tract infection, cholecystitis, cholangitis, diarrhea, hemolytic uremic syndrome, neonatal meningitis, urosepsis, intra-abdominal infection, meningitis, complicated pneumonia, wound infection, post-prostate biopsy-related infection, neonatal/infant sepsis, neutropenic fever, and other blood stream infection; pneumonia, bacteremia, and sepsis.

C98. A method for (i) inducing an immune response in a subject against extra-intestinal pathogenic *Escherichia coli*, (ii) inducing an immune response in a subject against extra-intestinal pathogenic *Escherichia coli*, or (iii) inducing the production of opsonophagocytic antibodies in a subject that are specific to extra-intestinal pathogenic *Escherichia coli*, wherein the method comprises administering to the subject an effective amount of the composition according to any one of clause C1 to clause C68.

C99. The method of clause C98, wherein the subject is at risk of developing a urinary tract infection.

C100. The method of clause C98, wherein the subject is at risk of developing bacteremia.

C101. The method of clause C98, wherein the subject is at risk of developing sepsis.

C102. A composition comprising a polypeptide derived from FimH or fragment thereof; and a (i) a conjugate of an an *E. coli* O25B antigen covalently coupled to a carrier protein, (ii) a conjugate of an *E. coli* O1A antigen covalently coupled to a carrier protein, (iii) a conjugate of an *E. coli* O2 antigen covalently coupled to a carrier protein, and (iv) a conjugate of an O6 antigen covalently coupled to a carrier protein, wherein the *E. coli* O25B antigen comprises the structure of Formula O25B, wherein n is an integer greater than 30.

C103. The composition of clause C102, wherein the carrier protein is selected from the group consisting of poly(L-lysine), detoxified Exotoxin A of *P. aeruginosa* (EPA), CRM197, maltose binding protein (MBP). Diphtheria toxoid, Tetanus toxoid, detoxified hemolysin A of *S. aureus*, clumping factor A, clumping factor B, Cholera toxin B subunit (CTB), cholera toxin, detoxified variants of cholera toxin, *Streptococcus pneumoniae* Pneumolysin and detoxified variants thereof, *C. jejuni* AcrA, *C. jejuni* natural glycoproteins and Streptococcal C5a peptidase (SCP).

C104. A method for (i) inducing an immune response in a subject against extra-intestinal pathogenic *Escherichia coli*, (ii) inducing an immune response in a subject against extra-intestinal pathogenic *Escherichia coli*, or (iii) inducing the production of opsonophagocytic antibodies in a subject that are specific to extra-intestinal pathogenic *Escherichia coli*, wherein the method comprises administering to the subject an effective amount of the composition of clause C1.

C105. The method of clause C104, wherein the subject is at risk of developing a urinary tract infection.

C106. The method of clause C104, wherein the subject is at risk of developing bacteremia.

C107. The method of clause C104, wherein the subject is at risk of developing sepsis.

C108. A composition comprising a polypeptide derived from FimH or fragment thereof; and a saccharide comprising an increase of at least 5 repeating units, compared to the corresponding wild-type O-polysaccharide of an *E. coli*.

C109. The composition according to clause C108, wherein the saccharide comprises Formula O25a and the *E. coli* is an *E. coli* serotype O25a.

C110. The composition according to clause C108, wherein the saccharide comprises Formula O25b and the *E. coli* is an *E. coli* serotype O25b.

C111. The composition according to clause C108, wherein the saccharide comprises Formula O2 and the *E. coli* is an *E. coli* serotype O2.

C112. The composition according to clause C108, wherein the saccharide comprises Formula O6 and the *E. coli* is an *E. coli* serotype O6.

C113. The composition according to clause C108, wherein the saccharide comprises Formula O1 and the *E. coli* is an *E. coli* serotype O1.

C114. The composition according to clause C108, wherein the saccharide comprises Formula O17 and the *E. coli* is an *E. coli* serotype O17.

C115. The composition according to clause C108, wherein the saccharide comprises a structure selected from: Formula O1, Formula O2, Formula O3, Formula O4, Formula O5, Formula O6, Formula O7, Formula O8, Formula O9, Formula O10, Formula O11, Formula O12, Formula O13, Formula O14, Formula O15, Formula O16, Formula O17, Formula O18, Formula O19, Formula O20, Formula O21, Formula O22, Formula O23, Formula O24, Formula O25, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula O63, Formula O64, Formula O65, Formula O66, Formula O68, Formula O69, Formula O70, Formula O71, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, 0145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 5 to 1000.

C116. The composition according to clause C108, wherein the *E. coli* is *E. coli* serotype selected from the group consisting of: O1, O2, O3, O4, O5, O6, O7, O8, O9, O10, O11, O12, O13, O14, O15, O16, O17, O18, O19, O20, O21, O22, O23, O24, O25, O25b, O26, O27, O28, O29, O30, O32, O33, O34, O35, O36, O37, O38, O39, O40, O41, O42, O43, O44, O45, O46, O48, O49, O50, O51, O52, O53, O54, O55, O56, O57, O58, O59, O60, O61, O62, O63, O64, O65, O66, O68, O69, O70, O71, O73, O74, O75, O76, O77, O78, O79, O80, O81, O82, O83, O84, O85, O86, O87, O88, O89, O90, O91, O92, O93, O95, O96, O97, O98, O99, O100, O101, O102, O103, O104, O105, O106, O107, O108, O109, O110, O111, O112, O113, O114, O115, O116, O117, O118, O119, O120, O121, O123, O124, O125, O126, O127, O128, O129, O130, O131, O132, O133, O134, O135, O136, O137, O138, O139, O140, O141, O142, O143, O144, O145, O146, O147, O148, O149, O150, O151, O152, O153, O154, O155, O156, O157, O158, O159, O160, O161, O162, O163, O164, O165, O166, O167, O168, O169, O170, O171, O172, O173, O174, O175, O176, O177, O178, O179, O180, O181, O182, O183, O184, O185, O186, and O187.

C117. The composition according to clause C108, wherein the saccharide is produced by increasing repeating units of O-polysaccharides produced by a Gram-negative bacterium in culture comprising overexpressing wzz family proteins in a Gram-negative bacterium to generate said saccharide.

C118. The composition according to clause C117, wherein the overexpressed wzz family protein is selected from the group consisting of wzzB, wzz, wzz$_{SF}$, wzz$_{ST}$, fepE, wzz$_{fepE}$, wzz1 and wzz2.

C119. The composition according to clause C117, wherein the overexpressed wzz family protein is wzzB.

C120. The composition according to clause C117, wherein the overexpressed wzz family protein is fepE.

C121. The composition according to clause C117, wherein the overexpressed wzz family protein is wzzB and fepE.

C122. The composition according to clause C108, wherein the saccharide is synthetically synthesized.

C123. A composition comprising a polypeptide derived from FimH or fragment thereof; and a conjugate comprising a saccharide according to clause C108, covalently bound to a carrier protein.

C124. The composition according to clause C123, wherein the carrier protein is CRM$_{197}$.

C125. The composition according to clause C123, wherein the saccharide comprises a structure selected from: Formula O1, Formula O2, Formula O3, Formula O4, Formula O5, Formula O6, Formula O7, Formula O8, Formula O9, Formula O10, Formula O11, Formula O12, Formula O13, Formula O14, Formula O15, Formula O16, Formula O17, Formula O18 Formula O19, Formula O20, Formula O21, Formula O22, Formula O23, Formula O24, Formula O25, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula O63, Formula O64, Formula O65, Formula O66, Formula O68, Formula O69, Formula O70, Formula O71, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 5 to 1000.

C126. The composition according to clause C123, wherein said saccharide comprises an increase of at least 5 repeating units, compared to the corresponding wild-type O-polysaccharide.

C127. The composition according to clause C1, further comprising a pharmaceutically acceptable diluent.

C128. The composition according to clause C127, further comprising an adjuvant.

C129. The composition according to clause C127, further comprising aluminum.

C130. The composition according to clause C127, further comprising QS-21.

C131. The composition according to clause C127, wherein the composition does not include an adjuvant.

C132. A method for inducing an immune response in a subject comprising administering to the subject a composition according to clause C127.

C133. The composition according to clause C123, further comprising a pharmaceutically acceptable diluent.

C134. A method for inducing an immune response in a subject comprising administering to the subject a composition according to clause C133.

C135. The method according to clauses C132 or C134, wherein the immune response comprises induction of an anti-*E. coli* O-specific polysaccharide serum antibody.

C136. The method according to clause C135, wherein the anti-*E. coli* O-specific polysaccharide serum antibody is an IgG antibody.

C137. The method according to clause C135, wherein the anti-*E. coli* O-specific polysaccharide serum antibody is an IgG antibody has bactericidal activity against *E. coli*.

C138. An immunogenic composition comprising a polypeptide derived from FimH or fragment thereof; and a saccharide derived from *E. coli*, conjugated to a carrier protein through a (2-((2-oxoethyl)thio)ethyl)carbamate (eTEC) spacer, wherein the polysaccharide is covalently linked to the eTEC spacer through a carbamate linkage, and wherein the carrier protein is covalently linked to the eTEC spacer through an amide linkage.

C139. The immunogenic composition according to clause C138, further comprising a pharmaceutically acceptable excipient, carrier or diluent.

C140. The immunogenic composition according to clause C138, wherein the saccharide is an O-antigen derived from *E. coli*.

C141. The immunogenic composition according to clause C138, wherein the saccharide comprises a structure selected from: Formula O1, Formula O2, Formula O3, Formula O4, Formula O5, Formula O6, Formula O7, Formula O8, Formula O9, Formula O10, Formula O11, Formula O12, Formula O13, Formula O14, Formula O15, Formula O16, Formula O17 Formula O18, Formula O19, Formula O20, Formula O21, Formula O22, Formula O23, Formula O24, Formula O25, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula O63, Formula O64, Formula O65, Formula O66, Formula O68, Formula O69, Formula O70, Formula O71, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 5 to 1000.

C142. The immunogenic composition according to clause C138, wherein the saccharide has a degree of O-acetylation between 75-100%.

C143. The immunogenic composition according to clause C138, wherein the carrier protein is CRM197.

C144. The immunogenic composition according to clause C143, wherein the CRM197 comprises 2 to 20 lysine residues covalently linked to the polysaccharide through an eTEC spacer.

C145. The immunogenic composition according to clause C143, wherein the CRM197 comprises 4 to 16 lysine residues covalently linked to the polysaccharide through an eTEC spacer.

C146. The immunogenic composition according to clause C138, further comprising an additional antigen.

C147. The immunogenic composition according to clause C138, further comprising an adjuvant.

C148. The immunogenic composition according to clause C147, wherein the adjuvant is an aluminum-based adjuvant selected from the group consisting of aluminum phosphate, aluminum sulfate and aluminum hydroxide.

C149. The immunogenic composition according to clause C138, wherein the composition does not comprise an adjuvant.

C150. An immunogenic composition comprising a polypeptide derived from FimH or fragment thereof; and a glycoconjugate comprising a saccharide derived from *E. coli* conjugated to a carrier protein, wherein the glycoconjugate is prepared using reductive amination.

C151. The immunogenic composition according to clause C150, further comprising a pharmaceutically acceptable excipient, carrier or diluent.

C152. The immunogenic composition according to clause C150, wherein the saccharide is an O-antigen derived from *E. coli*.

C153. The immunogenic composition according to clause C150, wherein the saccharide comprises a structure selected from: Formula O1, Formula O2, Formula O3, Formula O4, Formula O5, Formula O6, Formula O7, Formula O8, Formula O9, Formula O10, Formula O11, Formula O12, Formula O13, Formula O14, Formula O15, Formula O16, Formula O17, Formula O18, Formula O19, Formula O20, Formula O21, Formula O22, Formula O23, Formula O24, Formula O25, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula O63, Formula O64, Formula O65, Formula O66, Formula O68, Formula O69, Formula O70, Formula O71, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, 0145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 5 to 1000.

C154. The immunogenic composition according to clause C150, wherein the saccharide has a degree of O-acetylation between 75-100%.

C155. The immunogenic composition according to clause C150, wherein the carrier protein is CRM197.

C156. The immunogenic composition according to clause C150, further comprising an additional antigen.

C157. The immunogenic composition according to clause C150, further comprising an adjuvant.

C158. The immunogenic composition according to clause C157, wherein the adjuvant is an aluminum-based adjuvant selected from the group consisting of aluminum phosphate, aluminum sulfate and aluminum hydroxide.

C159. The immunogenic composition according to clause C150, wherein the composition does not comprise an adjuvant.

C160. A method for inducing an immune response in a subject comprising administering to the subject a composition according to any one of clauses C138-C159.

C161. The method according to clause C160, wherein the immune response comprises induction of an anti-E. coli O-specific polysaccharide serum antibody.

C162. The method according to clause C135, wherein the anti-E. coli O-specific polysaccharide serum antibody is an IgG antibody.

C163. The method according to clause C135, wherein the anti-E. coli O-specific polysaccharide serum antibody is an IgG antibody has bactericidal activity against E. coli.

C164. A composition comprising a polypeptide derived from FimH or fragment thereof; and a saccharide comprising a structure selected from any one of Formula O1, Formula O1A, Formula O1B, Formula O1C, Formula O2, Formula O3, Formula O4, Formula O4:K52, Formula O4:K6, Formula O5, Formula O5ab, Formula O5ac, Formula O6, Formula O6:K2; K13; K15, Formula O6:K54, Formula O7, Formula O8, Formula O9, Formula O10, Formula O11, Formula O12, Formula O13, Formula O14, Formula O15, Formula O16, Formula O17, Formula O18, Formula O18A, Formula O18ac, Formula O18A1, Formula O18B, Formula O18B1, Formula O19, Formula O20, Formula O21, Formula O22, Formula O23, Formula O23A, Formula O24, Formula O25, Formula O25a, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O45, Formula O45rel, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D$_1$, Formula O63, Formula O64, Formula O65, Formula O66, Formula O68, Formula O69, Formula O70, Formula O71, Formula O73, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, Formula O187, wherein n is greater than the number of repeat units in the corresponding wild-type E. coli polysaccharide.

C165. The composition according to clause C164, wherein n is an integer from 31 to 100.

C166. The composition according to clause C164, wherein the saccharide comprises a structure according to any one of Formula O1A, Formula O1B, and Formula O1C, Formula O2, Formula O6, and Formula O25B.

C167. The composition according to clause C164, wherein the saccharide is produced in a recombinant host cell that expresses a wzz family protein having at least 90% sequence identity to any one of SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, and SEQ ID NO: 39.

C168. The composition according to clause C167, wherein the protein comprises any one of SEQ ID NO: 30, SEQ ID NO: 31, SEQ ID NO: 32, SEQ ID NO: 33, SEQ ID NO: 34.

C169. The saccharide according to clause C164, wherein the saccharide is synthetically synthesized.

C170. A composition comprising a polypeptide derived from FimH or fragment thereof; and a conjugate comprising a carrier protein covalently bound to a saccharide, said saccharide comprising a structure selected from any one of Formula O1, Formula O1A, Formula O1B, Formula O1C, Formula O2, Formula O3, Formula O4, Formula O4:K52, Formula O4:K6, Formula O5, Formula O5ab, Formula O5ac, Formula O6, Formula O6:K2; K13; K15, Formula O6:K54, Formula O7, Formula O8, Formula O9, Formula O10, Formula O11, Formula O12, Formula O13, Formula O14, Formula O15, Formula O16, Formula O17, Formula O18, Formula O18A, Formula O18ac, Formula O18A1, Formula O18B, Formula O18B1, Formula O19, Formula O20, Formula O21, Formula O22, Formula O23, Formula O23A, Formula O24, Formula O25, Formula O25a, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O45, Formula O45rel, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D$_1$, Formula O63, Formula O64, Formula O65, Formula O66, Formula O68, Formula O69, Formula O70, Formula O71, Formula O73, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, or Formula O187, wherein n is an integer from 1 to 100.

C171. The composition according to clause C170, wherein the saccharide comprises any one of the following Formula O25b, Formula O1A, Formula O2, and Formula O6.

C172. The composition according to clause C170, wherein the saccharide further comprises any one of an *E. coli* R1 moiety, *E. coli* R2 moiety, *E. coli* R3 moiety, *E. coli* R4 moiety, and *E. coli* K-12 moiety.

C173. The composition according to clause C170, wherein the saccharide does not further comprise any one of an *E. coli* R1 moiety, *E. coli* R2 moiety, *E. coli* R3 moiety, *E. coli* R4 moiety, and *E. coli* K-12 moiety. The composition according to clause C170, wherein the saccharide does not further comprise an *E. coli* R2 moiety.

C174. The composition according to clause C170, wherein the saccharide further comprises a 3-deoxy-d-manno-oct-2-ulosonic acid (KDO) moiety.

C175. The composition according to clause C170, wherein the carrier protein is selected from any one of CRM$_{197}$, diphtheria toxin fragment B (DTFB), DTFB C8, Diphtheria toxoid (DT), tetanus toxoid (TT), fragment C of TT, pertussis toxoid, cholera toxoid, or exotoxin A from *Pseudomonas aeruginosa*; detoxified Exotoxin A of *P. aeruginosa* (EPA), maltose binding protein (MBP), detoxified hemolysin A of *S. aureus*, clumping factor A, clumping factor B, Cholera toxin B subunit (CTB), *Streptococcus pneumoniae* Pneumolysin and detoxified variants thereof, *C. jejuni* AcrA, *C. jejuni* natural glycoproteins and Streptococcal C5a peptidase (SCP).

C176. The composition according to clause C170, wherein the carrier protein is CRM$_{197}$.

C177. The composition according to clause C170, wherein the carrier protein is tetanus toxoid.

C178. The composition according to clause C170, wherein the ratio of saccharide to protein is at least 0.5 to at most 2.

C179. The composition according to clause C170, wherein the conjugate is prepared via reductive amination.

C180. The composition according to clause C170, wherein the saccharide is conjugated to the carrier protein through a (2-((2-oxoethyl)thio)ethyl)carbamate (eTEC) spacer.

C181. The composition according to clause C170, wherein the saccharide is a single-end linked conjugated saccharide.

C182. The composition according to clause C174, wherein the saccharide is conjugated to the carrier protein through a 3-deoxy-d-manno-oct-2-ulosonic acid (KDO) residue.

C183. The composition according to clause C170, wherein the conjugate is prepared via CDAP chemistry.

C184. A composition comprising a polypeptide derived from FimH or fragment thereof; and (a) a conjugate comprising a carrier protein covalently bound to a saccharide comprising Formula O25b, wherein n is an integer from 31 to 90, (b) a conjugate comprising a carrier protein covalently bound to a saccharide comprising Formula O1A, wherein n is an integer from 31 to 90, (c) a conjugate comprising a carrier protein covalently bound to a saccharide comprising Formula O2, wherein n is an integer from 31 to 90, and (d) a conjugate comprising a carrier protein covalently bound to a saccharide comprising and Formula O6, wherein n is an integer from 31 to 90.

C185. The composition according to clause C184, further comprising a conjugate comprising a carrier protein covalently bound to a saccharide comprising a structure selected from any one of the following: Formula O15, Formula O16, Formula O17, Formula O18 and Formula O75, wherein n is an integer from 31 to 90.

C186. The composition according to clause C184, comprising at most 25% free saccharide as compared to the total amount of saccharide in the composition.

C187. A method of eliciting an immune response against *Escherichia coli* in a mammal, comprising administering to the mammal an effective amount of the composition according to any one of clauses C184 to C186.

C188. The method according to clause C187, wherein the immune response comprises opsonophagocytic antibodies against *E. coli*.

C189. The method according to clause C187, wherein the immune response protects the mammal from an *E. coli* infection.

C190. A mammalian cell comprising (a) a first gene of interest encoding a polypeptide derived from *E. coli* or a fragment thereof, wherein the gene is integrated between at least two recombination target sites (RTS).

C191. The embodiment of clause C190, wherein the two RTS are chromosomally-integrated within the NL1 locus or the NL2 locus.

C192. The embodiment of clause C190, wherein the first gene of interest further comprises a reporter gene, a gene encoding a difficult to express protein, an ancillary gene or a combination thereof.

C193. The embodiment of clause C190, further comprising a second gene of interest that is integrated within a second chromosomal locus distinct from the locus of (a), wherein the second gene of interest comprises a reporter gene, a gene encoding a difficult to express protein, an ancillary gene or a combination thereof.

C194. A recombinant mammalian cell, comprising a polynucleotide encoding a polypeptide derived from *E. coli* or a fragment thereof.

C195. The recombinant cell according to C194, wherein the polypeptide is derived from *E. coli* fimbrial H (FimH).

C196. The recombinant cell according to C195, wherein the polypeptide comprises a phenylalanine residue at the N-terminus of the polypeptide.

C197. The recombinant cell according to C195, wherein the polypeptide comprises a phenylalanine residue within the first 20 residue positions of the N-terminus.

C198. The recombinant cell according to C195, wherein the polypeptide comprises a phenylalanine residue at position 1 of the polypeptide.

C199. The recombinant cell according to C198, wherein the polypeptide does not comprise a glycine residue immediately before the phenylalanine residue at position 1 of the polypeptide.

C200. The recombinant cell according to C195, wherein the polypeptide does not comprise an N-glycosylation site at position 7 of the polypeptide.

C201. The recombinant cell according to C199, wherein the polypeptide does not comprise an Asn residue at position 7 of the polypeptide.

C202. The recombinant cell according to C201, wherein the polypeptide comprises a residue selected from the group consisting of Ser, Asp, Thr, and Gln at position 7.

C203. The recombinant cell according to C198, wherein the polypeptide does not comprise an N-glycosylation site at position 70 of the polypeptide.

C204. The recombinant cell according to C203, wherein the polypeptide does not comprise an Asn residue at position 70 of the polypeptide.

C205. The recombinant cell according to C203, wherein the polypeptide does not comprise a Ser residue at position 70 of the polypeptide.

C206. The recombinant cell according to C194, wherein the polypeptide comprises a residue substitution selected from the group consisting of Ser, Asp, Thr, and Gln at an N-glycosylation site of the polypeptide.

C207. The recombinant cell according to C206, wherein the N-glycosylation site comprises position N235 of the polypeptide.

C208. The recombinant cell according to C206, wherein the N-glycosylation site comprises position N228 of the polypeptide.

C209. The recombinant cell according to C206, wherein the N-glycosylation site comprises position N235 and position N228 of the polypeptide.

C210. The recombinant cell according to C195, wherein the polypeptide comprises SEQ ID NO: 3.

C211. The recombinant cell according to C195, wherein the polypeptide comprises SEQ ID NO: 2.

C212. The recombinant cell according to C194, wherein the polypeptide comprises an aliphatic hydrophobic amino acid residue at position 1 of the polypeptide.

C213. The recombinant cell according to C212, wherein the aliphatic hydrophobic amino acid residue is selected from the group consisting of Ile, Leu, and Val.

C214. The recombinant cell according to C194, wherein the polypeptide comprises a fragment of FimH.

C215. The recombinant cell according to C214, wherein the polypeptide comprises a lectin domain of FimH.

C216. The recombinant cell according to C215, wherein the lectin domain comprises a mass of about 17022 Daltons.

C217. The recombinant cell according to C194, wherein the polypeptide is complexed with a FimC polypeptide or a fragment thereof.

C218. The recombinant cell according to C217, wherein the FimC polypeptide or a fragment thereof comprises a glycine residue at position 37 of the FimC polypeptide or a fragment thereof.

C219. The recombinant cell according to C195, wherein the polypeptide is in the low affinity conformation.

C220. The recombinant cell according to C195, wherein the polypeptide is stabilized by FimG.

C221. The recombinant cell according to C195, wherein the polypeptide is stabilized by a donor-strand peptide of FimG (DsG).

C222. The recombinant cell according to C221, wherein the polynucleotide sequence further encodes a linker sequence.

C223. The recombinant cell according to C222, wherein the linker comprises at least 4 amino acid residues and at most 15 amino acid residues.

C224. The recombinant cell according to C222, wherein the linker comprises at least 5 amino acid residues and at most 10 amino acid residues.

C225. The recombinant cell according to C222, wherein the linker comprises 7 amino acid residues.

C226. The recombinant cell according to C194, wherein the polypeptide does not comprise a signal peptide selected from the group consisting of a native FimH leader peptide, influenza hemagglutinin signal peptide, and a human respiratory syncytial virus A (strain A2) fusion glycoprotein F0 signal peptide.

C227. The recombinant cell according to C194, wherein the polypeptide comprises a murine IgK signal peptide sequence.

C228. The recombinant cell according to C194, wherein the polypeptide comprises any one signal peptide sequence selected from human IgG receptor FcRn large subunit p51 signal peptide and a human IL10 protein signal peptide.

C229. The recombinant cell according to C195, wherein the polypeptide comprises a mutation of arginine to proline at amino acid position 60 (R60P), according to the numbering of SEQ ID NO: 3.

C230. The recombinant cell according to C194, wherein the expression level of the polypeptide is greater than the expression level of the corresponding wild-type polypeptide expressed in the periplasm of a wild-type *E. coli* cell.

C231. The recombinant cell according to C194, wherein the expression level of the polypeptide is greater than 10 mg/L.

C232. The recombinant cell according to C194, wherein the polynucleotide sequence is integrated into the genomic DNA of said mammalian cell.

C233. The recombinant cell according to C194, wherein the polynucleotide sequence is codon optimized for expression in the cell.

C234. The recombinant cell according to C194, wherein the cell is a human embryonic kidney cell.

C235. The recombinant cell according to C234, wherein the human embryonic kidney cell comprises a HEK293 cell.

C236. The recombinant cell according to C235, wherein the HEK293 cell is selected from any one of HEK293T cells, HEK293TS cells, and HEK293E cells.

C237. The recombinant cell according to C195, wherein the cell is a CHO cell.

C238. The recombinant cell according to C237, wherein said CHO cell is a CHO-K1 cell, CHO-DUXB11, CHO-DG44 cell, or CHO—S cell.

C239. The recombinant cell according to C194, wherein the polypeptide is soluble.
C240. The recombinant cell according to C194, wherein the polypeptide is secreted from the cell.
C241. The recombinant cell according to C195, wherein the polypeptide comprises a N28Q substitution, according to the numbering of SEQ ID NO: 1.
C242. The recombinant cell according to C195, wherein the polypeptide comprises a N28D substitution, according to the numbering of SEQ ID NO: 1.
C243. The recombinant cell according to C195, wherein the polypeptide comprises a N28S substitution, according to the numbering of SEQ ID NO: 1.
C244. The recombinant cell according to C195, wherein the polypeptide comprises a substitution selected from any one of N28Q, V48C, and L55C, according to the numbering of SEQ ID NO: 1.
C245. The recombinant cell according to C195, wherein the polypeptide comprises a substitution N92S according to the numbering of SEQ ID NO: 1.
C246. The recombinant cell according to C194, wherein the polypeptide derived from FimH or fragment thereof comprises a substation selected from any one of V48C and L55C, according to the numbering of SEQ ID NO: 1.
C247. A culture comprising the recombinant cell of C194, wherein said culture is at least 5 liter in size.
C248. The culture according to C242, wherein the yield of the polypeptide or fragment thereof is at least 0.05 g/L.
C249. The culture according to C248, wherein the yield of the polypeptide or fragment thereof is at least 0.10 g/L.
C250. A method for producing a polypeptide derived from *E. coli* or a fragment thereof, comprising culturing a recombinant mammalian cell according to C194 under a suitable condition, thereby expressing the polypeptide or fragment thereof; and harvesting the polypeptide or fragment thereof.
C251. The method according to C250, further comprising purifying the polypeptide or fragment thereof.
C252. The method according to C250, wherein the cell comprises a nucleic acid encoding any one of SEQ ID NO: 5, SEQ ID NO: 6, SEQ ID NO: 7, SEQ ID NO: 8, and SEQ ID NO: 27.
C253. The method according to C250, wherein the yield of the polypeptide or fragment thereof is at least 0.05 g/L.
C254. The method according to C250, wherein the yield of the polypeptide or fragment thereof is at least 0.10 g/L.
C255. A composition comprising a polypeptide having at least 70% identity to any one of SEQ ID NO: 1, SEQ ID NO: 2, SEQ ID NO: 3, SEQ ID NO: 4, SEQ ID NO: 20, SEQ ID NO: 23, SEQ ID NO: 24, SEQ ID NO: 26, SEQ ID NO: 28, and SEQ ID NO: 29.
C256. The composition according to C255, further comprising a saccharide comprising a structure selected from any one Formula in Table 1.
C257. The composition according to C256, wherein the saccharide is covalently bound a carrier protein.
C258. The composition according to C257, wherein the carrier protein is selected from any one of poly(L-lysine), $CRM_{197}$, diphtheria toxin fragment B (DTFB), DTFB C8, Diphtheria toxoid (DT), tetanus toxoid (TT), fragment C of TT, pertussis toxoid, cholera toxoid, or exotoxin A from *Pseudomonas aeruginosa*; detoxified Exotoxin A of *P. aeruginosa* (EPA), maltose binding protein (MBP), detoxified hemolysin A of *S. aureus*, clumping factor A, clumping factor B, Cholera toxin B subunit (CTB), *Streptococcus pneumoniae* Pneumolysin and detoxified variants thereof, *C. jejuni* AcrA, *C. jejuni* natural glycoproteins and Streptococcal C5a peptidase (SCP).
C259. The composition according to C257, wherein the carrier protein is $CRM_{197}$.
C260. The composition according to C257, wherein the carrier protein is tetanus toxoid (TT).
C261. The composition according to C257, wherein the carrier protein is poly(L-lysine).
C262. The composition according to C257, wherein the saccharide is covalently bound a carrier protein by reductive amination.
C263. The composition according to C257, wherein the saccharide is covalently bound a carrier protein by CDAP chemistry.
C264. The composition according to C257, wherein the saccharide is covalently bound a carrier protein by single-end linked conjugation.
C265. The composition according to C257, wherein the saccharide is covalently bound a carrier protein through a (2-((2-oxoethyl)thio)ethyl)carbamate (eTEC) spacer.
C266. A polypeptide comprising the amino acid sequence selected from the group consisting of SEQ ID NO: 5, SEQ ID NO: 6, SEQ ID NO: 7, SEQ ID NO: 8, and SEQ ID NO: 27.
C267. A composition comprising a polypeptide derived from FimH or a fragment thereof; and a saccharide comprising a structure selected from any one of Formula O1, Formula O1A, Formula O1B, Formula O1C, Formula O2, Formula O3, Formula O4, Formula O4:K52, Formula O4:K6, Formula O5, Formula O5ab, Formula O5ac, Formula O6, Formula O6:K2; K13; K15, Formula O6:K54, Formula O7, Formula O8, Formula O9, Formula O10, Formula O11, Formula O12, Formula O13, Formula O14, Formula O15, Formula O16, Formula O17, Formula O18, Formula O18A, Formula O18ac, Formula O18A1, Formula O18B, Formula O18B1, Formula O19, Formula O20, Formula O21, Formula O22, Formula O23, Formula O23A, Formula O24, Formula O25, Formula O25a, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O45, Formula O45rel, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula $62D_1$, Formula O63, Formula O64, Formula O65, Formula O66, Formula O68, Formula O69, Formula O70, Formula O71, Formula O73, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, Formula O187.

C268. The composition according to Clause C267, further comprising at least one saccharide derived from any one *K. pneumoniae* type selected from the group consisting of O1, O2, O3, and O5.

C269. The composition according to Clause C267, further comprising a saccharide derived from *Klebsiella pneumoniae* type O1.

C270. The composition according to Clause C267, further comprising a saccharide derived from *K. pneumoniae* type O2.

C271. The composition according to Clause C267, further comprising a saccharide derived from *K. pneumoniae* type O3.

C272. The composition according to Clause C267, further comprising a saccharide derived from *K. pneumoniae* type O5.

C273. The composition according to Clause C267, further comprising a saccharide derived from *K. pneumoniae* type O1 and a saccharide derived from *K. pneumoniae* type O2.

C274. The composition according to Clause C268, wherein the saccharide derived from *K. pneumoniae* is conjugated to a carrier protein; and the saccharide derived from *E. coli* is conjugated to a carrier protein.

C275. The composition according to Clause C267, further comprising a polypeptide derived from *K. pneumoniae*.

C276. A composition comprising a polypeptide derived from FimH or a fragment thereof; and at least one saccharide derived from any one *K. pneumoniae* type selected from the group consisting of O1, O2, O3, and O5.

C277. The composition according to Clause C276, further comprising at least one saccharide comprising a structure selected from any one of Formula O1, Formula O1A, Formula O1B, Formula O1C, Formula O2, Formula O3, Formula O4, Formula O4:K52, Formula O4:K6, Formula O5, Formula O5ab, Formula O5ac, Formula O6, Formula O6:K2; K13; K15, Formula O6:K54, Formula O7, Formula O8, Formula O9, Formula O10, Formula O11, Formula O12, Formula O13, Formula O14, Formula O15, Formula O16, Formula O17, Formula O18, Formula O18A, Formula O18ac, Formula O18A1, Formula O18B, Formula O18B1, Formula O19, Formula O20, Formula O21, Formula O22, Formula O23, Formula O23A, Formula O24, Formula O25, Formula O25a, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O45, Formula O45rel, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D$_1$, Formula O63, Formula O64, Formula O65, Formula O66, Formula O68, Formula O69, Formula O70, Formula O71, Formula O73, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, Formula O187.

C278. The composition according to Clause C277, wherein the saccharide derived from *K. pneumoniae* is conjugated to a carrier protein; and the saccharide derived from *E. coli* is conjugated to a carrier protein.

C279. The composition according to Clause C277, further comprising a polypeptide derived from *K. pneumoniae*.

C280. A composition comprising at least one saccharide derived from any one *K. pneumoniae* type selected from the group consisting of O1, O2, O3, and O5; and at least one saccharide comprising a structure selected from any one of Formula O1, Formula O1A, Formula O1B, Formula O1C, Formula O2, Formula O3, Formula O4, Formula O4:K52, Formula O4:K6, Formula O5, Formula O5ab, Formula O5ac, Formula O6, Formula O6:K2; K13; K15, Formula O6:K54, Formula O7, Formula O8, Formula O9, Formula O10, Formula O11, Formula O12, Formula O13, Formula O14, Formula O15, Formula O16, Formula O17, Formula O18, Formula O18A, Formula O18ac, Formula O18A1, Formula O18B, Formula O18B1, Formula O19, Formula O20, Formula O21, Formula O22, Formula O23, Formula O23A, Formula O24, Formula O25, Formula O25a, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O45, Formula O45rel, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D$_1$, Formula O63, Formula O64, Formula O65, Formula O66, Formula O68, Formula O69, Formula O70, Formula O71, Formula O73, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, Formula O187.

C281. The composition according to Clause C280, further comprising a polypeptide derived from FimH or a fragment thereof.

C282. The composition according to Clause C280, wherein the *E. coli* saccharide comprises Formula O8.

C283. The composition according to Clause C280, wherein the *E. coli* saccharide comprises Formula O9.

C284. The composition according to Clause C280, further comprising a polypeptide derived from *K. pneumoniae*.

C285. The composition according to any of Clauses C267-C284, wherein the saccharide is covalently bound to a carrier protein.

C286. The composition according to Clause C285, wherein the saccharide further comprises a 3-deoxy-d-manno-oct-2-ulosonic acid (KDO) moiety.

C287. The composition according to Clause C285, wherein the saccharide comprises Lipid A.

C288. The composition according to any one of clauses C285-C287, wherein the saccharide is synthetically synthesized.

C289. The composition according to Clause C285, wherein the carrier protein is selected from any one of CRM197, diphtheria toxin fragment B (DTFB), DTFB C8, Diphtheria toxoid (DT), tetanus toxoid (TT), fragment C of TT, pertussis toxoid, cholera toxoid, or exotoxin A from *Pseudomonas aeruginosa*; detoxified Exotoxin A of *P. aeruginosa* (EPA), maltose binding protein (MBP), detoxified hemolysin A of *S. aureus*, clumping factor A, clumping factor B, Cholera toxin B subunit (CTB), *Streptococcus pneumoniae* Pneumolysin and detoxified variants thereof, *C. jejuni* AcrA, *C. jejuni* natural glycoproteins and Streptococcal C5a peptidase (SCP).

C290. A method of eliciting an immune response against *Escherichia coli* in a mammal, comprising administering to the mammal an effective amount of the composition according to any one of Clauses C267-C289.

C291. The method according to Clause C290, wherein the immune response comprises opsonophagocytic antibodies against *E. coli*.

C292. The method according to Clause C290, wherein the immune response protects the mammal from an *E. coli* infection.

C293. A method of eliciting an immune response against *Klebsiella pneumoniae* in a mammal, comprising administering to the mammal an effective amount of the composition according to any one of Clauses C267-C289.

C294. The method according to Clause C293, wherein the immune response comprises opsonophagocytic antibodies against *Klebsiella pneumoniae*.

C295. The method according to Clause C293, wherein the immune response protects the mammal from a *Klebsiella pneumoniae* infection.

C296. The compositions and methods according to any one of Clauses C1-C266, further comprising at least one saccharide derived from any one of *K. pneumoniae* type selected from the group consisting of O1, O2, O3, and O5.

C297. The compositions and methods of Clause C296, wherein the *K. pneumoniae* serotype O1 comprises variant O1V1 or O1V2.

C298. The compositions and methods of Clause C296, wherein the *K. pneumoniae* serotype O2 comprises variant O2V1 or O2V2.

C299. Use of the compositions set forth in any one of Clauses C1-C298 as set forth herein.

C300. A composition comprising
  (i) a polypeptide derived from fimbrial H (FimH) or a fragment thereof; and
  (ii) one or more conjugates, wherein the conjugate comprises a carrierprotein covalently bound to a saccharide, said saccharide comprising a structure selected from the group consisting of Formula O1, Formula O1A, Formula O1B, Formula O1C, Formula O2, Formula O3, Formula O4, Formula O4:K52, Formula O4:K6, Formula O5, Formula O5ab, Formula O5ac, Formula O6, Formula O6:K2; K13; K15, Formula O6:K54, Formula O7, Formula O8, Formula O9, Formula O10, Formula O11, Formula O12, Formula O13, Formula O14, Formula O15, Formula O16, Formula O17, Formula O18, Formula O18A, Formula O18ac, Formula O18A1, Formula O18B, Formula O18B1, Formula O19, Formula O20, Formula O21, Formula O22, Formula O23, Formula O23A, Formula O24, Formula O25, Formula O25a, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O45, Formula O45rel, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D$_1$, Formula O63, Formula O64, Formula O65, Formula O66, Formula O68, Formula O69, Formula O70, Formula O71, Formula O73, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 1 to 100.

C301. The composition according to clause C300, wherein the saccharide is selected from the group consisting of Formula O25b, Formula O1A, Formula O2, Formula O6, Formula O8 and Formula O9.

C302. The composition according to clause C301, wherein the saccharide is selected from the group consisting of Formula O25b, Formula O1A, Formula O2, and Formula O6.

C303. A composition comprising a polypeptide derived from Fimbrial antigen H (FimH) or a fragment thereof; and
  (a) a conjugate comprising a carrier protein covalently bound to a saccharide comprising Formula O25b, wherein n is an integer from 31 to 90,
  (b) a conjugate comprising a carrier protein covalently bound to a saccharide comprising Formula O1A, wherein n is an integer from 31 to 90,
  (c) a conjugate comprising a carrier protein covalently bound to a saccharide comprising Formula O2, wherein n is an integer from 31 to 90,
  (d) a conjugate comprising a carrier protein covalently bound to a saccharide comprising and Formula O6, wherein n is an integer from 31 to 90,
  (e) a conjugate comprising a carrier protein covalently bound to a saccharide comprising and Formula O8, wherein n is an integer from 31 to 90, and
  (f) a conjugate comprising a carrier protein covalently bound to a saccharide comprising and Formula O9, wherein n is an integer from 31 to 90.

C304. The composition of clause C303 comprising a polypeptide derived from Fimbrial antigen H (FimH) or a fragment thereof; and
  (a) a conjugate comprising a carrier protein covalently bound to a saccharide comprising Formula O25b, wherein n is an integer from 31 to 90,
  (b) a conjugate comprising a carrier protein covalently bound to a saccharide comprising Formula O1A, wherein n is an integer from 31 to 90,
  (c) a conjugate comprising a carrier protein covalently bound to a saccharide comprising Formula O2, wherein n is an integer from 31 to 90, and
  (d) a conjugate comprising a carrier protein covalently bound to a saccharide comprising and Formula O6, wherein n is an integer from 31 to 90.

C305. The composition according to clauses C303 or C304, further comprising one or more conjugates having a saccharide selected from the group consisting of Formula O15, Formula O16, Formula O17, Formula O18 and Formula O75, wherein n is an integer from 31 to 90.7. The composition according to any one of clauses 1-6, wherein the saccharide further comprises any one of an *E. coli* R1 moiety, *E. coli* R2 moiety, *E. coli* R3 moiety, *E. coli* R4 moiety, and *E. coli* K-12 moiety.

C306. The composition according to any one of clauses C300-C304, wherein the saccharide does not further comprise any one of an *E. coli* R1 moiety, *E. coli* R2 moiety, *E. coli* R3 moiety, *E. coli* R4 moiety, and *E. coli* K-12 moiety.

C307. The composition according to clause C306, wherein the saccharide does not further comprise an *E. coli* R2 moiety.

C308. The composition according to any one of clauses C300-C307, wherein the saccharide further comprises a 3-deoxy-d-manno-oct-2-ulosonic acid (KDO) moiety.

C309. The composition according to any one of clauses C300-C308, wherein the carrier protein is selected from the group consisting of CRM197, diphtheria toxin fragment B (DTFB), DTFB C8, Diphtheria toxoid (DT), tetanus toxoid (TT), fragment C of TT, pertussis toxoid, cholera toxoid, or exotoxin A from *Pseudomonas aeruginosa*; detoxified Exotoxin A of *P. aeruginosa* (EPA), maltose binding protein (MBP), detoxified hemolysin A of *S. aureus* clumping factor A, clumping factor B, Cholera toxin B subunit (CTB), *Streptococcus pneumoniae* Pneumolysin and detoxified variants thereof, *C. jejuni* AcrA, *C. jejuni* natural glycoproteins, and Streptococcal C5a peptidase (SCP) or a variant thereof.

C310. The composition according to clause C309, wherein the carrier protein is CRM197.

C311. The composition according to clause C309, wherein the carrier protein is tetanus toxoid.

C312. The composition according to any one of clauses C300-C311, wherein the ratio of saccharide to protein is at least 0.5 to at most 2.

C313. The composition according to any one of clauses C300-C312, wherein the conjugate is prepared via reductive amination.

C314. The composition according to any one of clauses C300-C312, wherein the saccharide is conjugated to the carrier protein through a (2-((2-oxoethyl)thio)ethyl)carbamate (eTEC) spacer.

C315. The composition according to any one of clauses C300-C314, wherein the saccharide is a single-end linked conjugated saccharide.

C316. The composition according to clause C308, wherein the saccharide is conjugated to the carrier protein through a 3-deoxy-d-manno-oct-2-ulosonic acid (KDO) residue.

C317. The composition according to any one of clauses C300-C313, wherein the conjugate is prepared via CDAP chemistry.

C318. The composition according to any one of clauses C300-C317, wherein the polypeptide is derived from *E. coli* fimbrial H (FimH).

C319. The composition according to clause C318, wherein the polypeptide comprises a phenylalanine residue at the N-terminus of the polypeptide.

C320. The composition according to clause C318, wherein the polypeptide comprises a phenylalanine residue within the first 20 residue positions of the N-terminus.

C321. The composition according to clause C314, wherein the polypeptide comprises a phenylalanine residue at position 1 of the polypeptide.

C322. The composition according to clause C317, wherein the polypeptide does not comprise a glycine residue immediately before the phenylalanine residue at position 1 of the polypeptide.

C323. The composition according to clause C314, wherein the polypeptide does not comprise an N-glycosylation site at position 7 of the polypeptide.
C324. The composition according to clause C318, wherein the polypeptide does not comprise an Asn residue at position 7 of the polypeptide.
C325. The composition according to clause C320, wherein the polypeptide comprises a residue selected from the group consisting of Ser, Asp, Thr, and Gln at position 7.
C326. The composition according to clause C317, wherein the polypeptide does not comprise an N-glycosylation site at position 70 of the polypeptide.
C327. The composition according to clause C322, wherein the polypeptide does not comprise an Asn residue at position 70 of the polypeptide.
C328. The composition according to clause C322, wherein the polypeptide does not comprise a Ser residue at position 70 of the polypeptide.
C329. The composition according to clause C314, wherein the polypeptide comprises a residue substitution selected from the group consisting of Ser, Asp, Thr, and Gln at an N-glycosylation site of the polypeptide.
C330. The composition according to clause C325, wherein the N-glycosylation site comprises position N235 of the polypeptide.
C331. The composition according to clause C325, wherein the N-glycosylation site comprises position N228 of the polypeptide.
C332. The composition according to clause C325, wherein the N-glycosylation site comprises position N235 and position N228 of the polypeptide.
C333. The composition according to clause C314, wherein the polypeptide comprises SEQ ID NO: 2.
C334. The composition according to clause C314, wherein the polypeptide comprises SEQ ID NO: 3.
C335. The composition according to clause C314, wherein the polypeptide comprises amino acids having an amino acid sequence selected from the group consisting of SEQ ID NO: 5, SEQ ID NO: 6, SEQ ID NO: 7, SEQ ID NO: 8, SEQ ID NO: 27, SEQ ID NO: 110, SEQ ID NO: 111, SEQ ID NO: 112, and SEQ ID NO: 113.
C336. The composition of cliam C314, wherein the polypeptide comprises amino acids having an amino acid sequence having at least 70% identity to the group consisting of SEQ ID NO: 1, SEQ ID NO: 2, SEQ ID NO: 3, SEQ ID NO: 4, SEQ ID NO: 20, SEQ ID NO: 23, SEQ ID NO: 24, SEQ ID NO: 26, SEQ ID NO: 28, SEQ ID NO: 29, SEQ ID NO: 110, SEQ ID NO: 111, SEQ ID NO: 112 and SEQ ID NO: 113.
C337. The composition according to clause C314, wherein the polypeptide comprises an aliphatic hydrophobic amino acid residue at position 1 of the polypeptide.
C338. The composition according to clause C333, wherein the aliphatic hydrophobic amino acid residue is selected from the group consisting of Ile, Leu, and Val.
C339. The composition according to clause C314, wherein the polypeptide comprises a fragment of FimH.
C340. The composition according to clause C335, wherein the polypeptide comprises a lectin domain of FimH.
C341. The composition according to clause C336, wherein the lectin domain comprises a mass of about 17022 Daltons.
C342. The composition according to clause C314, wherein the polypeptide is complexed with a FimC polypeptide or a fragment thereof.
C343. The composition according to clause C338, wherein the FimC polypeptide or a fragment thereof comprises a glycine residue at position 37 of the FimC polypeptide or a fragment thereof.
C344. The composition according to clause C314, wherein the polypeptide is in the low affinity conformation.
C345. The composition according to clause C314, wherein the polypeptide is stabilized by FimG.
C346. The composition according to clause C314, wherein the polypeptide is stabilized by a donor-strand peptide of FimG (DsG).
C347. The composition according to clause C346, wherein the polypeptide further comprises a linker.
C348. The composition according to clause C343, wherein the linker comprises at least 4 amino acid residues and at most 15 amino acid residues.
C349. The composition according to clause C343, wherein the linker comprises at least 5 amino acid residues and at most 10 amino acid residues.
C350. The composition according to clause C343, wherein the linker comprises 7 amino acid residues.
C351. The composition according to clause C314, wherein the polypeptide does not comprise a signal peptide selected from the group consisting of a native FimH leader peptide, influenza hemagglutinin signal peptide, and a human respiratory syncytial virus A (strain A2) fusion glycoprotein F0 signal peptide.
C352. The composition according to clause C314, wherein the polypeptide comprises a murine IgK signal peptide sequence.
C353. The composition according to clause C314, wherein the polypeptide comprises any one signal peptide sequence selected from human IgG receptor FcRn large subunit p51 signal peptide and a human IL10 protein signal peptide.
C354. The composition according to clause C314, wherein the polypeptide comprises a mutation of arginine to proline at amino acid position 60 (R60P), according to the numbering of SEQ ID NO: 3.
C355. The composition according to clauses C300-C354, comprising at most 25% free saccharide as compared to the total amount of saccharide in the composition.
C356. The composition of any one of clauses C300-C354, further comprising one or more conjugates, wherein the conjugate comprises a carrier protein covalently bound to a K. pneumoniae O-antigen selected from O1 and O2.
C357. The composition of clause C356, wherein the K. pneumoniae O-antigen is selected from the group consisting of a) serotype O1 subtype v1 (O1v1), b) serotype O1 subtype v2 (O1v2), c) serotype O2 subtype v1 (O2v1), and d) serotype O2 subtype v2 (O2v2).
C358. A composition comprising
 (i) one or more conjugates comprising a carrier protein covalently bound to a K. pneumoniae O-antigen selected from the group consisting of serotype O1 subtype v1 (O1v1), serotype O1 subtype v2 (O1v2), serotype O2 subtype v1 (O2v1), and serotype O2 subtype v2 (O2v2); and
 (ii) one or more conjugates, wherein the conjugate comprises a carrier protein covalently bound to a saccharide, said saccharide comprising a structure selected from the group consisting of Formula O1, Formula O1A, Formula O1B, Formula O1C, Formula O2, Formula O3, Formula O4, Formula O4:K52, Formula O4:K6, Formula O5, Formula O5ab, Formula O5ac, Formula O6, Formula O6:K2; K13; K15; Formula O6:K54, Formula O7, Formula O8, Formula O9, Formula O10, Formula O11, Formula O12, Formula O13, Formula O14, Formula O15, Formula O16, Formula O17, Formula O18, Formula O18A, Formula O18ac, Formula O18A1, Formula O18B, Formula O18B1, Formula O19, Formula O20, Formula O21, Formula O22, Formula O23, Formula O23A, Formula O24, Formula O25, Formula O25a, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O45, Formula O45rel, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D$_1$, Formula O63, Formula O64, Formula O65, Formula O66, Formula O68, Formula O69, Formula O70, Formula O71, Formula O73, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 1 to 100.

C359. The composition according to clause C358, wherein the saccharide is selected from the group consisting of Formula O25b, Formula O1A, Formula O2, Formula O6, Formula O8 and Formula O9.

C360. The composition according to clause C359, wherein the saccharide is selected from the group consisting of Formula O25b, Formula O1A, Formula O2, and Formula O6.

C361. A composition comprising one or more conjugates comprising a carrier protein covalently bound to a *K. pneumoniae* O-antigen selected from the group consisting of serotype O1 subtype v1 (O1v1), serotype O1 subtype v2 (O1v2), serotype O2 subtype v1 (O2v1), and serotype O2 subtype v2 (O2v2); and (a) a conjugate comprising a carrier protein covalently bound to a saccharide comprising Formula O25b, wherein n is an integer from 31 to 90,
(b) a conjugate comprising a carrier protein covalently bound to a saccharide comprising Formula O1A, wherein n is an integer from 31 to 90,
(c) a conjugate comprising a carrier protein covalently bound to a saccharide comprising Formula O2, wherein n is an integer from 31 to 90,
(d) a conjugate comprising a carrier protein covalently bound to a saccharide comprising and Formula O6, wherein n is an integer from 31 to 90,
(e) a conjugate comprising a carrier protein covalently bound to a saccharide comprising and Formula O8, wherein n is an integer from 31 to 90, and
(f) a conjugate comprising a carrier protein covalently bound to a saccharide comprising and Formula O9, wherein n is an integer from 31 to 90.

C362. The composition of clause C361 comprising (i) one or more conjugates comprising a carrier protein covalently bound to a *K. pneumoniae* O-antigen selected from the group consisting of serotype O1 subtype v1 (O1v1), serotype O1 subtype v2 (O1v2), serotype O2 subtype v1 (O2v1), and serotype O2 subtype v2 (O2v2); and (a) a conjugate comprising a carrier protein covalently bound to a saccharide comprising Formula O25b, wherein n is an integer from 31 to 90,
(b) a conjugate comprising a carrier protein covalently bound to a saccharide comprising Formula O1A, wherein n is an integer from 31 to 90,
(c) a conjugate comprising a carrier protein covalently bound to a saccharide comprising Formula O2, wherein n is an integer from 31 to 90, and
(d) a conjugate comprising a carrier protein covalently bound to a saccharide comprising and Formula O6, wherein n is an integer from 31 to 90.

C363. The composition according to clauses C361 or C362, further comprising one or more conjugates having a saccharide selected from the group consisting of Formula O15, Formula O16, Formula O17, Formula O18 and Formula O75, wherein n is an integer from 31 to 90.

C364. The composition according to any one of clauses C358-C363, wherein the saccharide further comprises any one of an *E. coli* R1 moiety, *E. coli* R2 moiety, *E. coli* R3 moiety, *E. coli* R4 moiety, and *E. coli* K-12 moiety.

C365. The composition according to any one of clauses C358-C363, wherein the saccharide does not further comprise any one of an *E. coli* R1 moiety, *E. coli* R2 moiety, *E. coli* R3 moiety, *E. coli* R4 moiety, and *E. coli* K-12 moiety.

C366. The composition according to clause 67, wherein the saccharide does not further comprise an *E. coli* R2 moiety.

C367. The composition according to any one of clauses C358-C366, wherein the saccharide further comprises a 3-deoxy-d-manno-oct-2-ulosonic acid (KDO) moiety.

C368. The composition according to any one of clauses C358-C367, wherein the carrier protein is selected from the group consisting of CRM197, diphtheria toxin fragment B (DTFB), DTFB C8, Diphtheria toxoid (DT), tetanus toxoid (TT), fragment C of TT, pertussis toxoid, cholera toxoid, or exotoxin A from *Pseudomonas aeruginosa*; detoxified Exotoxin A of *P. aeruginosa* (EPA), maltose binding protein (MBP), detoxified hemolysin A of *S. aureus* clumping factor A, clumping factor B, Cholera toxin B subunit (CTB), *Streptococcus pneumoniae* Pneumolysin and detoxified variants thereof, *C. jejuni* AcrA, *C. jejuni* natural glycoproteins, and Streptococcal C5a peptidase (SCP) or a variant thereof.

C369. The composition according to clause C368, wherein the carrier protein is CRM197.
C370. The composition according to clause C368, wherein the carrier protein is tetanus toxoid.
C371. The composition according to any one of clauses C358-C370, wherein the ratio of saccharide to protein is at least 0.5 to at most 2.
C372. The composition according to any one of clauses C358-C371, wherein the conjugate is prepared via reductive amination.
C373. The composition according to any one of clauses C358-C371, wherein the saccharide is conjugated to the carrier protein through a (2-((2-oxoethyl)thio)ethyl)carbamate (eTEC) spacer.
C374. The composition according to any one of clauses C358-C373, wherein the saccharide is a single-end linked conjugated saccharide.
C375. The composition according to clause C367, wherein the saccharide is conjugated to the carrier protein through a 3-deoxy-d-manno-oct-2-ulosonic acid (KDO) residue.
C376. The composition according to any one of clauses C358-C372, wherein the conjugate is prepared via CDAP chemistry.
C377. The composition according to clauses C358-C376, comprising at most 25% free saccharide as compared to the total amount of saccharide in the composition.
C378. The composition of any one of clauses C300-C377 further comprising an adjuvant.
C379. The composition of clause C378, wherein the adjuvant comprises aluminum.
C380. The composition of clause C378, wherein the adjuvant comprises QS21.
C381. The composition of clause C378, wherein the adjuvant comprises MPLA.
C382. The composition of clause C380 or C381, wherein the adjuvant is a liposomal adjuvant.
C383. A method of eliciting an immune response against *Escherichia coli* in a mammal, comprising administering to the mammal an effective amount of the composition according to any one of clauses C300-C382.
C384. The method according to clause C383, wherein the immune response comprises opsonophagocytic antibodies against *E. coli*.
C385. The method according to clause C383, wherein the immune response protects the mammal from an *E. coli* infection.
C386. Use of the composition of any one of clauses C300-C382 for inducing an immune response against *E. coli*.
C387. Use of the composition of any one of clauses C300-C382 in the manufacture of a medicament for inducing an immune response against *E. coli*.
C388. The use of clause C386 or C387, wherein the immune response comprises opsonophagocytic antibodies against *E. coli*.
C389. The use of clause C386 or C387, wherein the immune response protects the mammal from an *E. coli* infection.
C390. A method of eliciting an immune response against *K. pneumoniae* in a mammal, comprising administering to the mammal an effective amount of the composition according to any one of clauses C300-C382.
C391. The method according to clause C390, wherein the immune response comprises opsonophagocytic antibodies against *K. pneumoniae*.
C392. The method according to clause C390, wherein the immune response protects the mammal from a *K. pneumoniae* infection.
C393. Use of the composition of any one of clauses C300C382 for inducing an immune response against *K. pneumoniae*.
C394. Use of the composition of any one of clauses C300C382 in the manufacture of a medicament for inducing an immune response against *K. pneumoniae*.
C395. The use of clause C386 or C387, wherein the immune response comprises opsonophagocytic antibodies against *K. pneumoniae*.
C396. The use of clause C386 or C387, wherein the immune response protects the mammal from an *K. pneumoniae* infection.
C397. A nucleic acid comprising nucleotides encoding the polypeptides of any one of clauses C1-C382.
C398. The nucleic acid of clause C397, wherein the nucleic acid is RNA.
C399. A nanoparticle comprising the nucleic acid of clause C397 or C398.
C400. The composition according to any one of clauses 303, 304, 305, 359, 360, 361, 362 or 363, further comprising one or more conjugates having a saccharide selected from the group consisting of Formula O4, Formula O11, Formula O13, Formula O21 and Formula O86, wherein n is an integer from 1 to 100, preferably from 31 to 90.

The invention claimed is:

1. A composition comprising
   (i) a fimbrial H (FimH) polypeptide, a polypeptide derived from FimH, a functional fragment of a FimH polypeptide, or a functional fragment of a polypeptide derived from FimH; and
   (ii) one or more conjugates, wherein the conjugate comprises a carrier protein covalently bound to an *Escherichia coli* saccharide, said saccharide comprising a structure selected from the group consisting of Formula O1, Formula O1A, Formula O1B, Formula O1C, Formula O2, Formula O3, Formula O4, Formula O4:K52, Formula O4:K6, Formula O5, Formula O5ab, Formula O5ac, Formula O6, Formula O6:K2, Formula O6:K13, Formula O6:K15, Formula O6:K54, Formula O7, Formula O8, Formula O9, Formula O10, Formula O11, Formula O12, Formula O13, Formula O14, Formula O15, Formula O16, Formula O17, Formula O18, Formula O18A, Formula O18ac, Formula O18A1, Formula O18B, Formula O18B1, Formula O19, Formula O20, Formula O21, Formula O22, Formula O23, Formula O23A, Formula O24, Formula O25, Formula O25a, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O45rel, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D$_1$, Formula O63, Formula O64, Formula O65, Formula O66, Formula O68, Formula O69, Formula O70, Formula O71, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187,
   wherein n is an integer from 31 to 100 in the Formula thereof for each saccharide molecule.

2. A composition comprising a fimbrial H (FimH) polypeptide, a polypeptide derived from FimH, a functional fragment of a FimH polypeptide, or a functional fragment of a polypeptide derived from FimH thereof; and
   (a) a conjugate comprising a carrier protein covalently bound to an *Escherichia coli* saccharide comprising Formula O25b, wherein n is an integer from 31 to 90 in the Formula thereof for each saccharide molecule,
   (b) a conjugate comprising a carrier protein covalently bound to an *Escherichia coli* saccharide comprising Formula O1A, wherein n is an integer from 31 to 90 in the Formula thereof for each saccharide molecule,
   (c) a conjugate comprising a carrier protein covalently bound to an *Escherichia coli* saccharide comprising Formula O2, wherein n is an integer from 31 to 90 in the Formula thereof for each saccharide molecule,
   (d) a conjugate comprising a carrier protein covalently bound to an *Escherichia coli* saccharide comprising Formula O6, wherein n is an integer from 31 to 90 in the Formula thereof for each saccharide molecule,
   (e) a conjugate comprising a carrier protein covalently bound to an *Escherichia coli* saccharide comprising Formula O8, wherein n is an integer from 31 to 90 in the Formula thereof for each saccharide molecule, and
   (f) a conjugate comprising a carrier protein covalently bound to an *Escherichia coli* saccharide comprising Formula O9, wherein n is an integer from 31 to 90 in the Formula thereof for each saccharide molecule.

3. The composition of claim 1, comprising
   (a) a conjugate comprising a carrier protein covalently bound to an *Escherichia coli* saccharide comprising Formula O25b, wherein n is an integer from 31 to 90 in the Formula thereof for each saccharide molecule,
   (b) a conjugate comprising a carrier protein covalently bound to an *Escherichia coli* saccharide comprising Formula O1A, wherein n is an integer from 31 to 90 in the Formula thereof for each saccharide molecule,
   (c) a conjugate comprising a carrier protein covalently bound to an *Escherichia coli* saccharide comprising Formula O2, wherein n is an integer from 31 to 90 in the Formula thereof for each saccharide molecule, and
   (d) a conjugate comprising a carrier protein covalently bound to an *Escherichia coli* saccharide comprising Formula O6, wherein n is an integer from 31 to 90 in the Formula thereof for each saccharide molecule.

4. The composition according to claim 3, further comprising one or more conjugates comprising an *Escherichia coli* saccharide selected from the group consisting of Formula O15, Formula O16, Formula O17, Formula O18 and Formula O75, wherein n is an integer from 31 to 90 in the Formula thereof for each saccharide molecule.

5. The composition according to claim 1, wherein the carrier protein is selected from the group consisting of CRM$_{197}$, diphtheria toxin fragment B (DTFB), DTFB C8, Diphtheria toxoid (DT), tetanus toxoid (TT), fragment C of TT, pertussis toxoid, cholera toxoid, exotoxin A from *Pseudomonas aeruginosa*, detoxified Exotoxin A of *P. aeruginosa* (EPA), maltose binding protein (MBP), detoxified hemolysin A of *S. aureus*, clumping factor A, clumping factor B, Cholera toxin B subunit (CTB), *Streptococcus pneumoniae* Pneumolysin or detoxified variants thereof, *C. jejuni* AcrA, and *C. jejuni* natural glycoproteins.

6. The composition according to claim 1, wherein the polypeptide or functional fragment is *Escherichia coli* fimbrial H (FimH) or derived from *Escherichia coli* FimH.

7. The composition according to claim 6, comprising a functional fragment of FimH.

8. The composition according to claim 7, wherein the functional fragment comprises a lectin domain of FimH.

9. The composition according to claim 6, wherein the polypeptide is complexed with a FimC polypeptide or a functional fragment of a FimC polypeptide.

10. The composition according to claim 6, wherein the polypeptide is stabilized by a donor-strand peptide of FimG (DsG).

11. The composition according to claim 1, further comprising one or more conjugates, wherein the conjugate comprises a carrier protein covalently bound to a *K pneumoniae* O-antigen selected from O1 and O2.

12. A composition comprising
(i) one or more conjugates comprising a carrier protein covalently bound to a *K pneumoniae* O-antigen selected from the group consisting of serotype O1 subtype v1 (O1v1), serotype O1 subtype v2 (O1v2), serotype O2 subtype v1 (O2v1), and serotype O2 subtype v2 (O2v2); and
(ii) one or more conjugates, wherein the conjugate comprises a carrier protein covalently bound to an *Escherichia coli* saccharide, said saccharide comprising a structure selected from the group consisting of Formula O1, Formula O1A, Formula O1B, Formula O1C, Formula O2, Formula O3, Formula O4, Formula O4:K52, Formula O4:K6, Formula O5, Formula O5ab, Formula O5ac, Formula O6, Formula O6:K2, Formula O6:K13, Formula O6:K15, Formula O6:K54, Formula O7, Formula O8, Formula O9, Formula O10, Formula O11, Formula O12, Formula O13, Formula O14, Formula O15, Formula O16, Formula O17, Formula O18, Formula O18A, Formula O18ac, Formula O18A1, Formula O18B, Formula O18B1, Formula O19, Formula O20, Formula O21, Formula O22, Formula O23, Formula O23A, Formula O24, Formula O25, Formula O25a, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O45, Formula O45rel, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D1, Formula O63, Formula O64, Formula O65, Formula O66, Formula O68, Formula O69, Formula O70, Formula O71, Formula O73, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O1110444, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187,
wherein n is an integer from 31 to 100 in the Formula thereof for each saccharide molecule.

13. The composition according to claim 12, wherein the saccharide is selected from the group consisting of Formula O25b, Formula O1A, Formula O2, Formula O6, Formula O8 and Formula O9.

14. The composition according to claim 13, wherein the saccharide is selected from the group consisting of Formula O25b, Formula O1A, Formula O2, and Formula O6.

15. A composition comprising one or more conjugates comprising a carrier protein covalently bound to a *K pneumoniae* O-antigen selected from the group consisting of serotype O1 subtype v1 (O1v1), serotype O1 subtype v2 (O1v2), serotype O2 subtype v1 (O2v1), and serotype O2 subtype v2 (O2v2); and
(a) a conjugate comprising a carrier protein covalently bound to an *Escherichia coli* saccharide comprising Formula O25b, wherein n is an integer from 31 to 90 in the Formula thereof for each saccharide molecule,
(b) a conjugate comprising a carrier protein covalently bound to an *Escherichia coli* saccharide comprising Formula O1A, wherein n is an integer from 31 to 90 in the Formula thereof for each saccharide molecule,
(c) a conjugate comprising a carrier protein covalently bound to an *Escherichia coli* saccharide comprising Formula O2, wherein n is an integer from 31 to 90 in the Formula thereof for each saccharide molecule, and
(d) a conjugate comprising a carrier protein covalently bound to an *Escherichia coli* saccharide comprising and Formula O6, wherein n is an integer from 31 to 90 in the Formula thereof for each saccharide molecule.

16. The composition according to claim 15, further comprising one or more conjugates having an *Escherichia coli* saccharide selected from the group consisting of Formula O8, Formula O9, Formula O15, Formula O16, Formula O17, Formula O18 and Formula O75, wherein n is an integer from 31 to 90 in the Formula thereof for each saccharide molecule.

17. The composition of claim 1, further comprising an adjuvant.

* * * * *

SEQUENCE LISTING

```
<160> NUMBER OF SEQ ID NOS: 113

<210> SEQ ID NO 1
<211> LENGTH: 300
<212> TYPE: PRT
<213> ORGANISM: Artificial Sequence
<220> FEATURE:
<223> OTHER INFORMATION: Synthetic

<400> SEQUENCE: 1

Met Lys Arg Val Ile Thr Leu Phe Ala Val Leu Leu Met Gly Trp Ser
1               5                   10                  15

Val Asn Ala Trp Ser Phe Ala Cys Lys Thr Ala Asn Gly Thr Ala Ile
            20                  25                  30

Pro Ile Gly Gly Gly Ser Ala Asn Val Tyr Val Asn Leu Ala Pro Val
        35                  40                  45
```

Val Asn Val Gly Gln Asn Leu Val Asp Leu Ser Thr Gln Ile Phe
 50                  55                  60

Cys His Asn Asp Tyr Pro Glu Thr Ile Thr Asp Tyr Val Thr Leu Gln
 65                  70                  75                  80

Arg Gly Ser Ala Tyr Gly Gly Val Leu Ser Asn Phe Ser Gly Thr Val
                 85                  90                  95

Lys Tyr Ser Gly Ser Ser Tyr Pro Phe Pro Thr Thr Ser Glu Thr Pro
            100                 105                 110

Arg Val Val Tyr Asn Ser Arg Thr Asp Lys Pro Trp Pro Val Ala Leu
                115                 120                 125

Tyr Leu Thr Pro Val Ser Ser Ala Gly Gly Val Ala Ile Lys Ala Gly
130                 135                 140

Ser Leu Ile Ala Val Leu Ile Leu Arg Gln Thr Asn Asn Tyr Asn Ser
145                 150                 155                 160

Asp Asp Phe Gln Phe Val Trp Asn Ile Tyr Ala Asn Asn Asp Val Val
                165                 170                 175

Val Pro Thr Gly Gly Cys Asp Val Ser Ala Arg Asp Val Thr Val Thr
                180                 185                 190

Leu Pro Asp Tyr Pro Gly Ser Val Pro Ile Pro Leu Thr Val Tyr Cys
                195                 200                 205

Ala Lys Ser Gln Asn Leu Gly Tyr Tyr Leu Ser Gly Thr Thr Ala Asp
210                 215                 220

Ala Gly Asn Ser Ile Phe Thr Asn Thr Ala Ser Phe Ser Pro Ala Gln
225                 230                 235                 240

Gly Val Gly Val Gln Leu Thr Arg Asn Gly Thr Ile Ile Pro Ala Asn
                245                 250                 255

Asn Thr Val Ser Leu Gly Ala Val Gly Thr Ser Ala Val Ser Leu Gly
                260                 265                 270

Leu Thr Ala Asn Tyr Ala Arg Thr Gly Gly Gln Val Thr Ala Gly Asn
                275                 280                 285

Val Gln Ser Ile Ile Gly Val Thr Phe Val Tyr Gln
290                 295                 300

<210> SEQ ID NO 2
<211> LENGTH: 279
<212> TYPE: PRT
<213> ORGANISM: Artificial Sequence
<220> FEATURE:
<223> OTHER INFORMATION: Synthetic

<400> SEQUENCE: 2

Phe Ala Cys Lys Thr Ala Asn Gly Thr Ala Ile Pro Ile Gly Gly Gly
 1               5                  10                  15

Ser Ala Asn Val Tyr Val Asn Leu Ala Pro Val Val Asn Val Gly Gln
                20                  25                  30

Asn Leu Val Val Asp Leu Ser Thr Gln Ile Phe Cys His Asn Asp Tyr
             35                  40                  45

Pro Glu Thr Ile Thr Asp Tyr Val Thr Leu Gln Arg Gly Ser Ala Tyr
         50                  55                  60

Gly Gly Val Leu Ser Asn Phe Ser Gly Thr Val Lys Tyr Ser Gly Ser
 65                  70                  75                  80

Ser Tyr Pro Phe Pro Thr Thr Ser Glu Thr Pro Arg Val Val Tyr Asn
                 85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
            115                 120                 125

Leu Ile Leu Arg Gln Thr Asn Asn Tyr Asn Ser Asp Asp Phe Gln Phe
130                 135                 140

Val Trp Asn Ile Tyr Ala Asn Asn Asp Val Val Pro Thr Gly Gly
145                 150                 155                 160

Cys Asp Val Ser Ala Arg Asp Val Thr Val Thr Leu Pro Asp Tyr Pro
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr Thr Ala Asp Ala Gly Asn Ser Ile
            195                 200                 205

Phe Thr Asn Thr Ala Ser Phe Ser Pro Ala Gln Gly Val Gly Val Gln
    210                 215                 220

Leu Thr Arg Asn Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln
            275

<210> SEQ ID NO 3
<211> LENGTH: 156
<212> TYPE: PRT
<213> ORGANISM: Artificial Sequence
<220> FEATURE:
<223> OTHER INFORMATION: Synthetic

<400> SEQUENCE: 3

Phe Ala Cys Lys Thr Ala Asn Gly Thr Ala Ile Pro Ile Gly Gly Gly
1               5                   10                  15

Ser Ala Asn Val Tyr Val Asn Leu Ala Pro Val Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
    50                  55                  60

Gly Gly Val Leu Ser Asn Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
130                 135                 140

Val Trp Asn Ile Tyr Ala Asn Asn Asp Val Val Val
145                 150                 155

<210> SEQ ID NO 4
<211> LENGTH: 120
<212> TYPE: PRT
<213> ORGANISM: Artificial Sequence
<220> FEATURE:

<223> OTHER INFORMATION: Synthetic

<400> SEQUENCE: 4

```
Gly Cys Asp Val Ser Ala Arg Asp Val Thr Val Thr Leu Pro Asp Tyr
1               5                   10                  15

Pro Gly Ser Val Pro Ile Pro Leu Thr Val Tyr Cys Ala Lys Ser Gln
            20                  25                  30

Asn Leu Gly Tyr Tyr Leu Ser Gly Thr Thr Ala Asp Ala Gly Asn Ser
        35                  40                  45

Ile Phe Thr Asn Thr Ala Ser Phe Ser Pro Ala Gln Gly Val Gly Val
    50                  55                  60

Gln Leu Thr Arg Asn Gly Thr Ile Ile Pro Ala Asn Asn Thr Val Ser
65                  70                  75                  80

Leu Gly Ala Val Gly Thr Ser Ala Val Ser Leu Gly Leu Thr Ala Asn
                85                  90                  95

Tyr Ala Arg Thr Gly Gly Gln Val Thr Ala Gly Asn Val Gln Ser Ile
            100                 105                 110

Ile Gly Val Thr Phe Val Tyr Gln
        115                 120
```

<210> SEQ ID NO 5
<211> LENGTH: 330
<212> TYPE: PRT
<213> ORGANISM: Artificial Sequence
<220> FEATURE:
<223> OTHER INFORMATION: Synthetic

<400> SEQUENCE: 5

```
Val Glu Thr Asp Thr Leu Leu Leu Trp Val Leu Leu Leu Trp Val Pro
1               5                   10                  15

Gly Ser Thr Gly Phe Ala Cys Lys Thr Ala Ser Gly Thr Ala Ile Pro
            20                  25                  30

Ile Gly Gly Gly Ser Ala Asn Val Tyr Val Asn Leu Ala Pro Cys Val
        35                  40                  45

Asn Val Gly Gln Asn Cys Val Val Asp Leu Ser Thr Gln Ile Phe Cys
    50                  55                  60

His Asn Asp Tyr Pro Glu Thr Ile Thr Asp Tyr Val Thr Leu Gln Arg
65                  70                  75                  80

Gly Ser Ala Tyr Gly Val Leu Ser Ser Phe Ser Gly Thr Val Lys
                85                  90                  95

Tyr Ser Gly Ser Ser Tyr Pro Phe Pro Thr Thr Ser Glu Thr Pro Arg
            100                 105                 110

Val Val Tyr Asn Ser Arg Thr Asp Lys Pro Trp Pro Val Ala Leu Tyr
        115                 120                 125

Leu Thr Pro Val Ser Ser Ala Gly Gly Val Ala Ile Lys Ala Gly Ser
    130                 135                 140

Leu Ile Ala Val Leu Ile Leu Arg Gln Thr Asn Asn Tyr Asn Ser Asp
145                 150                 155                 160

Asp Phe Gln Phe Val Trp Asn Ile Tyr Ala Asn Asn Asp Val Val
                165                 170                 175

Pro Thr Gly Gly Cys Asp Val Ser Ala Arg Asp Val Thr Val Thr Leu
            180                 185                 190

Pro Asp Tyr Pro Gly Ser Val Pro Ile Pro Leu Thr Val Tyr Cys Ala
        195                 200                 205

Lys Ser Gln Asn Leu Gly Tyr Tyr Leu Ser Gly Thr Thr Ala Asp Ala
    210                 215                 220
```

Gly Asn Ser Ile Phe Thr Asn Thr Ala Ser Phe Ser Pro Ala Gln Gly
225                 230                 235                 240

Val Gly Val Gln Leu Thr Arg Gln Gly Thr Ile Ile Pro Ala Asn Asn
            245                 250                 255

Thr Val Ser Leu Gly Ala Val Gly Thr Ser Ala Val Ser Leu Gly Leu
        260                 265                 270

Thr Ala Asn Tyr Ala Arg Thr Gly Gln Val Thr Ala Gly Asn Val
        275                 280                 285

Gln Ser Ile Ile Gly Val Thr Phe Val Tyr Gln Gly Ser Ser Gly
    290                 295                 300

Gly Gly Ala Asp Val Thr Ile Thr Val Asn Gly Lys Val Val Ala Lys
305                 310                 315                 320

Gly Gly His His His His His His His
                325                 330

<210> SEQ ID NO 6
<211> LENGTH: 330
<212> TYPE: PRT
<213> ORGANISM: Artificial Sequence
<220> FEATURE:
<223> OTHER INFORMATION: Synthetic

<400> SEQUENCE: 6

Met Glu Thr Asp Thr Leu Leu Leu Trp Val Leu Leu Leu Trp Val Pro
1               5                   10                  15

Gly Ser Thr Gly Phe Ala Cys Lys Thr Ala Ser Gly Thr Ala Ile Pro
            20                  25                  30

Ile Gly Gly Gly Ser Ala Asn Val Tyr Val Asn Leu Ala Pro Val Val
        35                  40                  45

Asn Val Gly Gln Asn Leu Val Val Asp Leu Ser Thr Gln Ile Phe Cys
    50                  55                  60

His Asn Asp Tyr Pro Glu Thr Ile Thr Asp Tyr Val Thr Leu Gln Arg
65                  70                  75                  80

Gly Ser Ala Tyr Gly Gly Val Leu Ser Ser Phe Ser Gly Thr Val Lys
                85                  90                  95

Tyr Ser Gly Ser Ser Tyr Pro Phe Pro Thr Thr Ser Glu Thr Pro Arg
            100                 105                 110

Val Val Tyr Asn Ser Arg Thr Asp Lys Pro Trp Pro Val Ala Leu Tyr
        115                 120                 125

Leu Thr Pro Val Ser Ser Ala Gly Gly Val Ala Ile Lys Ala Gly Ser
    130                 135                 140

Leu Ile Ala Val Leu Ile Leu Arg Gln Thr Asn Asn Tyr Asn Ser Asp
145                 150                 155                 160

Asp Phe Gln Phe Val Trp Asn Ile Tyr Ala Asn Asn Asp Val Val Val
                165                 170                 175

Pro Thr Gly Gly Cys Asp Val Ser Ala Arg Asp Val Thr Val Thr Leu
            180                 185                 190

Pro Asp Tyr Pro Gly Ser Val Pro Ile Pro Leu Thr Val Tyr Cys Ala
        195                 200                 205

Lys Ser Gln Asn Leu Gly Tyr Tyr Leu Ser Gly Thr Thr Ala Asp Ala
    210                 215                 220

Gly Asn Ser Ile Phe Thr Asn Thr Ala Ser Phe Ser Pro Ala Gln Gly
225                 230                 235                 240

Val Gly Val Gln Leu Thr Arg Gln Gly Thr Ile Ile Pro Ala Asn Asn
                245                 250                 255

Thr Val Ser Leu Gly Ala Val Gly Thr Ser Ala Val Ser Leu Gly Leu
              260                 265                 270

Thr Ala Asn Tyr Ala Arg Thr Gly Gln Val Thr Ala Gly Asn Val
              275                 280                 285

Gln Ser Ile Ile Gly Val Thr Phe Val Tyr Gln Gly Gly Ser Ser Gly
290                 295                 300

Gly Gly Ala Asp Val Thr Ile Thr Val Asn Gly Lys Val Val Ala Lys
305                 310                 315                 320

Gly Gly His His His His His His
              325                 330

<210> SEQ ID NO 7
<211> LENGTH: 188
<212> TYPE: PRT
<213> ORGANISM: Artificial Sequence
<220> FEATURE:
<223> OTHER INFORMATION: Synthetic

<400> SEQUENCE: 7

Met Glu Thr Asp Thr Leu Leu Leu Trp Val Leu Leu Leu Trp Val Pro
1               5                   10                  15

Gly Ser Thr Gly Phe Ala Cys Lys Thr Ala Ser Gly Thr Ala Ile Pro
                20                  25                  30

Ile Gly Gly Gly Ser Ala Asn Val Tyr Val Asn Leu Ala Pro Val Val
            35                  40                  45

Asn Val Gly Gln Asn Leu Val Val Asp Leu Ser Thr Gln Ile Phe Cys
        50                  55                  60

His Asn Asp Tyr Pro Glu Thr Ile Thr Asp Tyr Val Thr Leu Gln Arg
65                  70                  75                  80

Gly Ser Ala Tyr Gly Val Leu Ser Ser Phe Ser Gly Thr Val Lys
                85                  90                  95

Tyr Ser Gly Ser Ser Tyr Pro Phe Pro Thr Thr Ser Glu Thr Pro Arg
            100                 105                 110

Val Val Tyr Asn Ser Arg Thr Asp Lys Pro Trp Pro Val Ala Leu Tyr
        115                 120                 125

Leu Thr Pro Val Ser Ser Ala Gly Gly Val Ala Ile Lys Ala Gly Ser
    130                 135                 140

Leu Ile Ala Val Leu Ile Leu Arg Gln Thr Asn Asn Tyr Asn Ser Asp
145                 150                 155                 160

Asp Phe Gln Phe Val Trp Asn Ile Tyr Ala Asn Asn Asp Val Val Val
                165                 170                 175

Pro Thr Gly Gly His His His His His His His
            180                 185

<210> SEQ ID NO 8
<211> LENGTH: 188
<212> TYPE: PRT
<213> ORGANISM: Artificial Sequence
<220> FEATURE:
<223> OTHER INFORMATION: Synthetic

<400> SEQUENCE: 8

Met Glu Thr Asp Thr Leu Leu Leu Trp Val Leu Leu Leu Trp Val Pro
1               5                   10                  15

Gly Ser Thr Gly Phe Ala Cys Lys Thr Ala Ser Gly Thr Ala Ile Pro
                20                  25                  30

Ile Gly Gly Gly Ser Ala Asn Val Tyr Val Asn Leu Ala Pro Cys Val

```
                35                  40                  45
Asn Val Gly Gln Asn Cys Val Val Asp Leu Ser Thr Gln Ile Phe Cys
             50                  55                  60
His Asn Asp Tyr Pro Glu Thr Ile Thr Asp Tyr Val Thr Leu Gln Arg
 65                  70                  75                  80
Gly Ser Ala Tyr Gly Val Leu Ser Ser Phe Ser Gly Thr Val Lys
                 85                  90                  95
Tyr Ser Gly Ser Ser Tyr Pro Phe Pro Thr Thr Ser Glu Thr Pro Arg
                100                 105                 110
Val Val Tyr Asn Ser Arg Thr Asp Lys Pro Trp Pro Val Ala Leu Tyr
                115                 120                 125
Leu Thr Pro Val Ser Ser Ala Gly Gly Val Ala Ile Lys Ala Gly Ser
130                 135                 140
Leu Ile Ala Val Leu Ile Leu Arg Gln Thr Asn Asn Tyr Asn Ser Asp
145                 150                 155                 160
Asp Phe Gln Phe Val Trp Asn Ile Tyr Ala Asn Asn Asp Val Val Val
                165                 170                 175
Pro Thr Gly Gly His His His His His His
                180                 185
```

<210> SEQ ID NO 9
<211> LENGTH: 14
<212> TYPE: PRT
<213> ORGANISM: Artificial Sequence
<220> FEATURE:
<223> OTHER INFORMATION: Synthetic

<400> SEQUENCE: 9

```
Ala Asp Val Thr Ile Thr Val Asn Gly Lys Val Val Ala Lys
 1               5                  10
```

<210> SEQ ID NO 10
<211> LENGTH: 241
<212> TYPE: PRT
<213> ORGANISM: Artificial Sequence
<220> FEATURE:
<223> OTHER INFORMATION: Synthetic

<400> SEQUENCE: 10

```
Met Ser Asn Lys Asn Val Asn Val Arg Lys Ser Gln Glu Ile Thr Phe
 1               5                  10                  15
Cys Leu Leu Ala Gly Ile Leu Met Phe Met Ala Met Val Ala Gly
                 20                  25                  30
Arg Ala Glu Ala Gly Val Ala Leu Gly Ala Thr Arg Val Ile Tyr Pro
                 35                  40                  45
Ala Gly Gln Lys Gln Val Gln Leu Ala Val Thr Asn Asn Asp Glu Asn
             50                  55                  60
Ser Thr Tyr Leu Ile Gln Ser Trp Val Glu Asn Ala Asp Gly Val Lys
 65                  70                  75                  80
Asp Gly Arg Phe Ile Val Thr Pro Pro Leu Phe Ala Met Lys Gly Lys
                 85                  90                  95
Lys Glu Asn Thr Leu Arg Ile Leu Asp Ala Thr Asn Asn Gln Leu Pro
                100                 105                 110
Gln Asp Arg Glu Ser Leu Phe Trp Met Asn Val Lys Ala Ile Pro Ser
                115                 120                 125
Met Asp Lys Ser Lys Leu Thr Glu Asn Thr Leu Gln Leu Ala Ile Ile
130                 135                 140
```

-continued

```
Ser Arg Ile Lys Leu Tyr Tyr Arg Pro Ala Lys Leu Ala Leu Pro Pro
145                 150                 155                 160

Asp Gln Ala Ala Glu Lys Leu Arg Phe Arg Arg Ser Ala Asn Ser Leu
                165                 170                 175

Thr Leu Ile Asn Pro Thr Pro Tyr Tyr Leu Thr Val Thr Glu Leu Asn
            180                 185                 190

Ala Gly Thr Arg Val Leu Glu Asn Ala Leu Val Pro Pro Met Gly Glu
        195                 200                 205

Ser Thr Val Lys Leu Pro Ser Asp Ala Gly Ser Asn Ile Thr Tyr Arg
    210                 215                 220

Thr Ile Asn Asp Tyr Gly Ala Leu Thr Pro Lys Met Thr Gly Val Met
225                 230                 235                 240

Glu
```

<210> SEQ ID NO 11
<211> LENGTH: 4
<212> TYPE: PRT
<213> ORGANISM: Artificial Sequence
<220> FEATURE:
<223> OTHER INFORMATION: Synthetic

<400> SEQUENCE: 11

```
Asp Asn Lys Gln
1
```

<210> SEQ ID NO 12
<211> LENGTH: 5
<212> TYPE: PRT
<213> ORGANISM: Artificial Sequence
<220> FEATURE:
<223> OTHER INFORMATION: Synthetic

<400> SEQUENCE: 12

```
Gly Gly Ser Gly Gly
1               5
```

<210> SEQ ID NO 13
<211> LENGTH: 6
<212> TYPE: PRT
<213> ORGANISM: Artificial Sequence
<220> FEATURE:
<223> OTHER INFORMATION: Synthetic

<400> SEQUENCE: 13

```
Gly Gly Ser Ser Gly Gly
1               5
```

<210> SEQ ID NO 14
<211> LENGTH: 7
<212> TYPE: PRT
<213> ORGANISM: Artificial Sequence
<220> FEATURE:
<223> OTHER INFORMATION: Synthetic

<400> SEQUENCE: 14

```
Gly Gly Ser Ser Gly Gly Gly
1               5
```

<210> SEQ ID NO 15
<211> LENGTH: 8
<212> TYPE: PRT
<213> ORGANISM: Artificial Sequence
<220> FEATURE:
<223> OTHER INFORMATION: Synthetic

```
<400> SEQUENCE: 15

Gly Gly Gly Ser Ser Gly Gly Gly
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gly Gly Gly Ser Gly Ser Gly Gly Gly
1               5

<210> SEQ ID NO 17
<211> LENGTH: 10
<212> TYPE: PRT
<213> ORGANISM: Artificial Sequence
<220> FEATURE:
<223> OTHER INFORMATION: Synthetic

<400> SEQUENCE: 17

Gly Gly Gly Ser Gly Gly Ser Gly Gly Gly
1               5                   10

<210> SEQ ID NO 18
<211> LENGTH: 21
<212> TYPE: PRT
<213> ORGANISM: Artificial Sequence
<220> FEATURE:
<223> OTHER INFORMATION: Synthetic

<400> SEQUENCE: 18

Met Lys Arg Val Ile Thr Leu Phe Ala Val Leu Leu Met Gly Trp Ser
1               5                   10                  15

Val Asn Ala Trp Ser
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic

<400> SEQUENCE: 19

Val Glu Thr Asp Thr Leu Leu Leu Trp Val Leu Leu Leu Trp Val Pro
1               5                   10                  15

Gly Ser Thr Gly
            20

<210> SEQ ID NO 20
<211> LENGTH: 279
<212> TYPE: PRT
<213> ORGANISM: Artificial Sequence
<220> FEATURE:
<223> OTHER INFORMATION: Synthetic

<400> SEQUENCE: 20

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Cys Val Asn Val Gly Gln
                20                  25                  30
```

Asn Cys Val Val Asp Leu Ser Thr Gln Ile Phe Cys His Asn Asp Tyr
                35                  40                  45

Pro Glu Thr Ile Thr Asp Tyr Val Thr Leu Gln Arg Gly Ser Ala Tyr
    50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
                100                 105                 110

Ser Ser Ala Gly Gly Val Ala Ile Lys Ala Gly Ser Leu Ile Ala Val
                115                 120                 125

Leu Ile Leu Arg Gln Thr Asn Asn Tyr Asn Ser Asp Asp Phe Gln Phe
                130                 135                 140

Val Trp Asn Ile Tyr Ala Asn Asn Asp Val Val Pro Thr Gly Gly
145                 150                 155                 160

Cys Asp Val Ser Ala Arg Asp Val Thr Val Thr Leu Pro Asp Tyr Pro
                165                 170                 175

Gly Ser Val Pro Ile Pro Leu Thr Val Tyr Cys Ala Lys Ser Gln Asn
                180                 185                 190

Leu Gly Tyr Tyr Leu Ser Gly Thr Thr Ala Asp Ala Gly Asn Ser Ile
                195                 200                 205

Phe Thr Asn Thr Ala Ser Phe Ser Pro Ala Gln Gly Val Gly Val Gln
                210                 215                 220

Leu Thr Arg Gln Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
                260                 265                 270

Gly Val Thr Phe Val Tyr Gln
                275

<210> SEQ ID NO 21
<211> LENGTH: 24
<212> TYPE: PRT
<213> ORGANISM: Artificial Sequence
<220> FEATURE:
<223> OTHER INFORMATION: Synthetic

<400> SEQUENCE: 21

Ala Asp Val Thr Ile Thr Val Asn Gly Lys Val Val Ala Lys Gly Gly
1               5                   10                  15

His His His His His His His His
                20

<210> SEQ ID NO 22
<211> LENGTH: 20
<212> TYPE: PRT
<213> ORGANISM: Artificial Sequence
<220> FEATURE:
<223> OTHER INFORMATION: Synthetic

<400> SEQUENCE: 22

Met Glu Thr Asp Thr Leu Leu Leu Trp Val Leu Leu Leu Trp Val Pro
1               5                   10                  15

Gly Ser Thr Gly

20

<210> SEQ ID NO 23
<211> LENGTH: 279
<212> TYPE: PRT
<213> ORGANISM: Artificial Sequence
<220> FEATURE:
<223> OTHER INFORMATION: Synthetic

<400> SEQUENCE: 23

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
130                 135                 140

Val Trp Asn Ile Tyr Ala Asn Asn Asp Val Val Val Pro Thr Gly Gly
145                 150                 155                 160

Cys Asp Val Ser Ala Arg Asp Val Thr Val Thr Leu Pro Asp Tyr Pro
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr Thr Ala Asp Ala Gly Asn Ser Ile
        195                 200                 205

Phe Thr Asn Thr Ala Ser Phe Ser Pro Ala Gln Gly Val Gly Val Gln
210                 215                 220

Leu Thr Arg Gln Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln
        275

<210> SEQ ID NO 24
<211> LENGTH: 160
<212> TYPE: PRT
<213> ORGANISM: Artificial Sequence
<220> FEATURE:
<223> OTHER INFORMATION: Synthetic

<400> SEQUENCE: 24

Phe Ala Cys Lys Thr Ala Ser Gly Thr Ala Ile Pro Ile Gly Gly Gly
1               5                   10                  15

```
Ser Ala Asn Val Tyr Val Asn Leu Ala Pro Val Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
 50                  55                  60

Gly Gly Val Leu Ser Ser Phe Ser Gly Thr Val Lys Tyr Ser Gly Ser
 65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
130                 135                 140

Val Trp Asn Ile Tyr Ala Asn Asn Asp Val Val Val Pro Thr Gly Gly
145                 150                 155                 160

<210> SEQ ID NO 25
<211> LENGTH: 8
<212> TYPE: PRT
<213> ORGANISM: Artificial Sequence
<220> FEATURE:
<223> OTHER INFORMATION: Synthetic

<400> SEQUENCE: 25

His His His His His His His His
1               5

<210> SEQ ID NO 26
<211> LENGTH: 160
<212> TYPE: PRT
<213> ORGANISM: Artificial Sequence
<220> FEATURE:
<223> OTHER INFORMATION: Synthetic

<400> SEQUENCE: 26

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Cys Val Asn Val Gly Gln
                20                  25                  30

Asn Cys Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
 50                  55                  60

Gly Gly Val Leu Ser Ser Phe Ser Gly Thr Val Lys Tyr Ser Gly Ser
 65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
130                 135                 140

Val Trp Asn Ile Tyr Ala Asn Asn Asp Val Val Val Pro Thr Gly Gly
145                 150                 155                 160
```

<210> SEQ ID NO 27
<211> LENGTH: 168
<212> TYPE: PRT
<213> ORGANISM: Artificial Sequence
<220> FEATURE:
<223> OTHER INFORMATION: Synthetic

<400> SEQUENCE: 27

```
Phe Ala Cys Lys Thr Ala Asn Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Asn Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Pro Thr Gly Gly
145                 150                 155                 160

His His His His His His His His
                165
```

<210> SEQ ID NO 28
<211> LENGTH: 279
<212> TYPE: PRT
<213> ORGANISM: Artificial Sequence
<220> FEATURE:
<223> OTHER INFORMATION: Synthetic

<400> SEQUENCE: 28

```
Phe Ala Cys Lys Thr Ala Asn Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Asn Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
```

```
            130                 135                 140
Val Trp Asn Ile Tyr Ala Asn Asn Asp Val Val Pro Thr Gly Gly
145                 150                 155                 160

Cys Asp Val Ser Ala Arg Asp Val Thr Val Thr Leu Pro Asp Tyr Pro
                165                 170                 175

Gly Ser Val Pro Ile Pro Leu Thr Val Tyr Cys Ala Lys Ser Gln Asn
                180                 185                 190

Leu Gly Tyr Tyr Leu Ser Gly Thr Thr Ala Asp Ala Gly Asn Ser Ile
                195                 200                 205

Phe Thr Asn Thr Ala Ser Phe Ser Pro Ala Gln Gly Val Gly Val Gln
                210                 215                 220

Leu Thr Arg Asn Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
                260                 265                 270

Gly Val Thr Phe Val Tyr Gln
                275

<210> SEQ ID NO 29
<211> LENGTH: 279
<212> TYPE: PRT
<213> ORGANISM: Artificial Sequence
<220> FEATURE:
<223> OTHER INFORMATION: Synthetic

<400> SEQUENCE: 29

Phe Ala Cys Lys Thr Ala Asn Gly Thr Ala Ile Pro Ile Gly Gly Gly
1               5                   10                  15

Ser Ala Asn Val Tyr Val Asn Leu Ala Pro Ala Val Asn Val Gly Gln
                20                  25                  30

Asn Leu Val Val Asp Leu Ser Thr Gln Ile Phe Cys His Asn Asp Tyr
                35                  40                  45

Pro Glu Thr Ile Thr Asp Tyr Val Thr Leu Gln Arg Gly Ala Ala Tyr
                50                  55                  60

Gly Gly Val Leu Ser Ser Phe Ser Gly Thr Val Lys Tyr Asn Gly Ser
65                  70                  75                  80

Ser Tyr Pro Phe Pro Thr Ser Glu Thr Pro Arg Val Val Tyr Asn
                85                  90                  95

Ser Arg Thr Asp Lys Pro Trp Pro Val Ala Leu Tyr Leu Thr Pro Val
                100                 105                 110

Ser Ser Ala Gly Gly Val Ala Ile Lys Ala Gly Ser Leu Ile Ala Val
                115                 120                 125

Leu Ile Leu Arg Gln Thr Asn Asn Tyr Asn Ser Asp Phe Gln Phe
                130                 135                 140

Val Trp Asn Ile Tyr Ala Asn Asn Asp Val Val Pro Thr Gly Gly
145                 150                 155                 160

Cys Asp Val Ser Ala Arg Asp Val Thr Val Thr Leu Pro Asp Tyr Pro
                165                 170                 175

Gly Ser Val Pro Ile Pro Leu Thr Val Tyr Cys Ala Lys Ser Gln Asn
                180                 185                 190

Leu Gly Tyr Tyr Leu Ser Gly Thr Thr Ala Asp Ala Gly Asn Ser Ile
                195                 200                 205

Phe Thr Asn Thr Ala Ser Phe Ser Pro Ala Gln Gly Val Gly Val Gln
```

```
              210                 215                 220
Leu Thr Arg Asn Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
                260                 265                 270

Gly Val Thr Phe Val Tyr Gln
                275

<210> SEQ ID NO 30
<211> LENGTH: 325
<212> TYPE: PRT
<213> ORGANISM: Artificial Sequence
<220> FEATURE:
<223> OTHER INFORMATION: Synthetic

<400> SEQUENCE: 30

Met Arg Val Glu Asn Asn Val Ser Gly Gln Asn His Asp Pro Glu
1               5                   10                  15

Gln Ile Asp Leu Ile Asp Leu Val Gln Leu Trp Arg Gly Lys Met
                20                  25                  30

Thr Ile Ile Ile Ser Val Ile Val Ala Ile Ala Leu Ala Ile Gly Tyr
                35                  40                  45

Leu Ala Val Ala Lys Glu Lys Trp Thr Ser Thr Ala Ile Ile Thr Gln
50                  55                  60

Pro Asp Val Gly Gln Ile Ala Gly Tyr Asn Asn Ala Met Asn Val Ile
65                  70                  75                  80

Tyr Gly Gln Ala Ala Pro Lys Val Ser Asp Leu Gln Glu Thr Leu Ile
                85                  90                  95

Gly Arg Phe Ser Ser Ala Phe Ser Ala Leu Ala Glu Thr Leu Asp Asn
                100                 105                 110

Gln Glu Glu Pro Glu Lys Leu Thr Ile Glu Pro Ser Val Lys Asn Gln
                115                 120                 125

Gln Leu Pro Leu Thr Val Ser Tyr Val Gly Gln Thr Ala Glu Gly Ala
130                 135                 140

Gln Met Lys Leu Ala Gln Tyr Ile Gln Gln Val Asp Asp Lys Val Asn
145                 150                 155                 160

Gln Glu Leu Glu Lys Asp Leu Lys Asp Asn Ile Ala Leu Gly Arg Lys
                165                 170                 175

Asn Leu Gln Asp Ser Leu Arg Thr Gln Glu Val Val Ala Gln Glu Gln
                180                 185                 190

Lys Asp Leu Arg Ile Arg Gln Ile Gln Glu Ala Leu Gln Tyr Ala Asn
                195                 200                 205

Gln Glu Gln Val Thr Lys Pro Gln Val Gln Gln Thr Glu Asp Val Thr
210                 215                 220

Gln Asp Thr Leu Phe Leu Leu Gly Ser Glu Ala Leu Glu Ser Met Ile
225                 230                 235                 240

Lys His Glu Ala Thr Arg Pro Leu Val Phe Ser Ser Asn Tyr Tyr Gln
                245                 250                 255

Thr Arg Gln Asn Leu Leu Asp Ile Glu Ser Leu Lys Val Asp Asp Leu
                260                 265                 270

Asp Ile His Ala Tyr Arg Tyr Val Met Lys Pro Thr Leu Pro Ile Arg
                275                 280                 285

Arg Asp Ser Pro Lys Lys Ala Ile Thr Leu Ile Leu Ala Val Leu Leu
```

```
              290                 295                 300
Gly Gly Met Val Gly Ala Gly Ile Val Leu Gly Arg Asn Ala Leu Arg
305                 310                 315                 320

Asn Tyr Asn Ala Lys
                325

<210> SEQ ID NO 31
<211> LENGTH: 326
<212> TYPE: PRT
<213> ORGANISM: Artificial Sequence
<220> FEATURE:
<223> OTHER INFORMATION: Synthetic

<400> SEQUENCE: 31

Met Arg Val Glu Asn Asn Val Ser Gly Gln Asn Asn Asp Pro Glu
1               5                   10                  15

Gln Ile Asp Leu Ile Asp Leu Val Gln Leu Trp Arg Gly Lys Met
                20                  25                  30

Thr Ile Ile Ile Ser Val Ile Val Ala Ile Ala Leu Ala Ile Gly Tyr
                35                  40                  45

Leu Ala Val Ala Lys Glu Lys Trp Thr Ser Thr Ala Ile Ile Thr Gln
50                  55                  60

Pro Asp Val Gly Gln Ile Ala Gly Tyr Asn Asn Ala Met Asn Val Ile
65                  70                  75                  80

Tyr Gly Gln Ala Ala Pro Lys Val Ser Asp Leu Gln Glu Thr Leu Ile
                85                  90                  95

Gly Arg Phe Ser Ser Ala Phe Ser Ala Leu Ala Glu Thr Leu Asp Asn
                100                 105                 110

Gln Asp Glu Pro Glu Lys Leu Thr Ile Glu Pro Ser Val Lys Asn Gln
                115                 120                 125

Gln Leu Pro Leu Thr Val Ser Tyr Val Gly Gln Thr Ala Glu Gly Ala
130                 135                 140

Gln Met Lys Leu Ala Gln Tyr Ile Gln Gln Val Asp Asp Lys Val Asn
145                 150                 155                 160

Gln Glu Leu Glu Lys Asp Leu Lys Asp Asn Ile Ala Leu Gly Arg Lys
                165                 170                 175

Asn Leu Gln Asp Ser Leu Arg Thr Gln Glu Val Val Ala Gln Glu Gln
                180                 185                 190

Lys Asp Leu Arg Ile Arg Gln Ile Gln Glu Ala Leu Gln Tyr Ala Asn
                195                 200                 205

Gln Ala Gln Val Thr Lys Pro Gln Ile Gln Gln Thr Gly Glu Asp Ile
210                 215                 220

Thr Gln Asp Thr Leu Phe Leu Leu Gly Ser Glu Ala Leu Glu Ser Met
225                 230                 235                 240

Ile Lys His Glu Ala Thr Arg Pro Leu Val Phe Ser Pro Asn Tyr Tyr
                245                 250                 255

Gln Thr Arg Gln Asn Leu Leu Asp Ile Glu Ser Leu Lys Val Asp Asp
                260                 265                 270

Leu Asp Ile His Ala Tyr Arg Tyr Val Met Lys Pro Thr Leu Pro Ile
                275                 280                 285

Arg Arg Asp Ser Pro Lys Lys Ala Ile Thr Leu Ile Leu Ala Val Leu
                290                 295                 300

Leu Gly Gly Met Val Gly Ala Gly Ile Val Leu Gly Arg Asn Ala Leu
305                 310                 315                 320

Arg Asn Tyr Asn Ala Lys
```

<210> SEQ ID NO 32
<211> LENGTH: 326
<212> TYPE: PRT
<213> ORGANISM: Artificial Sequence
<220> FEATURE:
<223> OTHER INFORMATION: Synthetic

<400> SEQUENCE: 32

Met Arg Val Glu Asn Asn Val Ser Gly Gln Asn His Asp Pro Glu
1               5                   10                  15

Gln Ile Asp Leu Ile Asp Leu Leu Val Gln Leu Trp Arg Gly Lys Met
            20                  25                  30

Thr Ile Ile Ile Ser Val Val Ala Ile Ala Leu Ala Ile Gly Tyr
        35                  40                  45

Leu Ala Val Ala Lys Glu Lys Trp Thr Ser Thr Ala Ile Ile Thr Gln
    50                  55                  60

Pro Asp Val Gly Gln Ile Ala Gly Tyr Asn Asn Ala Met Asn Val Ile
65                  70                  75                  80

Tyr Gly Gln Ala Ala Pro Lys Val Ser Asp Leu Gln Glu Thr Leu Ile
                85                  90                  95

Gly Arg Phe Ser Phe Ala Phe Ser Ala Leu Ala Glu Thr Leu Asp Asn
            100                 105                 110

Gln Lys Glu Pro Glu Lys Leu Thr Ile Glu Pro Ser Val Lys Asn Gln
        115                 120                 125

Gln Leu Pro Leu Thr Val Ser Tyr Val Gly Gln Thr Ala Glu Asp Ala
    130                 135                 140

Gln Met Lys Leu Ala Gln Tyr Ile Gln Gln Val Asp Lys Val Asn
145                 150                 155                 160

Gln Glu Leu Glu Lys Asp Leu Lys Asp Asn Leu Ala Leu Gly Arg Lys
                165                 170                 175

Asn Leu Gln Asp Ser Leu Arg Thr Gln Glu Val Val Ala Gln Glu Gln
            180                 185                 190

Lys Asp Leu Arg Ile Arg Gln Ile Gln Glu Ala Leu Gln Tyr Ala Asn
        195                 200                 205

Gln Ala Gln Val Thr Lys Pro Gln Ile Gln Thr Gly Glu Asp Ile
    210                 215                 220

Thr Gln Asp Thr Leu Phe Leu Leu Gly Ser Glu Ala Leu Glu Ser Met
225                 230                 235                 240

Ile Lys His Glu Ala Thr Arg Pro Leu Val Phe Ser Pro Asn Tyr Tyr
                245                 250                 255

Gln Thr Arg Gln Asn Leu Leu Asp Ile Glu Asn Leu Lys Val Asp Asp
            260                 265                 270

Leu Asp Ile His Ala Tyr Arg Tyr Val Met Lys Pro Thr Leu Pro Ile
        275                 280                 285

Arg Arg Asp Ser Pro Lys Lys Ala Ile Thr Leu Ile Leu Ala Val Leu
    290                 295                 300

Leu Gly Gly Met Val Gly Ala Gly Ile Val Leu Gly Arg Asn Ala Leu
305                 310                 315                 320

Arg Asn Tyr Asn Ser Lys
                325

<210> SEQ ID NO 33
<211> LENGTH: 326
<212> TYPE: PRT

<213> ORGANISM: Artificial Sequence
<220> FEATURE:
<223> OTHER INFORMATION: Synthetic

<400> SEQUENCE: 33

```
Met Arg Val Glu Asn Asn Val Ser Gly Gln Asn His Asp Pro Glu
1               5                  10                  15

Gln Ile Asp Leu Ile Asp Leu Leu Val Gln Leu Trp Arg Gly Lys Met
            20                  25                  30

Thr Ile Ile Ser Val Ile Ala Ile Ala Leu Ala Ile Gly Tyr
        35                  40                  45

Leu Ala Val Ala Lys Glu Lys Trp Thr Ser Thr Ala Ile Ile Thr Gln
50                  55                  60

Pro Asp Val Gly Gln Ile Ala Gly Tyr Asn Asn Ala Met Asn Val Ile
65                  70                  75                  80

Tyr Gly Gln Ala Ala Pro Lys Val Ser Asp Leu Gln Glu Thr Leu Ile
                85                  90                  95

Gly Arg Phe Ser Ser Ala Phe Ser Ala Leu Ala Glu Thr Leu Asp Asn
                100                 105                 110

Gln Glu Glu Arg Glu Lys Leu Thr Ile Glu Pro Ser Val Lys Asn Gln
            115                 120                 125

Gln Leu Pro Leu Thr Val Ser Tyr Val Gly Gln Thr Ala Glu Gly Ala
130                 135                 140

Gln Met Lys Leu Ala Gln Tyr Ile Gln Gln Val Asp Asp Lys Val Asn
145                 150                 155                 160

Gln Glu Leu Glu Lys Asp Leu Lys Asp Asn Ile Ala Leu Gly Arg Lys
                165                 170                 175

Asn Leu Gln Asp Ser Leu Arg Thr Gln Glu Val Val Ala Gln Glu Gln
                180                 185                 190

Lys Asp Leu Arg Ile Arg Gln Ile Gln Glu Ala Leu Gln Tyr Ala Asn
            195                 200                 205

Gln Ala Gln Val Thr Lys Pro Gln Ile Gln Gln Thr Gly Glu Asp Ile
210                 215                 220

Thr Gln Asp Thr Leu Phe Leu Leu Gly Ser Glu Ala Leu Glu Ser Met
225                 230                 235                 240

Ile Lys His Glu Ala Thr Arg Pro Leu Val Phe Ser Pro Asn Tyr Tyr
                245                 250                 255

Gln Thr Arg Gln Asn Leu Leu Asp Ile Glu Ser Leu Lys Val Asp Asp
                260                 265                 270

Leu Asp Ile His Ala Tyr Arg Tyr Val Met Lys Pro Met Leu Pro Ile
            275                 280                 285

Arg Arg Asp Ser Pro Lys Lys Ala Ile Thr Leu Ile Leu Ala Val Leu
290                 295                 300

Leu Gly Gly Met Val Gly Ala Gly Ile Val Leu Gly Arg Asn Ala Leu
305                 310                 315                 320

Arg Asn Tyr Asn Ala Lys
                325
```

<210> SEQ ID NO 34
<211> LENGTH: 327
<212> TYPE: PRT
<213> ORGANISM: Artificial Sequence
<220> FEATURE:
<223> OTHER INFORMATION: Synthetic

<400> SEQUENCE: 34

Met Thr Val Asp Ser Asn Thr Ser Ser Gly Arg Gly Asn Asp Pro Glu
1               5                   10                  15

Gln Ile Asp Leu Ile Glu Leu Leu Gln Leu Trp Arg Gly Lys Met
        20                  25                  30

Thr Ile Ile Val Ala Val Ile Ile Ala Ile Leu Leu Ala Val Gly Tyr
            35                  40                  45

Leu Met Ile Ala Lys Glu Lys Trp Ser Thr Ala Ile Ile Thr Gln
    50                  55                  60

Pro Asp Ala Ala Gln Val Ala Thr Tyr Thr Asn Ala Leu Asn Val Leu
65                  70                  75                  80

Tyr Gly Gly Asn Ala Pro Lys Ile Ser Glu Val Gln Ala Asn Phe Ile
                85                  90                  95

Ser Arg Phe Ser Ser Ala Phe Ser Ala Leu Ser Glu Val Leu Asp Asn
            100                 105                 110

Gln Lys Glu Arg Glu Lys Leu Thr Ile Glu Gln Ser Val Lys Gly Gln
        115                 120                 125

Ala Leu Pro Leu Ser Val Ser Tyr Val Ser Thr Thr Ala Glu Gly Ala
    130                 135                 140

Gln Arg Arg Leu Ala Glu Tyr Ile Gln Gln Val Asp Glu Glu Val Ala
145                 150                 155                 160

Lys Glu Leu Glu Val Asp Leu Lys Asp Asn Ile Thr Leu Gln Thr Lys
                165                 170                 175

Thr Leu Gln Glu Ser Leu Glu Thr Gln Glu Val Val Ala Gln Glu Gln
            180                 185                 190

Lys Asp Leu Arg Ile Lys Gln Ile Glu Glu Ala Leu Arg Tyr Ala Asp
        195                 200                 205

Glu Ala Lys Ile Thr Gln Pro Gln Ile Gln Gln Thr Gln Asp Val Thr
    210                 215                 220

Gln Asp Thr Met Phe Leu Leu Gly Ser Asp Ala Leu Lys Ser Met Ile
225                 230                 235                 240

Gln Asn Glu Ala Thr Arg Pro Leu Val Phe Ser Pro Ala Tyr Tyr Gln
                245                 250                 255

Thr Lys Gln Thr Leu Leu Asp Ile Lys Asn Leu Lys Val Thr Ala Asp
            260                 265                 270

Thr Val His Val Tyr Arg Tyr Val Met Lys Pro Thr Leu Pro Val Arg
        275                 280                 285

Arg Asp Ser Pro Lys Thr Ala Ile Thr Leu Val Leu Ala Val Leu Leu
    290                 295                 300

Gly Gly Met Ile Gly Ala Gly Ile Val Leu Gly Arg Asn Ala Leu Arg
305                 310                 315                 320

Ser Tyr Lys Pro Lys Ala Leu
                325

<210> SEQ ID NO 35
<211> LENGTH: 377
<212> TYPE: PRT
<213> ORGANISM: Artificial Sequence
<220> FEATURE:
<223> OTHER INFORMATION: Synthetic

<400> SEQUENCE: 35

Met Ser Ser Leu Asn Ile Lys Gln Gly Ser Asp Ala His Phe Pro Asp
1               5                   10                  15

Tyr Pro Leu Ala Ser Pro Ser Asn Asn Glu Ile Asp Leu Leu Asn Leu
            20                  25                  30

```
Ile Ser Val Leu Trp Arg Ala Lys Lys Thr Val Met Ala Val Val Phe
         35                  40                  45

Ala Phe Ala Cys Ala Gly Leu Leu Ile Ser Phe Ile Leu Pro Gln Lys
 50                  55                  60

Trp Thr Ser Ala Ala Val Val Thr Pro Pro Glu Pro Val Gln Trp Gln
 65                  70                  75                  80

Glu Leu Glu Lys Ser Phe Thr Lys Leu Arg Val Leu Asp Leu Asp Ile
                 85                  90                  95

Lys Ile Asp Arg Thr Glu Ala Phe Asn Leu Phe Ile Lys Lys Phe Gln
            100                 105                 110

Ser Val Ser Leu Leu Glu Glu Tyr Leu Arg Ser Ser Pro Tyr Val Met
            115                 120                 125

Asp Gln Leu Lys Glu Ala Lys Ile Asp Glu Leu Asp Leu His Arg Ala
        130                 135                 140

Ile Val Ala Leu Ser Glu Lys Met Lys Ala Val Asp Asp Asn Ala Ser
145                 150                 155                 160

Lys Lys Lys Asp Glu Pro Ser Leu Tyr Thr Ser Trp Thr Leu Ser Phe
                165                 170                 175

Thr Ala Pro Thr Ser Glu Glu Ala Gln Thr Val Leu Ser Gly Tyr Ile
            180                 185                 190

Asp Tyr Ile Ser Thr Leu Val Val Lys Glu Ser Leu Glu Asn Val Arg
            195                 200                 205

Asn Lys Leu Glu Ile Lys Thr Gln Phe Glu Lys Glu Lys Leu Ala Gln
        210                 215                 220

Asp Arg Ile Lys Thr Lys Asn Gln Leu Asp Ala Asn Ile Gln Arg Leu
225                 230                 235                 240

Asn Tyr Ser Leu Asp Ile Ala Asn Ala Ala Gly Ile Lys Lys Pro Val
                245                 250                 255

Tyr Ser Asn Gly Gln Ala Val Lys Asp Asp Pro Asp Phe Ser Ile Ser
            260                 265                 270

Leu Gly Ala Asp Gly Ile Glu Arg Lys Leu Glu Ile Glu Lys Ala Val
        275                 280                 285

Thr Asp Val Ala Glu Leu Asn Gly Glu Leu Arg Asn Arg Gln Tyr Leu
290                 295                 300

Val Glu Gln Leu Thr Lys Ala His Val Asn Asp Val Asn Phe Thr Pro
305                 310                 315                 320

Phe Lys Tyr Gln Leu Ser Pro Ser Leu Pro Val Lys Lys Asp Gly Pro
                325                 330                 335

Gly Lys Ala Ile Ile Val Ile Leu Ser Ala Leu Ile Gly Gly Met Val
            340                 345                 350

Ala Cys Gly Gly Val Leu Leu Arg Tyr Ala Met Ala Ser Arg Lys Gln
            355                 360                 365

Asp Ala Met Met Ala Asp His Leu Val
            370                 375

<210> SEQ ID NO 36
<211> LENGTH: 377
<212> TYPE: PRT
<213> ORGANISM: Artificial Sequence
<220> FEATURE:
<223> OTHER INFORMATION: Synthetic

<400> SEQUENCE: 36

Met Ser Ser Leu Asn Ile Lys Gln Gly Ser Glu Ala His Phe Pro Glu
 1               5                  10                  15
```

```
Tyr Pro Leu Ala Ser Pro Ser Asn Asn Glu Ile Asp Leu Leu Asn Leu
             20                  25                  30

Ile Glu Val Leu Trp Arg Ala Lys Lys Thr Val Met Ala Val Val Phe
 35                  40                  45

Ala Phe Ala Cys Ala Gly Leu Leu Ile Ser Phe Ile Leu Pro Gln Lys
 50                  55                  60

Trp Thr Ser Ala Ala Val Val Thr Pro Pro Glu Pro Val Gln Trp Gln
65                   70                  75                  80

Glu Leu Glu Lys Thr Phe Thr Lys Leu Arg Val Leu Asp Leu Asp Ile
                 85                  90                  95

Lys Ile Asp Arg Thr Glu Ala Phe Asn Leu Phe Ile Lys Lys Phe Gln
            100                 105                 110

Ser Val Ser Leu Leu Glu Glu Tyr Leu Arg Ser Ser Pro Tyr Val Met
            115                 120                 125

Asp Gln Leu Lys Glu Ala Lys Ile Asp Pro Leu Asp Leu His Arg Ala
        130                 135                 140

Ile Val Ala Leu Ser Glu Lys Met Lys Ala Val Asp Asp Asn Ala Ser
145                 150                 155                 160

Lys Lys Lys Asp Glu Ser Ala Leu Tyr Thr Ser Trp Thr Leu Ser Phe
                165                 170                 175

Thr Ala Pro Thr Ser Glu Glu Ala Gln Lys Val Leu Ala Gly Tyr Ile
            180                 185                 190

Asp Tyr Ile Ser Ala Leu Val Val Lys Glu Ser Ile Glu Asn Val Arg
        195                 200                 205

Asn Lys Leu Glu Ile Lys Thr Gln Phe Glu Lys Glu Lys Leu Ala Gln
210                 215                 220

Asp Arg Ile Lys Thr Lys Asn Gln Leu Asp Ala Asn Ile Gln Arg Leu
225                 230                 235                 240

Asn Tyr Ser Leu Asp Ile Ala Asn Ala Ala Gly Ile Lys Lys Pro Val
                245                 250                 255

Tyr Ser Asn Gly Gln Ala Val Lys Asp Asp Pro Asp Phe Ser Ile Ser
            260                 265                 270

Leu Gly Ala Asp Gly Ile Glu Arg Lys Leu Glu Ile Glu Lys Ala Val
        275                 280                 285

Thr Asp Val Ala Glu Leu Asn Gly Glu Leu Arg Asn Arg Gln Tyr Leu
290                 295                 300

Val Glu Gln Leu Thr Lys Thr Asn Ile Asn Asp Val Asn Phe Thr Pro
305                 310                 315                 320

Phe Lys Tyr Gln Leu Arg Pro Ser Leu Pro Val Lys Lys Asp Gly Gln
                325                 330                 335

Gly Lys Ala Ile Ile Val Ile Leu Ser Ala Leu Val Gly Gly Met Val
            340                 345                 350

Ala Cys Gly Gly Val Leu Leu Arg His Ala Met Ala Ser Arg Lys Gln
        355                 360                 365

Asp Ala Met Met Ala Asp His Leu Val
    370                 375

<210> SEQ ID NO 37
<211> LENGTH: 377
<212> TYPE: PRT
<213> ORGANISM: Artificial Sequence
<220> FEATURE:
<223> OTHER INFORMATION: Synthetic

<400> SEQUENCE: 37
```

```
Met Ser Ser Leu Asn Ile Lys Gln Gly Ser Asp Ala His Phe Pro Asp
1               5                   10                  15

Tyr Pro Leu Ala Ser Pro Ser Asn Asn Glu Ile Asp Leu Leu Asn Leu
            20                  25                  30

Ile Ser Val Leu Trp Arg Ala Lys Lys Thr Val Met Ala Val Val Phe
        35                  40                  45

Ala Phe Ala Cys Ala Gly Leu Leu Ile Ser Phe Ile Leu Pro Gln Lys
    50                  55                  60

Trp Thr Ser Ala Ala Val Val Thr Pro Pro Glu Pro Val Gln Trp Gln
65                  70                  75                  80

Glu Leu Glu Lys Ser Phe Thr Lys Leu Arg Val Leu Asp Leu Asp Ile
                85                  90                  95

Lys Ile Asp Arg Thr Glu Ala Phe Asn Leu Phe Ile Lys Lys Phe Gln
            100                 105                 110

Ser Val Ser Leu Leu Glu Glu Tyr Leu Arg Ser Ser Pro Tyr Val Met
        115                 120                 125

Asp Gln Leu Lys Glu Ala Lys Ile Asp Glu Leu Asp Leu His Arg Ala
    130                 135                 140

Ile Val Ala Leu Ser Glu Lys Met Lys Ala Val Asp Asp Asn Ala Ser
145                 150                 155                 160

Lys Lys Lys Asp Glu Pro Ser Leu Tyr Thr Ser Trp Thr Leu Ser Phe
                165                 170                 175

Thr Ala Pro Thr Ser Glu Glu Ala Gln Thr Val Leu Ser Gly Tyr Ile
            180                 185                 190

Asp Tyr Ile Ser Thr Leu Val Val Lys Glu Ser Leu Glu Asn Val Arg
    195                 200                 205

Asn Lys Leu Glu Ile Lys Thr Gln Phe Glu Lys Glu Lys Leu Ala Gln
210                 215                 220

Asp Arg Ile Lys Thr Lys Asn Gln Leu Asp Ala Asn Ile Gln Arg Leu
225                 230                 235                 240

Asn Tyr Ser Leu Asp Ile Ala Asn Ala Ala Gly Ile Lys Lys Pro Val
                245                 250                 255

Tyr Ser Asn Gly Gln Ala Val Lys Asp Asp Pro Asp Phe Ser Ile Ser
            260                 265                 270

Leu Gly Ala Asp Gly Ile Glu Arg Lys Leu Glu Ile Glu Lys Ala Val
    275                 280                 285

Thr Asp Val Ala Glu Leu Asn Gly Glu Leu Arg Asn Arg Gln Tyr Leu
290                 295                 300

Val Glu Gln Leu Thr Lys Ala His Val Asn Asp Val Asn Phe Thr Pro
305                 310                 315                 320

Phe Lys Tyr Gln Leu Ser Pro Ser Leu Pro Val Lys Lys Asp Gly Pro
                325                 330                 335

Gly Lys Ala Ile Ile Val Ile Leu Ser Ala Leu Ile Gly Gly Met Val
            340                 345                 350

Ala Cys Gly Gly Val Leu Leu Arg Tyr Ala Met Ala Ser Arg Lys Gln
    355                 360                 365

Asp Ala Met Met Ala Asp His Leu Val
    370                 375

<210> SEQ ID NO 38
<211> LENGTH: 377
<212> TYPE: PRT
<213> ORGANISM: Artificial Sequence
<220> FEATURE:
<223> OTHER INFORMATION: Synthetic
```

<400> SEQUENCE: 38

Met Ser Ser Leu Asn Ile Lys Gln Gly Ser Asp Ala His Phe Pro Asp
1               5                   10                  15

Tyr Pro Leu Ala Ser Pro Ser Asn Asn Glu Ile Asp Leu Leu Asn Leu
            20                  25                  30

Ile Ser Val Leu Trp Arg Ala Lys Lys Thr Val Met Ala Val Val Phe
        35                  40                  45

Ala Phe Ala Cys Ala Gly Leu Leu Ile Ser Phe Ile Leu Pro Gln Lys
    50                  55                  60

Trp Thr Ser Ala Ala Val Val Thr Pro Pro Glu Pro Val Gln Trp Gln
65                  70                  75                  80

Glu Leu Glu Lys Thr Phe Thr Lys Leu Arg Val Leu Asp Leu Asp Ile
                85                  90                  95

Lys Ile Asp Arg Thr Glu Ala Phe Asn Leu Phe Ile Lys Lys Phe Gln
            100                 105                 110

Ser Val Ser Leu Leu Glu Glu Tyr Leu Arg Ser Pro Tyr Val Met
        115                 120                 125

Asp Gln Leu Lys Glu Ala Lys Ile Asp Glu Leu Asp Leu His Arg Ala
    130                 135                 140

Ile Val Ala Leu Ser Glu Lys Met Lys Ala Val Asp Asp Asn Ala Ser
145                 150                 155                 160

Lys Lys Lys Asp Glu Pro Ser Leu Tyr Thr Ser Trp Thr Leu Ser Phe
                165                 170                 175

Thr Ala Pro Thr Ser Glu Glu Ala Gln Thr Val Leu Ser Gly Tyr Ile
            180                 185                 190

Asp Tyr Ile Ser Ala Leu Val Val Lys Glu Ser Ile Glu Asn Val Arg
    195                 200                 205

Asn Lys Leu Glu Ile Lys Thr Gln Phe Glu Lys Glu Lys Leu Ala Gln
210                 215                 220

Asp Arg Ile Lys Met Lys Asn Gln Leu Asp Ala Asn Ile Gln Arg Leu
225                 230                 235                 240

Asn Tyr Ser Leu Asp Ile Ala Asn Ala Ala Gly Ile Lys Lys Pro Val
                245                 250                 255

Tyr Ser Asn Gly Gln Ala Val Lys Asp Asp Pro Asp Phe Ser Ile Ser
            260                 265                 270

Leu Gly Ala Asp Gly Ile Glu Arg Lys Leu Glu Ile Glu Lys Ala Val
    275                 280                 285

Thr Asp Val Ala Glu Leu Asn Gly Glu Leu Arg Asn Arg Gln Tyr Leu
290                 295                 300

Val Glu Gln Leu Thr Lys Ala Asn Ile Asn Asp Val Asn Phe Thr Pro
305                 310                 315                 320

Phe Lys Tyr Gln Leu Ser Pro Ser Leu Pro Val Lys Lys Asp Gly Pro
                325                 330                 335

Gly Lys Ala Ile Ile Val Ile Leu Ser Ala Leu Ile Gly Gly Met Val
            340                 345                 350

Ala Cys Gly Ser Val Leu Leu Arg Tyr Ala Met Ala Ser Arg Lys Gln
    355                 360                 365

Asp Ala Met Met Ala Asp His Leu Val
    370                 375

<210> SEQ ID NO 39
<211> LENGTH: 378
<212> TYPE: PRT

<213> ORGANISM: Artificial Sequence
<220> FEATURE:
<223> OTHER INFORMATION: Synthetic

<400> SEQUENCE: 39

```
Met Pro Ser Leu Asn Val Lys Gln Glu Lys Asn Gln Ser Phe Ala Gly
1               5                   10                  15

Tyr Ser Leu Pro Pro Ala Asn Ser His Glu Ile Asp Leu Phe Ser Leu
            20                  25                  30

Ile Glu Val Leu Trp Gln Ala Lys Arg Arg Ile Leu Ala Thr Val Phe
        35                  40                  45

Ala Phe Ala Cys Val Gly Leu Leu Ser Phe Leu Leu Pro Gln Lys
    50                  55                  60

Trp Thr Ser Gln Ala Ile Val Thr Pro Ala Glu Ser Val Gln Trp Gln
65                  70                  75                  80

Gly Leu Glu Arg Thr Leu Thr Ala Leu Arg Val Leu Asp Met Glu Val
                85                  90                  95

Ser Val Asp Arg Gly Ser Val Phe Asn Leu Phe Ile Lys Lys Phe Ser
            100                 105                 110

Ser Pro Ser Leu Leu Glu Glu Tyr Leu Arg Ser Ser Pro Tyr Val Met
        115                 120                 125

Asp Gln Leu Lys Gly Ala Gln Ile Asp Glu Gln Asp Leu His Arg Ala
    130                 135                 140

Ile Val Leu Leu Ser Glu Lys Met Lys Ala Val Asp Ser Asn Val Gly
145                 150                 155                 160

Lys Lys Asn Glu Thr Ser Leu Phe Thr Ser Trp Thr Leu Ser Phe Thr
                165                 170                 175

Ala Pro Thr Arg Glu Glu Ala Gln Lys Val Leu Ala Gly Tyr Ile Gln
            180                 185                 190

Tyr Ile Ser Asp Ile Val Val Lys Glu Thr Leu Glu Asn Ile Arg Asn
        195                 200                 205

Gln Leu Glu Ile Lys Thr Arg Tyr Glu Gln Glu Lys Leu Ala Met Asp
    210                 215                 220

Arg Val Arg Leu Lys Asn Gln Leu Asp Ala Asn Ile Gln Arg Leu His
225                 230                 235                 240

Tyr Ser Leu Glu Ile Ala Asn Ala Ala Gly Ile Lys Arg Pro Val Tyr
                245                 250                 255

Ser Asn Gly Gln Ala Val Lys Asp Asp Pro Asp Phe Ser Ile Ser Leu
            260                 265                 270

Gly Ala Asp Gly Ile Ser Arg Lys Leu Glu Ile Glu Lys Gly Val Thr
        275                 280                 285

Asp Val Ala Glu Ile Asp Gly Asp Leu Arg Asn Arg Gln Tyr His Val
    290                 295                 300

Glu Gln Leu Ala Ala Met Asn Val Ser Asp Val Lys Phe Thr Pro Phe
305                 310                 315                 320

Lys Tyr Gln Leu Ser Pro Ser Leu Pro Val Lys Asp Gly Pro Gly
                325                 330                 335

Lys Ala Ile Ile Ile Ile Leu Ala Ala Leu Ile Gly Gly Met Met Ala
            340                 345                 350

Cys Gly Gly Val Leu Leu Arg His Ala Met Val Ser Arg Lys Met Glu
        355                 360                 365

Asn Ala Leu Ala Ile Asp Glu Arg Leu Val
    370                 375
```

```
<210> SEQ ID NO 40
<211> LENGTH: 22
<212> TYPE: DNA
<213> ORGANISM: Artificial Sequence
<220> FEATURE:
<223> OTHER INFORMATION: Synthetic

<400> SEQUENCE: 40
gaagcaaacc gtacgcgtaa ag                                              22

<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41
cgaccagctc ttacacggcg                                                 20

<210> SEQ ID NO 42
<211> LENGTH: 36
<212> TYPE: DNA
<213> ORGANISM: Artificial Sequence
<220> FEATURE:
<223> OTHER INFORMATION: Synthetic

<400> SEQUENCE: 42
gaaataggac cactaataaa tacacaaatt aataac                               36

<210> SEQ ID NO 43
<211> LENGTH: 21
<212> TYPE: DNA
<213> ORGANISM: Artificial Sequence
<220> FEATURE:
<223> OTHER INFORMATION: Synthetic

<400> SEQUENCE: 43
ataattgacg atccggttgc c                                               21

<210> SEQ ID NO 44
<211> LENGTH: 27
<212> TYPE: DNA
<213> ORGANISM: Artificial Sequence
<220> FEATURE:
<223> OTHER INFORMATION: Synthetic

<400> SEQUENCE: 44
gctatttacg ccctgattgt cttttgt                                         27

<210> SEQ ID NO 45
<211> LENGTH: 22
<212> TYPE: DNA
<213> ORGANISM: Artificial Sequence
<220> FEATURE:
<223> OTHER INFORMATION: Synthetic

<400> SEQUENCE: 45
attgagaacc tgcgtaaacg gc                                              22

<210> SEQ ID NO 46
<211> LENGTH: 24
<212> TYPE: DNA
<213> ORGANISM: Artificial Sequence
<220> FEATURE:
<223> OTHER INFORMATION: Synthetic
```

```
<400> SEQUENCE: 46
tgaagagcgg ttcagataac ttcc                                              24

<210> SEQ ID NO 47
<211> LENGTH: 21
<212> TYPE: DNA
<213> ORGANISM: Artificial Sequence
<220> FEATURE:
<223> OTHER INFORMATION: Synthetic

<400> SEQUENCE: 47
cgatccggaa acctcctaca c                                                 21

<210> SEQ ID NO 48
<211> LENGTH: 26
<212> TYPE: DNA
<213> ORGANISM: Artificial Sequence
<220> FEATURE:
<223> OTHER INFORMATION: Synthetic

<400> SEQUENCE: 48
gattattcgc gcaacgctaa acagat                                            26

<210> SEQ ID NO 49
<211> LENGTH: 23
<212> TYPE: DNA
<213> ORGANISM: Artificial Sequence
<220> FEATURE:
<223> OTHER INFORMATION: Synthetic

<400> SEQUENCE: 49
tgatcattga cgatccggta gcc                                               23

<210> SEQ ID NO 50
<211> LENGTH: 70
<212> TYPE: DNA
<213> ORGANISM: Artificial Sequence
<220> FEATURE:
<223> OTHER INFORMATION: Synthetic

<400> SEQUENCE: 50
cggtagctgt aaagccaggg gcggtagcgt ggtttaaacc caagcaacag atcggcgtcg       60
tcggtatgga                                                              70

<210> SEQ ID NO 51
<211> LENGTH: 78
<212> TYPE: DNA
<213> ORGANISM: Artificial Sequence
<220> FEATURE:
<223> OTHER INFORMATION: Synthetic

<400> SEQUENCE: 51
agcttccata ccgacgacgc cgatctgttg ctgggtttta aaccacgcta ccgcccctgg       60
ctttacagct accgagct                                                     78

<210> SEQ ID NO 52
<211> LENGTH: 30
<212> TYPE: DNA
<213> ORGANISM: Artificial Sequence
<220> FEATURE:
<223> OTHER INFORMATION: Synthetic

<400> SEQUENCE: 52
ggtagctgta aagccagggg cggtagcgtg                                        30
```

<210> SEQ ID NO 53
<211> LENGTH: 30
<212> TYPE: DNA
<213> ORGANISM: Artificial Sequence
<220> FEATURE:
<223> OTHER INFORMATION: Synthetic

<400> SEQUENCE: 53
ccataccgac gacgccgatc tgttgcttgg                                    30

<210> SEQ ID NO 54
<211> LENGTH: 19
<212> TYPE: PRT
<213> ORGANISM: Artificial Sequence
<220> FEATURE:
<223> OTHER INFORMATION: Synthetic

<400> SEQUENCE: 54

Glu Thr Asp Thr Leu Leu Leu Trp Val Leu Leu Trp Val Pro Gly
1               5                   10                  15

Ser Thr Gly

<210> SEQ ID NO 55
<211> LENGTH: 23
<212> TYPE: PRT
<213> ORGANISM: Homo sapiens

<400> SEQUENCE: 55

Met Gly Val Pro Arg Pro Gln Pro Trp Ala Leu Gly Leu Leu Leu Phe
1               5                   10                  15

Leu Leu Pro Gly Ser Leu Gly
            20

<210> SEQ ID NO 56
<211> LENGTH: 18
<212> TYPE: PRT
<213> ORGANISM: Homo sapiens

<400> SEQUENCE: 56

Met His Ser Ser Ala Leu Leu Cys Cys Leu Val Leu Leu Thr Gly Val
1               5                   10                  15

Arg Ala

<210> SEQ ID NO 57
<211> LENGTH: 25
<212> TYPE: PRT
<213> ORGANISM: Human respiratory syncytial virus A (strain A2)

<400> SEQUENCE: 57

Met Glu Leu Leu Ile Leu Lys Ala Asn Ala Ile Thr Thr Ile Leu Thr
1               5                   10                  15

Ala Val Thr Phe Cys Phe Ala Ser Gly
            20                  25

<210> SEQ ID NO 58
<211> LENGTH: 15
<212> TYPE: PRT
<213> ORGANISM: Influenza A virus (strain A/Japan/305/1957 H2N2)

<400> SEQUENCE: 58

Met Ala Ile Ile Tyr Leu Ile Leu Leu Phe Thr Ala Val Arg Gly
1               5                   10                  15

<210> SEQ ID NO 59
<211> LENGTH: 207
<212> TYPE: PRT
<213> ORGANISM: Artificial Sequence
<220> FEATURE:
<223> OTHER INFORMATION: Synthetic

<400> SEQUENCE: 59

```
Met Glu Gly Met Asp Pro Leu Ala Val Leu Ala Glu Ser Arg Leu Leu
1               5                   10                  15

Pro Leu Leu Thr Val Arg Gly Gly Glu Asp Leu Ala Gly Leu Ala Thr
                20                  25                  30

Val Leu Glu Leu Met Gly Val Gly Ala Leu Glu Ile Thr Leu Arg Thr
            35                  40                  45

Glu Lys Gly Leu Glu Ala Leu Lys Ala Leu Arg Lys Ser Gly Leu Leu
        50                  55                  60

Leu Gly Ala Gly Thr Val Arg Ser Pro Lys Glu Ala Glu Ala Ala Leu
65                  70                  75                  80

Glu Ala Gly Ala Ala Phe Leu Val Ser Pro Gly Leu Leu Glu Glu Val
                85                  90                  95

Ala Ala Leu Ala Gln Ala Arg Gly Val Pro Tyr Leu Pro Gly Val Leu
                100                 105                 110

Thr Pro Thr Glu Val Glu Arg Ala Leu Ala Leu Gly Leu Ser Ala Leu
            115                 120                 125

Lys Phe Phe Pro Ala Glu Pro Phe Gln Gly Val Arg Val Leu Arg Ala
        130                 135                 140

Tyr Ala Glu Val Phe Pro Glu Val Arg Phe Leu Pro Thr Gly Gly Ile
145                 150                 155                 160

Lys Glu Glu His Leu Pro His Tyr Ala Ala Leu Pro Asn Leu Leu Ala
                165                 170                 175

Val Gly Gly Ser Trp Leu Leu Gln Gly Asp Leu Ala Ala Val Met Lys
                180                 185                 190

Lys Val Lys Ala Ala Lys Ala Leu Leu Ser Pro Gln Ala Pro Gly
            195                 200                 205
```

<210> SEQ ID NO 60
<211> LENGTH: 156
<212> TYPE: PRT
<213> ORGANISM: Artificial Sequence
<220> FEATURE:
<223> OTHER INFORMATION: Synthetic

<400> SEQUENCE: 60

```
Met Thr Lys Lys Val Gly Ile Val Asp Thr Thr Phe Ala Arg Val Asp
1               5                   10                  15

Met Ala Glu Ala Ala Ile Arg Thr Leu Lys Ala Leu Ser Pro Asn Ile
                20                  25                  30

Lys Ile Ile Arg Lys Thr Val Pro Gly Ile Lys Asp Leu Pro Val Ala
            35                  40                  45

Cys Lys Lys Leu Leu Glu Glu Glu Gly Cys Asp Ile Val Met Ala Leu
        50                  55                  60

Gly Met Pro Gly Lys Ala Glu Lys Asp Lys Val Cys Ala His Glu Ala
65                  70                  75                  80

Ser Leu Gly Leu Met Leu Ala Gln Leu Met Thr Asn Lys His Ile Ile
                85                  90                  95

Glu Val Phe Val His Glu Asp Glu Ala Lys Asp Asp Asp Glu Leu Asp
```

```
                    100                 105                 110
Ile Leu Ala Leu Val Arg Ala Ile Glu His Ala Ala Asn Val Tyr Tyr
            115                 120                 125

Leu Leu Phe Lys Pro Glu Tyr Leu Thr Arg Met Ala Gly Lys Gly Leu
        130                 135                 140

Arg Gln Gly Arg Glu Asp Ala Gly Pro Ala Arg Glu
145                 150                 155

<210> SEQ ID NO 61
<211> LENGTH: 156
<212> TYPE: PRT
<213> ORGANISM: Artificial Sequence
<220> FEATURE:
<223> OTHER INFORMATION: Synthetic

<400> SEQUENCE: 61

Met Thr Lys Lys Val Gly Ile Val Asp Thr Thr Phe Ala Arg Val Asp
1               5                   10                  15

Met Ala Ser Ala Ala Ile Leu Thr Leu Lys Met Glu Ser Pro Asn Ile
            20                  25                  30

Lys Ile Ile Arg Lys Thr Val Pro Gly Ile Lys Asp Leu Pro Val Ala
        35                  40                  45

Cys Lys Lys Leu Leu Glu Glu Gly Cys Asp Ile Val Met Ala Leu
    50                  55                  60

Gly Met Pro Gly Lys Ala Glu Lys Asp Lys Val Cys Ala His Glu Ala
65                  70                  75                  80

Ser Leu Gly Leu Met Leu Ala Gln Leu Met Thr Asn Lys His Ile Ile
                85                  90                  95

Glu Val Phe Val His Glu Asp Glu Ala Lys Asp Asp Ala Glu Leu Lys
                100                 105                 110

Ile Leu Ala Ala Arg Arg Ala Ile Glu His Ala Leu Asn Val Tyr Tyr
            115                 120                 125

Leu Leu Phe Lys Pro Glu Tyr Leu Thr Arg Met Ala Gly Lys Gly Leu
        130                 135                 140

Arg Gln Gly Phe Glu Asp Ala Gly Pro Ala Arg Glu
145                 150                 155

<210> SEQ ID NO 62
<211> LENGTH: 209
<212> TYPE: PRT
<213> ORGANISM: Artificial Sequence
<220> FEATURE:
<223> OTHER INFORMATION: Synthetic

<400> SEQUENCE: 62

Met Ser Thr Ile Asn Asn Gln Leu Lys Ala Leu Lys Val Ile Pro Val
1               5                   10                  15

Ile Ala Ile Asp Asn Ala Glu Asp Ile Ile Pro Leu Gly Lys Val Leu
            20                  25                  30

Ala Glu Asn Gly Leu Pro Ala Ala Glu Ile Thr Phe Arg Ser Ser Ala
        35                  40                  45

Ala Val Lys Ala Ile Met Leu Leu Arg Ser Ala Gln Pro Glu Met Leu
    50                  55                  60

Ile Gly Ala Gly Thr Ile Leu Asn Gly Val Gln Ala Leu Ala Ala Lys
65                  70                  75                  80

Glu Ala Gly Ala Thr Phe Val Val Ser Pro Gly Phe Asn Pro Asn Thr
                85                  90                  95
```

```
Val Arg Ala Cys Gln Ile Ile Gly Ile Asp Ile Val Pro Gly Val Asn
                100                 105                 110

Asn Pro Ser Thr Val Glu Ala Ala Leu Glu Met Gly Leu Thr Thr Leu
            115                 120                 125

Lys Phe Phe Pro Ala Glu Ala Ser Gly Gly Ile Ser Met Val Lys Ser
        130                 135                 140

Leu Val Gly Pro Tyr Gly Asp Ile Arg Leu Met Pro Thr Gly Gly Ile
145                 150                 155                 160

Thr Pro Ser Asn Ile Asp Asn Tyr Leu Ala Ile Pro Gln Val Leu Ala
                165                 170                 175

Cys Gly Gly Thr Trp Met Val Asp Lys Lys Leu Val Thr Asn Gly Glu
            180                 185                 190

Trp Asp Glu Ile Ala Arg Leu Thr Arg Glu Ile Val Glu Gln Val Asn
        195                 200                 205

Pro
```

<210> SEQ ID NO 63
<211> LENGTH: 114
<212> TYPE: PRT
<213> ORGANISM: Artificial Sequence
<220> FEATURE:
<223> OTHER INFORMATION: Synthetic

<400> SEQUENCE: 63

```
Met Pro Ile Phe Thr Leu Asn Thr Asn Ile Lys Ala Thr Asp Val Pro
1               5                   10                  15

Ser Asp Phe Leu Ser Leu Thr Ser Arg Leu Val Gly Leu Ile Leu Ser
            20                  25                  30

Lys Pro Gly Ser Tyr Val Ala Val His Ile Asn Thr Asp Gln Gln Leu
        35                  40                  45

Ser Phe Gly Gly Ser Thr Asn Pro Ala Ala Phe Gly Thr Leu Met Ser
    50                  55                  60

Ile Gly Gly Ile Glu Pro Ser Lys Asn Arg Asp His Ser Ala Val Leu
65                  70                  75                  80

Phe Asp His Leu Asn Ala Met Leu Gly Ile Pro Lys Asn Arg Met Tyr
                85                  90                  95

Ile His Phe Val Asn Leu Asn Gly Asp Asp Val Gly Trp Asn Gly Thr
            100                 105                 110

Thr Phe
```

<210> SEQ ID NO 64
<211> LENGTH: 157
<212> TYPE: PRT
<213> ORGANISM: Artificial Sequence
<220> FEATURE:
<223> OTHER INFORMATION: Synthetic

<400> SEQUENCE: 64

```
Met Asn Gln His Ser His Lys Asp Tyr Glu Thr Val Arg Ile Ala Val
1               5                   10                  15

Val Arg Ala Arg Trp His Ala Asp Ile Val Asp Ala Cys Val Glu Ala
            20                  25                  30

Phe Glu Ile Ala Met Ala Ala Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
```

```
                65                  70                  75                  80
Val Asn Gly Gly Ile Tyr Arg His Glu Phe Val Ala Ser Ala Val Ile
                    85                  90                  95

Asp Gly Met Met Asn Val Gln Leu Ser Thr Gly Val Pro Val Leu Ser
                100                 105                 110

Ala Val Leu Thr Pro His Arg Tyr Arg Asp Ser Ala Glu His His Arg
            115                 120                 125

Phe Phe Ala Ala His Phe Ala Val Lys Gly Val Glu Ala Ala Arg Ala
        130                 135                 140

Cys Ile Glu Ile Leu Ala Ala Arg Glu Lys Ile Ala Ala
145                 150                 155

<210> SEQ ID NO 65
<211> LENGTH: 205
<212> TYPE: PRT
<213> ORGANISM: Artificial Sequence
<220> FEATURE:
<223> OTHER INFORMATION: Synthetic

<400> SEQUENCE: 65

Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
                20                  25                  30

Ala Gly Gly Val His Leu Ile Glu Ile Thr Phe Thr Val Pro Asp Ala
            35                  40                  45

Asp Thr Val Ile Lys Ala Leu Ser Val Leu Lys Glu Lys Gly Ala Ile
        50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
                100                 105                 110

Thr Pro Thr Glu Leu Val Lys Ala Met Lys Leu Gly His Thr Ile Leu
            115                 120                 125

Lys Leu Phe Pro Gly Glu Val Val Gly Pro Gln Phe Val Lys Ala Met
        130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Pro Asp Glu Val Arg Glu Lys
                180                 185                 190

Ala Lys Ala Phe Val Glu Lys Ile Arg Gly Cys Thr Glu
            195                 200                 205

<210> SEQ ID NO 66
<211> LENGTH: 157
<212> TYPE: PRT
<213> ORGANISM: Artificial Sequence
<220> FEATURE:
<223> OTHER INFORMATION: Synthetic

<400> SEQUENCE: 66

Met Asn Gln His Ser His Lys Asp Tyr Glu Thr Val Arg Ile Ala Val
1               5                   10                  15
```

Val Arg Ala Arg Trp His Ala Glu Ile Val Asp Ala Cys Val Ser Ala
            20                  25                  30

Phe Glu Ala Ala Met Ala Asp Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asp Gly Met Met Asn Val Gln Leu Ser Thr Gly Val Pro Val Leu Ser
            100                 105                 110

Ala Val Leu Thr Pro His Arg Tyr Arg Asp Ser Asp Ala His Thr Leu
        115                 120                 125

Leu Phe Leu Ala Leu Phe Ala Val Lys Gly Met Glu Ala Ala Arg Ala
    130                 135                 140

Cys Val Glu Ile Leu Ala Ala Arg Glu Lys Ile Ala Ala
145                 150                 155

<210> SEQ ID NO 67
<211> LENGTH: 177
<212> TYPE: PRT
<213> ORGANISM: Artificial Sequence
<220> FEATURE:
<223> OTHER INFORMATION: Synthetic

<400> SEQUENCE: 67

Met Phe Thr Lys Ser Gly Asp Asp Gly Asn Thr Asn Val Ile Asn Lys
1               5                   10                  15

Arg Val Gly Lys Asp Ser Pro Leu Val Asn Phe Leu Gly Asp Leu Asp
            20                  25                  30

Glu Leu Asn Ser Phe Ile Gly Phe Ala Ile Ser Lys Ile Pro Trp Glu
        35                  40                  45

Asp Met Lys Lys Asp Leu Glu Arg Val Gln Val Glu Leu Phe Glu Ile
    50                  55                  60

Gly Glu Asp Leu Ser Thr Gln Ser Ser Lys Lys Ile Asp Glu Ser
65                  70                  75                  80

Tyr Val Leu Trp Leu Leu Ala Ala Thr Ala Ile Tyr Arg Ile Glu Ser
                85                  90                  95

Gly Pro Val Lys Leu Phe Val Ile Pro Gly Gly Ser Glu Glu Ala Ser
            100                 105                 110

Val Leu His Val Thr Arg Ser Val Ala Arg Arg Val Glu Arg Asn Ala
        115                 120                 125

Val Lys Tyr Thr Lys Glu Leu Pro Glu Ile Asn Arg Met Ile Ile Val
    130                 135                 140

Tyr Leu Asn Arg Leu Ser Ser Leu Leu Phe Ala Met Ala Leu Val Ala
145                 150                 155                 160

Asn Lys Arg Arg Asn Gln Ser Glu Lys Ile Tyr Glu Ile Gly Lys Ser
                165                 170                 175

Trp

<210> SEQ ID NO 68
<211> LENGTH: 157
<212> TYPE: PRT
<213> ORGANISM: Artificial Sequence
<220> FEATURE:
<223> OTHER INFORMATION: Synthetic

<400> SEQUENCE: 68

```
Met Asn Gln His Ser His Lys Asp Tyr Glu Thr Val Arg Ile Ala Val
1               5                   10                  15

Val Arg Ala Arg Trp His Ala Asp Ile Val Asp Gln Cys Val Arg Ala
            20                  25                  30

Phe Glu Glu Ala Met Ala Asp Ala Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asp Gly Met Met Asn Val Gln Leu Ser Thr Gly Val Pro Val Leu Ser
            100                 105                 110

Ala Val Leu Thr Pro His Arg Tyr Arg Ser Ser Arg Glu His His Glu
        115                 120                 125

Phe Phe Arg Glu His Phe Met Val Lys Gly Val Glu Ala Ala Ala Ala
    130                 135                 140

Cys Ile Thr Ile Leu Ala Ala Arg Glu Lys Ile Ala Ala
145                 150                 155
```

<210> SEQ ID NO 69
<211> LENGTH: 201
<212> TYPE: PRT
<213> ORGANISM: Artificial Sequence
<220> FEATURE:
<223> OTHER INFORMATION: Synthetic

<400> SEQUENCE: 69

```
Met Gly His Thr Lys Gly Pro Thr Pro Gln Gln His Asp Gly Ser Ala
1               5                   10                  15

Leu Arg Ile Gly Ile Val His Ala Arg Trp Asn Lys Thr Ile Ile Met
            20                  25                  30

Pro Leu Leu Ile Gly Thr Ile Ala Lys Leu Leu Glu Cys Gly Val Lys
        35                  40                  45

Ala Ser Asn Ile Val Val Gln Ser Val Pro Gly Ser Trp Glu Leu Pro
    50                  55                  60

Ile Ala Val Gln Arg Leu Tyr Ser Ala Ser Gln Leu Gln Thr Pro Ser
65                  70                  75                  80

Ser Gly Pro Ser Leu Ser Ala Gly Asp Leu Leu Gly Ser Ser Thr Thr
                85                  90                  95

Asp Leu Thr Ala Leu Pro Thr Thr Thr Ala Ser Ser Thr Gly Pro Phe
            100                 105                 110

Asp Ala Leu Ile Ala Ile Gly Val Leu Ile Lys Gly Glu Thr Met His
        115                 120                 125

Phe Glu Tyr Ile Ala Asp Ser Val Ser His Gly Leu Met Arg Val Gln
    130                 135                 140

Leu Asp Thr Gly Val Pro Val Ile Phe Gly Val Leu Thr Val Leu Thr
145                 150                 155                 160

Asp Asp Gln Ala Lys Ala Arg Ala Gly Val Ile Glu Gly Ser His Asn
                165                 170                 175

His Gly Glu Asp Trp Gly Leu Ala Ala Val Glu Met Gly Val Arg Arg
            180                 185                 190
```

```
Arg Asp Trp Ala Ala Gly Lys Thr Glu
        195                 200
```

<210> SEQ ID NO 70
<211> LENGTH: 237
<212> TYPE: PRT
<213> ORGANISM: Artificial Sequence
<220> FEATURE:
<223> OTHER INFORMATION: Synthetic

<400> SEQUENCE: 70

```
Met Tyr Glu Val Asp His Ala Asp Val Tyr Asp Leu Phe Tyr Leu Gly
1               5                   10                  15

Arg Gly Lys Asp Tyr Ala Ala Glu Ala Ser Asp Ile Ala Asp Leu Val
            20                  25                  30

Arg Ser Arg Thr Pro Glu Ala Ser Ser Leu Leu Asp Val Ala Cys Gly
        35                  40                  45

Thr Gly Thr His Leu Glu His Phe Thr Lys Glu Phe Gly Asp Thr Ala
50                  55                  60

Gly Leu Glu Leu Ser Glu Asp Met Leu Thr His Ala Arg Lys Arg Leu
65                  70                  75                  80

Pro Asp Ala Thr Leu His Gln Gly Asp Met Arg Asp Phe Gln Leu Gly
                85                  90                  95

Arg Lys Phe Ser Ala Val Val Ser Met Phe Ser Ser Val Gly Tyr Leu
            100                 105                 110

Lys Thr Val Ala Glu Leu Gly Ala Ala Val Ala Ser Phe Ala Glu His
        115                 120                 125

Leu Glu Pro Gly Gly Val Val Val Glu Pro Trp Trp Phe Pro Glu
130                 135                 140

Thr Phe Ala Asp Gly Trp Val Ser Ala Asp Val Val Arg Arg Asp Gly
145                 150                 155                 160

Arg Thr Val Ala Arg Val Ser His Ser Val Arg Glu Gly Asn Ala Thr
                165                 170                 175

Arg Met Glu Val His Phe Thr Val Ala Asp Pro Gly Lys Gly Val Arg
            180                 185                 190

His Phe Ser Asp Val His Leu Ile Thr Leu Phe His Gln Arg Glu Tyr
        195                 200                 205

Glu Ala Ala Phe Met Ala Ala Gly Leu Arg Val Glu Tyr Leu Glu Gly
    210                 215                 220

Gly Pro Ser Gly Arg Gly Leu Phe Val Gly Val Pro Ala
225                 230                 235
```

<210> SEQ ID NO 71
<211> LENGTH: 138
<212> TYPE: PRT
<213> ORGANISM: Artificial Sequence
<220> FEATURE:
<223> OTHER INFORMATION: Synthetic

<400> SEQUENCE: 71

```
Met Gly Met Lys Glu Lys Phe Val Leu Ile Ile Thr His Gly Asp Phe
1               5                   10                  15

Gly Lys Gly Leu Leu Ser Gly Ala Glu Val Ile Ile Gly Lys Gln Glu
            20                  25                  30

Asn Val His Thr Val Gly Leu Asn Leu Gly Asp Asn Ile Glu Lys Val
        35                  40                  45

Ala Lys Glu Val Met Arg Ile Ile Ile Ala Lys Leu Ala Glu Asp Lys
50                  55                  60
```

```
Glu Ile Ile Ile Val Val Asp Leu Phe Gly Gly Ser Pro Phe Asn Ile
 65                  70                  75                  80

Ala Leu Glu Met Met Lys Thr Phe Asp Val Lys Val Ile Thr Gly Ile
                 85                  90                  95

Asn Met Pro Met Leu Val Glu Leu Leu Thr Ser Ile Asn Val Tyr Asp
            100                 105                 110

Thr Thr Glu Leu Leu Glu Asn Ile Ser Lys Ile Gly Lys Asp Gly Ile
        115                 120                 125

Lys Val Ile Glu Lys Ser Ser Leu Lys Met
130                 135

<210> SEQ ID NO 72
<211> LENGTH: 154
<212> TYPE: PRT
<213> ORGANISM: Artificial Sequence
<220> FEATURE:
<223> OTHER INFORMATION: Synthetic

<400> SEQUENCE: 72

Met Lys Tyr Asp Gly Ser Lys Leu Arg Ile Gly Ile Leu His Ala Arg
 1               5                  10                  15

Trp Asn Leu Glu Ile Ile Ala Ala Leu Val Ala Gly Ala Ile Lys Arg
                 20                  25                  30

Leu Gln Glu Phe Gly Val Lys Ala Glu Asn Ile Ile Glu Thr Val
             35                  40                  45

Pro Gly Ser Phe Glu Leu Pro Tyr Gly Ser Lys Leu Phe Val Glu Lys
         50                  55                  60

Gln Lys Arg Leu Gly Lys Pro Leu Asp Ala Ile Ile Pro Ile Gly Val
 65                  70                  75                  80

Leu Ile Lys Gly Ser Thr Met His Phe Glu Tyr Ile Cys Asp Ser Thr
                 85                  90                  95

Thr His Gln Leu Met Lys Leu Asn Phe Glu Leu Gly Ile Pro Val Ile
            100                 105                 110

Phe Gly Val Leu Thr Cys Leu Thr Asp Glu Gln Ala Glu Ala Arg Ala
        115                 120                 125

Gly Leu Ile Glu Gly Lys Met His Asn His Gly Glu Asp Trp Gly Ala
    130                 135                 140

Ala Ala Val Glu Met Ala Thr Lys Phe Asn
145                 150

<210> SEQ ID NO 73
<211> LENGTH: 164
<212> TYPE: PRT
<213> ORGANISM: Artificial Sequence
<220> FEATURE:
<223> OTHER INFORMATION: Synthetic

<400> SEQUENCE: 73

Met Ala Val Lys Gly Leu Gly Glu Val Asp Gln Lys Tyr Asp Gly Ser
 1               5                  10                  15

Lys Leu Arg Ile Gly Ile Leu His Ala Arg Trp Asn Arg Lys Ile Ile
                 20                  25                  30

Leu Ala Leu Val Ala Gly Ala Leu Arg Leu Leu Glu Phe Gly Val
             35                  40                  45

Lys Ala Glu Asn Ile Ile Ile Glu Thr Val Pro Gly Ser Phe Glu Leu
         50                  55                  60

Pro Tyr Gly Ser Lys Leu Phe Val Glu Lys Gln Lys Arg Leu Gly Lys
```

```
            65                  70                  75                  80

Pro Leu Asp Ala Ile Ile Pro Ile Gly Val Leu Ile Lys Gly Ser Thr
                85                  90                  95

Met His Phe Glu Tyr Ile Cys Asp Ser Thr Thr His Gln Leu Met Lys
            100                 105                 110

Leu Asn Phe Glu Leu Gly Ile Pro Val Ile Phe Gly Val Leu Thr Cys
            115                 120                 125

Leu Thr Asp Glu Gln Ala Glu Ala Arg Ala Gly Leu Ile Glu Gly Lys
        130                 135                 140

Met His Asn His Gly Glu Asp Trp Gly Ala Ala Val Glu Met Ala
145                 150                 155                 160

Thr Lys Phe Asn

<210> SEQ ID NO 74
<211> LENGTH: 175
<212> TYPE: PRT
<213> ORGANISM: Artificial Sequence
<220> FEATURE:
<223> OTHER INFORMATION: Synthetic

<400> SEQUENCE: 74

Met Gly Ala Asn Trp Tyr Leu Asp Asn Glu Ser Ser Arg Leu Ser Phe
1               5                   10                  15

Thr Ser Thr Lys Asn Ala Asp Ile Ala Glu Val His Arg Phe Leu Val
            20                  25                  30

Leu His Gly Lys Val Asp Pro Lys Gly Leu Ala Glu Val Glu Val Glu
        35                  40                  45

Thr Glu Ser Ile Ser Thr Gly Ile Pro Leu Arg Asp Met Leu Leu Arg
    50                  55                  60

Val Leu Val Phe Gln Val Ser Lys Phe Pro Val Ala Gln Ile Asn Ala
65                  70                  75                  80

Gln Leu Asp Met Arg Pro Ile Asn Asn Leu Ala Pro Gly Ala Gln Leu
                85                  90                  95

Glu Leu Arg Leu Pro Leu Thr Val Ser Leu Arg Gly Lys Ser His Ser
            100                 105                 110

Tyr Asn Ala Glu Leu Leu Ala Thr Arg Leu Asp Glu Arg Arg Phe Gln
            115                 120                 125

Val Val Thr Leu Glu Pro Leu Val Ile His Ala Gln Asp Phe Asp Met
        130                 135                 140

Val Arg Ala Phe Asn Ala Leu Arg Leu Val Ala Gly Leu Ser Ala Val
145                 150                 155                 160

Ser Leu Ser Val Pro Val Gly Ala Val Leu Ile Phe Thr Ala Arg
                165                 170                 175

<210> SEQ ID NO 75
<211> LENGTH: 208
<212> TYPE: PRT
<213> ORGANISM: Artificial Sequence
<220> FEATURE:
<223> OTHER INFORMATION: Synthetic

<400> SEQUENCE: 75

Met Thr Asp Tyr Ile Arg Asp Gly Ser Ala Ile Lys Ala Leu Ser Phe
1               5                   10                  15

Ala Ile Ile Leu Ala Glu Ala Asp Leu Arg His Ile Pro Gln Asp Leu
            20                  25                  30

Gln Arg Leu Ala Val Arg Val Ile His Ala Cys Gly Met Val Asp Val
```

```
                35                  40                  45
Ala Asn Asp Leu Ala Phe Ser Glu Gly Ala Gly Lys Ala Gly Arg Asn
 50                  55                  60

Ala Leu Leu Ala Gly Ala Pro Ile Leu Cys Asp Ala Arg Met Val Ala
 65                  70                  75                  80

Glu Gly Ile Thr Arg Ser Arg Leu Pro Ala Asp Asn Arg Val Ile Tyr
                 85                  90                  95

Thr Leu Ser Asp Pro Ser Val Pro Glu Leu Ala Lys Lys Ile Gly Asn
            100                 105                 110

Thr Arg Ser Ala Ala Ala Leu Asp Leu Trp Leu Pro His Ile Glu Gly
            115                 120                 125

Ser Ile Val Ala Ile Gly Asn Ala Pro Thr Ala Leu Phe Arg Leu Phe
        130                 135                 140

Glu Leu Leu Asp Ala Gly Ala Pro Lys Pro Ala Leu Ile Ile Gly Met
145                 150                 155                 160

Pro Val Gly Phe Val Gly Ala Ala Glu Ser Lys Asp Glu Leu Ala Ala
                165                 170                 175

Asn Ser Arg Gly Val Pro Tyr Val Ile Val Arg Gly Arg Arg Gly Gly
            180                 185                 190

Ser Ala Met Thr Ala Ala Ala Val Asn Ala Leu Ala Ser Glu Arg Glu
        195                 200                 205

<210> SEQ ID NO 76
<211> LENGTH: 128
<212> TYPE: PRT
<213> ORGANISM: Artificial Sequence
<220> FEATURE:
<223> OTHER INFORMATION: Synthetic

<400> SEQUENCE: 76

Met Ile Thr Val Phe Gly Leu Lys Ser Lys Leu Ala Pro Arg Arg Glu
  1               5                  10                  15

Lys Leu Ala Glu Val Ile Tyr Ser Ser Leu His Leu Gly Leu Asp Ile
                 20                  25                  30

Pro Lys Gly Lys His Ala Ile Arg Phe Leu Cys Leu Glu Lys Glu Asp
             35                  40                  45

Phe Tyr Tyr Pro Phe Asp Arg Ser Asp Asp Tyr Thr Val Ile Glu Ile
 50                  55                  60

Asn Leu Met Ala Gly Arg Ser Glu Glu Thr Lys Met Leu Leu Ile Phe
 65                  70                  75                  80

Leu Leu Phe Ile Ala Leu Glu Arg Lys Leu Gly Ile Arg Ala His Asp
                 85                  90                  95

Val Glu Ile Thr Ile Lys Glu Gln Pro Ala His Cys Trp Gly Phe Arg
            100                 105                 110

Gly Arg Thr Gly Asp Ser Ala Arg Asp Leu Asp Tyr Asp Ile Tyr Val
        115                 120                 125

<210> SEQ ID NO 77
<211> LENGTH: 235
<212> TYPE: PRT
<213> ORGANISM: Artificial Sequence
<220> FEATURE:
<223> OTHER INFORMATION: Synthetic

<400> SEQUENCE: 77

Met Gly Ser Asp Leu Gln Lys Leu Gln Arg Phe Ser Thr Cys Asp Ile
  1               5                  10                  15
```

```
Ser Asp Gly Leu Leu Asn Val Tyr Asn Ile Pro Thr Gly Gly Tyr Phe
            20                  25                  30

Pro Asn Leu Thr Ala Ile Ser Pro Gln Asn Ser Ser Ile Val Gly
        35                  40                  45

Thr Ala Tyr Thr Val Leu Phe Ala Pro Ile Asp Asp Pro Arg Pro Ala
50                  55                  60

Val Asn Tyr Ile Asp Ser Val Pro Pro Asn Ser Ile Leu Val Leu Ala
65                  70                  75                  80

Leu Glu Pro His Leu Gln Ser Gln Phe His Pro Phe Ile Lys Ile Thr
                85                  90                  95

Gln Ala Met Tyr Gly Gly Leu Met Ser Thr Arg Ala Gln Tyr Leu Lys
            100                 105                 110

Ser Asn Gly Thr Val Val Phe Gly Arg Ile Arg Asp Val Asp Glu His
            115                 120                 125

Arg Thr Leu Asn His Pro Val Phe Ala Tyr Gly Val Gly Ser Cys Ala
        130                 135                 140

Pro Lys Ala Val Val Lys Ala Val Gly Thr Asn Val Gln Leu Lys Ile
145                 150                 155                 160

Leu Thr Ser Asp Gly Val Thr Gln Thr Ile Cys Pro Gly Asp Tyr Ile
                165                 170                 175

Ala Gly Asp Asn Asn Gly Ile Val Arg Ile Pro Val Gln Glu Thr Asp
            180                 185                 190

Ile Ser Lys Leu Val Thr Tyr Ile Glu Lys Ser Ile Glu Val Asp Arg
            195                 200                 205

Leu Val Ser Glu Ala Ile Lys Asn Gly Leu Pro Ala Lys Ala Ala Gln
        210                 215                 220

Thr Ala Arg Arg Met Val Leu Lys Asp Tyr Ile
225                 230                 235

<210> SEQ ID NO 78
<211> LENGTH: 162
<212> TYPE: PRT
<213> ORGANISM: Artificial Sequence
<220> FEATURE:
<223> OTHER INFORMATION: Synthetic

<400> SEQUENCE: 78

Met Ser Gly Met Arg Val Tyr Leu Gly Ala Asp His Ala Gly Tyr Glu
1               5                   10                  15

Leu Lys Gln Ala Ile Ile Ala Phe Leu Lys Met Thr Gly His Glu Pro
            20                  25                  30

Ile Asp Cys Gly Ala Leu Arg Tyr Asp Ala Asp Asp Tyr Pro Ala
        35                  40                  45

Phe Cys Ile Ala Ala Ala Thr Arg Thr Val Ala Asp Pro Gly Ser Leu
50                  55                  60

Gly Ile Val Leu Gly Gly Ser Gly Asn Gly Glu Gln Ile Ala Ala Asn
65                  70                  75                  80

Lys Val Pro Gly Ala Arg Cys Ala Leu Ala Trp Ser Val Gln Thr Ala
            85                  90                  95

Ala Leu Ala Arg Glu His Asn Asn Ala Gln Leu Ile Gly Ile Gly Gly
            100                 105                 110

Arg Met His Thr Leu Glu Glu Ala Leu Arg Ile Val Lys Ala Phe Val
        115                 120                 125

Thr Thr Pro Trp Ser Lys Ala Gln Arg His Gln Arg Ile Asp Ile
        130                 135                 140
```

Leu Ala Glu Tyr Glu Arg Thr His Glu Ala Pro Pro Val Pro Gly Ala
145                 150                 155                 160

Pro Ala

<210> SEQ ID NO 79
<211> LENGTH: 157
<212> TYPE: PRT
<213> ORGANISM: Artificial Sequence
<220> FEATURE:
<223> OTHER INFORMATION: Synthetic

<400> SEQUENCE: 79

Met Gly Asp Asp Ala Arg Ile Ala Ala Ile Gly Asp Val Asp Glu Leu
1               5                   10                  15

Asn Ser Gln Ile Gly Val Leu Leu Ala Glu Pro Leu Pro Asp Asp Val
                20                  25                  30

Arg Ala Ala Leu Ser Ala Ile Gln His Asp Leu Phe Asp Leu Gly Gly
            35                  40                  45

Glu Leu Cys Ile Pro Gly His Ala Ala Ile Thr Glu Asp His Leu Leu
    50                  55                  60

Arg Leu Ala Leu Trp Leu Val His Tyr Asn Gly Gln Leu Pro Pro Leu
65                  70                  75                  80

Glu Glu Phe Ile Leu Pro Gly Gly Ala Arg Gly Ala Ala Leu Ala His
                85                  90                  95

Val Cys Arg Thr Val Cys Arg Arg Ala Glu Arg Ser Ile Lys Ala Leu
            100                 105                 110

Gly Ala Ser Glu Pro Leu Asn Ile Ala Pro Ala Ala Tyr Val Asn Leu
        115                 120                 125

Leu Ser Asp Leu Leu Phe Val Leu Ala Arg Val Leu Asn Arg Ala Ala
    130                 135                 140

Gly Gly Ala Asp Val Leu Trp Asp Arg Thr Arg Ala His
145                 150                 155

<210> SEQ ID NO 80
<211> LENGTH: 157
<212> TYPE: PRT
<213> ORGANISM: Artificial Sequence
<220> FEATURE:
<223> OTHER INFORMATION: Synthetic

<400> SEQUENCE: 80

Met Ile Leu Ser Ala Glu Gln Ser Phe Thr Leu Arg His Pro His Gly
1               5                   10                  15

Gln Ala Ala Ala Leu Ala Phe Val Arg Glu Pro Ala Ala Leu Ala
                20                  25                  30

Gly Val Gln Arg Leu Arg Gly Leu Asp Ser Asp Gly Glu Gln Val Trp
            35                  40                  45

Gly Glu Leu Leu Val Arg Val Pro Leu Leu Gly Glu Val Asp Leu Pro
    50                  55                  60

Phe Arg Ser Glu Ile Val Arg Thr Pro Gln Gly Ala Glu Leu Arg Pro
65                  70                  75                  80

Leu Thr Leu Thr Gly Glu Arg Ala Trp Val Ala Val Ser Gly Gln Ala
                85                  90                  95

Thr Ala Ala Glu Gly Gly Glu Met Ala Phe Ala Phe Gln Phe Gln Ala
            100                 105                 110

His Leu Ala Thr Pro Glu Ala Glu Gly Glu Gly Gly Ala Ala Phe Glu
        115                 120                 125

```
Val Met Val Gln Ala Ala Gly Val Thr Leu Leu Leu Val Ala Met
    130                 135                 140

Ala Leu Pro Gln Gly Leu Ala Ala Gly Leu Pro Pro Ala
145                 150                 155

<210> SEQ ID NO 81
<211> LENGTH: 156
<212> TYPE: PRT
<213> ORGANISM: Artificial Sequence
<220> FEATURE:
<223> OTHER INFORMATION: Synthetic

<400> SEQUENCE: 81

Met Thr Lys Lys Val Gly Ile Val Asp Thr Thr Phe Ala Arg Val Asp
1               5                   10                  15

Met Ala Ser Ala Ala Ile Leu Thr Leu Lys Met Glu Ser Pro Asn Ile
                20                  25                  30

Lys Ile Ile Arg Lys Thr Val Pro Gly Ile Lys Asp Leu Pro Val Ala
            35                  40                  45

Cys Lys Lys Leu Leu Glu Glu Glu Gly Cys Asp Ile Val Met Ala Leu
        50                  55                  60

Gly Met Pro Gly Lys Lys Glu Lys Asp Lys Val Cys Ala His Glu Ala
65                  70                  75                  80

Ser Leu Gly Leu Met Leu Ala Gln Leu Met Thr Asn Lys His Ile Ile
                85                  90                  95

Glu Val Phe Val His Glu Asp Glu Ala Lys Asp Ala Glu Leu Lys
                100                 105                 110

Ile Leu Ala Ala Arg Arg Ala Ile Glu His Ala Leu Asn Val Tyr Tyr
            115                 120                 125

Leu Leu Phe Lys Pro Glu Tyr Leu Thr Arg Met Ala Gly Lys Gly Leu
        130                 135                 140

Arg Gln Gly Phe Glu Asp Ala Gly Pro Ala Arg Glu
145                 150                 155

<210> SEQ ID NO 82
<211> LENGTH: 209
<212> TYPE: PRT
<213> ORGANISM: Artificial Sequence
<220> FEATURE:
<223> OTHER INFORMATION: Synthetic

<400> SEQUENCE: 82

Met Asp Asp Ile Asn Asn Gln Leu Lys Arg Leu Lys Val Ile Pro Val
1               5                   10                  15

Ile Ala Ile Asp Asn Ala Glu Asp Ile Ile Pro Leu Gly Lys Val Leu
                20                  25                  30

Ala Glu Asn Gly Leu Pro Ala Ala Glu Ile Thr Phe Arg Ser Ser Ala
            35                  40                  45

Ala Val Lys Ala Ile Met Leu Leu Arg Ser Ala Gln Pro Glu Met Leu
        50                  55                  60

Ile Gly Ala Gly Thr Ile Leu Asn Gly Val Gln Ala Leu Ala Ala Lys
65                  70                  75                  80

Glu Ala Gly Ala Asp Phe Val Val Ser Pro Gly Phe Asn Pro Asn Thr
                85                  90                  95

Val Arg Ala Cys Gln Ile Ile Gly Ile Asp Ile Val Pro Gly Val Asn
            100                 105                 110

Asn Pro Ser Thr Val Glu Gln Ala Leu Glu Met Gly Leu Thr Thr Leu
        115                 120                 125
```

Lys Phe Phe Pro Ala Glu Ala Ser Gly Gly Ile Ser Met Val Lys Ser
            130                 135                 140

Leu Val Gly Pro Tyr Gly Asp Ile Arg Leu Met Pro Thr Gly Gly Ile
145                 150                 155                 160

Thr Pro Asp Asn Ile Asp Asn Tyr Leu Ala Ile Pro Gln Val Leu Ala
                165                 170                 175

Cys Gly Gly Thr Trp Met Val Asp Lys Lys Leu Val Arg Asn Gly Glu
            180                 185                 190

Trp Asp Glu Ile Ala Arg Leu Thr Arg Glu Ile Val Glu Gln Val Asn
                195                 200                 205

Pro

<210> SEQ ID NO 83
<211> LENGTH: 114
<212> TYPE: PRT
<213> ORGANISM: Artificial Sequence
<220> FEATURE:
<223> OTHER INFORMATION: Synthetic

<400> SEQUENCE: 83

Met Pro Ile Phe Thr Leu Asn Thr Asn Ile Lys Ala Asp Asp Val Pro
1               5                   10                  15

Ser Asp Phe Leu Ser Leu Thr Ser Arg Leu Val Gly Leu Ile Leu Ser
            20                  25                  30

Lys Pro Gly Ser Tyr Val Ala Val His Ile Asn Thr Asp Gln Gln Leu
        35                  40                  45

Ser Phe Gly Gly Ser Thr Asn Pro Ala Ala Phe Gly Thr Leu Met Ser
    50                  55                  60

Ile Gly Gly Ile Glu Pro Asp Lys Asn Arg Asp His Ser Ala Val Leu
65                  70                  75                  80

Phe Asp His Leu Asn Ala Met Leu Gly Ile Pro Lys Asn Arg Met Tyr
                85                  90                  95

Ile His Phe Val Asn Leu Asn Gly Asp Asp Val Gly Trp Asn Gly Thr
            100                 105                 110

Thr Phe

<210> SEQ ID NO 84
<211> LENGTH: 114
<212> TYPE: PRT
<213> ORGANISM: Artificial Sequence
<220> FEATURE:
<223> OTHER INFORMATION: Synthetic

<400> SEQUENCE: 84

Met Pro Ile Phe Thr Leu Asn Thr Asn Ile Lys Ala Asp Asp Val Pro
1               5                   10                  15

Ser Asp Phe Leu Ser Leu Thr Ser Arg Leu Val Gly Leu Ile Leu Ser
            20                  25                  30

Glu Pro Gly Ser Tyr Val Ala Val His Ile Asn Thr Asp Gln Gln Leu
        35                  40                  45

Ser Phe Gly Gly Ser Thr Asn Pro Ala Ala Phe Gly Thr Leu Met Ser
    50                  55                  60

Ile Gly Gly Ile Glu Pro Asp Lys Asn Glu Asp His Ser Ala Val Leu
65                  70                  75                  80

Phe Asp His Leu Asn Ala Met Leu Gly Ile Pro Lys Asn Arg Met Tyr
                85                  90                  95

```
Ile His Phe Val Asp Leu Asp Gly Asp Val Gly Trp Asn Gly Thr
                100                 105                 110
Thr Phe
```

<210> SEQ ID NO 85
<211> LENGTH: 157
<212> TYPE: PRT
<213> ORGANISM: Artificial Sequence
<220> FEATURE:
<223> OTHER INFORMATION: Synthetic

<400> SEQUENCE: 85

```
Met Asn Gln His Ser His Lys Asp His Glu Thr Val Arg Ile Ala Val
1               5                   10                  15

Val Arg Ala Arg Trp His Ala Asp Ile Val Asp Ala Cys Val Glu Ala
                20                  25                  30

Phe Glu Ile Ala Met Ala Ala Ile Gly Gly Asp Arg Phe Ala Val Asp
                35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asp Gly Met Met Asn Val Gln Leu Asp Thr Gly Val Pro Val Leu Ser
                100                 105                 110

Ala Val Leu Thr Pro His Arg Tyr Arg Asp Ser Asp Glu His His Arg
                115                 120                 125

Phe Phe Ala Ala His Phe Ala Val Lys Gly Val Glu Ala Ala Arg Ala
                130                 135                 140

Cys Ile Glu Ile Leu Asn Ala Arg Glu Lys Ile Ala Ala
145                 150                 155
```

<210> SEQ ID NO 86
<211> LENGTH: 157
<212> TYPE: PRT
<213> ORGANISM: Artificial Sequence
<220> FEATURE:
<223> OTHER INFORMATION: Synthetic

<400> SEQUENCE: 86

```
Met Asn Gln His Ser His Lys Asp His Glu Thr Val Arg Ile Ala Val
1               5                   10                  15

Val Arg Ala Arg Trp His Ala Asp Ile Val Asp Ala Cys Val Glu Ala
                20                  25                  30

Phe Glu Ile Ala Met Ala Ala Ile Gly Gly Asp Arg Phe Ala Val Asp
                35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asp Gly Gly Ile Tyr Asp His Glu Phe Val Ala Ser Ala Val Ile
                85                  90                  95

Asp Gly Met Met Asn Val Gln Leu Asp Thr Gly Val Pro Val Leu Ser
                100                 105                 110

Ala Val Leu Thr Pro His Glu Tyr Glu Asp Ser Asp Glu Asp His Glu
                115                 120                 125
```

Phe Phe Ala Ala His Phe Ala Val Lys Gly Val Glu Ala Ala Arg Ala
         130                 135                 140

Cys Ile Glu Ile Leu Asn Ala Arg Glu Lys Ile Ala Ala
145                 150                 155

<210> SEQ ID NO 87
<211> LENGTH: 205
<212> TYPE: PRT
<213> ORGANISM: Artificial Sequence
<220> FEATURE:
<223> OTHER INFORMATION: Synthetic

<400> SEQUENCE: 87

Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
            20                  25                  30

Ala Gly Gly Val His Leu Ile Glu Ile Thr Phe Thr Val Pro Asp Ala
        35                  40                  45

Asp Thr Val Ile Lys Ala Leu Ser Val Leu Lys Glu Lys Gly Ala Ile
    50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Asp Ile Leu
        115                 120                 125

Lys Leu Phe Pro Gly Glu Val Val Gly Pro Gln Phe Val Lys Ala Met
    130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Asp Ala Leu Val Lys Gly Asp Pro Asp Glu Val Arg Glu Lys
            180                 185                 190

Ala Lys Lys Phe Val Gly Lys Ile Arg Gly Cys Thr Glu
        195                 200                 205

<210> SEQ ID NO 88
<211> LENGTH: 205
<212> TYPE: PRT
<213> ORGANISM: Artificial Sequence
<220> FEATURE:
<223> OTHER INFORMATION: Synthetic

<400> SEQUENCE: 88

Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
            20                  25                  30

Ala Gly Gly Val His Leu Ile Glu Ile Thr Phe Thr Val Pro Asp Ala
        35                  40                  45

Asp Thr Val Ile Lys Ala Leu Ser Val Leu Lys Glu Lys Gly Ala Ile
    50                  55                  60

Ile Gly Ala Gly Thr Val Thr Ser Val Glu Gln Cys Arg Lys Ala Val
65                  70                  75                  80

```
Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Asp Ile Leu
        115                 120                 125

Lys Leu Phe Pro Gly Glu Val Val Gly Pro Glu Phe Val Glu Ala Met
130                 135                 140

Lys Gly Pro Phe Pro Asn Val Lys Phe Val Pro Thr Gly Gly Val Asp
145                 150                 155                 160

Leu Asp Asp Val Cys Glu Trp Phe Asp Ala Gly Val Leu Ala Val Gly
                165                 170                 175

Val Gly Asp Ala Leu Val Glu Gly Asp Pro Asp Glu Val Arg Glu Asp
            180                 185                 190

Ala Lys Glu Phe Val Glu Glu Ile Arg Gly Cys Thr Glu
            195                 200                 205

<210> SEQ ID NO 89
<211> LENGTH: 205
<212> TYPE: PRT
<213> ORGANISM: Artificial Sequence
<220> FEATURE:
<223> OTHER INFORMATION: Synthetic

<400> SEQUENCE: 89

Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
            20                  25                  30

Ala Gly Gly Val His Leu Ile Glu Ile Thr Phe Thr Val Pro Asp Ala
        35                  40                  45

Asp Thr Val Ile Lys Ala Leu Ser Val Leu Lys Glu Lys Gly Ala Ile
    50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Asp Ile Leu
        115                 120                 125

Lys Leu Phe Pro Gly Glu Val Val Gly Pro Gln Phe Val Lys Ala Met
130                 135                 140

Lys Gly Pro Phe Pro Asn Val Lys Phe Val Pro Thr Gly Gly Val Asn
145                 150                 155                 160

Leu Asp Asn Val Cys Lys Trp Phe Lys Ala Gly Val Leu Ala Val Gly
                165                 170                 175

Val Gly Lys Ala Leu Val Lys Gly Lys Pro Asp Glu Val Arg Glu Lys
            180                 185                 190

Ala Lys Lys Phe Val Lys Lys Ile Arg Gly Cys Thr Glu
            195                 200                 205

<210> SEQ ID NO 90
<211> LENGTH: 157
<212> TYPE: PRT
<213> ORGANISM: Artificial Sequence
```

<220> FEATURE:
<223> OTHER INFORMATION: Synthetic

<400> SEQUENCE: 90

Met Asn Gln His Ser His Lys Asp His Glu Thr Val Arg Ile Ala Val
1               5                   10                  15

Val Arg Ala Arg Trp His Ala Glu Ile Val Asp Ala Cys Val Ser Ala
            20                  25                  30

Phe Glu Ala Ala Met Arg Asp Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asp Gly Met Met Asn Val Gln Leu Asp Thr Gly Val Pro Val Leu Ser
            100                 105                 110

Ala Val Leu Thr Pro His Arg Tyr Arg Asp Ser Asp Ala His Thr Leu
        115                 120                 125

Leu Phe Leu Ala Leu Phe Ala Val Lys Gly Met Glu Ala Ala Arg Ala
    130                 135                 140

Cys Val Glu Ile Leu Ala Ala Arg Glu Lys Ile Ala Ala
145                 150                 155

<210> SEQ ID NO 91
<211> LENGTH: 157
<212> TYPE: PRT
<213> ORGANISM: Artificial Sequence
<220> FEATURE:
<223> OTHER INFORMATION: Synthetic

<400> SEQUENCE: 91

Met Asn Gln His Ser His Lys Asp His Glu Thr Val Arg Ile Ala Val
1               5                   10                  15

Val Arg Ala Arg Trp His Ala Glu Ile Val Asp Ala Cys Val Ser Ala
            20                  25                  30

Phe Glu Ala Ala Met Arg Asp Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asp Gly Gly Ile Tyr Asp His Glu Phe Val Ala Ser Ala Val Ile
                85                  90                  95

Asp Gly Met Met Asn Val Gln Leu Asp Thr Gly Val Pro Val Leu Ser
            100                 105                 110

Ala Val Leu Thr Pro His Glu Tyr Glu Asp Ser Asp Ala Asp Thr Leu
        115                 120                 125

Leu Phe Leu Ala Leu Phe Ala Val Lys Gly Met Glu Ala Ala Arg Ala
    130                 135                 140

Cys Val Glu Ile Leu Ala Ala Arg Glu Lys Ile Ala Ala
145                 150                 155

<210> SEQ ID NO 92
<211> LENGTH: 157
<212> TYPE: PRT

```
<213> ORGANISM: Artificial Sequence
<220> FEATURE:
<223> OTHER INFORMATION: Synthetic

<400> SEQUENCE: 92

Met Asn Gln His Ser His Lys Asp His Glu Thr Val Arg Ile Ala Val
1               5                   10                  15

Val Arg Ala Arg Trp His Ala Glu Ile Val Asp Ala Cys Val Ser Ala
            20                  25                  30

Phe Glu Ala Ala Met Arg Asp Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asn Gly Met Met Asn Val Gln Leu Asn Thr Gly Val Pro Val Leu Ser
            100                 105                 110

Ala Val Leu Thr Pro His Asn Tyr Asp Lys Ser Lys Ala His Thr Leu
        115                 120                 125

Leu Phe Leu Ala Leu Phe Ala Val Lys Gly Met Glu Ala Ala Arg Ala
    130                 135                 140

Cys Val Glu Ile Leu Ala Ala Arg Glu Lys Ile Ala Ala
145                 150                 155

<210> SEQ ID NO 93
<211> LENGTH: 156
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (70)..(70)
<223> OTHER INFORMATION: Xaa is A or K

<400> SEQUENCE: 93

Met Thr Lys Lys Val Gly Ile Val Asp Thr Thr Phe Ala Arg Val Asp
1               5                   10                  15

Met Ala Ser Ala Ala Ile Leu Thr Leu Lys Met Glu Ser Pro Asn Ile
            20                  25                  30

Lys Ile Ile Arg Lys Thr Val Pro Gly Ile Lys Asp Leu Pro Val Ala
        35                  40                  45

Cys Lys Lys Leu Leu Glu Glu Gly Cys Asp Ile Val Met Ala Leu
    50                  55                  60

Gly Met Pro Gly Lys Xaa Glu Lys Asp Lys Val Cys Ala His Glu Ala
65                  70                  75                  80

Ser Leu Gly Leu Met Leu Ala Gln Leu Met Thr Asn Lys His Ile Ile
                85                  90                  95

Glu Val Phe Val His Glu Asp Glu Ala Lys Asp Ala Glu Leu Lys
            100                 105                 110

Ile Leu Ala Ala Arg Arg Ala Ile Glu His Ala Leu Asn Val Tyr Tyr
        115                 120                 125

Leu Leu Phe Lys Pro Glu Tyr Leu Thr Arg Met Ala Gly Lys Gly Leu
    130                 135                 140

Arg Gln Gly Phe Glu Asp Ala Gly Pro Ala Arg Glu
145                 150                 155
```

```
<210> SEQ ID NO 94
<211> LENGTH: 209
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is S or D
<220> FEATURE:
<221> NAME/KEY: MISC_FEATURE
<222> LOCATION: (3)..(3)
<223> OTHER INFORMATION: Xaa is T or D
<220> FEATURE:
<221> NAME/KEY: MISC_FEATURE
<222> LOCATION: (10)..(10)
<223> OTHER INFORMATION: Xaa is A or R
<220> FEATURE:
<221> NAME/KEY: MISC_FEATURE
<222> LOCATION: (85)..(85)
<223> OTHER INFORMATION: Xaa is T or D
<220> FEATURE:
<221> NAME/KEY: MISC_FEATURE
<222> LOCATION: (119)..(119)
<223> OTHER INFORMATION: Xaa is A or Q
<220> FEATURE:
<221> NAME/KEY: MISC_FEATURE
<222> LOCATION: (163)..(163)
<223> OTHER INFORMATION: Xaa is S or D
<220> FEATURE:
<221> NAME/KEY: MISC_FEATURE
<222> LOCATION: (189)..(189)
<223> OTHER INFORMATION: Xaa is T or R

<400> SEQUENCE: 94

Met Xaa Xaa Ile Asn Asn Gln Leu Lys Xaa Leu Lys Val Ile Pro Val
1               5                   10                  15

Ile Ala Ile Asp Asn Ala Glu Asp Ile Ile Pro Leu Gly Lys Val Leu
            20                  25                  30

Ala Glu Asn Gly Leu Pro Ala Ala Glu Ile Thr Phe Arg Ser Ser Ala
        35                  40                  45

Ala Val Lys Ala Ile Met Leu Leu Arg Ser Ala Gln Pro Glu Met Leu
    50                  55                  60

Ile Gly Ala Gly Thr Ile Leu Asn Gly Val Gln Ala Leu Ala Ala Lys
65                  70                  75                  80

Glu Ala Gly Ala Xaa Phe Val Val Ser Pro Gly Phe Asn Pro Asn Thr
                85                  90                  95

Val Arg Ala Cys Gln Ile Ile Gly Ile Asp Ile Val Pro Gly Val Asn
            100                 105                 110

Asn Pro Ser Thr Val Glu Xaa Ala Leu Glu Met Gly Leu Thr Thr Leu
        115                 120                 125

Lys Phe Phe Pro Ala Glu Ala Ser Gly Gly Ile Ser Met Val Lys Ser
    130                 135                 140

Leu Val Gly Pro Tyr Gly Asp Ile Arg Leu Met Pro Thr Gly Gly Ile
145                 150                 155                 160

Thr Pro Xaa Asn Ile Asp Asn Tyr Leu Ala Ile Pro Gln Val Leu Ala
                165                 170                 175

Cys Gly Gly Thr Trp Met Val Asp Lys Lys Leu Val Xaa Asn Gly Glu
            180                 185                 190

Trp Asp Glu Ile Ala Arg Leu Thr Arg Glu Ile Val Glu Gln Val Asn
        195                 200                 205

Pro
```

<210> SEQ ID NO 95
<211> LENGTH: 114
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (13)..(13)
<223> OTHER INFORMATION: Xaa is T or D
<220> FEATURE:
<221> NAME/KEY: MISC_FEATURE
<222> LOCATION: (33)..(33)
<223> OTHER INFORMATION: Xaa is K or E
<220> FEATURE:
<221> NAME/KEY: MISC_FEATURE
<222> LOCATION: (71)..(71)
<223> OTHER INFORMATION: Xaa is S or D
<220> FEATURE:
<221> NAME/KEY: MISC_FEATURE
<222> LOCATION: (74)..(74)
<223> OTHER INFORMATION: Xaa is R or E
<220> FEATURE:
<221> NAME/KEY: MISC_FEATURE
<222> LOCATION: (101)..(101)
<223> OTHER INFORMATION: Xaa is N or D
<220> FEATURE:
<221> NAME/KEY: MISC_FEATURE
<222> LOCATION: (103)..(103)
<223> OTHER INFORMATION: Xaa is N or D

<400> SEQUENCE: 95

Met Pro Ile Phe Thr Leu Asn Thr Asn Ile Lys Ala Xaa Asp Val Pro
1               5                   10                  15

Ser Asp Phe Leu Ser Leu Thr Ser Arg Leu Val Gly Leu Ile Leu Ser
                20                  25                  30

Xaa Pro Gly Ser Tyr Val Ala Val His Ile Asn Thr Asp Gln Gln Leu
            35                  40                  45

Ser Phe Gly Gly Ser Thr Asn Pro Ala Ala Phe Gly Thr Leu Met Ser
        50                  55                  60

Ile Gly Gly Ile Glu Pro Xaa Lys Asn Xaa Asp His Ser Ala Val Leu
65                  70                  75                  80

Phe Asp His Leu Asn Ala Met Leu Gly Ile Pro Lys Asn Arg Met Tyr
                85                  90                  95

Ile His Phe Val Xaa Leu Xaa Gly Asp Asp Val Gly Trp Asn Gly Thr
            100                 105                 110

Thr Phe

<210> SEQ ID NO 96
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa is Y or H
<220> FEATURE:
<221> NAME/KEY: MISC_FEATURE
<222> LOCATION: (82)..(82)
<223> OTHER INFORMATION: Xaa is N or D
<220> FEATURE:
<221> NAME/KEY: MISC_FEATURE
<222> LOCATION: (87)..(87)
<223> OTHER INFORMATION: Xaa is R or D
<220> FEATURE:
<221> NAME/KEY: MISC_FEATURE
<222> LOCATION: (105)..(105)
<223> OTHER INFORMATION: Xaa is S or D
<220> FEATURE:
<221> NAME/KEY: MISC_FEATURE
<222> LOCATION: (119)..(119)
<223> OTHER INFORMATION: Xaa is R or E
<220> FEATURE:
<221> NAME/KEY: MISC_FEATURE
<222> LOCATION: (121)..(121)
<223> OTHER INFORMATION: Xaa is R or E
<220> FEATURE:
<221> NAME/KEY: MISC_FEATURE
<222> LOCATION: (124)..(124)
<223> OTHER INFORMATION: Xaa is A or D
<220> FEATURE:
<221> NAME/KEY: MISC_FEATURE
<222> LOCATION: (126)..(126)
<223> OTHER INFORMATION: Xaa is H or D
<220> FEATURE:
<221> NAME/KEY: MISC_FEATURE
<222> LOCATION: (128)..(128)
<223> OTHER INFORMATION: Xaa is R or E
<220> FEATURE:
<221> NAME/KEY: MISC_FEATURE
<222> LOCATION: (150)..(150)
<223> OTHER INFORMATION: Xaa is A or N

<400> SEQUENCE: 96

Met Asn Gln His Ser His Lys Asp Xaa Glu Thr Val Arg Ile Ala Val
1               5                   10                  15

Val Arg Ala Arg Trp His Ala Asp Ile Val Asp Ala Cys Val Glu Ala
            20                  25                  30

Phe Glu Ile Ala Met Ala Ala Ile Gly Gly Asp Arg Phe Ala Val Asp
        35                  40                  45

Val Phe Asp Val Pro Gly Ala Tyr Glu Ile Pro Leu His Ala Arg Thr
50                  55                  60

Leu Ala Glu Thr Gly Arg Tyr Gly Ala Val Leu Gly Thr Ala Phe Val
65                  70                  75                  80

Val Xaa Gly Gly Ile Tyr Xaa His Glu Phe Val Ala Ser Ala Val Ile
                85                  90                  95

Asp Gly Met Met Asn Val Gln Leu Xaa Thr Gly Val Pro Val Leu Ser
            100                 105                 110

Ala Val Leu Thr Pro His Xaa Tyr Xaa Asp Ser Xaa Glu Xaa His Xaa
        115                 120                 125

Phe Phe Ala Ala His Phe Ala Val Lys Gly Val Glu Ala Ala Arg Ala
    130                 135                 140

Cys Ile Glu Ile Leu Xaa Ala Arg Glu Lys Ile Ala Ala
145                 150                 155

<210> SEQ ID NO 97
<211> LENGTH: 205
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (126)..(126)
<223> OTHER INFORMATION: Xaa is T or D
<220> FEATURE:
<221> NAME/KEY: MISC_FEATURE
<222> LOCATION: (139)..(139)
<223> OTHER INFORMATION: Xaa is Q or E
<220> FEATURE:
<221> NAME/KEY: MISC_FEATURE
<222> LOCATION: (142)..(142)
<223> OTHER INFORMATION: Xaa is K or E
<220> FEATURE:

```
<221> NAME/KEY: MISC_FEATURE
<222> LOCATION: (160)..(160)
<223> OTHER INFORMATION: Xaa is N or D
<220> FEATURE:
<221> NAME/KEY: MISC_FEATURE
<222> LOCATION: (163)..(163)
<223> OTHER INFORMATION: Xaa is N or D
<220> FEATURE:
<221> NAME/KEY: MISC_FEATURE
<222> LOCATION: (166)..(166)
<223> OTHER INFORMATION: Xaa is E or K
<220> FEATURE:
<221> NAME/KEY: MISC_FEATURE
<222> LOCATION: (169)..(169)
<223> OTHER INFORMATION: Xaa is D or K
<220> FEATURE:
<221> NAME/KEY: MISC_FEATURE
<222> LOCATION: (179)..(179)
<223> OTHER INFORMATION: Xaa is S, D or K
<220> FEATURE:
<221> NAME/KEY: MISC_FEATURE
<222> LOCATION: (183)..(183)
<223> OTHER INFORMATION: Xaa is K or E
<220> FEATURE:
<221> NAME/KEY: MISC_FEATURE
<222> LOCATION: (185)..(185)
<223> OTHER INFORMATION: Xaa is T, D, or K
<220> FEATURE:
<221> NAME/KEY: MISC_FEATURE
<222> LOCATION: (192)..(192)
<223> OTHER INFORMATION: Xaa is D or K
<220> FEATURE:
<221> NAME/KEY: MISC_FEATURE
<222> LOCATION: (195)..(195)
<223> OTHER INFORMATION: Xaa is A, E, or K
<220> FEATURE:
<221> NAME/KEY: MISC_FEATURE
<222> LOCATION: (198)..(198)
<223> OTHER INFORMATION: Xaa is E or K
<220> FEATURE:
<221> NAME/KEY: MISC_FEATURE
<222> LOCATION: (199)..(199)
<223> OTHER INFORMATION: Xaa is E or K

<400> SEQUENCE: 97

Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
            20                  25                  30

Ala Gly Gly Val His Leu Ile Glu Ile Thr Phe Thr Val Pro Asp Ala
        35                  40                  45

Asp Thr Val Ile Lys Ala Leu Ser Val Leu Lys Glu Lys Gly Ala Ile
    50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Xaa Ile Leu
        115                 120                 125

Lys Leu Phe Pro Gly Glu Val Val Gly Pro Xaa Phe Val Xaa Ala Met
    130                 135                 140

Lys Gly Pro Phe Pro Asn Val Lys Phe Val Pro Thr Gly Gly Val Xaa
145                 150                 155                 160

Leu Asp Xaa Val Cys Xaa Trp Phe Xaa Ala Gly Val Leu Ala Val Gly
                165                 170                 175
```

```
Val Gly Xaa Ala Leu Val Xaa Gly Xaa Pro Asp Glu Val Arg Glu Xaa
            180                 185                 190

Ala Lys Xaa Phe Val Xaa Xaa Ile Arg Gly Cys Thr Glu
        195                 200                 205

<210> SEQ ID NO 98
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa is Y or H
<220> FEATURE:
<221> NAME/KEY: MISC_FEATURE
<222> LOCATION: (38)..(38)
<223> OTHER INFORMATION: Xaa is A or R
<220> FEATURE:
<221> NAME/KEY: MISC_FEATURE
<222> LOCATION: (82)..(82)
<223> OTHER INFORMATION: Xaa is N or D
<220> FEATURE:
<221> NAME/KEY: MISC_FEATURE
<222> LOCATION: (87)..(87)
<223> OTHER INFORMATION: Xaa is R or D
<220> FEATURE:
<221> NAME/KEY: MISC_FEATURE
<222> LOCATION: (97)..(97)
<223> OTHER INFORMATION: Xaa is N or D
<220> FEATURE:
<221> NAME/KEY: MISC_FEATURE
<222> LOCATION: (105)..(105)
<223> OTHER INFORMATION: Xaa is S, N, or D
<220> FEATURE:
<221> NAME/KEY: MISC_FEATURE
<222> LOCATION: (119)..(119)
<223> OTHER INFORMATION: Xaa is R, E, or N
<220> FEATURE:
<221> NAME/KEY: MISC_FEATURE
<222> LOCATION: (121)..(121)
<223> OTHER INFORMATION: Xaa is R, E, or D
<220> FEATURE:
<221> NAME/KEY: MISC_FEATURE
<222> LOCATION: (122)..(122)
<223> OTHER INFORMATION: Xaa is K or D
<220> FEATURE:
<221> NAME/KEY: MISC_FEATURE
<222> LOCATION: (124)..(124)
<223> OTHER INFORMATION: Xaa is K or D
<220> FEATURE:
<221> NAME/KEY: MISC_FEATURE
<222> LOCATION: (126)..(126)
<223> OTHER INFORMATION: Xaa is H or D

<400> SEQUENCE: 98

Met Asn Gln His Ser His Lys Asp Xaa Glu Thr Val Arg Ile Ala Val
1               5                   10                  15

Val Arg Ala Arg Trp His Ala Glu Ile Val Asp Ala Cys Val Ser Ala
            20                  25                  30

Phe Glu Ala Ala Met Xaa Asp Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Xaa Gly Gly Ile Tyr Xaa His Glu Phe Val Ala Ser Ala Val Ile
                85                  90                  95

Xaa Gly Met Met Asn Val Gln Leu Xaa Thr Gly Val Pro Val Leu Ser
```

```
                100             105                 110
Ala Val Leu Thr Pro His Xaa Tyr Xaa Xaa Ser Xaa Ala Xaa Thr Leu
            115                 120                 125

Leu Phe Leu Ala Leu Phe Ala Val Lys Gly Met Glu Ala Ala Arg Ala
            130                 135             140

Cys Val Glu Ile Leu Ala Ala Arg Glu Lys Ile Ala Ala
145                 150                 155

<210> SEQ ID NO 99
<211> LENGTH: 142
<212> TYPE: DNA
<213> ORGANISM: Artificial Sequence
<220> FEATURE:
<223> OTHER INFORMATION: Synthetic

<400> SEQUENCE: 99
taatgcttaa gtcgaacaga aagtaatcgt attgtacacg gccgcataat cgaaattaat      60
acgactcact ataggggaat tgtgagcgga taacaattcc ccatcttagt atattagtta     120
agtataagaa ggagatatac tt                                              142

<210> SEQ ID NO 100
<211> LENGTH: 18
<212> TYPE: DNA
<213> ORGANISM: Artificial Sequence
<220> FEATURE:
<223> OTHER INFORMATION: Synthetic

<400> SEQUENCE: 100
taaagaagga gatatcat                                                    18

<210> SEQ ID NO 101
<211> LENGTH: 17
<212> TYPE: DNA
<213> ORGANISM: Artificial Sequence
<220> FEATURE:
<223> OTHER INFORMATION: Synthetic

<400> SEQUENCE: 101
tgagaaggag atatcat                                                     17

<210> SEQ ID NO 102
<211> LENGTH: 365
<212> TYPE: PRT
<213> ORGANISM: Homo sapiens

<400> SEQUENCE: 102

Met Gly Val Pro Arg Pro Gln Pro Trp Ala Leu Gly Leu Leu Leu Phe
1               5                   10                  15

Leu Leu Pro Gly Ser Leu Gly Ala Glu Ser His Leu Ser Leu Leu Tyr
            20                  25                  30

His Leu Thr Ala Val Ser Ser Pro Ala Pro Gly Thr Pro Ala Phe Trp
        35                  40                  45

Val Ser Gly Trp Leu Gly Pro Gln Gln Tyr Leu Ser Tyr Asn Ser Leu
    50                  55                  60

Arg Gly Glu Ala Glu Pro Cys Gly Ala Trp Val Trp Glu Asn Gln Val
65                  70                  75                  80

Ser Trp Tyr Trp Glu Lys Glu Thr Thr Asp Leu Arg Ile Lys Glu Lys
                85                  90                  95

Leu Phe Leu Glu Ala Phe Lys Ala Leu Gly Gly Lys Gly Pro Tyr Thr
            100                 105                 110
```

Leu Gln Gly Leu Leu Gly Cys Glu Leu Gly Pro Asp Asn Thr Ser Val
            115                 120                 125

Pro Thr Ala Lys Phe Ala Leu Asn Gly Glu Glu Phe Met Asn Phe Asp
        130                 135                 140

Leu Lys Gln Gly Thr Trp Gly Gly Asp Trp Pro Glu Ala Leu Ala Ile
145                 150                 155                 160

Ser Gln Arg Trp Gln Gln Asp Lys Ala Ala Asn Lys Glu Leu Thr
            165                 170                 175

Phe Leu Leu Phe Ser Cys Pro His Arg Leu Arg Glu His Leu Glu Arg
            180                 185                 190

Gly Arg Gly Asn Leu Glu Trp Lys Glu Pro Pro Ser Met Arg Leu Lys
            195                 200                 205

Ala Arg Pro Ser Ser Pro Gly Phe Ser Val Leu Thr Cys Ser Ala Phe
        210                 215                 220

Ser Phe Tyr Pro Pro Glu Leu Gln Leu Arg Phe Leu Arg Asn Gly Leu
225                 230                 235                 240

Ala Ala Gly Thr Gly Gln Gly Asp Phe Gly Pro Asn Ser Asp Gly Ser
            245                 250                 255

Phe His Ala Ser Ser Ser Leu Thr Val Lys Ser Gly Asp Glu His His
            260                 265                 270

Tyr Cys Cys Ile Val Gln His Ala Gly Leu Ala Gln Pro Leu Arg Val
            275                 280                 285

Glu Leu Glu Ser Pro Ala Lys Ser Ser Val Leu Val Val Gly Ile Val
        290                 295                 300

Ile Gly Val Leu Leu Leu Thr Ala Ala Ala Val Gly Gly Ala Leu Leu
305                 310                 315                 320

Trp Arg Arg Met Arg Ser Gly Leu Pro Ala Pro Trp Ile Ser Leu Arg
            325                 330                 335

Gly Asp Asp Thr Gly Val Leu Leu Pro Thr Pro Gly Glu Ala Gln Asp
            340                 345                 350

Ala Asp Leu Lys Asp Val Asn Val Ile Pro Ala Thr Ala
        355                 360                 365

<210> SEQ ID NO 103
<211> LENGTH: 62
<212> TYPE: PRT
<213> ORGANISM: Homo sapiens

<400> SEQUENCE: 103

Met Gly Val Pro Arg Pro Gln Pro Trp Ala Leu Gly Leu Leu Leu Phe
1               5                   10                  15

Leu Leu Pro Gly Ser Leu Gly Phe Ala Cys Lys Thr Ala Asn Gly Thr
            20                  25                  30

Ala Ile Pro Ile Gly Gly Gly Ser Ala Asn Val Tyr Val Asn Leu Ala
        35                  40                  45

Pro Val Val Asn Val Gly Gln Asn Leu Val Val Asp Leu Ser
    50                  55                  60

<210> SEQ ID NO 104
<211> LENGTH: 574
<212> TYPE: PRT
<213> ORGANISM: Human respiratory syncytial virus A (strain A2)

<400> SEQUENCE: 104

Met Glu Leu Leu Ile Leu Lys Ala Asn Ala Ile Thr Thr Ile Leu Thr
1               5

```
Ala Val Thr Phe Cys Phe Ala Ser Gly Gln Asn Ile Thr Glu Glu Phe
             20                  25                  30

Tyr Gln Ser Thr Cys Ser Ala Val Ser Lys Gly Tyr Leu Ser Ala Leu
         35                  40                  45

Arg Thr Gly Trp Tyr Thr Ser Val Ile Thr Ile Glu Leu Ser Asn Ile
 50                  55                  60

Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
             85                  90                  95

Met Gln Ser Thr Pro Pro Thr Asn Asn Arg Ala Arg Glu Leu Pro
             100                 105                 110

Arg Phe Met Asn Tyr Thr Leu Asn Asn Ala Lys Lys Thr Asn Val Thr
         115                 120                 125

Leu Ser Lys Lys Arg Lys Arg Arg Phe Leu Gly Phe Leu Leu Gly Val
 130                 135                 140

Gly Ser Ala Ile Ala Ser Gly Val Ala Val Ser Lys Val Leu His Leu
 145                 150                 155                 160

Glu Gly Glu Val Asn Lys Ile Lys Ser Ala Leu Leu Ser Thr Asn Lys
             165                 170                 175

Ala Val Val Ser Leu Ser Asn Gly Val Ser Val Leu Thr Ser Lys Val
             180                 185                 190

Leu Asp Leu Lys Asn Tyr Ile Asp Lys Gln Leu Leu Pro Ile Val Asn
             195                 200                 205

Lys Gln Ser Cys Ser Ile Ser Asn Ile Glu Thr Val Ile Glu Phe Gln
             210                 215                 220

Gln Lys Asn Asn Arg Leu Leu Glu Ile Thr Arg Glu Phe Ser Val Asn
 225                 230                 235                 240

Ala Gly Val Thr Thr Pro Val Ser Thr Tyr Met Leu Thr Asn Ser Glu
             245                 250                 255

Leu Leu Ser Leu Ile Asn Asp Met Pro Ile Thr Asn Asp Gln Lys Lys
             260                 265                 270

Leu Met Ser Asn Asn Val Gln Ile Val Arg Gln Gln Ser Tyr Ser Ile
             275                 280                 285

Met Ser Ile Ile Lys Glu Glu Val Leu Ala Tyr Val Val Gln Leu Pro
 290                 295                 300

Leu Tyr Gly Val Ile Asp Thr Pro Cys Trp Lys Leu His Thr Ser Pro
 305                 310                 315                 320

Leu Cys Thr Thr Asn Thr Lys Glu Gly Ser Asn Ile Cys Leu Thr Arg
             325                 330                 335

Thr Asp Arg Gly Trp Tyr Cys Asp Asn Ala Gly Ser Val Ser Phe Phe
             340                 345                 350

Pro Gln Ala Glu Thr Cys Lys Val Gln Ser Asn Arg Val Phe Cys Asp
             355                 360                 365

Thr Met Asn Ser Leu Thr Leu Pro Ser Glu Ile Asn Leu Cys Asn Val
             370                 375                 380

Asp Ile Phe Asn Pro Lys Tyr Asp Cys Lys Ile Met Thr Ser Lys Thr
 385                 390                 395                 400

Asp Val Ser Ser Ser Val Ile Thr Ser Leu Gly Ala Ile Val Ser Cys
                 405                 410                 415

Tyr Gly Lys Thr Lys Cys Thr Ala Ser Asn Lys Asn Arg Gly Ile Ile
             420                 425                 430
```

```
Lys Thr Phe Ser Asn Gly Cys Asp Tyr Val Ser Asn Lys Gly Met Asp
            435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
        530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 105
<211> LENGTH: 64
<212> TYPE: PRT
<213> ORGANISM: Human respiratory syncytial virus A (strain A2)

<400> SEQUENCE: 105

Met Glu Leu Leu Ile Leu Lys Ala Asn Ala Ile Thr Thr Ile Leu Thr
1               5                   10                  15

Ala Val Thr Phe Cys Phe Ala Ser Gly Phe Ala Cys Lys Thr Ala Asn
            20                  25                  30

Gly Thr Ala Ile Pro Ile Gly Gly Ser Ala Asn Val Tyr Val Asn
        35                  40                  45

Leu Ala Pro Val Val Asn Val Gly Gln Asn Leu Val Val Asp Leu Ser
    50                  55                  60

<210> SEQ ID NO 106
<211> LENGTH: 178
<212> TYPE: PRT
<213> ORGANISM: Homo sapiens

<400> SEQUENCE: 106

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125
```

-continued

```
Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 107
<211> LENGTH: 57
<212> TYPE: PRT
<213> ORGANISM: Homo sapiens

<400> SEQUENCE: 107

Met His Ser Ser Ala Leu Leu Cys Cys Leu Val Leu Leu Thr Gly Val
1               5                   10                  15

Arg Ala Phe Ala Cys Lys Thr Ala Asn Gly Thr Ala Ile Pro Ile Gly
            20                  25                  30

Gly Gly Ser Ala Asn Val Tyr Val Asn Leu Ala Pro Val Val Asn Val
        35                  40                  45

Gly Gln Asn Leu Val Val Asp Leu Ser
    50                  55

<210> SEQ ID NO 108
<211> LENGTH: 562
<212> TYPE: PRT
<213> ORGANISM: Influenza A virus (strain A/Japan/305/1957 H2N2)

<400> SEQUENCE: 108

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Asn Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Glu Gly Ser Asp Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Ile Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
```

```
    210                 215                 220

Pro Glu Ile Ala Thr Arg Pro Lys Val Asn Gly Gln Gly Gly Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Gly Asn Leu Glu Arg Arg
                405                 410                 415

Leu Glu Asn Leu Asn Lys Arg Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys Gly Val Lys Leu Ser Ser Met Gly Val Tyr Gln Ile Leu Ala
        515                 520                 525

Ile Tyr Ala Thr Val Ala Gly Ser Leu Ser Leu Ala Ile Met Met Ala
    530                 535                 540

Gly Ile Ser Phe Trp Met Cys Ser Asn Gly Ser Leu Gln Cys Arg Ile
545                 550                 555                 560

Cys Ile

<210> SEQ ID NO 109
<211> LENGTH: 54
<212> TYPE: PRT
<213> ORGANISM: Influenza A virus (strain A/Japan/305/1957 H2N2)

<400> SEQUENCE: 109

Met Ala Ile Ile Tyr Leu Ile Leu Leu Phe Thr Ala Val Arg Gly Phe
1               5                   10                  15

Ala Cys Lys Thr Ala Asn Gly Thr Ala Ile Pro Ile Gly Gly Gly Ser
```

```
                    20                  25                  30

Ala Asn Val Tyr Val Asn Leu Ala Pro Val Val Asn Val Gly Gln Asn
                35                  40                  45

Leu Val Val Asp Leu Ser
            50

<210> SEQ ID NO 110
<211> LENGTH: 310
<212> TYPE: PRT
<213> ORGANISM: Artificial Sequence
<220> FEATURE:
<223> OTHER INFORMATION: Synthetic

<400> SEQUENCE: 110

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Cys Val Asn Val Gly Gln
                20                  25                  30

Asn Cys Val Val Asp Leu Ser Thr Gln Ile Phe Cys His Asn Asp Tyr
                35                  40                  45

Pro Glu Thr Ile Thr Asp Tyr Val Thr Leu Gln Arg Gly Ser Ala Tyr
            50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
                100                 105                 110

Ser Ser Ala Gly Gly Val Ala Ile Lys Ala Gly Ser Leu Ile Ala Val
                115                 120                 125

Leu Ile Leu Arg Gln Thr Asn Asn Tyr Asn Ser Asp Asp Phe Gln Phe
            130                 135                 140

Val Trp Asn Ile Tyr Ala Asn Asn Asp Val Val Pro Thr Gly Gly
145                 150                 155                 160

Cys Asp Val Ser Ala Arg Asp Val Thr Val Thr Leu Pro Asp Tyr Pro
                165                 170                 175

Gly Ser Val Pro Ile Pro Leu Thr Val Tyr Cys Ala Lys Ser Gln Asn
                180                 185                 190

Leu Gly Tyr Tyr Leu Ser Gly Thr Ala Asp Ala Gly Asn Ser Ile
            195                 200                 205

Phe Thr Asn Thr Ala Ser Phe Ser Pro Ala Gln Gly Val Gly Val Gln
        210                 215                 220

Leu Thr Arg Gln Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
                260                 265                 270

Gly Val Thr Phe Val Tyr Gln Gly Gly Ser Ser Gly Gly Ala Asp
                275                 280                 285

Val Thr Ile Thr Val Asn Gly Lys Val Val Ala Lys Gly Gly His His
                290                 295                 300

His His His His His His
305                 310
```

```
<210> SEQ ID NO 111
<211> LENGTH: 168
<212> TYPE: PRT
<213> ORGANISM: Artificial Sequence
<220> FEATURE:
<223> OTHER INFORMATION: Synthetic

<400> SEQUENCE: 111

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Cys Val Asn Val Gly Gln
            20                  25                  30

Asn Cys Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

His His His His His His His His
                165

<210> SEQ ID NO 112
<211> LENGTH: 310
<212> TYPE: PRT
<213> ORGANISM: Artificial Sequence
<220> FEATURE:
<223> OTHER INFORMATION: Synthetic

<400> SEQUENCE: 112

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140
```

```
Val Trp Asn Ile Tyr Ala Asn Asn Asp Val Val Pro Thr Gly Gly
145                 150                 155                 160

Cys Asp Val Ser Ala Arg Asp Val Thr Val Thr Leu Pro Asp Tyr Pro
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr Thr Ala Asp Ala Gly Asn Ser Ile
        195                 200                 205

Phe Thr Asn Thr Ala Ser Ser Pro Ala Gln Gly Val Gly Val Gln
    210                 215                 220

Leu Thr Arg Gln Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
                260                 265                 270

Gly Val Thr Phe Val Tyr Gln Gly Gly Ser Ser Gly Gly Ala Asp
            275                 280                 285

Val Thr Ile Thr Val Asn Gly Lys Val Val Ala Lys Gly Gly His His
        290                 295                 300

His His His His His His
305                 310

<210> SEQ ID NO 113
<211> LENGTH: 168
<212> TYPE: PRT
<213> ORGANISM: Artificial Sequence
<220> FEATURE:
<223> OTHER INFORMATION: Synthetic

<400> SEQUENCE: 113

Phe Ala Cys Lys Thr Ala Ser Gly Thr Ala Ile Pro Ile Gly Gly Gly
1               5                   10                  15

Ser Ala Asn Val Tyr Val Asn Leu Ala Pro Val Val Asn Val Gly Gln
                20                  25                  30

Asn Leu Val Val Asp Leu Ser Thr Gln Ile Phe Cys His Asn Asp Tyr
            35                  40                  45

Pro Glu Thr Ile Thr Asp Tyr Val Thr Leu Gln Arg Gly Ser Ala Tyr
        50                  55                  60

Gly Gly Val Leu Ser Ser Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
                100                 105                 110

Ser Ser Ala Gly Gly Val Ala Ile Lys Ala Gly Ser Leu Ile Ala Val
            115                 120                 125

Leu Ile Leu Arg Gln Thr Asn Asn Tyr Asn Ser Asp Asp Phe Gln Phe
        130                 135                 140

Val Trp Asn Ile Tyr Ala Asn Asn Asp Val Val Pro Thr Gly Gly
145                 150                 155                 160

His His His His His His His
                165
```